US008088805B2

(12) United States Patent
Delorme et al.

(10) Patent No.: US 8,088,805 B2
(45) Date of Patent: *Jan. 3, 2012

(54) INHIBITORS OF HISTONE DEACETYLASE

(75) Inventors: Daniel Delorme, Saint-Lazare (CA);
Silvana Marcela Leit de Moradei,
Kirkland (CA); Sylvie Frechette, Verdun
(CA)

(73) Assignee: MethylGene Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/687,398

(22) Filed: Mar. 16, 2007

(65) Prior Publication Data

US 2007/0213330 A1 Sep. 13, 2007

Related U.S. Application Data

(62) Division of application No. 11/090,713, filed on Mar. 25, 2005, now Pat. No. 7,253,204.

(60) Provisional application No. 60/556,828, filed on Mar. 26, 2004.

(51) Int. Cl.
*A61K 31/428* (2006.01)
*C07D 277/62* (2006.01)
*C07D 277/70* (2006.01)
*C07D 277/82* (2006.01)

(52) U.S. Cl. ........ 514/367; 548/152; 548/159; 548/161; 548/178; 548/180

(58) Field of Classification Search .................. 514/367; 548/161, 178, 180
See application file for complete search history.

(56) References Cited

U.S. PATENT DOCUMENTS

| 3,576,869 | A | 4/1971 | Schellenbaum et al. |
| 5,137,918 | A | 8/1992 | Weisershausen et al. |
| 5,332,750 | A | 7/1994 | Mederski et al. |
| 5,366,878 | A | 11/1994 | Pederson et al. |
| 5,635,377 | A | 6/1997 | Pederson et al. |
| 5,652,355 | A | 7/1997 | Metelev et al. |
| 5,945,450 | A | 8/1999 | Takenouchi et al. |
| 6,034,251 | A | 3/2000 | Aslanian et al. |
| 6,174,905 | B1 | 1/2001 | Suzuki et al. |
| 6,376,515 | B2 | 4/2002 | Zhu et al. |
| 6,541,661 | B1 | 4/2003 | Delorme et al. |
| 6,632,815 | B2 | 10/2003 | Zhu et al. |
| 6,653,309 | B1 | 11/2003 | Saunders et al. |
| 6,777,217 | B1 | 8/2004 | Schreiber et al. |
| 6,897,220 | B2 | 5/2005 | Delorme et al. |
| 7,253,204 | B2 | 8/2007 | Delorme et al. |
| 7,282,608 | B2 | 10/2007 | Raeppel et al. |
| 2002/0061860 | A1 | 5/2002 | Li et al. |
| 2003/0096844 | A1 | 5/2003 | Kozlowski et al. |
| 2003/0232859 | A1 | 12/2003 | Kozlowski et al. |
| 2004/0010013 | A1 | 1/2004 | Friary et al. |
| 2004/0044051 | A1 | 3/2004 | Kozlowski et al. |
| 2004/0087798 | A1 | 5/2004 | Yamada |
| 2004/0106599 | A1* | 6/2004 | Delorme et al. ......... 514/217.05 |
| 2004/0132804 | A1 | 7/2004 | Tong et al. |
| 2004/0147569 | A1 | 7/2004 | Suzuki et al. |
| 2004/0186148 | A1 | 9/2004 | Shankar et al. |
| 2005/0096222 | A1 | 5/2005 | Hidaka et al. |
| 2005/0288282 | A1* | 12/2005 | Delorme et al. ........... 514/228.2 |
| 2006/0058298 | A1* | 3/2006 | Delorme et al. ........... 514/237.5 |

FOREIGN PATENT DOCUMENTS

| CA | 2 136 288 A1 | 11/1994 |
| CA | 2480356 A1 | 10/2003 |
| CA | 2484065 A1 | 11/2003 |
| CA | 2490579 A1 | 1/2004 |
| CA | 2615105 A1 | 1/2007 |
| DE | 14 70 097 A1 | 6/1969 |
| EP | 0 657 454 A1 | 11/1994 |
| EP | 0 847 992 A1 | 6/1998 |
| EP | 1 256 341 A1 | 11/2002 |
| JP | 258863 | 9/1996 |
| JP | 11269146 A | 10/1999 |
| JP | 1999269146 A | 10/1999 |
| JP | 1999-302173 A | 11/1999 |
| JP | 2001131130 A | 5/2001 |
| JP | 2003-137866 A | 5/2003 |
| JP | 2003221380 | 8/2003 |
| WO | 98/42672 A1 | 10/1998 |
| WO | 98/45252 A1 | 10/1998 |
| WO | 00/03704 A1 | 1/2000 |
| WO | 01/16106 A1 | 3/2001 |
| WO | 01/38322 A1 | 5/2001 |
| WO | 01/60354 A1 | 8/2001 |
| WO | 01/64643 A2 | 9/2001 |
| WO | 01/68585 A4 | 9/2001 |
| WO | 01/70675 A2 | 9/2001 |
| WO | 02/069947 A2 | 9/2002 |
| WO | 03/024448 A2 | 3/2003 |
| WO | WO 03-024448 * | 3/2003 |
| WO | 03/075929 A1 | 9/2003 |
| WO | 03/076395 A1 | 9/2003 |
| WO | 03/076400 A1 | 9/2003 |

(Continued)

OTHER PUBLICATIONS

WO2003024448 (2003), disclosed in the IDS.*
Csordas, Adam, "On the Biological Role of Histone Acetylation," Biochem. J., 1990, pp. 23-38, vol. 265, Great Britain.
Taunton, Jack, et al. "A Mammalian Histone Deacetylase Related to the Yeast Transcriptional Regulator Rpd3p," Science, 1996, pp. 408-411, vol. 272.
Grozinger, Christina M., et al., "Three Proteins Define a Class of Human Histone Deacetylases Related to Yeast Hda1p," PNAS, Proc. Natl. Acad. Sci., Apr. 1999, pp. 4868-4873, vol. 96.
Kao, Hung-Ying, et al., "Isolation of a Novel Histone Deacetylase Reveals that Class I and Class II Deacetylases Promote SMRT-Mediated Repression," Genes & Development, 2000, pp. 55-66, vol. 14.
Van Den Wyngaert, Ilse, et al. "Cloning and Characterization of Human Histone Deacetylase 8," FEBS Letters, 2000, pp. 77-83. vol. 478.

(Continued)

*Primary Examiner* — Yong Chu
(74) *Attorney, Agent, or Firm* — McDonnell Boehnen Hulbert & Berghoff LLP

(57) ABSTRACT

The invention relates to the inhibition of histone deacetylase. The invention provides compounds and methods for inhibiting histone deacetylase enzymatic activity. The invention also provides compositions and methods for treating cell proliferative diseases and conditions.

4 Claims, No Drawings

FOREIGN PATENT DOCUMENTS

| WO | 03/076401 A1 | 9/2003 |
|---|---|---|
| WO | 03/076421 A1 | 9/2003 |
| WO | 03/076422 A1 | 9/2003 |
| WO | 03/076430 A1 | 9/2003 |
| WO | 03/076438 A1 | 9/2003 |
| WO | 2003/087057 A1 | 10/2003 |
| WO | 03/092686 A1 | 11/2003 |
| WO | WO 2004005513 A2 * | 1/2004 |
| WO | 2004/058234 A2 | 7/2004 |
| WO | 2004/069133 A2 | 8/2004 |
| WO | 2004/069823 A1 | 8/2004 |
| WO | 2004/071400 A2 | 8/2004 |
| WO | 2005/030705 A1 | 4/2005 |
| WO | 2005/092899 A2 | 10/2005 |
| WO | 2006/122319 A | 11/2006 |
| WO | 2007/118137 A1 | 10/2007 |

OTHER PUBLICATIONS

Zhou, Xianbo, et al., "Cloning and Characterization of a Histone Deacetylase, HDAC9," PNAS, Sep. 11, 2001,pp. 10572-10577, vol. 98, No. 19.

Kao, Hung-Ying, et al., "Isolation and Characterization of Mammalian HDAC10, a Novel Histone Deacetylase," The Journal of Biological Chemistry, 2002, pp. 187-193, vol. 277, No. 1, The American Society for Biochemistry and Molecular Biology, Inc.

Gao, Lin, et al. "Cloning and Functional Characterization of HDAC11, a Novel Member of the Human Histone Deacetylase Family," The Journal of Biological Chemistry, 2002, pp. 25748-25755, vol. 277, No. 28, The American Society for Biochemistry and Molecular Biology, Inc.

Richon, Victoria M., et al., "A Class of Hybrid Polar Inducers of Transformed Cell Differentiation Inhibits Histone Deacetylases," Proc. Natl. Acad. Sci., Mar. 1998, pp. 3003-3007, vol. 95, Cell Biology.

Yoshida, Minoru et al., "Reversible Arrest of Proliferation of Rat 3Y1 Fibroblasts in Both the G1 and G2 Phases by Trichostatin A," Experimental Cell Research, 1988, pp. 122-131, vol. 177, Academic Press, Inc.

Finnin, Michael S., et al., "Structures of a Histone Deacetylase Homologue Bound to the TSA and SAHA Inhibitors," Nature, Sep. 1999, pp. 188-193, vol. 401, Macmillan Magazines Ltd.

Yoshida, Minoru, et al., "Potent and Specific Inhibition of Mammalian Histone Deacetylase Both In Vivo and In Vitro by Trichostatin A," The Journal of Biological Chemistry, 1990, pp. 17174-17179, vol. 265, No. 28, The American Society for Biochemistry and Molecular Biology, Inc.

Ramchandani, Shyam, et al., "Inhibition of Tumorigenesis by a Cytosine-DNA, Methyltransferase, Antisense Oligodeoxynucleotide," PNAS, 1997, pp. 684-689, vol. 94, The National Academy of Sciences of the USA.

Pon, Richard T., "Solid Phase Supports for Oligonucleotide Synthesis," Methods in Molecular Biology, 1993, pp. 465-496, vol. 20, Humana Press Inc., Totowa, New Jersey.

Alaimo, Robert J., "The Preparation and Characterization of 2-Amino-5,6-Dichloro and 2-Amino-6,7-Dichlorobenzothiazole," J. Het. Chem., 1971, pp. 309-310, vol. 8.

Zee-Cheng, Robert K. Y. et al., "Antileukemic Activity of Substituted Ureidothiazoles, Ureidothiadiazoles, and Related Compounds," Journal of Medicinal Chemistry, 1979, pp. 28-32, vol. 22, No. 1.

Taurins, Alfred, et al., "Synthesis of Pyridyl- and Quinolyl-Substituted 2-Aminothiazoles," J. Het. Chem., 1970, pp. 1137-1141, vol. 7.

Rosowsky, Andre, et al., "5-Deaza-7-Desmethylene Analogues of 5,10-Methylene-5,6,7,8-Tetrahydrofolic Acid and Related Compounds: Synthesis and In Vitro Biological Activity," J. Het Chem., 1994, pp. 1241-1250, vol. 31.

Meyer, Thomas, et al., "A Derivative of Staurosporine (CGP 41 251) Shows Selectivity for Protein Kinase C Inhibition and In Vitro Anti-Proliferative as Well as In Vivo Anti-Tumor Activity," Int. J. Cancer, 1989, pp. 851-856, vol. 43.

Anderson, Malcolm, et al., "Imidazo[1,2-a]pyridines: A Potent and Selective Class of Cyclin-Dependent Kinase Inhibitors Identified Through Structure-Based Hybridisation," Bioorganic & Medical Chemistry Letters, Mar. 2003, pp. 3021-3026, vol. 13.

Zlatoidský, P. et al., "Synthesis of 4-(4-Guanidinobenzoyloxy)Benzamides and 1-(4-Guanidinobenzoyloxy) Benzoyloxy Acetamides as Trypsin Inhibitors," Eur. J. Med. Chem., 1996, pp. 895-899, vol. 31.

Zimmermann, Jürg, et al., "Phenylamino-Pyrimidine (PAP)—Derivates: A New Class of Potent and Highly Selective PDGF-Receptor Autophosphorylation Inhibitors," Bioorganic & Medicinal Chemistry Letters, 1996, pp. 1221-1226, vol. 6, No. 11.

Barvian, Mark, et al., "Pyrido[2,3-d]Pyrimidin-7-one Inhibitors of Cyclin-Dependent Kinases," J. Med. Chem., 2001, p. 1016, vol. 43.

Barvian, Mark, et al., "Pyrido[2,3-d]Pyrimidin-7-one Inhibitors of Cyclin-Dependent Kinases," J. Med. Chem., vol. 43, 2000, pp. 4606-4616, No. 24.

Suzuki, Tsuneji, et al, "Synthesis and Histone Deacetylase Inhibitory Activity of New Benzamide Derivatives," J. Med. Chem., 1999, pp. 3001-3003, vol. 42, American Chemical Society.

Piper, James R. et al., "Analogues of Methotrexate in Rheumatoid Arthritis. 2. Effects of 5-Deazaaminopterin, 5,10-Dideazaaminopterin, and Analogues on Type II Collagen-Induced Arthritis in Mice," J. Med. Chem., 1997, pp. 377-381, vol. 40, No. 3, American Chemical Society.

Grell, Wolfgang, et al., "Repaglinide and Related Hypoglycemic Benzoic Acid Derivatives," J. Med. Chem, 1998, pp. 5219-5246, vol. 41, American Chemical Society.

Geoffroy, Otto J. et al., "Chemoselective One-Pot Reductive Deamination of Aryl Amines," Tetrahedron Letters, 2001, pp. 5367-5369, vol. 42.

Boger, Dale L. et al., "Total Synthesis of Distamycin A and 2640 Analogues: A Solution-Phase Combinatorial Approach to the Discovery of New, Bioactive DNA Binding Agents and Development of a Rapid, High-Throughput Screen for Determining Relative DNA Binding Affinity or DNA Binding Sequence Selectivity," J. Am. Chem. Soc., 2000, pp. 6382-6394, vol. 122, American Chemical Society.

Matsuoka, Hiroharu, et al., "Antirheumatic Agents: Novel Methotrexate Derivatives Bearing a Benzoxazine or Benzothiazine Moiety," J. Med. Chem., 1997, pp. 105-111, vol. 40.

Hennequin, Laurent F., et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., 2002, pp. 1300-1312, vol. 45, American Chemical Society.

Taylor, Edward C., et al., "Novel 5-Desmethylene Analogues of 5,10-Dideaza-5,6,7,8-Tetrahydrofolic Acid as Potential Anticancer Agents," J. Org. Chem., 1992, pp. 3218-3225, vol. 57, American Chemical Society.

Zhu, Zhijian, et al., "Synthesis of 2,6,7-Trichloro-1-(β-D-Ribofuranosyl)Naphtho[2,3-d]Imidazole: A Linear Dimensional Analogue of the Antiviral Agent TCRB," J. Org. Chem., 1998, pp. 977-983, vol. 63, American Chemical Society.

Suzuki et al., "Benzamide Analogs as Nuclear Receptor Agonists and Reinforcement Agents for Treatment of Cell Proliferation-, Hormone-, and Vitamin-related Diseases", JP 2000256194, CA 133:247304, 2000.

Suzuki et al., Benzamide Derivatives as Histone Deacetylase Inhibitors for Treating Tumors and Other Diseases, JP 11302173, CA 131:319669, 1999.

Suzuki et al., "Preparation of Cell Differentiation-Inducing N-Phenylbenzamides and Anticancers", JP 11269146, CA 131:257321, 1999.

Graneb et al., "A Novel Mitogenic Signaling Pathway of Bradykinin in the Human Colon Carcinoma Cell Line SW-480 Involves Sequential Activation of a Gq/11 Protein, Phosphatidylinositol 3-Kinase β, and Protein Kinase C∈", The Journal of Biological Chemistry, 273(48), 1998, 32016-32022.

Charles et al., "Synthesis of substituted Benzamides, Benzimidazoles and Benzoxazines as potential Anthelminitic and Antimicrobial Agents", Archiv Der Pharmazie, 1982, 97-103, 315(2).

European Patent Office Additional Exemplary Search for Application No. EP 02 763 627.3 dated Apr. 26, 2007, 53 pages.

Database Crossfire Beilstein (Online) Beilstein Institut zur Förderung der Chemischen Wissenschaftern, Frankfurt am Main, DE, N,N1-di (o-aminophenyl) terephthalamide, Database accession No. 5619310 XP-002229372, Third invention abstract & Indian J. Chem. Sect. B., vol. 25, 1986, pp. 1146-1149.

Database Crossfire Beilstein (Online) Beilstein Institut zur Förerung der Chemischen Wissenschaften, Frankfurt am Main, DE, Database accession No. 3016237 XP-002229373, 4, 6-dimino-N, N1-bis-(2-amino-phebyl)-isoph thalamide. Third invention abstract & Chem. Heterocycl. Compd. vol. 13, 1977, pp. 1029-1032.

Database Crossfire Beilstein (Online) Beilstein Institut zur Förerung der Chemischen Wissenschaftern, Frankfurt am Main, DE, Database accession No. 3458834 XP-002229374 4, 6-dimino-N, N1-bis-(2-amino-phenyl)-phtha lamide. Third invention abstract & Justus Liebigs Ann. Chem., vol. 347, 1906, p. 116.

Picard et al., "Desymmetrization Reactions: A Convenient Syntheseis of Aromatic Diamide Diamines" Synthesis, vol. 10, 2001, pp. 1471-1478.

Rabilloud, G. et al., "Reactions de condensation de 1 'o-phénediamine avec les benzoxazin-3, 1-ones-4 substituées en position 2" Bull. Soc. Chim. Fr., 1975, pp. 2682-2686.

Cecil Textbook of Medicine, ed. by Bennet, J.C., and Plum F., 1996, 1004-1010, vol. 1.

Ragione et al., "Genes Modulated by Histone Acetylation as New Effectors of Butyrate Activity", FEBS Letters 499, 2001, 199-204.

Turner et al., "Recent Advances in the Medicinal Chemistry of Antifungal Agents", Current Pharmaceutical Design, 1996, 209-224, vol. 2.

Sugar et al., "Comparison of Three Methods of Antifungal Susceptibility Testing with the Proposed NCCLS Standard Broth Macrodilution Assay: Lack of Effect of Phenol Red", Diagn. Microbiol. Infect. Dis., 1995, 129-133, vol. 21.

Snyder et al., "Common Bacteria Whose Susceptibility to Antimicrobials is No Longer Predictable", J. Med. Liban, 2000, 208-214, 48(4).

Ye et al., CNS Drug Rev., 2001 Summer, 7(2), 199-213.

STN International Search cited by examiner in U.S. Appl. No. 11/687,398, Feb. 10, 2008, 195 pages.

U.S. Appl. No. 12/043,450, filed Mar. 6, 2008.

Weidle et al., "XP-001098720—Inhibition of Histone Deacetylase: a New Strategy to Target Epigenetic Modification for Anticancer Treatment", Anticancer Research 20, 2000, pp. 1471-1486.

U.S. Appl. No. 11/620,917, filed Jan. 8, 2007.

\* cited by examiner

INHIBITORS OF HISTONE DEACETYLASE

CROSS REFERENCE TO RELATED APPLICATIONS

This application is a division of U.S. application Ser. No. 11/090,713, filed Mar. 25, 2005, which claims priority from U.S. Provisional Application Ser. No. 60/556,828, filed Mar. 26, 2004, which are incorporated herein by reference in their entirety.

BACKGROUND OF THE INVENTION

1. Field of the Invention

This invention relates to the inhibition of histone deacetylase. More particularly, the invention relates to compounds and methods for inhibiting histone deacetylase enzymatic activity.

2. Summary of the Related Art

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, *Biochem. J.*, 286: 23-38 (1990) teaches that histones are subject to posttranslational acetylation of the ε-amino groups of N-terminal lysine residues, a reaction that is catalyzed by histone acetyl transferase (HAT1). Acetylation neutralizes the positive charge of the lysine side chain, and is thought to impact chromatin structure. Indeed, Taunton et al., *Science*, 272: 408-411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). The molecular cloning of gene sequences encoding proteins with HDAC activity has established the existence of a set of discrete HDAC enzyme isoforms. Grozinger et al., *Proc. Natl. Acad. Sci. USA*, 96: 4868-4873 (1999), teaches that HDACs is divided into two classes, the first represented by yeast Rpd3-like proteins, and the second represented by yeast Hda1-like proteins. Grozinger et al. also teaches that the human HDAC1, HDAC2, and HDAC3 proteins are members of the first class of HDACs, and discloses new proteins, named HDAC4, HDAC5, and HDAC6, which are members of the second class of HDACs. Kao et al., *Genes & Dev.*, 14: 55-66 (2000), discloses HDAC7, a new member of the second class of HDACs. Van den Wyngaert, *FEBS*, 478: 77-83 (2000) discloses HDAC8, a new member of the first class of HDACs. Zhou, X. et al., *Proc. Natl. Acad. Sci. U.S.A.* 98 (19), 10572-10577 (2001) discloses cloning and characterization of HDAC9. Kao, H. Y. et al., *J. Biol. Chem.* 277 (1), 187-193 (2002) discloses isolation and characterization of mammalian HDAC10. Gao L. et al., *J Biol Chem.* 277(28): 25748-55 (2002) discloses cloning and functional characterization of HDAC11.

Richon et al., *Proc. Natl. Acad. Sci. USA*, 95: 3003-3007 (1998), discloses that HDAC activity is inhibited by trichostatin A (TSA), a natural product isolated from *Streptomyces hygroscopicus*, and by a synthetic compound, suberoylanilide hydroxamic acid (SAHA). Yoshida and Beppu, *Exper. Cell Res.*, 177: 122-131 (1988), teaches that TSA causes arrest of rat fibroblasts at the $G_1$ and $G_2$ phases of the cell cycle, implicating HDAC in cell cycle regulation. Indeed, Finnin et al., *Nature*, 401: 188-193 (1999), teaches that TSA and SAHA inhibit cell growth, induce terminal differentiation, and prevent the formation of tumors in mice. Suzuki et al., U.S. Pat. No. 6,174,905, EP 0847992, JP 258863/96, and Japanese Application No. 10138957, disclose benzamide derivatives that induce cell differentiation and inhibit HDAC. Delorme et al., WO 01/38322 and PCT IB01/00683, disclose additional compounds that serve as HDAC inhibitors.

These findings suggest that inhibition of HDAC activity represents a novel approach for intervening in cell cycle regulation and that HDAC inhibitors have great therapeutic potential in the treatment of cell proliferative diseases or conditions. To date, few inhibitors of histone deacetylase are known in the art. There is thus a need to identify additional HDAC inhibitors and to identify the structural features required for potent HDAC inhibitory activity.

BRIEF SUMMARY OF THE INVENTION

The invention provides compounds and methods for treating cell proliferative diseases. The invention provides new inhibitors of histone deacetylase enzymatic activity.

In a first aspect, the invention provides compounds that are useful as inhibitors of histone deacetylase.

In a second aspect, the invention provides a composition comprising an inhibitor of histone deacetylase according to the invention and a pharmaceutically acceptable carrier, excipient, or diluent.

In a third aspect, the invention provides a method of inhibiting histone deacetylase in a cell, comprising contacting a cell in which inhibition of histone deacetylase is desired with an inhibitor of histone deacetylase of the invention.

In a fourth aspect, the invention provides a method for treating cell proliferative diseases.

The foregoing merely summarizes certain aspects of the invention and is not intended to be limiting in nature. These aspects and other aspects and embodiments are described more fully below.

DETAILED DESCRIPTION OF THE PREFERRED EMBODIMENTS

The invention provides compounds and methods for inhibiting histone deacetylase enzymatic activity. The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

As used herein, the terms "histone deacetylase" and "HDAC" are intended to refer to any one of a family of enzymes that remove acetyl groups from the ε-amino groups of lysine residues at the N-terminus of a histone. Unless otherwise indicated by context, the term "histone" is meant to refer to any histone protein, including H1, H2A, H2B, H3, H4, and H5, from any species. Preferred histone deacetylases include class I and class II enzymes. Preferably the histone deacetylase is a human HDAC, including, but not limited to, HDAC-1, HDAC-2, HDAC-3, HDAC-4, HDAC-5, HDAC-6, HDAC-7, HDAC-8, HDAC-9, HDAC-10, and HDAC-11. In some other preferred embodiments, the histone deacetylase is derived from a protozoal or fungal source.

The terms "histone deacetylase inhibitor" and "inhibitor of histone deacetylase" are used to identify a compound having a structure as defined herein, which is capable of interacting with a histone deacetylase and inhibiting its enzymatic activity. "Inhibiting histone deacetylase enzymatic activity" means reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as $(A)_a$-B—, wherein a is 0 or 1. In such instances, when a is 0 the moiety is B— and when a is 1 the moiety is A-B—.

The term "hydrocarbyl" refers to a straight, branched, or cyclic alkyl, alkenyl, or alkynyl, each as defined herein. A "$C_0$" hydrocarbyl is used to refer to a covalent bond. Thus, "$C_0$-$C_3$-hydrocarbyl" includes a covalent bond, methyl, ethyl, ethenyl, ethynyl, propyl, propenyl, propynyl, and cyclopropyl.

The term "alkyl" as employed herein refers to straight and branched chain aliphatic groups having from 1 to 12 carbon atoms, preferably 1-8 carbon atoms, and more preferably 1-6 carbon atoms, which is optionally substituted with one, two or three substituents. Preferred alkyl groups include, without limitation, methyl, ethyl, propyl, isopropyl, butyl, isobutyl, sec-butyl, tert-butyl, pentyl, and hexyl. A "$C_0$" alkyl (as in "$C_0$-$C_3$-alkyl") is a covalent bond (like "$C_0$" hydrocarbyl).

The term "alkenyl" as used herein means an unsaturated straight or branched chain aliphatic group with one or more carbon-carbon double bonds, having from 2 to 12 carbon atoms, preferably 2-8 carbon atoms, and more preferably 2-6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2-8 carbon atoms, and more preferably 2-6 carbon atoms, which is optionally substituted with one, two or three substituents. Preferred alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butynylene.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, and N.

An "aryl" group is a $C_6$-$C_{14}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $(C_1$-$C_6)$alk ($C_6$-$C_{10}$)aryl, including, without limitation, benzyl, phenethyl, and naphthylmethyl.

A "heterocyclic" group (or "heterocyclyl) is an optionally substituted nonaromatic mono-, bi-, or tricyclic structure having from about 3 to about 14 atoms, wherein one or more atoms are selected from the group consisting of N, O, and S. One ring of a bicyclic heterocycle or two rings of a tricyclic heterocycle may be aromatic, as in indan and 9,10-dihydro anthracene. The heterocyclic group is optionally substituted on carbon with oxo or with one of the substituents listed above. The heterocyclic group may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

As used herein, the term "heteroaryl" refers to optionally substituted groups having 5 to 14 ring atoms, preferably 5, 6, 9, or 10 ring atoms; having 6, 10, or 14 pi electrons shared in a cyclic array; and having, in addition to carbon atoms, between one or more heteroatoms selected from the group consisting of N, O, and S. For example, a heteroaryl group may be pyrimidinyl, pyridinyl, benzimidazolyl, thienyl, benzothiazolyl, benzofuranyl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, triazolyl, and isoxazolyl.

A "heteroaralkyl" or "heteroarylalkyl" group comprises a heteroaryl group covalently linked to an alkyl group, either of which is independently optionally substituted or unsubstituted. Preferred heteroalkyl groups comprise a $C_1$-$C_6$ alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl.

An "arylene," "heteroarylene," or "heterocyclylene" group is an aryl, heteroaryl, or heterocyclyl group, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, haloalkoxy, aryloxy, heteroaryloxy, amino, acylamino, alkylcarbamoyl, arylcarbamoyl, aminoalkyl, acyl, carboxy, hydroxyalkyl, alkanesulfonyl, arenesulfonyl, sulfonamido, alkanesulfonamido, arenesulfonamido, aralkylsulfonamido, alkylcarbonyl, acyloxy, cyano, alkylthio, ureido, and ureidoalkyl groups. Preferred substituents, which are themselves not further substituted (unless expressly stated otherwise) are:

(a) halo, cyano, oxo, alkyl, alkoxy, alkylthio, haloalkoxy, aminoalkyl, aminoalkoxy, carboxy, formyl, nitro, amino, amidino, carbamoyl, guanidino, $C_3$-$C_7$ heterocycle, heterocyclylalkyl, heterocyclylcarbonyl, hydroxyalkyl, alkoxyalkyl, (b) $C_1$-$C_5$ alkyl or alkenyl or arylalkyl imino, carbamoyl, carbamate, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, heteroarylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, heteroaryloxy, arylalkyl ether, $C_3$-$C_7$ heterocyclylalkylether, aryl, aryl fused to a cycloalkyl or heterocycle or another aryl ring, $C_3$-$C_7$ heterocycle, heteroaryl, arylcarbamoyl, or any of these rings fused or spiro-fused to a cycloalkyl, heterocyclyl, or aryl, wherein any of the foregoing which are additionally substitutable is further optionally substituted with one more moieties listed in (a), above; and (c) —$(CH_2)_s$—$NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$-$C_8$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents from (a), above.

In addition, substituents on cyclic moieties (i.e., cycloalkyl, heterocyclyl, aryl, heteroaryl) include 5-6 membered mono-and 9-14 membered bi-cyclic moieties fused to the parent cyclic moiety to form a bi-or tri-cyclic fused ring system. For example, an optionally substituted phenyl includes, but not limited to, the following:

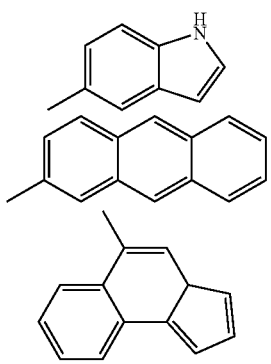

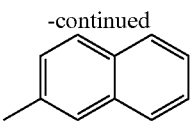

Preferred substituents on cyclic moieties (i.e., cycloalkyl, heterocyclyl, aryl, heteroaryl) also include groups of the formula —$K^1$—N(H)($R^{10}$), wherein $K^1$ is a chemical bond or $C_1$-$C_4$ alkylene;

$R^{10}$ is selected from the group consisting of Z' and -$Ak^2$-Z', wherein $Ak^2$ is $C_1$-$C_4$ alkylene; and Z' is cycloalkyl, aryl, heteroaryl, or heterocyclyl, each of which optionally is substituted, and each of which optionally is fused to one or more aryl or heteroaryl rings, or to one or more saturated or partially unsaturated cycloalkyl or heterocyclic rings.

Particularly preferred substituents on cyclic moieties (such as aryl, heteroaryl, cycloalkyl, heterocyclyl, or any of these rings fused to one or more aryl or heteroaryl rings, or to one or more saturated or partially unsaturated cycloalkyl or heterocyclic rings), include 1, 2, or 3 groups independently selected from the following:

a) alkoxy, cyano, amino, oxo, haloalkyl, halo, alkyl, $R_{50}$—C(O)—N($R_{32}$)—, $R_{50}$—O—C(O)—N($R_{32}$)—, $R_{50}$—NH—C(O)—N($R_{32}$)—, $R_{50}$—NH—C(O)—O—, ($R_{32}$)($R_{33}$)N-alkyl-, ($R_{32}$)($R_{33}$)N-alkyl-O—, ($R_{32}$)($R_{33}$)N-alkenylene-N($R_{32}$)—, N($R_{32}$)-aryl-N($R_{32}$)—C(O)-arylalkyl-N($R_{32}$)—;

wherein $R_{50}$ is cycloakyl, heterocyclyl-$C_1$-$C_6$ alkyl-, $R_{32}R_{33}$N-alkyl-, or alkyl;

b) aryl-$C_0$-$C_6$ alkyl-, heteroaryl-$C_0$-$C_6$ alkyl-, cycloalkyl-$C_0$-$C_6$ alkyl-, heterocyclyl-$C_0$-$C_6$ alkyl-, aryl-$C_0$-$C_6$ alkyl-N($R_{32}$)—, aryl-C(O)—, heteroaryl-$C_0$-$C_6$ alkyl-N($R_{32}$)—, heterocyclyl-$C_0$-$C_6$ alkyl-N($R_{32}$)—, aryl-O—, heteroaryl-O—, aryl-S—, heteroaryl-S—, aryl-$SO_2$—, heteroaryl-$SO_2$, aryl-C(O)N($R_{32}$)—, heteroaryl-C(O)N($R_{32}$)—, heteroaryl-C(H)($SO_2$-heteroaryl)-N($R_{32}$)—;

wherein $R_{32}$ and $R_{33}$ are independently H or $C_1$-$C_6$ alkyl, or $R_{32}$ and $R_{33}$ taken together with the N to which they are attached form a heterocyclyl or heteroaryl;

and wherein any of the rings described in paragraphs [0045]-[0048] are further optionally substituted with 1, 2, or 3 groups independently selected from alkyl, alkoxy, thioalkoxy, alkyl-$SO_2$—, amino, halo, cyano, haloalkyl, hydroxyalkyl, alkoxyalkoxyalkyl, COOH, alkanoyl, alkanoate, $NO_2$, hydroxy, haloalkoxy, ($R_{32}$)($R_{33}$)N—$C_0$-$C_6$ alkyl-, ($R_{32}$)($R_{33}$)N—$C_0$-$C_6$ alkyl-O—, ($R_{32}$)($R_{33}$)N—C(O)—, heteroaryl, alkyl-C(O)N($R_{32}$)—, aryl-O—, ($R_{32}$)($R_{33}$)N—$SO_2$—, aryl, and ($R_{32}$)($R_{33}$)N—alkyl-C(O)N($R_{32}$)—.

A "halohydrocarbyl" is a hydrocarbyl moiety in which from one to all hydrogens have been replaced with one or more halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally optionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluoro-3-propylphenyl. As another non-limiting example, substituted N-octyls include 2,4dimethyl-5-ethyl-octyl and 3-cyclopentyl-octyl. Included within this definition are methylenes (—$CH_2$—) substituted with oxygen to form carbonyl —CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Throughout the specification preferred embodiments of one or more chemical substituents are identified. Also preferred are combinations of preferred embodiments. For example, paragraph [0080] describes preferred embodiments of Cy in the compound of formula (1a) and paragraph [0078] describes preferred embodiments of W of the compound of formula (1a). Thus, also contemplated as within the scope of the invention are compounds of formula (1) in which Cy is as described in paragraph [0080] and W is as described in paragraph [0078].

Some compounds of the invention may have chiral centers and/or geometric isomeric centers (E- and Z-isomers), and it is to be understood that the invention encompasses all such optical, diastereoisomers and geometric isomers. The invention also comprises all tautomeric forms of the compounds disclosed herein. Where compounds of the invention include chiral centers, the invention encompasses the enantiomerically pure isomers of such compounds, the enantiomerically enriched mixtures of such compounds, and the racemic mixtures of such compounds.

The compounds of the invention may be administered in the form of an in vivo hydrolyzable ester or in vivo hydrolyzable amide. An in vivo hydrolyzable ester of a compound of the invention containing carboxy or hydroxy group is, for example, a pharmaceutically acceptable ester which is hydrolyzed in the human or animal body to produce the parent acid or alcohol. Suitable pharmaceutically acceptable esters for carboxy include $C_{1-6}$-alkoxymethyl esters (e.g., methoxymethyl), $C_{1-6}$-alkanoyloxymethyl esters (e.g., for example pivaloyloxymethyl), phthalidyl esters, $C_{3-8}$-cycloalkoxycarbonyloxy$C_{1-6}$-alkyl esters (e.g., 1-cyclohexylcarbonyloxyethyl); 1,3-dioxolen-2-onylmethyl esters (e.g., 5-methyl-1,3-dioxolen-2-onylmethyl; and $C_{1-6}$-alkoxycarbonyloxyethyl esters (e.g., 1-methoxycarbonyloxyethyl) and may be formed at any carboxy group in the compounds of this invention.

An in vivo hydrolyzable ester of a compound of the invention containing a hydroxy group includes inorganic esters such as phosphate esters and a-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl (to give carbamates), N,N-dialkylaminoacetyl and carboxyacetyl. Examples of substituents on benzoyl include morpholino and piperazino linked from a ring nitrogen atom via a methylene group to the 3-or 4-position of the benzoyl ring. A suitable value for an in vivo hydrolyzable amide of a compound of the invention containing a carboxy group is, for example, a N—$C_{1-6}$-alkyl or N,N-di-$C_{1-6}$-alkyl amide such as N-methyl, N-ethyl, N-propyl, N,N-dimethyl, N-ethyl-N-methyl or N,N-diethyl amide.

Compounds

In a first aspect, the invention provides novel inhibitors of histone deacetylase. In a first embodiment, the novel inhibitors of histone deacetylase are represented by formula (1):

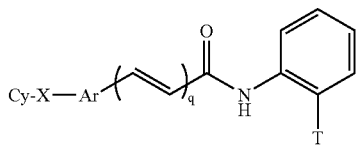

(1)

and pharmaceutically acceptable salts thereof, wherein

X is selected from the group consisting of a chemical bond, L, W-L, L-W, L-W-L, and L-W'-L-W', wherein Cy is aryl, heteroaryl, cycloalkyl or heterocyclyl, each of which is optionally substituted and each of which is optionally fused to one or more aryl or heteroaryl rings, or to one or more saturated or partially unsaturated cycloalkyl or heterocyclic rings, each of which rings is optionally substituted;

W, at each occurrence, is S, O, C=O, —NH—C(=O)—NH—, —NHSO$_2$—, or N(R$^9$), where R$^9$ is selected from the group consisting of hydrogen, alkyl, hydroxyalkyl, and t-butoxycarbonyl;

W' at each occurrence is independently a chemical bond, S, O, or NH; and

L, at each occurrence, is independently a chemical bond or $C_1$-$C_4$ alkylene; or Ar is arylene or heteroarylene, each of which is optionally substituted;

q is 0 or 1; and

T is $NH_2$ or OH;

provided that when Cy is naphthyl, X is —$CH_2$—, Ar is phenyl, and q is 0 or 1, T is not OH.

In some preferred embodiments of the compound according to paragraph [0059], q is 1, and T is $NH_2$.

Preferred compounds of the embodiments of paragraph [0070] include those wherein Ar is phenylene, and Cy-X— is

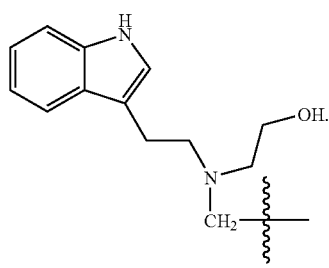

In some preferred embodiments of the compounds according to paragraph [0059], q is 0.

In a preferred embodiment, the HDAC inhibitors of the invention comprise compounds of paragraph [0072] having formula (1a):

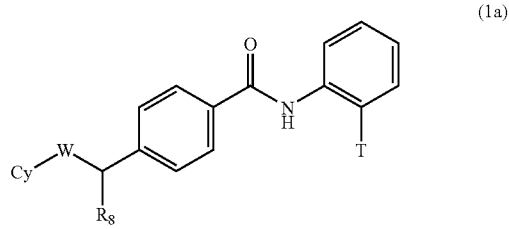

(1a)

and pharmaceutically acceptable salts thereof, wherein

Cy is aryl, heteroaryl, cycloalkyl or heterocyclyl, each of which is optionally substituted and each of which is optionally fused to one or more aryl or heteroaryl rings, or to one or more saturated or partially unsaturated cycloalkyl or heterocyclic rings, each of which rings is optionally substituted;

W is S, O, or N(R$_9$), wherein R$_9$ is hydrogen or $C_1$-$C_6$-alkyl;

R$_8$ is H or $C_1$-$C_4$ alkyl; and

T is $NH_2$ or OH.

In some preferred embodiments of the compounds according to paragraph [0073], W is NH or S.

Preferred compounds according to the invention, and particularly paragraph [0078], include those wherein Cy is selected from phenyl, pyridyl, pyrimidinyl, pyrazinyl, pyridazinyl, thiazolyl, benzothiazolyl, benzoimidazolyl, and benzotriazolyl, each of which is optionally substituted.

Preferred compounds according to paragraph [0080] include those of the structure 1a-1:

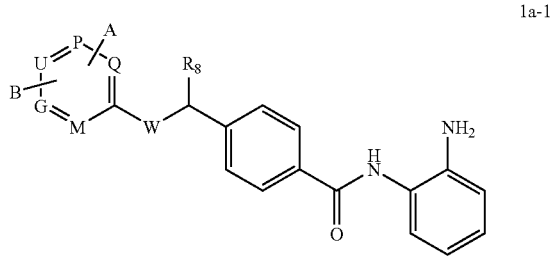

1a-1 and pharmaceutically acceptable salts thereof, wherein W is NH or S; P, Q, M, G and U are independently CH or N, provided that no more than two of P, Q, M, G and U are N and in the ring containing P, Q, M, G, and U, an annular S or O is not adjacent to another annular S or O; R$_8$ is H or $C_1$-$C_4$ alkyl; and A and B are as defined below.

Preferred compounds according to paragraph [0080] include those of the structure 1a-2:

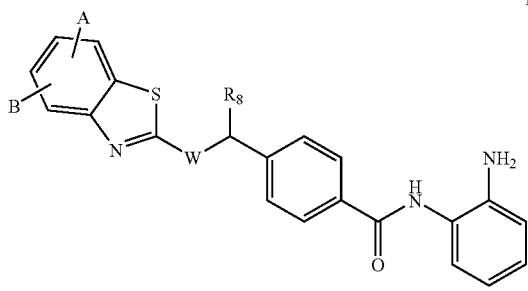

1a-2 and pharmaceutically acceptable salts thereof, wherein W is S or NH; $R_8$ is H or $C_1$-$C_4$ alkyl; and A and B are as defined below.

Preferred compounds according to paragraph [0080] include those of the structure 1a-3:

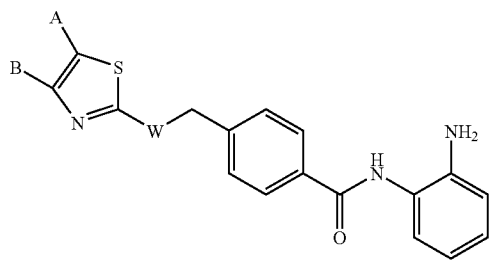

1a-3 and pharmaceutically acceptable salts thereof, wherein W is S or NH, and A and B are as defined below.

Preferred compounds according to paragraph [0085] include those wherein W is NH.

Preferred compounds according to paragraph [0080] include those of the structure 1a-4:

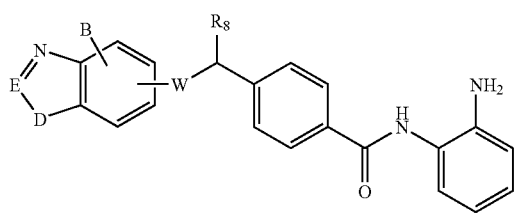

1a-4 and pharmaceutically acceptable salts thereof, wherein W is S or NH; D is N—$R_{10}$ or S, E is N or C-A; $R_8$ and $R_{10}$ are independently H or $C_1$-$C_4$ alkyl; and A and B are as described below.

Preferred compounds according to paragraph [0088] include those wherein W is NH.

Preferred compounds according to paragraph [0081] include those of the formula 1a-5:

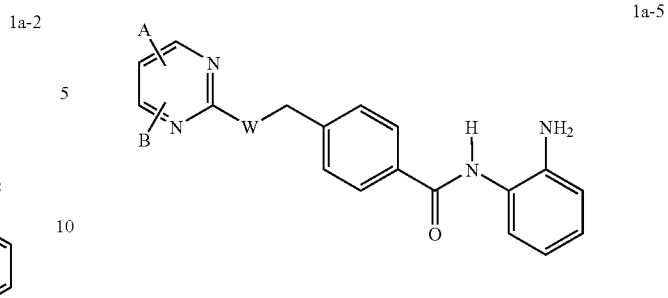

1a-5 and pharmaceutically acceptable salts thereof.

Preferred compounds according to paragraph [0091] include those wherein W is NH.

Preferred compounds according to paragraphs [0073] and [0078] also include those wherein W is NH and Cy is quinoxalinyl, phthalimidyl, or benzodioxolyl, each of which is optionally substituted with A and/or B, wherein A and B are as defined below.

In a further preferred embodiment, the HDAC inhibitors of the invention comprise compounds of paragraph [0059] having formula (1b):

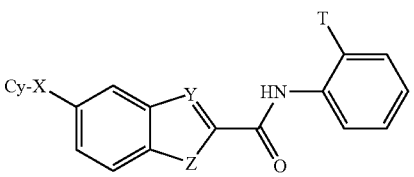

(1b)

and pharmaceutically acceptable salts thereof, wherein

Cy is aryl, heteroaryl, cycloalkyl or heterocyclyl, each of which is optionally substituted and each of which is optionally fused to one or more aryl or heteroaryl rings, or to one or more saturated or partially unsaturated cycloalkyl or heterocyclic rings, each of which rings is optionally substituted;

X is L, W-L, or L-W, wherein
  W, at each occurrence, is S, O, or NH; and
    L is —$CH_2$—;
Y is N or CH;
Z is O, S, $NR_{12}$ or $CH_2$;
  $R_{12}$ is H or $C_1$-$C_4$ alkyl; and
T is $NH_2$ or OH.

In some preferred embodiments of the compounds according to paragraph [0095], T is $NH_2$.

Preferred compounds according to each of paragraphs [0095] and [0105] include those wherein X is —S—$CH_2$—, —NH—$CH_2$— or —$CH_2$—NH—.

Preferred compounds according to paragraphs [0095], [0105], and [0106] include those wherein Cy is aryl or heteroaryl, each of which is optionally substituted.

Preferred compounds according to each of paragraphs [0095]-[0107] include those wherein Cy is phenyl, pyridyl, pyrimidinyl, or benzothiazolyl, each of which is optionally substituted.

Preferred compounds according to each of paragraphs [0095]-[0108] include those wherein Cy is substituted with A and/or B, wherein A and B are as defined in paragraph [0187].

Preferred compounds according to paragraph each of paragraphs [0095]-[0108] include those wherein Cy is optionally substituted with one two or three groups independently selected from alkoxy, acyl, morpholino, or phenyl optionally substituted with alkoxy.

In a further preferred embodiment, the HDAC inhibitors of the invention comprise compounds of paragraph [0059] having formula (1c):

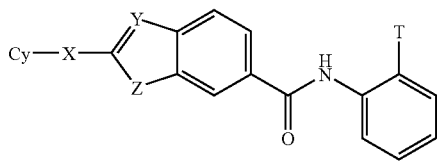

and pharmaceutically acceptable salts thereof, wherein
Cy is aryl, heteroaryl, cycloalkyl, or heterocyclyl, each of which is optionally substituted and each of which is optionally fused to one or more aryl or heteroaryl rings, or to one or more saturated or partially unsaturated cycloalkyl or heterocyclic rings, each of which rings is optionally substituted;
X is L, W-L, or L-W, wherein
  W, at each occurrence, is S, O, or NH; and
  L is —CH$_2$—;
Y is N or CH;
Z is O, S, NR$_{12}$ or CH$_2$;
  R$_{12}$ is H or C$_1$-C$_4$ alkyl; and
T is NH$_2$ or OH.

In some preferred embodiments of the compounds according to paragraph [0111], T is NH$_2$.

Preferred compounds according to each of paragraphs [0111]-[0121] include those wherein X is —S—CH$_2$—, —NH—CH$_2$— or —CH$_2$—NH—.

Preferred compounds according to each of paragraphs [0111]-[0122] include those wherein Cy is aryl or heteroaryl, each of which is optionally substituted.

Preferred compounds according to each of paragraphs [0111]-[0122] include those wherein Cy is phenyl, pyridyl, pyrimidinyl, or benzothiazolyl, each of which is optionally substituted.

Preferred compounds according to each of paragraphs [0111]-[0124] include those wherein Cy is substituted with A and/or B, wherein A and B are as defined in paragraph [0187].

Preferred compounds according to each of paragraphs [0111]-[0124] include those wherein Cy is optionally substituted with one two or three groups independently selected from alkoxy, haloalkoxy, acyl, morpholino, or phenyl optionally substituted with alkoxy.

In a further preferred embodiment, the HDAC inhibitors of the invention comprise compounds of paragraph [0059] having formula (1d):

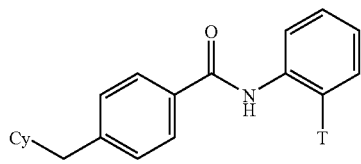

and pharmaceutically acceptable salts thereof, wherein
Cy is aryl, or heteroaryl, each of which is optionally substituted and each of which is optionally fused to one or more aryl or heteroaryl rings, or to one or more saturated or partially unsaturated cycloalkyl or heterocyclic rings, each of which rings is optionally substituted; and
T is NH$_2$ or OH.

In some preferred embodiments of the compounds according to paragraph [0127], T is NH$_2$.

Preferred compounds according to each of paragraphs [0127]-[0131] include those wherein Cy is optionally substituted heteroaryl or optionally substituted heterocyclyl, each of which is optionally fused to one or more aryl or heteroaryl rings, or to one or more saturated or partially unsaturated cycloalkyl or heterocyclic rings, each of which rings is optionally substituted.

Preferred compounds according to each of paragraphs [0127]-[0132] include those wherein Cy is:

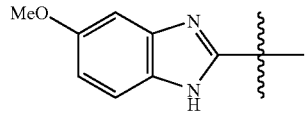

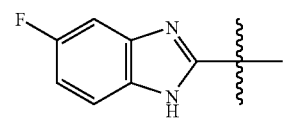

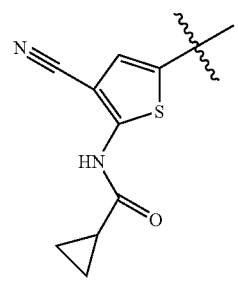

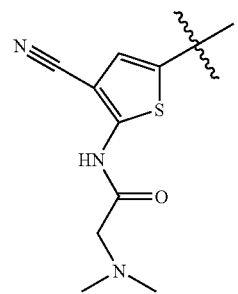

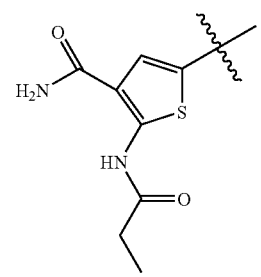

-continued

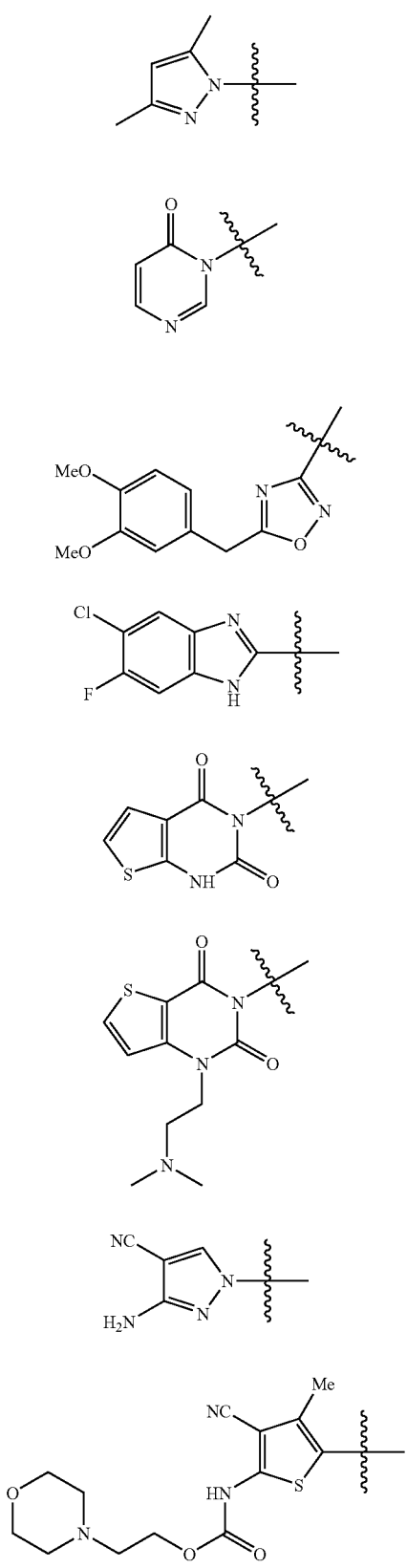

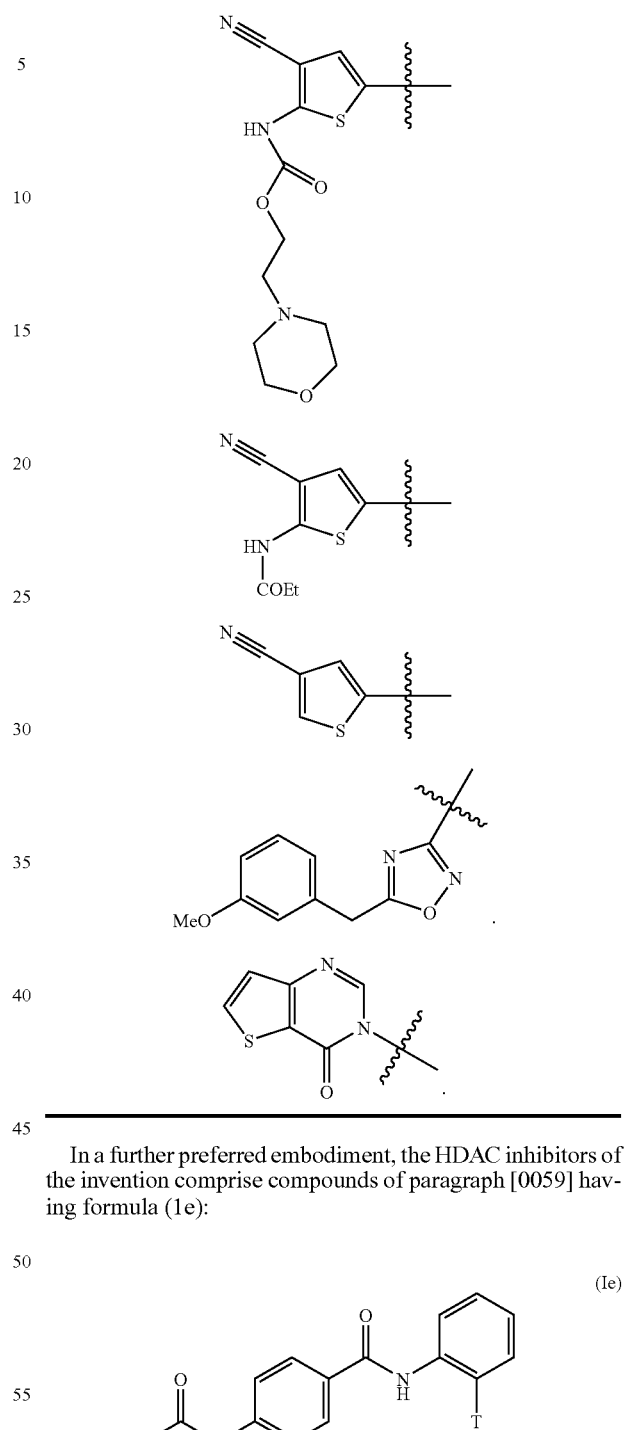

In a further preferred embodiment, the HDAC inhibitors of the invention comprise compounds of paragraph [0059] having formula (1e):

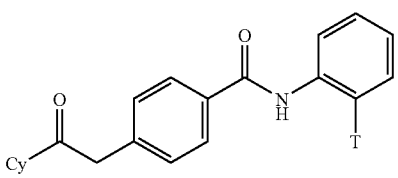

(Ie)

and pharmaceutically acceptable salts thereof, wherein
Cy is aryl, heteroaryl, cycloalkyl, or heterocyclyl, each of which is optionally substituted and each of which is optionally fused to one or more aryl or heteroaryl rings, or to one or more saturated or partially unsaturated cycloalkyl or heterocyclic rings, each of which rings is optionally substituted; and
T is $NH_2$ or OH In some preferred embodiments of the compounds according to paragraph [0134], T is NH$_2$.

Preferred compounds according to each of paragraphs [0134]-[0137] include those wherein Cy is heterocyclyl or heteroaryl, each of which is optionally substituted, and each of which contains at least one nitrogen atom as part of the ring.

Preferred compounds according to each of paragraphs [0134]-[0139] include those wherein Cy is bound to phenyl through a nitrogen atom.

Preferred compounds according to each of paragraphs [0134]-[0139] include those wherein Cy is heterocyclyl, which is optionally substituted.

Preferred compounds according to paragraph each of paragraphs [0134]-[0139] and [0140] include those wherein Cy is piperidinyl, or piperazinyl, each of which is optionally substituted.

Preferred compounds according to each of paragraphs [0134]-[0142] include those wherein Cy is optionally substituted with one or two substituents independently selected from A and B, wherein A and B are as defined in paragraph [0187].

Preferred compounds according to each of paragraphs [0134]-[0142] include those wherein Cy is optionally substituted with one or two substituents independently selected from:

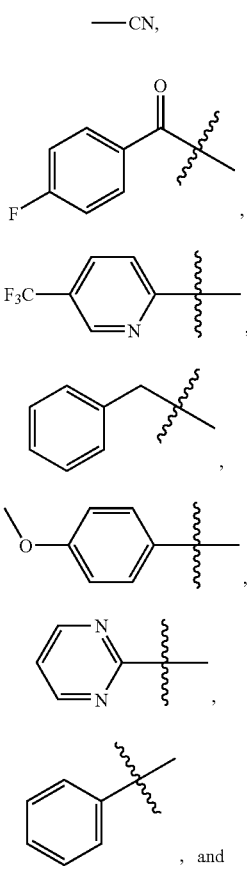

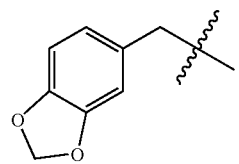

Preferred compounds according to paragraph [0072] include those wherein Ar is phenylene, indolyl or indolinyl, each of which is optionally substituted, and X is absent, CH$_2$, —O—CH$_2$—, —S—CH$_2$—, —S—C(CH$_3$)(H)—, or —N(R$_9$)—CH$_2$—

Preferred compounds according to paragraph [0145] include those wherein Ar is an indolyl or indolinyl group, X is CH$_2$ or —N(R$_9$)—CH$_2$—, and Cy is:

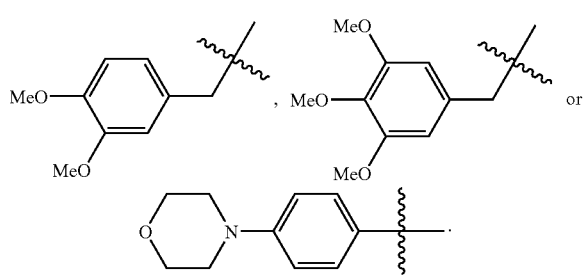

Preferred compounds according to paragraph [0145] include those wherein Ar is phenylene, X is —S—CH$_2$—, or —S—C(CH$_3$)(H)—, and Cy is:

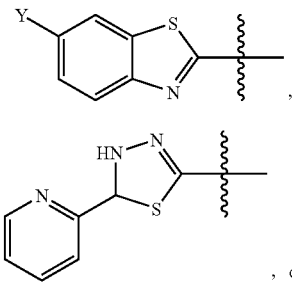

wherein Y is selected from:

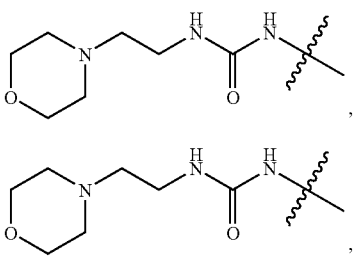

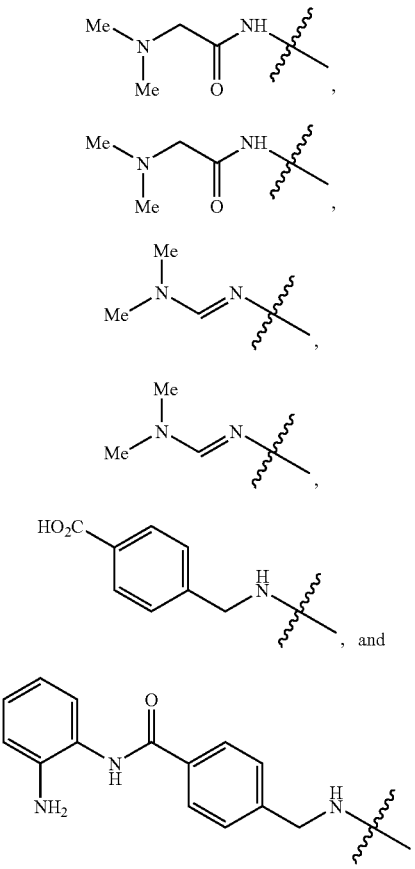

Preferred compounds according to paragraph 0 include those wherein Y' is H, and Y" is:

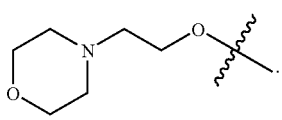

Preferred compounds according to paragraph [0145] include those of the formula (1f):

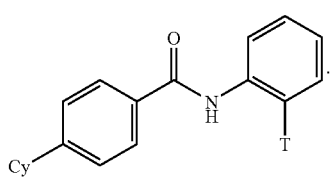

(1f)

Preferred compounds according to paragraph [0150] include those wherein Cy is heterocyclyl or heteroaryl, each of which is optionally substituted, and each of which contains at least one nitrogen atom as part of the ring.

Preferred compounds according to paragraph [0151] include those wherein Cy is bound to the phenyl through a nitrogen atom.

Preferred compounds according to paragraph [0150] include those wherein Cy is:

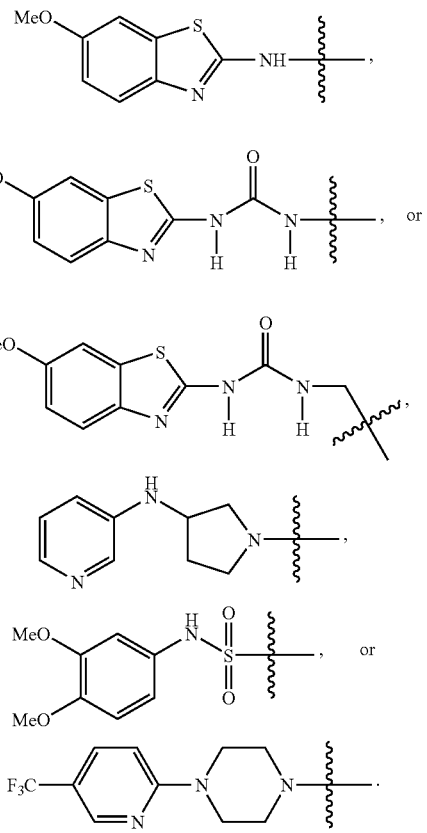

Preferred compounds according to paragraph [0150] include those of the formula (1f-1):

(1f-1)

and pharmaceutically acceptable salts thereof, wherein T is OH or NH$_2$ and A is as defined below.

Preferred compounds according to paragraph [0154] include those wherein T is NH$_2$.

Preferred compounds according to paragraph [0145] include those wherein Ar is phenylene, X is —O—CH$_2$—, and Cy is:

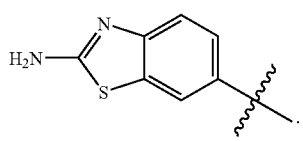

In a further preferred embodiment, the HDAC inhibitors of the invention comprise compounds of paragraph [0059] having formula (1 g):

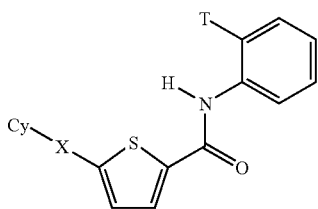

(1g)

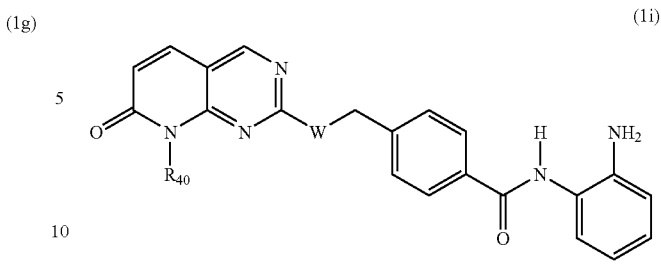

(1i)

and pharmaceutically acceptable salts thereof, wherein
Cy is aryl, or heteroaryl, cycloalkyl, or heterocyclyl, each of which is optionally substituted and each of which is optionally fused to one or more aryl or heteroaryl rings, or to one or more saturated or partially unsaturated cycloalkyl or heterocyclic rings, each of which rings is optionally substituted;

X is L, W-L, or L-W, wherein
  W, at each occurrence, is S, O, or NH; and
  L is —CH$_2$—;
T is NH$_2$ or OH.

Preferred compounds according to paragraph [0158] include those wherein Cy is optionally substituted heteroaryl. More preferably, Cy is optionally substituted pyrimidinyl. Also preferably, Cy is pyrimidinyl substituted with pyridyl.

Preferred compounds according to paragraph [0158] also include those wherein X is —NH—CH$_2$—.

Preferred compounds according to paragraph [0158] also include compounds wherein T is NH$_2$.

Preferred compounds according to paragraph [0059] include those of the formula (1 h):

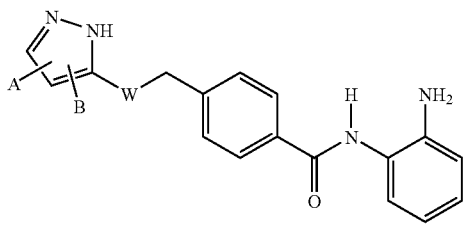

(1h)

and pharmaceutically acceptable salts thereof, where W is S, O, or NH and A and B are as described below.

Preferred compounds according to paragraph [0167] include those wherein W is NH.

Preferred compounds according to paragraph [0167] include those wherein A is optionally substituted pyridyl or optionally substituted phenyl.

Preferred compounds according to paragraph [0167] include those wherein B is H or halo. Preferably, halo is chloro.

Preferred compounds according to paragraph [0059] include those of the formula (1i):

and pharmaceutically acceptable salts thereof, where W is S, O, or NH and R40 is H or C$_1$-C$_6$ alkyl.

Preferred compounds according to paragraph [0173] include those wherein W is NH.

Preferred compounds according to paragraph [0173] include those wherein R$_{40}$ is H.

Preferred compounds according to paragraph [0173] include those wherein R$_{40}$ is methyl.

In a further preferred embodiment, the novel histone deacetylase inhibitors of the invention are compounds of formula (2)

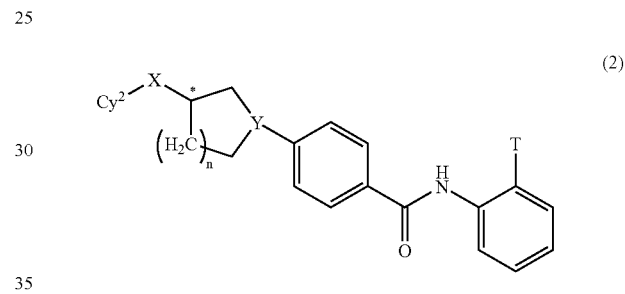

(2)

and pharmaceutically acceptable salts thereof, wherein
Cy$^2$ is aryl or heteroaryl, each of which is optionally substituted and wherein each of aryl, and heteroaryl is optionally fused to one or more aryl or heteroaryl rings, or to one or more saturated or partially unsaturated cycloalkyl or heterocyclic rings, each of which rings is optionally substituted;

X is selected from the group consisting of: a covalent bond, C$_0$-C$_4$-hydrocarbyl, C$_0$-C$_4$-hydrocarbyl-(CO)—C$_0$-C$_4$-hydrocarbyl, C$_0$-C$_4$-hydrocarbyl-(NR$^7$)—C$_0$-C$_4$-hydrocarbyl, C$_0$-C$_4$-hydrocarbyl-(S)—C$_0$-C$_4$-hydrocarbyl, C$_0$-C$_4$-hydrocarbyl-(O)—C$_0$-C$_4$-hydrocarbyl, C$_0$-C$_4$-hydrocarbyl-(SO)—C$_0$-C$_4$-hydrocarbyl, C$_0$-C$_4$-hydrocarbyl —(SO$_2$)—C$_0$-C$_4$-hydrocarbyl, C$_0$-C$_4$-hydrocarbyl —(NH)—(CO)—C$_0$-C$_4$-hydrocarbyl, C$_0$-C$_4$-hydrocarbyl —(CO)—(NH)—C$_0$-C$_4$-hydrocarbyl, —NH—CO—NH—, —NH—CS—NH—, —O—CO—O—, —O—CS—O—, —NH—C(NH)—NH—, —S(O)$_2$—N(R$^7$)—, —N(R$^7$)—S(O)$_2$—, —NH—C(O)—O—, and —O—C(O)—NH—, wherein R$^7$ is selected from the group consisting of hydrogen, C$_1$-C$_5$-alkyl, aryl, aralkyl, acyl, heterocyclyl, heteroaryl, SO$_2$-alkyl, SO$_2$-aryl, CO-alkyl, CO-aryl, CO—NH-alkyl, CO—NH-aryl, CO—O-alkyl and CO—O-aryl, each of which is optionally substituted, n is 0 to 4,
Y is N or CH,
T is NH$_2$ or OH.

Compounds of formula (2) contain a chiral center (indicated by the asterisk (*)). The invention encompasses both racemic mixtures and enantiomerically enriched mixtures of compounds of formula (2), as well as the enantiomerically pure isomers of compounds of formula (2). Preferably in enantiomerically enriched mixtures there is greater or equal to 80% of one enantiomer, more preferably greater than 90%, 95%, or 98%.

Groups A and B are the same or different and are independently selected from H, halogen, $C_1$-$C_4$ alkyl, optionally substituted alkoxy including aminoalkoxy, haloalkoxy and heteroarylalkoxy, alkoxyalkyl, haloalkyl, amino, nitro, alkylthio, acylamino, carbamoyl, or the following:

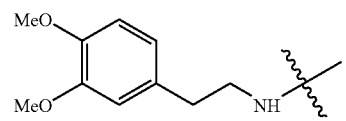
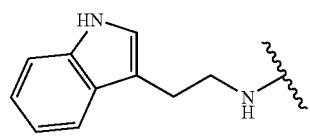
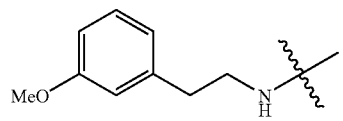
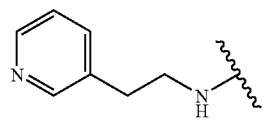
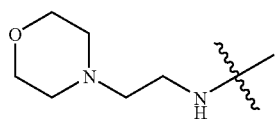
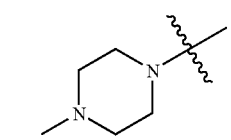
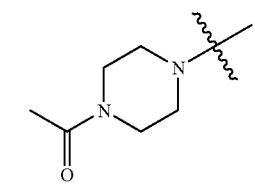
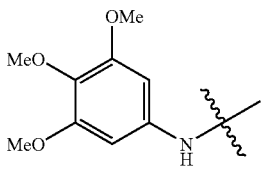
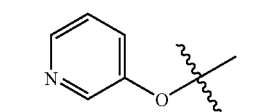

-continued

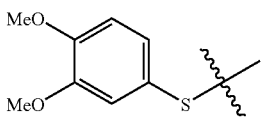
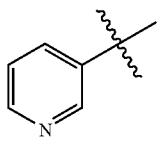
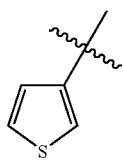
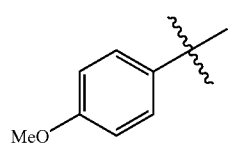
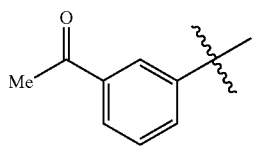
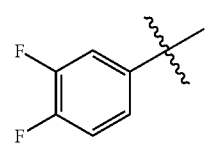
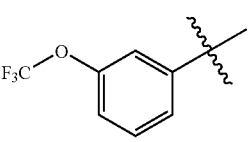
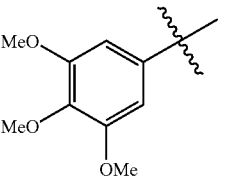
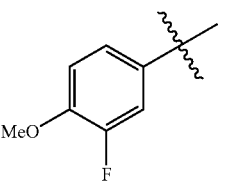
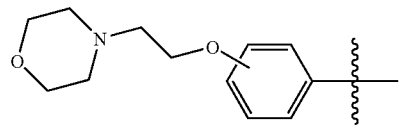

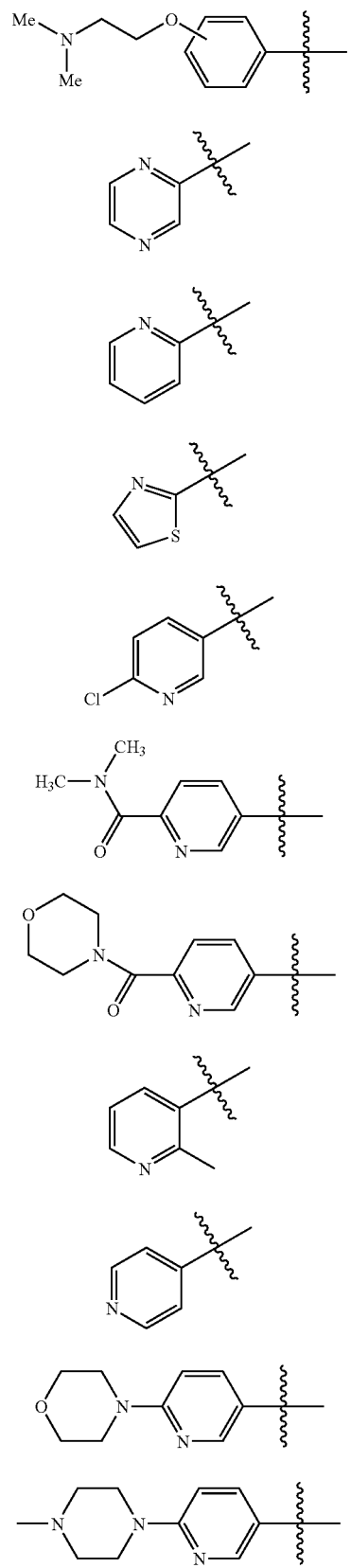
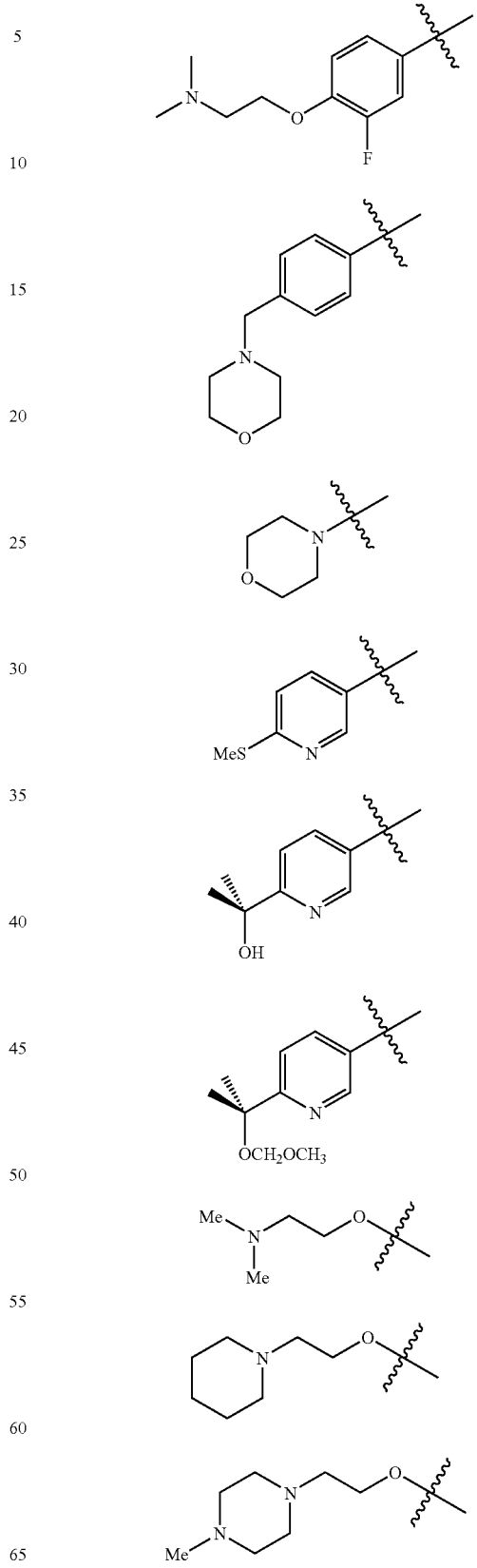

27
-continued
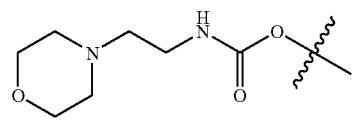
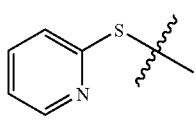
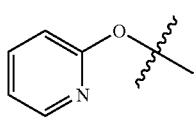
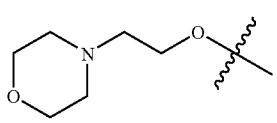
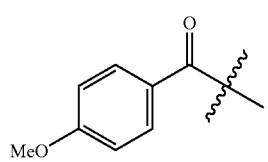
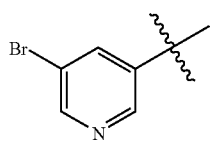
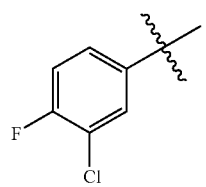
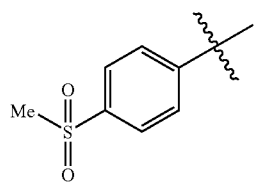
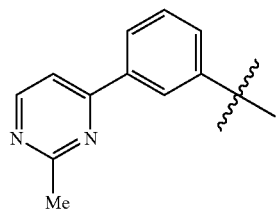
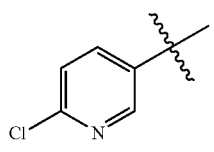
28
-continued
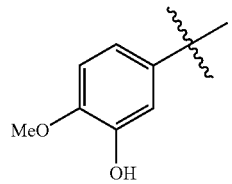
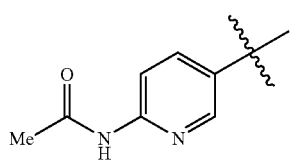
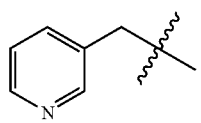
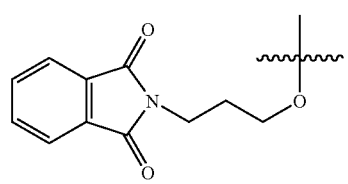
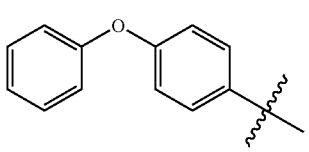
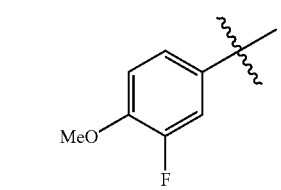
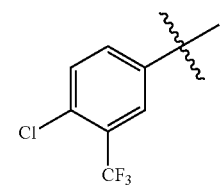
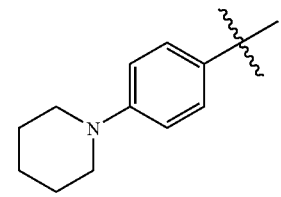
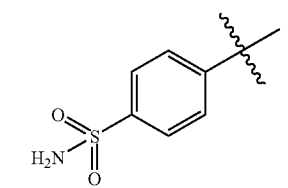

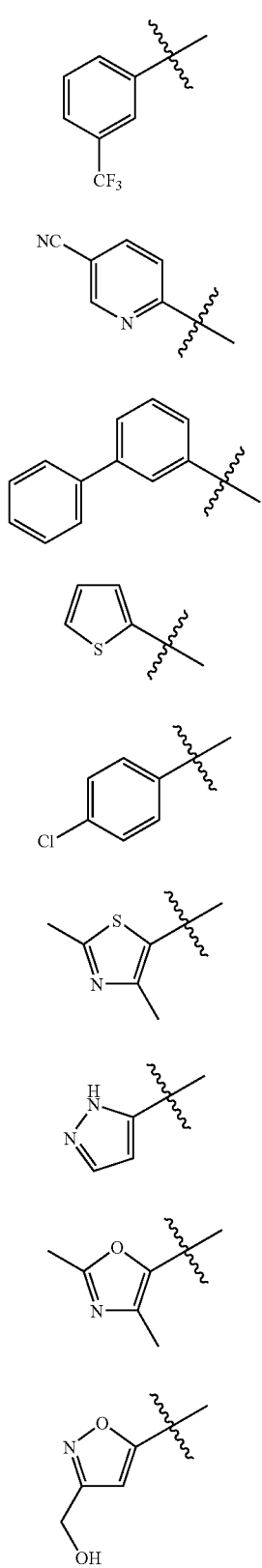
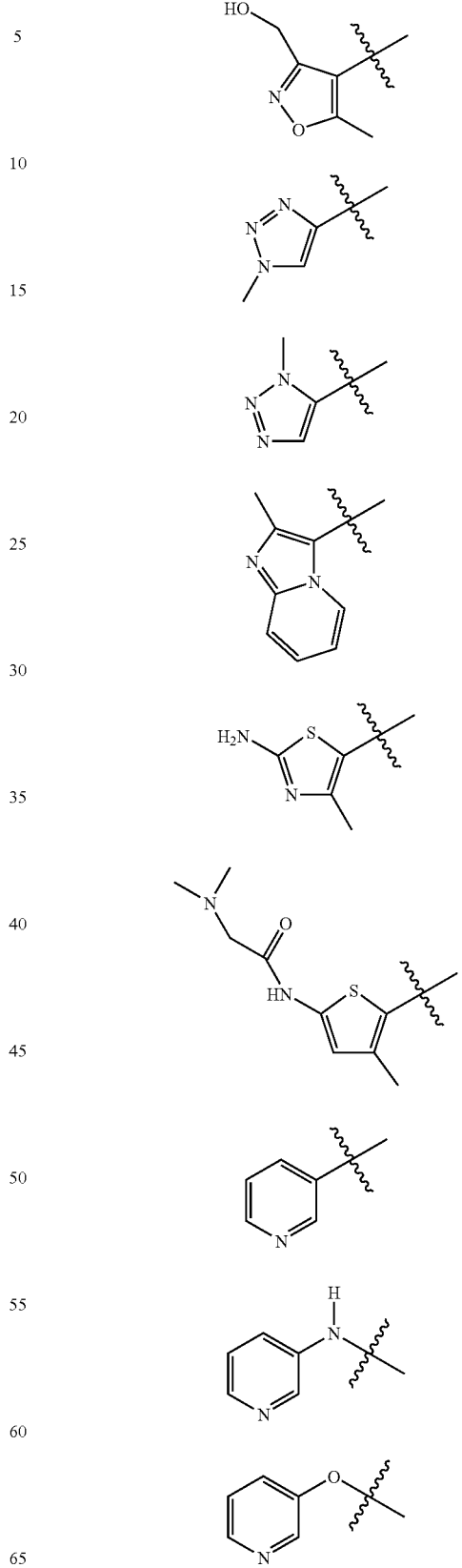

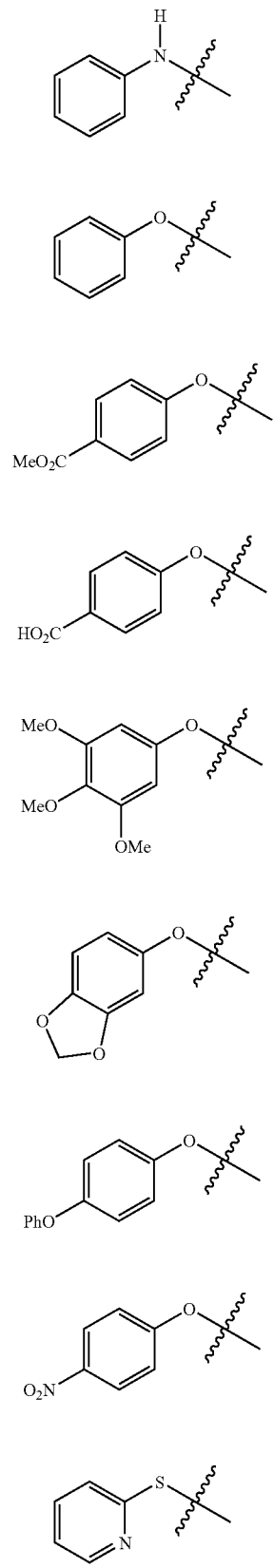

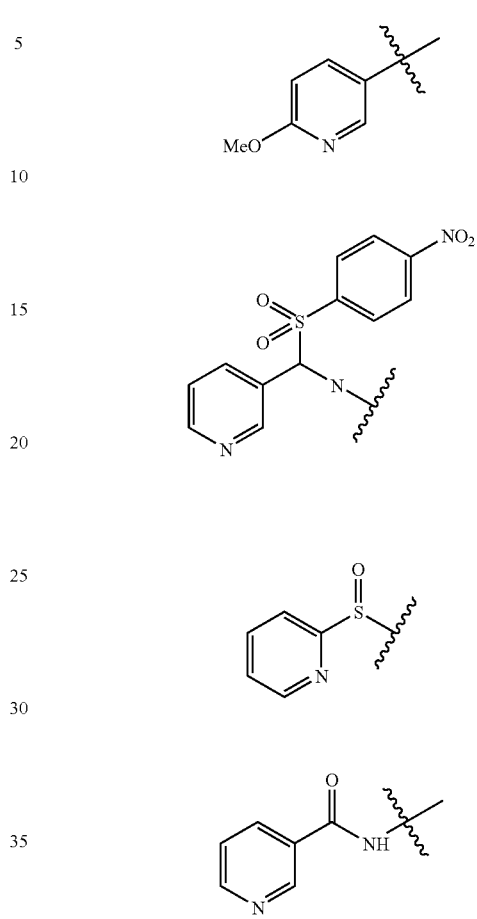

Synthesis

Compounds of formula (1), wherein Ar is pyridylene and X comprises —N(R[9])— preferably may be prepared according to the procedures illustrated in Scheme A. Dibromopyridine XIII or XIV is treated with amine RNH$_2$ to produce aminobromopyridine XV or XVI, respectively. Treatment of XV or XVI with diacetoxypalladium, diphenylphosphinoferrocene, DMF, diisopropylethylamine, and phenylenediamine under carbon monoxide yields anilinyl amide XVII or XVIII, respectively.

Treatment of XV or XVI with tert-butylacrylate, diisopropylethylamine, dibenzylacetone palladium, and tri-o-tolylphosphine (POT) in DMF under nitrogen affords compounds XIX and XX, respectively. The ester moiety of XIX or XX is hydrolyzed to produce the corresponding acid moiety in XXI or XXII, respectively, by reaction with trifluoroacetic acid in dichloromethane. Treatment of the acid XXI or XXII with phenylenediamine, BOP, and triethylamine affords the anilinyl amide XXIII or XXIV, respectively.

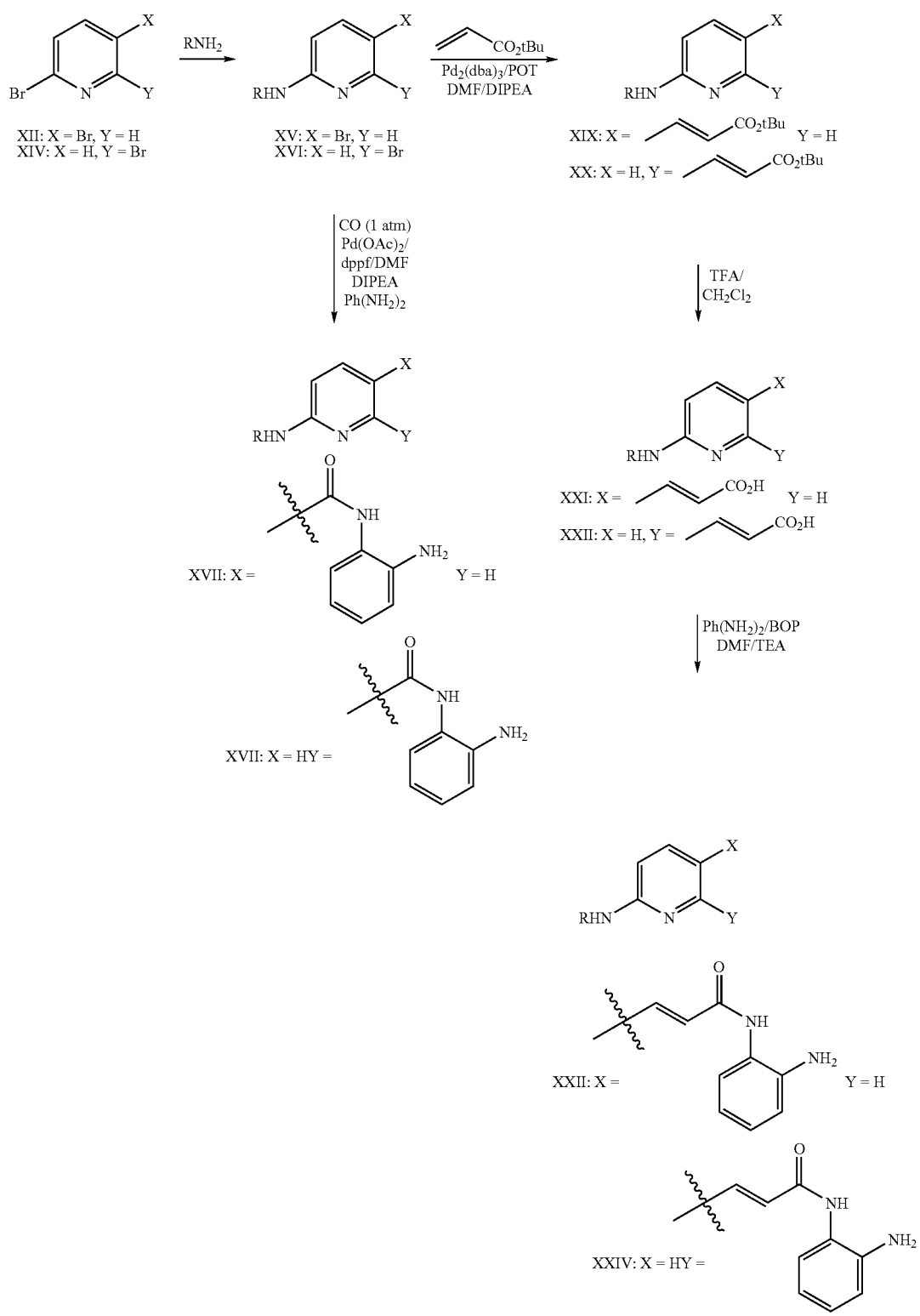

Compounds wherein X comprises —O—C(O)—NH— preferably may be prepared according to the synthetic route depicted in Scheme B. Thus, carbinol XXV is added to bromobenzylamine XXVI with carbonyldiimidazole (CDI), triethylamine, and 1,8-diazabicyclo[5.4.0]undec-7-ene (DBU) in DMF to produce compound XXVII. The remaining synthetic steps in the production of anilinyl amide XXVIII are as described above for Scheme A.

Scheme B

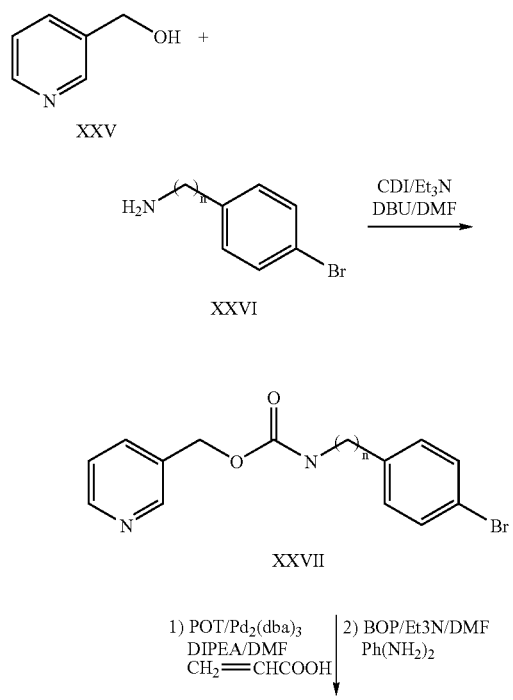

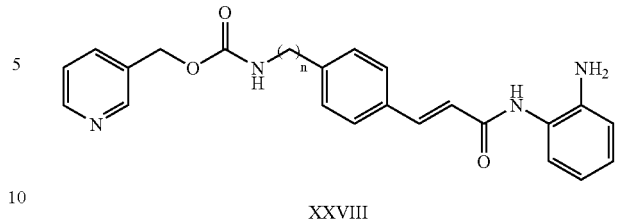

Compounds wherein X comprises —N(R⁹)—, preferably may be prepared as outlined in Scheme C. Amine XXIX is reacted with p-bromobenzylbromide in the presence of potassium carbonate in DMF to produce bromobenzylamine XXX. Treatment of XXX with nitroacrylanilide, dibenzylacetone palladium, POT, and diisopropylethylamine in DMF affords nitroanilide XXXI. Nitroanilide XXXI is converted to the corresponding anilinyl amide XXXII by treatment with stannous chloride in methanol and water.

Treatment of amine XXXI in formic acid with paraformaldehyde provides methylamine XXXIII. The nitroanilide moiety in XXXIII is then converted to the corresponding anilinyl amide moiety in XXXIV by treatment with stannous chloride in methanol and water.

Scheme C

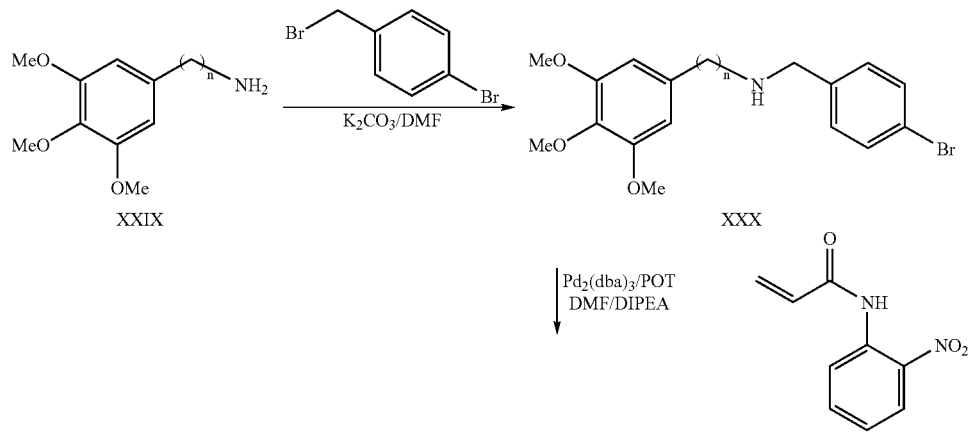

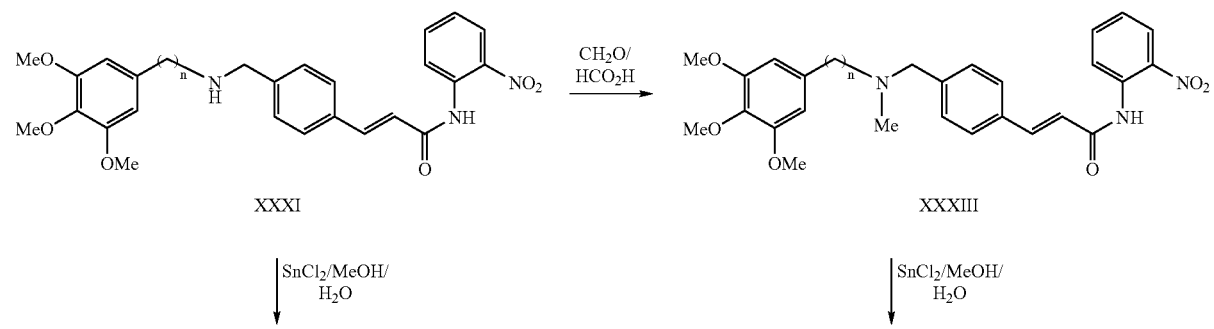

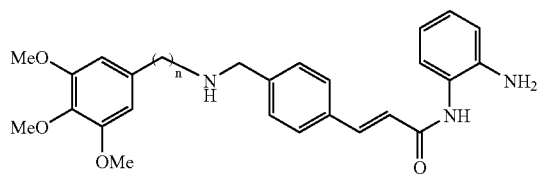

XXXII

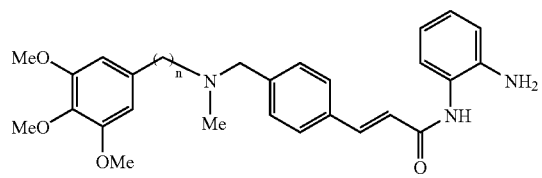

XXXIV

Alternatively, compounds wherein X comprises —N(R$^9$)— may be prepared according to the synthetic route depicted in Scheme D. Carboxylic acid XXXV in methanol is treated with hydrochloric acid to produce ester XXXVI. Conversion of the primary amine moiety in XXXVI to the secondary amine moiety in XXXVI is effected by treatment with a catalyst such as triethylamine, methoxybenzylchloride, sodium iodide, and potassium carbonate in DMF at 60° C. Ester XXXVI is converted to anilinyl amide XXXVII by treatment with sodium hydroxide, THF, and methanol, followed by BOP, triethylamine, and phenylenediamine in DMF, as described above for Scheme A.

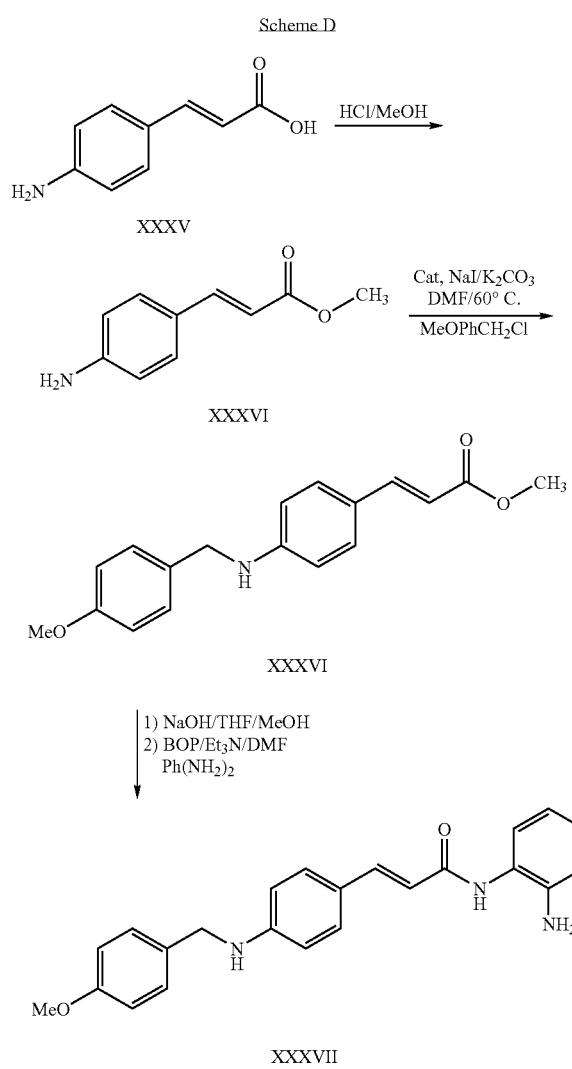

Compounds wherein X comprises

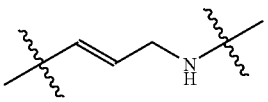

or —C(O)—NH—, preferably may be prepared according to the procedures illustrated in Scheme E. Addition of amine 68 to haloaryl compound XXXVIII or XXXIX and potassium carbonate in DMF provides arylamine XL or XLI, respectively. Anilinyl amide XLII or XLIII is then prepared using procedures analogous to those set forth in Schemes A-D above.

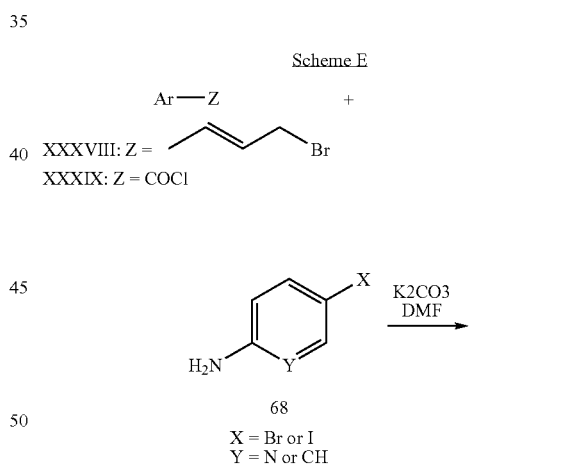

-continued

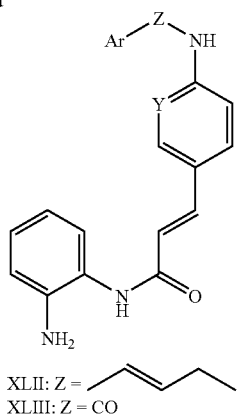

XLII: Z = /\_/\
XLIII: Z = CO

Compounds such as XLVII and XLIX preferably may be prepared as outlined in Scheme F. Dibromopyridine is combined with diaminoethane to produce amine XLIV. Treatment of amine XLIV with isatoic anhydride LV in methanol and water, followed by refluxing in formic acid affords compound XLVI. Treatment of amine XLIV with the reaction products of benzylaminodiacetic acid and acetic anhydride provides compound XLVIII. Bromopyridylamines XLVI and XLVIII are then converted to the corresponding diene anilinylamides XLVII and XLIX, respectively, by procedures analogous to those set forth in Schemes A-E above.

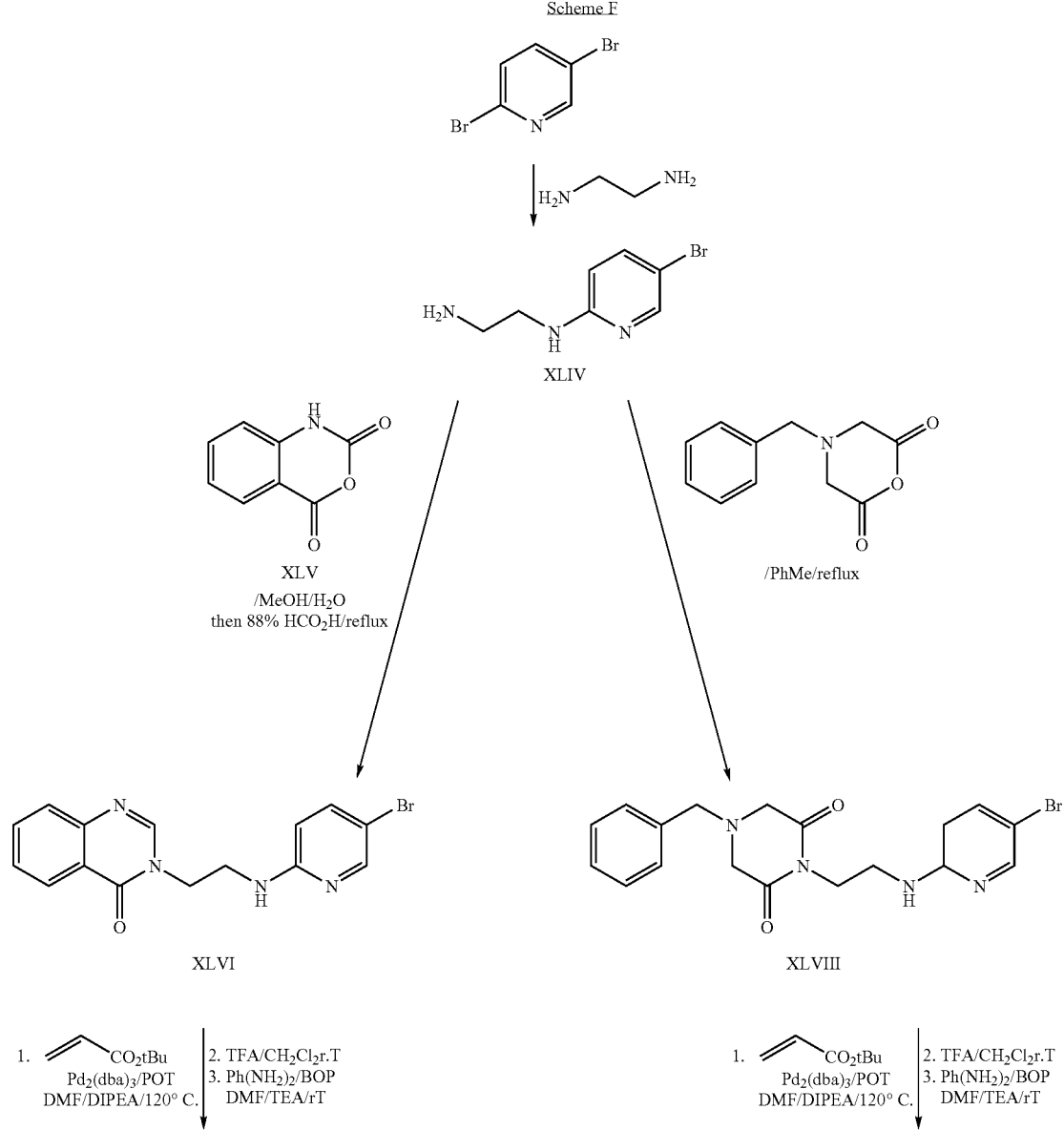

-continued

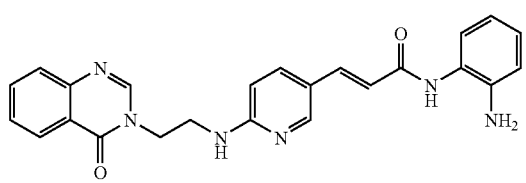

XLVII

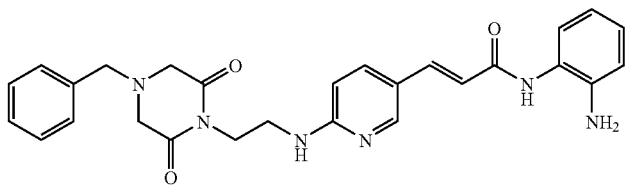

XLIX

Compounds such as LIV preferably may be prepared according to the synthetic route depicted in Scheme G. Trichlorotriazine is treated with aminoindan and diisopropylethylamine to produce dichloroaminotriazine L. Treatment with bromobenzylamine and diisopropylethylamine affords diaminochlorotriazine LI. Addition of ammonia gas and dioxane provides triaminotriazine LII. Treatment with protected acrylanilide, triethylamine, POT, and dibenzylacetone palladium then yields diene anilinylamide LIII, which is deprotected with trifluoroacetic acid to provide the final product LIV.

Compounds of formula (1), wherein Ar is quinolylene and X comprises —N($R^9$)— preferably may be prepared according to the procedures illustrated in Scheme H. Dihydroxyquinoline LV with dimethylaminopyridine (DMAP) in pyridine is treated with trifluoromethanesulfonic anhydride to provide bis(trifluoromethanesulfonyloxy)-quinoline LVI. Treatment of LVI with p-methoxybenzylamine affords aminoquinoline LVII. Anilinyl amides LVIII and LIX are then prepared using procedures analogous to those described above.

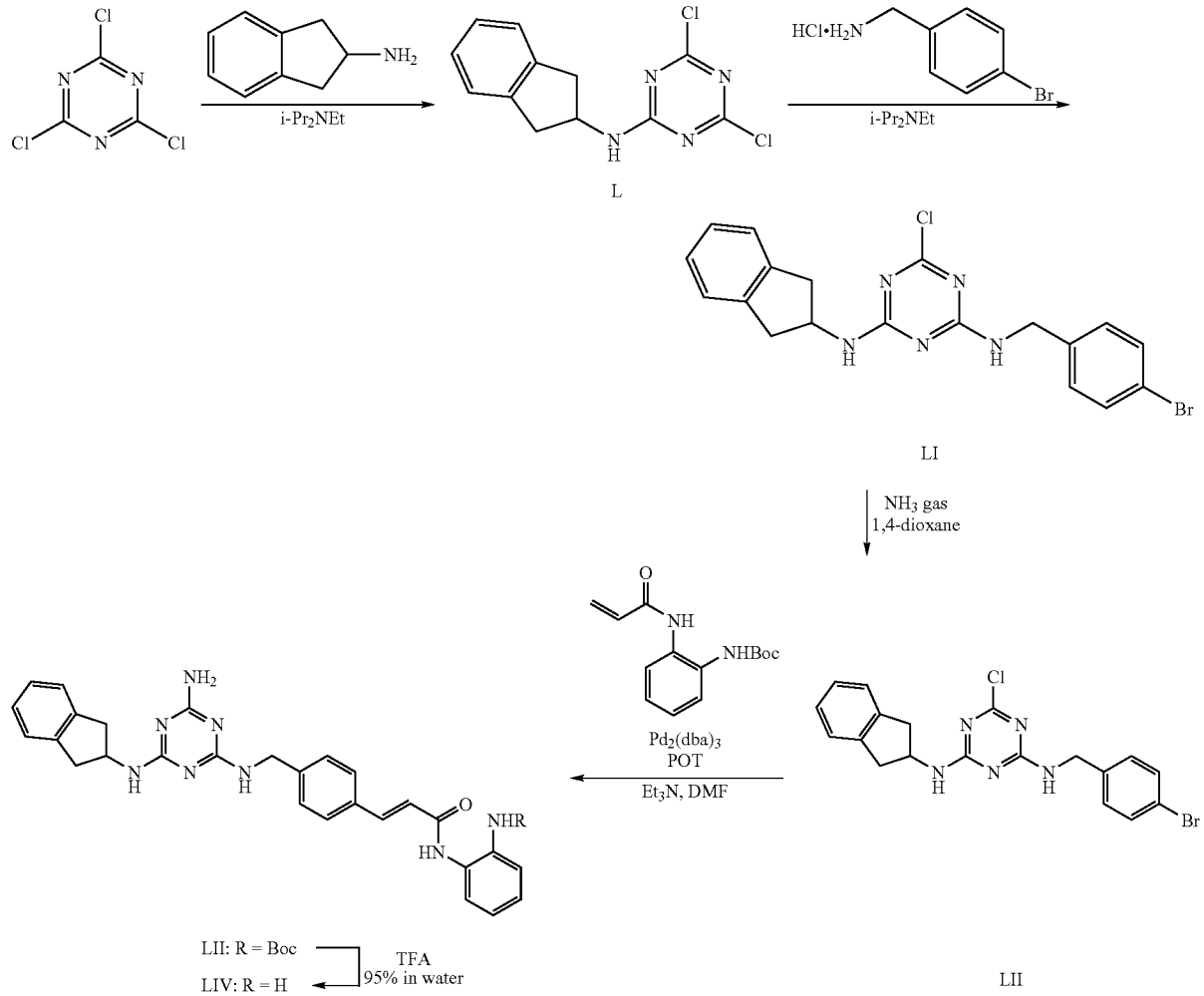

Scheme H

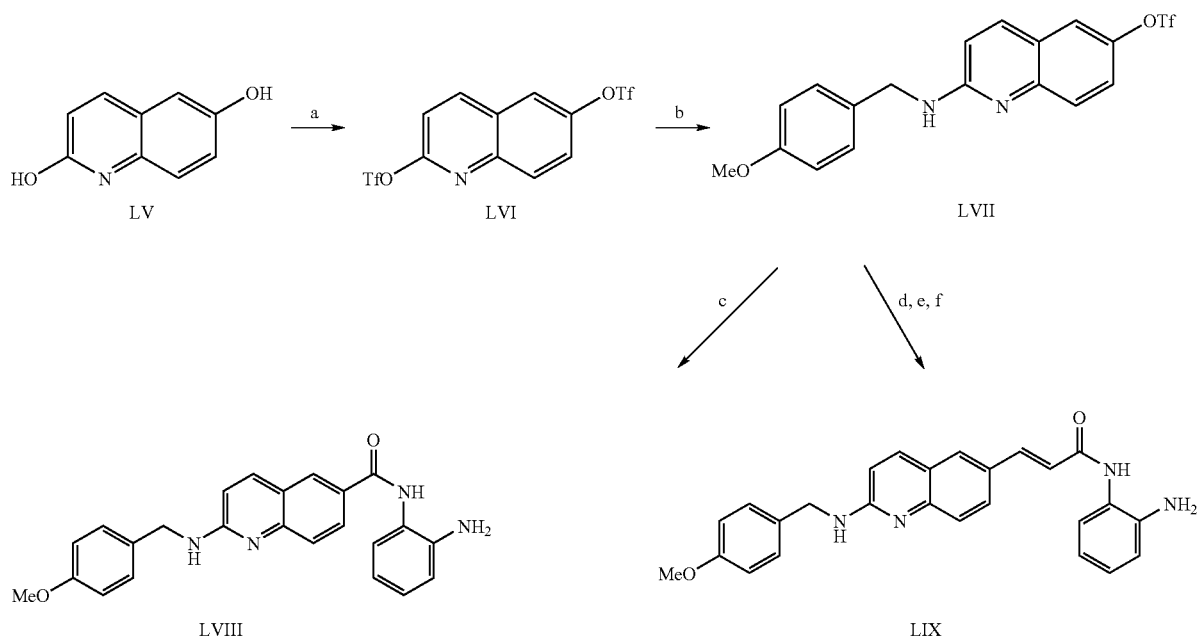

a. Tf₂O/Py/DMAP/0 C.
b. p-mrthoxybenzylamine/120 C.
c. 1,2-phenylenediamine/CO (40 psi)/ Pd(OAc)₂/dppf/DMF/DIPEA/70 C.
d. tButylacrylate/Pd₂(dba)₃/POT/DMF/DIPEA/120 C.
e. TFA/DCM/rT
f. 1,2-phenylenediamine/BOP/DMF/TEA/rT Compounds wherein X comprises a sulfur atom preferably may be prepared as outlined in Scheme I. Bromide LX is converted to diaryl ester LXI using procedures analogous to those described for Scheme D above. Ester LXI is converted to the corresponding acid LXIV by treatment with a hydroxide base, such as lithium hydroxide. Alternatively, ester LXI may be treated with chloroethylmorphonline, sodium iodide, potassium carbonate, triethylamine, and tetrabutylammonium iodide (TBAI) in DMF to produce ester LXIII, which is then converted to acid LXIV. Conversion of the acid LXIV to the anilinyl amide LXV is effected by treatment of the acid with 1,2-phenylenediamine in the presence of BOP reagent, triethylamine, and dimethylformamide (DMF).

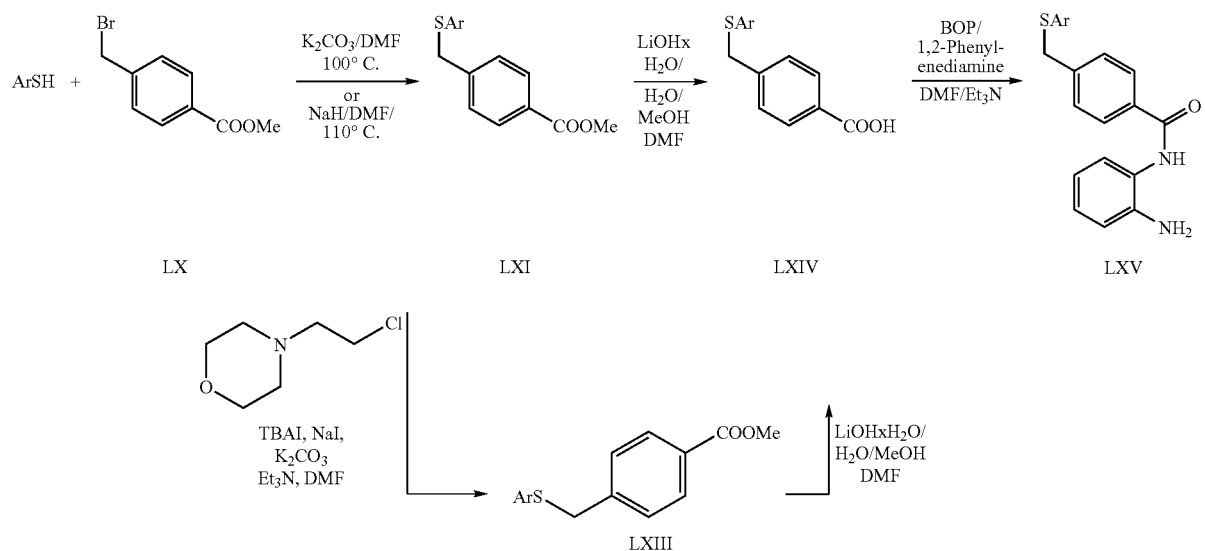

Alternatively, compounds wherein X comprises a sulfur atom, may be prepared according to the procedures illustrated in Scheme J. Sulfanyl anilinylamide LXVIII is prepared using procedures analogous to those set forth above.

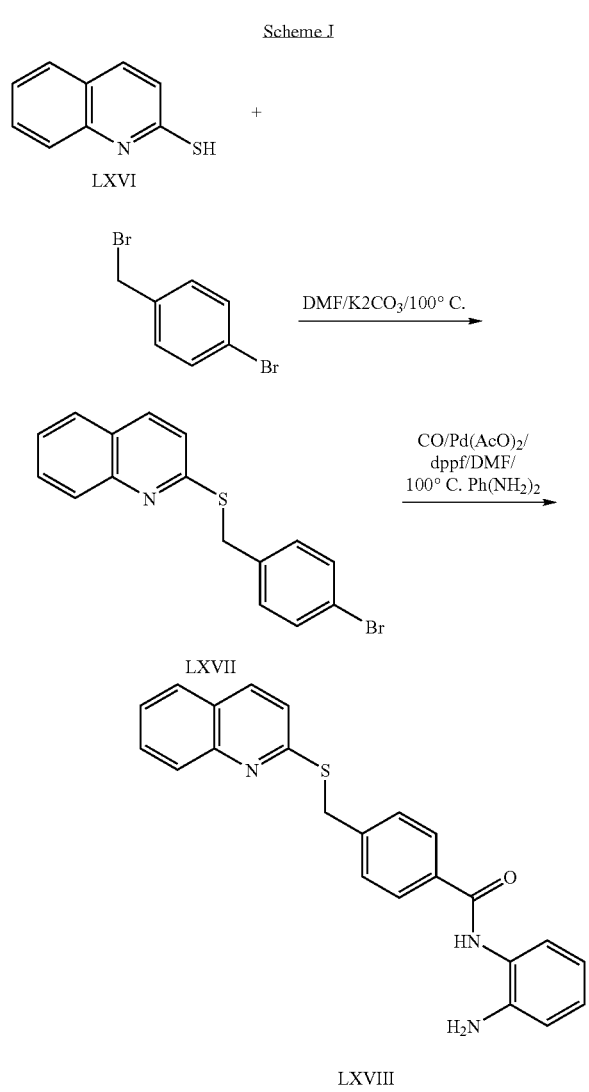

Compounds wherein X comprises —N(R⁹)— preferably may be prepared according to the synthetic route depicted in Scheme K. Amino anilinyl amide LXXI is prepared according to synthetic steps similar to those described above.

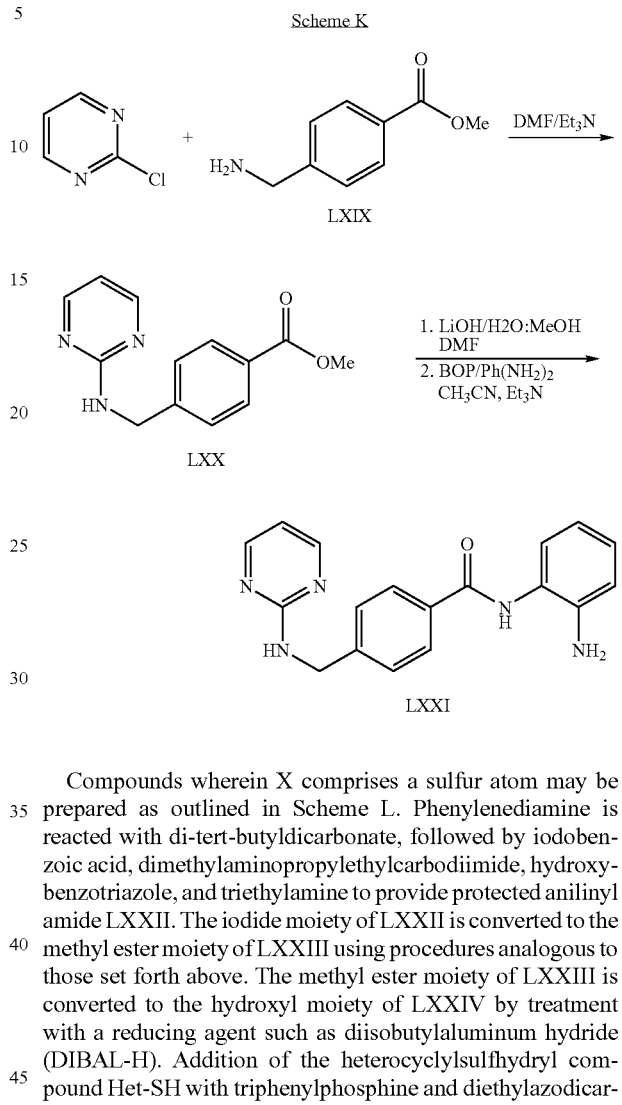

Compounds wherein X comprises a sulfur atom may be prepared as outlined in Scheme L. Phenylenediamine is reacted with di-tert-butyldicarbonate, followed by iodobenzoic acid, dimethylaminopropylethylcarbodiimide, hydroxybenzotriazole, and triethylamine to provide protected anilinyl amide LXXII. The iodide moiety of LXXII is converted to the methyl ester moiety of LXXIII using procedures analogous to those set forth above. The methyl ester moiety of LXXIII is converted to the hydroxyl moiety of LXXIV by treatment with a reducing agent such as diisobutylaluminum hydride (DIBAL-H). Addition of the heterocyclylsulfhydryl compound Het-SH with triphenylphosphine and diethylazodicarboxylate converts the hydroxyl moiety of LXXIV to the sulfanyl moiety of LXXV. LXXV is deprotected with trifluoroacetic acid to afford the sulfanyl anilinyl amide LXXVI.

Scheme L

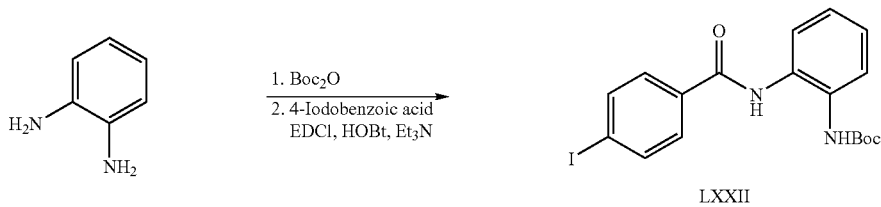

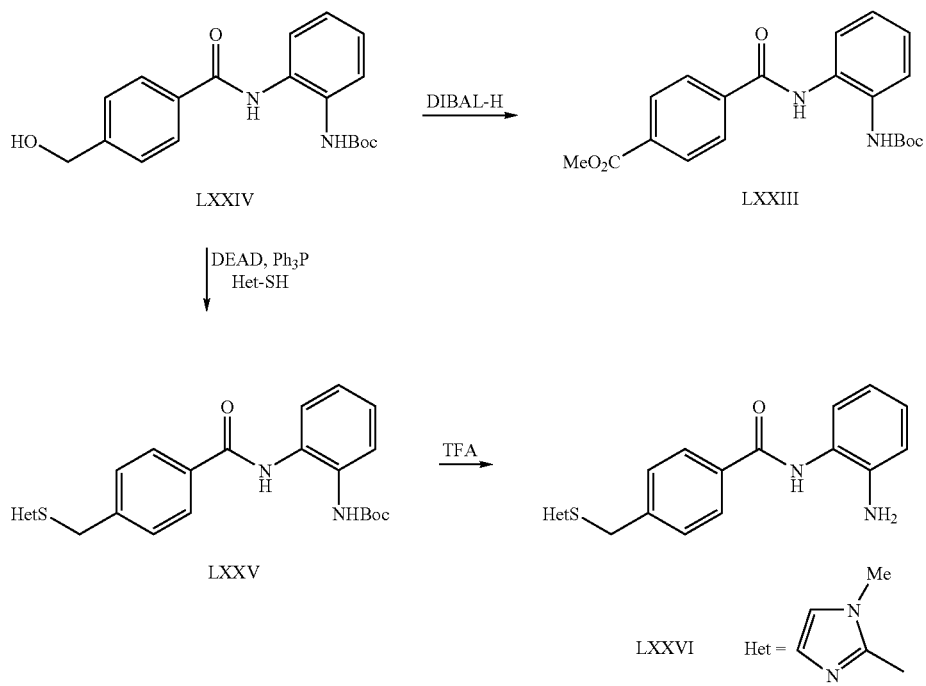

Compounds wherein X is a chemical bond may be prepared according to the synthetic route depicted in Scheme M. Thus, chloroarylanilinylamide LXXVII is treated with aryl boronic acid, benzene, ethanol, aqueous sodium carbonate, and triphenylphosphine palladium to afford the diarylanilinylamide LXXVIII.

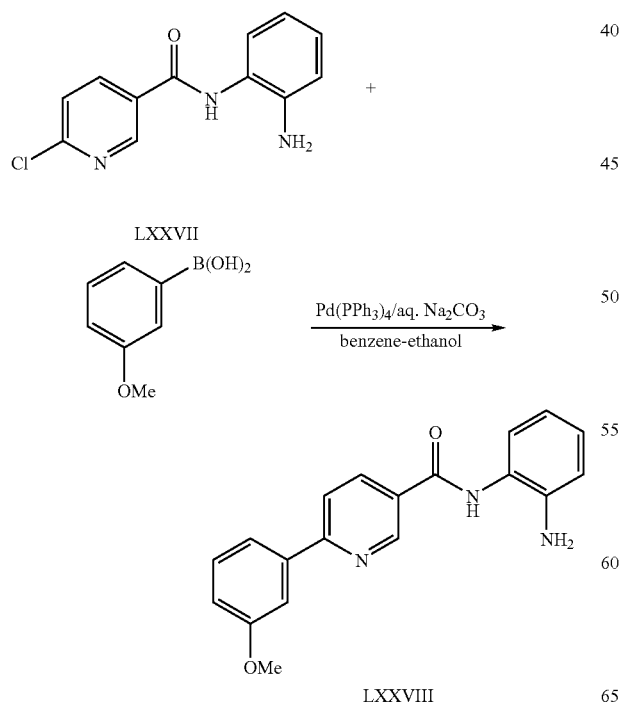

Compounds such as LXXXI preferably may be prepared according to the procedures illustrated in Scheme N. Thus, benzene-1,2-carbaldehyde LXXIX in acetic acid is treated with p-aminomethylbenzoic acid to produce the benzoic acid LXXX. The acid LXXX is converted to the corresponding anilinylamide LXXXI by treatment with hydroxybenzotriazole, ethylenedichloride, and phenylenediamine.

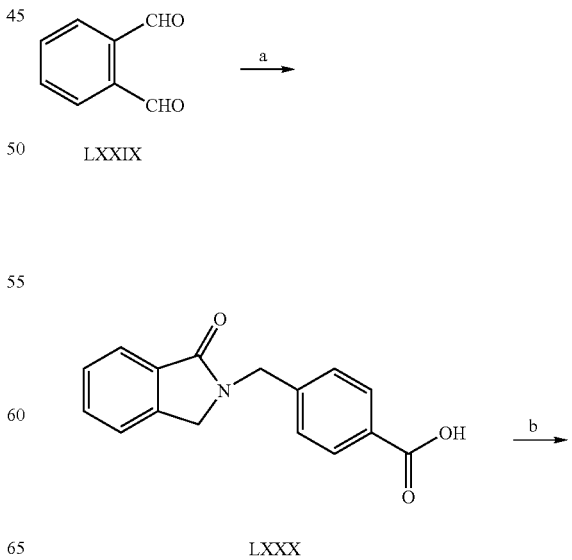

-continued

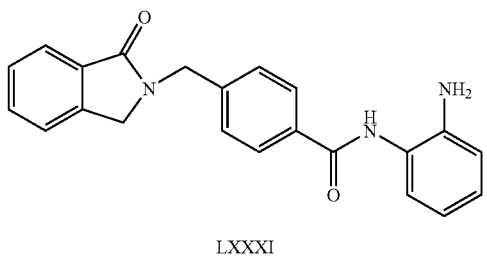

LXXXI a. p-aminomethylbenzoic acid/AcOH/5 min/reflux
b. HOBT/EDC/1,2-diamino benzene Compounds such as LXXXVI and LXXXIX preferably may be prepared according to the procedures illustrated in Scheme O. Phthalic anhydride LXXXV and p-aminomethylbenzoic acid are combined in acetic acid to produce an intermediate carboxylic acid, which is converted to the anilinylamide LXXXVI using procedures analogous to those set forth above.

The addition of 4-(2-aminoethyl)phenol to phthalic anhydride LXXXV in acetic acid affords the hydroxyl compound LXXXVII. The hydroxyl group of LXXXVII is converted to the triflate group of LXXXVIII by treatment with sodium hydride, THF, DMF, and phenylaminoditriflate. Treatment of LXXXVIII according to procedures analogous to those described for Scheme 3 above affords the anilinylamide LXXXIX.

Compounds such as XCI-XCVI preferably may be prepared according to the synthetic route depicted in Scheme P. Treatment of isatoic anhydride XC with p-aminomethylbenzoic acid in water and triethylamine, followed by formic acid affords an intermediate carboxylic acid, which is converted to anilinylamide XCI using procedures analogous to those described above.

Alternatively, treatment of isatoic acid XC with p-aminomethylbenzoic acid in water and triethylamine, followed by hydrochloric acid and sodium nitrite affords an intermediate carboxylic acid, which is converted to anilinylamide XCII using procedures analogous to those described above.

Alternatively, treatment of isatoic acid XC with p-aminomethylbenzoic acid in water and triethylamine affords benzoic acid XCIII. Treatment of XCIII with sodium hydroxide, dioxane, methylchloroformate, and methanol affords an intermediate quinazolinedione carboxylic acid, the acid moiety of which is then converted to the anilinylamide moiety of XCIV using procedures analogous to those described above. Alternatively, the intermediate quanzolinedione carboxylic acid in DMF is treated with potassium carbonate and methyl iodide to produce an intermediate benzoic acid methyl ester, which is converted to an intermediate benzoic acid by treatment with sodium hydroxide, methanol, and water. The benzoic acid is then converted to the corresponding anilinylamide XCV using procedures analogous to those described above.

Alternatively, treatment of XCIII with acetic anhydride followed by acetic acid produces an intermediate carboxylic acid, which is converted to anilinylamide XCVI using procedures analogous to those described above.

Scheme O

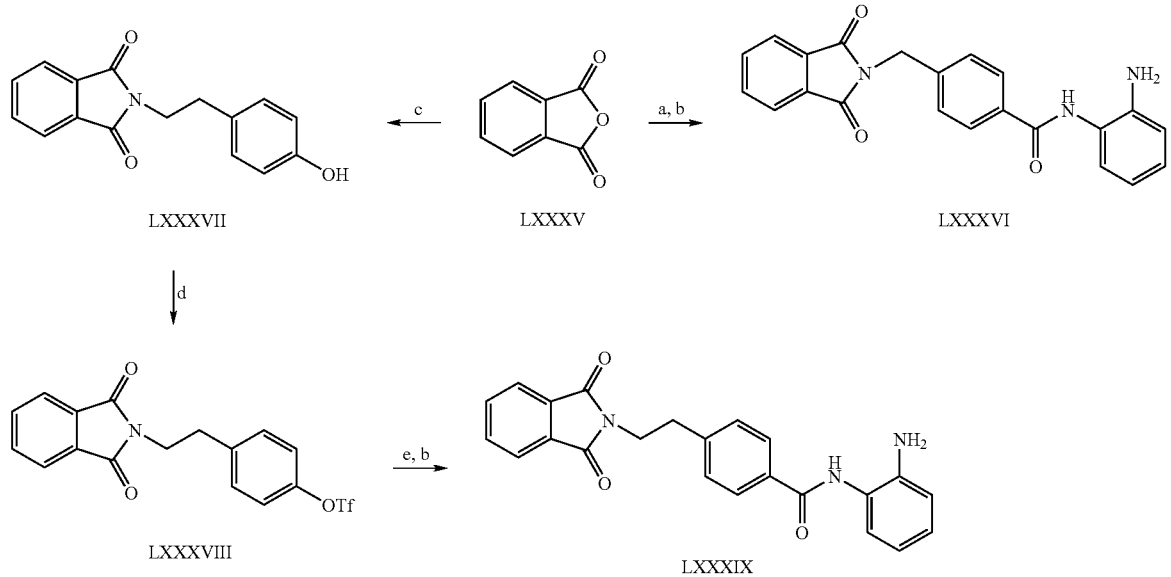

a. p-aminomethylbenzoic acid/AcOH/reflux/3 hrs
b. HOBT/EDC/1,2-diamino benzene
c. 4-(2-aminoethyl)phenol/AcOH/5 hrs/reflux
d. PhNTf$_2$/NaH/THF-DMF/30 min/0° C.
e. 1. CO/Pd(OAc)$_2$/dppf/Et$_3$N/MeOH-DMF/4 days/75° C.
   2. AcOH/HCl/3 hrs/reflux Scheme P

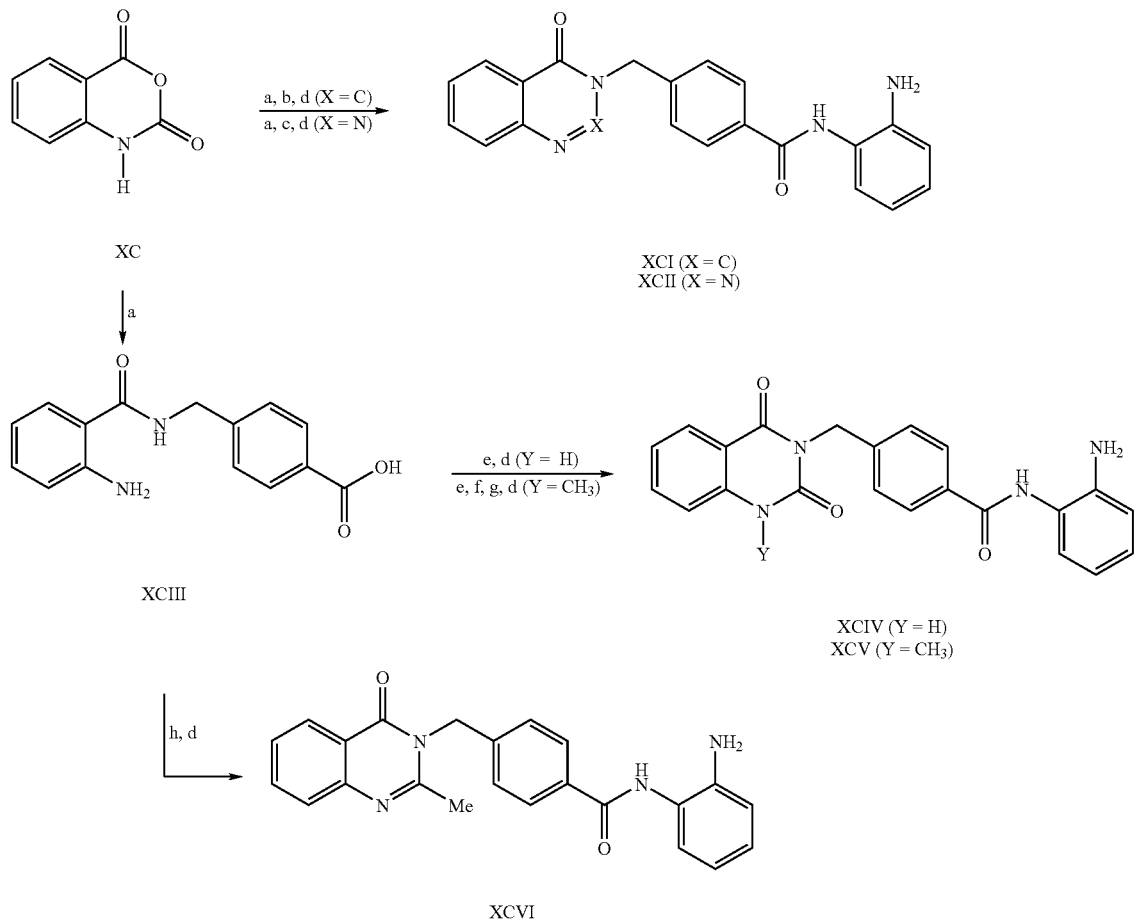

a. p-aminomethylbenzoic acid/H$_2$O/Et$_3$N/3 hrs/40° C.
b. HCOOH/reflux/6 hrs
c. NaNO$_2$/HCl/0° C./2 hrs, then rt/12 hrs
d. HOBT/EDC/1,2-diamino benzene
e. ClCOOMe/KOH/2 hrs, 0° C.
f. RI/K$_2$CO$_3$/DMF/rt
g. NaOH/MeOH/H$_2$O
h. Ac$_2$O/1 hour/reflux then AcOH/48 hrs/reflux Compounds such as C preferably may be prepared as outlined in Scheme Q. Alkylamine XCVII is treated with thiocarbonyl diimidazole in dichloromethane, followed by ammonium hydroxide to afford thiourea XCVIII. Treatment of thiourea XCVIII with methylmethoxyacrylate in dioxane and N-bromosuccinimide produces thiazole ester IC. The ester IC is converted to the corresponding anilinylamine C using procedures analogous to those set forth above.

Scheme Q

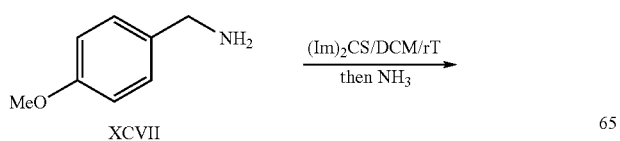

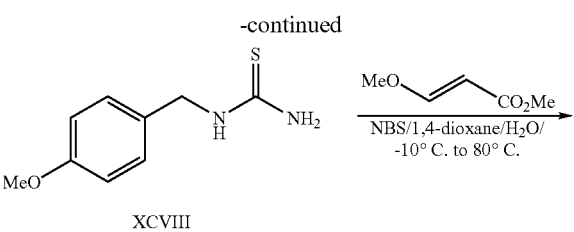

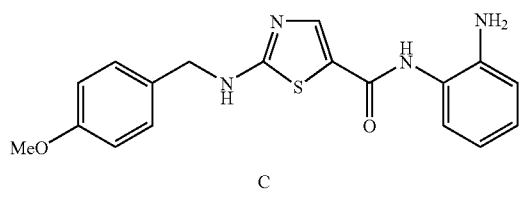

C

Compounds wherein X is a chemical bond and Cy has an amino substituent may be prepared according to the synthetic route depicted in R. Thus, protected iodoarylanilinylamide CI is treated according to procedures analogous to those described above to afford the diarylanilinylamide CII. The aldehyde moiety in CII is converted to the corresponding secondary amine moiety by treatment with the primary amine and sodium triacetoxyborohydride followed by glacial acetic acid. The resultant compound is deprotected to yield CIII using procedures analogous to those set forth in above.

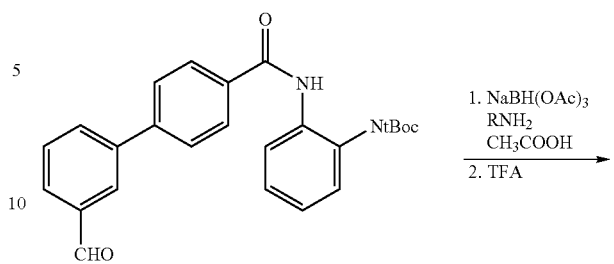

CII

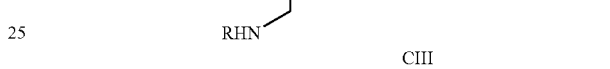

CIII

Compounds wherein X comprises an alkynylene moiety may be prepared as outlined in Scheme S. Treatment of protected iodoarylanilinylamide CI with triphenylphosphine palladium chloride, cuprous iodide, and 1-ethynylcyclohexylamine affords the alkynylarylanilinylamide CIV. The primary amine moiety in CIV is converted to the corresponding secondary amine and the aniline moiety is deprotected to afford CV using procedures analogous to those described above.

Scheme R

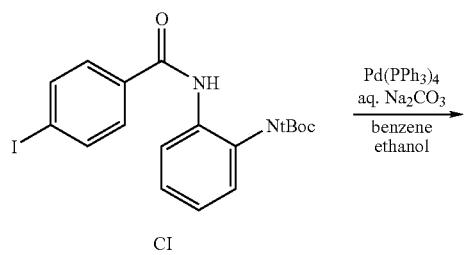

CI

Scheme S

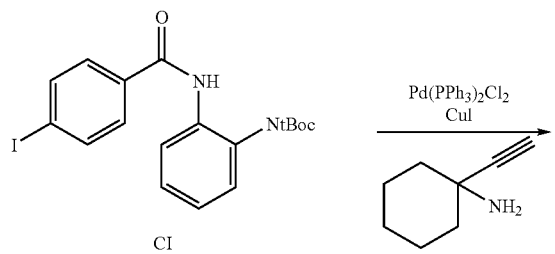

CI

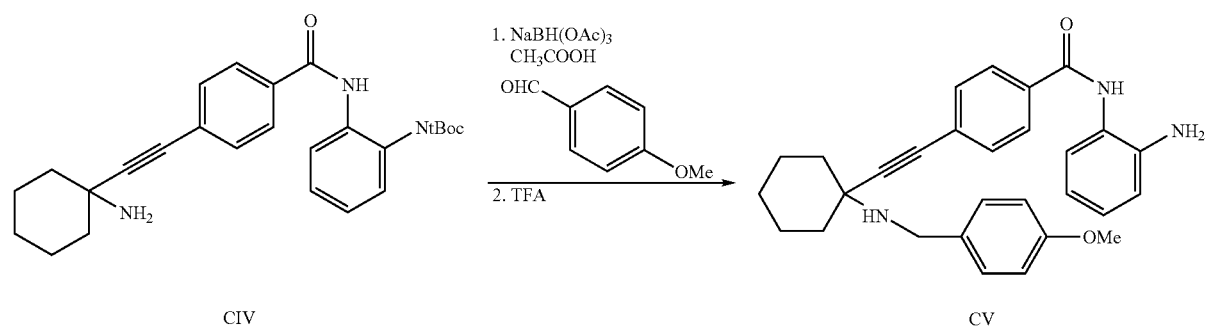

CIV        CV

Scheme T

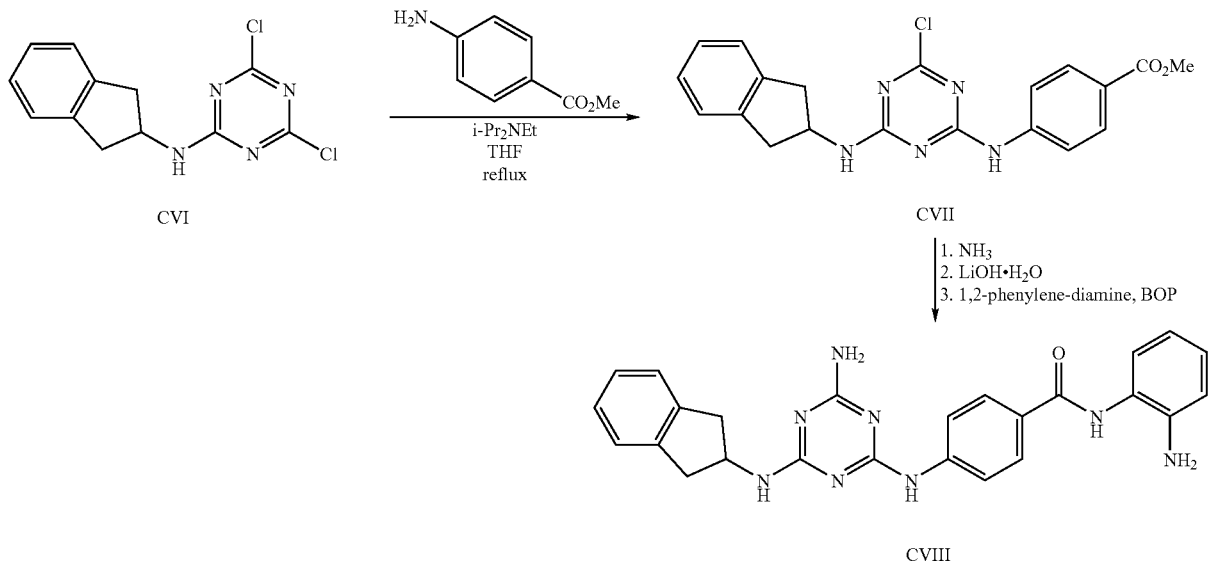

Compounds such as CVIII preferably may be prepared according to the synthetic route depicted in Scheme T. Dichloroaminotriazine CVI is treated with methyl-4-aminobenzoate in the presence of diisopropylethylamine to produce diaminotriazine CVII. Addition of ammonia gas and dioxane, followed by a saponification and a peptide coupling to yield CVIII.

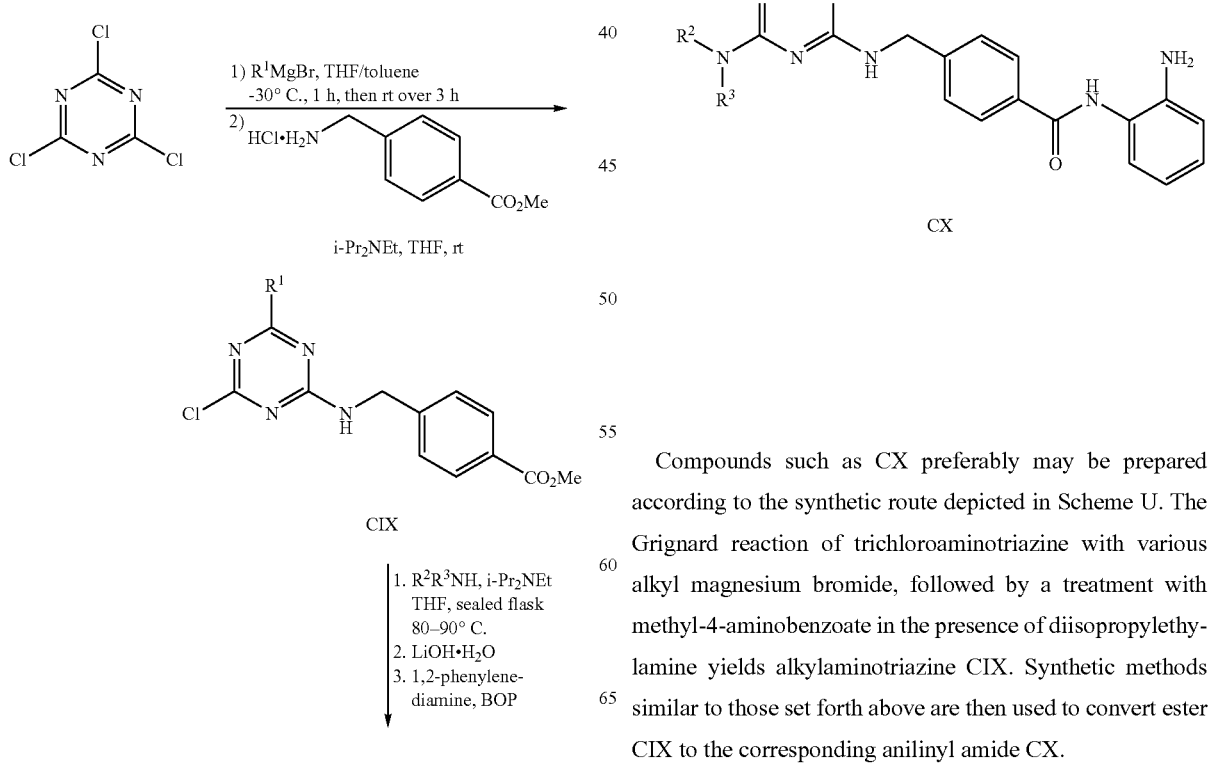

Compounds such as CX preferably may be prepared according to the synthetic route depicted in Scheme U. The Grignard reaction of trichloroaminotriazine with various alkyl magnesium bromide, followed by a treatment with methyl-4-aminobenzoate in the presence of diisopropylethylamine yields alkylaminotriazine CIX. Synthetic methods similar to those set forth above are then used to convert ester CIX to the corresponding anilinyl amide CX.

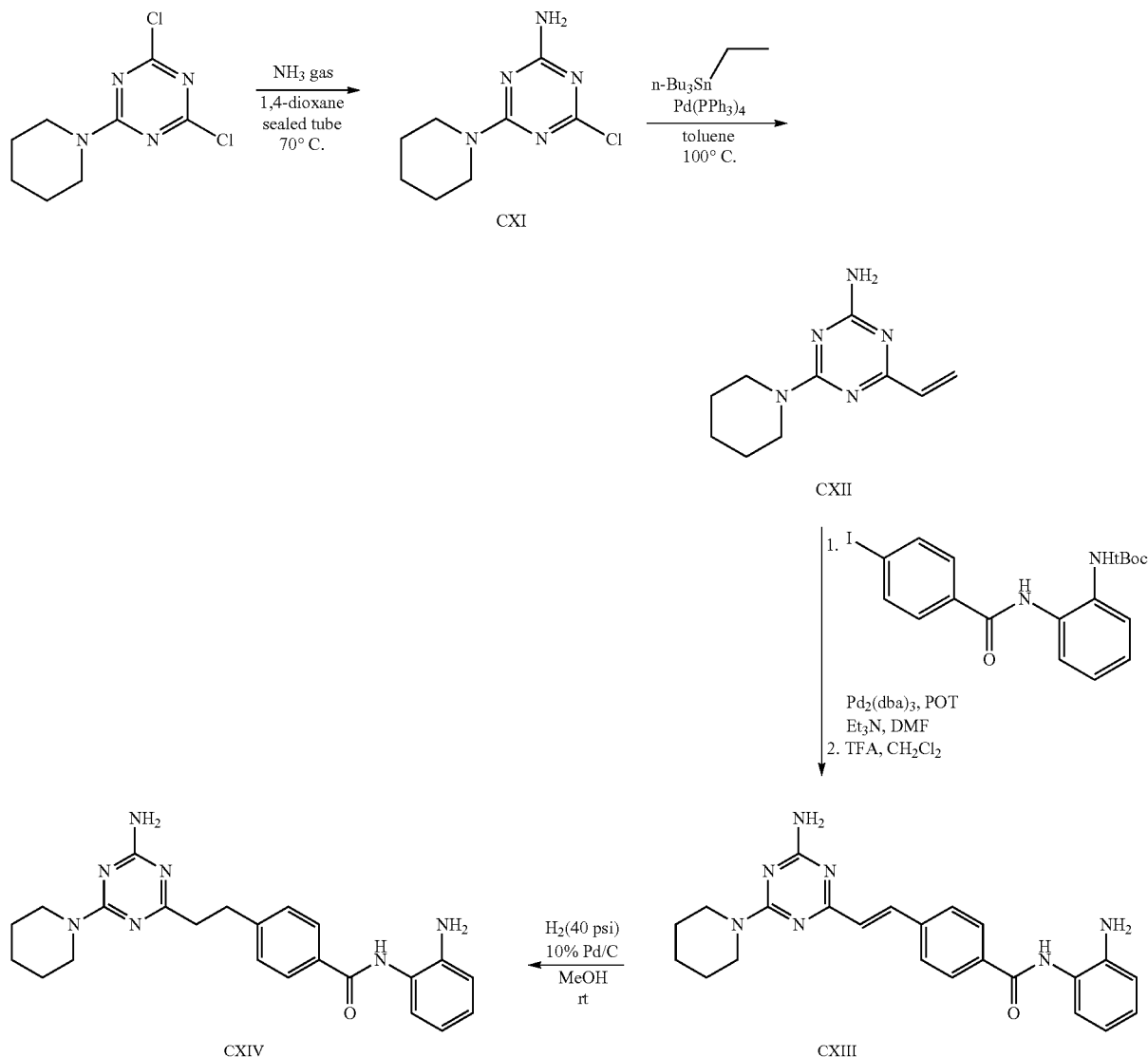

As shown in Scheme V, amination of dichlorotriazine affords CXI. Still coupling using vinyl stannane provides CXII. Treatment with protected iodoanilide, triethylamine, POT and dibenzylacetone palladium then yields anilinylamide, which is deprotected with trifluoroacetic acid to provide the alkene CXIII. Hydrogenation of the alkene affords the final compound CXIV.

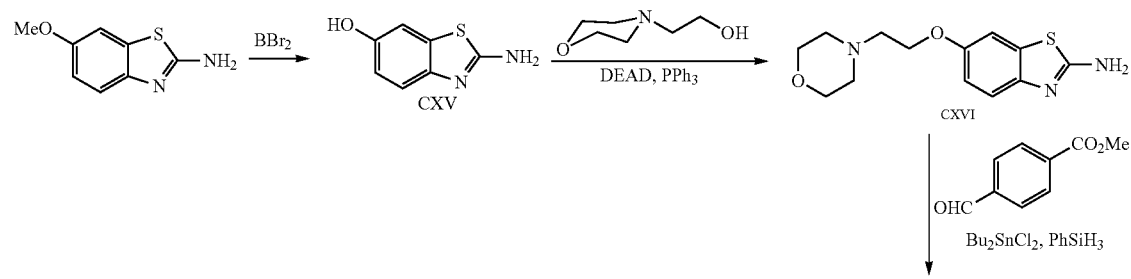

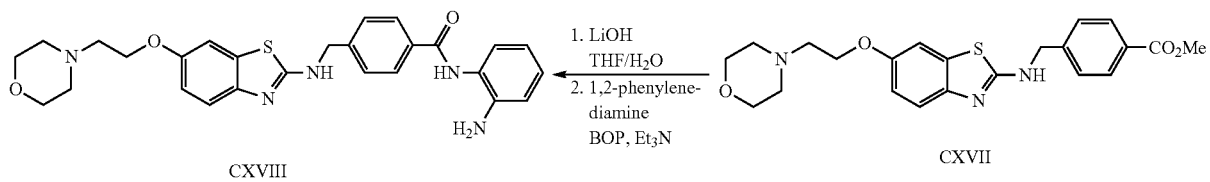

Compounds such as CXVIII preferably may be prepared according to the synthetic route depicted in Scheme W. Treatment of methoxyaminobenzothiazole with tribromide boron affords the corresponding acid CXV. Mitsunobu reaction using hydroxyethyl morpholine in the presence of diethylazodicarboxylate and triphenylphosphine yields the amine CXVI. Reductive amination with methyl-4-formylbenzoate using phenylsilane and tin catalyst yields to the ester CXVII. Saponification followed by the usual peptide coupling analogous to those described above provides the desired anilide CXVIII.

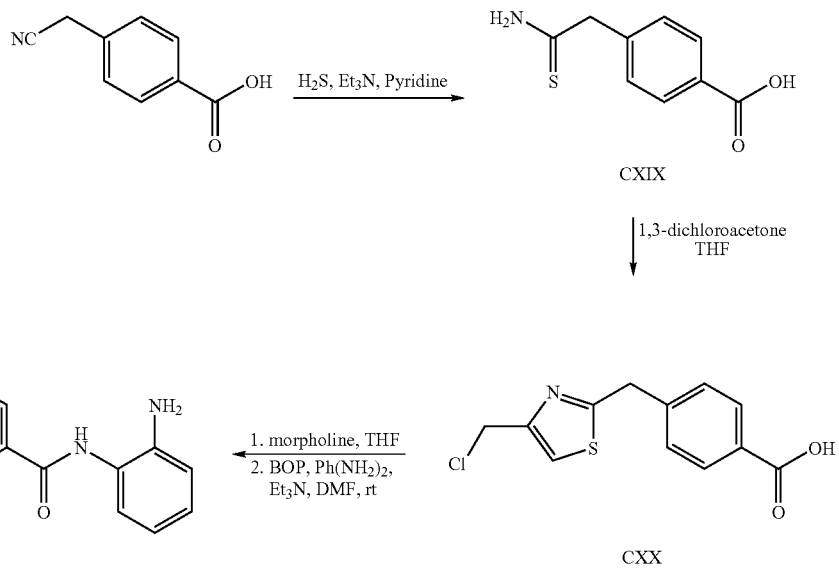

Treatment 4-methylcyanobenzoic acid with hydrogen sulfide affords CXIX, which is subjected to cyclization in the presence of 1,3-dichloroacetone to yield CXX. Treatment with morpholine followed by a peptide coupling using the standard condition produces CXXI.

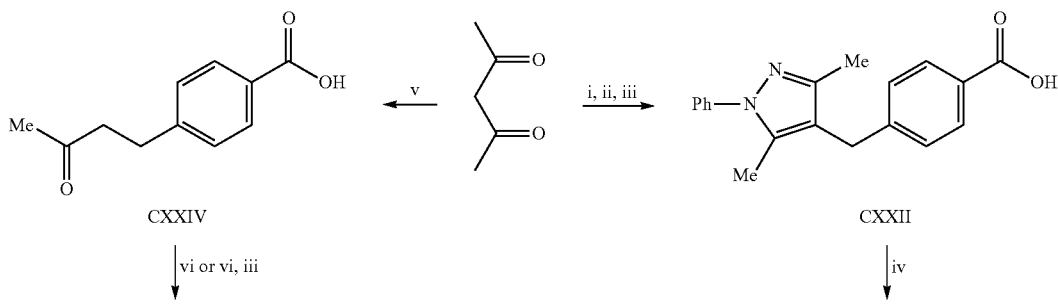

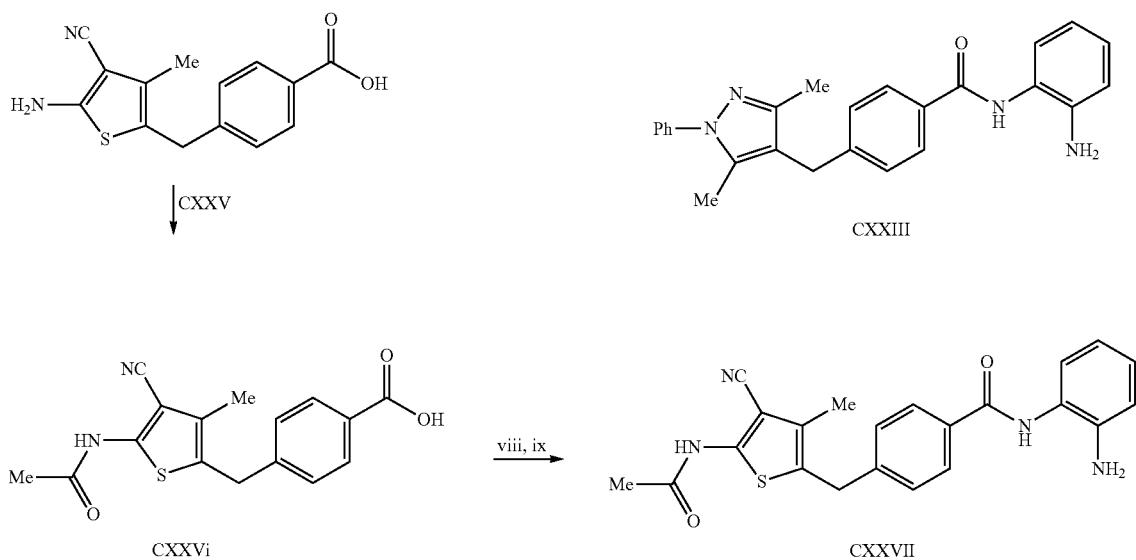

i: BrCH₂C₆H₄COOMe/MeONa/THF;
ii: PhNHNH₂;
iii: NaOH, then HCl
iv: HOBt/EDCxHCl then 1,2-diaminobenzene;
v: BrCH₂C₆H₄COOMe/MeONa/MeOH, then HCl/AcOH;
vi: CH₂(CN)₂/S₈/Et₂NH;
vii: AcCl;
viii: 2-N-Bocamino aniline;
ix: TFA;

Compounds such as CXXIII and CXXVII preferably may be prepared according to the synthetic scheme Y. Consecutive treatment of acetyl acetone with methyl bromomethylbenzoate in the presence of NaOMe and phenyl hydrazine followed by saponification, afforded the intermediate acid CXXII. This material was coupled with 1,2-diaminobenzene in a standard fashion to afford CXXIII.

Consecutive treatment of acetyl acetone with methyl bromomethylbenzoate in the presence of NaOMe and a 1:1 mixture AcOH—HCl (conc.) afforded the intermediate acid CXXIV. This keto-acid reacting with sulfur and malonodinitrile in the presence of a base, produced the thiophene CXXV, which was converted into the desired CXXVII using standard procedures.

Scheme Z

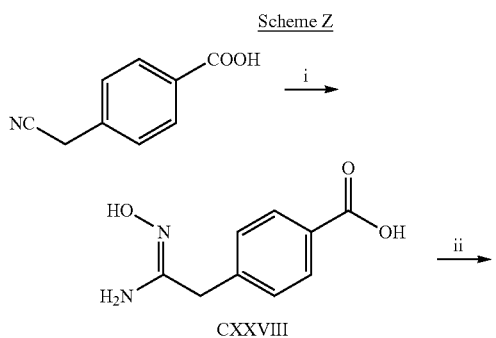

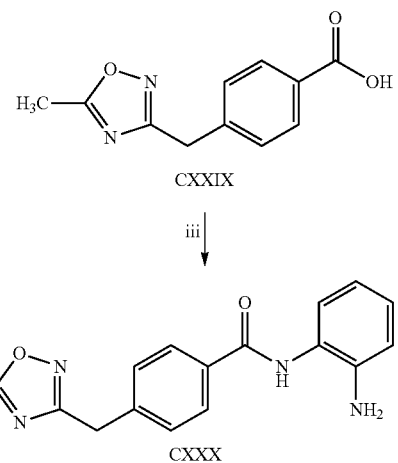

i: NH₂OH/EtOH;
ii: Ac₂O/pyridine;
iii: HOBt/EDCxHCl then 1,2-diaminobenzene;

Compounds such as CXXX preferably may be prepared according to the synthetic scheme Z. Treatment of 4-cyanomethylbenzoic acid with hydroxylamine produced the amidoxime CXXVIII, which upon treatment with acetic anhydride was converted into the oxadiazole CXXIX. The latter was coupled with 1,2-diaminobenzene in a standard fashion to afford CXXX.

Scheme AA

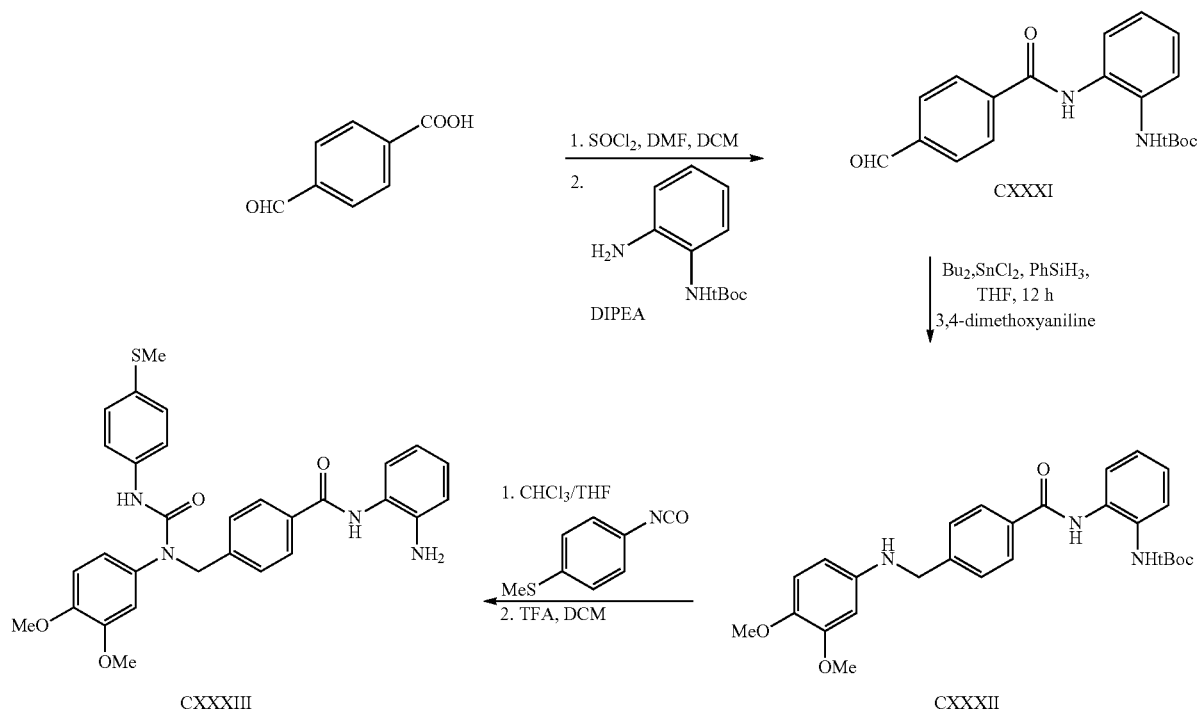

Compounds such as CXXXIII preferably may be prepared according to the synthetic route depicted in Scheme AA. Treatment of 4-formylbenzoic acid with thionyl chloride afford the acyl chloride which is coupled with protected anilide to produce CXXXI. Reductive amination with dimethoxyaniline using phenylsilane and tin catalyst yields to the protected anilide CXXXII. Treatment with isocyanate followed by deprotection with trifluoroacetic acid provides the ureidoanilide CXXXIII.

Pharmaceutical Compositions

In a second aspect, the invention provides pharmaceutical compositions comprising an inhibitor of histone deacetylase according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain preferred embodiments, compounds of the invention are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salts refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Inhibition of Histone Deacetylase

In a third aspect, the invention provides a method of inhibiting histone deacetylase in a cell, comprising contacting a cell in which inhibition of histone deacetylase is desired with an inhibitor of histone deacetylase according to the invention. Because compounds of the invention inhibit histone deacetylase, they are useful research tools for in vitro study of the role of histone deacetylase in biological processes. In addition, the compounds of the invention selectively inhibit certain isoforms of HDAC.

Measurement of the enzymatic activity of a histone deacetylase can be achieved using known methodologies. For example, Yoshida et al., J. Biol. Chem., 265: 17174-17179 (1990), describes the assessment of histone deacetylase enzymatic activity by the detection of acetylated histones in trichostatin A treated cells. Taunton et al., Science, 272: 408-411 (1996), similarly describes methods to measure histone deacetylase enzymatic activity using endogenous and recombinant HDAC-1.

In some preferred embodiments, the histone deacetylase inhibitor interacts with and reduces the activity of all histone deacetylases in the cell. In some other preferred embodiments according to this aspect of the invention, the histone deacetylase inhibitor interacts with and reduces the activity of fewer than all histone deacetylases in the cell. In certain preferred embodiments, the inhibitor interacts with and reduces the activity of one histone deacetylase (e.g., HDAC-1) or a sub-group of histone deacetylases (e.g., HDAC-1, HDAC-2, and HDAC-3) to a greater extent than other histone deacetylases. Where the inhibitor preferentially reduces the activity of a sub-group of histone deacetylases, the reduction in activity of each member of the sub-group may be the same or different. As discussed below, certain particularly preferred histone deacetylase inhibitors are those that interact with, and reduce the enzymatic activity of, histone deacetylases that are involved in tumorigenesis. Certain other preferred histone deacetylase inhibitors interact with and reduce the enzymatic activity of fungal histone deacetylases.

Preferably, the method according to the third aspect of the invention causes an inhibition of cell proliferation of the contacted cells. The phrase "inhibiting cell proliferation" is used to denote an ability of an inhibitor of histone deacetylase to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the inhibitor is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, an inhibitor of histone deacetylase according to the invention that inhibits cell proliferation in a contacted cell may induce the contacted cell to undergo growth retardation, to undergo growth arrest, to undergo programmed cell death (i.e., to apoptose), or to undergo necrotic cell death.

The cell proliferation inhibiting ability of the histone deacetylase inhibitors according to the invention allows the synchronization of a population of asynchronously growing cells. For example, the histone deacetylase inhibitors of the invention may be used to arrest a population of non-neoplastic cells grown in vitro in the G1 or G2 phase of the cell cycle. Such synchronization allows, for example, the identification of gene and/or gene products expressed during the G1 or G2 phase of the cell cycle. Such synchronization of cultured cells may also be useful for testing the efficacy of a new transfection protocol, where transfection efficiency varies and is dependent upon the particular cell cycle phase of the cell to be transfected. Use of the histone deacetylase inhibitors of the invention allows the synchronization of a population of cells, thereby aiding detection of enhanced transfection efficiency.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the histone deacetylase inhibitor induces cell differentiation in the contacted cell. Thus, a neoplastic cell, when contacted with an inhibitor of histone deacetylase may be induced to differentiate, resulting in the production of a non-neoplastic daughter cell that is phylogenetically more advanced than the contacted cell.

In some preferred embodiments, the contacted cell is in an animal. Thus, the invention provides a method for treating a cell proliferative disease or condition in an animal, comprising administering to an animal in need of such treatment a therapeutically effective amount of a histone deacetylase inhibitor of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a histone deacetylase inhibitor of the invention.

It is contemplated that some compounds of the invention have inhibitory activity against a histone deacetylase from a protozoal source. Thus, the invention also provides a method for treating or preventing a protozoal disease or infection, comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a protozoal histone deacetylase to a greater extent than it inhibits mammalian histone deacetylases, particularly human histone deacetylases.

The present invention further provides a method for treating a fungal disease or infection comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a fungal histone deacetylase to a greater extent than it inhibits mammalian histone deacetylases, particularly human histone deacetylases.

The term "therapeutically effective amount" is meant to denote a dosage sufficient to cause inhibition of histone deacetylase activity in the cells of the subject, or a dosage sufficient to inhibit cell proliferation or to induce cell differentiation in the subject. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

When administered systemically, the histone deacetylase inhibitor is preferably administered at a sufficient dosage to attain a blood level of the inhibitor from about 0.01 µM to about 100 µM, more preferably from about 0.05 µM to about 50 µM, still more preferably from about 0.1 µM to about 25 µM, and still yet more preferably from about 0.5 µM to about 25 µM. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the tissue, organ, or the particular animal or patient to be treated.

In certain preferred embodiments of the third aspect of the invention, the method further comprises contacting the cell with an antisense oligonucleotide that inhibits the expression of a histone deacetylase. The combined use of a nucleic acid level inhibitor (e.g., antisense oligonucleotide) and a protein level inhibitor (i.e., inhibitor of histone deacetylase enzyme activity) results in an improved inhibitory effect, thereby reducing the amounts of the inhibitors required to obtain a given inhibitory effect as compared to the amounts necessary when either is used individually. The antisense oligonucleotides according to this aspect of the invention are complementary to regions of RNA or double-stranded DNA that encode HDAC-1, HDAC-2, HDAC-3, HDAC-4, HDAC-5, HDAC-6, HDAC7, and/or HDAC-8 (see e.g., GenBank Accession Number U50079 for HDAC-1, GenBank Accession Number U31814 for HDAC-2, and GenBank Accession Number U75697 for HDAC-3).

For purposes of the invention, the term "oligonucleotide" includes polymers of two or more deoxyribonucleosides, ribonucleosides, or 2'-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane.

For purposes of the invention the term "2'-substituted ribonucleoside" includes ribonucleosides in which the hydroxyl group at the 2' position of the pentose moiety is substituted to produce a 2'-O-substituted ribonucleoside. Preferably, such substitution is with a lower alkyl group containing 1-6 saturated or unsaturated carbon atoms, or with an aryl or allyl group having 2-6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups. The term "2'-substituted ribonucleoside" also includes ribonucleosides in which the 2'-hydroxyl group is replaced with an amino group or with a halo group, preferably fluoro.

Particularly preferred antisense oligonucleotides utilized in this aspect of the invention include chimeric oligonucleotides and hybrid oligonucleotides.

For purposes of the invention, a "chimeric oligonucleotide" refers to an oligonucleotide having more than one type of internucleoside linkage. One preferred example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred example of such a hybrid oligonucleotide comprises a ribonucleotide or 2'-substituted ribonucleotide region, preferably comprising from about 2 to about 12 2'-substituted nucleotides, and a deoxyribonucleotide region. Preferably, such a hybrid oligonucleotide contains at least three consecutive deoxyribonucleosides and also contains ribonucleosides, 2'-substituted ribonucleosides, preferably 2'-O-substituted ribonucleosides, or combinations thereof (see e.g., Metelev and Agrawal, U.S. Pat. No. 5,652, 355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active. Useful assays for this purpose include quantitating the mRNA encoding a product of the gene, a Western blotting analysis assay for the product of the gene, an activity assay for an enzymatically active gene product, or a soft agar growth assay, or a reporter gene construct assay, or an in vivo tumor growth assay, all of which are described in detail in this specification or in Ramchandani et al. (1997) Proc. Natl. Acad. Sci. USA 94: 684-689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon, R. T. (1993) Methods in Molec. Biol. 20: 465-496).

Particularly preferred oligonucleotides have nucleotide sequences of from about 13 to about 35 nucleotides which include the nucleotide sequences shown in Table 1. Yet additional particularly preferred oligonucleotides have nucleotide sequences of from about 15 to about 26 nucleotides of the nucleotide sequences shown in Table 1.

TABLE 1

| Oligo | Target | Accession Number | Nucleotide Position | Sequence | position within Gene |
|---|---|---|---|---|---|
| HDAC1 AS1 | Human HDAC1 | U50079 | 1585-1604 | 5'-GAAACGTGAGGGACTCAGCA-3' (SEQ ID NO: 1) | 3'-UTR |
| HDAC1 AS2 | Human HDAC1 | U50079 | 1565-1584 | 5'-GGAAGCCAGAGCTGGAGAGG-3' (SEQ ID NO: 2) | 3'-UTR |
| HDAC1 MM | Human HDAC1 | U50079 | 1585-1604 | 5'-GTTAGGTGAGGCACTGAGGA-3' (SEQ ID NO: 3) | 3'-UTR |
| HDAC2 AS | Human HDAC2 | U31814 | 1643-1622 | 5'-GCTGAGCTGTTCTGATTTGG-3' (SEQ ID NO: 4) | 3'-UTR |
| HDAC2 MM | Human HDAC2 | U31814 | 1643-1622 | 5'-CGTGAGCACTTCTCATTTCC-3' (SEQ ID NO: 5) | 3'-UTR |
| HDAC3 AS | Human HDAC3 | AF039703 | 1276-1295 | 5'-CGCTTTCCTTGTCATTGACA-3' (SEQ ID NO: 6) | 3'-UTR |
| HDAC3 MM | Human HDAC3 | AF039703 | 1276-1295 | 5'-GCCTTTCCTACTCATTGTGT-3' (SEQ ID NO: 7) | 3'-UTR |
| HDAC4 AS1 | Human HDAC4 | AB006626 | 514-33 | 5'-GCTGCCTGCCGTGCCCACCC-3' (SEQ ID NO: 8) | 5'-UTR |
| HDAC4 MM1 | Human HDAC4 | AB006626 | 514-33 | 5'-CGTGCCTGCGCTGCCCACGG-3' (SEQ ID NO: 9) | 5'-UTR |
| HDAC4 AS2 | Human HDAC4 | AB006626 | 7710-29 | 5'-TACAGTCCATGCAACCTCCA-3' (SEQ ID NO: 10) | 3'-UTR |
| HDAC4 MM4 | Human HDAC4 | AB006626 | 7710-29 | 5'-ATCAGTCCAACCAACCTCGT-3' (SEQ ID NO: 11) | 3'-UTR |
| HDAC5 AS | Human HDAC5 | AF039691 | 2663-2682 | 5'-CTTCGGTCTCACCTGCTTGG-3' (SEQ ID NO: 12) | 3'-UTR |
| HDAC6 AS | Human HDAC6 | AJ011972 | 3791-3810 | 5'-CAGGCTGGAATGAGCTACAG-3' (SEQ ID NO: 13) | 3'-UTR |
| HDAC6 MM | Human HDAC6 | AJ011972 | 3791-3810 | 5'-GACGCTGCAATCAGGTAGAC-3' (SEQ ID NO: 14) | 3'-UTR |
| HDAC7 AS | Human HDAC7 | AF239243 | 2896-2915 | 5'-CTTCAGCCAGGATGCCCACA-3' (SEQ ID NO: 15) | 3'-UTR |
| HDAC8 AS1 | Human HDAC8 | AF230097 | 51-70 | 5'-CTCCGGCTCCTCCATCTTCC-3' (SEQ ID NO: 16) | 5'-UTR |
| HDAC8 AS2 | Human HDAC8 | AF230097 | 1328-1347 | 5'-AGCCAGCTGCCACTTGATGC-3' (SEQ ID NO: 17) | 3'-UTR |

The following examples are intended to further illustrate certain preferred embodiments of the invention, and are not intended to limit the scope of the invention.

EXAMPLES

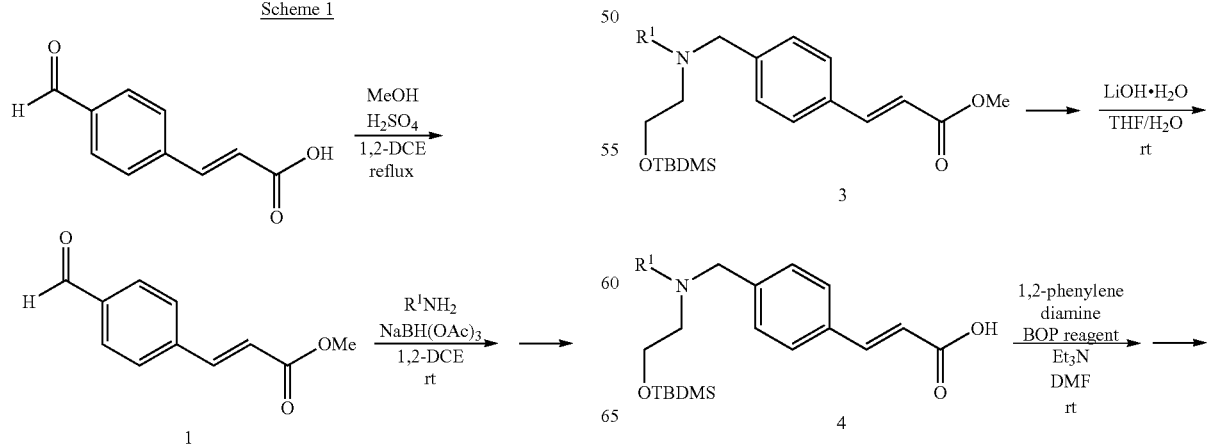

Scheme 1

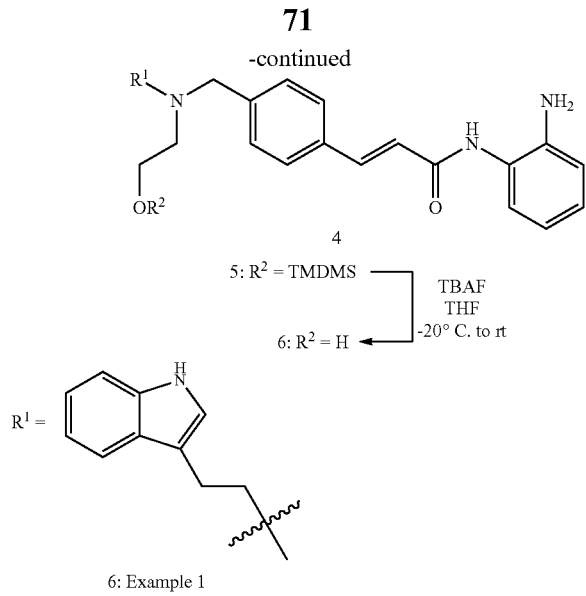

6: Example 1

Example 1

N-(2-Amino-phenyl)-3-[4-({(2-hydroxy-ethyl)-[2-(1H-indol-3-yl)-ethyl]-amino}-methyl)-phenyl]-acrylamide (6)

Step 1: Methyl 3-(4-formyl-phenyl)-acrylate (1)

To a stirred suspension at room temperature of 4-formyl-cinnamic acid (15.39 g, 87.36 mmol) in 1,2-dichloroethane (100 mL) was added concentrated sulfuric acid (8 mL) and anhydrous MeOH (15 mL), respectively. The reaction mixture was refluxed for 18 h, cooled to the room temperature and concentrated. The residue was diluted with AcOEt and washed with $H_2O$, saturated aqueous $NaHCO_3$, $H_2O$ and brine, dried over $MgSO_4$, filtered, and concentrated again. The crude product was purified by flash chromatography on silica gel (eluent AcOEt/hexane:20/80→30/70) to afford the title compound 2 (9.75 g, 51.26 mmol, 59% yield) as a pale yellow powder. $^1$H NMR (300 MHz, $CDCl_3$) δ(ppm): 10.04 (s, 1H), 7.91 (d, J=7.9 Hz, 2H), 7.80-7.60 (m, 3H), 6.56 (d, J=15.8 Hz, 1H), 3.84 (s, 3H).

Step 2: Methyl 3-(4-{[2-(1H-indol-3-yl)-ethylamino]-methyl}-phenyl)-acrylate (2)

To a stirred solution of 1 (3.00 g, 15.77 mmol) and tryptamine (2.78 g, 17.35 mmol) in anhydrous 1,2-dichloroethane (200 mL) under nitrogen was added $NaBH(OAc)_3$ (3.87 g, 17.35 mmol) at room temperature. The reaction mixture was stirred at room temperature for 39 hours, poured into 10% solution of $K_2CO_3$ and extracted with $CH_2Cl_2$. The organic layer was concentrated to form a residue which was purified by flash chromatography on silica gel (MeOH/$CH_2Cl_2$, 10/90) and co-precipitated in a mixture of AcOEt/hexane to afford the title compound 2 (4.39 g, 13.13 mmol, 83% yield) as a yellow solid. $^1$H NMR (400 MHz, DMSO-$d_6$) δ(ppm): 10.78 (s, 1H), 7.70-7.62 (m, 3H), 7.49 (d, J=8.0 Hz, 1H), 7.39 (d, J=8.2 Hz, 2H), 7.33 (dt, J=8.0, 0.9 Hz, 1H), 7.13 (d, J=2.2 Hz, 1H), 7.06 (ddd, J=7.0, 7.0, 1.2 Hz, 1H), 6.96 (ddd, J=6.9, 6.9, 1.1 Hz, 1H), 6.62 (d, J=16.0 Hz, 1H), 3.79 (s, 2H), 3.75 (s, 3H), 2.91-2.78 (m, 4H), 2.18 (bs, 1H).

Step 3: Methyl 3-[4-({[2-(tert-butyl-dimethyl-silanyloxy)-ethyl]-[2-(1H-indol-3-yl)-ethyl]-amino}-methyl)-phenyl]-acrylate (3)

To a stirred solution of 2 (2.82 g, 8.44 mmol) and diisopropylethylamine (2.21 mL, 12.66 mmol) in anhydrous DMSO (22 mL) at room temperature under nitrogen was added (2-bromo-ethoxy)-tert-butyl-dimethylsilane (2.17 mL, 10.12 mmol). The reaction mixture was heated at 50-55° C. for 24 h, poured into water and extracted with $CH_2Cl_2$. The organic layer was dried over $MgSO_4$, filtered, and concentrated. The crude product was purified by flash chromatography on silica gel (AcOEt/$CH_2Cl_2$, 15/85, plus a few drops of $NH_4OH$) to afford the title compound 3 (4.06 g, 8.24 mmol, 97% yield) as a dark orange oil.

$^1$H NMR (300 MHz, $CDCl_3$) δ(ppm): 7.95 (bs, 1H), 7.70 (d, J=15.8 Hz, 1H), 7.58-7.30 (m, 6H), 7.18 (t, J=7.5 Hz, 1H), 7.07 (t, J=7.5 Hz, 1H), 7.00 (bs, 1H), 6.43 (d, J=16.2 Hz, 1H), 3.88-3.68 (m, 7H), 3.04-2.66 (m, 6H), 0.88 (bs, 9H), 0.04 (bs, 6H).

Step 4: 3-[4-({[2-(tert-Butyl-dimethyl-silanyloxy)-ethyl]-[2-(1H-indol-3-yl)-ethyl]-amino}-methyl)-phenyl]-acrylic acid (4)

To a stirred solution of compound 3 (3.18 g, 6.45 mmol) in THF (40 mL) was added a solution of $LiOH.H_2O$ (677 mg, 16.14 mmol) in water (20 mL) at room temperature. After 24 h the reaction mixture was concentrated, diluted with water and acidified with 1N HCl until a pH 5-6. A precipitate was formed which was separated by filtration, rinsed with water and dried to afford the title compound 4 (2.43 g, 5.08 mmol, 79% yield) as an off-white solid. $^1$H NMR (400 MHz, DMSO-$d_6$) δ(ppm): 12.34 (bs, 1H), 10.75 (s, 1H), 7.63 (d, J=8.2 Hz, 2H), 7.59 (d, J=15.8 Hz, 1H), 7.44-7.35 (m, 3H), 7.32 (d, J=8.0 Hz, 1H), 7.11 (d, J=2.3 Hz, 1H), 7.05 (td, J=7.5, 1.0 Hz, 1H), 6.92 (td, J=7.4, 0.9 Hz, 1H), 6.51 (d, J=15.8 Hz, 1H), 3.79 (s, 2H), 3.69 (t, J=6.4 Hz, 2H), 2.93-2.74 (m, 4H), 2.69 (t, J=6.2 Hz, 2H), 0.88 (s, 9H), 0.05 (s, 6H).

Step 5: N-(2-Amino-phenyl)-3-[4-({[2-(tert-butyl-dimethyl-silanyloxy)-ethyl]-[2-(1H-indol-3-yl)-ethyl]-amino}-methyl)-phenyl]-acrylamide (5)

To a stirred solution of 4 (1.30 g, 2.72 mmol) in anhydrous DMF (20 mL) at room temperature under nitrogen were added $Et_3N$ (330 μl, 3.26 mmol) and BOP reagent (1.32 g, 2.99 mmol), respectively. After 30 min, a solution of 1,2-phenylenediamine (352 mg, 3.26 mmol), $Et_3N$ (1.14 mL, 8.15 mmol) in anhydrous DMF (3 mL) was added dropwise. After 3 h the reaction mixture was poured into saturated aqueous solution of $NH_4Cl$, and extracted with AcOEt. The extract was washed with saturated $NH_4Cl$, water and brine, dried over $MgSO_4$, filtered, concentrated and purified by flash chromatography on silica gel (MeOH/$CH_2Cl_2$, 5/95 plus several drops of $NH_4OH$), to afford the title compound 5 (1.49 g, 2.62 mmol, 96% yield) as a yellow sticky foam. $^1$H NMR (300 MHz, DMSO-$d_6$) δ(ppm): 10.78 (s, 1H), 9.40 (s, 1H), 7.59 (d, J=8.0 Hz, 2H), 7.58 (d, J=15.8 Hz, 1H), 7.45 (d, J=7.9 Hz, 2H), 7.40 (t, J=7.7 Hz, 2H), 7.35 (d, J=8.4 Hz, 1H), 7.14 (s, 1H), 7.07 (t, J=7.5 Hz, 1H), 7.05-6.85 (m, 3H), 6.79 (d, J=7.9 Hz, 1H), 6.62 (t, J=7.5 Hz, 1H), 4.98 (bs, 2H), 3.80 (s, 2H), 3.71 (t, J=6.2 Hz, 2H), 2.95-2.75 (m, 4H), 2.71 (t, J=6.2 Hz, 2H), 0.89 (s, 9H), 0.05 (s, 6H).

Step 6: N-(2-Amino-phenyl)-3-[4-({(2-hydroxy-ethyl)-[2-(1H-indol-3-yl)-ethyl]-amino}-methyl)-phenyl]-acrylamide (6)

To a stirred solution at −20° C. of 5 (1.49 g, 2.62 mmol) in anhydrous THF (30 mL) under nitrogen was slowly added a solution of TBAF (2.88 mL, 2.88 mmol, 1.0M in THF). The reaction mixture was allowed to warm-up to the room temperature over 1 h and was stirred for additional 22 hours. MeOH was added and the reaction mixture was concentrated, diluted with AcOEt, and successively washed with saturated aqueous solution of $NaHCO_3$, $H_2O$, a saturated aqueous solution of $NH_4Cl$ and brine, dried over $MgSO_4$, filtered, and concentrated. The residue was purified by flash chromatography on silica gel (MeOH/$CH_2Cl_2$, 5/95→10/90 plus several drops of $NH_4OH$) and triturated with a mixture of AcOEt/$CH_2Cl_2$/hexane to afford the title compound 6 (956 mg, 2.10 mmol, 80% yield) as a pale yellow solid. $^1$H NMR (400 MHz, DMSO-$d_6$) δ(ppm): 10.76 (s, 1H), 9.39 (s, 1H), AB system ($δ_A$=7.58, $δ_B$=7.44, $J_{AB}$=8.0 Hz, 4H), 7.56 (d, J=15.7 Hz, 1H), 7.42-7.34 (m, 2H), 7.33 (d, J=8.0 Hz, 1H), 7.12 (d, J=2.3 Hz, 1H), 7.05 (td, J=7.2, 1.2 Hz, 1H), 6.98-6.90 (m, 2H), 6.90 (d, J=15.8 Hz, 1H), 6.77 (dd, J=8.0, 1.4 Hz, 1H), 6.60 (ddd, J=7.5, 7.5, 1.4 Hz, 1H), 4.98 (bs, 2H), 4.43 (t, J=5.4 Hz, 1H), 3.78 (s, 2H), 3.56 (td, J=6.3, 5.6 Hz, 2H), 2.94-2.84 (m, 2H), 2.82-2.74 (m, 2H), 2.68 (t, J=6.5 Hz, 2H).

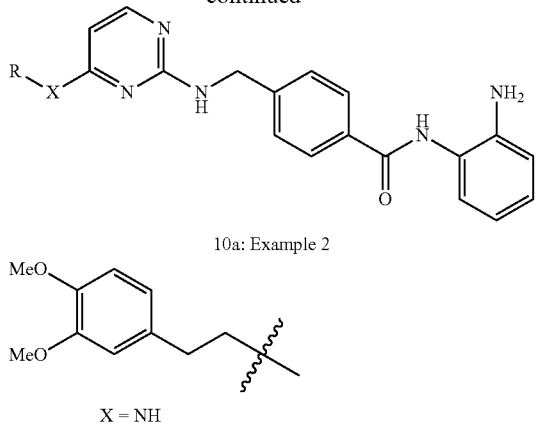

10a: Example 2

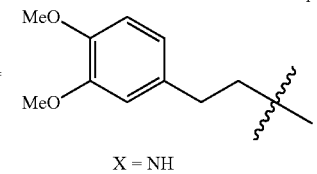

X = NH

Example 2

N-(2-Amino-phenyl)-4-({4-[2-(3,4-dimethoxy-phenyl)-ethylamino]-pyrimidin-2-ylamino}-methyl)-benzamide (10a)

Step 1: (2-Chloro-pyrimidin-4-yl)-[2-(3,4-dimethoxy-phenyl)-ethyl]-amine (7)

To a stirred solution of 2,4-dichloropyrimidine (500 mg, 3.36 mmol) in anhydrous DMF (10 mL) at room temperature under nitrogen were slowly added i-$Pr_2NEt$ (1.06 mL, 6.10 mmol) and 3,4-dimethoxyphenethylamine (531 μl, 3.05 mmol), respectively. After 24 h the reaction mixture was diluted with AcOEt and successively washed with saturated aqueous solution of $NH_4Cl$ and brine, dried over anhydrous $MgSO_4$, filtered and concentrated. The residue was purified by flash chromatography on silica gel (MeOH/$CH_2Cl_2$: 2/98→5/95) to afford the title compound 7a (744 mg, 2.53 mmol, 83% yield) as pale yellow oil.

Step 2: Methyl 4-({4-[2-(3,4-dimethoxy-phenyl)-ethylamino]-pyrimidin-2-ylamino}-methyl)-benzoate (8)

In a sealed flask, a mixture of 7 (744 mg, 2.53 mmol), methyl 4-(aminomethyl)benzoate (628 mg, 3.80 mmol) and i-$Pr_2NEt$ (882 μl, 5.07 mmol) in isopropanol (50 mL) was heated to 120-125° C. for 7 days (during this period of time an excess of methyl 4-(aminomethyl)benzoate was added to the reaction mixture). The reaction mixture was allowed to cool to the room temperature, concentrated and purified by flash chromatography on silica gel (MeOH/$CH_2Cl_2$, 5/95→10/90 plus several drops of $NH_4OH$) to afford the title compound 8 (671 mg, 1.59 mmol, 63% yield) as an orange sticky solid.

Step 3: 4-({4-[2-(3,4-Dimethoxy-phenyl)-ethylamino]-pyrimidin-2-ylamino}-methyl)-benzoic acid (9)

To a stirred solution of compound 8 (670 mg, 1.59 mmol) in THF (15 mL) at room temperature was added a solution of LiOH.$H_2O$ (166 mg, 3.97 mmol) in water (5 mL). After 24 h, the reaction mixture was concentrated, diluted with water and acidified with 2N HCl (pH at 5-6). A precipitate formed, which was separated by filtration, rinsed with water and dried to afford the title compound 9 (600 mg, 1.47 mmol, 93%

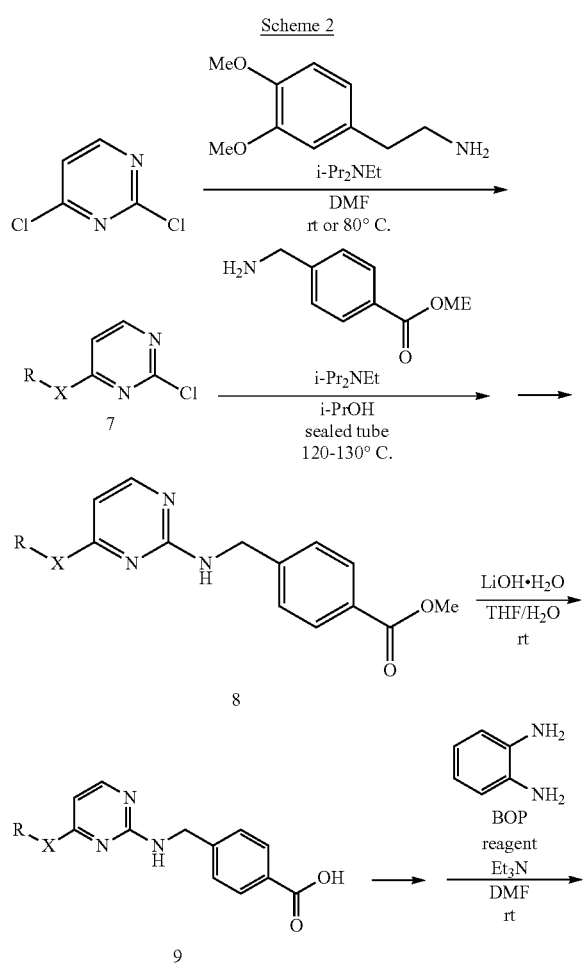

Scheme 2 yield) as an off-white solid. ¹H NMR (400 MHz, DMSO-$d_6$) δ(ppm): AB system ($δ_A$=7.87, $δ_B$=7.41, J=8.2 Hz, 4H), 7.68-7.58 (m, 1H), 7.12-6.56 (m, 5H), 5.75 (d, J=5.5 Hz, 1H), 4.53 (d, J=6.3 Hz, 2H), 3.74 and 3.72 (2s, 6H), 3.48-3.30 (m, 2H), 2.80-2.60 (m, 2H).

Step 4: N-(2-Amino-phenyl)-4-({4-[2-(3,4-dimethoxy-phenyl)-ethylamino]-pyrimidin-2-ylamino}-methyl)-benzamide (10a)

To a stirred solution of 9a (300 mg, 0.73 mmol) in anhydrous DMF (10 mL) at room temperature under nitrogen were added Et₃N (123 µl, 0.88 mmol) and BOP reagent (358 mg, 0.81 mmol), respectively. After 30 min, a solution of 1,2-phenylenediamine (95 mg, 0.88 mmol), Et₃N (307 µl, 2.20 mmol) in anhydrous DMF (2 mL) was added drop wise. After stirring overnight, the reaction mixture was poured into a saturated aqueous solution of NH₄Cl, and extracted with AcOEt. The organic layer was successively washed with saturated NH₄Cl, water and brine, dried over MgSO₄, filtered, and concentrated. The residue was purified by flash chromatography on silica gel (MeOH/CH₂Cl₂: 5/95→10/90 plus a few drops of NH₄OH) and co-precipitated in a mixture of AcOEt/MeOH/hexane to afford the title compound 10a (280 mg, 0.56 mmol, 76% yield) as an off-white solid. ¹H NMR (400 MHz, DMSO-$d_6$) δ(ppm): 9.60 (s, 1H), AB system ($δ_A$=7.91, $δ_B$=7.43, J=8.0 Hz, 4H), 7.71-7.58 (m, 1H), 7.17 (d, J=7.4 Hz, 1H), 7.20-7.00 (m, 2H), 6.98 (t, J=7.5 Hz, 1H), 6.86 (d, J=8.0 Hz, 1H), 6.84-6.64 (m, 3H), 6.61 (t, J=7.4 Hz, 1H), 5.76 (d, J=5.3 Hz, 1H), 4.90 (bs, 2H), 4.54 (d, J=6.1 Hz, 2H), 3.74 (s, 6H), 3.50-3.35 (m, 2H), 2.80-2.62 (m, 2H).

Examples 3-11

Examples 3-11 (compounds 10b-10j) were prepared using the same procedures as described for the compound 10a, example 2 (scheme 2).

TABLE 1

10b-j

| Cmpd | Ex | R-X | Name | Characterization |
|---|---|---|---|---|
| 10b | 3 | (1H-indol-3-yl)ethylamino | N-(2-Amino-phenyl)-4-({4-[2-(1H-indol-3-yl)-ethylamino]-pyrimidin-2-ylamino}-methyl)-benzamide | ¹H NMR (400 MHz, DMSO-$d_6$) δ(ppm): 10.82 (s, 1H), 9.60 (s, 1H), AB system ($δ_A$ = 7.90, $δ_B$ = 7.43, $J_{AB}$ = 8.1 Hz, 4H), 7.64 (bs, 1H), 7.52 (d, J = 7.2 Hz, 1H), 7.34 (d, J = 8.0 Hz, 1H), 7.25-6.90 (m, 7H), 6.79 (dd, J = 8.0, 1.4 Hz, 1H), 6.61 (td, J = 7.5, 1.4 Hz, 1H), 5.76 (d, J = 5.1 Hz, 1H), 4.90(s, 2H), 4.54 (d, J = 6.1 Hz, 2H), 3.63-3.43 (m, 2H), 2.93 (t, J = 7.3 Hz, 2H). |
| 10c | 4 | 3-methoxyphenyl ethylamino | N-(2-Amino-phenyl)-4-({4-[2-(3-methoxy-phenyl)-ethylamino]-pyrimidin-2-ylamino}-methyl)-benzamide | ¹H NMR (400 MHz, DMSO-$d_6$) δ (ppm): 9.60 (s, 1H), AB system ($δ_A$ = 7.91, $δ_B$ = 7.43, J = 8.2 Hz, 4H), 7.64 (bs, 1H), 7.25-6.92 (m, 5H), 6.87-6.68 (m, 4H), 6.61 (td, J = 7.5, 1.4 Hz, 1H), 5.75 (d, J = 5.3 Hz, 1H), 4.90 (bs, 2H), 4.54(d, J = 6.3 Hz, 2H), 3.75 (s, 3H), 3.52-3.38 (m, 2H), 2.84-2.70 (m, 2H). |
| 10d | 5 | pyridin-3-yl ethylamino | N-(2-Amino-phenyl)-4-{[4-(2-pyridin-3-yl-ethylamino)-pyrimidin-2-ylamino]-methyl}-benzamide | ¹H NMR (400 MHz, DMSO-$d_6$) δ (ppm): 9.60 (s, 1H), 8.47-8.33 (m, 2H), AB system ($δ_A$ = 7.91, $δ_B$ = 7.42, J = 8.0 Hz, 4H), 7.70-7.50 (m, 2H), 7.36-7.28 (m, 1H), 7.25-7.03 (m, 2H), 7.17 (d, J = 7.4 Hz, 1H), 6.98 (t, J = 7.5 Hz, 1H), 6.79 (d, J = 8.2 Hz, 1H), 6.61 (t, J = 7.5 Hz, 1H), 5.75 (d, J = 5.9 Hz, 1H), 4.90 (bs, 2H), 4.53 (d, J = 6.1 Hz, 2H), 3.53-3.39 (m, 2H), 2.88-2.73 (m, 2H). |
| 10e | 6 | 2-morpholin-4-yl ethylamino | N-(2-Amino-phenyl)-4-{[4-(2-morpholin-4-yl-ethylamino)-pyrimidin-2-ylamino]-methyl}-benzamide | ¹H NMR (400 MHz, DMSO-$d_6$) δ (ppm): 9.61 (s, 1H), AB system ($δ_A$ = 7.91, $δ_B$ = 7.41, J = 8.0 Hz, 4H), 7.68-7.57 (m, 1H), 7.25-6.85 (m, 2H), 7.16 (d, J = 7.4 Hz, 1H), 6.98 (t, J = 7.5 Hz, 1H), 6.79 (d, J = 7.8 Hz, 1H), 6.61 (t, J = 7.3 Hz, 1H), 5.77 (d, J = 5.5 Hz, 1H), 4.90 (bs, 2H), 4.51 (d, J = 6.3 Hz, 2H), 3.66-3.50 (m, 4H), 3.40-3.26 (m, 2H), 2.50-2.24 (m, 6H). |

TABLE 1-continued 10b-j

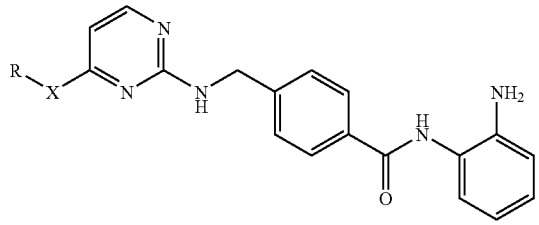

| Cmpd | Ex | R-X | Name | Characterization |
|---|---|---|---|---|
| 10F | 7 | 4-methylpiperazin-1-yl (N-methylpiperazine attached) | N-(2-Amino-phenyl)-4-{[4-(4-methyl-piperazin-1-yl)-pyrimidin-2-ylamino]-methyl}-benzamide | $^1$H NMR (400 MHz, CD$_3$OD) δ (ppm): 7.90 (d, J = 8.2 Hz, 2H), 7.74 (d, J = 5.9 Hz, 1H), 7.44 (d, J = 8.2 Hz, 2H), 7.16 (m, 1H), 7.06 (m, 1H), 6.89 (m, 1H), 6.75 (m, 1H), 6.05 (d, J = 6.7 Hz, 1H), 4.58 (s, 2H), 3.60 (m, 4H), 2.42 (m, 4H), 2.18 (s, 3H). |
| 10g | 8 | 4-acetylpiperazin-1-yl | 4-{[4-(4-Acetyl-piperazin-1-yl)-pyrimidin-2-ylamino]-methyl}-N-(2-amino-phenyl)-benzamide | $^1$H NMR (400 MHz, DMSO-d$_6$) δ (ppm): 9.78 (s, 1H), 8.71 (s, 1H), 7.96 (d, J = 7.8 Hz, 2H), 7.89 (d, J = 7.0 Hz, 1H), 7.46 (d, J = 8.2 Hz, 2H), 7.19 (d, J = 7.8 Hz, 1H), 7.0 (dd, J = 7.8, 7.4 Hz, 1H), 6.86 (d, J = 7.8 Hz, 1H), 6.70 (m, 1H), 6.51 (d, J = 7.0 Hz, 1H), 4.62 (d, J = 5.9 Hz, 2H), 3.76 (m, 4H), 3.34 (m, 6H), 2.03 (s, 3H). |
| 10h | 9 | 3,4,5-trimethoxyphenylamino | N-(2-Amino-phenyl)-4-{[4-(3,4,5-trimethoxy-phenylamino)-pyrimidin-2-ylamino]-methyl}-benzamide | $^1$H NMR (400 MHz, DMSO-d$_6$) δ (ppm): 9.50 (s, 1H), 9.07 (s, 1H), 7.81 (d, J = 8.2 Hz, 2H), 7.74 (d, J = 5.7 Hz, 1H), 7.31 (d, J = 8.0 Hz, 3H), 7.05 (d, J = 6.7 Hz, 1H), 6.96 (s, 2H), 6.87 (m, 1H), 6.68 (m, 1H), 6.50 (m, 1H), 5.93 (d, J = 5.7 Hz, 1H), 4.82 (bs, 2H), 4.54 (bs, 2H), 3.75-3.40 (m, 9H). |
| 10i | 10 | pyridin-3-yloxy | N-(2-Amino-phenyl)-4-{[4-(pyridin-3-yloxy)-pyrimidin-2-ylamino]-methyl}-benzamide | $^1$H NMR (500 MHz, DMSO-d$_6$) δ (ppm): 9.58 (s, 1H), 8.49 (bs, 1H), 8.20 (m, 1H), 8.03 (bs, 1H), 7.81 (m, 3H), 7.59 (bs, 1H), 7.50 (bs, 1H), 7.36 (bs, 1H), 7.14 (m, 1H), 7.04 (bs, 1H), 6.96 (m, 1H), 6.76 (m, 1H), 6.59 (m, 1H), 6.28 (bs, 2H), 4.87 (s, 2H), 4.49 (s, 1H), 4.16 (s, 1H). |
| 10j | 11 | 3,4-dimethoxyphenylsulfanyl | N-(2-Amino-phenyl)-4-{[4-(3,4-dimethoxy-phenylsulfanyl)-pyrimidin-2-ylamino]-methyl}-benzamide | $^1$H NMR (300 MHz, DMSO-d$_6$) δ (ppm): 9.64 (s, 1H), 8.03 (d, J = 5.3 Hz, 1H), 7.94 (m, 3H), 7.39 (bs, 2H), 7.19 (m, 4H), 7.02 (dd, J = 7.5, 7.5 Hz, 1H), 6.84 (d, J = 7.5 Hz, 1H), 6.66 (dd, J = 7.5, 7.5 Hz, 1H), 6.04 (bs, 1H), 4.93 (s, 2H), 4.53 (bs, 2H), 3.88 (s, 3H), 3.82 (s, 3H). |

Scheme 3

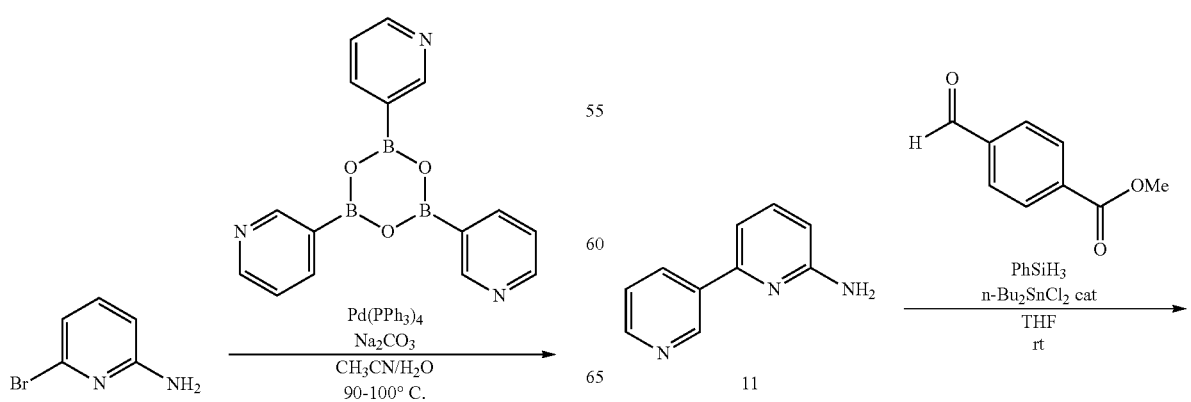

-continued

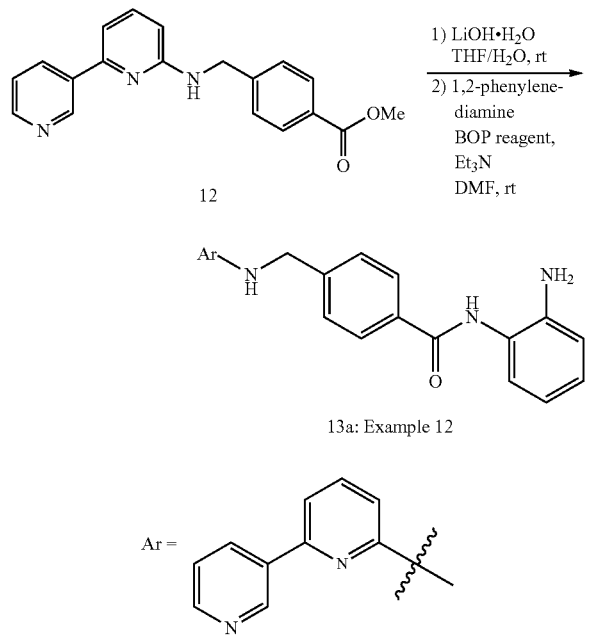

Example 12

N-(2-Amino-phenyl)-4-([2,3']bipyridinyl-6-ylaminomethyl)-benzamide (13a)

Step 1: [2,3']Bipyridinyl-6-ylamine (11)

To a stirred degassed suspension of a mixture of 2-amino-6-bromopyridine (5.38 g, 31.09 mmol), 2,4,6-(3-pyridinyl)-cyclotriboroxane (3.80 g, 12.07 mmol) and aqueous $Na_2CO_3$ (100 mL, 0.4M) in acetonitrile (100 mL) at room temperature $Pd(PPh_3)_4$ (1.70 g, 1.47 mmol) was added. The reaction mixture was heated at 95° for 1 to 2 days under nitrogen, cooled to the room temperature and filtered. The filtrate was concentrated purified by flash chromatography on silica gel (MeOH/$CH_2Cl_2$: 5/95→10/90 plus a few drops of $NH_4OH$) and co-precipitated with a mixture of AcOEt/$CH_2Cl_2$/hexane to afford the title compound 11 (4.091 g, 23.90 mmol, 77% yield) as a pale yellow solid. $^1$H NMR (400 MHz, DMSO-$d_6$) δ(ppm): 9.16 (dd, J=2.2, 0.8 Hz, 1H), 8.57 (dd, J=4.7, 1.6 Hz 1H), 8.33-8.28 (m, 1H), 7.54-7.44 (m, 2H), 7.14 (dd, J=7.3, 0.5 Hz, 1H), 6.49 (dd, J=8.2, 0.4 Hz 1H), 6.12 (bs, 2H).

Step 2: Methyl 4-([2,3']bipyridinyl-6-ylaminomethyl)-benzoate (12)

To a stirred suspension of a mixture of 11 (3.00 g, 17.52 mmol), methyl 4-formylbenzoate (4.62 g, 28.11 mmol, 1.5-2.0 equiv.) and dibutyl tin dichloride 160 mg, 0.53 mmol) in anhydrous THF (15 mL) at room temperature was added phenylsilane (2.34 mL, 19.28 mmol) in three portions over two days. After stirring for 2 to 7 days the reaction mixture was filtered, filtrate was concentrated and purified by flash chromatography on silica gel (MeOH/$CH_2Cl_2$, 2/98→10/90) to afford the title compound 12 (5.50 g, 17.22 mmol, 98% yield) as a pale yellow solid. $^1$H NMR (400 MHz, DMSO-$d_6$) δ(ppm): 9.11 (dd, J=2.3, 0.7 Hz, 1H), 8.55 (dd, J=4.7, 1.8 Hz 1H), 8.29-8.24 (m, 1H), 7.93 (d, J=8.4 Hz, 2H), 7.57-7.40 (m, 5H), 7.18 (d, J=7.2 Hz, 1H), 6.59 (d, J=8.2 Hz 1H), 4.69 (d, J=6.1 Hz, 2H), 3.85 (s, 3H).

Step 3: N-(2-Amino-phenyl)-4-([2,3']bipyridinyl-6-ylaminomethyl)-benzamide (13a)

The title compound 13a (Example 12) was obtained from 12 as an off-white solid in two steps following the same procedure as in Example 2, steps 3 and 4 (Scheme 2). $^1$H NMR (400 MHz, DMSO-$d_6$) δ(ppm): 9.60 (s, 1H), 9.16 (dd, J=2.2, 0.9 Hz, 1H), 8.56 (dd, J=4.8, 1.7 Hz 1H), 8.31 (ddd, J=7.8, 2.3, 1.7 Hz, 1H), 7.95 (d, J=8.2 Hz, 2H), 7.57-7.48 (m, 3H), 7.46 (ddd, J=8.0, 4.7, 0.8 Hz, 1H), 7.42 (t, J=6.1 Hz, 1H), 7.19 (dd, J=7.2, 0.6 Hz, 1H), 7.17 (dd, J=7.3, 1.0 Hz, 1H), 6.98 (td, J=7.5, 1.4, 1H), 6.79 (dd, J=7.8, 1.4 Hz 1H), 6.65-6.57 (m, 2H), 4.90 (bs, 2H), 4.69 (d, J=6.1 Hz, 2H).

Examples 13-16

Examples 13-16 (compounds 13b-13e) were prepared using the same procedures as described for compound 13a, example 12 (scheme 3).

TABLE 2

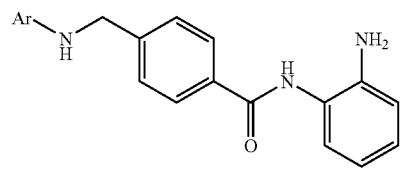

13b-e

| Cmpd | Ex | Ar | Name | Characterization |
|---|---|---|---|---|
| 13b | 13 | ![3-pyridin-3-yl-phenyl] | N-(2-Amino-phenyl)-4-[(3-pyridin-3-yl-phenylamino)-methyl]-benzamide | $^1$H NMR (400 MHz, DMSO-$d_6$) δ (ppm): 9.57 (s, 1H), 8.73 (dd, J = 2.6, 1.0 Hz, 2H), 8.50 (dd, J = 4.8, 1.6 Hz, 1H), 7.93-7.88 (m, 3H), 7.49 (d, J = 8.4 Hz, 2H), 7.42 (ddd, J = 8.0, 4.8, 0.8 Hz, 1H), 7.14 (q, J = 7.6 Hz, 2H), 6.93 (td, J = 8.0, 1.6 Hz, 1H), 6.86-6.81 (m, 2H), 6.74 (dd, J = 8.0, 1.2 Hz, 1H), 6.63-6.52 (m, 3H), 4.86 (s, 2H), 4.43 (d, J = 6.0 Hz, 2H). |

TABLE 2-continued

| Cmpd | Ex | Ar | Name | Characterization |
|---|---|---|---|---|
| 13c | 14 | (3-pyridyl)-phenyl | N-(2-Amino-phenyl)-4-[(4-pyridin-3-yl-phenylamino)-methyl]-benzamide | ¹H NMR (400 MHz, DMSO-d₆) δ (ppm): 9.58 (s, 1H), 8.73 (d, J = 2.0 Hz, 1H), 8.38 (dd, J = 4.4, 1.2 Hz, 1H), 7.91 (d, J = 8.0 Hz, 2H), 7.90-7.86 (m, 1H), 7.47 (d, J = 8.0 Hz, 2H), 7.42 (d, J = 8.8 Hz, 2H), 7.34 (ddd, J = 8.0, 4.8, 0.8 Hz, 1H), 7.12 (d, J = 8.0, 1.2 Hz, 1H), 6.94(td, J = 7.6, 1.6 Hz, 1H), 6.75 (dd, J = 8.0, 1.2 Hz, 1H), 6.70-6.63 (m, 3H), 6.56 (td, J = 7.6, 1.6 Hz, 1H), 4.87 (s, 2H), 4.41 (d, J = 6.4 Hz, 2H). |
| 13d | 15 | [3,3']bipyridinyl-6-yl | N-(2-Amino-phenyl)-4-([3,3']bipyridinyl-6-ylaminomethyl)-benzamide | ¹H NMR (400 MHz, DMSO-d₆) δ (ppm): 9.62 (s, 1H), 8.83 (dd, J = 2.4, 0.7 Hz, 1H), 8.48 (dd, J = 4.7, 1.6 Hz 1H), 8.38 (d, J = 2.5 Hz, 1H), 7.99 (ddd, J = 7.9, 2.3, 1.6 Hz, 1H), 7.95 (d, J = 8.2 Hz, 2H), 7.82 (dd, J = 8.8, 2.5 Hz, 1H), 7.54-7.45 (m, 3H), 7.43 (ddd, J = 7.9, 4.7, 0.7 Hz, 1H), 7.18 (d, J = 7.0 Hz, 1H), 6.99 (td, J = 7.6, 1.6 Hz, 1H), 6.79 (dd, J = 8.0, 1.4 Hz 1H), 6.68 (d, J = 8.6 Hz, 1H), 6.61 (td, J = 7.5, 1.3 Hz, 1H), 4.91 (bs, 2H), 4.65 (d, J = 6.1 Hz, 2H). |
| 13e | 16 | 5-pyridin-3-yl-pyrimidin-2-yl | N-(2-Amino-phenyl)-4-[(5-pyridin-3-yl-pyrimidin-2-ylamino)-methyl]-benzamide | ¹H NMR (400 MHz, DMSO-d₆) δ (ppm): 9.62 (s, 1H), 8.88 (d, J = 2.2 Hz, 1H), 8.72 (bs, 2H), 8.54 (dd, J = 4.7, 1.6 Hz, 1H), 8.15 (t, J = 6.5 Hz, 1H), 8.06 (dt, J = 8.0, 2.0 Hz, 1H), 7.94 (d, J = 8.2 Hz, 2H), 7.48-7.45 (m, 3H), 7.17 (d, J = 7.6 Hz, 1H), 6.98 (td, J = 7.6, 1.3 Hz, 1H), 6.79 (dd, J = 8.0, 1.2 Hz, 1H), 6.61 (td, J = 7.7, 1.2 Hz, 1H), 4.91 (s, 2H), 4.66 (d, J = 6.3 Hz, 2H). |

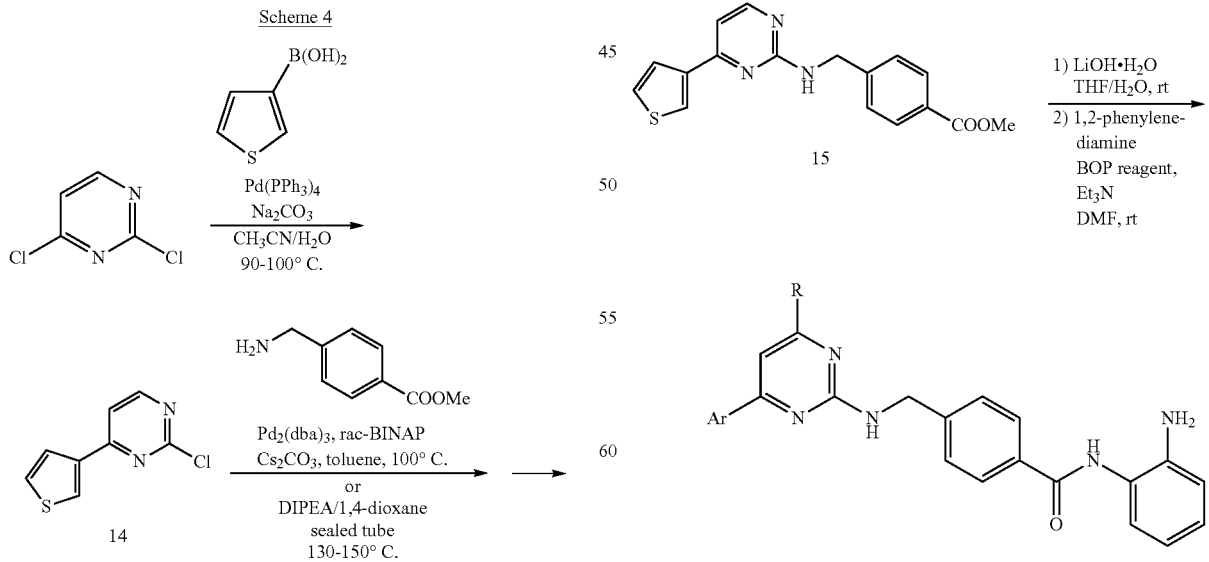

Scheme 4

-continued

R = H; Ar = 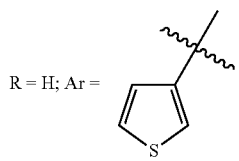

Example 17

N-(2-Amino-phenyl)-4-[(4-thiophen-3-yl-pyrimidin-2-ylamino)-methyl]-benzamide. (16a)

Step 1: 2-Chloro-4-thiophen-3-yl-pyrimidine (14)

To a solution of 3-thiopheneboronic acid (500 mg, 3.91 mmol) and 2,4-dichloropyrimidine (1.16 g, 7.81 mmol) in acetonitrile (20 mL) was added a 0.4 M solution of $Na_2CO_3$ (20 mL) followed by $Pd(PPh_3)_4$ (450 mg, 0.39 mmol). The suspension was degassed and heated at 90° C. for 16 h under nitrogen, cooled down, concentrated and extracted with EtOAc. Organic layer was successively washed with saturated solution of $NH_4Cl$, brine, dried over anhydrous $Na_2SO_4$, filtered and concentrated. The residue was purified by flash chromatography on silica gel (EtOAc/$CH_2Cl_2$: 2/98) to afford the title compound 14 (680 mg, 3.46 mmol, 88% yield). $^1$H NMR: (400 MHz, $CDCl_3$) δ (ppm): 8.56 (d, J=5.2 Hz, 1H), 8.19 (dd, J=3.2, 1.2 Hz, 1H), 7.66 (dd, J=5.2, 1.2 Hz, 1H), 7.46 (d, J=5.2 Hz, 1H), 7.43 (dd, J=5.2, 2.8 Hz, 1H).

Step 2: Methyl 4-[(4-thiophen-3-yl-pyrimidin-2-ylamino)-methyl]-benzoate (15)

To a solution of 14 (680 mg, 3.46 mmol) and methyl 4-(aminomethyl)benzoate (686 mg, 4.51 mmol) in dry 1,4-dioxane (10 mL) was added DIPEA (1.50 mL, 8.65 mmol) and the mixture was heated for 48 h at 130° C. in a sealed tube. Solvents were removed under vacuum and the residue was triturated with a mixture of $EtOAc/Et_2O$, to form a solid, which was collected by filtration and dried. This material was purified by flash chromatography on silica gel (EtOAc/$CH_2Cl_2$: 30/70) to afford the title compound 15 (540 mg, 1.66 mmol, 48% yield). $^1$H NMR: (400 MHz, DMSO-$d_6$) δ (ppm): 8.29-8.23 (m, 2H), 7.88 (d, J=8.4 Hz, 2H), 7.84-7.77 (m, 1H), 7.69-7.59 (m, 2H), 7.52-7.43 (m, 2H), 7.03 (d, J=5.2 Hz, 1H), 4.60 (d, J=6.4 Hz, 2H), 3.81 (s, 3H).

Steps 3: N-(2-Amino-phenyl)-4-[(4-thiophen-3-yl-pyrimidin-2-ylamino)-methyl]-benzamide (16a)

The title compound 16a (example 17) was obtained from 15 as an off-white solid in two steps following the same procedure as in Example 2, steps 3 and 4 (Scheme 2). $^1$H NMR: (400 MHz, DMSO-$d_6$) δ (ppm): 9.59 (s, 1H), 8.32-8.27 (m, 2H), 7.91 (d, J=8.0 Hz, 2H), 7.83 (t, J=6.4 Hz, 1H), 7.71 (d, J=4.8 Hz, 1H), 7.68-7.63 (m, 1H), 7.54-7.44 (m, 2H), 7.15 (d, J=8.0 Hz, 1H), 7.06 (d, J=5.2 Hz, 1H), 6.96 (td, J=7.6, 1.6 Hz, 1H), 6.77 (dd, J=8.0, 1.2 Hz, 1H), 6.59 (td, J=7.6, 1.2 Hz, 1H), 4.89 (s, 2H), 4.62 (d, J=6.4 Hz, 2H).

Examples 18-24

Examples 18-24 (compounds 16b-16 h) were prepared using the same procedure as described for compound 16a, example 17, (scheme 4).

TABLE 3

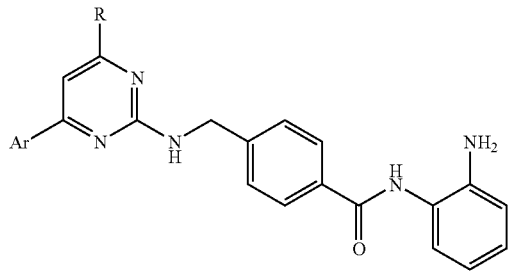

16b-h

| Cmpd | Ex. | Ar | R | Name | Characterization |
|---|---|---|---|---|---|
| 16b | 18 | ![4-methoxyphenyl] | H | N-(2-Amino phenyl)-4-{[4-(4-methoxy-phenyl)-pyrimidin-2-ylamino]-methyl}-benzamide | $^1$H NMR (400 MHz, DMSO-$d_6$) δ (ppm): 9.56 (s, 1H), 8.26 (d, J = 5.2, 1H), 8.03 (d, J = 8.8 Hz, 2H), 7.89 (d, J = 8.0 Hz, 2H), 7.79 (t, J = 6.4 Hz, 1H), 7.45 (d, J = 8.4 Hz, 2H), 7.12 (d, J = 7.2 Hz, 1H), 7.09 (d, J = 5.2 Hz, 1H), 7.02 (d, J = 8.8 Hz, 2H), 6.55 (td, J = 7.2, 1.2 Hz, 1H), 6.74 (dd, J = 8.0, 1.2 Hz, 1H), 6.56 (t, J = 7.6 Hz, 1H), 4.86 (s, 2H), 4.62 (d, J = 6.0 Hz, 2H), 3.81 (s, 3H). |
| 16c | 19 | ![3-acetylphenyl] | H | 4-{[4-(3-Acetyl-phenyl)-pyrimidin-2-ylamino]-methyl}-N-(2-amino-phenyl)-benzamide | $^1$H NMR (400 MHz, DMSO-$d_6$) δ (ppm): 9.55 (s, 1H), 8.58 (s, 1H), 8.36 (d, J = 4.8 Hz, 1H), 8.28 (d, J = 7.2 Hz, 1H), 8.10-7.98 (m, 1H), 8.00 (t, J = 6.0 Hz, 1H), 7.88 (d, J = 8.4 Hz, 2H), 7.62 (t, J = 7.6 Hz, 1H), 7.47 (bs, 2H), 7.24 (d, J = 5.2 Hz, 1H), 7.09 (d, J = 7.6 Hz, 1H), 6.92 (td, J = 7.6, 1.6 Hz, 1H), 6.72 (d, J = 8.0 Hz, 1H), 6.54 (t, J = 7.6 Hz, 1H), 4.85 (s, 2H), 4.61 (d, J = 6.0 Hz, 2H), 2.63 (s, 3H). |

TABLE 3-continued 16b-h

[Structure: pyrimidine with Ar and R substituents, linked via NH-CH2 to benzamide with 2-aminophenyl group]

| Cmpd | Ex. | Ar | R | Name | Characterization |
|---|---|---|---|---|---|
| 16d | 20 | 3,4-difluorophenyl | H | N-(2-Amino-phenyl)-4-{[4-(3,4-difluoro-phenyl)-pyrimidin-2-ylamino]-methyl}-benzamide | $^1$H NMR (400 MHz, DMSO-d$_6$) δ (ppm): 9.55 (s, 1H), 8.35 (d, J = 5.2, 1H), 8.14-8.04 (m, 1H), 7.99-7.91 (m, 2H), 7.88 (d, J = 8.0 Hz, 2H), 7.60-7.38 (m, 3H), 7.19 (d, J = 5.2 Hz, 1H), 7.10 (d, J = 8.4 Hz, 1H), 6.92 (td, J = 7.6, 1.6 Hz, 1H), 6.73 (dd, J = 7.6, 1.6 Hz, 1H), 6.55 (t, J = 6.8 Hz, 1H), 4.85 (m, 1H), 4.61 (d, J = 4.8 Hz, 2H). |
| 16e | 21 | 3-trifluoromethoxyphenyl | H | N-(2-Amino-phenyl)-4-{[4-(3-trifluoromethoxy-phenyl)-pyrimidin-2-ylamino]-methyl}-benzamide | $^1$H NMR (400 MHz, DMSO-d$_6$) δ (ppm): 9.56 (s, 1H), 8.37 (d, J = 5.2, 1H), 8.12-7.95 (m, 3H), 7.88 (d, J = 8.0 Hz, 2H), 7.65-7.57 (m, 1H), 7.53-7.40 (m, 3H), 7.22 (d, J = 5.2 Hz, 1H), 7.10 (d, J = 8.0 Hz, 1H), 6.92 (td, J = 7.6, 1.2 Hz, 1H), 6.73 (dd, J = 8.0, 1.2 Hz, 1H), 6.55 (t, J = 7.2 Hz, 1H), 4.84 (m, 2H), 4.60 (d, J = 6.4 Hz, 2H). |
| 16f | 22 | pyridin-3-yl | NH$_2$ | N-(2-Amino phenyl)-4-[(4-amino-6-pyridin-3-yl-pyrimidin-2-ylamino)-methyl]-benzamide | $^1$H NMR (400 MHz, DMSO-d$_6$) δ (ppm): 9.60 (s, 1H), 9.06 (d, J = 1.6 Hz, 1H), 8.62 (d, J = 3.7 Hz, 1H), 8.22 (bd, J = 7.8 Hz, 1H), 7.93 (d, J = 8.2 Hz, 2H), 7.56-7.44 (m, 3H), 7.35-7.15 (m, 1H), 7.17 (d, J = 7.4 Hz, 1H), 6.98 (td, J = 7.6, 1.5 Hz, 1H), 6.78 (dd, J = 8.0, 1.4 Hz, 1H), 6.61 (t, J = 7.4 Hz, 1H), 6.65-6.45 (m, 2H), 6.30 (s, 1H), 5.04-4.80 (m, 2H), 4.62 (d, J = 6.3 Hz, 2H). |
| 16g | 23 | 3,4,5-trimethoxyphenyl | H | N-(2-Amino-phenyl)-4-{[4-(3,4,5-trimethoxy-phenyl)-pyrimidin-2-ylamino]-methyl}-benzamide | $^1$H NMR (300 MHz, DMSO-d$_6$) δ (ppm): 9.64 (s, 1H), 8.40 (d, J = 5.3 Hz, 1H), 7.97 (d, J = 7.9 Hz, 3H), 7.56 (d, J = 7.5 Hz, 2H), 7.41 (s, 2H), 7.28 (d, J = 5.3 Hz, 1H), 7.20 (d, J = 7.5 Hz, 1H), 7.02 (dd, J = 7.9, 7.0 Hz, 1H), 6.83 (d, J = 7.9 Hz, 1H), 6.64 (dd, J = 7.5, 7.5 Hz, 1H), 4.92 (s, 2H), 4.67 (d, J = 6.2 Hz, 2H), 3.90 (s, 3H), 3.77 (s, 3H). |
| 16h | 24 | 3-fluoro-4-methoxyphenyl | H | N-(2-Amino-phenyl)-4-{[4-(3-fluoro-4-methoxy-phenyl)-pyrimidin-2-ylamino]-methyl}-benzamide | $^1$H NMR (400 MHz, DMSO-d$_6$) δ (ppm): 9.49 (s, 1H), 8.22 (d, J = 5.1 Hz, 1H), 7.80 (m, 5H), 7.39 (d, J = 6.3 Hz, 2H), 7.18 (t, J = 8.4 Hz, 1H), 7.06 (m, 2H), 6.86 (m, 1H), 6.67 (m, 1H), 6.49 (m, 1H), 4.78 (s, 2H), 4.54 (d, J = 5.9 Hz, 2H), 3.82 (s, 3H). |

Scheme 5

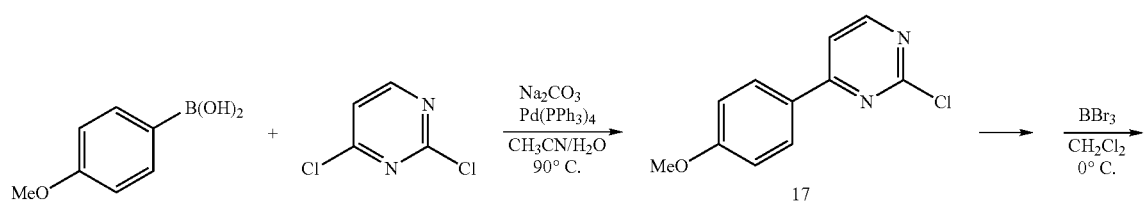

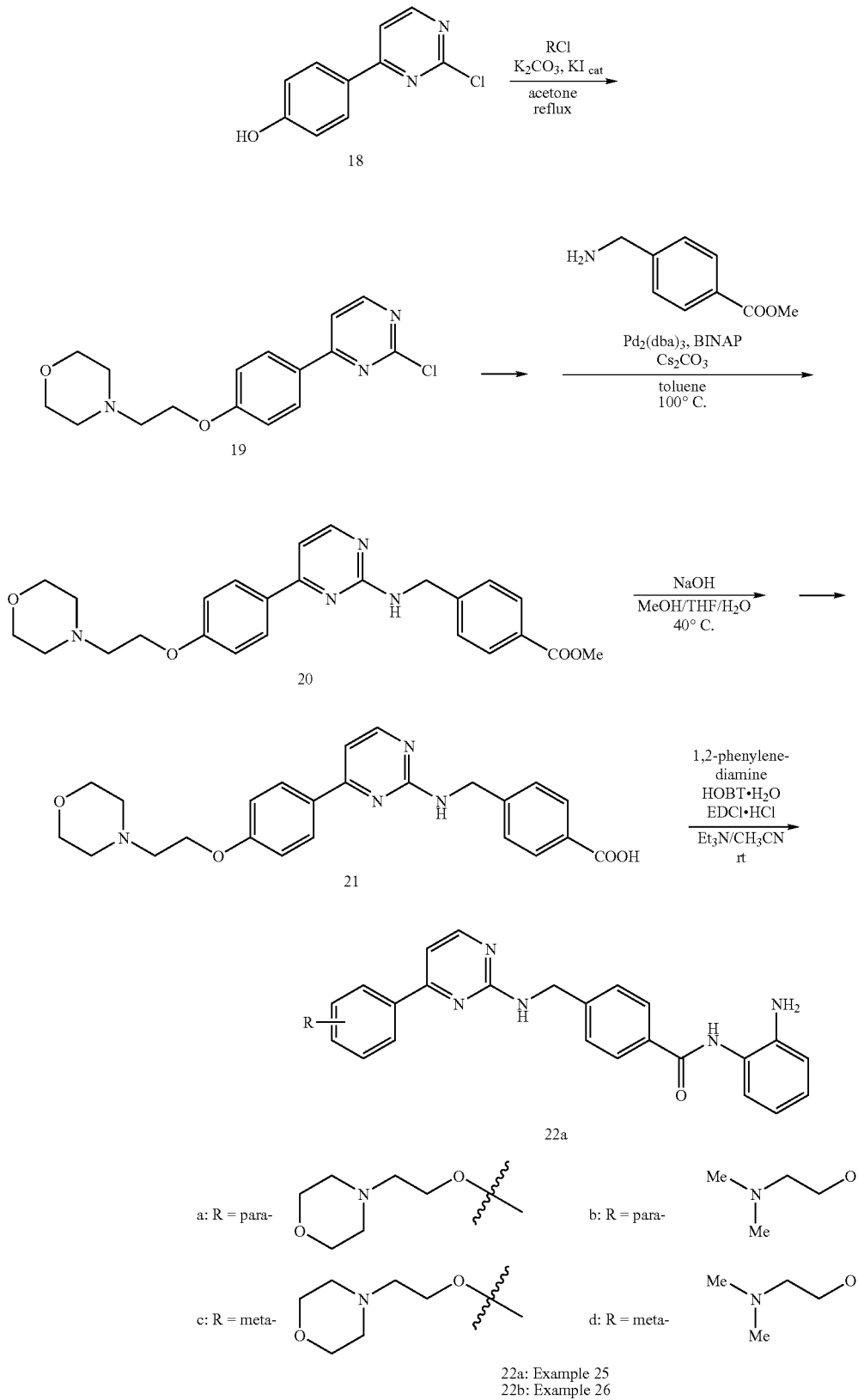
a: R = para- (morpholinoethoxy)
b: R = para- (dimethylaminoethoxy)
c: R = meta- (morpholinoethoxy)
d: R = meta- (dimethylaminoethoxy)
22a: Example 25
22b: Example 26
22c: Example 27
22d: Example 28

Example 25

N-(2-Amino-phenyl)-4-({4-[4-(2-morpholin-4-yl-ethoxy)-phenyl]-pyrimidin-2-ylamino}-methyl)-benzamide (22a)

Step 1: 2-Chloro-4-(4-methoxy-phenyl)-pyrimidine (17)

To a solution of 4-methoxyphenylboronic acid (3.0 g, 19.7 mmol) and 2,4-dichloropyrimidine (5.9 g, 39.0 mmol) in dry acetonitrile (120 mL) was added a 0.4 M solution of $Na_2CO_3$ (120 mL) followed by $Pd(PPh_3)_4$ (400 mg, 0.35 mmol). The suspension was degassed and heated at 90° C. for 16 h, cooled down and concentrated to produce a precipitate which was collected by filtration, washed with water, dried and purified by flash chromatography on silica gel (EtOAc/$CH_2Cl_2$: 5/95) to afford the title compound 17 (4.25 g, 19.3 mmol, 97% yield).

Step 2: 4-(2-Chloro-pyrimidin-4-yl)-phenol (18)

To a solution of 17 (3.7 g, 16.8 mmol) in dry dichloromethane (42 mL) at 0° C. was added boron tribromide (3.17 mL, 33.5 mmol). The mixture was stirred vigorously at room temperature for 16 h, cooled down to 0° C. Ice-water was poured-in and the stirring was continued for 30 min. The reaction mixture was concentrated to form a precipitate which was collected by filtration, washed with water, dried and purified by flash chromatography on silica gel (MeOH/$CH_2Cl_2$: 2/98) to afford the title compound 18 (3.28 g, 15.9 mmol, 94% yield). $^1$H NMR: (400 MHz, DMSO-$d_6$) δ (ppm): 10.26 (s, 1H), 8.66 (d, J=5.6 Hz, 1H), 8.05 (td, J=8.4, 1.6 Hz, 2H), 7.96 (d, J=5.6 Hz, 1H), 6.90 (td, J=8.4, 1.6 Hz, 2H).

Step 3: 4-{2-[4-(2-Chloro-pyrimidin-4-yl)-phenoxy]-ethyl}-morpholine (19)

To a solution of 18 (1.8 g, 8.71 mmol) in acetone (80 mL) were added 4-(2-chloroethyl)morpholine hydrochloride (1.95 g, 10.5 mmol), potassium iodide (360 mg, 2.2 mmol) and potassium carbonate (6.0 g, 44.0 mmol), respectively. The reaction mixture was refluxed for 16 h and concentrated. The residue was diluted with water and the aqueous phase was extracted twice with EtOAc. The combined organic extracts were dried over anhydrous $Na_2SO_4$, filtered and concentrated to form a residue was purified by flash chromatography on silica gel (EtOAc/$CH_2Cl_2$, 50/50 to MeOH/$CH_2Cl_2$: 2/98) to afford the title compound 19 (2.7 g, 8.4 mmol, 96% yield).

Step 4: Methyl 4-({4-[4-(2-morpholin-4-yl-ethoxy)-phenyl]-pyrimidin-2-ylamino}-methyl)-benzoate (20)

To a solution of 19 (2.7 g, 8.4 mmol) and methyl 4-(aminomethyl)benzoate hydrochloride (2.7 g, 13.5 mmol) in dry toluene (33 mL) was added cesium carbonate (8.2 g, 25.3 mmol) followed by $Pd_2(dba)_3$ (464 mg, 0.51 mmol) and rac-BINAP (473 mg, 0.76 mmol). The solution was degassed and heated at 100° C. for 16 h. The reaction mixture was partitioned between water and EtOAc and the phases were separated. The organic layer was successively washed with brine, dried over anhydrous $Na_2SO_4$, filtered and concentrated to form a residue which was purified by flash chromatography on silica gel (MeOH/$CH_2Cl_2$: 2/98) to afford the title compound 20 (1.9 g, 4.2 mmol, 50% yield).

Step 5: 4-({4-[4-(2-Morpholin-4-yl-ethoxy)-phenyl]-pyrimidin-2-ylamino}-methyl)-benzoic acid (21)

To a solution of 20 (1.9 g, 4.2 mmol) in a mixture of THF (8 mL), MeOH (8 mL) and water (4 mL) was added NaOH (373 mg, 9.3 mmol). The mixture was heated at 40° C. for 16 h, then acidified to pH 6 by adding 1N HCl, concentrated, and dried under high vacuum to afford the title compound 21, which was used without further purification.

Step 6: N-(2-Amino-phenyl)-4-({4-[4-(2-morpholin-4-yl-ethoxy)-phenyl]-pyrimidin-2-ylamino}-methyl)-benzamide (22a)

To a solution of 21 (crude from the previous step) in dry acetonitrile (50 mL) was added 1,2-phenylenediamine (1.83 g, 16.9 mmol) followed by $Et_3N$ (2.65 mL, 19.0 mmol), HOBt.$H_2O$ (1.03 g, 7.6 mmol) and EDCI.HCl (1.62 g, 8.5 mmol). The mixture was stirred at room temperature for 72 h, filtered to remove salts and filtrate was concentrated to form a residue, which was purified by flash chromatography on silica gel (MeOH/$CH_2Cl_2$: 2/98 to 5/95). Trituration of this material with a mixture of EtOAc/$CH_2Cl_2$, allowed affording the title compound 22a (696 mg, 1.3 mmol, 31% yield over 2 steps) as a white solid. $^1$H NMR: (400 MHz, DMSO-$d_6$) δ (ppm): 9.55 (s, 1H), 8.25 (d, J=5.2 Hz, 1H), 8.00 (d, J=8.4 Hz, 2H), 7.88 (d, J=8.4 Hz, 2H), 7.77 (t, J=6.4 Hz, 1H), 7.44 (d, J=7.2 Hz, 2H), 7.11 (d, J=7.6 Hz, 1H), 7.07 (d, J=5.2 Hz, 1H), 7.01 (d, J=8.4 Hz, 2H), 6.92 (td, J=7.6, 1.6 Hz, 1H), 6.73 (dd, J=8.0, 1.6 Hz, 1H), 6.55 (td, J=7.4, 1.2 Hz, 1H), 4.85 (s, 2H), 4.61 (d, J=5.6 Hz, 2H), 4.13 (t, J=5.6 Hz, 2H), 3.55 (t, J=4.4 Hz, 4H), 2.68 (t, J=5.6 Hz, 2H), 2.45 (t, J=4.4 Hz, 4H).

Example 26

N-(2-Amino-phenyl)-4-({4-[3-(2-dimethylamino-ethoxy)-phenyl]-pyrimidin-2-ylamino}-methyl)-benzamide hydrochloride (22b)

The title compound 22b was obtained in 6 steps following the same procedure as in example 25, steps 1-6 (Scheme 5) starting from 3-methoxyphenylboronic acid and using 2-(dimethylamine)ethyl chloride hydrochloride as the alkylating reagent in step 3. The compound was obtained as the hydrochloride salt by solubilizing it in a mixture of MeOH and EtOAc and by adding in a solution of 1N HCl in $Et_2O$. The white precipitate was filtered off, washed with EtOAc and dried under high vacuum. $^1$H NMR (400 MHz, CDCl$_3$) δ (ppm): 8.31 (d, J=5.2 Hz, 1H), 7.91 (d, J=7.6 Hz, 2H), 7.50 (d, J=7.6 Hz, 1H), 7.45 (d, J=8.4 Hz, 2H), 7.32 (t, J=8.0 Hz, 1H), 7.34-7.28 (m, 1H), 7.05 (td, J=7.6, 1.6 Hz, 1H), 7.00-6.96 (m, 1H), 6.97 (d, J=4.8 Hz, 1H), 6.82-6.77 (m, 2H), 6.04 (bs, 1H), 4.74 (d, J=6.0 Hz, 2H), 4.11 (t, J=5.2 Hz, 2H), 2.94 (t, J=5.2 Hz, 2H), 2.45 (s, 6H).

Example 27

N-(2-Amino-phenyl)-4-({4-[3-(2-morpholin-4-yl-ethoxy)-phenyl]-pyrimidin-2-ylamino}-methyl)-benzamide (22c)

The title compound 22c was obtained in 6 steps following the same procedure as in example 25 (steps 1-6, scheme 5) starting from 3-methoxyphenylboronic acid and using 4-(2- chloroethyl)morpholine hydrochloride as the alkylating reagent in step 3. $^1$H NMR (400 MHz, DMSO-d$_6$) δ (ppm): 9.54 (s, 1H), 8.31 (d, J=5.2 Hz, 1H), 7.92-7.83 (m, 3H), 7.65-7.52 (m, 2H), 7.45 (d, J=6.4 Hz, 2H), 7.35 (t, J=8.4 Hz, 1H), 7.15 (d, J=5.2 Hz, 1H), 7.11 (d, J=6.8 Hz, 1H), 7.03 (d, J=6.8 Hz, 1H), 6.92 (td, J=7.6, 1.2 Hz, 1H), 6.73 (dd, J=7.6, 1.2 Hz, 1H), 6.55 (t, J=6.8 Hz, 1H), 4.85 (s, 2H), 4.61 (d, J=6.0 Hz, 2H), 4.14-4.06 (m, 2H), 3.55 (t, J=4.8 Hz, 4H), 2.70 (t, J=5.6 Hz, 2H), 2.50-2.44 (m, 4H).

Example 28

N-(2-Amino-phenyl)-4-({4-[4-(2-dimethylamino-ethoxy)-phenyl]-pyrimidin-2-ylamino}-methyl)-benzamide (22d)

The title compound 22d was obtained in 6 steps following the same procedure as in example 25, (steps 1-6, scheme 5) starting from 4-methoxyphenylboronic acid and using 2-(dimethylamine)ethyl chloride hydrochloride as the alkylating reagent in step 3. $^1$H NMR (400 MHz, DMSO-d$_6$) δ (ppm): 10.52-10.35 (bs, 1H), 9.97 (s, 1H), 8.29 (d, J=5.2 Hz, 1H), 8.06 (d, J=8.8 Hz, 2H), 7.96 (d, J=8.0 Hz, 2H), 8.10-7.85 (m, 1H), 7.52-7.40 (m, 2H), 7.31 (t, J=7.6 Hz, 1H), 7.20-7.00 (m, 5H), 6.96-6.88 (m, 1H), 4.70-4.58 (m, 2H), 4.45-4.38 (t, J=4.8 Hz, 2H), 3.54-3.46 (m, 2H), 2.83 (s, 6H).

Scheme 6

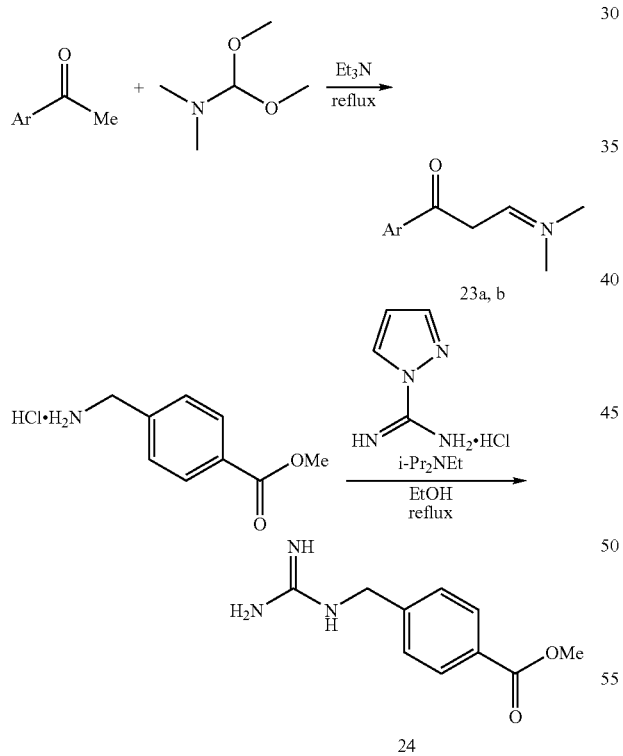

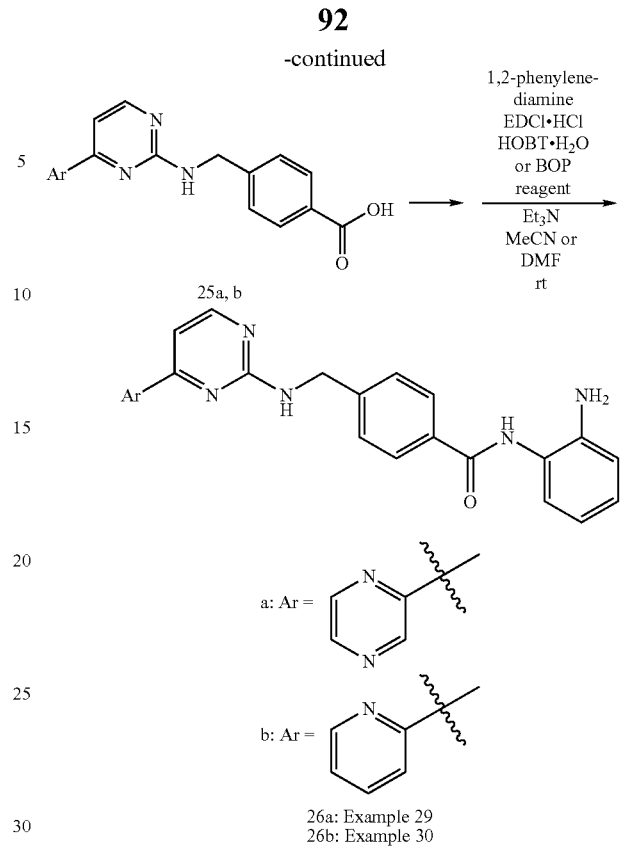

26a: Example 29
26b: Example 30

Example 29

N-(2-Amino-phenyl)-4-[(4-pyrazin-2-yl-pyrimidin-2-ylamino)-methyl]-benzamide (26a)

Step 1: 3-Dimethylamino-1-pyrazin-2-yl-propenone (23a)

A solution of acetylpyrazine (5 g, 40.9 mmol) in N,N-dimethylformamide dimethyl acetal (10.9 mL, 81.8 mmol) and Et$_3$N (5.7 mL) was heated at 110° C. for 16 h. The heating was stopped and a precipitate was formed while it was allowed to cool down to room temperature. The suspension was diluted with tert-butyl methyl ether; the solid was separated by filtration and washed with tert-butyl methyl ether. This material was triturated with the same solvent, filtered off and dried to afford the title compound 23a as a yellow solid (5.9 g, 33.3 mmol, 81% yield). $^1$H NMR (400 MHz, DMSO-d$_6$) δ (ppm): 9.09 (s, 1H), 8.73 (d, J=2.4 Hz, 1H), 8.66 (dd, J=2.4, 1.6 Hz, 1H), 7.84 (d, J=12.4 Hz, 1H), 6.30-6.20 (m, 1H), 3.19 (s, 3H), 2.93 (s, 3H).

Step 2: 4-guanidinomethyl-benzoic acid methyl ester dihydrate (24)

To a solution of methyl 4-(aminomethyl)benzoate hydrochloride (5 g) in dry ethanol (25 mL) was added 1H-pyrazole-1-carboxamidine hydrochloride (4.4 g) followed by DIPEA (13.0 mL) and the mixture was refluxed for 3 h. Ethanol was removed under vacuum. To the remaining viscous oil saturated solution of NaHCO$_3$ (50 mL) was slowly added under vigorous stirring followed by addition of 300 ml water (resultant pH 9). A white solid is formed and stirring was continued for 1 h. This material was filtered off, washed with water (200 mL) and tert-butyl methyl ether (50 mL), and dried to give the title compound 24 as a white powder (4.7 g, 91%). $^1$H NMR (400 MHz, DMSO-$d_6$) δ (ppm): 7.91 (d, J=8.0 Hz, 2H), 7.39 (d, J=8.0 Hz, 2H), 4.39 (s, 2H), 3.83 (s, 3H), 3.80-2.80 [m, 4H+2H$_2$O (determined by elemental analysis]).

Step 3 Method A: 4-[(4-Pyrazin-2-yl-pyrimidin-2-ylamino)-methyl]-benzoic acid (25a)

A suspension of 24 (6.2 g, 25.4 mmol) and 23a (3.0 g, 16.9 mmol) in anhydrous methanol (40 mL) was stirred and heated to reflux for 10 min, then a solution of sodium methoxide 95% (3.65 g, 67.6 mmol) in methanol (40 mL) was slowly added. After refluxing for 24 h, 20 mL of 2.5N NaOH in water were added and the refluxing was maintained for additional 24 h. The mixture was allowed to cool to the room temperature methanol was removed under reduced pressure, 100 mL of water were added and the resultant mixture was extracted with AcOEt. The aqueous phase was separated and acidified to pH 5-6 with 2N HCl to form a precipitate which was collected by filtration, rinsed with water and dried to afford the desired carboxylic acid 25a (4.55 g, 14.8 mmol, 87%) as a white solid.

Step 4: N-(2-Amino-phenyl)-4-[(4-pyrazin-2-yl-pyrimidin-2-ylamino)-methyl]-benzamide (26a)

To a solution of 25a (1 g, 3.3 mmol) in dry acetonitrile (35 mL) was added 1,2-phenylenediamine (0.88 g, 8.1 mmol) followed by Et$_3$N (2.7 mL, 19.1 mmol), HOBt.H$_2$O (803 mg, 5.9 mmol) and EDCI.HCl (1.89 g, 9.9 mmol). The mixture was stirred at room temperature for 16 h to form a suspension which was collected by filtration, washed successively with MeCN, water and again MeCN, triturated with MeOH, filtered and dried to afford the title compound 26a (730 mg, 1.84 mmol, 55% yield). $^1$H NMR (400 MHz, DMSO-$d_6$) δ (ppm): 9.57 (s, 1H), 9.43 (s, 1H), 8.75 (d, J=4.8 Hz, 2H), 8.49 (d, J=5.2 Hz, 1H), 8.11 (t, J=5.2 Hz, 1H), 7.91 (d, J=8.4 Hz, 2H), 7.59-7.37 (m, 2H), 7.44 (d, J=5.2 Hz, 1H), 7.12 (d, J=7.6 Hz, 1H), 6.94 (td, J=7.6, 1.6 Hz, 1H), 6.75 (dd, J=8.0, 1.2 Hz, 1H), 6.57 (t, J=7.2 Hz, 1H), 4.86 (s, 2H), 4.66 (d, J=5.2 Hz, 2H).

Example 30

N-(2-Amino-phenyl)-4-[(4-pyridin-2-yl-pyrimidin-2-ylamino)-methyl]-benzamide (26b)

Compound 26b was prepared following the same procedure as in example 29, steps 1, 2 and 4 (scheme 6). For the step 3, method B was used:

Step 3 Method B: 4-[(4-Pyridin-2-yl-pyrimidin-2-ylamino)-methyl]-benzoic acid (25b)

To a solution of 24 (0.85 g, 4.83 mmol) and 3-dimethylamino-1-pyridin-2-yl-propenone 23b (1.0 g, 4.83 mmol) in i-PrOH (20 mL) were added molecular sieves (0.2 g, 4 Å, powder, >5 μm). The reaction mixture was refluxed for 16 h then the cloudy solution was filtered through a celite pad. The mother liquor was concentrated to the half of its volume, a solid was formed which was collected by filtration and dried to give a pale yellow crystalline material (0.62 g, 1.94 mmol, 40% yield). This compound (0.456 g, 1.43 mmol) was dissolved in a mixture of THF (3 mL), MeOH (3 mL) and water (1.5 mL), then NaOH (0.125 g, 3.14 mmol) was added and the reaction mixture was stirred at 40° C. for 16 h, cooled down to the room temperature, acidified to pH 5-6 by adding 1N HCl (3.2 mL), and concentrated to remove the organic solvents. A precipitate was formed which was collected by filtration, washed with water and dried afford the title compound 25b (0.542 g, 1.37 mmol, 96% yield).

Examples 31-33

Examples 31-33 (compounds 26b-26d) were prepared using the same procedure as described for compound 26a (example 29, scheme 6).

TABLE 4

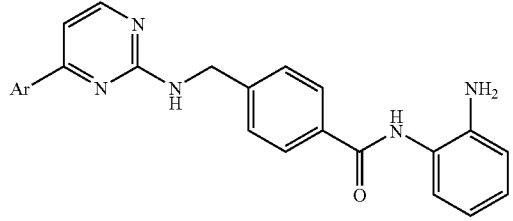

| Cmpd | Ex | Ar | Name | Characterization |
|---|---|---|---|---|
| 26b | 31 | 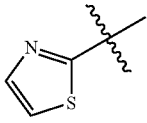 | N-(2-Amino-phenyl)-4-[(4-pyridin-2-yl-pyrimidin-2-ylamino)-methyl]-benzamide | $^1$H NMR (400 MHz, DMSO-$d_6$) δ (ppm): 9.55 (s, 1H), 8.65 (d, J = 4.3 Hz, 1H), 8.41 (d, J = 4.7 Hz,1H), 8.29 (d, J = 7.8 Hz, 1H), 7.94 (m, 2H), 7.88 (d, J = 8.2 Hz, 2H), 7.46-7.50 (m, 4H), 7.11 (d, J = 7.4 Hz, 1H), 6.92 (m, 1H), 6.73 (dd, J = 7.8, 1.2 Hz, 1H), 6.55 (m, 1H), 4.84 (s, 2H), 4.64 (d, J = 5.9 Hz, 2H). |
| 26c | 32 | | N-(2-Amino-phenyl)-4-[(4-thiazol-2-yl-pyrimidin-2-ylamino)-methyl]-benzamide | $^1$H NMR (400 MHz, DMSO-$d_6$) δ (ppm): 9.56 (s, 1H), 8.43 (d, J = 5.2, 1H), 8.18-8.08 (m, 1H), 8.02 (s, 1H), 7.95 (s, 1H), 7.90 (d, J = 8.4 Hz, 2H), 7.56-7.37 (m, 2H), 7.27-7.18 (m, 1H), 7.12 (d, J = 7.6 Hz, 1H), 6.94 (td, J = 7.6, 1.6 Hz, 1H), 6.74 (dd, J = 8.0, 1.2 HZ, 1H), 6.56 (t, J = 7.2 Hz, 1H), 4.86 (s, 2H), 4.59 (d, J = 6.8 Hz, 2H). |

TABLE 4-continued

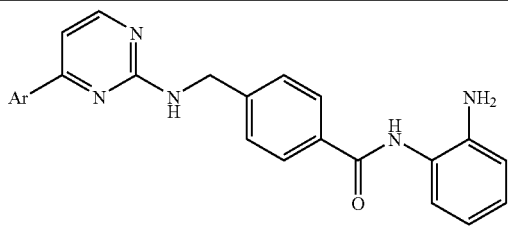

| Cmpd | Ex | Ar | Name | Characterization |
|---|---|---|---|---|
| 26d | 33 | ![6-chloro-pyridin-3-yl] | N-(2-Amino-phenyl)-4-{[4-(6-chloro-pyridin-3-yl)-pyrimidin-2-ylamino]-methyl}-benzamide | $^1$H NMR (400 MHz, DMSO-$d_6$) δ (ppm): 9.57 (s, 1H), 9.06 (s, 1H), 8.46 (m, 1H), 8.41 (d, J = 5.1 Hz, 1H), 8.05 (m, 1H), 7.90 (d, J = 8.7 Hz, 2H), 7.66 (d, J = 7.6 Hz, 1H), 7.47 (m, 2H), 7.27 (d, J = 5.1 Hz, 1H), 7.12 (d, J = 7.4 Hz, 1H), 6.94 (m, 1H), 6.75 (dd, J = 8.0, 1.4 Hz, 1H), 6.57 (m, 1H), 4.87 (s, 2H), 4.64 (d, J = 6.1 Hz, 2H). |

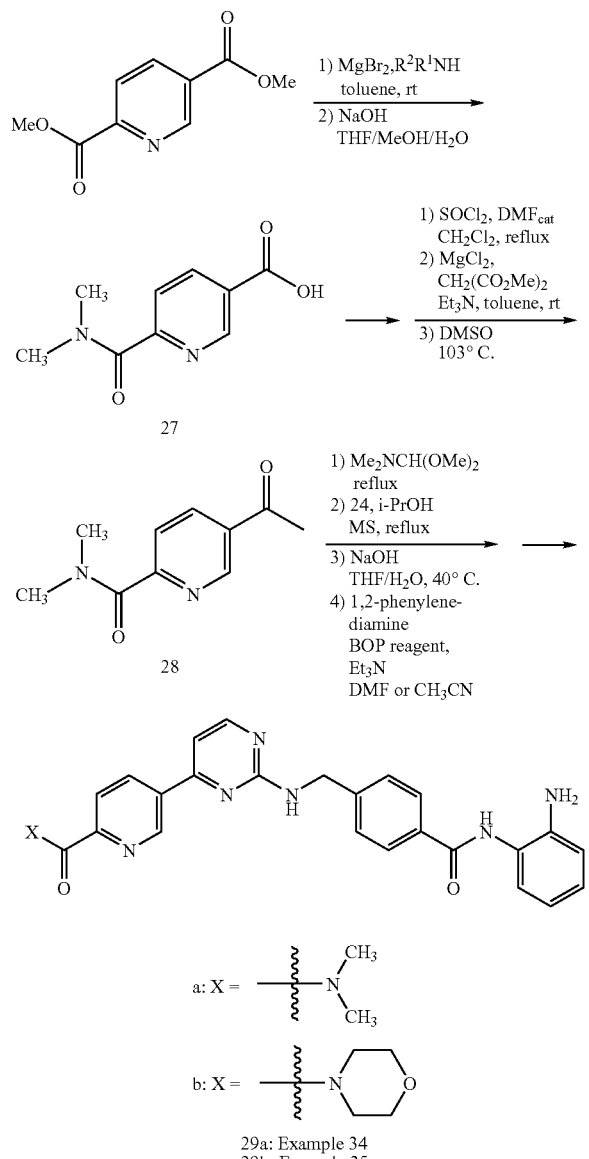

Scheme 7

29a: Example 34
29b: Example 35

Example 34

5-{2-[4-(2-Amino-phenylcarbamoyl)-benzylamino]-pyrimidin-4-yl}-pyridine-2-carboxylic acid dimethylamide (29a)

Step 1: 6-Dimethylcarbamoyl-nicotinic acid (27)

To a suspension of pyridine-2,5-dicarboxylic acid dimethyl ester (10.1 g, 51.6 mmol) and MgBr$_2$ (4.75 g, 25.8 mmol) in THF (200 mL) was added drop-wise a solution of dimethylamine (51.6 mL, 103.2 mmol, 2N in THF) at room temperature under nitrogen over a period of 10 min. The reaction mixture was stirred overnight and quenched with 1N HCl (52 mL) and H$_2$O (50 mL), extracted with EtOAc (200 mL×3). The organic phase was washed with brine, dried over Na$_2$SO$_4$, filtered and concentrated. The crude residue was dissolved in a mixture of DMF (10 mL), AcOEt (50 mL), MeOH (20 mL) and DCM (50 mL), the formed solution was partially evaporated to produce a crystalline material, which was removed by filtration. The mother liquor was collected and evaporated to form a solid, which was dissolved in a mixture of THF (67 mL) and MeOH (67 mL). To this solution NaOH (2.95 g, 73.7 mmol) in H$_2$O (33.5 mL) was added. The reaction mixture was heated at 40° C. for few hours, acidified (pH 3) to form a solid precipitate, which was collected by filtration and dried to afford the title compound 27 (4.937 g, 50% yield over two steps).

Step 2: 5-Acetyl-pyridine-2-carboxylic acid dimethylamide (28)

A suspension of 27 (4.937 g, 25.41 mmol), SOCl$_2$ (2.41 mL, 33 mmol) and DMF (0.9 mL, 5.1 mmol) in CH$_2$Cl$_2$ (51 mL) was refluxed for 3 h. The reaction mixture was cooled to room temperature and evaporated to dryness. The residue was suspended in toluene and Et$_3$N (4.25 mL, 30.5 mmol) was added. The resulting suspension was canulated to a stirred and pre-formed suspension of dimethyl malonate (3.49 mL, 30.5 mmol), MgCl$_2$ (1.742 g, 18.3 mmol), Et$_3$N (10.2 mL, 73.2 mmol) in toluene (25 mL) over 2 hours. The resulting reaction mixture was stirred overnight and quenched with 1N HCl (50 mL) and water (50 mL) and extracted with EtOAc (200 mL×3). The combined organic layer was washed with brine (100 mL), dried over Na$_2$SO$_4$ and filtered. The filtrate was evaporated to dryness to give brown oil (5.21 g) which was dissolved in DMSO (15.4 mL) and H₂O (0.62 mL) and then heated at 130° C. for 2 h, cooled down to room temperature, diluted with H₂O (100 mL), extracted with EtOAc. The organic layer was washed with brine (100 mL), dried over Na₂SO₄, filtered, and concentrated. The residue was purified by flash chromatography on silica gel (AcOEt/hexane, 70/30 to 100/0) to afford the title compound 28 (430 mg, 9% yield) as a brown crystalline solid.

Step 3: 5-{2-[4-(2-Amino-phenylcarbamoyl)-benzylamino]-pyrimidin-4-yl}-pyridine-2-carboxylic acid dimethylamide (29a)

The title compound 29a (example 34) was obtained from 28 as an off-white solid in 4 steps following the same procedure as in example 29, steps 1, 3 (Method B) and 4 (Scheme 6). ¹H NMR (400 MHz, DMSO-d₆) δ(ppm): 9.57 (s, 1H), 9.20 (s, 1H), 8.50 (m, 1H), 8.41 (d, J=4.9 Hz, 1H), 8.04 (m, 1H), 7.89 (d, J=7.8 Hz, 2H), 7.65 (m, 1H), 7.46 (m, 2H), 7.29 (d, J=5.1 Hz, 1H), 7.11 (d, J=7.4 Hz, 1H), 6.93 (m, 1H), 6.74 (m, 1H), 6.56 (m, 1H), 4.86 (s, 2H), 4.65 (m, 2H), 3.02 (s, 3H), 2.94 (s, 3H).

Examples 35

N-(2-Amino-phenyl)-4-({4-[6-(morpholine-4-carbonyl)-pyridin-3-yl]-pyrimidin-2-ylamino}-methyl)-benzamide (29b)

The title compound was prepared using the same procedures as described for the compound 29a, example 34 (scheme 7). ¹H NMR (400 MHz, DMSO-d₆) δ(ppm): 9.55 (s, 1H), 9.21 (s, 1H), 8.52 (m, 1H), 8.42 (d, J=4.9 Hz, 1H), 8.03 (t, J=6.2 Hz, 1H), 7.90 (d, J=8.0 Hz, 2H), 7.71 (d, J=8.0 Hz, 1H), 7.47 (m, 2H), 7.29 (d, J=5.1 Hz, 1H), 7.12 (d, J=7.6 Hz, 1H), 6.93 (m, 1H), 6.74 (d, J=7.8 Hz, 1H), 6.56 (m, 1H), 4.85 (s, 2H), 4.64 (d, J=4.9 Hz, 2H), 3.66 (s, 4H), 3.55 (m, 2H), 3.44 (m, 2H).

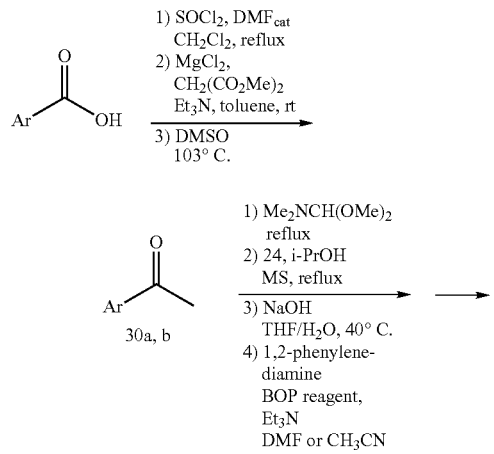

Scheme 8

1) SOCl₂, DMF_cat
CH₂Cl₂, reflux
2) MgCl₂,
CH₂(CO₂Me)₂
Et₃N, toluene, rt
3) DMSO
103° C.

1) Me₂NCH(OMe)₂
reflux
2) 24, i-PrOH
MS, reflux
3) NaOH
THF/H₂O, 40° C.
4) 1,2-phenylene-
diamine
BOP reagent,
Et₃N
DMF or CH₃CN

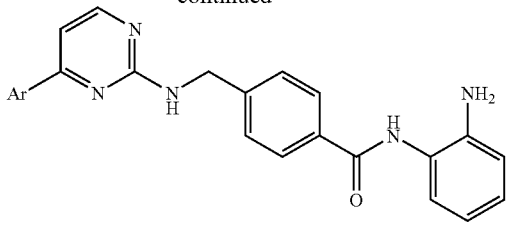
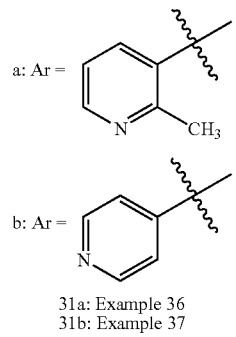

31a: Example 36
31b: Example 37

Example 36

N-(2-Amino-phenyl)-4-{[4-(2-methyl-pyridin-3-yl)-pyrimidin-2-ylamino]-methyl}-benzamide (31a)

Step 1: 1-(2-Methyl-pyridin-3-yl)-ethanone (30a)

The title compound 30a was obtained from 2-methylnicotinic acid in 92% yield as a brown crystalline solid following the same procedure as in example 34, (step 2 scheme 7).

Step 2: N-(2-Amino-phenyl)-4-{[4-(2-methyl-pyridin-3-yl)-pyrimidin-2-ylamino]-methyl}-benzamide (31a)

The title compound 31a (example 36) was obtained from 30a as an off-white solid in 4 steps following the same procedures as in example 29, steps 1, 3 (Method B) and 4 (Scheme 6). ¹H NMR (400 MHz, DMSO-d₆) δ(ppm): 9.57 (s, 1H), 8.46 (m, 1H), 8.40 (m, 1H), 7.54 (t, J=6.4 Hz, 1H), 7.88 (d, J=8.2 Hz, 2H), 7.75 (d, J=6.3 Hz, 1H), 7.40 (d, J=7.8 Hz, 2H), 7.29 (m, 1H), 7.11 (d, J=7.2 Hz, 1H), 6.93 (m, 1H), 6.79 (d, J=4.9 Hz, 1H), 6.73 (dd, J=8.0, 1.4 Hz, 1H), 6.55 (m, 1H), 4.86 (s, 2H), 4.48 (d, J=6.3 Hz, 2H), 2.66-2.82 (m, 3H).

Example 37

N-(2-Amino-phenyl)-4-[(4-pyridin-4-yl-pyrimidin-2-ylamino)-methyl]-benzamide (31b)

The title compound 31b was prepared using the same procedures as described for compound 31a (example 36, scheme 8). ¹H NMR (400 MHz, DMSO-d₆) δ(ppm): 9.56 (s, 1H), 8.70 (d, J=5.3 Hz, 2H), 8.44 (d, J=5.1 Hz, 1H), 8.05 (t, J=6.3 Hz, 1H), 7.98 (d, J=6.1 Hz, 2H), 7.90 (d, J=8.2 Hz, 2H), 7.47 (bs, 2H), 7.27 (d, J=5.1 Hz, 1H), 7.12 (d, J=7.6 Hz, 1H), 6.93 (m, 1H), 6.74 (dd, J=8.0, 1.4 Hz, 1H), 6.56 (m, 1H), 4.86 (s, 2H), 4.64 (d, J=5.9 Hz, 2H).

Scheme 9

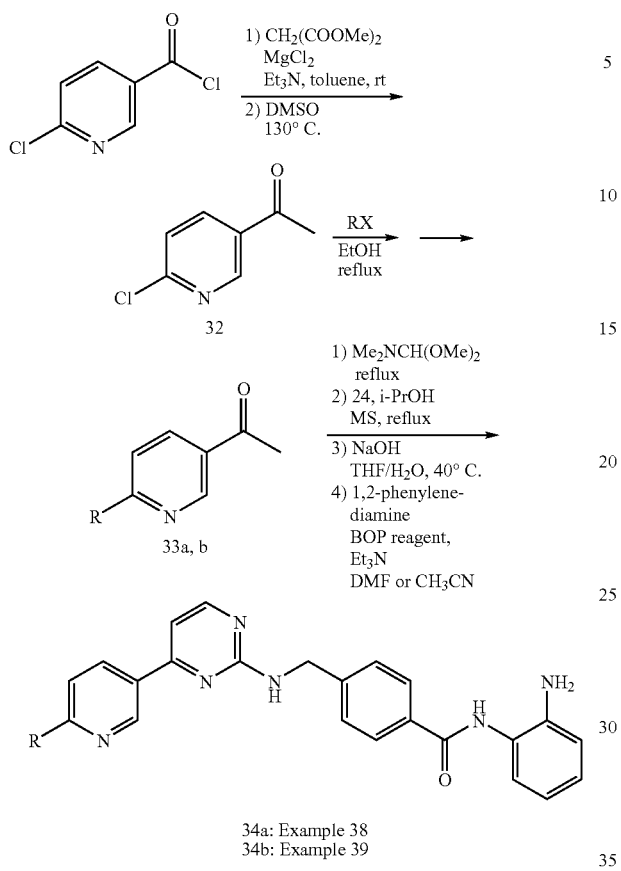

34a: Example 38
34b: Example 39

Example 38

N-(2-Amino-phenyl)-4-{[4-(6-morpholin-4-yl-pyridin-3-yl)-pyrimidin-2-ylamino]-methyl}-benzamide (34a)

Step 1: 1-(6-Chloro-pyridin-3-yl)-ethanone (32)

A suspension of dimethyl malonate (7.8 mL, 68.3 mmol), $MgCl_2$ (3.872 g, 40.7 mmol), $Et_3N$ (19.1 mL, 136.9 mmol) in toluene (15 mL) at room temperature under nitrogen was stirred for 2 h. To this mixture a suspension of 6-chloro-nicotinoyl chloride (3.872 g, 40.7 mmol) and $Et_3N$ (4.25 mL, 30.5 mmol) in toluene (46 mL) was added via canula. The resultant reaction mixture was stirred overnight, quenched with 1N HCl (100 mL) and water (100 mL) and extracted with EtOAc. The organic layer was washed with brine (100 mL), dried over $Na_2SO_4$, filtered and concentrated to give white crystalline material (6.5 g) which was dissolved in a mixture DMSO (9 mL) and $H_2O$ (0.37 mL), heated at 130° C. for 5 h, cooled down to room temperature and treated with water (10 mL). A precipitate formed which was collected by filtration, rinsed with water and dried to afford the title compound 32 (1.8 g, 28% yield) as pale yellow crystalline solid.

Step 2: 1-(6-Morpholin-4-yl-pyridin-3-yl)-ethanone (33a)

A solution of 32 (1.25 g, 7.9 mmol) and morpholine (2.20 mL, 25.2 mmol) in EtOH (22 mL) was refluxed for 12 h and then evaporated to dryness. The residue was dissolved in EtOAc (200 mL), washed with saturated $NaHCO_3$ (50 mL×2) and brine (50 mL), dried over $Na_2SO_4$, filtered and evaporated to afford the title compound 33a (1.66 g, quantitative yield) as a pale yellow solid.

Step 3: N-(2-Amino-phenyl)-4-{[4-(6-morpholin-4-yl-pyridin-3-yl)-pyrimidin-2-ylamino]-methyl}-benzamide (34a)

The title compound 34a (example 38) was obtained from 33a as off-white solid in 4 steps following the same procedure as in example 29, steps 1, 3 (Method B) and 4 (scheme 6). $^1$H NMR (400 MHz, DMSO-$d_6$) δ(ppm): 9.57 (s, 1H), 8.84 (s, 1H), 8.24 (d, J=5.3 Hz, 1H), 8.18 (m, 1H), 7.90 (d, J=7.3 Hz, 2H), 7.78 (m, 1H), 7.46 (d, J=7.8 Hz, 2H), 7.13 (m, 1H), 7.08 (d, J=5.3 Hz, 1H), 6.95 (d, J=7.6 Hz, 1H), 6.91 (m, 1H), 6.75 (d, J=7.8 Hz, 1H), 5.57 (dd, J=7.2, 7.6 Hz, 1H), 4.87 (s, 2H), 4.61 (d, J=6.1 Hz, 2H), 3.70 (m, 4H), 3.56 (m, 4H).

Example 39

N-(2-Amino-phenyl)-4-({4-[6-(4-methyl-piperazin-1-yl)-pyridin-3-yl]-pyrimidin-2-ylamino}-methyl)-benzamide (34b)

Title compound 34b was prepared using the same procedure as described for compound 34a (example 38, scheme 9). $^1$H NMR (400 MHz, DMSO-$d_6$) δ(ppm): 9.55 (s, 1H), 8.81 (d, J=2.2 Hz, 1H), 8.22 (d, J=5.3 Hz, 1H), 8.14 (t, J=8.6 Hz, 1H), 7.89 (d, J=8.2 Hz, 2H), 7.75 (t, J=6.2 Hz, 1H), 7.45 (d, J=8.0 Hz, 2H), 7.12 (d, J=7.4 Hz, 1H), 7.05 (d, J=5.3 Hz, 1H), 6.93 (m, 1H), 6.88 (d, J=8.2 Hz, 1H), 6.74 (dd, J=8.0, 1.4 Hz, 1H), 6.56 (m, 1H), 4.87 (s, 2H), 4.62 (d, J=6.5 Hz, 2H), 3.59 (m, 4H), 2.38 (m, 4H), 2.21 (s, 3H).

Scheme 10

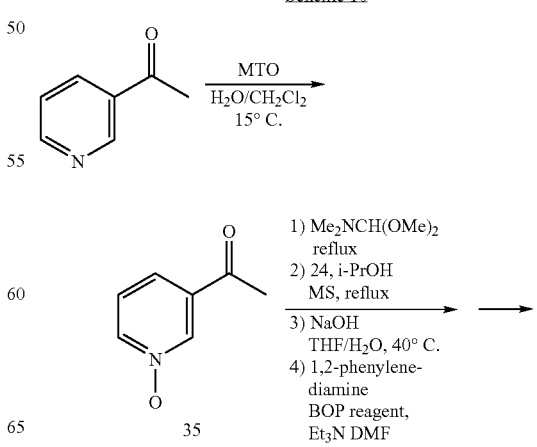

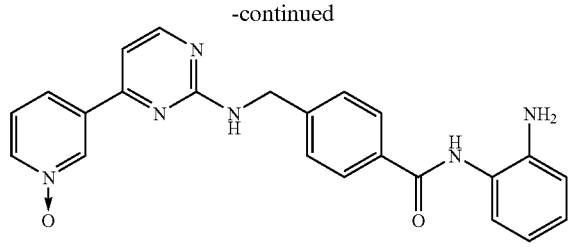

36: Example 40

Example 40

N-(2-Amino-phenyl)-4-{[4-(1-oxy-pyridin-3-yl)-pyrimidin-2-ylamino]-methyl}-benzamide (36)

Step 1: 1-(1-Oxy-pyridin-3-yl)-ethanone (35)

To a solution of 1-pyridin-3-yl-ethanone (1.00 g, 8.3 mmol) in $CH_2Cl_2$ (8.3 mL) at room temperature was added MTO (methyltrioxorhenium, 113 mg, 0.45 mmol) and the reaction mixture was cooled to 15° C. Aqueous solution of $H_2O_2$ (30%, 1.13 mL, 9.96 mmol) was added drop wise over a period of 20 min and the reaction mixture was stirred for 5 h at 15° C. and cooled to 0° C. Aqueous solution of $Na_2S_2O_3$ (20%, 20 mL) was added, the mixture was stirred for 10 min, extracted with EtOAc. The aqueous layer was collected and freeze-dried to form a solid material, which was purified by flash chromatography on silica gel (MeOH/$CH_2Cl_2$, 10/90) to afford the title compound 35 (1.3 g, quantitative yield).

Step 2: N-(2-Amino-phenyl)-4-{[4-(1-oxy-pyridin-3-yl)-pyrimidin-2-ylamino]-methyl}-benzamide (36)

The title compound 36 (example 40) was obtained from 35 as a pale yellow solid in 4 steps following the same procedure as in example 29, steps 1, 3 (Method B) and 4 (scheme 6). $^1$H NMR (400 MHz, DMSO-$d_6$) δ(ppm): 9.61 (s, 1H), 8.81 (bs, 1H), 8.45 (m, 1H), 8.33 (d, J=5.1 Hz, 1H), 8.12 (bs, 1H), 7.99 (d, J=7.8 Hz, 1H), 7.93 (d, J=8.0 Hz, 2H), 7.55 (t, J=7.0 Hz, 1H), 7.50 (m, 2H), 7.29 (d, J=5.1 Hz, 1H), 7.16 (d, J=7.4 Hz, 1H), 6.97 (m, 1H), 6.78 (dd, J=8.0, 1.2 Hz, 1H), 6.60 (m, 1H), 4.91 (s, 2H), 4.67 (d, J=6.3 Hz, 2H).

Scheme 11

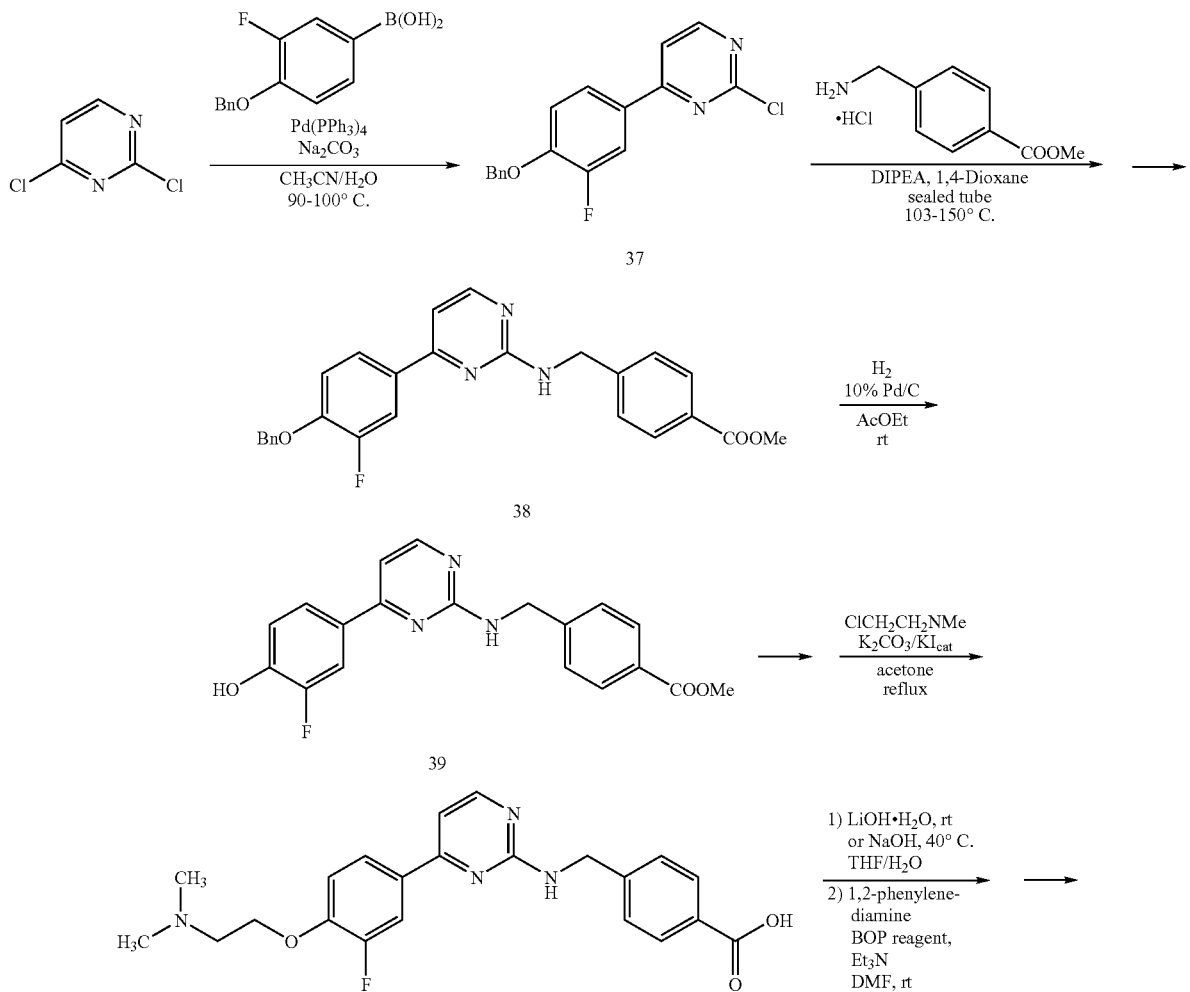

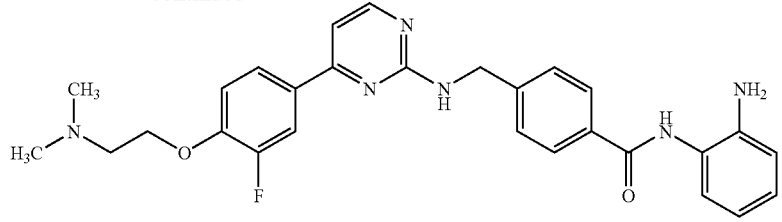

41: Example 41

Example 41

N-(2-Amino-phenyl)-4-({4-[4-(2-dimethylamino-ethoxy)-3-fluoro-phenyl]-pyrimidin-2-ylamino}-methyl)-benzamide (41)

Step 1: 4-(4-Benzyloxy-3-fluoro-phenyl)-2-chloro-pyrimidine (37)

The title compound 37 was obtained following the same procedure as in Example 25, step 1 (Scheme 5) starting with 4-benzyloxy-3-fluorobenzeneboronic acid. $^1$H NMR (400 MHz, CDCl$_3$) δ (ppm): 8.60 (d, J=5.2 Hz, 1H), 7.90 (dd, J=12.0, 2.4 Hz, 1H), 7.84-7.80 (m, 1H), 7.54 (d, J=5.2 Hz, 1H), 7.48-7.32 (m, 5H), 7.10 (t, J=8.4 Hz, 1H), 5.24 (s, 2H).

Step 2: 4-{[4-(4-Benzyloxy-3-fluoro-phenyl)-pyrimidin-2-ylamino]-methyl}-benzoic acid methyl ester (38)

The title compound 38 was obtained from 37 following the same procedure as in example 17 (step 2, scheme 4). $^1$H NMR (400 MHz, CDCl$_3$) δ (ppm): 8.23 (d, J=4.4 Hz, 1H), 7.98 (d, J=8.4 Hz, 2H), 7.78 (dd, J=12.4, 2.0 Hz, 1H), 7.67 (ddd, J=8.0, 2.0, 1.2 Hz, 1H), 7.47-7.29 (m, 7H), 7.01 (t, J=8.4 Hz, 1H), 6.88 (d, J=5.6 Hz, 1H), 6.06-5.95 (m, 1H), 5.18 (s, 2H), 4.75 (d, J=6.4 Hz, 2H), 3.90 (s, 3H).

Step 3: Methyl 4-{[4-(3-fluoro-4-hydroxy-phenyl)-pyrimidin-2-ylamino]-methyl}-benzoate (39)

To a degassed solution of 38 (950 mg, 2.14 mmol) in EtOAc (100 mL) at room temperature under N$_2$ was added 10% Pd/C (220 mg, 0.21 mmol). The mixture was hydrogenated for 5 days (1 atm, balloon), filtered through a celite pad, rinsed with MeOH and EtOAc and the filtrate was concentrated to afford the title compound 39 (450 mg, 1.27 mmol, 59% yield).

Step 4: Methyl 4-({4-[4-(2-dimethylamino-ethoxy)-3-fluoro-phenyl]-pyrimidin-2-ylamino}-methyl)-benzoate (40)

To a solution of 39 (450 mg, 1.27 mmol) in acetone (25 mL) was added 2-(dimethylamino)ethyl chloride hydrochloride (220 mg, 1.53 mmol) followed by potassium iodide (53 mg, 0.32 mmol) and potassium carbonate (878 mg, 6.35 mmol). The reaction mixture was refluxed for 20 h, then saturated solution of NH$_4$Cl was added, pH of the mixture was adjusted to 8 and acetone was removed under reduced pressure. The formed solid was collected by filtration, washed with water, dried and purified by flash chromatography on silica gel (MeOH/DCM/NH$_4$OH: 10/89/1) to afford the title compound 40 (525 mg, 1.24 mmol, 97% yield).

Steps 5: N-(2-Amino-phenyl)-4-({4-[4-(2-dimethylamino-ethoxy)-3-fluoro-phenyl]-pyrimidin-2-ylamino}-methyl)-benzamide (41)

The title compound 41 (Example 41) was obtained from 40 as off-white solid in two steps following the same procedure as in example 25, steps 5 and 6 (scheme 5). $^1$H NMR: (400 MHz, DMSO-d$_6$) δ (ppm): 9.55 (s, 1H), 8.27 (d, J=5.2 Hz, 1H), 7.95-7.75 (m, 5H), 7.50-7.35 (m, 2H), 7.25 (t, J=8.0 Hz, 1H), 7.14-7.06 (m, 2H), 6.92 (t, J=7.6 Hz, 1H), 6.72 (d, J=8.0 Hz, 1H), 6.54 (t, J=7.6 Hz, 1H), 4.85 (s, 2H), 4.60 (d, J=5.2 Hz, 2H), 4.17 (t, J=5.6 Hz, 2H), 2.66 (t, J=5.6 Hz, 2H), 2.21 (s, 6H).

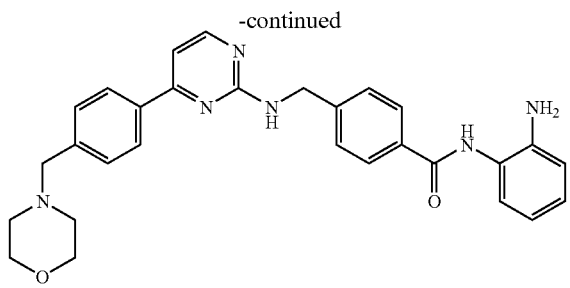

44: Example 42

Example 42

N-(2-Amino-phenyl)-4-{[4-(4-morpholin-4-ylmethyl-phenyl)-pyrimidin-2-ylamino]-methyl}-benzamide (44)

Step 1: 4-(2-Chloro-pyrimidin-4-yl)-benzaldehyde (42)

The title compound 42 was obtained following the same procedure as in example 25, step 1 (scheme 5), starting with 4-formylphenylboronic acid. $^1$H NMR: (400 MHz, CDCl$_3$) δ (ppm): 10.11 (s, 1H), 8.73 (d, J=4.8 Hz, 1H), 8.27 (td, J=8.4, 1.6 Hz, 2H), 8.03 (td, J=8.4, 1.6 Hz, 2H), 7.73 (d, J=4.8 Hz, 1H).

Step 2: 4-[4-(2-Chloro-pyrimidin-4-yl)-benzyl]-morpholine (43)

To a solution of 42 (950 mg, 4.35 mmol) and morpholine (455 μL, 5.21 mmol) in dry 1,2-dichloroethane (10 mL) at room temperature was added AcOH (2 drops) followed by NaBH(OAc)$_3$ (1.1 g, 5.21 mmol) and the mixture was stirred for 16 h. A solution of 10% K$_2$CO$_3$ was added to the reaction mixture followed by dichloromethane and the phases were separated. The aqueous phase was extracted with CH$_2$Cl$_2$ and organic layer was dried over anhydrous Na$_2$SO$_4$, filtered to form a residue which was purified by flash chromatography on silica gel (EtOAc/CH$_2$Cl$_2$: 20/80) to afford the title compound 43 (460 mg, 1.59 mmol, 36% yield).

Steps 3: N-(2-Amino-phenyl)-4-{[4-(4-morpholin-4-ylmethyl-phenyl)-pyrimidin-2-ylamino]-methyl}-benzamide (44)

The title compound 44 was obtained from 43 in three steps following the same procedure as in example 2, steps 2-4 (scheme 2) and was isolated as the hydrochloride salt by dissolving it in a mixture of dichloromethane and EtOAc by adding a 1N HCl in Et$_2$O solution. The precipitate was filtered off, washed with EtOAc and dried under high vacuum.

$^1$H NMR (400 MHz, CDCl$_3$) δ (ppm): 8.33 (d, J=5.2 Hz, 1H), 8.00-7.93 (m, 1H), 7.95 (d, J=8.0 Hz, 2H), 7.85 (d, J=8.0 Hz, 2H), 7.47 (d, J=8.0 Hz, 2H), 7.44 (d, J=8.0 Hz, 2H), 7.29 (d, J=8.4 Hz, 1H), 7.07 (td, J=7.6, 1.2 Hz, 1H), 7.00 (d, J=5.2 Hz, 1H), 6.85-6.78 (m, 2H), 5.83 (t, J=6.0 Hz, 1H), 4.78 (d, J=6.0 Hz, 2H), 3.74 (t, J=4.0 Hz, 4H), 3.59 (s, 2H), 2.51 (bs, 4H).

Scheme 13

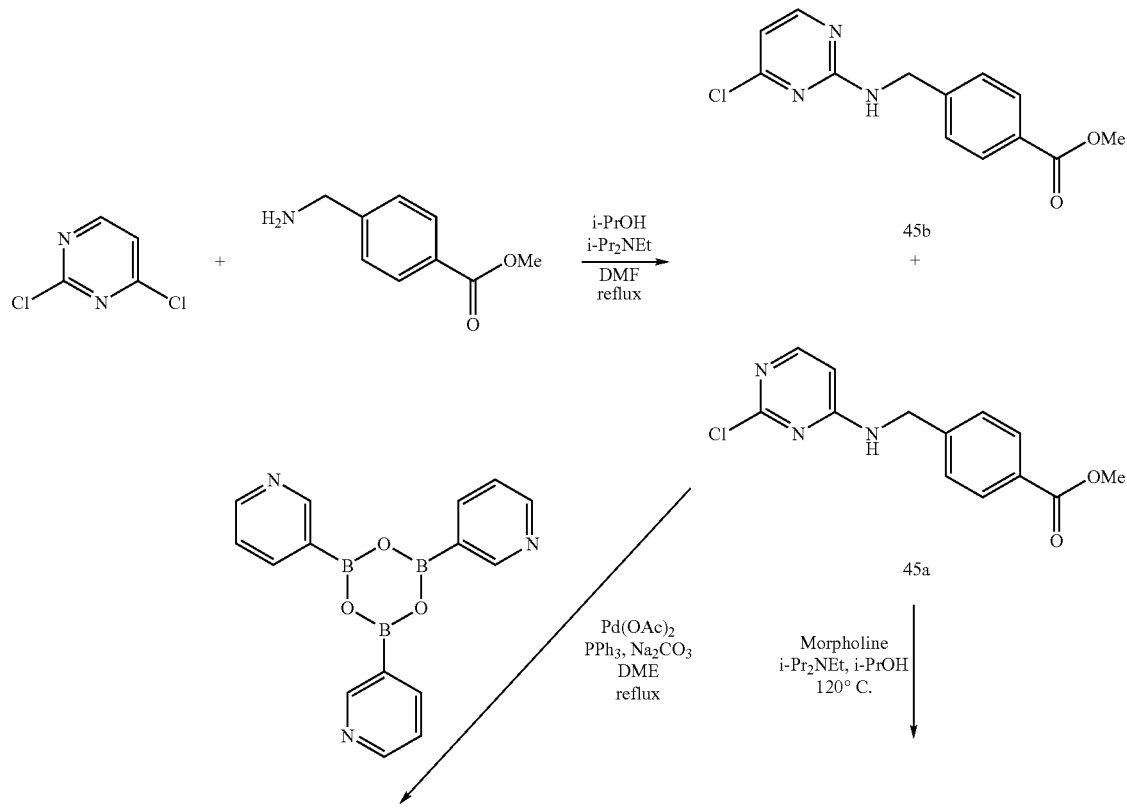

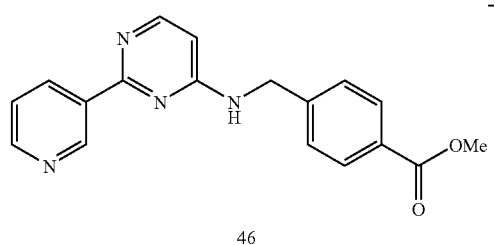

46

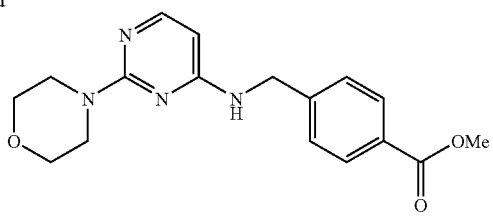

48

1) NaOH in H₂O;THF/MeOH; 40° C.
2) 1,2-phenylenediamine; BOP reagent, Et₃N; DMF or CH₃CN 1) NaOH in H₂O;THF/MeOH; 40° C.
2) 1,2-phenylenediamine; BOP reagent, Et₃N; DMF or CH₃CN

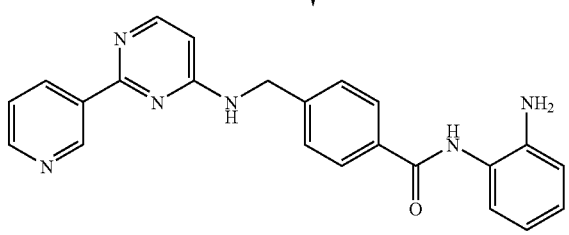

47: Example 43

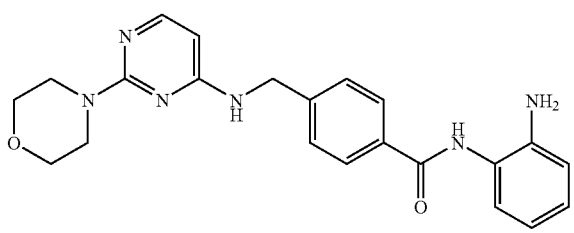

49: Example 44

Example 43

N-(2-Amino-phenyl)-4-[(2-pyridin-3-yl-pyrimidin-4-ylamino)-methyl]-benzamide (47)

Step 1: 4-[(2-Chloro-pyrimidin-4-ylamino)-methyl]-benzoic acid methyl ester (45a) and 4-[(4-chloro-pyrimidin-2-ylamino)-methyl]-benzoic acid methyl ester (45b)

A mixture of 2,4-dichloropyrimidine (4.51 g, 30.3 mmol), methyl 4-aminomethyl-benzoate (5.00 g, 30.3 mmol), DIPEA (10.4 mL, 60.6 mmol) in i-PrOH (60 mL) and DMF (40 mL) was refluxed for 5 h. After evaporation of the reaction mixture to dryness the residue was purified by flash chromatography on silica gel (EtOAc/hexane:40/60→60/40+1% of Et₃N) to afford the title compounds 45a (3.454 g, 41% yield) and 45b (1.52 g, 14% yield, contaminated with the starting material).

45a, ¹H NMR (400 MHz, DMSO-d₆) δ(ppm): 8.45 (bs, 1H), 7.90-7.94 (m, 3H), 7.42 (d, J=8.4 Hz, 2H), 6.53 (d, J=5.9 Hz, 1H), 4.58 (d, J=5.3 Hz, 2H), 3.83 (s, 3H)).

45b, ¹H NMR (400 MHz, DMSO-d₆) δ(ppm): 8.27 (t, J=6.5 Hz, 1H), 8.21 (bs, 1H), 7.88 (d, J=8.2 Hz, 2H), 7.40 (d, J=8.2 Hz, 2H), 6.69 (d, J=5.1 Hz, 1H), 4.55 (bs, 2H), 3.82 (s, 3H).

Step 2: Methyl 4-[(2-Pyridin-3-yl-pyrimidin-4-ylamino)-methyl]-benzoate (46)

To a suspension of 3-pyridine boroxin (189 mg, 0.60 mmol), 45a (500 mg, 1.81 mmol), Pd(OAc)₂ (41 mg, 0.18 mmol) and PPh₃ (95 mg, 0.36 mmol) in DME (1.8 mL) was added a solution of Na₂CO₃ (590 mg dissolved in the minimum quantity of water, 5.60 mmol) at room temperature. The reaction mixture was purged with nitrogen and refluxed for 4 days, evaporated to dryness and purified by flash chromatography on silica gel (EtOAc/hexane:30/70+1% of Et₃N) to afford the title compound 46 (152 mg, 26% yield) as a pale yellow solid.

Step 3: N-(2-Amino-phenyl)-4-[(2-pyridin-3-yl-pyrimidin-4-ylamino)-methyl]-benzamide (47)

The title compound 47 (example 43) was obtained from 46 as an off-white solid in two steps following the same procedure as in Example 34, step 3 (reactions 3 and 4) (Scheme 7). ¹H NMR (400 MHz, DMSO-d₆) δ(ppm): 9.50 (s, 1H), 9.30 (d, J=1.6 Hz, 1H), 8.54 (dd, J=4.7, 1.6 Hz, 1H), 8.46 (ddd, J=8.0, 2.0, 2.0 Hz, 1H), 8.11 (dd, J 6.3, 6.1 Hz, 2H), 7.85 (d, J=8.2 Hz, 2H), 7.38-7.43 (m, 3H), 7.05 (m, 1H), 6.86 (m, 1H), 6.67 (dd, J=7.9, 1.5 Hz, 1H), 6.49 (m, 2H), 4.79 (s, 2H), 4.66 (s, 2 H).

Example 44

N-(2-Amino-phenyl)-4-[(2-morpholin-4-yl-pyrimidin-4-ylamino)-methyl]-benzamide (49)

Step 2: Methyl 4-[(2-morpholin-4-yl-pyrimidin-4-ylamino)-methyl]-benzoate (48a)

A mixture of 45a (2.50 g, 9.0 mmol), morpholine (0.95 mL, 10.8 mmol) and i-Pr₂NEt (3.12 mmol) in i-PrOH (18.0 mL) in a sealed flask was heated at 120° C. overnight and cooled down to room temperature. A precipitate was formed which was collected by filtration, rinsed with i-PrOH and dried to afford the title compound 48 (2.96 g, quantitative yield).

Step 3: N-(2-Amino-phenyl)-4-[(2-morpholin-4-yl-pyrimidin-4-ylamino)-methyl]-benzamide (49)

The title compound 49 (example 44) was obtained from 48 as an off-white solid in two steps following the same procedure as in example 34, step 3 (reactions 3 and 4) (scheme 7). ¹H NMR (400 MHz, DMSO-d₆) δ(ppm): 9.56 (s, 1H), 7.89

(d, J=8.2 Hz, 2H), 7.72 (d, J=5.7 Hz, 1H), 7.56 (bs, 1H), 7.40 (d, J=8.2 Hz, 2H), 7.13 (d, J=7.8 Hz, 1H), 6.94 (m, 1H), 6.75 (m, 1H), 6.57 (m, 1H), 5.83 (bs, 1H), 4.87 (s, 2H), 4.51 (bs, 2H), 3.56 (s, 8H).

to afford the title compound 50 (2.74 g, 13.43 mmol, 64% yield) as a pale yellow oily liquid. $^1$H NMR (400 MHz, CDCl$_3$) δ(ppm): 8.49 (dd, J=2.3, 0.6 Hz, 1H), 7.60 (dd, J=8.5, 2.4 Hz, 1H), 7.09 (dd, J=8.6, 0.8 Hz, 1H), 2.57 (s, 3H).

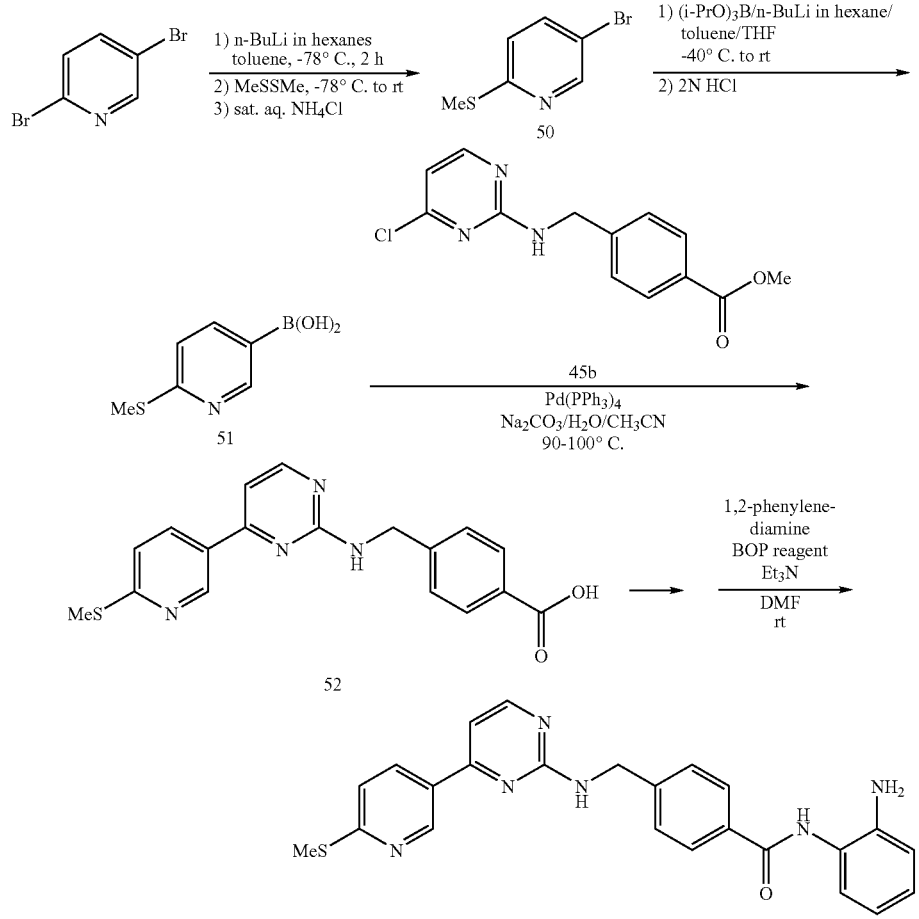

53: Example 45

Example 45

N-(2-Amino-phenyl)-4-{[4-(6-methylsulfanyl-pyridin-3-yl)-pyrimidin-2-ylamino]-methyl}-benzamide (53)

Step 1: 5-Bromo-2-methylsulfanyl-pyridine (50)

To a stirred solution of 2,5-dibromopyridine (5.00 g, 21.11 mmol) in anhydrous toluene (300 mL) at −78° C. under nitrogen was slowly added a solution of n-BuLi (10.13 mL, 25.33 mmol, 2.5M in hexanes). After 2 h at −78° C., methyl disulfide (2.47 mL, 27.44 mmol) was added. The reaction mixture was stirred for 1 h at −78° C. and was allowed to warm to room temperature, quenched with saturated NH$_4$Cl to form a two-phase system. The organic layer was separated, washed with sat NH$_4$C$_1$, H$_2$O and brine, dried over anhydrous MgSO$_4$, filtered and concentrated. The residue was purified by flash chromatography on silica gel (AcOEt/hexane, 5/95)

Step 2: 5-(2-methylsulfanyl-pyridinyl)-boronic acid (51)

To a stirred solution of 50 (2.74 g, 13.43 mmol) and triisopropylborate (3.72 mL, 16.11 mmol) in a mixture of anhydrous toluene/THF (20 mL/5 mL) at −40° C. under nitrogen was added dropwise a solution of n-BuLi (6.98 mL, 17.45 mmol, 2.5M in hexanes). After stirring for 1 h at −40° C., the mixture was allowed to warm to room temperature and quenched with 2N HCl. The resultant suspension was filtered; the precipitate was rinsed with H$_2$O and AcOEt. The filtrate was neutralized with 1N NaOH (pH 7) and extracted with AcOEt. The organic layer and the precipitate were combined, solvent was evaporated and the solid residue was triturated with MeCN-MeOH to afford the title compound 51 (1.84 g, 10.88 mmol, 81% yield) as a pale yellow solid.

Step 3: 4-{[4-(6-Methylsulfanyl-pyridin-3-yl)-pyrimidin-2-ylamino]-methyl}-benzoic acid (52)

To a degassed stirred suspension of a mixture of 51 (593 mg, 3.51 mmol), 45b (500 mg, 1.80 mmol) and solution of Na$_2$CO$_3$ (15 mL, 0.4M) in acetonitrile (15 mL) at room temperature Pd(PPh$_3$)$_4$ (126 mg, 0.11 mmol) was added. The reaction mixture was heated at 90-95° C. for 24 h under nitrogen. Then, 1M NaOH (amount) was added and the heating was continued for additional 2 h. After cooling to the room temperature the reaction mixture was filtered, filtrate was extracted with AcOEt, the aqueous layer was collected, filtered, concentrated and acidified with 2N HCl (pH at 5-6). A precipitate was formed which was collected by filtration and dried to afford the title compound 52 (396 mg, 1.12 mmol, 62% yield) as a beige solid.

Step 4: N-(2-Amino-phenyl)-4-{[4-(6-methylsulfanyl-pyridin-3-yl)-pyrimidin-2-ylamino]-methyl}-benzamide (53)

The title compound 53 (example 45) was obtained from 52 as an off-white solid in one step following the same procedure as in example 2, step 4 (scheme 2). $^1$H NMR (400 MHz, DMSO-d$_6$) δ(ppm): 9.60 (s, 1H), 9.12 (d, J=1.8 Hz, 1H), 8.39 (d, J=5.3 Hz 1H), 8.29 (bd, J=8.0 Hz, 1H), 7.98 (t, J=6.4 Hz, 1H), 7.94 (d, J=8.2 Hz, 2H), 7.56-7.38 (m, 3H), 7.24 (d, J=5.1 Hz, 1H), 7.17 (d, J=7.0 Hz, 1H), 6.98 (td, J=7.5, 1.4 Hz, 1H), 6.79 (dd, J=7.9, 1.3 Hz 1H), 6.60 (td, J=7.2, 1.2 Hz, 1H), 4.90 (s, 2H), 4.67 (bd, J=6.3 Hz, 2H), 2.60 (s, 3H).

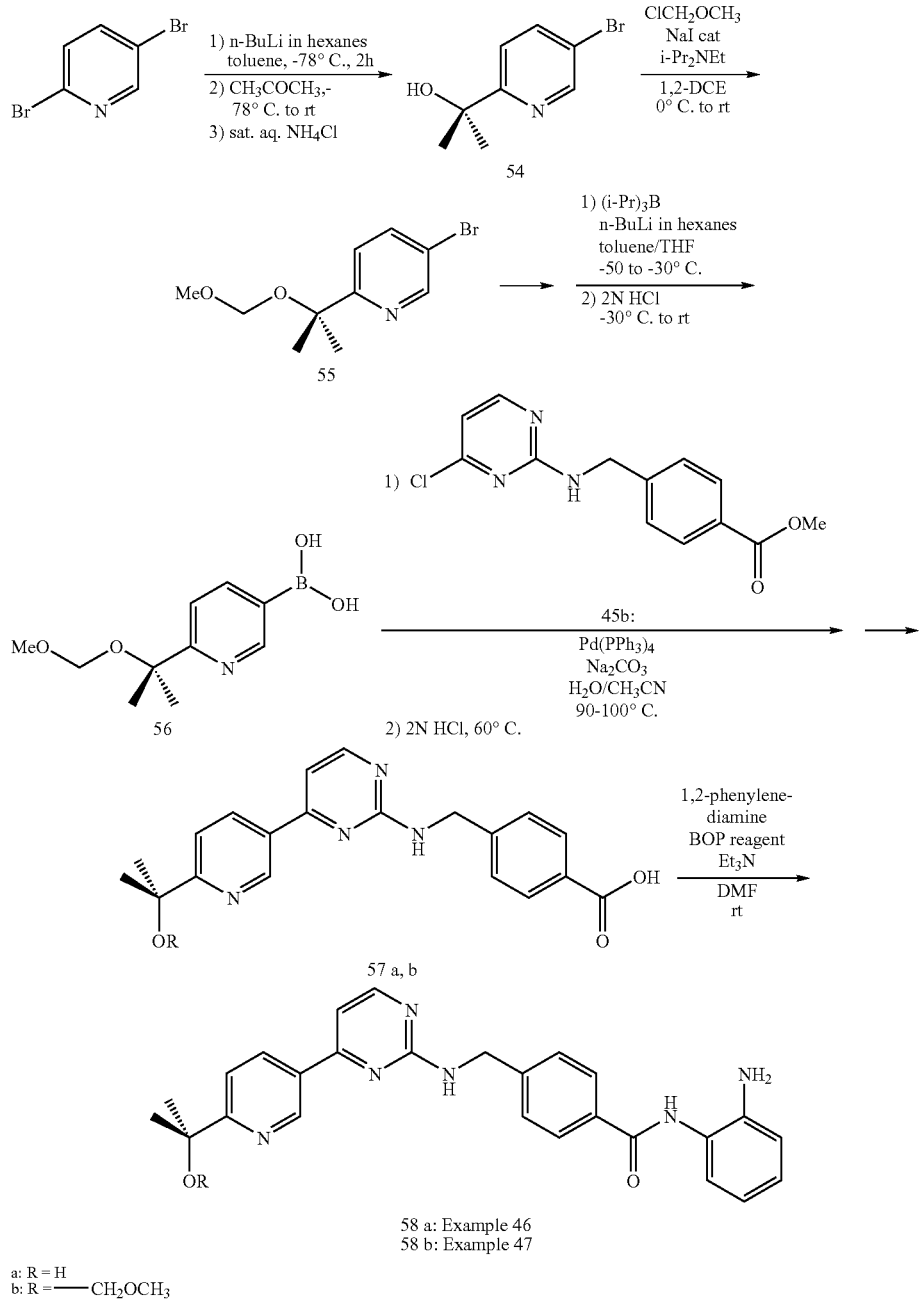

Scheme 15

58 a: Example 46
58 b: Example 47 a: R = H
b: R = —CH$_2$OCH$_3$

Example 46

N-(2-Amino-phenyl)-4-({4-[6-(1-hydroxy-1-methyl-ethyl)-pyridin-3-yl]-pyrimidin-2-ylamino}-methyl)-benzamide (58a)

Step 1: 2-(5-Bromo-pyridin-2-yl)-propan-2-ol (54a)

To a stirred solution of 2,5-dibromopyridine (2.00 g, 8.44 mmol) in anhydrous toluene (100 mL) at −78° C. under nitrogen was slowly added a solution of n-BuLi (4.05 mL, 10.13 mmol, 2.5M in hexanes). After 2 h at −78° C., acetone (806 μl, 10.98 mmol) was added. After stirring for 1 h, the reaction mixture was allowed to warm to 0° C. and was quenched with a saturated $NH_4Cl$. A two-phase system was formed; the organic layer was separated, washed with saturated $NH_4Cl$, $H_2O$ and brine, dried over anhydrous $MgSO_4$, filtered and concentrated. The residue was purified by flash chromatography on silica gel (AcOEt/$CH_2Cl_2$: 20/80) to afford the title compound 54 (1.37 g, 6.34 mmol, 75% yield) as a pale yellow oily liquid. $^1$H NMR (400 MHz, $CDCl_3$) δ(ppm): ABX System ($δ_A$=7.32, $δ_B$=7.82, $δ_X$=8.58, $J_{AB}$=8.4 Hz, $J_{BX}$=2.3 Hz, $J_{AX}$=0 Hz, 3H), 4.47 (bs, 1H), 1.57 (s, 6H).

Step 2: 5-Bromo-2-(1-methoxymethoxy-1-methyl-ethyl)-pyridine: (55)

To a stirred solution of 54 (1.36 g, 6.29 mmol) and i-$Pr_2NEt$ (2.19 mL, 12.59 mmol) in anhydrous dichloromethane (20 mL) at 0° C. under nitrogen was slowly added chloromethyl methyl ether (1.17 mL, 14.63 mmol). After 30 min, the reaction mixture was allowed to warm to room temperature, stirred for two days, concentrated and purified by flash chromatography on silica gel (AcOEt/hexane:5/95) to afford the title compound 55 (1.56 g, 6.00 mmol, 95% yield) as a pale yellow oily liquid. $^1$H NMR (400 MHz, $CDCl_3$) δ(ppm): ABX System ($δ_A$=7.50, $δ_B$=7.80, $δ_X$=8.60, $J_{AB}$=8.4 Hz, $J_{BX}$=2.4 Hz, $J_{AX}$=0.8 Hz, 3H), 4.73 (s, 2H), 3.41 (s, 3H), 1.64 (s, 6H)).

Step 3: 5-(2-[1-methoxymethoxy-1-methyl-ethyl]-pyridinyl)-boronic acid (56)

To a stirred solution of 55 (2.90 g, 11.15 mmol) and triisopropylborate (3.09 mL, 13.38 mmol) in a mixture of anhydrous toluene/THF (20 mL/5 mL) at −50° C. under nitrogen was added dropwise a solution of n-BuLi (7.87 mL, 13.38 mmol, 1.7M in hexanes) over 10 min. After 45 min at −50° C., the mixture was allowed to warm to room temperature and was quenched with 2N HCl (30 mL) at −30° C. After decantation, the pH of the aqueous layer was adjusted to 7 with 1N NaOH, and extracted with AcOEt. The extract was evaporated and the residue was dried under vacuum to afford the title compound 56a (2.33 g, 10.37 mmol, 93% yield) as beige sticky foam. $^1$H NMR (400 MHz, DMSO-$d_6$) δ(ppm): ABX System ($δ_A$=7.55, $δ_B$=8.11, $δ_X$=8.83, $J_{AB}$=7.8 Hz, $J_{BX}$=1.8 Hz, $J_{AX}$=0.9 Hz, 3H), 8.32 (s, 2H), 4.68 (s, 2H), 3.31 (s, 3H), 1.56 (s, 6H)).

Step 4: 4-({4-[6-(1-Hydroxy-1-methyl-ethyl)-pyridin-3-yl]-pyrimidin-2-ylamino}-methyl)-benzoic acid (57a)

To a degassed stirred suspension of a mixture of 56 (550 mg, 2.44 mmol), 45b (510 mg, 1.84 mmol, not pure) and an aqueous solution of $Na_2CO_3$ (10 mL, 0.4M) in acetonitrile (15 mL) at room temperature Pd($PPh_3$)$_4$ (106 mg, 0.09 mmol) was added. The reaction mixture was heated at 95-100° C. for 24 h under nitrogen, cooled to room temperature, filtered, filtrate was concentrated, diluted with water, washed with AcOEt, acidified with 2N HCl (25 mL) and warmed at 60° C. for 4 h. The reaction mixture was allowed to cool to room temperature and the pH was adjusted to 5-6 with 2N NaOH. A precipitate formed which was collected by filtration, rinsed with water and dried to afford the title compound 57a (303 mg, 0.83 mmol, 45% yield) as a pale yellow solid. $^1$H NMR (400 MHz, DMSO-$d_6$) δ(ppm): 12.82 (bs, 1H), 9.20-9.08 (m, 1H), 8.46-8.32 (m, 2H, included at 8.40 ppm, d, J=5.1 Hz), 7.98 (t, J=6.2 Hz, 1H), 7.90 (d, J=8.2 Hz, 2H), 7.84-7.72 (m, 1H), 7.58-7.42 (m, 2H), 7.25 (d, J=5.1 Hz, 1H), 5.34 (s, 1H), 4.67 (d, J=5.7 Hz, 2H), 1.50 (s, 6H).

Step 5: N-(2-Amino-phenyl)-4-({4-[6-(1-hydroxy-1-methyl-ethyl)-pyridin-3-yl]-pyrimidin-2-ylamino}-methyl)-benzamide (58a)

The title compound 58a (example 46) was obtained from 57a as off-white solid in one step following the same procedure as in Example 2, step 4 (Scheme 2). $^1$H NMR (400 MHz, DMSO-$d_6$) δ(ppm): 9.60 (s, 1H), 9.15 (d, J=2.0 Hz, 1H), 8.45-8.35 (m, 2H, included at 8.41 ppm, d, J=5.1 Hz), 8.00 (t, J=6.4 Hz, 1H), 7.94 (d, J=8.2 Hz, 2H), 7.79 (bd, J=8.2 Hz, 1H), 7.58-7.43 (m, 2H), 7.25 (d, J=5.1 Hz, 1H), 7.16 (d, J=7.4 Hz, 1H), 6.98 (td, J=7.6, 1.5 Hz, 1H), 6.78 (dd, J=8.0, 1.4 Hz 1H), 6.60 (t, J=7.4 Hz, 1H), 5.37 (s, 1H), 4.90 (s, 2H), 4.68 (d, J=5.7 Hz, 2H), 1.50 (s, 6H).

Example 47

N-(2-Amino-phenyl)-4-({4-[6-(1-methoxymethoxy-1-methyl-ethyl)-pyridin-3-yl]-pyrimidin-2-ylamino}-methyl)-benzamide (58b)

The title compound 58b (example 47) was obtained from 56a as off-white solid in two steps following the same procedures as in example 46, step 4 (note: no acid hydrolysis at 60° C.) and 5 (Scheme 15). $^1$H NMR (400 MHz, DMSO-$d_6$) δ(ppm): 9.61 (s, 1H), 9.18 (s, 1H), 8.50-8.32 (m, 2H, included at 8.42 ppm, d, J=5.1 Hz), 8.02 (t, J=6.0 Hz, 1H), 7.94 (d, J=8.0 Hz, 2H), 7.72 (bd, J=7.6 Hz, 1H), 7.59-7.42 (m, 2H), 7.26 (d, J=5.1 Hz, 1H), 7.16 (d, J=7.8 Hz, 1H), 6.98 (td, J=7.6, 1.4 Hz, 1H), 6.79 (d, J=7.8 Hz, 1H), 6.60 (t, J=7.4 Hz, 1H), 4.91 (s, 2H), 4.72 (s, 2H), 4.68 (d, J=5.3 Hz, 2H), 3.32 (s, 3H), 1.60 (s, 6H).

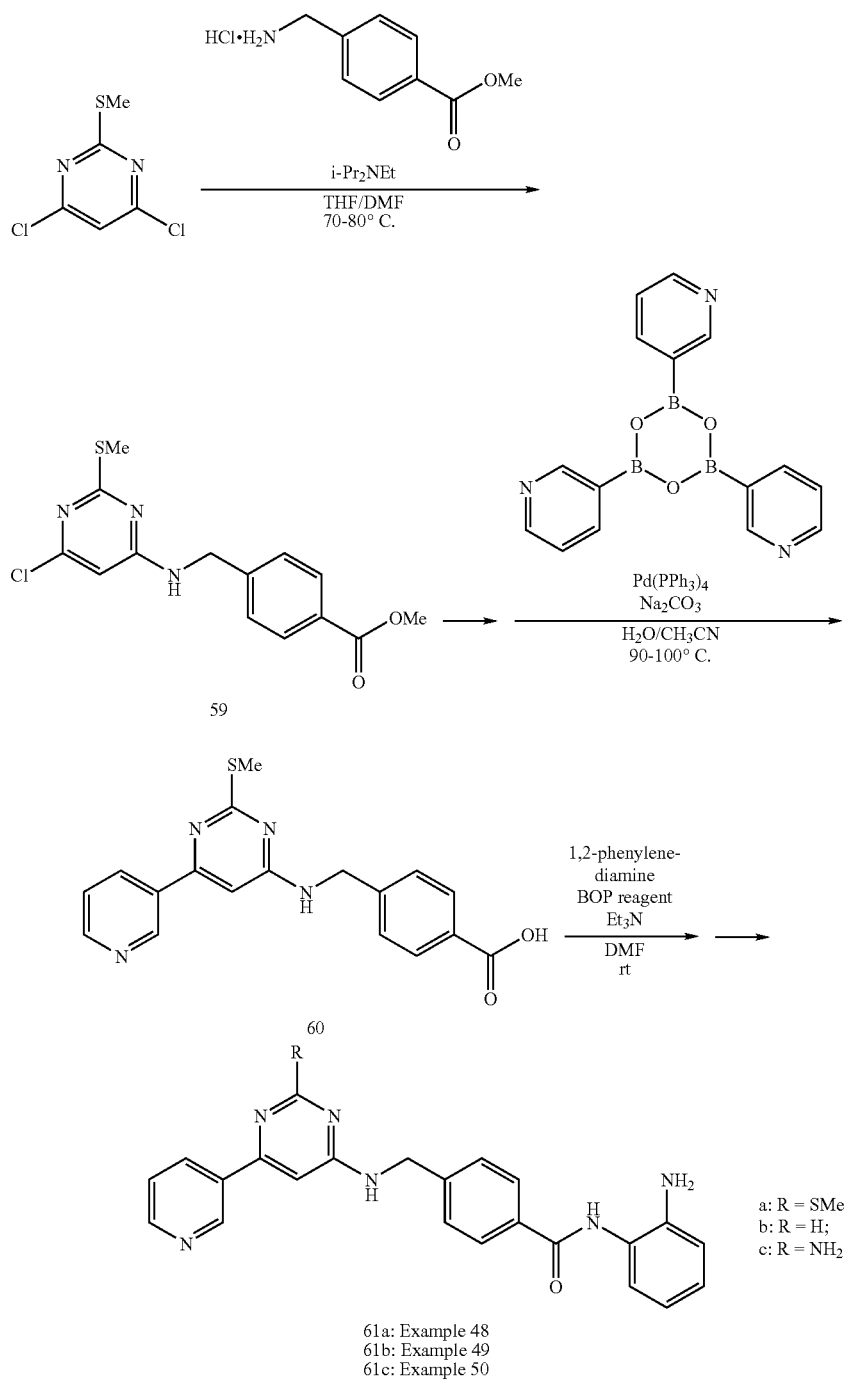

Example 48

N-(2-Amino-phenyl)-4-[(2-methylsulfanyl-6-pyridin-3-yl-pyrimidin-4-ylamino)-methyl]-benzamide (61a)

Step 1: Methyl 4-[(6-Chloro-2-methylsulfanyl-pyrimidin-4-ylamino)-methyl]-benzoate (59)

A stirred suspension of 4,6-dichloro-2-(methylthio)pyrimidine (657 mg, 3.37 mmol) or 4,6-dichloro-2-(R)-pyrimidine, methyl 4-(aminomethyl)benzoate.HCl (744 mg, 3.69 mmol) and i-Pr$_2$NEt (2.34 mL, 13.43 mmol) in a mixture of anhydrous THF/DMF (10 mL/2 mL) under nitrogen was heated at 70-80° C. for 24 h. The mixture was allowed to cool down to room temperature, poured into a saturated NaHCO$_3$ and extracted with AcOEt. The organic layer was washed with water, saturated NH$_4$C$_1$, H$_2$O and brine, dried over anhydrous MgSO$_4$, filtered and concentrated. The residue was purified by flash chromatography on silica gel (eluent AcOEt/CH$_2$Cl$_2$, 30/70, then 40/60) to afford the title compound 59a (929 mg, 2.87 mmol, 85% yield) as a beige powder.

Step 2: 4-[(2-Methylsulfanyl-6-pyridin-3-yl-pyrimidin-4-ylamino)-methyl]-benzoic acid (60)

To a degassed stirred suspension of a mixture of 59 (925 mg, 2.86 mmol), 2,4,6-(3-pyridinyl)-cyclotriboroxane (360 mg, 1.14 mmol) and aqueous of $Na_2CO_3$ (20 mL, 0.4M) in acetonitrile (20 mL) at room temperature was $Pd(PPh_3)_4$ (165 mg, 0.14 mmol) was added. The reaction mixture was heated at 95° for one to two days under nitrogen. 1M NaOH (5 mL) was added to the reaction mixture and the heating was maintained for another 1 h. The mixture was allowed to cool to room temperature and filtered. The filtrate was extracted with AcOEt, the aqueous layer was separated, concentrated, and acidified with 2N HCl (pH at 5-7). A precipitate formed which was collected by filtration and dried to afford the title compound 60 (770 mg, 2.19 mmol, 76% yield) as a beige solid. $^1$H NMR (400 MHz, DMSO-$d_6$) δ(ppm): 12.89 (bs 1H), 9.15 (bs, 1H), 8.72-8.64 (m, 1H), 8.39-8.20 (m, 2H), 7.93 (d, J=8.4 Hz, 2H), 7.58-7.40 (m, 3H), 6.84 (s, 1H), 4.69 (d, J=5.1 Hz 2H), 2.48 (bs, 3H).

Step 3: N-(2-Amino-phenyl)-4-[(2-methylsulfanyl-6-pyridin-3-yl-pyrimidin-4-ylamino)-methyl]-benzamide (61a)

The title compound 61a (Example 48) was obtained from 60 as off-white solid in one step following the same procedure as in example 2, step 4 (scheme 2). $^1$H NMR (400 MHz, DMSO-$d_6$) δ(ppm): 9.64 (s, 1H), 9.16 (bs, 1H), 8.68 (dd, J=4.7, 1.6 Hz 1H), 8.45-8.25 (m, 1H), 8.27 (t, J=5.9 Hz, 1H), 7.97 (d, J=8.2 Hz, 2H), 7.58-7.42 (m, 3H), 7.17 (d, J=7.6 Hz, 1H), 6.98 (td, J=7.5, 1.4 Hz, 1H), 6.85 (s, 1H), 6.79 (dd, J=7.9, 1.1 Hz 1H), 6.61 (t, J=7.2 Hz, 1H), 4.92 (s, 2H), 4.69 (bs, 2H), 2.50 (s, 3H).

Examples 49-50

Examples 49, 50 (compounds 61b-c) were prepared using the same procedures as described for compound 61a (example 48, scheme 16).

TABLE 5

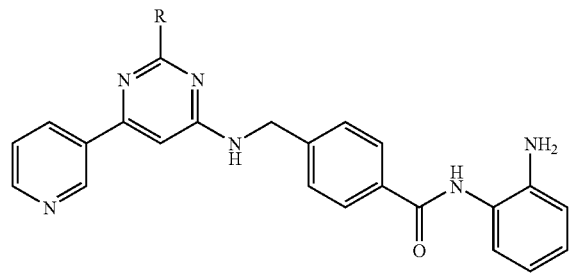

| Cmpd | Ex | R | Name | Characterization |
|---|---|---|---|---|
| 61b | 49 | H | N-(2-Amino-phenyl)-4-[(6-pyridin-3-yl-pyrimidin-4-ylamino)-methyl]-benzamide | $^1$H NMR (400 MHz, DMSO-$d_6$) δ (ppm): 9.64 (s, 1H), 9.19 (bs, 1H), 8.69 (d, J = 3.7 Hz 1H), 8.56 (s, 1H), 8.36 (d, J = 6.3 Hz, 1H), 8.20 (t, J = 6.0 Hz, 1H), 7.96 (d, J = 8.0 Hz, 2H), 7.52-7.40 (m, 3H), 7.17 (d, J = 7.0 Hz, 1H), 7.13 (s, 1H), 6.98 (t, J = 7.5 Hz, 1H), 6.79 (d, J = 7.6 Hz 1H), 6.61 (t, J = 7.5 Hz, 1H), 4.92 (s, 2H), 4.71 (bs, 2H). |
| 61c | 50 | $NH_2$ | N-(2-Amino-phenyl)-4-[(2-amino-6-pyridin-3-yl-pyrimidin-4-ylamino)-methyl]-benzamide | $^1$H NMR (400 MHz, DMSO-$d_6$) δ (ppm): 9.63 (s, 1H), 9.08 (d, J = 1.8 Hz, 1H), 8.63 (dd, J = 4.7, 1.6 Hz 1H), 8.24 (d, J = 7.8 Hz, 1H), 7.96 (d, J = 8.0 Hz, 2H), 7.63 (bs, 1H), 7.54-7.43 (m, 3H), 7.17 (d, J = 7.2 Hz, 1H), 6.98 (td, J = 7.6, 1.2 Hz, 1H), 6.79 (d, J = 6.8 Hz 1H), 6.61 (t, J = 7.5 Hz, 1H), 6.38 (s, 1H), 6.19 (bs, 2H). 4.92 (s, 2H), 4.65 (bs, 2H). |

Scheme 17

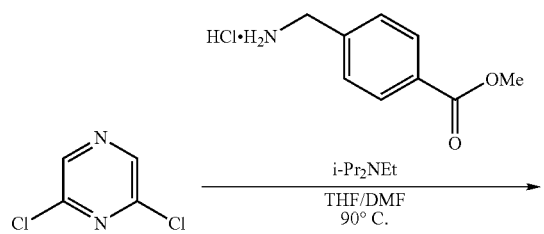

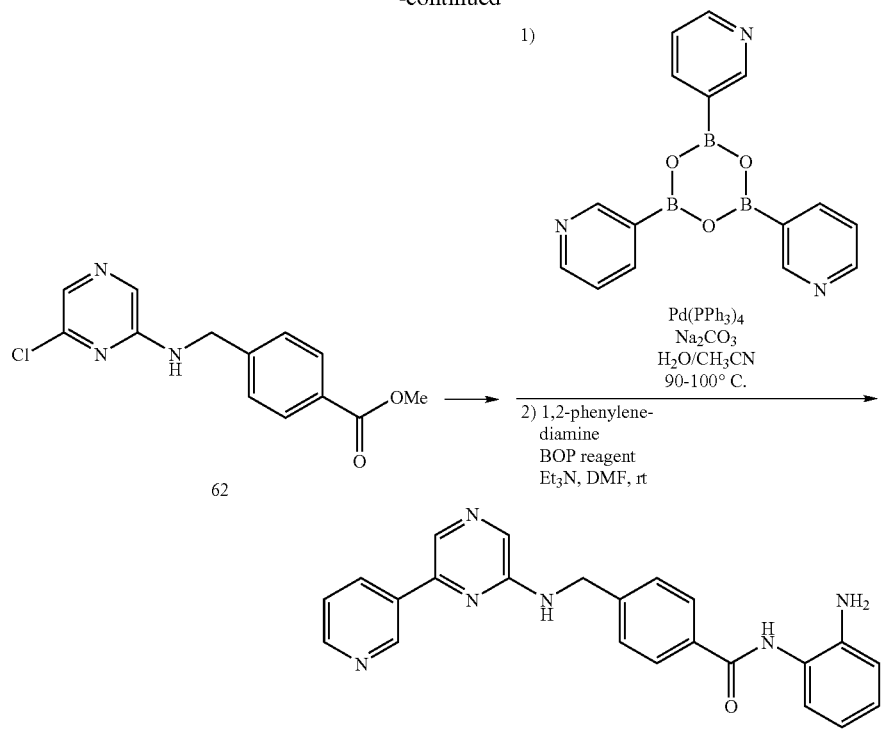

Example 51

N-(2-Amino-phenyl)-4-[(6-pyridin-3-yl-pyrazin-2-ylamino)-methyl]-benzamide (63)

Step 1: 4-[(6-Chloro-pyrazin-2-ylamino)-methyl]-benzoic acid methyl ester (62)

A stirred suspension of 2,6-dichloropyrazine (500 mg, 3.36 mmol), methyl 4-(aminomethyl)benzoate.HCl (744 mg, 3.69 mmol) and i-Pr$_2$NEt (2.05 mL, 11.75 mmol) in a mixture of anhydrous THF/DMF (10 mL/2 mL) under nitrogen was heated at 90° C. for 24 h. The mixture was allowed to cool down to room temperature, was poured into saturated aqueous NH$_4$Cl and extracted with AcOEt. The organic layer was washed with H$_2$O and brine, dried over anhydrous MgSO$_4$, filtered and concentrated. The residue was purified by flash chromatography on silica gel (AcOEt/CH$_2$Cl$_2$: 20/80→30/70) to afford the title compound 62 (300 mg, 1.08 mmol, 32% yield) as a pale yellow solid. $^1$H NMR (400 MHz, DMSO-d$_6$) δ(ppm): 8.18 (t, J=6.0 Hz, 1H), 7.97 (s, 1H), AB system ($\delta_A$=7.95, $\delta_B$=7.49, J$_{AB}$=8.5 Hz, 4H), 7.75 (s, 1H), 4.58 (d, J=5.9 Hz, 2H), 3.87 (s, 3H).

Step 2: N-(2-Amino-phenyl)-4-[(6-pyridin-3-yl-pyrazin-2-ylamino)-methyl]-benzamide (63)

The title compound 63 (example 51) was obtained from 62 as a beige powder in two steps following the same procedure as in Example 48, steps 2 and 3 (Scheme 16). $^1$H NMR (400 MHz, DMSO-d$_6$) δ(ppm): 9.62 (s, 1H), 9.19 (dd, J=2.3, 0.8 Hz, 1H), 8.62 (dd, J=4.7, 1.6 Hz 1H), 8.40 (s, 1H), 8.36 (ddd, J=8.4, 2.0, 2.0 Hz, 1H), 8.06 (s, 1H), 8.01-7.92 (m, 3H), 7.54 (d, J=8.2 Hz, 2H), 7.51 (ddd, J=7.8, 4.7, 0.8 Hz, 1H), 7.16 (bd, J=6.7 Hz, 1H), 6.98 (td, J=7.6, 1.5 Hz, 1H), 6.78 (dd, J=8.0, 1.4 Hz 1H), 6.60 (td, J=7.5, 1.3 Hz, 1H), 4.91 (s, 2H), 4.71 (d, J=6.1 Hz, 2H).

Scheme 18

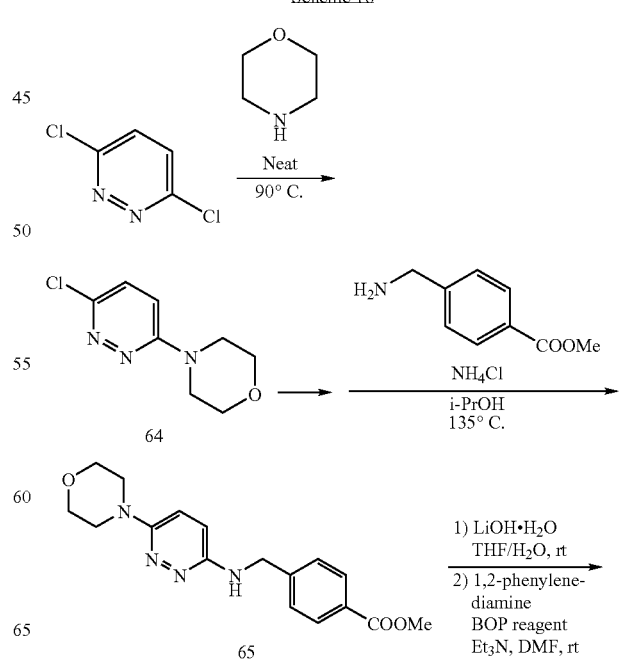

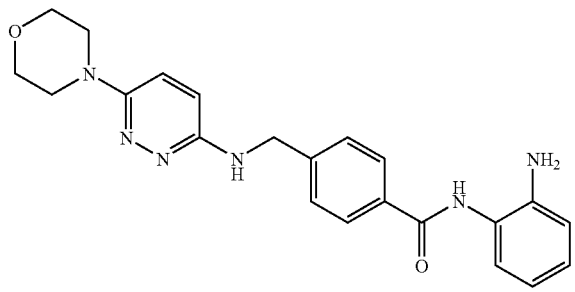

66: Example 52

Example 52

N-(2-Amino-phenyl)-4-[(6-morpholin-4-yl-pyridazin-3-ylamino)-methyl]-benzamide (66)

Step 1: 4-(6-Chloro-pyridazin-3-yl)-morpholine (64)

A 50 mL flask equipped with a reflux condenser was charged with morpholine (2.93 mL, 33.5 mmol) and 3,6-dichloropyridazine (5.00 g, 33.5 mmol). The mixture was heated at 90° C. for 6 h, the resultant solid was partitioned between EtOAc, water and saturated $NH_4Cl$. Organic layer was separated, dried over anhydrous $Na_2SO_4$, filtered, and evaporated to afford the title compound 64 (5.3 g, 26.5 mmol, 79% yield).

Step 2: Methyl 4-[(6-morpholin-4-yl-pyridazin-3-ylamino)-methyl]-benzoate (65)

To a solution of 64 (2.0 g, 10.0 mmol) and methyl 4-(aminomethyl)benzoate hydrochloride (2.2 g, 11.0 mmol) in i-PrOH (200 mL) was added $NH_4Cl$ (2.14 g, 40.0 mmol). The reaction mixture was heated at 150° C. for 72 h and concentrated. The residue was dissolved in water and the aqueous phase was extracted with the aqueous phase was separated, treated with 1N NaOH (pH 8) and extracted with EtOAc. The extract was dried over anhydrous $Na_2SO_4$, filtered and concentrated. The residue was purified by flash chromatography on silica gel ($MeOH/CH_2Cl_2$: 2/98 to 5/95) to afford the title compound 65 (270 mg, 0.82 mmol, 8% yield). $^1H$ NMR: (400 MHz, $CDCl_3$) δ (ppm): 7.97 (d, J=8.0 Hz, 2H), 7.42 (d, J=8.0 Hz, 2H), 6.90 (d, J=9.2 Hz, 1H), 6.69 (d, J=9.2 Hz, 1H), 5.16-5.06 (bs, 1H), 4.67 (s, 2H), 3.90 (s, 3H), 3.82 (t, J=4.8 Hz, 4H), 3.41 (t, J=4.8 Hz, 4H).

Steps 3: N-(2-Amino-phenyl)-4-[(6-morpholin-4-yl-pyridazin-3-ylamino)-methyl]-benzamide (66)

The title compound 66 (example 52) was obtained from 65 as an off-white solid in two steps following the same procedure as in Example 2, steps 3 and 4 (Scheme 2). $^1H$ NMR: (400 MHz, DMSO-$d_6$) δ (ppm): 9.57 (s, 1H), 7.89 (d, J=8.0 Hz, 2H), 7.42 (d, J=8.0 Hz, 2H), 7.15-7.12 (m, 1H), 7.13 (d, J=9.6 Hz, 1H), 6.94 (t, J=7.6 Hz, 1H), 6.88 (t, J=6.0 Hz, 1H), 6.83 (d, J=9.6 Hz, 1H), 6.75 (dd, J=8.0, 1.2 Hz, 1H), 6.57 (t, J=8.0 Hz, 1H), 4.86 (s, 2H), 4.54 (d, J=6.4 Hz, 2H), 3.69 (t, J=4.8 Hz, 4H), 3.24 (t, J=4.8 Hz, 4H).

Scheme 19

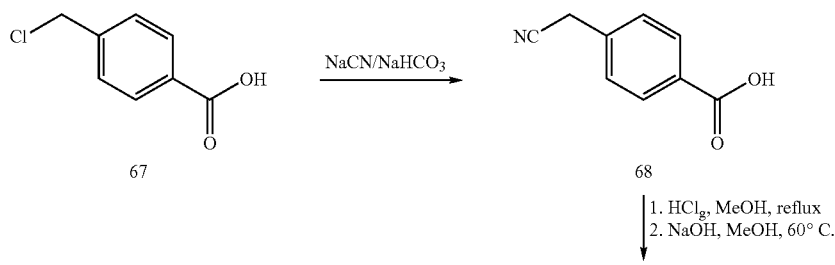

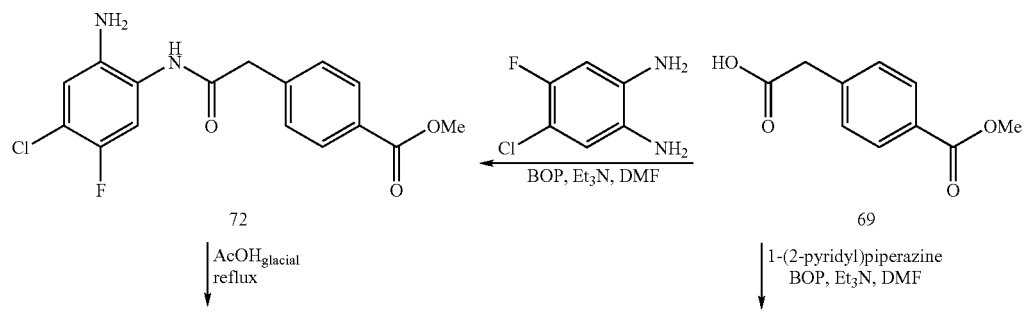

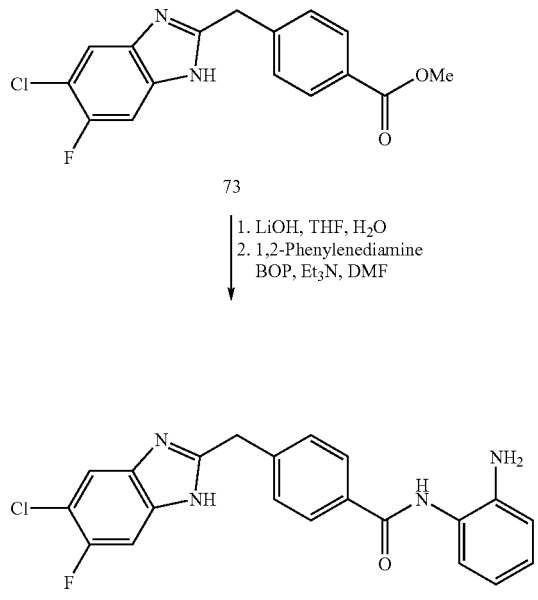

73

1. LiOH, THF, H₂O
2. 1,2-Phenylenediamine
   BOP, Et₃N, DMF

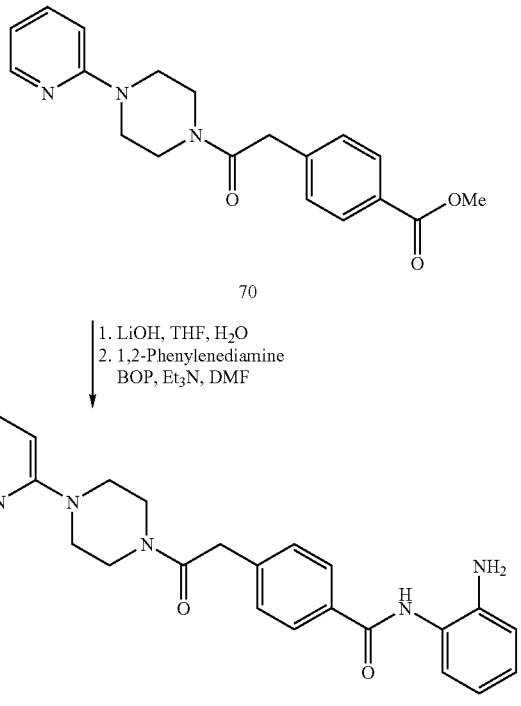

70

1. LiOH, THF, H₂O
2. 1,2-Phenylenediamine
   BOP, Et₃N, DMF

74: Example 54

71: Example 53

Example 53

N-(2-Amino-phenyl)-4-[2-oxo-2-(4-pyrimidin-2-yl-piperazin-1-yl)-ethyl]-benzamide (71)

Step 1: 4-Cyanomethyl-benzoic acid (68)

The title compound was obtained according to the procedure described in *J. Med. Chem.* 1997, 40, 377-384, starting from 4-chloromethylbenzoic acid (67).

Step 2: 4-Carboxymethyl-benzoic acid methyl ester (69)

The title compound was obtained according to the procedures described in *J. Med. Chem.* 1998, 41, 5219-5246, as a beige solid (85% yield). $^1$H NMR (DMSO-d$_6$) δ (ppm): 12.49 (s, 1H), 7.89 (d, J=1.8 Hz, 2H), 7.39 (d, J=8.2 Hz, 2H), 3.84 (s, 3H), 3.79 (s, 2H).

Step 3: Methyl 4-[2-Oxo-2-(4-pyridin-2-yl-piperazin-1-yl)-ethyl]-benzoate (70)

Following the procedure described in example 1, step 5 (scheme 1) the title compound 70 was obtained as a pale yellow solid (70% yield). $^1$H-NMR (DMSO) δ: 8.36 (d, J=4.7 Hz, 2H), 7.89 (d, J=8.4 Hz, 2H), 7.38 (d, J=8.4 Hz, 2H), 6.65 (t, J=4.8 Hz, 1H), 3.87 (s, 2H), 3.83 (s, 3H), 3.71-3.66 (m, 4H), 3.60-3.53 (m, 4H).

Step 4: N-(2-Amino-phenyl)-4-[2-oxo-2-(4-pyrimidin-2-yl-piperazin-1-yl)-ethyl]-benzamide (71)

Following the procedures described in Example 1 steps 4 and 5 the title compound 71 was obtained as a beige solid (225 mg, 69%). $^1$H NMR: (DMSO) δ (ppm): 9.62 (s, 1H), 8.36 (d, J=4.7 Hz, 2H), 7.90 (d, J=8.0 Hz, 2H), 7.36 (d, J=8.2 Hz, 2H), 7.13 (d, J=6.8 Hz, 1H), 6.95 (td, J=7.5, 1.4 Hz, 1H), 6.76 (dd, J=8.0, 1.4 Hz, 1H), 6.70 (t, J=4.8 Hz, 1H), 6.57 (tdd, J=7.6, 1.4 Hz, 1H), 4.90 (s, 2H), 3.87 (s, 2H), 3.72-3.68 (m, 4H), 3.62-3.55 (m, 4H).

Example 54

N-(2-Amino-phenyl)-4-(5-chloro-6-fluoro-1H-benzoimidazol-2-ylmethyl)-benzamide (74)

Step 1: 4-[(2-Amino-4-chloro-5-fluoro-phenylcarbamoyl)-methyl]-benzoic acid methyl ester (72)

Following the procedure described in example 1, step 5 (scheme 1) the title compound 72 was obtained as orange oil (69% yield). LRMS: 336.1 (calc.), 337.5 (obt.).

Step 2: 4-(5-Chloro-6-fluoro-1H-benzoimidazol-2-ylmethyl)-benzoic acid methyl ester (73)

Compound 72 (333 mg, 0.99 mmol) was dissolved in AcOH (10 ml) and the solution was refluxed, for 24 h. AcOH was evaporated and the residue was dissolved in AcOEt, washed with aqueous NH₄Cl, NaHCO₃ and brine, and dried over MgSO₄. Evaporation of EtOAc provided the title compound 73 as a brownish powder (297 mg, 95%).
$^1$H NMR (DMSO-d$_6$) δ (ppm): 7.90 (d, J=1.8 Hz, 2H), 7.88 (d, J=1.9 Hz, 1H), 7.66 (d, J=7 Hz, 1H), 7.51 (d, J=9.8 Hz, 2H), 4.26 (s, 2H), 3.32 (s, 3H).
LRMS: 318.1 (calc.), 319.4 (obt.)

Step 3: N-(2-Amino-phenyl)-4-(5-chloro-6-fluoro-1H-benzoimidazol-2-ylmethyl)-benzamide (74)

Following the procedures described in example 1, steps 4 and 5 the title compound 74 was obtained as a yellow solid (53% yield). $^1$H NMR: (DMSO) δ (ppm): 9.59 (s, 1H), 7.91 (d, J=8.0 Hz, 2H), 7.67 (d, J=6.9 Hz, 1H), 7.51 (d, J=9.7 Hz, 1H), 7.43 (d, J=8.4 Hz, 2H), 7.13 (d, J=7.2 Hz, 1H), 6.74 (td, J=7.6 Hz, 1H), 7.52 (dd, J=4.7, 4.7 Hz, 1H), 6.57 (dd, J=7.0, 1.4 Hz, 2H), 4.87 (s, 2H), 4.26 (s, 2H).

Scheme 20

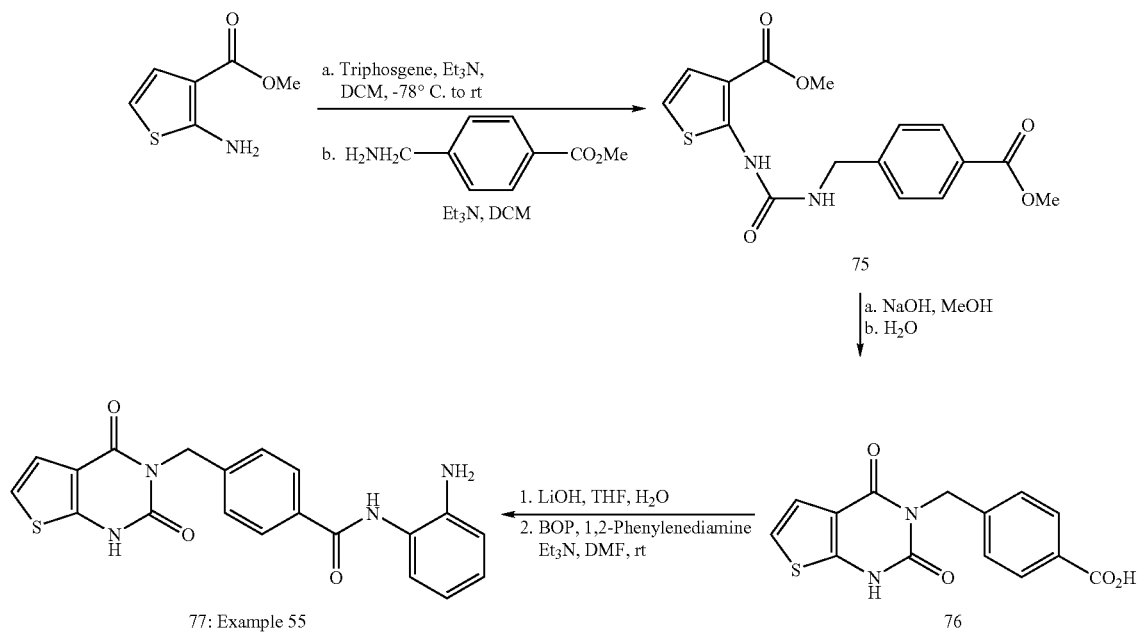

Example 55

N-(2-Amino-phenyl)-4-(2,4-dioxo-1,4-dihydro-2H-thieno[2,3-d]pyrimidin-3-ylmethyl)-benzamide (77)

The title compound 77 was obtained starting from 2-amino-thiophene-3-carboxylic acid methyl ester via the intermediates 75 and 76 (scheme 20) following the same procedures described in Patent Application WO 03/024448 (69% yield). $^1$H NMR (DMSO) δ (ppm): 9.59 (s, 1H), 7.88 (d, J=8.2 Hz, 2H), 7.38 (d, J=8.2 Hz, 2H), 7.18-7.11 (m, 3H), 7.45 (bs, 1H), 6.94 (td, J=7.6, 1.6 Hz, 1H), 6.75 (dd, J=7.8, 1.4 Hz, 1H), 6.57 (td, J=7.5, 1.4 Hz, 1H), 5.09 (s, 2H), 4.87 (bs, 2H). LRMS: 392.1 (calc.), 393.4 (obt.).

Scheme 21

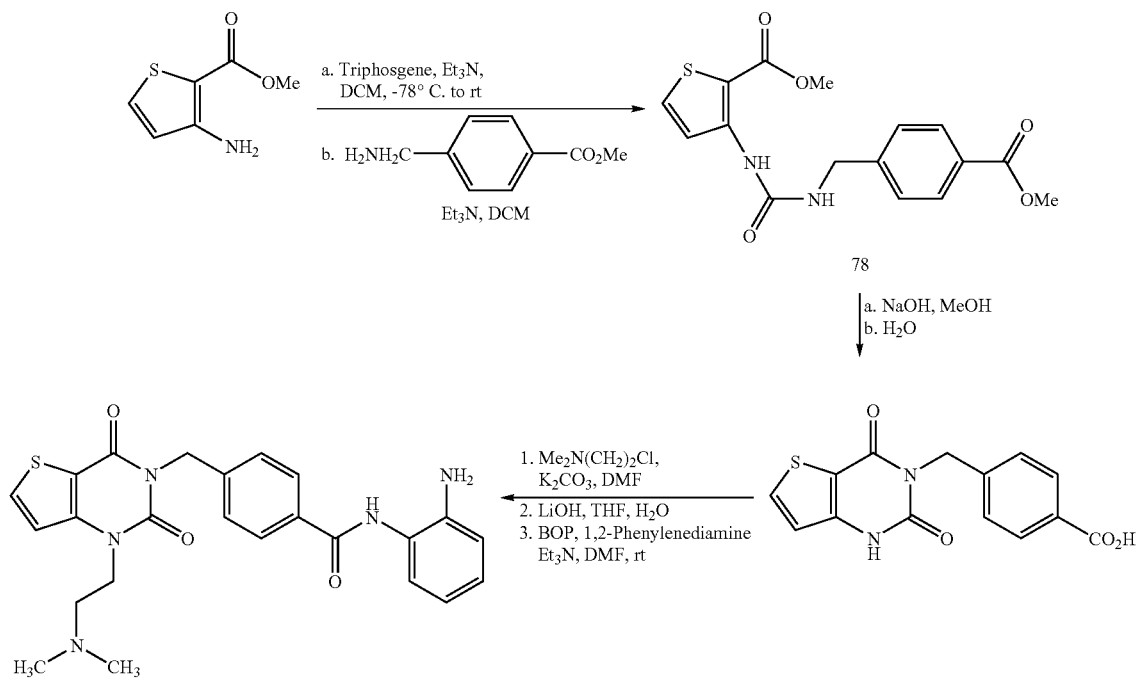

Example 56

N-(2-Amino-phenyl)-4-[1-(2-dimethylamino-ethyl)-2,4-dioxo-1,4-dihydro-2H-thieno[3,2-d]pyrimidin-3-ylmethyl]-benzamide (80)

The title compound 80 was obtained starting from 3-amino-thiophene-2-carboxylic acid methyl ester via the intermediates 78 and 79 as a yellow solid following the same procedures described in the Patent Application WO 03/024448. $^1$H NMR (DMSO) δ (ppm): 9.60 (s, 1H), 8.22 (d, J=5.5 Hz, 1H), 7.89 (d, J=8.2 Hz, 2H), 7.41-7.39 (m, 3H), 7.13 (d, J=7.4 Hz, 1H), 6.95 (td, J=7.6, 1.6 Hz, 1H), 6.75 (dd, J=7.8, 1.6 Hz, 1H), 6.57 (td, J=7.4, 1.2 Hz, 1H), 5.16 (s, 2H), 4.88 (bs, 2H), 4.23 (m, 2H), 2.81 (m, 2H). LRMS: 463.2 (calc.), 464.4 (obt.).

1.28 mM) was added at 5° C. Cooling was removed, the reaction mixture stirred at rt for 1 hr and added via canula to a solution of 4-(5-amino-4-cyano-3-methyl-thiophen-2-ylm-ethyl)-benzoic acid (81, 350 mg, 1.28 mM) (described in the Patent Application WO 03/024448) and DBU (382 μl, 2.56 mM) in anhydrous THF (20 ml) at rt. The combined mixture stirred 3 hrs, THF was evaporated and the remaining solid residue was suspended in water, acidified with conc. HCl (pH 4) and collected by filtration. Trituration of this material with 25 ml acetone provided the title compound 82 (85 mg, 15% yield). LRMS: 429.5 (calc.) 430.4 (found).

Scheme 22

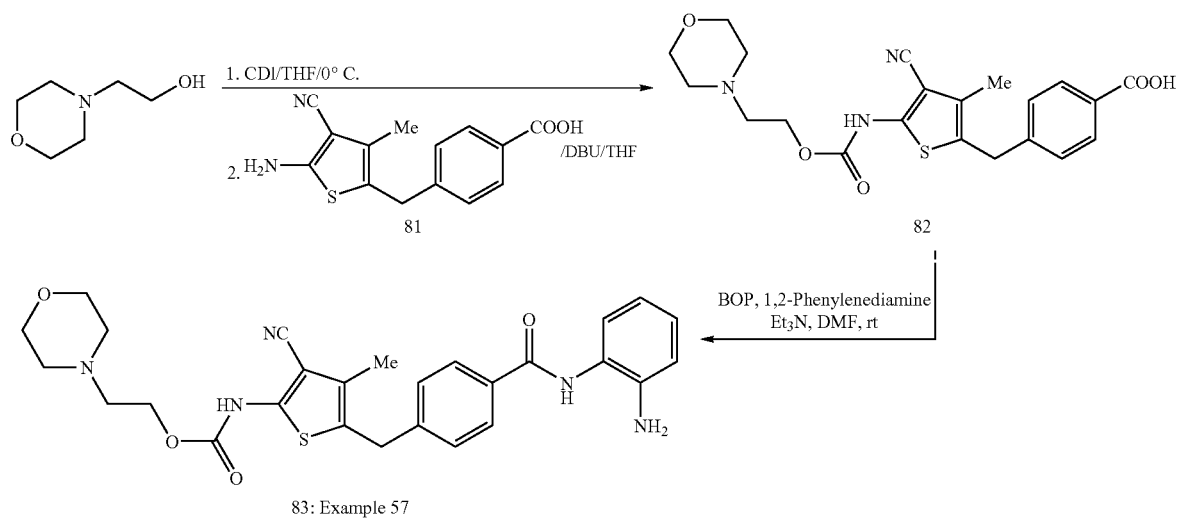

83: Example 57

Example 57

{5-[4-(2-Amino-phenylcarbamoyl)-benzyl]-3-cyano-4-methyl-thiophen-2-yl}-carbamic acid 2-morpholin-4-yl-ethyl ester (83)

Step 1: 4-[4-Cyano-3-methyl-5-(2-morpholin-4-yl-ethoxycarbonylamino)-thiophen-2-ylmethyl]-benzoic acid (82)

To a solution of carbonyl diimidazole (207 mg, 1.28 mM) in anhydrous THF (10 ml) hydroxyethyl morpholine (114 μl, Step 2: {5-[4-(2-Amino-phenylcarbamoyl)-benzyl]-3-cyano-4-methyl-thiophen-2-yl}-carbamic acid 2-morpholin-4-yl-ethyl ester (83)

Following the procedure described in example 1, step 5 the title compound 83 was obtained as a solid (26% yield). $^1$H NMR: (300 MHz, DMSO-d$_6$, δ (ppm): 9.61 (s, 1H), 7.92 (d, J=7.91, 2H), 7.34 (d, J=7.91, 2H), 7.15 (d, J=7.47, 1H), 6.97 (t, J=7.03, 1H), 6.77 (d, J=7.03, 1H), 6.59 (t, J=7.47, 1H), 4.88 (brs, 2H), 4.22 (t, J=5.50, 2H), 4.10 (s, 2H), 3.55 (t, J=4.40, 4H), 2.56 (t, J=5.50, 2H), 2.43-2.39 (m, 4H), 2.18 (s, 3H). LRMS: 519.6 (calc. 520.5 (found).

Scheme 23

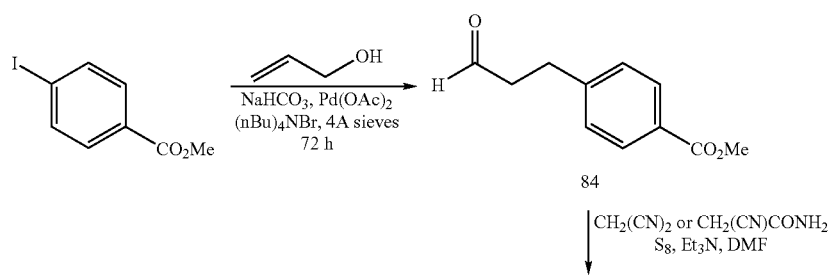

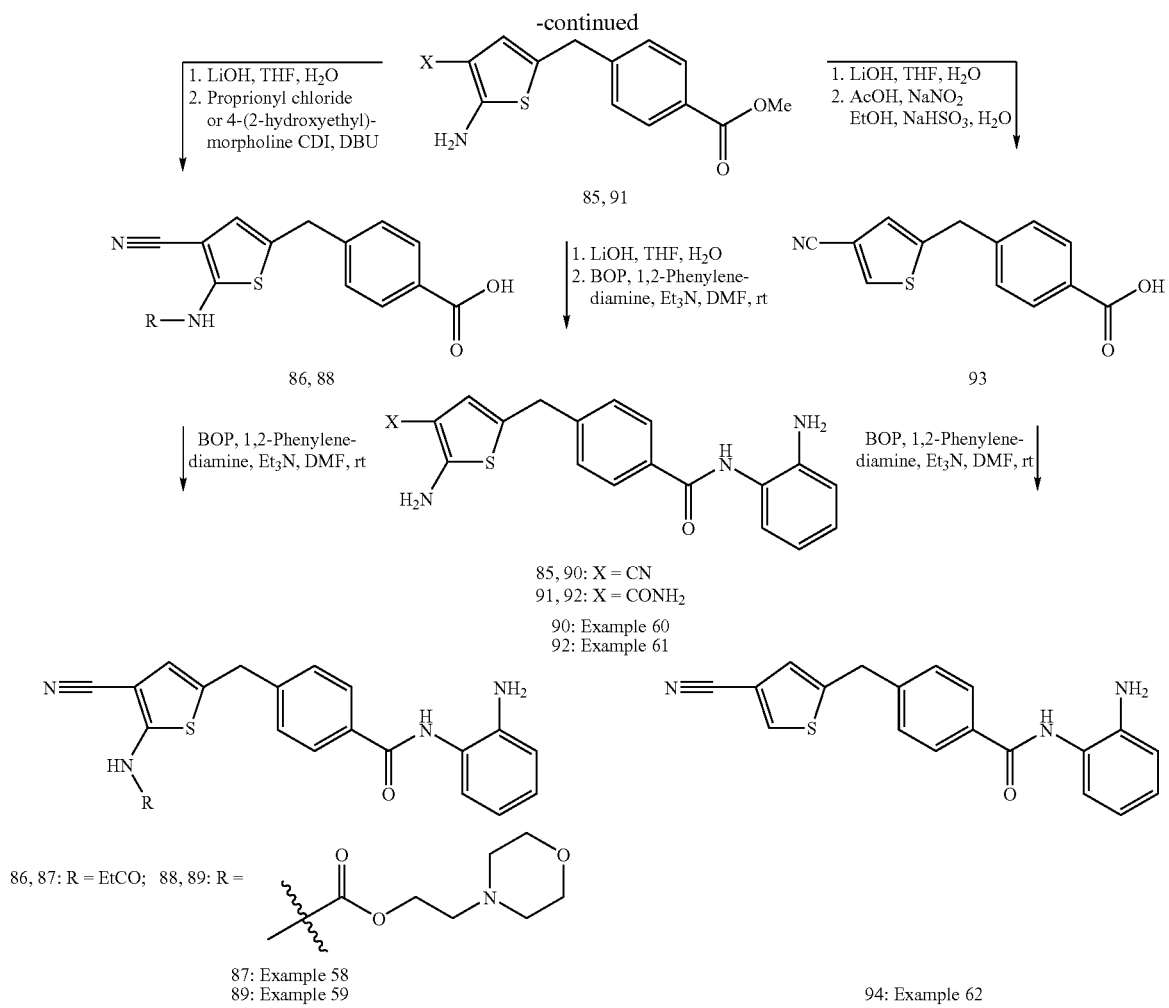

86, 87: R = EtCO;  88, 89: R = [morpholine ester group]

87: Example 58
89: Example 59

94: Example 62

Example 58

N-(2-Amino-phenyl)-4-(4-cyano-5-propionylamino-thiophen-2-ylmethyl)-benzamide (87)

Step 1: 4-(3-Oxo-propyl)-benzoic acid methyl ester (84)

The title compound 84 was obtained according to the procedure described in *J. Org. Chem.*; 1992; 57(11); 3218-3225, starting from 4-iodobenzoic acid methyl ester.

Step 2: 4-(5-Amino-4-cyano-thiophen-2-ylmethyl)-benzoic acid methyl ester (85)

To a suspension of sulfur (309 mg, 4.22 mmol) and methyl 4-(3-oxo-propyl)benzoate (84) (812 mg, 4.22 mmol) in DMF (4 ml) at 0° C. was slowly added Et$_3$N (353 µl, 2.53 mmol) at 0° C. The reaction mixture was stirred 1 h at room temperature and a solution of malononitrile (279 mg, 4.22 mmol) in DMF (6 ml) was slowly added. The reaction mixture was stirred at room temperature for 16 h, poured into 300 ml of ice/water to yield an orange precipitate, which was filtered, rinsed with cold water and dried to afford the title compound 85 (1.04 g, 90%) as an orange solid. LRMS: 272.1 (Calc.); 265.0 (found).

Steps 3, 4: N-(2-Amino-phenyl)-4-(4-cyano-5-propionylamino-thiophen-2-ylmethyl)-benzamide (87)

The title compound 87 was obtained starting from the cyano-compound 85 via the intermediate 86 as a yellow solid following the same procedures as described in Patent Application WO 03/024448, for a similar compound (63% yield). $^1$H NMR (DMSO) δ (ppm): 11.26 (s, 1H), 9.61 (s, 1H), 7.92 (d, J=7.5 Hz, 2H), 7.39 (d, J=7.5 Hz, 2H), 7.15 (d, J=7.5 Hz, 1H), 6.95 (s, 2H), 6.77 (d, J=8.0 Hz, 1H), 6.58 (m, 1H), 5.76-5.75 (m, 1H), 4.88 (s, 2H), 4.12 (s, 2H), 2.50 (m, 3H), 1.05-1.03 (m, 3H). LRMS: 404.1 (calc.), 405.1 (obt.).

Example 59

{5-[4-(2-Amino-phenylcarbamoyl)-benzyl]-3-cyano-thiophen-2-yl}-carbamic acid 2-morpholin-4-yl-ethyl ester (89)

The title compound 89 was obtained starting from the cyano compound 85 via the intermediate 88 similarly to the compound 87, example 58 (scheme 23) as a yellow solid (15% yield). $^1$H NMR: (300 MHz, DMSO-d$_6$, δ (ppm): 9.60 (bs, 1H), 7.91 (d, J=7.8 Hz, 2H), 7.38 (d, J=8.2 Hz, 2H), 7.13 (d, J=7.8 Hz, 1H), 6.97-6.93 (m, 2H), 6.76 (dd, J=7.8, 1.2 Hz, 1H), 6.58 (ddd, J=7.4, 7.4, 1.2 Hz, 1H), 4.89 (bs, 2H), 4.22 (t, J=5.5 Hz, 2H), 4.12 (s, 2H), 3.55 (t, J=4.7 Hz, 4H), 2.56 (t, J=5.7 Hz, 2H), 2.41 (m, 4H).

Example 60

4-(5-Amino-4-cyano-thiophen-2-ylmethyl)-N-(2-amino-phenyl)-benzamide (90)

The title compound 90 was obtained starting from the compound 85 as an orange solid following the same procedures described in example 1 steps 4 and 5, (67% yield). $^1$H NMR: (DMSO) δ (ppm): 9.60 (bs, 1H), 7.90 (d, J=8.2 Hz, 2H), 7.33 (d, J=8.2 Hz, 2H), 7.13 (d, J=6.7 Hz, 1H), 7.03 (bs, 1H), 6.95 (ddd, J=7.6, 7.6, 1.6 Hz, 1H), 6.76 (dd, J=6.6, 1.6 Hz, 1H), 6.58 (ddd, J=7.4, 7.4, 1.7 Hz, 1H), 6.52 (s, 1H), 4.89 (bs, 2H), 3.95 (s, 2H). LRMS: 348.1 (Calc.); 349.2 (found).

Example 61

2-Amino-5-[4-(2-amino-phenylcarbamoyl)-benzyl]-thiophene-3-carboxylic acid amide (92)

Step 2: 4-(5-Amino-4-carbamoyl-thiophen-2-ylmethyl)-benzoic acid methyl ester (91)

The title compound 91 was obtained as a yellow solid by following the same procedure as described in Example 58 step 2 (replacing malononitrile by 2-cyano-acetamide), (88% yield). LRMS: 304.1 (calc.); 305.1 (found).

Step 3-4: 2-Amino-5-[4-(2-amino-phenylcarbamoyl)-benzyl]-thiophene-3-carboxylic acid amide (92)

The title compound 92 was obtained as an orange solid starting from the compound 91 and following the same procedures as described in example 1 steps 4 and 5 (54% yield). $^1$H NMR: (DMSO) δ (ppm): 9.62(s, 1H), 7.90 (d, J=8.2 Hz, 1H), 7.32 (d, J=8.2 Hz, 1H), 7.14-7.12 (m, 3H), 6.95 (td, J=7.6, 1.6 Hz, 1H), 6.84(s, 1H), 6.76 (dd, J=7.8, 1.2 Hz, 1H), 6.58 (td, J=7.4, 1.2 Hz, 1H), 4.87 (s, 2H), 3.93 (s, 2H). LRMS: 366.1 (Calc.); 367.4 (found).

Example 62

N-(2-Amino-phenyl)-4-(4-cyano-thiophen-2-ylmethyl)-benzamide (94)

Step 4: 4-(4-Cyano-thiophen-2-ylmethyl)-benzoic acid (93)

Starting from the cyano compound 85 and following the procedures described in example 1, step 4 (ester hydrolysis) and a procedure described in *Tetrahedron Lett.;* 2001; 42(32); 5367-5370 (de-amination) the title compound 93 was obtained as a brown solid (76% yield). LRMS: 243.1 (calcd.), 244.3 (found).

Step 5: N-(2-Amino-phenyl)-4-(4-cyano-thiophen-2-ylmethyl)-benzamide (94)

The title compound 94 was obtained as an orange solid starting from the compound 93 by following the same procedures described in example 1 step 5 (41% yield).

$^1$H NMR: (DMSO) δ (ppm): 9.61 (bs, 1H), 8.38 (d, J=1.4 Hz, 1H), 7.92 (d, J=8.0 Hz, 2H), 7.40 (d, J=8.2 Hz, 2H), 7.33 (d, J=1.4 Hz, 1H), 7.13 (d, J=6.8 Hz, 1H), 6.95 (td, J=7.6, 1.6 Hz, 1H), 6.75 (dd, J=8.0, 1.4 Hz, 1H), 6.57 (td, J=7.4, 1.2 Hz, 1H), 4.89 (bs, 2H), 4.27 (s, 2H). LRMS: 333.1 (Calc.); 334.4 (found).

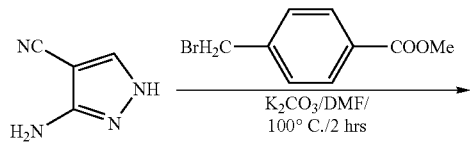

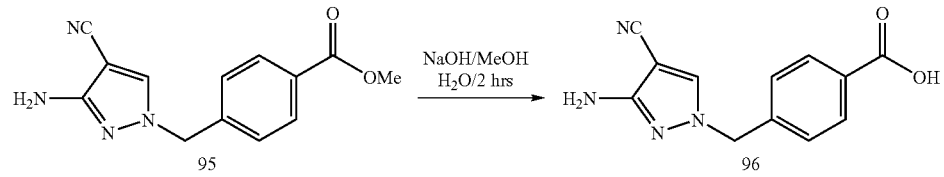

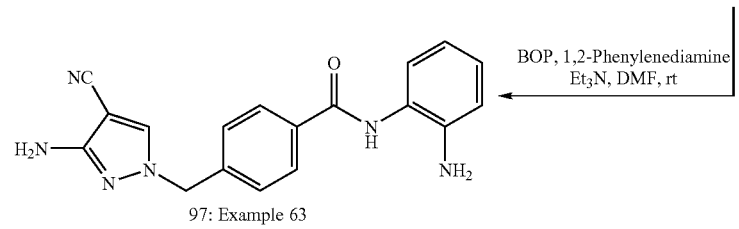

97: Example 63

Example 63

4-(3-Amino-4-cyano-pyrazol-1-ylmethyl)-N-(2-amino-phenyl)-benzamide (97)

Step 1: 4-(3-Amino-4-cyano-pyrazol-1-ylmethyl)-benzoic acid methyl ester (95)

To a solution of 3-amino-1H-pyrazole-4-carbonitrile (1.211 g, 11.21 mmol) in anhydrous DMF (20 ml) $K_2CO_3$ (5.414 g, 39.24 mmol) was added. The suspension was stirred 5 min at room temperature and treated with p-bromomethyl-benzoic acid methyl ester (2.568 g, 11.21 mmol), stirred for 2.5 hrs at 100° C., cooled and filtered. Filtrate was evaporated to form an oily residue, which was dissolved in a mixture $Et_2O$-acetone and kept overnight at −10° C. A crystalline material was formed which was triturated with hot EtOAc, again kept overnight at −10° C. and was collected by filtration to form the title compound 95 (675 mg, 24% yield). LRMS: 256.3 (calc.), 257.3 (found).

Step 2: 4-(3-Amino-4-cyano-pyrazol-1-ylmethyl)-benzoic acid (96)

To a solution of NaOH (343 mg, 8.58 mmol) in a mixture of water (10 ml) and MeOH (20 ml) the ester 95 (732 mg, 2.86 mmol) was added. The reaction mixture was refluxed 2 min and stirred for additional 2 hrs at ambient temperature. MeOH was removed under reduced pressure and remaining aqueous solution was acidified with conc. HCl (pH 3-4) to form a precipitate which was collected by filtration to afford the title compound (96) (640 mg, 92% yield). LRMS: 242.2 (calc.), 241.1 (found).

Step 3: 4-(3-Amino-4-cyano-pyrazol-1-ylmethyl)-N-(2-amino-phenyl)-benzamide (97)

The title compound 97 was obtained as a white solid starting from the compound 96 following the same procedures as described in example 1 step 5. Crude product was purified by flash chromatography, eluent $MeOH$—$CH_2Cl_2$ (2:23) followed by trituration with $CH_2Cl_2$, to afford the title compound 97 (58% yield). $^1H$ NMR: (400 MHz, DMSO-$d_6$, δ (ppm): 9.61 (s, 1H), 8.27 (s, 1H), 7.92 (d, J=8.2, 2H), 7.33 (d, J=8.2, 2H), 7.13 (d (dd), J=7.8, 1H), 6.95 (dd, J=1.4 Hz, J=7.8 Hz, 1H), 6.75 (dd, J=1.2 Hz, j=7.8 Hz, 1H), 6.57 (dd, J=1.2 Hz, 7.6 Hz, 1H), 5.60 (s, 2H), 5.16 (s, 2H), 4.89 (s, 2H). LRMS: 332.4 (calc.), 333.4 (found).

Scheme 25

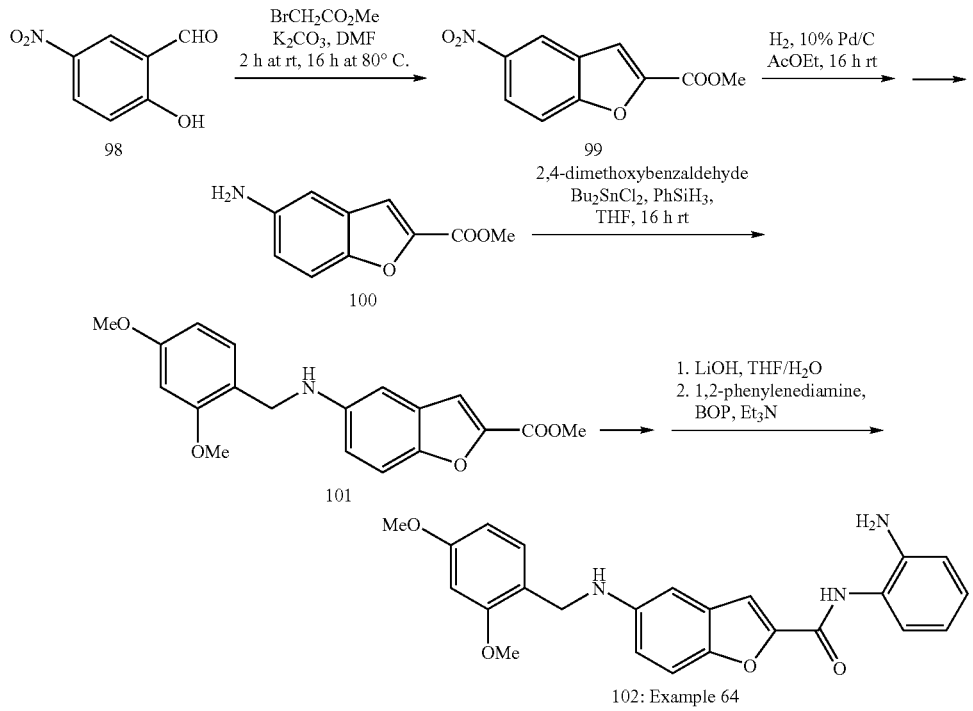

Example 64

5-(2,4-Dimethoxy-benzylamino)-benzofuran-2-carboxylic acid (2-amino-phenyl)-amide (102)

Steps 1-2: 5-Amino-benzofuran-2-carboxylic acid methyl ester (100)

The title compound 100 was obtained following the procedures described in *J. Am. Chem. Soc.* 2000, 122, (6382-6394), starting from 2-hydroxy-5-nitro-benzaldehyde (98) via the intermediate ester 99 (74% yield).

Steps 3-4: 5-(2,4-Dimethoxy-benzylamino)-benzofuran-2-carboxylic acid (2-amino-phenyl)-amide (102)

The title compound 102 was obtained as a orange solid via the intermediates 100 and 101 by following the same procedures as described in example 12, step 2 (scheme 3), and example 1, steps 4 and 5 (scheme 1) (76 mg, 41%). $^1H$ NMR: (DMSO) δ (ppm): 9.69 (s, 1H), 7.44 (s, 1H), 7.37 (d, J=8.8 Hz, 1H), 7.17-7.15 (m, 2H), 6.96 (td, J=7.5, 1.4 Hz, 1H), 6.84 (dd, J=9.0, 2.3 Hz, 1H), 6.76 (dd, J=8.0, 2.3 Hz, 1H), 6.67 (d, J=2.3 Hz, 1H), 6.60-6.56 (m, 2H), 6.45 (dd, J=8.2, 2.3 Hz, 1H), 5.94 (t, J=6.0 Hz, 1H), 4.92 (s, 2H), 4.15 (d, J=5.7 Hz, 1H), 3.83 (s, 3H), 3.73 (s, 3H). LRMS: 417.2 (calc.); 418.5 (obt.).

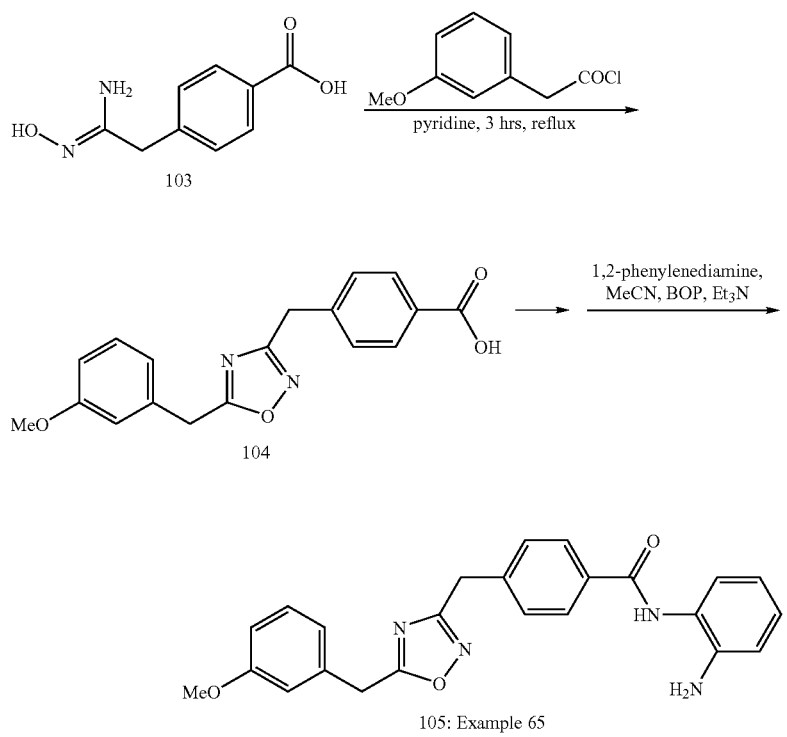

Example 65

N-(2-Amino-phenyl)-4-[5-(3-methoxy-benzyl)-[1,2,4]oxadiazol-3-ylmethyl]-benzamide (105)

Step 1. 4-[5-(3-Methoxy-benzyl)-[1,2,4]oxadiazol-3-ylmethyl]-benzoic acid (104)

To a suspension of 4-(N-hydroxycarbamidoylmethyl)-benzoic acid (103) (described in the Patent Application WO 03/024448) (464 mg, 2.40 mmol) in anhydrous pyridine (10 ml) (3-methoxy-phenyl)-acetyl chloride (418 mg, 2.27 mmol) was added and the reaction mixture was refluxed for 3 hrs, cooled, quenched with water (10 ml) and evaporated to form a solid residue. This material was re-dissolved in CH$_2$Cl$_2$, decolorized with charcoal and purified 3 times by flash chromatography with the eluents being CH$_2$Cl$_2$-MeOH (19:1), CH$_2$Cl$_2$-acetone (19:1, then 9:1) and acetone-hexane (3:2), to afford the title compound 104 (96 mg, 13%). LRMS: 324.3 (calcd.), 323.3 [M−H]$^-$ (found).

N-(2-Amino-phenyl)-4-[5-(3-methoxy-benzyl)-[1,2,4]oxadiazol-3-ylmethyl]-benzamide (105)

The title compound 105 was obtained as a white solid following the same procedures described in example 1 step 5 (scheme 1). The crude product was purified twice by flash chromatography, eluents MeOH—CH$_2$Cl$_2$ (1:19), then EtOAc—CH$_2$Cl$_2$ (1:2), to afford the title compound in 41% yield. LRMS: 414.5 (calcd.), 415.4 [MH]$^+$ (found). $^1$H NMR: (400 MHz, DMSO-d$_6$, δ (ppm): 9.61 (s, 1H), 7.91 (d, J=8.22, 2H), 7.41 (d, J=8.22, 2H), 7.25 (t, J=7.83, 1H), 7.14 (d, J=6.65, 1H), 6.96 (m, 1H), 6.89-6.84 (m, 3H), 6.76 (dd, J=8.02, 1.37, 1H), 6.58 (dt, J=7.63, 1.30, 1H), 4.89 (s, 2H), 4.29 (s, 2H), 4.16 (s, 2H), 3.73 (s, 3H).

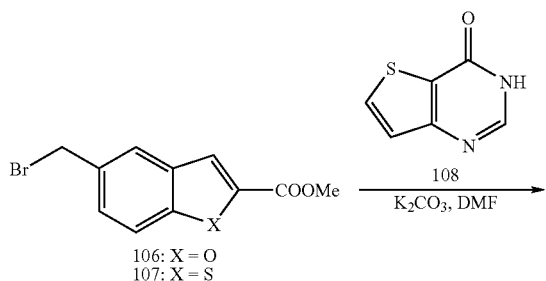

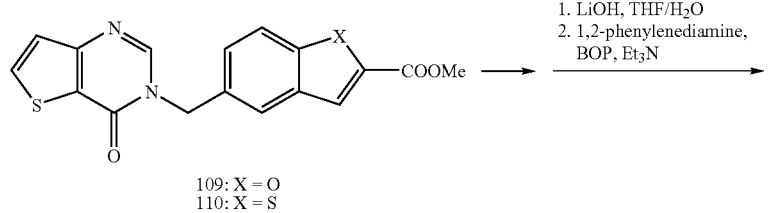

109: X = O
110: X = S

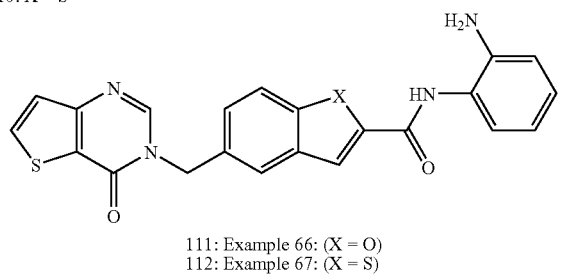

111: Example 66: (X = O)
112: Example 67: (X = S)

Example 66

5-(4-Oxo-4H-thieno[3,2-d]pyrimidin-3-ylmethyl)-benzofuran-2-carboxylic acid (2-amino-phenyl)-amide (111)

The title compound 111 was obtained starting from the compound 106 [reacting with 3H-thieno[3,2-d]pyrimidin-4-one (108)] via the intermediate 109, following the procedures described in the Patent Application WO 03/024448. $^1$H NMR: (DMSO) δ (ppm): 9.87 (s, 1H); 8.72 (s, 1H); 8.20 (d, J=5.5 Hz, 1H); 7.81 (s, 1H); 7.68 (m, 2H); 7.54 (dd, J=8.6, 1.6 Hz, 1H), 7.42 (d, J=5.5 Hz, 1H); 7.17 (d, J=6.6 Hz, 1H); 6.98 (dt, J=7.8, 1.6 Hz, 1H); 6.77 (dd, J=8.2, 1.6 Hz, 1H), 6.59 (dt, J=7.4, 1.6 Hz, 1H); 5.35 (s, 2H); 4.96 (s, 2H). LRMS: 416.1 (calc.), 417.4 (obt.).

Example 67

5-(4-Oxo-4H-thieno[3,2-d]pyrimidin-3-ylmethyl)-benzo[b]thiophene-2-carboxylic acid (2-amino-phenyl)-amide (112)

The title compound 112 was obtained starting from the compound 107 [reacting with 3H-thieno[3,2-d]pyrimidin-4-one (108)] via the intermediate 110, following the procedures described in the Patent Application WO 03/024448. $^1$H NMR: (DMSO) δ (ppm): 9.89 (s, 1H), 8.74 (s, 1H), 8.29 (s, 1H), 8.21 (d, J=5.28, 1H), 8.03 (d, J=8.22, 1H), 7.98 (s, 1H), 7.51 (dd, J=8.51, 1.67, 1H), 7.43 (d, J=5.28, 1H), 7.17 (dd, J=7.73, 1.27, 1H), 6.99 (m, 1H), 6.79 (dd, J=8.22, 1.37, 1H), 6.60 (dt, J=7.43, 1.37, 1H), 5.38 (s, 2H), 5.00 (s, 2H). LRMS: 432.1 (calc.), 433.3 (obt.)

Scheme 28

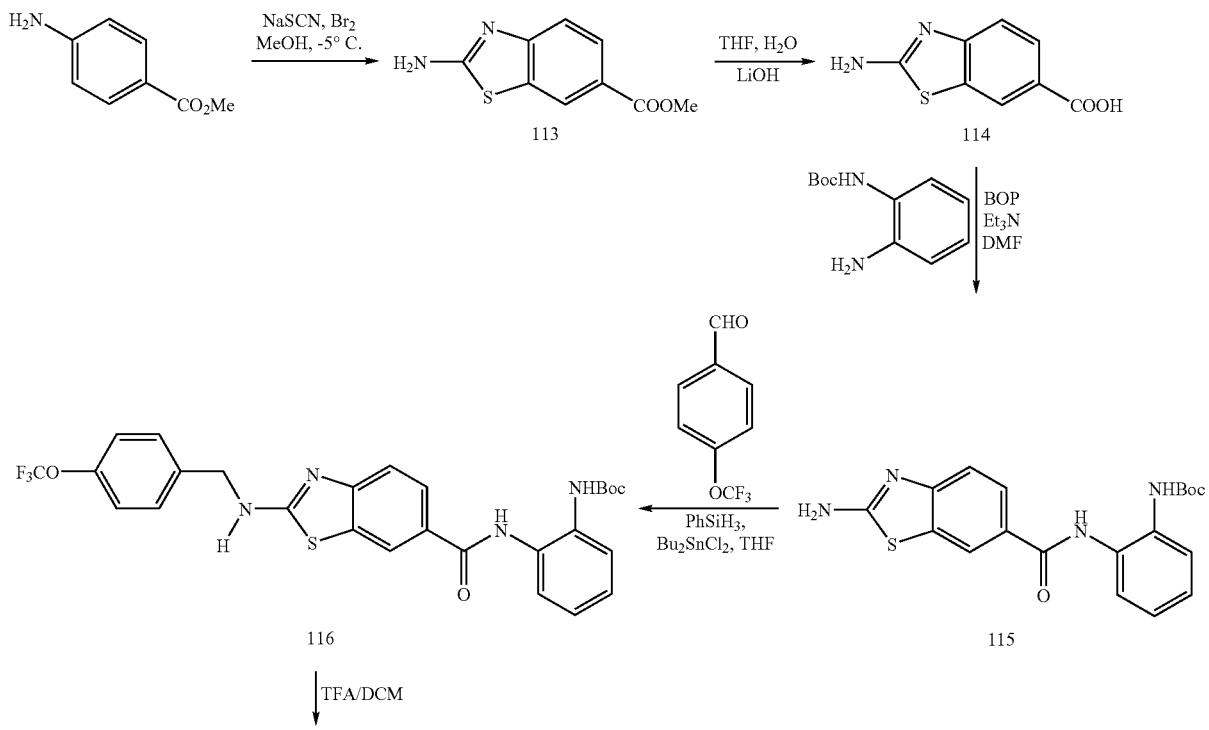

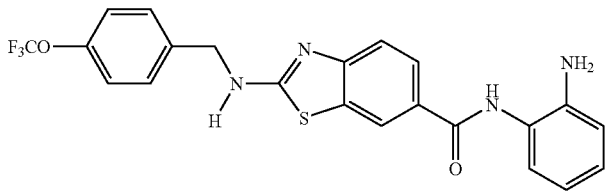

117: Example 68

Example 68

Step 5: 2-(4-Trifluoromethoxy-benzylamino)-benzothiazole-6-carboxylic acid (2-amino-phenyl)-amide (117)

Step 1: 2-Amino-benzothiazole-6-carboxylic acid methyl ester (113)

The title compound was obtained following the procedure described in *J. Med. Chem.* 1997; 40 (105-111), starting from 4-amino-benzoic acid methyl ester.

Step 2: 2-Amino-benzothiazole-6-carboxylic acid (114)

The title compound 114 was obtained following the procedure described in example 1 step 4 (97% yield). $^1$H-NMR (DMSO) δ: 12.58 (s, 1H), 8.23 (d, J=1.8 Hz, 1H); 7.85 (s, 2H); 7.78 (dd, J=8.4, 1.8 Hz, 1H); 7.33 (d, J=7.8 Hz, 1H).

Step 3: {2-[(2-Amino-benzothiazole-6-carbonyl)-amino]-phenyl}-carbamic acid tert-butyl ester (115)

The acid 114 (1.80 g, 9.27 mmol) was combined with (2-amino-phenyl)-carbamic acid tert-butyl ester (2.31 g, 11.1 mmol) and BOP (4.91 g, 11.1 mmol) in DMF. To this solution Et$_3$N (5.16 ml, 37.1 mmol) was added and the mixture was stirred overnight at room temperature under nitrogen, concentrated in vacuo and purified by flash column chromatography (30% hexane/EtOAc). To further purify the product, the mixture was partitioned between EtOAc and water, organic layer was separated, dried over MgSO$_4$ and evaporated give the title compound 115 (1.84 g, 52%). $^1$H-NMR (DMSO) δ: 9.72 (s, 1H), 8.66 (m, 1H); 8.22 (d, J=1.8 Hz, 1H); 7.80 (m, 3H); 7.50 (m, 2H); 7.37 (m, 1H); 7.14 (m, 2H); 1.44 (s, 9H).

Step 4: 2-(4-Trifluoromethoxy-phenyl)-benzothiazole-6-carboxylic acid (2-aminophenyl)-amide (116)

To a solution of 115 (300 mg, 0.78 mmol), 4-(trifluoromethoxy)benzaldehyde (123 μl, 0.86 mmol), and dibutyltin dichloride (24 mg, 0.08 mmol) in THF was added phenylsilane (106 μl, 0.86 mmol). The mixture was stirred overnight at room temperature under nitrogen, additional aldehyde and phenylsilane were added and the stirring continued until no more starting material was present. The THF was evaporated off the mixture and the residue was purified by flash column chromatography (EtOAc/hexane 30/70, then 50/50), to give the title compound 116 (314 mg, 72%). $^1$H-NMR (DMSO) δ: 9.77 (s, 1H), 8.89 (t, J=5.7 Hz, 1H); 8.69 (s, 1H); 8.29 (d, J=1.8 Hz, 1H); 7.84 (dd, J=8.4, 1.8 Hz, 1H); 7.50 (m, 5H); 7.37 (d, J=7.8 Hz, 2H); 7.17 (m, 2H); 4.69 (d, J=5.7 Hz, 2H); 1.47 (s, 9H).

Step 5: 2-(4-Trifluoromethoxy-benzylamino)-benzothiazole-6-carboxylic acid (2-amino-phenyl)-amide (117)

To a solution of 116 (306 mg, 0.55 mmol) in DCM was added TFA (2.0 ml). This mixture was stirred at room temperature for 4 hours and concentrated. The residue was dissolved in EtOAc, washed with NaHCO$_3$, dried over MgSO$_4$ and concentrated again. The residue was purified by flash column chromatography (30% hexane in EtOAc) to give the title compound 117 as a yellow solid (252 mg, 100%). $^1$H-NMR (DMSO) δ: 9.56 (s, 1H), 8.83 (t, J=5.8 Hz, 1H), 8.30 (d, J=1.8 Hz, 1H); 7.85 (dd, J=8.4, 1.6 Hz, 1H); 7.49 (d, J=8.4 Hz, 2H); 7.43 (d, J=8.4 Hz, 1H); 7.34 (d, J=8.4 Hz, 2H); 7.15 (d, J=7.6 Hz. 1H); 6.94 (brt, J=7.8 Hz, 1H); 6.77 (d, J=7.8 Hz, 1H); 6.59 (t, J=7.5 Hz, 1H); 4.66 (d, J=5.7 Hz, 2H). LRMS: 458.1 (calc.), 459.2 (obt.)

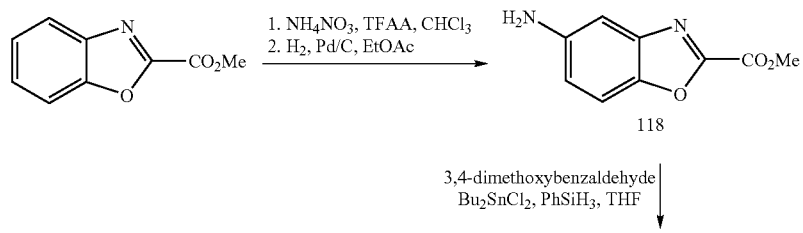

Scheme 29

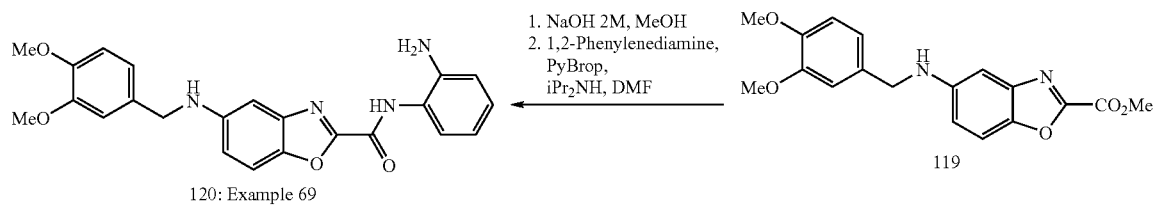

Example 69

6-(3,4-Dimethoxy-benzylamino)-benzooxazole-2-carboxylic acid (2-amino-phenyl)-amide (120)

Step 1: 5-Amino-benzooxazole-2-carboxylic acid methyl ester (118)

The title compound 118 was obtained following the procedures described in *J. Am. Chem. Soc.* 2000; 122 (6382-6394) starting from benzooxazole-2-carboxylic acid methyl ester.

Step 2: 5-(3,4-Dimethoxy-benzylamino)-benzooxazole-2-carboxylic acid methyl ester (119)

The title compound 119 was obtained as a solid following the same procedure as described in example 68 step 4 (scheme 28) (90% yield). LRMS: 342.1 (Calc.); 343.4 (found).

Steps 4-5: 6-(3,4-Dimethoxy-benzylamino)-benzooxazole-2-carboxylic acid (2-amino-phenyl)-amide (120)

The title compound 120 was obtained following the procedures described in example 1, step 5 (scheme 1) (31% yield). $^1$H NMR: (DMSO) δ (ppm): 10.06 (s, 1H), 7.56 (d, J=8.80, 1H), 7.22 (dd, J=7.83, 1.37, 1H), 7.02 (d, J=1.57, 1H), 6.98 (m, 1H), 6.92 (d, J=1.76, 1H), 6.88 (d, J=1.96, 1H), 6.86 (d, J=2.35, 1H), 6.82 (d, J=1.96, 1H), 6.78 (dd, J=7.93, 1.27, 1H), 6.60 (m, 1H), 4.99 (brs, 2H), 4.28 (d, J=5.48, 2H), 3.76 (s, 3H), 3.73 (s, 3H). LRMS: 418 (calc.), 419.5 (obt.).

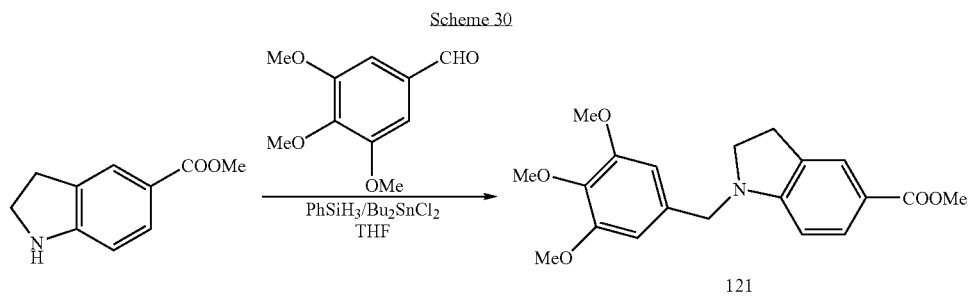

Scheme 30

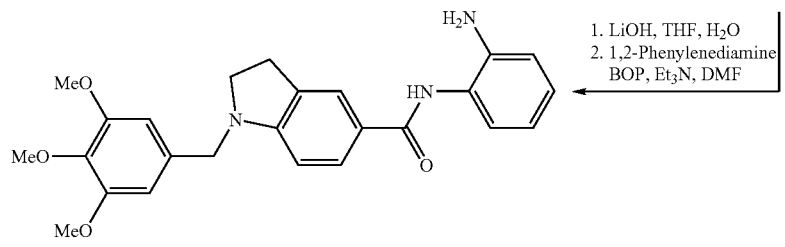

122: Example 70

Example 70

1-(3,4,5-Trimethoxy-benzyl)-2,3-dihydro-1H-indole-5-carboxylic acid (2-amino-phenyl)-amide (122)

The title compound 122 was obtained following the procedure described in example 68 step 4 (scheme 28) (to produce the intermediate 121) and procedures described in example 1, steps 4 and 5 (scheme 1) (33% yield). $^{1}$H-NMR (DMSO) δ: 9.29 (s, 1H), 7.71 (dd, J=8.22, 1.77, 1H), 7.66 (brm, 1H), 7.12 (dd, J=7.93, 1.47, 1H), 6.93-6.89 (m, 3H), 6.84 (dd, J=8.22, 1.96, 1H), 6.75 (dd, J=8.02, 1.37, 1H), 6.65 (d, J=8.41, 1H), 6.57 (dt, J=7.53, 1.30, 1H), 4.82 (s, 2H), 3.73 (s, 6H), 3.41 (t, J=8.51, 2H), 2.98 (t, J=8.51, 2H). LRMS: 435.2 (Calc.); 436.5 (found).

(482.3 mg, 2.71 mmol) and dibutyltin dichloride (76 mg, 0.25 mmol) in THF was added phenylsilane (334 μl, 2.71 mmol). The mixture was stirred at room temperature overnight under nitrogen, THF was evaporated off the mixture and the residue was purified by flash chromatography (hexane/EtOAc, 20/80) to afford the title compound 123 (881 mg, 98%). $^{1}$H-NMR (DMSO) δ: 8.00 (d, J=1.0 Hz, 1H), 7.70 (d, J=8.2 Hz, 1H); 7.58 (dd, J=8.4, 1.6 Hz, 1H); 7.52 (d, J=2.0 Hz, 1H); 6.70 (d, J=9.0 Hz, 2H); 6.59 (d, J=9.0 Hz, 2H); 5.48 (t, J=5.8 Hz, 1H); 4.31 (d, J=5.7 Hz, 2H); 3.83 (s, 3H); 3.68 (t, J=4.7 Hz, 4H); 2.86 (t, J=4.7 Hz, 4H).

Step 2: 3-{[tert-Butoxycarbonyl-(4-morpholin-4-yl-phenyl)-amino]-methyl}-1H-indole-6-carboxylic acid methyl ester (124)

To a solution of 123 (689 mg, 1.89 mmol) in THF (100 ml) Et$_3$N (289 μl, 2.08 mmol) was added dropwise. (BOC)$_2$O was Scheme 32

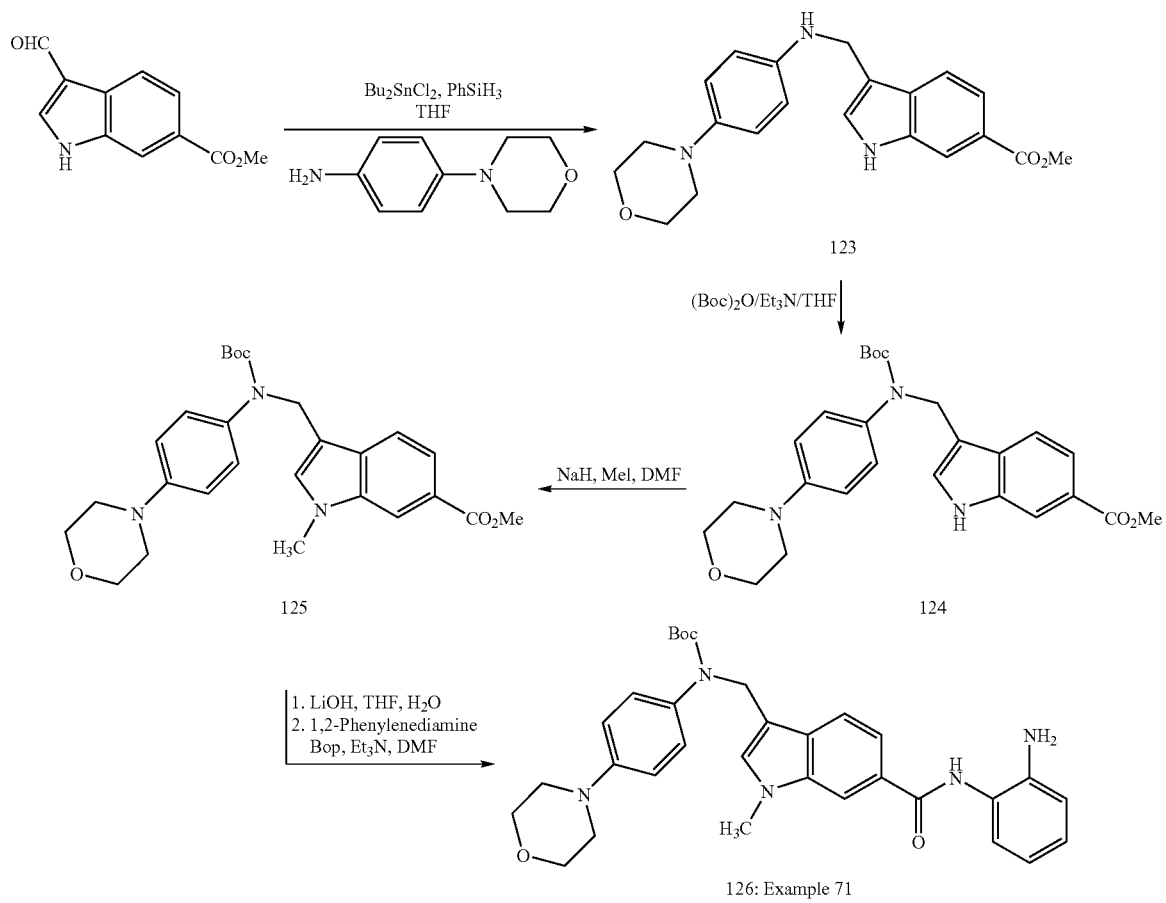

126: Example 71

Example 71

[6-(2-Amino-phenylcarbamoyl)-1-methyl-1H-indol-3-ylmethyl]-(4-morpholin-4-yl-phenyl)-carbamic acid tert-butyl ester (126)

Step 1: 3-[(4-Morpholin-4-yl-phenylamino)-methyl]-1H-indole-6-carboxylic acid methyl ester (123)

To a solution of 3-formyl-1H-indole-6-carboxylic acid methyl ester (500 mg, 2.46 mmol), 4-morpholinoaniline added slowly and the mixture was stirred at room temperature overnight under nitrogen, THF was evaporated off and the residue was partitioned between water and CH$_2$Cl$_2$. Organic layer was separated, dried over MgSO$_4$, evaporated to form another residue which was purified by flash column chromatography (EtOAc/hexane, 7:3) to afford the title compound 124 (692 mg, 79%). $^{1}$H-NMR (CDCl$_3$) δ: 8.24 (m, 1H), 8.09 (m, 1H); 7.76 (dd, J=8.2, 1.4 Hz, 1H); 7.55 (d, J=8.8 Hz, 1H); 7.13 (d, J=2.5 Hz, 1H); 6.93 (m, 3H); 4.97 (s, 2H); 3.94 (s, 3H); 3.89 (m, 4H); 3.16 (m, 4H); 1.47 (s, 9H).

Step 3: 3-{[tert-Butoxycarbonyl-(4-morpholin-4-yl-phenyl)-amino]-methyl}-1-methyl-1H-indole-6-carboxylic acid methyl ester (125)

To a solution of the ester 124 (473 mg, 1.02 mmol) in DMF (15 ml) was added 60% NaH (45 mg, 1.12 mmol). The solution was stirred for one hour at room temperature under nitrogen, cooled to 0° C., treated with MeI (170 µl, 1.12 mmol), warmed to room temperature and stirred overnight under nitrogen. The mixture was partitioned between water and AcOEt, organic layer was collected, dried over MgSO$_4$ and concentrated in vacuo to yield 454 mg (93%). $^1$H-NMR (DMSO) δ: 7.99 (m, 1H); 7.56 (dd, J=1.4, 8.2 Hz, 1H); 7.47 (m, 1H); 7.27 (s, 1H); 6.86 (d, J=8.8 Hz, 2H); 6.75 (d, J=9.0 Hz, 2H); 4.86 (s, 2H); 3.83 (s, 3H); 3.76 (s, 3H); 3.67 (t, J=4.8 Hz, 4H); 3.01 (t, J=4.8 Hz, 4H); 1.37 (s, 9H).

Steps 4-5: [6-(2-Amino-phenylcarbamoyl)-1-methyl-1H-indol-3-ylmethyl]-(4-morpholin-4-yl-phenyl)-carbamic acid tert-butyl ester (126)

The procedures described in example 1 steps 4 and 5 (scheme 1) were followed to afford the title compound 126 as a solid (134 mg, 33%). $^1$H-NMR (DMSO) δ: 9.59 (s, 1H); 8.06 (s, 1H); 7.61 (dd, J=1.6, 8.4 Hz, 1H); 7.48 (m, 1H); 7.21 (s, 1H); 7.15 (dd, J=7.8, 1.4 Hz, 1H); 6.94 (dt, J=7.8, 1.6 Hz, 1H); 6.86 (m, 2H); 6.76 (m, 3H); 6.58 (dt, J=7.4, 1.4 Hz, 1H); 4.88 (s, 2H); 4.87 (s, 2H); 3.76 (s, 3H); 3.68 (t, J=4.8 Hz, 4H); 3.02 (t, J=4.8 Hz, 4H); 1.39 (s, 9H). LRMS: 556.2 (Calc.); 557.5 (found).

Scheme 32

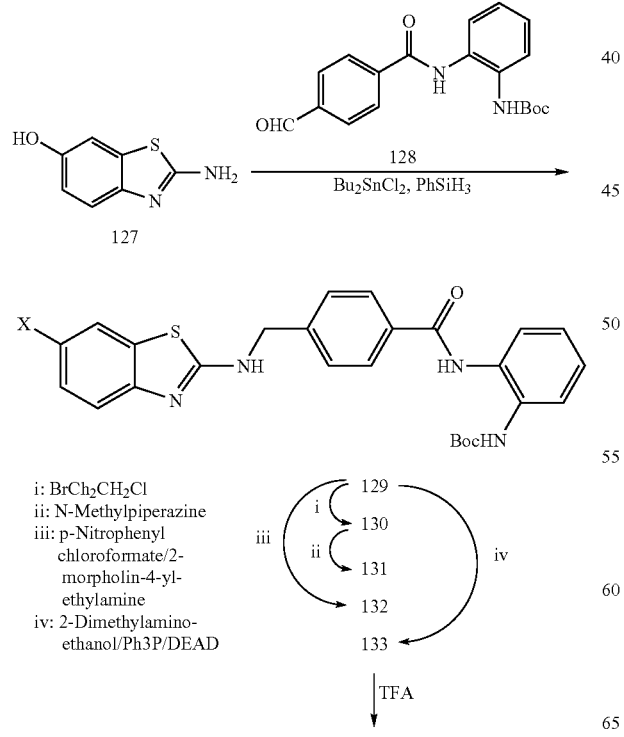

i: BrCH$_2$CH$_2$Cl
ii: N-Methylpiperazine
iii: p-Nitrophenyl chloroformate/2-morpholin-4-yl-ethylamine
iv: 2-Dimethylamino-ethanol/Ph$_3$P/DEAD

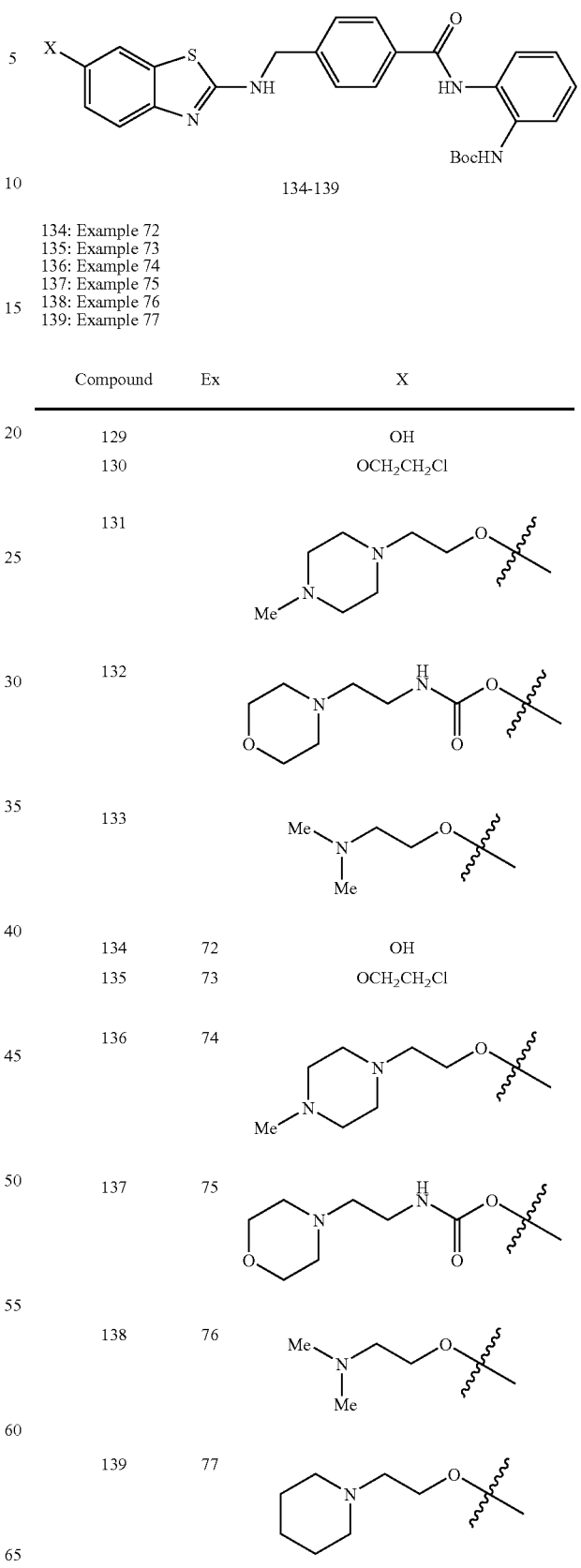

| Compound | Ex | X |
|---|---|---|
| 129 | | OH |
| 130 | | OCH$_2$CH$_2$Cl |
| 131 | | (4-methylpiperazin-1-yl)ethoxy |
| 132 | | (morpholin-4-yl)ethyl-NHC(O)O- |
| 133 | | Me$_2$N-CH$_2$CH$_2$-O- |
| 134 | 72 | OH |
| 135 | 73 | OCH$_2$CH$_2$Cl |
| 136 | 74 | (4-methylpiperazin-1-yl)ethoxy |
| 137 | 75 | (morpholin-4-yl)ethyl-NHC(O)O- |
| 138 | 76 | Me$_2$N-CH$_2$CH$_2$-O- |
| 139 | 77 | (piperidin-1-yl)ethoxy |

134: Example 72
135: Example 73
136: Example 74
137: Example 75
138: Example 76
139: Example 77

Example 72

N-(2-Amino-phenyl)-4-[(6-hydroxy-benzothiazol-2-ylamino)-methyl]-benzamide (134)

Step 1: (2-{4-[(6-Hydroxy-benzothiazol-2-ylamino)-methyl]-benzoylamino}-phenyl)-carbamic acid tert-butyl ester (129)

The title compound 129 was obtained following the same procedure as for the reductive amination described in Scheme 3, step 2 (example 12) starting from aminothiazole 127 and aldehyde 128 (described in the Patent Application WO 03/024448) (96% yield). $^1$H NMR: (acetone-$d_6$) δ(ppm): 9.60 (s, 1H), 8.25 (bs, 1H), 7.99 (d, J=8.2 Hz, 2H), 7.69 (d, J=7.4 Hz, 1H), 7.61-7.58 (m, 3H), 7.39 (bs, 1H), 7.27 (d, J=8.6 Hz, 1H), 7.19 (quint.d, J=7.4, 2.0 Hz, 2H), 7.12 (d, J=2.3 Hz, 1H), 6.79 (dd, J=8.6, 2.7 Hz, 1H), 4.78 (s, 2H), 1.48 (s, 9H). m/z: 491.5 (MH$^+$).

Step 2: N-(2-Amino-phenyl)-4-[(6-hydroxy-benzothiazol-2-ylamino)-methyl]-benzamide (134)

The title compound 134 was obtained starting from compound 129 following the same procedure as for the Boc cleavage described in scheme 28, step 5 (example 68) (53% yield). $^1$H NMR: (DMSO-$d_6$) δ(ppm): 9.58 (s, 1H), 9.12 (s, 1H), 8.25 (t, J=6.3 Hz, 1H), 7.91 (d, J=7.8 Hz, 2H), 7.45 (d, J=8.2 Hz, 2H), 7.15 (d, J=8.6 Hz, 1H) 7.12 (s, 1H), 7.02 (d, J=2.7 Hz, 1H), 6.94 (t, J=6.7 Hz, 1H), 6.75 (dd, J=8.2, 1.2 Hz, 1H), 6.63 (dd, J=8.6, 2.3 Hz, 1H), 6.56 (t, J=7.8 Hz, 1H), 4.87 (s, 2H), 4.59 (d, J=5.5 Hz, 2H). m/z: 391.2 (MH$^+$).

Example 73

N-(2-Amino-phenyl)-4-{[6-(2-chloro-ethoxy)-benzothiazol-2-ylamino]-methyl}-benzamide (135)

Step 1: [2-(4-{[6-(2-Chloro-ethoxy)-benzothiazol-2-ylamino]-methyl}-benzoylamino)-phenyl]-carbamic acid tert-butyl ester (130)

The title compound 130 was obtained following the procedure described in *J. Med. Chem.*, 2002, 45 (6), 1300-1312, and using compound 129 as starting material. (43% yield). $^1$H NMR: (DMSO-$d_6$) δ(ppm): 9.59 (bs, 1H), 8.25 (bs, 1H), 7.99 (d, J=8.0 Hz, 2H), 7.69 (dd, J=7.4, 1.4 Hz, 1H), 7.60 (d, J=8.4 Hz, 2H), 7.35 (d, J=8.4 Hz, 1H), 7.32 (d, J=2.5 Hz, 1H), 7.19 (quint.d, J=7.2, 2.3 Hz, 2H), 6.91 (dd, J=8.6, 2.5 Hz, 1H), 4.79 (s, 2H), 4.30 (t, J=5.3 Hz, 2H), 3.92 (t, J=5.5 Hz, 3H), 1.48 (s, 9H). m/z: 553.5, 554.5 (M$^+$, M+1).

Step 2. N-(2-Amino-phenyl)-4-{[6-(2-chloro-ethoxy)-benzothiazol-2-ylamino]-methyl}-benzamide (135)

The title compound 135 was obtained starting from compound 130 following the same procedures as for the Boc cleavage described in scheme 28, step 5 (example 68) (48% yield). $^1$H NMR: (DMSO-$d_6$) δ(ppm): 9.59 (s, 1H), 8.39 (t, J=5.5 Hz, 1H), 7.92 (d, J=8.0 Hz, 2H), 7.46 (d, J=8.2 Hz, 2H), 7.35 (d, J=2.5 Hz, 1H), 7.27 (d, J=8.8 Hz, 1H), 7.13 (d, J=6.8 Hz, 1H), 7.00 (d, J=8.0, 1.4 Hz, 1H), 6.94 (td, J=8.0, 1.4 Hz, 1H), 6.83 (dd, J=8.8, 6.1 Hz, 1H), 6.75 (dd, J=8.0, 1.4 Hz, 1H), 6.57 (t, J=8.6 Hz, 1H), 4.88 (s, 2H), 4.63 (d, J=6.1 Hz, 2H), 4.21 (t, J=5.1 Hz, 2H), 3.92 (t, J=5.3 Hz, 2H). mz: 453.4, 455.4 (M$^+$, M+1).

Example 74

N-(2-Amino-phenyl)-4-({6-[2-(4-methyl-piperazin-1-yl)-ethoxy]-benzothiazol-2-ylamino}-methyl)-benzamide (136)

Step 1: {2-[4-({6-[2-(4-Methyl-piperazin-1-yl)-ethoxy]-benzothiazol-2-ylamino}-methyl)-benzoylamino]-phenyl}-carbamic acid tert-butyl ester (131)

The title compound 131 was obtained following the procedure described in *J. Med. Chem.*, 2002, 45, (6), 1300-1312, and using compound 130 as starting material. (91% yield). $^1$H NMR: (Acetone-$d_6$) δ(ppm): 7.99 (d, J=8.2 Hz, 2H), 7.69 (d, J=7.2 Hz, 1H), 7.59 (d, J=8.6 Hz, 2H), 7.56 (d, J=2.0 Hz, 1H), 7.33 (d, J=8.8 Hz, 1H), 7.28 (d, J=2.5 Hz, 1H), 7.21 (quint.d, J=7.2, 1.2 Hz, 2H), 7.03-6.93 (m, 1H), 6.87 (dd, J=8.8, 2.7 Hz, 1H), 4.79 (s, 2H), 4.11 (t, J=5.9 Hz, 2H), 2.75 (t, J=5.7 Hz, 2H), 2.67-2.51 (m, 4H), 2.48-2.38 (m, 4H), 2.21 (s, 3H), 1.49 (s, 9H).

Step 2: N-(2-Amino-phenyl)-4-({6-[2-(4-methyl-piperazin-1-yl)-ethoxy]-benzothiazol-2-ylamino}-methyl)-benzamide (136)

The title compound 136 was obtained starting from compound 131 following the same procedures as for the Boc cleavage described in scheme 28, step 5 (example 68) (60% yield). $^1$H NMR: (CDCl$_3$) δ(ppm): 7.97 (d, J=7.9 Hz, 2H), 7.58 (d, J=7.9 Hz, 2H), 7.51 (d, J=8.8 Hz, 1H), 7.42 (d, J=8.0 Hz, 1H), 7.22-7.17 (m, 2H), 6.99-6.92 (m, 3H), 4.78 (s, 2H), 4.20-4.18 (m, 2H), 2.97-2.87 (m, 8H), 2.70-2.66 (m, 2H), 2.61 (s, 3H). m/z: 517.5 (MH$^+$).

Example 75

(2-Morpholin-4-yl-ethyl)-carbamic acid 2-[4-(2-amino-phenylcarbamoyl)-benzylamino]-benzothiazol-6-yl ester (137)

Step 1: [2-(4-{[6-(2-Morpholin-4-yl-ethylcarbamoyloxy)-benzothiazol-2-ylamino]-methyl}-benzoylamino)-phenyl]-carbamic acid tert-butyl ester (132)

To a solution of p-nitrophenylchloroformate (171 mg, 0.848 mmol) in THF (15 mL) cooled to −78° C. under N$_2$ atmosphere was added Et$_3$N (236 μL, 1.70 mmol). Then a suspension of the intermediate 129 (416 mg, 0.848 mmol) in THF (4.2 mL) was added via canula. The resulting yellow mixture was stirred at −78° C. for 1 h and at 0° C. for 1.5 h, heated at 40° C. for 16 h and cooled to r.t. Then, neat 4-(2-aminoethyl)morpholine (119 μL, 0.848 mmol) was added and the solution was stirred for 4 h, quenched by addition of MeOH. It was allowed to stir for 30 min. and concentrated. The resulting material was purified by flash chromatography using MeOH/DCM (3:97) affording the title compound 132 (165 mg, 30% yield). $^1$H NMR: (DMSO-$d_6$) δ(ppm): 9.77 (s, 1H), 8.64 (bs, 1H), 8.56 (t, J=5.9 Hz, 1H), 7.90 (d, J=8.2 Hz, 2H), 7.60 (t, J=5.9 Hz, 1H), 7.50 (d, J=8.0 Hz, 2H), 7.50-7.48 (m, 2H), 7.45 (d, J=2.3 Hz, 1H), 7.30 (d, J=8.8 Hz, 1H), 7.17 (t, J=7.6 Hz, 1H), 7.12 (t, J=7.8 Hz, 1H), 6.90 (dd, J=8.2, 2.0 Hz, 1H), 4.67 (d, J=6.0 Hz, 2H), 3.56 (t, J=4.1 Hz, 4H), 3.31 (t, J=6.1 Hz, 2H), 3.16 (q, J=6.1 Hz, 2H), 2.39 (t, J=6.8 Hz, 4H), 1.42 (s, 9H). m/z: 647.7 (MH$^+$).

Step 2: (2-Morpholin-4-yl-ethyl)-carbamic acid 2-[4-(2-amino-phenylcarbamoyl)-benzylamino]-benzothiazol-6-yl ester (137)

The title compound 137 was obtained starting from compound 132 following the same procedure as for the Boc cleavage described in scheme 28, step 5 (example 68) (55% yield). $^1$H NMR: (DMSO-d$_6$): $^1$H NMR: (DMSO-d$_6$): 9.60 (s, 1H), 8.56 (t, J=6.3 Hz, 1H), 7.93 (d, J=8.4 Hz, 2H), 7.61 (t, J=5.5 Hz, 1H), 7.47 (d, J=7.8 Hz, 2H), 7.46 (d, J=2.3 Hz, 1H), 7.31 (d, J=8.6 Hz, 1H), 7.14 (d, J=6.8 Hz, 2H), 6.95 (t, J=6.5 Hz, 1H), 6.92 (dd, J=8.8, 2.5 Hz, 1H), 6.75 (d, J=7.8 Hz, 1H), 6.57 (t, J=7.4 Hz, 1H), 4.88 (s, 2H), 4.66 (d, J=5.9 Hz, 2H), 3.57 (t, J=4.5 Hz, 4H), 3.33-3.31 (m, 2H), 2.41-2.38 (m, 6H). m/z: 547.5 (MH$^+$).

Example 76

N-(2-Amino-phenyl)-4-{[6-(2-dimethylamino-ethoxy)-benzothiazol-2-ylamino]-methyl}-benzamide (138)

Step 1: [2-(4-{[6-(2-Dimethylamino-ethoxy)-benzothiazol-2-ylamino]-methyl}-benzoylamino)-phenyl]-carbamic acid tert-butyl ester (133)

To a suspension of compound 129 (1.00 g, 2.04 mmol) in THF (6.8 mL) at room temperature under N$_2$ atmosphere were successively added N,N-dimethylethanolamine (225 µL, 2.24 mmol) and triphenylphosphine (696 mg, 2.65 mmol) followed by diisopropyl azodicarboxylate (550 µL, 2.65 mmol). Heat was evolved and the mixture turned dark red. It was stirred for 4 h, THF was removed in vacuo and the dark residue was partitioned between EtOAc and H$_2$O. Organic phase was collected and extracted with HCl 1N. Acidic extract was separated and neutralized with saturated aqueous NaHCO$_3$ under vigorous stirring. A white precipitate was formed which was collected by filtration to afford the title compound 133 (430 mg, 37% yield). $^1$H NMR: (acetone-d$_6$) δ(ppm): 7.99 (d, J=8.4 Hz, 2H), 7.70 (dd, J=8.0, 2.2 Hz, 1H), 7.59 (d, J=8.4 Hz, 2H), 7.56 (d, J=1.6 Hz, 1H), 7.33 (d, J=9.0 Hz, 1H), 7.27 (d, J=2.5 Hz, 1H), 7.19 (quint.d, J=7.8, 2.4 Hz, 2H), 6.87 (dd, J=8.8, 2.5 Hz, 1H), 4.80 (s, 2H), 4.08 (t, J=5.9 Hz, 2H), 2.67 (t, J=5.7 Hz, 2H), 2.27 (s, 6H), 1.48 (s, 9H). m/z: 562.5 (MH$^+$).

Step 2: N-(2-Amino-phenyl)-4-{[6-(2-dimethylamino-ethoxy)-benzothiazol-2-ylamino]-methyl}-benzamide (138)

The title compound 138 was obtained starting from the compound 133 following the same procedures as for the Boc cleavage described in scheme 28, step 5 (example 68) (82% yield). $^1$H NMR: (CD$_3$OD) δ(ppm): 7.96 (d, J=8.2 Hz, 2H), 7.53 (d, J=8.2 Hz, 2H), 7.32 (d, J=8.8 Hz, 1H), 7.23 (d, J=2.5 Hz, 1H), 7.17 (d, J=9.0 Hz, 1H), 7.07 (td, J=9.0, 1.6 Hz, 1H), 6.90 (dd, J=8.8, 2.7 Hz, 1H), 6.89 (dd, J=6.5, 1.6 Hz, 1H), 6.76 (t, J=6.5 Hz, 1H), 4.71 (s, 2H), 4.10 (t, J=5.3 Hz, 2H), 2.79 (t, J=5.5 Hz, 2H), 2.36 (s, 6H). m/z: 462.5 (MH$^+$).

Example 77

N-(2-Amino-phenyl)-4-{[6-(2-piperidin-1-yl-ethoxy)-benzothiazol-2-ylamino]-methyl}-benzamide (139)

The title compound 139 was obtained following the same procedures (two-step reaction sequence) described in example 76 but substituting N,N-dimethylethanolamine for 1-piperidineethanol (52% yield over two steps). $^1$H NMR: (CD$_3$OD) δ(ppm): 7.96 (d, J=8.4 Hz, 2H), 7.53 (d, J=8.2 Hz, 2H), 7.36 (d, J=8.8 Hz, 1H), 7.32 (d, J=2.5 Hz, 1H), 7.17 (d, J=8.0 Hz, 1H), 7.07 (td, J=6.1, 1.2 Hz, 1H), 6.97 (dd, J=8.8, 2.7 Hz, 1H), 6.90 (d, J=7.8 Hz, 1H), 6.77 (t, J=7.2 Hz, 1H), 4.71 (s, 2H), 4.35 (t, J=4.9 Hz, 2H), 3.64-3.60 (m, 2H), 3.56 (t, J=4.9 Hz, 2H), 3.10-3.01 (m, 2H), 2.05-1.92 (m, 2H), 1.90-1.81 (m, 4H). m/z: 502.5 (MH$^+$).

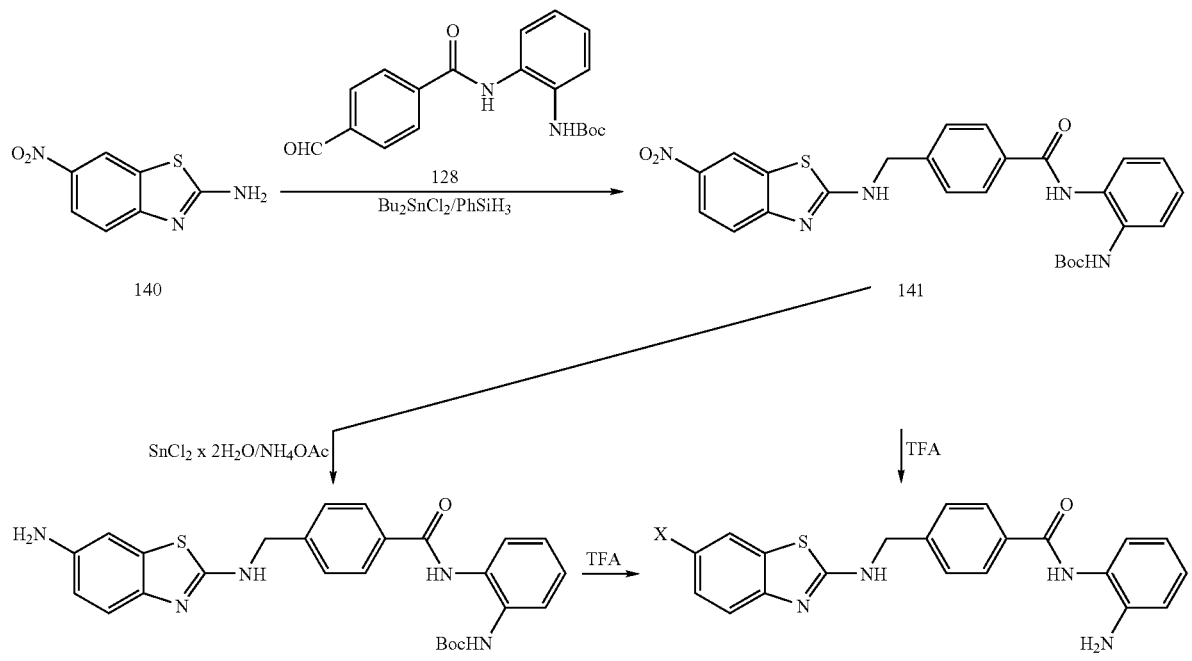

Example 78

N-(2-Amino-phenyl)-4-[(6-nitro-benzothiazol-2-ylamino)-methyl]-benzamide (142)

Step 1: (2-{4-[(6-Nitro-benzothiazol-2-ylamino)-methyl]-benzoylamino}-phenyl)-carbamic acid tert-butyl ester (141)

The title compound 141 was obtained starting from compounds 140 and 128 (described in the Patent Application WO 03/024448), following the same procedure as for the reductive amination described in scheme 3, step 2 (example 12) (66% yield). $^1$H NMR: (CD$_3$OD) δ(ppm): 9.78 (s, 1H), 9.28 (bs, 1H), 8.71 (d, J=2.5 Hz, 1H), 8.64 (bs, 1H), 8.09 (dd, J=9.0, 2.5 Hz, 1H), 7.92 (d, J=8.2 Hz, 2H), 7.51 (dd, J=8.6, 2.2 Hz, 2H), 7.46 (d, J=9.0, 2H), 7.17 (td, J=7.4, 1.8 Hz, 1H), 7.12 (td, J=7.1, 1.8 Hz, 1H), 4.75 (bs, 2H), 1.42 (s, 9H). m/z: 542.2 (M+Na).

Step 2: N-(2-Amino-phenyl)-4-[(6-nitro-benzothiazol-2-ylamino)-methyl]-benzamide (142)

The title compound 142 was obtained following the same procedure as for the Boc cleavage described in scheme 28, step 5 (example 68) using compound 141 as the starting material (98% yield). $^1$H NMR: (DMSO-d$_6$): 10.06 (s, 1H), 9.30 (bs, 1H), 8.71 (d, J=2.3 Hz, 1H), 8.09 (dd, J=9.0, 2.3 Hz, 1H), 9.97 (d, J=8.2 Hz, 2H), 7.51 (d, J=8.2 Hz, 2H), 7.46 (d, J=8.8 Hz, 1H), 7.30 (d, J=7.0 Hz, 1H), 7.17 (t, J=7.8 Hz, 1H), 7.10 (d, J=7.8 Hz, 1H), 7.03 (t, J=7.2 Hz, 1H), 4.75 (d, J=5.5 Hz, 2H). m/z: 420.5 (MH$^+$).

Example 79

4-[(6-Amino-benzothiazol-2-ylamino)-methyl]-N-(2-amino-phenyl)-benzamide (144)

Step 1: (2-{4-[(6-Amino-benzothiazol-2-ylamino)-methyl]-benzoylamino}-phenyl)-carbamic acid tert-butyl ester (143)

To a suspension of compound 141 (200 mg, 0.385 mmol) in a mixture of THF/MeOH/H$_2$O (10 mL/10 mL/10 mL) were successively added tin(II) chloride dihydrate (1.35 g, 8.46 mmol) and ammonium acetate (1.09 g, 14.12 mmol). The mixture was refluxed for 2 days, the tin salts were filtered off and the filtrate was concentrated in vacuo. The residue was partitioned between EtOAc and H$_2$O (brine was added to break the emulsion). Organic phase was successively washed with saturated aqueous NaHCO$_3$ and brine, dried over MgSO$_4$, and concentrated in vacuo to afford the title compound 143 (145 mg, 77% yield). $^1$H NMR: (DMSO-d$_6$) δ (ppm): 12.89 (bs, 1H), 10.79 (s, 1H), 8.12 (d, J=2.0 Hz, 1H), 8.05 (d, J=8.8 Hz, 2H), 7.90-7.68 (m, 3H), 7.62 (d, J=8.4 Hz, 2H), 7.48 (bs, 1H), 7.21 (dd, J=4.9, 3.7 Hz, 1H), 4.65 (s, 2H). m/z: 490.5 (MH$^+$).

Step 2: 4-[(6-Amino-benzothiazol-2-ylamino)-methyl]-N-(2-amino-phenyl)-benzamide (144)

The title compound 144 was obtained following the same procedures as for the Boc-cleavage described in scheme 28, step 5 (example 68) using compound 143 as starting material. (58% yield). $^1$H NMR: (DMSO-d$_6$): 9.58 (s, 1H), 8.09 (t, J=5.9 Hz, 1H), 7.91 (d, J=8.0 Hz, 2H), 7.45 (d, J=8.4 Hz, 2H), 7.13 (d, J=7.0 Hz, 1H), 7.05 (d, J=8.6 Hz, 1H), 6.94 (t, J=6.8 Hz, 1H), 6.81 (d, J=2.2 Hz, 1H), 6.75 (dd, J=6.7, 1.2 Hz, 1H), 6.57 (t, J=6.5 Hz, 1H), 6.48 (dd, J=8.4, 2.2 Hz, 1H), 5.19 (s, 2H), 4.81 (s, 2H), 4.58 (d, J=5.9 Hz, 2H). m/z: 390.5 (MH$^+$)

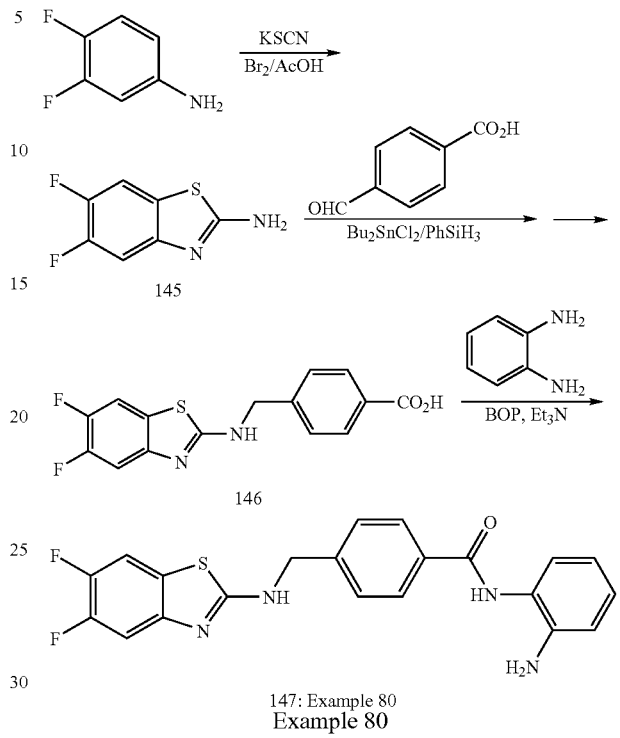

Scheme 34

147: Example 80

Example 80

N-(2-Amino-phenyl)-4-[(5,6-difluoro-benzothiazol-2-ylamino)-methyl]-benzamide (147)

Step 1: 5,6-Difluoro-benzothiazol-2-ylamine (145)

The title compound 145 was obtained following the procedure described in *J. Het. Chem,* 1971, 8 (309-310) starting from 4,5-difluoroaniline (95% yield). $^1$H NMR: (DMSO-d$_6$) δ(ppm): 7.78 (dd, J=10.6, 8.6 Hz, 1H), 7.61 (s, 2H), 7.32 (dd, J=11.9, 7.2 Hz, 1H). m/z: 337.5 (M+Na$^+$)

Step 2: 4-[(5,6-Difluoro-benzothiazol-2-ylamino)-methyl]-benzoic acid (146)

The title compound 146 was obtained starting from the compound 145 following the same procedure as for the reductive amination described in scheme 3, step 2 (example 12) (63% yield). $^1$H NMR: (DMSO-d$_6$) δ (ppm): 8.72 (t, J=5.9 Hz, 1H), 7.89 (d, J=8.4 Hz, 2H), 7.82 (dd, J=10.4, 8.0 Hz, 1H), 7.44 (d, J=8.4 Hz, 2H), 7.40 (dd, J=11.9, 7.4 Hz, 1H), 4.65 (d, J=5.7 Hz, 2H). m/z: 315.2 (MH$^+$).

Step 3: N-(2-Amino-phenyl)-4-[(5,6-difluoro-benzothiazol-2-ylamino)-methyl]-benzamide (147)

The title compound 147 was obtained starting from the compound 146 following the same procedure as for the BOP coupling reaction described in scheme 1, step 5 (example 1) (32% yield). $^1$H NMR: (DMSO-d$_6$): 9.59 (s, 1H), 8.73 (t, J=5.9 Hz, 1H), 7.93 (d, J=8.2 Hz, 2H), 7.83 (dd, J=10.4, 8.0 Hz, 1H), 7.45 (d, J=8.2 Hz, 2H), 7.40 (dd, J=11.9, 7.2 Hz, 1H), 7.13 (d, J=7.8 Hz, 1H), 6.94 (td, J=7.8, 1.4 Hz, 1H), 6.75 (dd, J=7.8, 1.4 Hz, 1H), 6.57 (td, J=7.6, 1.2 Hz, 1H), 4.87 (s, 2H), 4.65 (d, J=5.9 Hz, 2H). m/z: 411.4 (MH$^+$).

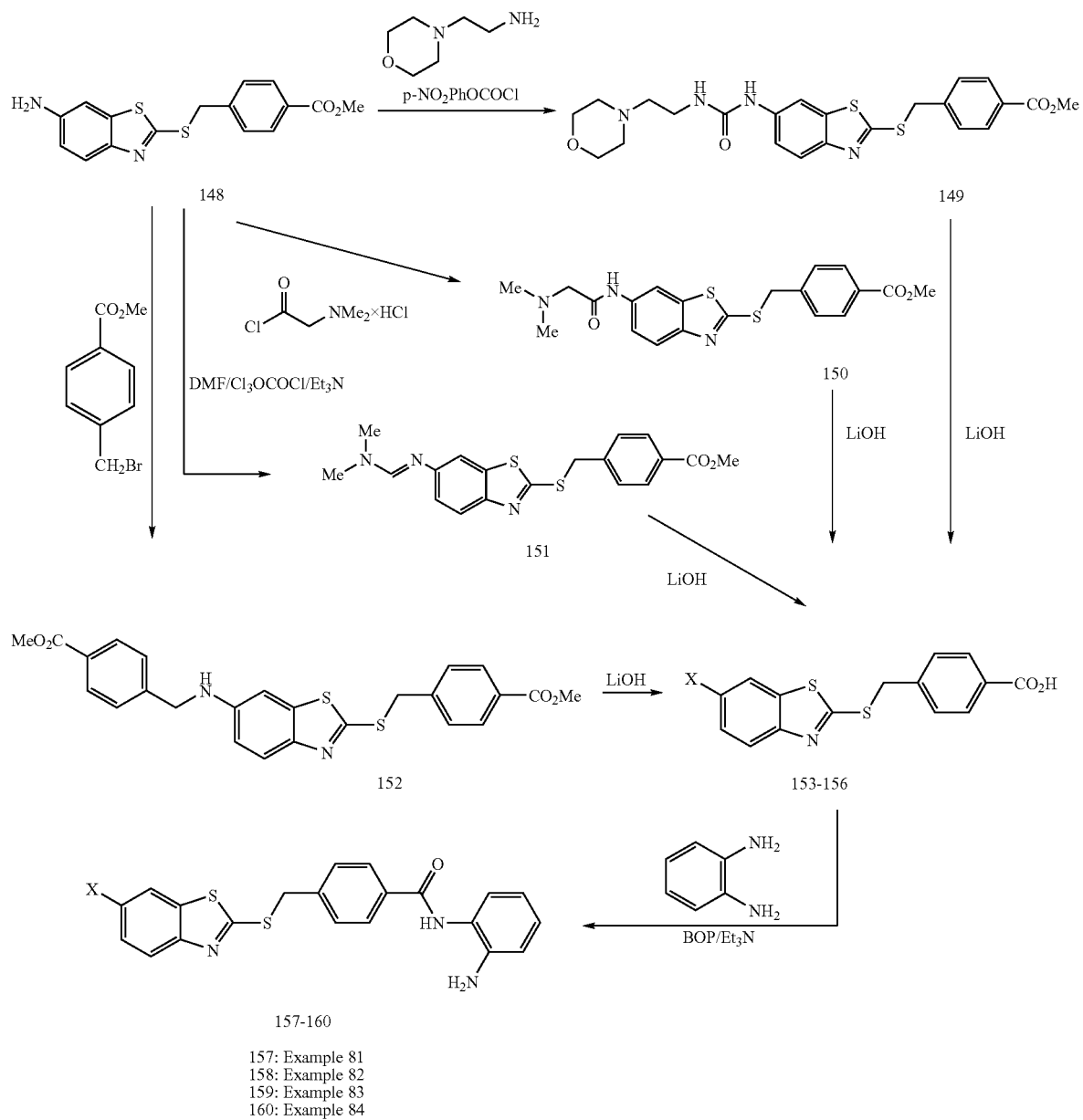

| 156 | 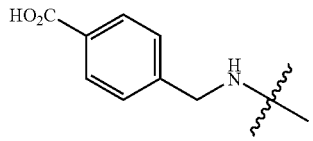 | 160 | 84 | 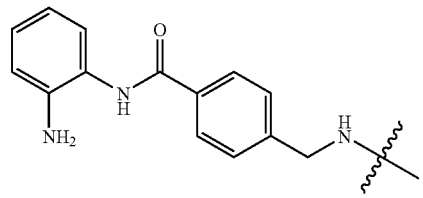 |

Example 81

N-(2-Amino-phenyl)-4-{6-[3-(2-morpholin-4-yl-ethyl)-ureido]-benzothiazol-2-ylsulfanylmethyl}-benzamide (157)

Step 1: 4-{6-[3-(2-Morpholin-4-yl-ethyl)-ureido]-benzothiazol-2-ylsulfanylmethyl}-benzoic acid methyl ester (149)

The title compound 149 was obtained following the same procedure as for the carbamate formation described in scheme 32, step 1 (example 75), but substituting compound 129 for compound 148 (described in the Patent Application WO 03/024448) (70% yield). $^{1}$H NMR: (DMSO-$d_6$) δ (ppm): 9.28 (bs, 1H), 8.18 (d, J=2.3 Hz, 1H), 7.90 (d, J=8.2 Hz, 2H), 7.77 (d, J=8.6 Hz, 1H), 7.61 (d, J=8.2 Hz, 2H), 7.42 (dd, J=8.8, 2.2 Hz, 1H), 4.68 (s, 2H), 3.82 (s, 3H), 3.59-3.58 (m, 4H), 3.33-3.32 (m, 2H), 3.21 (q, J=6.1 Hz, 2H), 2.38-2.37 (m, 4H). m/z: 487.4 (MH$^+$).

Step 2: 4-{6-[3-(2-Morpholin-4-yl-ethyl)-ureido]-benzothiazol-2-ylsulfanylmethyl}-benzoic acid methyl ester (153)

The title compound 153 was obtained following the same procedure as for the hydrolysis described in scheme 1, step 4 (example 1) using compound 149 as starting material (50% yield). $^{1}$H NMR: (DMSO-$d_6$) δ(ppm): 9.75 (bs, 1H), 8.22 (d, J=2.2 Hz, 1H), 7.90 (d, J=8.4 Hz, 2H), 7.76 (d, J=8.8 Hz, 1H), 7.61 (d, J=8.4 Hz, 2H), 7.55 (d, J=6.3 Hz, 1H), 7.49 (dd, J=8.8, 2.2 Hz, 1H), 4.68 (s, 2H), 3.58 (t, J=4.3 Hz, 4H), 3.34-3.32 (m, 2H), 3.21 (q, J=5.9 Hz, 2H), 2.38 (t, J=6.3 Hz, 4H). m/z: 473.4 (MH$^+$).

Step 3: N-(2-Amino-phenyl)-4-{6-[3-(2-morpholin-4-yl-ethyl)-ureido]-benzothiazol-2-ylsulfanylmethyl}-benzamide (157)

The title compound 157 was obtained following the same procedures as the BOP coupling described in scheme 1, step 5 (example 1) using compound 153 as starting material (26% yield). $^{1}$H NMR: (DMSO-$d_6$) δ (ppm): 9.59 (s, 1H), 8.84 (s, 1H), 8.13 (d, J=2.2 Hz, 1H), 7.90 (d, J=8.2 Hz, 2H), 7.71 (d, J=8.6 Hz, 1H), 7.58 (d, J=8.2 Hz, 2H), 7.30 (dd, J=8.8, 2.2 Hz 1H), 7.12 (d, J=7.0 Hz, 1H), 6.94 (t, J=7.0 Hz, 1H), 6.74 (dd, J=8.1, 1.5 Hz, 1H), 6.56 (t, J=7.4 Hz, 1H), 6.14 (t, J=4.9 Hz, 1H), 4.88 (bs, 2H), 4.66 (s, 2H) 3.58 (t, J=4.5 Hz, 4H), 3.31-3.30 (m, 2H), 3.21 (q, J=5.7 Hz, 2H), 2.38 (t, J=6.3 Hz, 4H). m/z: 563.5 (MH$^+$).

Example 82

N-(2-Amino-phenyl)-4-[6-(2-dimethylamino-acetylamino)-benzothiazol-2-ylsulfanylmethyl]-benzamide (158)

Step 1: 4-[6-(2-Dimethylamino-acetylamino)-benzothiazol-2-ylsulfanylmethyl]-benzoic acid methyl ester (150)

NaHCO$_3$ (356 mg, 4.24 mmol) was added to a suspension of compound 148 (described in the Patent Application WO 03/024448) (701 mg, 2.12 mmol) and Me$_2$NCH$_2$COCl.HCl (670 mg, 4.24 mmol) in CH$_3$CN followed by addition of Et$_3$N (295 μl, 2.12 mmol). The mixture was stirred at room temperature 24 h, concentrated in vacuo and the residue was partitioned between DCM and H$_2$O. The aqueous layer was collected, neutralized with NaHCO$_3$ and extracted with fresh DCM, dried over Na$_2$SO$_4$ and concentrated in vacuo. The residue was purified by flash chromatography on silica gel affording the title compound 150 (485 mg, 55% yield). $^{1}$H NMR: (DMSO-$d_6$) δ(ppm): 9.95 (s, 1H), 8.41 (d, J=2.0 Hz, 1H), 7.91 (d, J=8.2 Hz, 2H), 7.79 (d, J=8.8 Hz, 1H), 7.63 (d, J=8.2 Hz, 2H), 7.63 (dd, J=8.8, 2.1 Hz, 1H), 4.71 (s, 2H), 3.84 (s, 3H), 3.11 (s, 2H), 2.30 (s, 6H). m/z: 416.4 (MH$^+$).

Step 2: 4-[6-(2-Dimethylamino-acetylamino)-benzothiazol-2-ylsulfanylmethyl]-benzoic acid (154)

The title compound 154 was obtained following same procedure as for the hydrolysis described in scheme 1, step 4 (example 1) using compound 150 as starting material (78% yield). $^{1}$H NMR: (DMSO-$d_6$) δ(ppm): 9.95 (s, 1H), 8.41 (d, J=2.0 Hz, 1H), 7.86 (d, J=8.2 Hz, 2H), 7.79 (d, J=8.8 Hz, 1H), 7.63 (dd, J=9.0, 2.0 Hz, 1H), 7.55 (d, J=8.2 Hz, 2H), 4.68 (s, 2H), 3.11 (s, 2H), 2.30 (s, 6H). m/z: 402.4 (MH$^+$).

Step 3: N-(2-Amino-phenyl)-4-[6-(2-dimethylamino-acetylamino)-benzothiazol-2-ylsulfanylmethyl]-benzamide (158)

Title compound 158 was obtained following the same procedures as the BOP coupling described in scheme 1, step 5 (example 1) using compound 154 as starting material (28% yield). $^1$H NMR: (DMSO-d$_6$) δ (ppm): 9.93 (s, 1H), 9.59 (s, 1H), 8.39 (d, J=2.0 Hz, 1H), 7.90 (d, J=8.0 Hz, 2H), 7.79 (d, J=9.0 Hz, 1H), 7.62 (dd, J=8.8, 2.2 Hz, 1H), 7.60 (d, J=8.2 Hz, 2H), 7.12 (d, J=7.6 Hz, 1H), 6.94 (t, J=8.0 Hz, 1H), 6.74 (dd, J=8.0, 1.6 Hz, 1H), 6.56 (t, J=7.5 Hz, 1H), 4.88 (s, 2H), 4.69 (s, 2H), 3.09 (s, 2H), 2.28 (s, 6H). HRMS: m/z: 491.1455±0.0014 (M$^+$).

Example 83

N-(2-Amino-phenyl)-4-[6-(dimethylamino-methyleneamino)-benzothiazol-2-ylsulfanylmethyl]-benzamide (159)

Step 1: 4-[6-(Dimethylamino-methyleneamino)-benzothiazol-2-ylsulfanylmethyl]-benzoic acid methyl ester (151)

To a pre-cooled (−78° C.) solution of trichloromethylchloroformate (74 μL, 608 mmol) in THF (2 mL) under N$_2$ atmosphere was added via canula a solution of compound 148 (described in the Patent Application WO 03/024448) (201 mg, 608 mmol) in a mixture of THF and DMF (3.5 mL, 0.5 mL respectively) followed by addition of Et$_3$N (169 μL, 1.22 mmol). The solution was stirred at −78° C. for 1 h and at 0° C. for 2 h and allowed to warm to rt overnight. The solvents were removed in vacuo, and the residue was partitioned between H$_2$O and a mixture of DCM/MeOH (9:1), dried over MgSO$_4$ and concentrated in vacuo, affording the title compound 151 (136 mg, 58% yield). $^1$H NMR: (DMSO-d$_6$) δ(ppm): 7.92 (d, J=8.4 Hz, 2H), 7.81 (s, 1H), 7.69 (d, J=8.6 Hz, 1H), 7.62 (d, J=8.2 Hz, 2H), 7.46 (d, J=2.2 Hz, 1H), 7.04 (dd, J=8.6, 2.2 Hz, 1H), 4.68 (s, 2H), 3.84 (s, 3H), 3.04 (bs, 3H), 2.95 (bs, 3H). m/z: 386.4 (MH$^+$).

Step 2: 4-[6-(Dimethylamino-methyleneamino)-benzothiazol-2-ylsulfanylmethyl]-benzoic acid (155)

The title compound 155 was obtained following same procedure as for the hydrolysis described in scheme 1, step 4 (example 1) using compound 151 as starting material (45% yield). $^1$H NMR: (DMSO-d$_6$) δ (ppm): 7.89 (d, J=8.2 Hz, 2H), 7.80 (s, 1H), 7.69 (d, J=8.6 Hz, 1H), 7.59 (d, J=8.2 Hz, 2H), 7.45 (d, J=2.2 Hz, 1H), 7.04 (dd, J=8.6, 2.2 Hz, 1H), 4.67 (s, 2H), 3.03 (bs, 3H), 2.94 (bs, 3H). m/z: 372.3 (MH$^+$).

Step 3: N-(2-Amino-phenyl)-4-[6-(dimethylamino-methyleneamino)-benzothiazol-2-ylsulfanylmethyl]-benzamide (159)

The title compound 159 was obtained following the same procedures as for the BOP coupling described in scheme 1, step 5 (example 1) using compound 155 as starting material. (25% yield). $^1$H NMR: (DMSO-d$_6$) δ(ppm): 9.60 (s, 1H), 7.91 (d, J=8.2 Hz, 2H), 7.79 (s, 1H), 7.69 (d, J=8.6 Hz, 1H), 7.60 (d, J=8.2 Hz, 2H), 7.44 (d, J=2.2 Hz, 1H), 7.13 (d, J=8.0 Hz, 1H), 7.03 (dd, J=8.6, 2.3 Hz, 1H), 6.95 (t, J=7.0 Hz, 1H), 6.75 (d, J=9.2 Hz, 1H), 6.57 (t, J=7.4 Hz, 1H), 4.89 (s, 2H), 4.67 (s, 2H), 3.02 (s, 3H), 2.93 (s, 3H). m/z: 462.5 (MH$^+$).

Example 84

N-(2-Amino-phenyl)-4-{6-[N-(2-Amino-phenyl)-4-benzylamide]-benzothiazol-2-ylsulfanylmethyl}-benzamide (160)

Step 1: N-(4-methylbenzoic acid methyl ester)-benzothiazol-2-ylsulfanylmethyl}-benzoic acid methyl ester (152)

To a solution of compound 148 (9.52 g, 28.8 mmol) in DMF (30 mL) was added DCM (130 mL) and methyl-(4-bromomethyl)benzoate (6.60 g, 28.8 mmol) was added and the mixture was stirred at rt for 16 h. The solvents were concentrated in vacuo and the resulting solid was partitioned between EtOAc and H$_2$O. The organic layer was washed with HCl 1N, brine, dried over MgSO$_4$ and concentrated in vacuo. The crude material was purified by flash chromatography using EtOAc/Hex (45:55) followed by Biotage pre-packed silica gel column using MeOH/DCM (2:98) and crystallization in a mixture of CHCl$_3$ and Et$_2$O affording the title compound 152 (2.66 g, 19% yield). $^1$H NMR: (DMSO-d$_6$) δ(ppm): 7.89 (d, J=8.0 Hz, 2H), 7.87 (d, J=7.8 Hz, 2H), 7.55 (d, J=8.4 Hz, 2H), 7.54 (d, J=8.8 Hz, 1H), 7.47 (d, J=8.4 Hz, 2H), 6.93 (d, J=2.3 Hz, 1H), 6.77 (dd, J=8.8, 2.5 Hz, 1H), 6.70 (t, J=6.1 Hz, 1H), 4.58 (s, 2H), 4.38 (d, J=6.3 Hz, 2H), 3.81 (s, 3H), 3.81 (s, 3H). m/z: 479.4 (MH$^+$).

Step 2: N-(4-methylbenzoic acid)-benzothiazol-2-ylsulfanylmethyl}-benzoic acid (156)

The title compound 156 was obtained following same procedure as for the hydrolysis described in scheme 1, step 4 (example 1) using compound 152 as starting material and doubling the amount of lithium hydroxide (37% yield). m/z: 451.4 (MH$^+$).

Step 3: N-(2-Amino-phenyl)-4-{6-[N-(2-Amino-phenyl)-4-benzamide]-benzothiazol-2-ylsulfanylmethyl}-benzamide (160)

The title compound 160 was obtained following the same procedures as for the BOP coupling described in scheme 1, step 5 (example 1) using compound 156 as starting material and doubling the amount of all reagents (5% yield). $^1$H NMR: (Acetone-d$_6$) d(ppm): 7.98 (d, J=8.0 Hz, 2H), 7.96 (d, J=8.2 Hz, 2H), 7.63 (d, J=9.0 Hz, 1H), 7.62 (d, J=7.4 Hz, 2H), 7.55 (d, J=8.0 Hz, 2H), 7.28 (d, J=8.2 Hz, 2H), 7.04 (d, J=2.5 Hz, 1H), 6.99 (t, J=7.4 Hz, 2H), 6.91 (dd, J=8.8, 2.3 Hz, 1H), 6.85 (d, J=7.4 Hz, 2H), 6.66 (t, J=7.4 Hz, 2H), 4.65 (s, 2H), 4.54 (s, 2H). m/z: 631.5 (MH$^+$).

159 160

Scheme 36

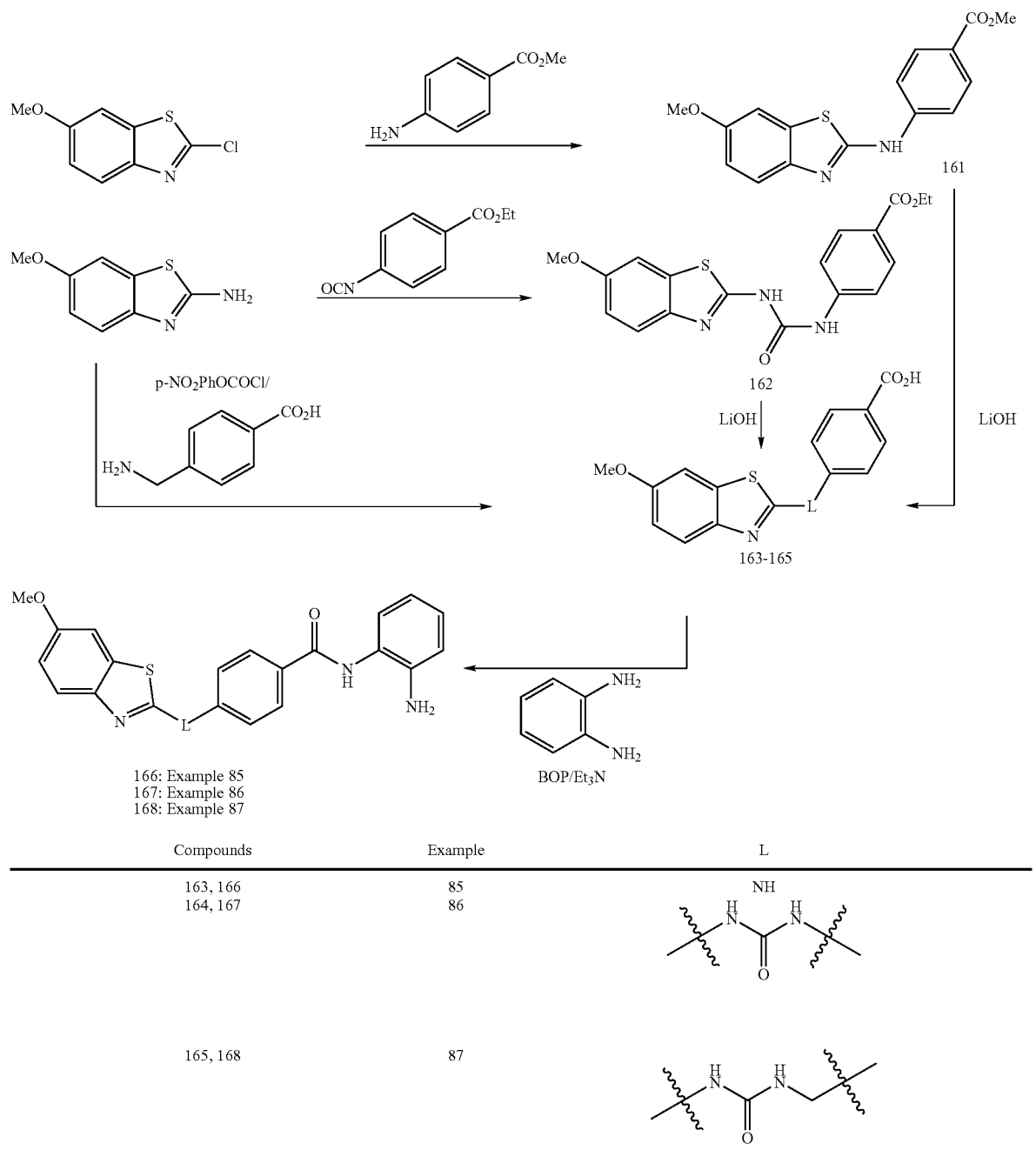

| Compounds | Example | L |
|---|---|---|
| 163, 166 | 85 | |
| 164, 167 | 86 | NH, H-N-C(=O)-N-H (urea linker) |
| 165, 168 | 87 | H-N-C(=O)-N-H (urea linker with methylene) |

Example 85

N-(2-Amino-phenyl)-4-(6-methoxy-benzothiazol-2-ylamino)-benzamide (166)

Step 1: 4-(6-Methoxy-benzothiazol-2-ylamino)-benzoic acid methyl ester (161)

To a solution of 2-chloro-6-methoxybenzothiazole (1.00 g, 5.03 mmol) in DMF (10 mL) was added methyl 4-aminobenzoate (760 mg, 5.03 mmol) followed by addition of powdered $K_2CO_3$ (1.81 g, 15.09 mmol). The mixture was stirred at 90° C. for 16 h and at 120° C. for 24 h and then at 140° C. for 3 days. It was allowed to cool down to rt and NaH (60% in mineral oil, 201 mg, 5.03 mmol) was added. The mixture was stirred at rt for 16 h and quenched with $H_2O$. The solvent was removed in vacuo at 80° C. and the residue was partitioned between $H_2O$ and EtOAc. The organic layer was washed with HCl 1N, saturated $NaHCO_3$ and brine, dried over $MgSO_4$ and concentrated in vacuo. The crude material was purified by flash chromatography using EtOAc/Hex and increasing polarity from 20:80 to 50:50 throughout elution, affording the title compound 161 (150 mg, 9% yield). m/z: 315.2 (MH+).

Step 2:
4-(6-Methoxy-benzothiazol-2-ylamino)-benzoic acid (163)

The title compound 163 was obtained following same procedure as for the hydrolysis described in scheme 1, step 4 (example 1) using compound 161 as starting material (66% yield). m/z: 301.2 (MH+).

Step 3: N-(2-Amino-phenyl)-4-(6-methoxy-benzothiazol-2-ylamino)-benzamide (166)

The title compound 166 was obtained following the same procedures as for the BOP coupling described in scheme 1, step 5 (example 1) using compound 163 as starting material. (53% yield). $^1$H NMR: (DMSO-$d_6$) δ(ppm): 10.62 (s, 1H), 9.53 (s, 1H), 7.98 (d, J=8.8 Hz, 2H), 7.84 (d, J=9.2 Hz, 2H), 7.57 (d, J=8.8 Hz, 1H), 7.47 (d, J=2.0 Hz, 1H), 6.59 (t, J=7.2 Hz, 1H), 4.89 (s, 2H), 3.78 (s, 3H). m/z: 391.4 (MH+).

Example 86

N-(2-Amino-phenyl)-4-[3-(6-methoxy-benzothiazol-2-yl)-ureido]-benzamide (167)

Step 1: 4-[3-(6-Methoxy-benzothiazol-2-yl)-ureido]-benzoic acid ethyl ester (162)

The title compound 162 was obtained following the procedure described in J. Med. Chem., 1979, 22 (1), 28-32, starting from 2-amino-6-methoxybenzothiazole (93% yield). $^1$H NMR: (DMSO-$d_6$) δ(ppm): 9.63 (bs, 1H), 7.91 (d, J=8.4 Hz, 2H), 7.65 (d, J=8.0 Hz, 2H), 7.55-7.51 (m, 2H), 6.98 (d, J=8.8 Hz, 1H), 4.28 (q, J=6.8 Hz, 2H), 3.79 (s, 3H), 1.32 (t, J=7.2 Hz, 3H). m/z: 372.3 (MH+).

Step 2: 4-[3-(6-Methoxy-benzothiazol-2-yl)-ureido]-benzoic acid (164)

The title compound 164 was obtained following same procedure as for the hydrolysis described in scheme 1, step 4 (example 1) using compound 162 as starting material (99% yield). $^1$H NMR: (DMSO-$d_6$) δ (ppm): 7.94 (d, J=8.4 Hz, 2H), 7.70 (d, J=8.0 Hz, 2H), 7.57 (d, J=8.4 Hz, 1H), 7.49 (d, J=2.4 Hz, 1H), 6.96 (dd, J=8.8, 2.4 Hz, 1H), 3.80 (s, 3H). m/z: 344.3 (MH+).

Step 3: N-(2-Amino-phenyl)-4-[3-(6-methoxy-benzothiazol-2-yl)-ureido]-benzamide (167)

The title compound 167 was obtained following the same procedures as the BOP coupling described in scheme 1, step 5 (example 1) using compound 164 as starting material. (50% yield). $^1$H NMR: (DMSO-$d_6$) δ(ppm): 9.58 (s, H), 9.54 (bs, 1H), 7.96 (d, J=8.4 Hz, 2H), 7.93 (s, 1H), 7.63 (d, J=8.8 Hz, 2H), 7.54 (d, J=9.2 Hz, 1H), 7.52 (d, J=2.0 Hz, 1H), 7.14 (d, J=7.6 Hz, 1H), 6.98 (dd, J=8.0, 1.6 Hz, 1H), 6.94 (d, J=8.0 Hz, 1H), 6.77 (d, J=8.0 Hz, 1H), 6.59 (t, J=7.2 Hz, 1H), 4.89 (bs, 2H), 3.80 (s, 3H). m/z: 434.4 (MH+).

Example 87

N-(2-Amino-phenyl)-4-[3-(6-methoxy-benzothiazol-2-yl)-ureidomethyl]-benzamide (168)

Step 1: 4-[3-(6-Methoxy-benzothiazol-2-yl)-ureidomethyl]-benzoic acid (165)

The title compound 165 was obtained following the same procedure as for the carbamate formation described in scheme 32, step 1 (example 75) substituting compound 129 for 2-amino-6-methoxybenzothiazole and using 4-aminomethylbenzoic acid instead of 4-(2-aminoethyl)-morpholine (28% yield). $^1$H NMR: (DMSO-$d_6$) δ(ppm): 7.92 (t, J=8.0 Hz, 2H), 7.51 (d, J=8.5 Hz, 1H), 7.47 (s, 1H), 7.42 (d, J=8.5 Hz, 1H), 6.95 (d, J=7.0 Hz, 1H), 4.45 (s, 2H), 3.77 (s, 3H). m/z: 358.3 (MH+).

Step 2: N-(2-Amino-phenyl)-4-[3-(6-methoxy-benzothiazol-2-yl)-ureidomethyl]-benzamide (168)

The title compound 168 was obtained following the same procedures as the BOP coupling described in scheme 1, step 5 (example 1) using compound 165 as starting material. (1.5% yield). $^1$H NMR: (DMSO-$d_6$) δ(ppm): 10.75 (bs, 14H), 9.63 (s, 1H), 7.97-7.91 (m, 2H), 7.53-7.43 (m, 3H), 7.33 (s, 1H), 7.16 (s, 1H), 6.96-6.95 (m, 2H), 6.78 (d, J=8.0 Hz, 1H), 6.60-6.58 (m, 1H), 4.88 (bs, 2H), 4.45 (s, 2H), 3.78 (s, 3H).

Scheme 37

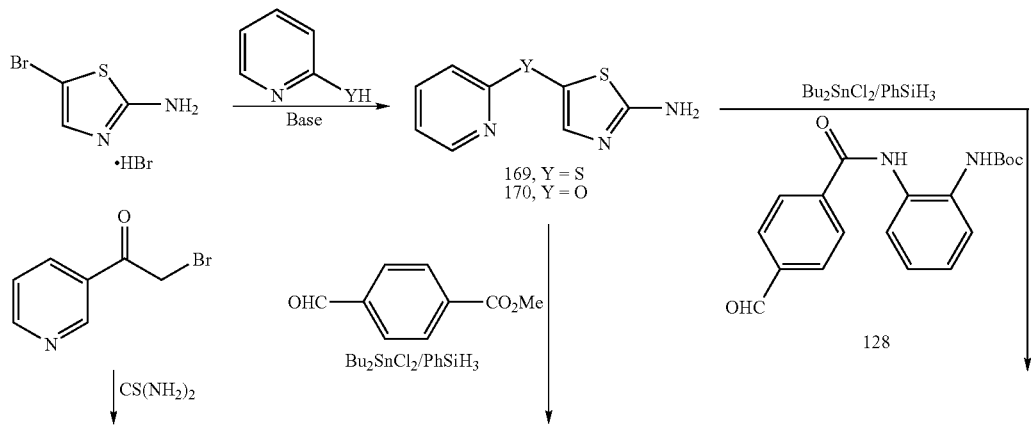

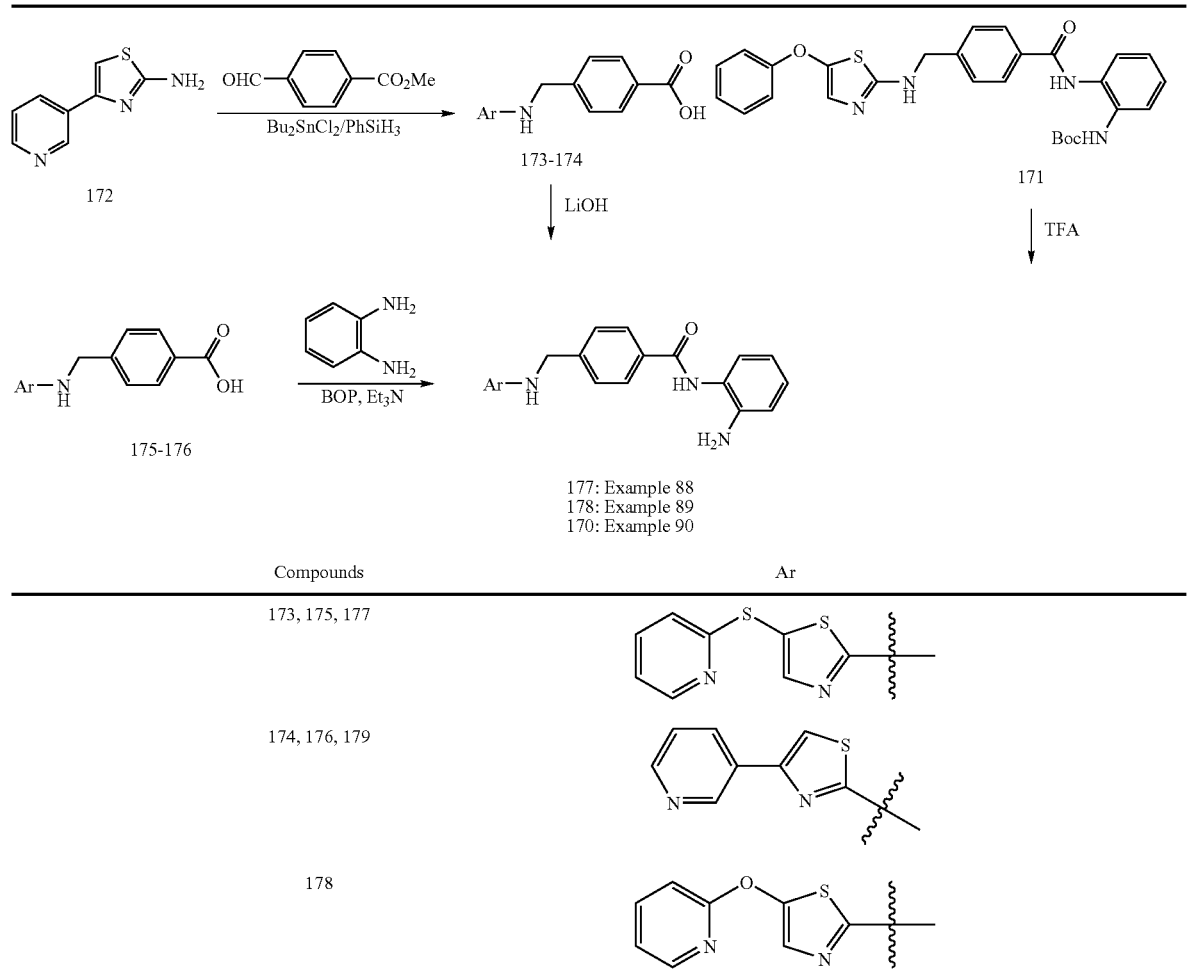

| Compounds | Ar |
|---|---|
| 173, 175, 177 | pyridin-2-yl-S-thiazol-5-yl |
| 174, 176, 179 | pyridin-3-yl-thiazol-4-yl |
| 178 | pyridin-2-yl-O-thiazol-5-yl |

Example 88

N-(2-Amino-phenyl)-4-{[5-(pyridin-2-ylsulfanyl)-thiazol-2-ylamino]-methyl}-benzamide (177)

Step 1: 5-(Pyridin-2-ylsulfanyl)-thiazol-2-ylamine (169)

To a solution of 2-amino-5-bromothiazole hydrobromide (1.00 g, 3.85 mmol) in DMF (8 mL) was added 2-mercaptopyridine (428 mg, 3.85 mmol) followed by addition of powdered $K_2CO_3$ (1.81 g, 15.09 mmol). The mixture was stirred at 80° C. for 1 h and at rt for 16 h. The solvent was removed in vacuo at 80° C. and the compound was partitioned between $H_2O$ and EtOAc. The aqueous layer was extracted with EtOAc and the organic phase was extracted with HCl 1N. The acidic extract was neutralized with saturated $NaHCO_3$ and the precipitate was extracted with EtOAc, washed with brine, dried over $MgSO_4$ and concentrated in vacuo to afford the title compound 169 (589 mg, 73% yield). $^1$H NMR: (Acetone-$d_6$) δ(ppm): 8.36 (s, 1H), 7.66 (s, 1H), 7.20 (s, 1H), 7.12-7.05 (m, 2H), 6.84 (s, 2H). m/z: 210.1 (MH$^+$).

Step 2: 4-{[5-(Pyridin-2-ylsulfanyl)-thiazol-2-ylamino]-methyl}-benzoic acid methyl ester (173)

The title compound 173 was obtained starting from the compound 169 following the same procedures as for the reductive amination described in scheme 3, step 2 (example 12) (50% yield). $^1$H NMR: (Acetone-$d_6$) δ(ppm): 8.37 (d, J=4.0 Hz, 1H), 7.99 (d, J=8.5 Hz, 2H), 7.83 (bs, 1H), 7.67 (td, J=8.0, 1.5 Hz, 1H), 7.56 (d, J=7.5 Hz, 2H), 7.28 (s, 1H), 7.13 (dd, J=6.5, 5.0 Hz, 1H), 7.07 (d, J=8.0 Hz, 1H), 4.72 (bs, 2H), 3.88 (s, 3H). m/z: 358.1 (MH$^+$).

Step 3: 4-{[5-(Pyridin-2-ylsulfanyl)-thiazol-2-ylamino]-methyl}-benzoic acid (175)

The title compound 175 was obtained following the same procedures as for the hydrolysis described in scheme 1, step 4 (example 1) using compound 173 as starting material. (81% yield). $^1$H NMR: (acetone-$d_6$) δ (ppm): 8.37 (d, J=4.0 Hz, 1H), 7.99 (d, J=8.5 Hz, 2H), 7.83 (bs, 1H), 7.67 (td, J=8.0, 1.5 Hz, 1H), 7.56 (d, J=7.5 Hz, 2H), 7.28 (s, 1H), 7.13 (dd, J=6.5, 5.0 Hz, 1H), 7.07 (d, J=8.0 Hz, 1H), 4.72 (bs, 2H), 3.88 (s, 3H). m/z: 344.0 (MH$^+$).

Step 4: N-(2-Amino-phenyl)-4-{[5-(pyridin-2-ylsulfanyl)-thiazol-2-ylamino]-methyl}-benzamide (177)

The title compound 177 was obtained following the same procedures as for the BOP coupling described in scheme 1, step 5 (example 1) using compound 175 as starting material. (53% yield). $^1$H NMR: (DMSO-d$_6$) δ(ppm): 9.63 (s, 1H), 8.74 (t, J=5.9 Hz, 1H), 8.40 (d, J=3.7 Hz, 1H), 7.96 (d, J=8.4 Hz, 2H), 7.72 (td, J=7.6, 2.0 Hz, 1H), 7.48 (d, J=7.8 Hz, 2H), 7.34 (s, 1H), 7.19-7.15 (m, 2H), 7.05 (d, J=8.2 Hz, 1H), 6.97 (t, J=8.0 Hz, 1H), 6.78 (d, J=7.8 Hz, 1H), 6.60 (t, J=7.8 Hz, 1H), 4.91 (s, 2H), 4.59 (d, J=6.1 Hz, 2H). mz: 434.4 (MH$^+$).

Example 89

N-(2-Amino-phenyl)-4-{[5-(pyridin-2-yloxy)-thiazol-2-ylamino]-methyl}-benzamide (178)

Step 1: 5-(Pyridin-3-yloxy)-thiazol-2-ylamine (170)

To a suspension of (NaH 60% in mineral oil, 169 mg, 4.23 mmol) in DME (10 mL) was added 2-hydroxypyridine (366 mg, 3.85 mmol). [Hydrogen evolution was observed]. Then, powdered K$_2$CO$_3$ (2.31 g, 19.2 mmol) was added followed by portion-wise addition of 2-amino-5-bromothiazole hydrobromide (1.00 g, 3.85 mmol). The mixture was refluxed with stirring for 16 h and allowed to cool down to room temperature, quenched with water and partitioned between water and EtOAc. The aqueous layer was extracted with EtOAc and organic phase was extracted with HCl 1N. The acidic extract was neutralized with saturated NaHCO$_3$ and the precipitate was extracted first with EtOAc and then with a mixture of MeOH/CHCl$_3$ (20:85). The combined organic extracts were dried over MgSO$_4$ and concentrated in vacuo. The residue was crystallized by addition of a mixture of MeOH/CHCl$_3$ (5:95) affording the title compound 170 (21 mg, 3%). $^1$H NMR: (CD$_3$OD) δ(ppm): 9.05 (dd, J=7.2, 2.0 Hz, 1H), 8.70 (ddd, J=9.2, 6.7, 2.2 Hz, 1H), 8.44 (s, 1H), 7.73 (d, J=8.8 Hz, 1H), 7.59 (bs, 2H), 7.58 (td, J=6.8, 1.4 Hz, 1H). m/z: 194.2 (MH$^+$).

Step 2: [2-(4-{[5-(Pyridin-3-yloxy)-thiazol-2-ylamino]-methyl}-benzoylamino)-phenyl]-carbamic acid tert-butyl ester (173)

The title compound 173 was obtained following same procedure as for the reductive amination described in scheme 3, step 2 (example 12) reacting compound 170 with compound 128 (described in the Patent Application WO 03/024448) (46% yield). $^1$H NMR: (acetone-d$_6$) δ (ppm): 9.66 (s, 1H), 8.30 (s, 1H), 7.97 (d, J=8.2 Hz, 2H), 7.79 (ddd, J=7.0, 2.0, 0.6 Hz, 1H), 7.68 (dd, J=7.6, 1.6 Hz, 1H), 7.60 (dd, J=7.8, 1.8 Hz, 1H), 7.55 (d, J=8.2 Hz, 2H), 7.45 (ddd, J=9.4, 6.7, 2.0 Hz, 1H), 7.27 (s, 1H), 7.21 (td, J=7.4, 1.8 Hz, 1H), 7.16 (dt, J=7.4, 1.8 Hz, 1H), 6.50 (d, J=9.2 Hz, 1H), 6.33 (td, J=6.7, 1.4 Hz, 1H), 4.67 (s, 2H), 1.99 (s, 9H). m/z: 518.5 (MH$^+$).

Step 3: N-(2-Amino-phenyl)-4-{[5-(pyridin-2-yloxy)-thiazol-2-ylamino]-methyl}-benzamide (178)

The title compound 178 was obtained following the same procedures as for the Boc cleavage described in scheme 28, step 5 (example 68) using compound 171 as starting material. (82% yield). $^1$H NMR: (acetone-d$_6$) δ (ppm): 8.00 (d, J=8.4 Hz, 2H), 7.82 (dd, J=6.3, 1.4 Hz, 1H), 7.56 (d, J=8.2 Hz, 2H), 7.46 (ddd, J=13.7, 6.7, 2.2 Hz, 1H), 7.30 (d, J=6.7 Hz, 1H), 7.28 (s, 1H), 6.99 (td, J=13.7, 7.2 Hz, 1H), 6.87 (dd, J=6.7, 1.2 Hz, 1H), 6.67 (t, J=7.2 Hz, 1H), 6.49 (d, J=8.8 Hz, 1H), 6.34 (td, J=6.7, 5.3 Hz, 1H), 4.69 (s, 2H). m/z: 434.4 (MHz).

Example 90

N-(2-Amino-phenyl)-4-[(4-pyridin-3-yl-thiazol-2-ylamino)-methyl]-benzamide (179)

Step 1: 4-Pyridin-3-yl-thiazol-2-ylamine (172)

The title compound 172 was obtained following the procedure described in *J. Heterocycl. Chem.*, 1970, 7, (1137-1141). (94% yield). $^1$H NMR: (CD$_3$OD) δ(ppm): 8.94 (dd, J=2.3, 0.8 Hz, 1H), 8.41 (dd, J=4.7, 1.6 Hz, 1H), 8.18 (dt, J=8.6, 1.6 Hz, 1H), 7.43 (ddd, J=9.0, 3.9, 0.8 Hz, 1H), 7.03 (s, 1H). m/z: 178.1 (MH$^+$).

Step 2: 4-[(4-Pyridin-3-yl-thiazol-2-ylamino)-methyl]-benzoic acid methyl ester (174)

The title compound 174 was obtained following the same procedures as for the reductive amination described in scheme 3, step 2 (example 12) using compound 172 as starting material (33% yield). $^1$H NMR: (Acetone-d$_6$) δ(ppm): 9.07 (dd, J=2.3, 0.8 Hz, 1H), 8.45 (dd, J=4.7, 1.6 Hz, 1H), 8.16 (dt, J=8.6, 1.6 Hz, 1H), 7.98 (d, J=8.6 Hz, 2H), 7.60 (d, J=8.6 Hz, 2H), 7.52-7.49 (m, 1H), 7.34 (ddd, J=7.8, 4.7, 0.8, 1H), 7.14 (s, 1H), 4.76 (s, 2H), 3.87 (s, 3H). m/z: 326.3 (MH$^+$).

Step 3: 4-[(4-Pyridin-3-yl-thiazol-2-ylamino)-methyl]-benzoic acid (176)

The title compound 176 was obtained following the same procedure as for the hydrolysis described in scheme 1, step 4 (example 1) using compound 174 as starting material (27% yield). $^1$H NMR: (DMSO-d$_6$) δ (ppm): 8.99 (dd, J=2.0, 0.8, 1H), 8.42 (dd, J=4.7, 1.6 Hz, 1H), 8.23 (t, J=5.9 Hz, 1H), 8.11 (dt, J=8.2, 2.0 Hz, 1H), 7.76 (d, J=8.2 Hz, 2H), 7.36 (ddd, J=7.8, 4.7, 0.8 Hz, 1H), 7.23 (d, J=8.2 Hz, 2H), 7.21 (s, 1H), 7.47 (d, J=5.5 Hz, 2H). m/z: 312.3 (MH$^+$).

Step 4: N-(2-Amino-phenyl)-4-[(4-pyridin-3-yl-thiazol-2-ylamino)-methyl]-benzamide (179)

The title compound 179 was obtained following the same procedures as the BOP coupling described in scheme 1, step 5 (example 1) using compound 176 as starting material (94% yield). $^1$H NMR (CDCl$_3$) δ(ppm): 10.00 (s, 1H), 9.00 (dd, J=3.1, 0.8 Hz, 1H), 8.43 (dd, J=4.7, 1.6 Hz, 1H), 8.33 (t, J=6.3 Hz, 1H), 8.11 (dt, J=7.8, 2.3 Hz, 1H), 7.89 (d, J=8.6 Hz, 2H), 7.62 (dd, J=5.9, 3.5 Hz, 1H), 7.50 (d, J=8.6 Hz, 2H), 7.37 (dd, J=7.8, 4.7 Hz, 1H), 7.26 (dd, J=5.5, 3.5 Hz, 1H), 7.24 (s, 1H), 4.56 (d, J=5.9 Hz, 2H). m/z: 402.1 (MH$^+$).

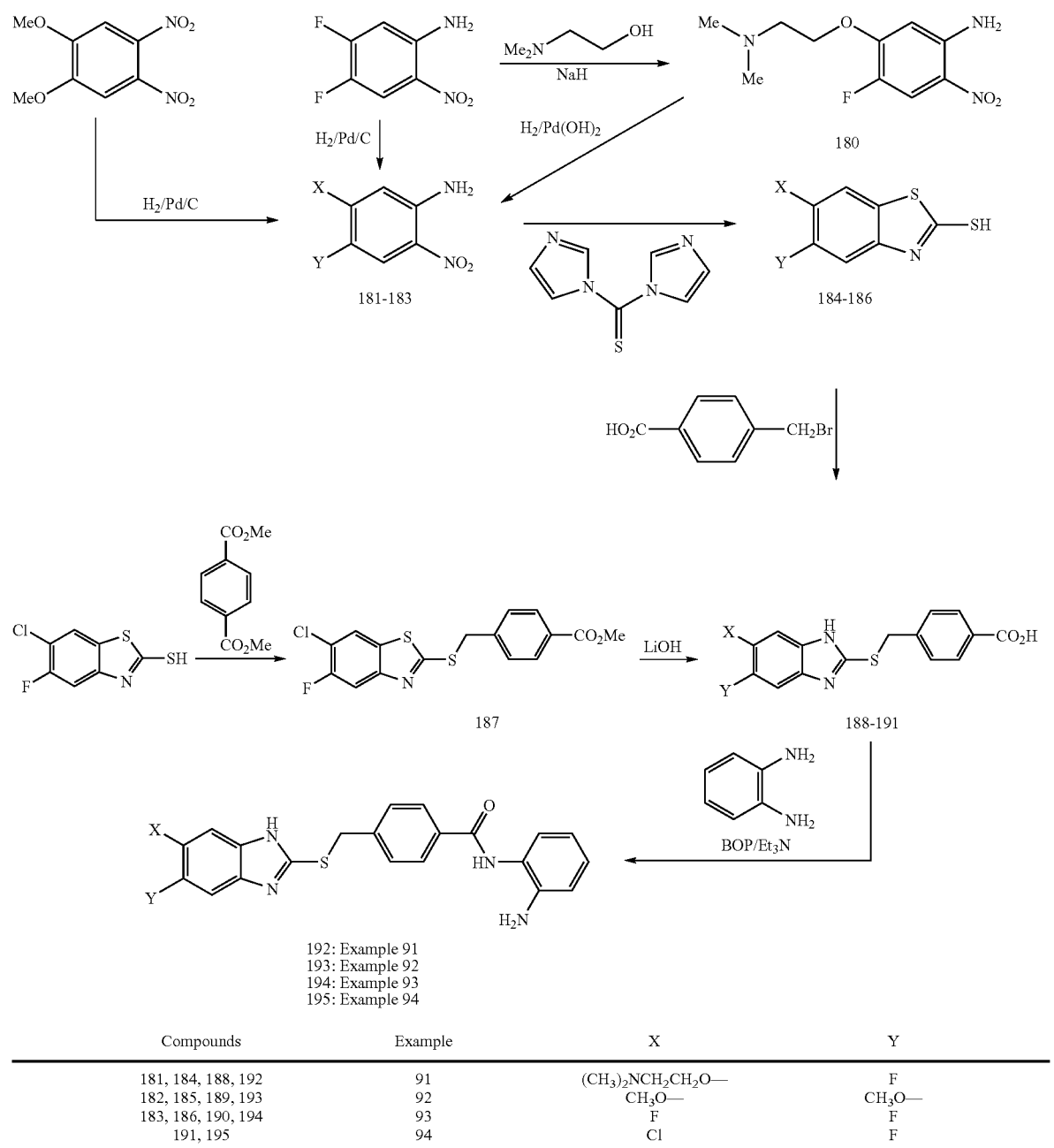

| Compounds | Example | X | Y |
|---|---|---|---|
| 181, 184, 188, 192 | 91 | (CH₃)₂NCH₂CH₂O— | F |
| 182, 185, 189, 193 | 92 | CH₃O— | CH₃O— |
| 183, 186, 190, 194 | 93 | F | F |
| 191, 195 | 94 | Cl | F |

Example 91

N-(2-Amino-phenyl)-4-[6-(2-dimethylamino-ethoxy)-5-fluoro-1H-benzoimidazol-2-ylsulfanylmethyl]-benzamide (192)

Step 1: 5-(2-Dimethylamino-ethoxy)-4-fluoro-2-nitro-phenylamine (180)

A flame-dried round-bottomed flask was charged with 4,5-difluoro-2-nitroaniline (2.00 g, 11.49 mmol) and N,N-dimethylethanolamine. Pyridine (44 mL) was added followed by slow addition of NaH (60% in mineral oil, 965 mg, 24.1 mmol). The mixture was put under $N_2$ atmosphere, stirred at rt for 16 h and quenched with $H_2O$. Solvents were removed in vacuo and the residue was partitioned between $H_2O$ and EtOAc. The organic layer was extracted twice with HCl 1N, the combined acidic extracts were neutralized with saturated $NaHCO_3$ to form a precipitate which was allowed to stand overnight, collected by filtration and purified by flash chromatography using $MeOH/CHCl_3$ with increasing polarity (10:90 to 15:85) to afford the title compound 180 (1.30 g, 47% yield). $^1$H NMR: ($CD_3OD$) δ (ppm): 7.76 (d, J=11.7 Hz, 1H), 6.53 (d, J=7.4 Hz, 1H), 4.19 (t, J=5.5 Hz, 2H), 2.84 (t, J=5.5 Hz, 2H), 2.37 (s, 6H). m/z: 244.2 ($MH^+$).

Step 2: 4-(2-Dimethylamino-ethoxy)-5-fluoro-benzene-1,2-diamine (181)

A solution of intermediate 180 (220 mg, 0.904 mmol) in acetic acid (3.6 mL) was degassed and put under N₂ atmosphere. A catalytic amount of Pd(OH)₂ was added and the black mixture was hydrogenated (1 atm) at rt for 16 h, filtered through a celite pad and rinsed with MeOH. The filtrate was concentrated in vacuo at 80° C. to afford the title compound 181 as a mixture with AcONHEt₃ (252 mg, 75%). ¹H NMR: (CD₃OD) δ (ppm): 6.54 (d, J=7.8 Hz, 1H), 6.51 (d, J=12.3 Hz, 1H), 4.21 (t, J=5.1 Hz, 2H), 3.40 (t, J=5.1 Hz, 2H), 2.89 (s, 6H). m/z: 214.1 (MH⁺).

Step 3: 6-(2-Dimethylamino-ethoxy)-5-fluoro-1H-benzoimidazole-2-thiol (184)

The title compound 184 was obtained following the procedure described in *J. Med. Chem.*, 1998, 63, 977-983, starting from the compound 181 (96% yield). ¹H NMR: (CD₃OD) δ(ppm): 7.16 (d, J=1.2 Hz, 0.5H), 7.07 (d, J=10.4 Hz, 1H), 7.04 (d, J=7.2 Hz, 0.5H), 4.37 (t, J=4.9 Hz, 2H), 3.50 (t, J=5.1 Hz, 2H), 2.92 (s, 6H). m/z: 256.2 (MH⁺).

Step 4: 4-[6-(2-Dimethylamino-ethoxy)-5-fluoro-1H-benzoimidazol-2-ylsulfanylmethyl]-benzoic acid (188)

The title compound 188 was obtained following same procedure as for the alkylation described in scheme 27, step 1 (examples 66 and 67) reacting compound 184 with F-bromotoluic acid (100% yield). ¹H NMR: (DMSO-d₆) δ (ppm): 12.65 (s, 1H), 7.92 (s, 1H), 7.83 (d, J=8.2 Hz, 2H), 7.51 (d, J=8.0 Hz, 2H), 7.30-7.27 (m, 1H), 4.58 (s, 2H), 4.40 (t, J=4.9 Hz, 2H), 3.54 (t, J=4.9 Hz, 2H), 2.88 (s, 6H). m/z: 390.2 (MH⁺).

Step 5: N-(2-Amino-phenyl)-4-[6-(2-dimethylamino-ethoxy)-5-fluoro-1H-benzoimidazol-2-ylsulfanylmethyl]-benzamide (192)

The title compound 192 was obtained following the same procedure as for the BOP coupling described in scheme 1, step 5 (example 1) using compound 188 as starting material. (30% yield). ¹H NMR: (acetone-d₆) δ (ppm): 9.02 (bs, 1H), 7.95 (d, J=8.0 Hz, 2H), 7.61 (d, J=8.0 Hz, 2H), 7.27 (d, J=7.6 Hz, 1H), 7.28-7.10 (m, 2H), 6.99 (td, J=8.0, 1.6 Hz, 1H), 6.86 (dd, J=7.8, 1.2 Hz, 1H), 6.66 (t, J=8.8 Hz, 1H), 4.65 (s, 2H), 4.63 (bs, 2H), 4.22 (bs, 2H), 2.87 (bs, 2H), 2.41 (s, 6H). m/z: 480.4 (MH⁺).

Example 92

N-(2-Amino-phenyl)-4-(5,6-dimethoxy-1H-benzoimidazol-2-ylsulfanylmethyl)-benzamide (193)

Step 1: 4,5-Dimethoxy-benzene-1,2-diamine (182)

A solution of 1,2-dimethoxy-4,5-dinitrobenzene (500 mg, 2.19 mmol) in MeOH (10 mL) was degassed and put under N₂ atmosphere. A catalytic amount of Pd on charcoal (10%) was quenched with MeOH (1 mL) and transferred in one shot as a suspension in MeOH into the solution. Acetic acid (1.5 mL) was added and the black mixture was put under H₂ atmosphere (1 atm), stirred at rt for 16 h. The mixture was filtered through a celite pad and rinsed with MeOH. The filtrate was concentrated in vacuo at 80° C. to afford the title compound 182 (residual acetic acid could not be removed from the product). ¹H NMR: (DMSO-d₆) δ(ppm): 6.23 (s, 2H), 3.56 (s, 6H). m/z: 169.3. (MH⁺).

Step 2: 5,6-Dimethoxy-1H-benzoimidazole-2-thiol (185)

The title compound 185 was obtained following the procedure described in *J. Med. Chem.*, 1998, 63, 977-983, starting from compound 182. (44% yield for 2 steps). ¹H NMR: (DMSO-d₆) δ(ppm): 12.29 (s, 2H), 6.71 (s, 2H), 3.74 (s, 6H). m/z: 211.2 (MH⁺).

Step 3: 4-(5,6-Dimethoxy-1H-benzoimidazol-2-ylsulfanylmethyl)-benzoic acid (189)

The title compound 189 was obtained following same procedure as for the alkylation described in scheme 27, step 1 (example 66 and 67) reacting compound 185 with □-bromotoluic acid (60% yield). ¹H NMR: (DMSO-d₆) δ(ppm): 7.83 (d, J=8.2 Hz, 2H), 7.43 (d, J=8.4 Hz, 2H), 7.06 (s, 2H), 4.61 (s, 2H). m/z: 345.2 (MH⁺).

Step 4: N-(2-Amino-phenyl)-4-(5,6-dimethoxy-1H-benzoimidazol-2-ylsulfanylmethyl)-benzamide (193)

The title compound 193 was obtained following the same procedures as for the BOP coupling described in scheme 1, step 5 (example 1) using compound 189 as starting material. (148 mg, 59% yield). ¹H NMR: (DMSO-d₆) δ(ppm): 12.30 (s, 1H), 9.55 (s, 1H), 7.85 (d, J=8.0 Hz, 2H), 7.48 (d, J=8.4 Hz, 2H), 7.10 (d, J=7.8 Hz, 2H), 6.92 (td, J=7.2, 1.6 Hz, 1H), 6.91-6.85 (bs, 1H), 6.73 (dd, J=8.2, 1.2 Hz, 1H), 6.55 (td, J=7.8, 1.6 Hz, 1H), 4.85 (s, 2H), 4.52 (s, 2H), 3.74 (s, 6H). m/z: 435.5 (MH⁺).

Example 93

N-(2-Amino-phenyl)-4-(5,6-difluoro-1H-benzoimidazol-2-ylsulfanylmethyl)-benzamide (194)

Step 1: 4,5-Difluoro-benzene-1,2-diamine (183)

The title compound 183 was obtained following the same procedure described as example 92, step 1 (scheme 38), but substituting 1,2-dimethoxy-4,5-dinitrobenzene for 4,5-difluoro-2nitroaniline (97% yield). ¹H NMR: (CD₃OD) δ (ppm): 6.53 (t, J=10.0 Hz, 2H). m/z: 145.3 (MH⁺).

Step 2: 5,6-Difluoro-1H-benzoimidazole-2-thiol (186)

The title compound 186 was obtained following the procedure described in *J. Med. Chem.*, 1998, 63, 977-983 starting from compound 183 (60% yield). ¹H NMR: (CD₃OD) δ(ppm): 7.48 (s, 0.5H), 7.13 (d, J=8.4 Hz, 1H), 7.11 (d, J=6.4 Hz, 1H), 1.99 (s, 1.5H). m/z: 187.1 (MH⁺).

Step 3: 4-(5,6-Difluoro-1H-benzoimidazol-2-ylsulfanylmethyl)-benzoic acid (190)

The title compound 190 was obtained following same procedure as for the alkylation described in scheme 27, step 1 (example 66 and 67) reacting compound 186 with □-bromotoluic acid (59% yield). ¹H NMR: (DMSO-d₆) δ(ppm): 9.07 (s, 0.5H), 7.84 (d, J=8.0 Hz, 2H), 7.68 (s, 1.5H), 7.52 (d, J=8.2 Hz, 2H), 5.53-5.45 (m, 2H), 4.60 (s, 2H). m/z: 321.2 (MH⁺).

Step 4: N-(2-Amino-phenyl)-4-(5,6-difluoro-1H-benzoimidazol-2-ylsulfanylmethyl)-benzamide (194)

The title compound 194 was obtained following the same procedures as the BOP coupling described in scheme 1, step 5 (example 1) using compound 186 as starting material (39% yield). ¹H NMR: (DMSO-d₆) δ (ppm): 9.59 (s, 1H), 7.88 (d, J=8.0 Hz, 2H), 7.54 (d, J=8.0 Hz, 2H), 7.55-7.40 (m, 2H), 7.13 (d, J=7.6 Hz, 1H), 6.95 (t, J=7.6 Hz, 1H), 6.76 (d, J=7.4 Hz, 1H), 6.58 (t, J=7.4 Hz, 1H), 4.61 (s, 2H). m/z: 411.4 (MH⁺).

Example 94

N-(2-Amino-phenyl)-4-(5-chloro-6-fluoro-1H-benzoimidazol-2-ylsulfanylmethyl)-benzamide (195)

Step 1: 4-(6-Chloro-5-fluoro-1H-benzoimidazol-2-ylsulfanylmethyl)-benzoic acid methyl ester (187)

The title compound 187 was obtained following same procedure as for the alkylation described in scheme 27, step 1 (example 66 and 67) reacting 6-chloro-5-fluorobenzimidazole-2-thiol with methyl 4-(bromomethyl)benzoate (54% yield). ¹H NMR: (DMSO-d₆) δ (ppm): (parent, missing protons: 7.85 (d, J=8.4 Hz, 2H), 7.55 (d, J=8.4 Hz, 2H), 3.80 (s, 2H), 3.34 (s, 3H). m/z: 351.2 (MH⁺).

Step 2: 4-(5-Chloro-6-fluoro-1H-benzoimidazol-2-ylsulfanylmethyl)-benzoic acid (191)

The title compound 191 was obtained following the same procedure as for the hydrolysis described in scheme 1, step 4 (example 1) using compound 187 as starting material (83% yield). ¹H NMR: (DMSO-d₆) δ (ppm): 7.88 (d, J=8.2 Hz, 2H), 7.67 (d, J=6.8 Hz, 1H), 7.55 (d, J=8.2 Hz, 2H), 7.53 (d, J=6.8 Hz, 1H), 4.65 (s, 2H). m/z: 337.2 (MH⁺).

Step 3: N-(2-Amino-phenyl)-4-(5-chloro-6-fluoro-1H-benzoimidazol-2-ylsulfanylmethyl)-benzamide (195)

The title compound 195 was obtained following the same procedures as the BOP coupling described in scheme 1, step 5 (example 1) using compound 191 as starting material (62% yield). ¹H NMR: (DMSO-d₆) δ (ppm): 12.87 (bs, 1H), 9.56 (s, 1H), 7.87 (d, J=8.0 Hz, 2H), 7.62-7.57 (m, 1H), 7.53 (d, J=8.2 Hz, 2H), 7.52-7.48 (m, 1H), 7.10 (d, J=7.8 Hz, 1H), 6.92 (td, J=8.0, 1.6 Hz, 1H), 6.73 (dd, J=7.8, 1.4 Hz, 1H), 6.55 (t, J=7.4 Hz, 1H), 4.86 (s, 2H), 4.61 (s, 2H). m/z: 427.4 (MH⁺).

Scheme 39

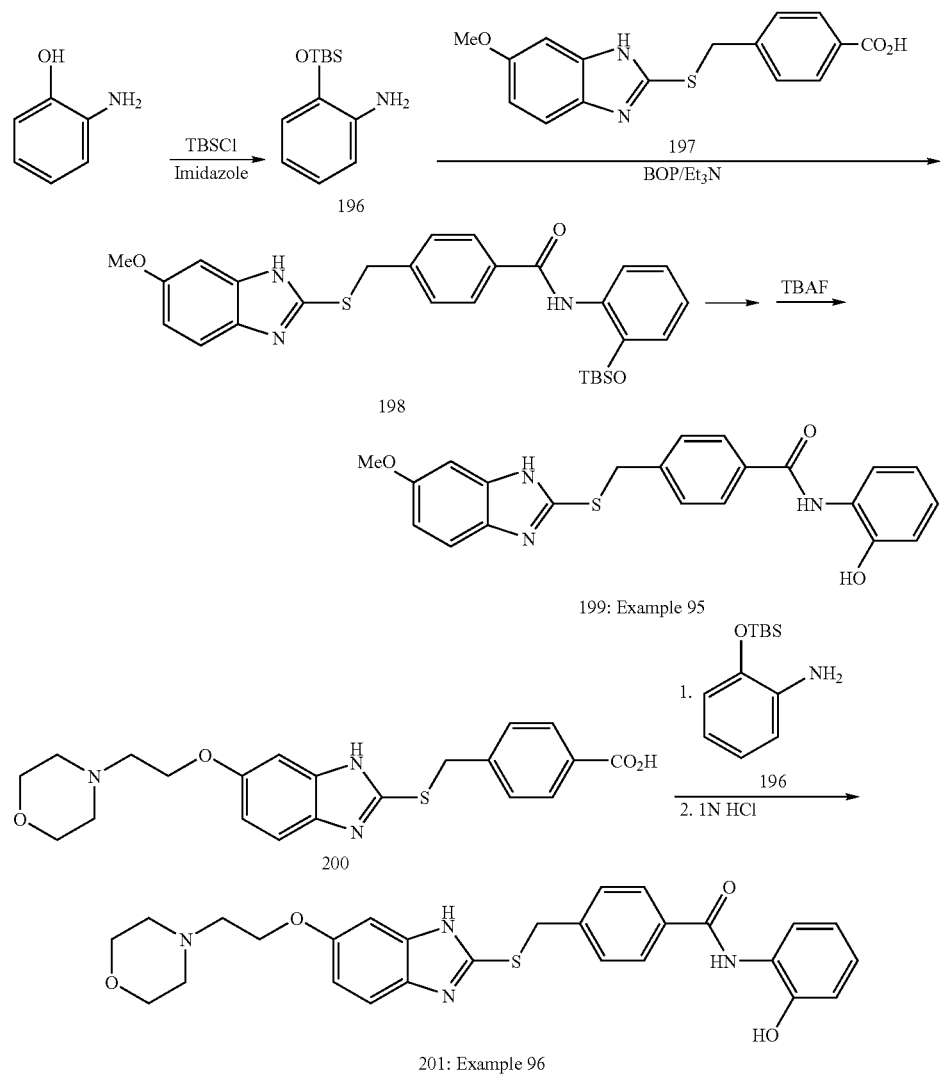

199: Example 95

201: Example 96

Example 95

N-(2-Hydroxy-phenyl)-4-(5-methoxy-1H-benzoimidazol-2-ylsulfanylmethyl)-benzamide (199)

Step 1: 2-(tert-Butyl-dimethyl-silanyloxy)-phenylamine (196)

To a stirred solution of 2-aminophenol (3.00 g, 27.5 mmol) in DCM (150 ml) was added tert-butyldimethylsilyl chloride (4.35 ml, 28.9 mmol) and Et$_3$N (4.02 ml, 28.9 mmol). The reaction mixture was stirred 16 h at room temperature. The organic phase was washed with water and brine, dried over anhydrous MgSO$_4$, filtered and concentrated. The residue was purified by flash chromatography (5% AcOEt in hexane) to afford the title compound 196 (5.56 g, 91% yield). $^1$H NMR (CDCl$_3$) δ (ppm): 7.61 (s, 1H), 7.16 (s, 1H), 6.58 (s, 2H), 6.45 (s, 1H), 6.09 (s, 1H), 3.97 (s, 3H), 3.93 (s, 3H), 3.84 (s, 3H), 3.83 (s, 6H). m/z: 224.1 (MH$^+$).

Step 2: N-[2-(tert-Butyl-dimethyl-silanyloxy)-phenyl]-4-(5-methoxy-1H-benzoimidazol-2-ylsulfanylmethyl)-benzamide (198)

The title compound 198 was obtained following the same procedures as for the BOP coupling described in scheme 1, step 5 (example 1) reacting the compound 197 (described in the Patent Application WO 03/024448) with the compound 196. m/z: 520.3 (MH$^+$).

Step 3: N-(2-Hydroxy-phenyl)-4-(5-methoxy-1H-benzoimidazol-2-ylsulfanylmethyl)-benzamide (199)

To a stirred solution of compound 198 (313 mg, 0.600 mmol) in THF (15 ml) was added TBAF 1M in THF (1.20 ml, 1.20 mmol). The reaction mixture was stirred 16 h at room temperature. The solvent was evaporated and the residue was dissolved in EtOAc, washed with sat. NH$_4$Cl and brine, dried over anhydrous MgSO$_4$, filtered and concentrated to afford the title compound 199 (150 mg, 61% yield) as a white powder. $^1$H NMR (DMSO-d$_6$) δ (ppm): 9.72 (bs, 1H), 9.49 (bs, 1H), 7.90 (d, J=8.1 Hz, 2H), 7.63 (d, J=8.1 Hz, 1H), 7.58 (d, J=8.8 Hz, 2H), 7.51 (d, J=9.5 Hz, 1H), 7.08-6.89 (m, 4H), 6.81 (dd, J=7.0, 7.0 Hz, 1H), 4.76 (s, 2H), 3.81 (s, 3 H). m/z: 406.2 (MH$^+$).

Example 96

N-(2-Hydroxy-phenyl)-4-{[6-(2-morpholin-4-yl-ethoxy)-benzothiazol-2-ylamino]-methyl}-benzamide (201)

Title compound 201 was obtained following the same procedures described in example 95 substituting compound 197 for compound 200 (described in the Patent Application WO 03/024448) and using 1N HCl instead of TBAF in the last step (26% yield). $^1$H NMR: (CD$_3$OD) δ (ppm): 7.93 (d, J=8.5 Hz, 2H), 7.79 (d, J=7.5 Hz, 1H), 7.55 (d, J=8.0 Hz, 2H), 7.33 (d, J=8.5 Hz, 1H), 7.23 (s, 1H), 7.04 (t, J=7.0 Hz, 1H), 6.92-6.85 (m, 3H), 7.40 (s, 2H), 4.14-4.12 (m, 2H), 3.72-3.70 (m, 4H), 2.81-2.79 (m, 2H), 2.62-2.60 (m, 4H). m/z: 505.5 (MH$^+$).

Scheme 40

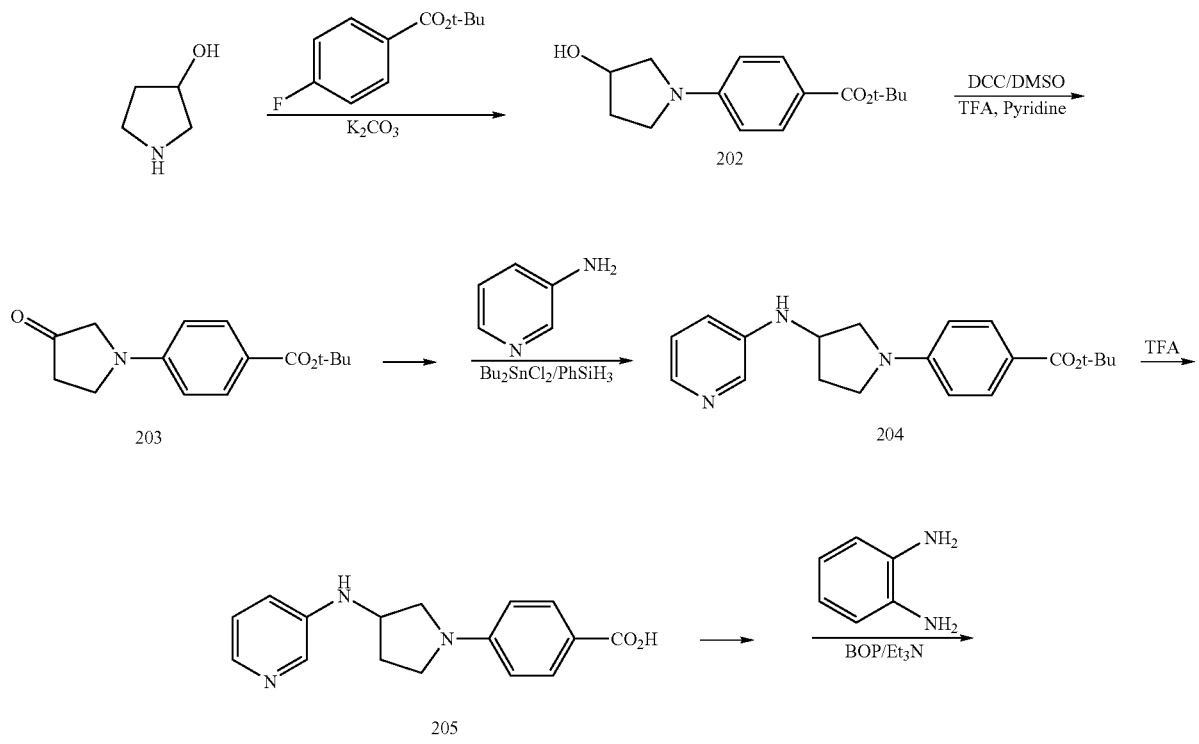

-continued

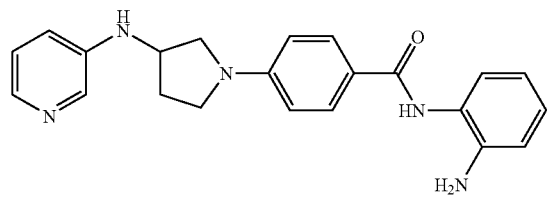

206: Example 97

Example 97

N-(2-Amino-phenyl)-4-[3-(pyridin-3-ylamino)-pyrrolidin-1-yl]-benzamide (206)

Step 1: 4-(3-Hydroxy-pyrrolidin-1-yl)-benzoic acid tert-butyl ester (202)

The title compound 202 was obtained following the procedure described in *J. Heterocycl. Chem.*, 1994, 31, 1241, (91% yield). $^1$H NMR: (CD$_3$OD) δ(ppm): 7.77 (d, J=9.0 Hz, 2H), 6.54 (d, J=9.0 Hz, 2H), 4.57-4.53 (m, 1H), 3.57-3.50 (m, 2H), 3.45 (td, J=9.4, 3.3 Hz, 1H), 3.29 (dd, J=12.7, 1.6 Hz, 1H), 2.22-2.13 (m, 1H), 2.10-2.03 (m, 1H), 1.59 (s, 9H). m/z: 264.4 (MH$^+$).

Step 2: 4-(3-Oxo-pyrrolidin-1-yl)-benzoic acid tert-butyl ester (203)

The title compound 203 was obtained following the procedure described in *J. Heterocycl. Chem.*, 1994, 31, 1241 (73% yield). $^1$H NMR: (DMSO-d$_6$) δ(ppm): 7.74 (d, J=8.8 Hz, 2H), 6.67(d, J=9.0 Hz, 2H), 3.75 (s, 2H), 3.69 (t, J=7.4 Hz, 2H), 2.72 (t, J=7.6 Hz, 2H), 1.52 (s, 9H). m/z: 262.4 (MH$^+$).

Step 3: 4-[3-(Pyridin-3-ylamino)-pyrrolidin-1-yl]-benzoic acid tert-butyl ester (204)

The title compound 204 was obtained following the procedure as for the reductive amination described in scheme 3, step 2 (example 12) starting from compound 203 and using 3-aminopyridine instead of 6-(pyridin-3-yl)pyridin-2-amine (11) (76% yield). $^1$H NMR: (acetone-d$_6$) δ (ppm): 8.08 (d, J=2.7 Hz, 1H), 7.85 (dd, J=4.3, 1.6 Hz, 1H), 7.79 (d, J=9.0 Hz, 2H), 7.09 (ddd, J=8.2, 4.5, 0.8 Hz, 1H), 7.06 (ddd, J=8.2, 2.7, 1.6 Hz, 1H), 6.58 (d, J=9.0 Hz, 2H), 4.33 (quint, J=4.9 Hz, 1H), 3.79 (dd, J=10.2, 6.1 Hz, 1H), 3.60-3.54 (m, 1H), 3.51-3.45 (m, 1H), 3.32 (dd, J=7.2, 4.1 Hz, 1H), 2.44 (sext., J=7.6 Hz, 1H), 2.18-2.11 (m, 1H), 1.56 (s, 9H). m/z: 340.4 (MH$^+$).

Step 4: 4-[3-(Pyridin-3-ylamino)-pyrrolidin-1-yl]-benzoic acid (205)

The title compound 205 was obtained following the same procedures as for the Boc cleavage described in scheme 28, step 5 (example 68) using compound 204 as starting material (96% yield). $^1$H NMR: (DMSO-d$_6$) d (ppm): 8.09 (d, J=2.0 Hz, 1H), 8.02(d, J=3.5 Hz, 1H), 7.74 (d, J=8.8 Hz, 2H), 7.68-7.62 (m, 2H), 7.29-7.26 (m, 1H), 6.57 (d, J=8.8 Hz, 2H), 4.29-4.26 (m, 1H), 3.71 (dd, J=10.6, 5.7 Hz, 1H), 3.51-3.42 (m, 2H), 3.23 (dd, J=10.6, 3.5 Hz, 1H), 2.35 (sext., J=7.2 Hz, 1H), 2.06-1.98 (m, 1H). m/z: 284.4 (MH$^+$).

Step 5: N-(2-Amino-phenyl)-4-[3-(pyridin-3-ylamino)-pyrrolidin-1-yl]-benzamide (206)

The title compound 206 was obtained following the same procedures as for the BOP coupling described in scheme 1, step 5 (example 1) using compound 205 as starting material (10% yield). $^1$H NMR: (CD$_3$OD) δ(ppm): 8.14 (s, 1H), 7.96 (d, J=2.3 Hz, 1H), 7.86 (d, J=9.0 Hz, 2H), 7.77 (dd, J=4.7, 1.4 Hz, 1H), 7.61-7.58 (m, 1H), 7.25 (dd, J=6.1, 3.1 Hz, 1H), 7.18 (ddd, J=8.4, 4.7, 0.8 Hz, 1H), 7.15 (dd, J=8.0, 1.6 Hz, 1H), 7.11 (ddd, J=8.2, 2.7, 1.4 Hz, 1H), 7.05 (td, J=7.2, 1.4 Hz, 1H), 6.89 (dd, J=8.0, 1.4 Hz, 1H), 6.76 (td, J=7.6, 1.4 Hz, 1H), 6.64 (d, J=8.8 Hz, 2H), 4.26 (quint, J=4.3 Hz, 1H), 3.78 (dd, J=10.0, 6.1 Hz, 1H), 3.62-3.56 (m, 1H), 3.53-3.47 (m, 1H), 3.31-3.29 (m, 1H), 2.42 (sext., J=7.4 Hz, 1H), 2.12-2.08 (m, 1H). m/z: 374.4 (MH$^+$).

Scheme 41

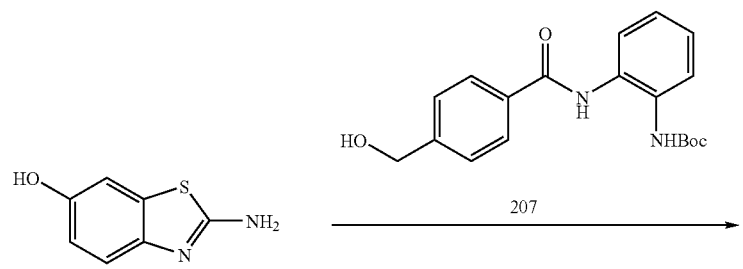

207

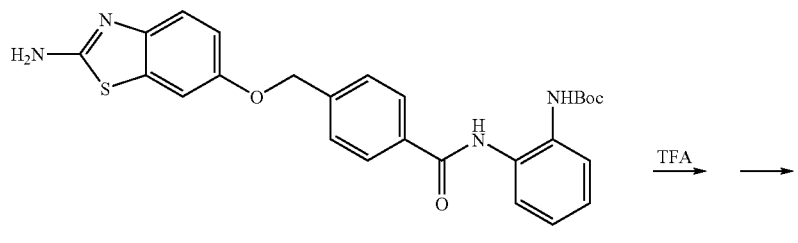

208

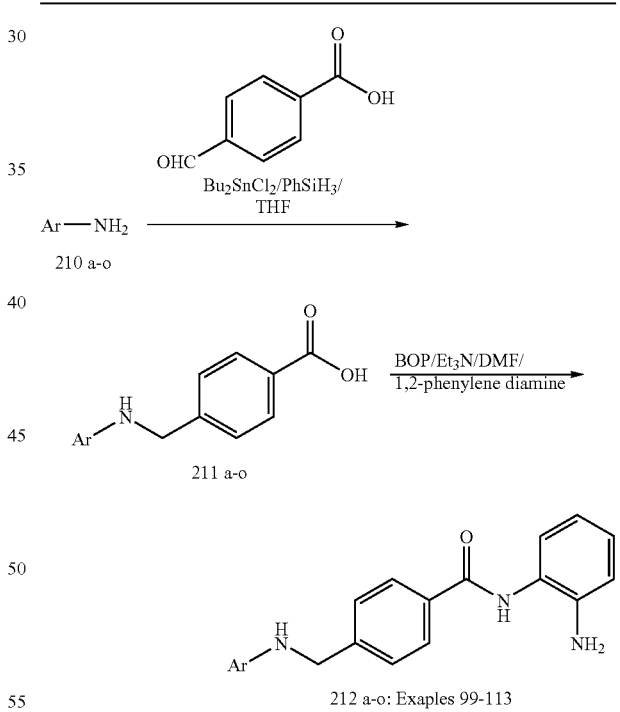

209: Example 98

Example 98

4-(2-Amino-benzothiazol-6-yloxymethyl)-N-(2-amino-phenyl)-benzamide (209)

Step 1: {2-[4-(2-Amino-benzothiazol-6-yloxy)-benzoylamino]-phenyl}-carbamic acid tert-butyl ester (208)

The title compound 208 was obtained following the same procedure as applied for the synthesis of compound 133 (scheme 32), using compound 207 (described in the Patent Application WO 03/024448) instead of dimethylamino-ethanol and substituting compound 129 (scheme 32) for compound 127 (also mentioned in the scheme 32) (43% yield). $^1$H NMR (DMSO-d$_6$) δ (ppm): 9.81 (s, 1H), 8.66 (s, 1H), 7.94 (d, J=8.4 Hz, 2H), 7.58 (d, J=8.4 Hz, 2H), 7.51 (d, J=8.2 Hz, 2H), 7.37 (d, J=2.5 Hz 1H), 7.23 (d, J=8.8 Hz, 1H), 7.18 (td, J=7.8, 1.8 Hz, 1H), 7.13 (td, J=7.6, 1.6 Hz, 1H), 6.89 (dd, J=8.6, 2.5 Hz, 1H), 5.18 (s, 2H), 1.43 (s, 9H). m/z: 491.4 (MH$^+$).

Step 2: N-(2-Amino-phenyl)-4-[3-(6-methoxy-benzothiazol-2-yl)-ureido]-benzamide (209)

The title compound 209 was obtained following the same procedures as the Boc cleavage described in scheme 28, step 5 (example 68) using compound 208 as starting material. (28% yield). $^1$H NMR: (DMSO-d$_6$) δ(ppm): 9.63 (s, 1H), 7.96 (d, J=8.2 Hz, 2H), 7.54 (d, J=8.2 Hz, 2H), 7.37 (d, J=2.5 Hz, 1H), 7.23 (s, 2H), 7.21 (d, J=8.8 Hz, 1H), 7.14 (d, J=8.0 Hz, 1H), 6.95 (td, J=8.8, 2.3 Hz, 1H), 6.89 (dd, J=8.6, 2.5 Hz, 1H), 6.75 (d, J=6.7 Hz, 1H), 6.57 (t, J=6.7 Hz, 1H), 5.16 (s, 2H), 4.89 (s, 2H). m/z: 391.4 (MH$^+$).

Scheme 42

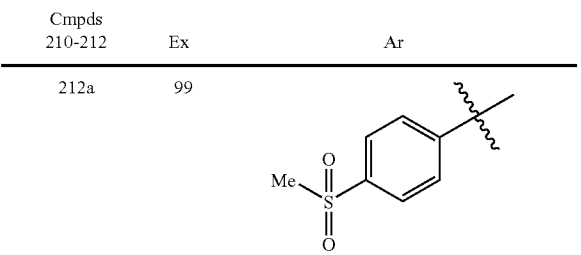

| Cmpds 210-212 | Ex | Ar |
|---|---|---|
| 212a | 99 | (4-methylsulfonyl-phenyl)methyl |

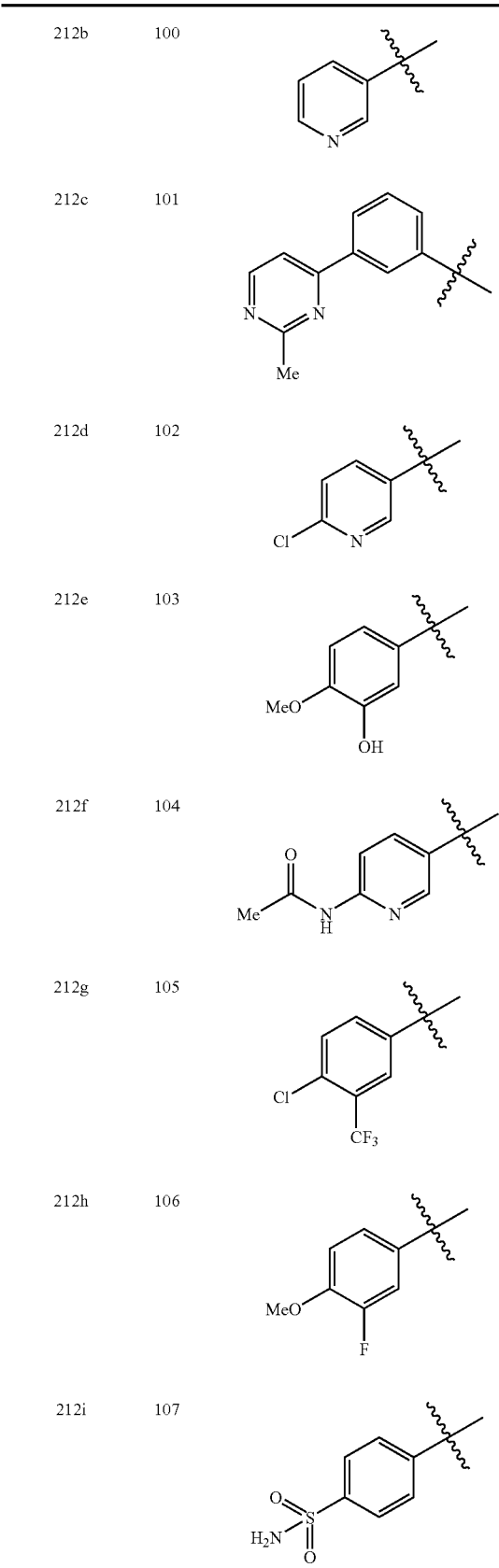
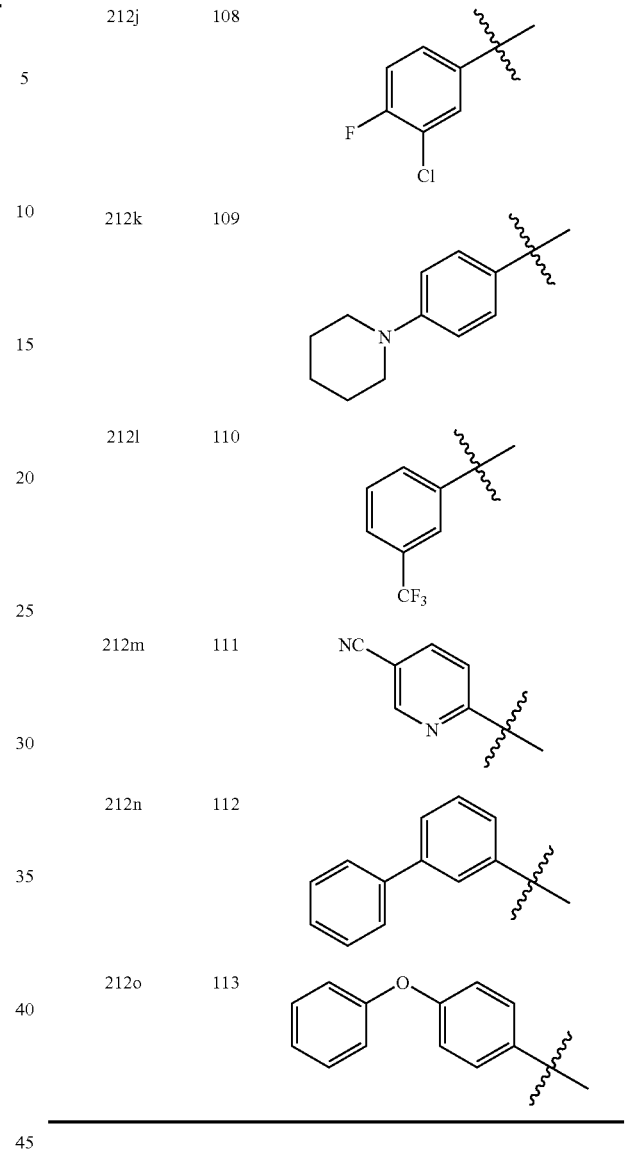

Example 99

N-(2-Amino-phenyl)-4-[(4-methanesulfonyl-phenylamino)-methyl]-benzamide (212a)

Step 1:
4-[(4-Methanesulfonyl-phenylamino)-methyl]-benzoic acid (211a)

Title compound was obtained by reacting 4-methanesulfonyl-phenylamine (210a) with 4-formyl-benzoic acid, following the procedure described in the scheme 3, step 2 (example 12). $^1$H NMR, (DMSO) δ (ppm): 7.87 (d, J=7.6 Hz, 2H), 7.50 (d, J=8.2 Hz, 2H), 7.41 (d, J=7.6 Hz, 2H), 6.64 (d, J=8.0 Hz, 2H), 4.42 (s, 2H), 3.00 (s, 3H). LRMS: (calc.) 305.4; (obt.) 304.3 (MH)$^+$.

Step 2: N-(2-Amino-phenyl)-4-[(4-methanesulfonyl-phenylamino)-methyl]-benzamide (212a)

The compound was obtained by reacting the acid 211a with 1,2-phenylenediamine following the procedure described in the scheme 1, step 5 (example 1). ¹H NMR: (DMSO) δ (ppm): 9.57 (bs, 1H), 7.90 (d, J=8.4 Hz, 1H), 7.50 (d, J=8.2 Hz, 2H), 7.43 (d, J=8.4 Hz, 2H), 7.35 (t, J=6.0 Hz, 1H), 7.11 (d, J=7.6 Hz, 1H), 6.93 (dt, J=1.6, 8.0 Hz, 1H), 6.73 (dd, J=1.6, 8.0 Hz, 1H), 6.66 (d, J=8.8 Hz, 2H), 6.55 (dt, J=1.2, 7.6 Hz, 1H), 4.88 (bs, 2H), 4.43 (d, J=6.0 Hz, 2H). LRMS: (calc.) 395.5; (obt.) 396.4 (MH)⁺.

Examples 100-113

Examples 100-113 (compounds 212b-o) were prepared using the same procedures as described for the compound 212a, example 99 (scheme 42, table 1) starting from the arylamines 210b-o via the intermediate acids 211b-o (scheme 42).

TABLE 6

| Ex. | Cmpd | Ar | Name | Characterization | Scheme |
|---|---|---|---|---|---|
| 100 | 212b | pyridin-3-yl | N-(2-Amino-phenyl)-4-(pyridin-3-ylaminomethyl)-benzamide | ¹H NMR: (DMSO-d₆) δ(ppm): 9.60(bs, 1H), 7.98(d, J=2.7 Hz, 1H), 7.92(d, J'7.8 Hz, 2H), 7.82(d, J=4.3 Hz, 1H), 7.46(d, J=8.2 Hz, 2H), 7.25(dd, J=5.1, 4.7 Hz, 1H), 7.13(d, J=7.8 Hz, 2H), 6.85(dt, J=1.5, 7.4 Hz, 1H), 6.75(dd, J=1.6, 7.8 Hz, 1H), 6.58(ddd, J=7.8, 7.0 Hz, 1H), 4.43(s, 2H). | 42 |
| 101 | 212c | 3-(2-methyl-pyrimidin-4-yl)-phenyl | N-(2-Amino-Hz 1H), phenyl)-4-{[3-(2-methyl-pyrimidin-4-yl)-phenylamino]-methyl}-benzamide | ¹H NMR: (CDCl₃) δ(ppm): 9.26(bs, 1H), 8.34(dd, J=1.8, 5.3 Hz, 1H), 7.59(d, J=7.8 Hz, 2H), 7.37(d, J=4.9 Hz, 1H), 7.17(d, J=8.2 Hz, 2H), 7.12(s, 1H), 6.96(d, J=8.0 Hz, 1H), 6.85(t J=7.8 Hz, 1H), 6.80(d, J=7.2 Hz, 1H), 6.62(dd, J=6.0, 7.6 Hz, 1H), 6.43(d, J=8.0 Hz, 1H), 6.38-6.33(m, 1H), 6.25(dd, J=6.2, 7.6 Hz, 1H), 4.10(s, 2H), 3.01(s, 3H). | 42 |
| 102 | 212d | 6-chloro-pyridin-3-yl | N-(2-Amino-phenyl)-4-[(6-chloro-pyridin-3-ylamino)-methyl]-benzainide | ¹H NMR: (DMSO-d₆) δ(ppm): 9.43(bs, 1H), 7.77(d, J=8.0 Hz, 2H), 7.56(d, J=1.8 Hz, 1H), 7.30(d, J=8.2 Hz, 2H), 6.99-6.96(m, 2H), 6.84-6.78(m, 2H), 6.66(t, J=6.2 Hz, 1H), 6.61(d, 1H), 6.42(t, J=7.4 Hz, 1H), 4.73(s, 2H), 4.24(d, J=6.3Hz, 2H). | 42 |
| 103 | 212e | 3-hydroxy-4-methoxy-phenyl | N-(2-Amino-phenyl)-4-[(3-hydroxy-4-methoxy-phenylamino)-methyl]-benzamide | ¹H NMR: (DMSO-d₆) δ(ppm): 9.58(bs, 1H), 8.58(s, 1H), 7.90(d, J=7.6 Hz, 2H), 7.43(d, J=8.0 Hz, 2H), 7.14(d J=7.6 Hz, 1H), 6.95(dd, J=6.8, 8.4 Hz, 1H) 6.76(d, J=8.0 Hz, 1H) 6.62-6.52(m, 2H), 6.09(d, J=2.4 Hz, 1H), 5.93-5.87(m, 2H), 4.88(s, 2H), 4.25(d, J=6.0 Hz, 2H), 3.60(s, 3H). | 42 |
| 104 | 212f | 6-acetylamino-pyridin-3-yl | 4-[(6-Acetylamino-pyridin-3-ylamino)-methyl]-N-(2-amino-phenyl)-benzamide | ¹H NMR: (DMSO-d₆): 9.98(bs, 1H), 9.57(bs, 1H), 7.88(d, J=8.0 Hz, 2H), 7.70(d, J=8.8 Hz, 1H), 7.62(d, J=2.8 Hz, 1H), 7.44(d, J=8.0 Hz, 2H), 7.11(d, J=7.6 Hz, 1H), 6.95-6.90(m, 2H), 6.73(d, J=8.0 Hz, 1H), 6.54(t, J=7.6 Hz, 1H), 6.36(t, J=6.0 Hz, 1H), 4.87(s, 2H), 4.33(d, J=6.0 Hz, 2H), 1.97(s, 3H). | 42 |
| 105 | 212g | 4-chloro-3-trifluoromethyl-phenyl | N-(2-Amino-phenyl)-4-[(4-chloro-3-trifluoromethyl-phenylamino)-methyl]-benzamide | ¹H NMR: (DMSO-d₆): 9.60(bs, 1H), 7.92(d, J=8.0 Hz, 2H), 7.44(d, J=8.4 Hz, 2H), 7.30(d, J=8.4 Hz, 1H), 7.12(d, J=7.6 Hz, 1H), 7.05-6.91(m, 2H), 6.79-6.74(m, 2H), 6.56(dd, J=6.8, 7.6 Hz, 1H), 4.88(s, 2H), 4.40(d, J=6.0 Hz, 2H). | 42 |

TABLE 6-continued

| Ex. | Cmpd | Ar | Name | Characterization | Scheme |
|---|---|---|---|---|---|
| 106 | 212h | 3-fluoro-4-methoxyphenyl (MeO, F) | N-(2-Amino-phenyl)-4-[(3-fluoro-4-methoxy-phenylamino)-methyl]-benzamide | $^1$H NMR: (DMSO-d$_6$): 9.56(bs, 1H), 7.89(d, J=8.0 Hz, 2H), 7.43(d, J=8.0 Hz, 2H), 7.12(d, J=7.6 Hz, 1H), 6.93(dt, J=1.2, 8.0 Hz, 1H), 6.85(t, J=8.8 Hz, 1H), 6.74(d, J=7.6 Hz, 1H), 6.56(t, J=7.6 Hz, 1H), 6.40(dd, J=2.4, 14.0 Hz, 1H), 6.28(bd, J=10.0 Hz, 1H), 6.23(t, J=6.4 Hz, 1H), 4.87(s, 2H), 4.28(s, 2H). | 42 |
| 107 | 212i | 4-methanesulfonyl-phenyl (H$_2$NSO$_2$) | N-(2-Amino-phenyl)-4-[(4-methanesulfonyl-phenylamino)-methyl]-benzamide | $^1$H NMR: (DMSO-d$_6$): 9.55(bs, 1H), 7.88(d, J=8.0 Hz, 2H), 7.45-7.40(m, 4H), 7.12-7.07(m, 1H), 6.92(dd, J=1.6, 8.8 Hz, 1H), 6.87(s, 2H), 6.73(dd, 1H), 6.59(d, J=8.8 Hz, 2H), 6.53(t, J=7.6 Hz, 1H), 4.85(bs, 2H), 4.41(d, J=6.4 Hz, 2H). | 42 |
| 108 | 212j | 3-chloro-4-fluoro-phenyl (F, Cl) | N-(2-Amino-phenyl)-4-[(3-chloro-4-fluoro-phenylamino)-methyl]-benzamide | $^1$H NMR: (DMSO-d$_6$): 9.58(bs, 1H), 7.90(d, J=8.0 Hz, 2H), 7.41(d, J=8.4 Hz, 2H), 7.12(d, J=6.4 Hz, 1H), 7.08(t, J=9.2 Hz, 1H), 6.94(dt, J=1.6, 8.0 Hz, 1H), 6.75(dd, J=1.6, 8.0 Hz, 1H), 6.63-6.60(m, 1H), 6.58-6.48(m, 3H), 4.87(bs, 2H), 4.32(d, J=6.0 Hz, 2H). | 42 |
| 109 | 212k | 4-piperidin-1-yl-phenyl | N-(2-Amino-phenyl)-4-[(4-piperidin-1-yl-phenylamino)-methyl]-benzamide | $^1$H NMR: (DMSO-d$_6$): 9.56(bs, 1H), 7.88(d, J=8.0 Hz, 2H), 7.43(d, J=8.0 Hz, 2H), 7.12(d, J=8.0 Hz, 1H), 6.94(t, J=7.3 Hz, 1H), 6.74(d, J=8.0 Hz, 1H), 6.68(d, J=8.0 Hz, 2H), 6.56(t, J=8.0 Hz, 1H), 6.45(d, J=8.8 Hz, 2H), 4.86(bs, 2H), 4.27(d, J=6.0 Hz, 2H), 2.84-2.82(m, 4H), 1.61-1.55(m, 4H), 1.46-1.43(m, 2H). | 42 |
| 110 | 212l | 3-trifluoromethyl-phenyl (CF$_3$) | N-(2-Amino-phenyl)-4-[(3-trifluoromethyl-phenylamino)-methyl]-benzamide | $^1$H NMR: (DMSO-d$_6$): 9.58(bs, 1H), 7.91(d, J=8.0 Hz, 2H), 7.45(d, J=8.4 Hz, 2H), 7.22(dd, J=7.6, 8.4 Hz, 1H), 7.13(d, J=6.8 Hz, 1H), 6.93(dt, J=1.6, 8.0 Hz, 1H), 6.86-6.83(m, 2H), 6.78(dd, J=2.0, 8.0 Hz, 2H), 6.75(dd, J=1.6, 8.0 Hz, 1H), 6.56(dt, J=1.6, 7.6 Hz, 1H), 4.87(bs, 2H), 4.40(d, J=6.4 Hz, 2H). | 42 |
| 111 | 212m | 5-cyano-pyridin-2-yl (NC, N) | N-(2-Amino-phenyl)-4-[(5-cyano-pyridin-2-ylamino)-methyl]-benzamide | $^1$H NMR: (DMSO-d$_6$): 9.57(bs, 1H), 8.36(d, J=2.0 Hz, 1H), 8.17(t, J=6.4 Hz, 1H), 7.90(d, J=8.0 Hz, 2H), 7.68(dd, J=2.0, 8.8 Hz, 1H), 7.39(d, J=8.0 Hz, 2H), 7.13(d, J=8.0 Hz, 1H), 6.94(t, J=8.4 Hz, 1H), 6.75(dd, J=1.2, 7.6 Hz, 1H), 6.60-6.54(m, 2H), 4.87(bs, 2H), 4.61(d, J=5.6 Hz, 2H). | 42 |

TABLE 6-continued

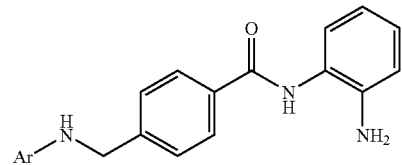

| Ex. | Cmpd | Ar | Name | Characterization | Scheme |
|---|---|---|---|---|---|
| 112 | 212n | (biphenyl-3-yl) | N-(2-Amino-phenyl)-4-(biphenyl-3-ylaminomethyl)-benzamide | $^1$H NMR: (Acetone-$d_6$) δ(ppm): 8.62(s, 1H), 8.40-8.37(m, 1H), 7.86(d, J=8.4 Hz, 2H), 7.58(d, J=8.2 Hz, 2H), 7.54(dd, J=8.6, 1.4 Hz, 2H), 7.39(t, J=7.2 Hz, 2H), 7.30(d, J=7.2 Hz, 1H), 7.17(t, J=7.6 Hz, 1H), 7.11(td, J=7.8, 1.6 Hz, 1H), 7.06(td, J=7.6, 1.6 Hz, 1H), 6.93(t, J=2.0 Hz, 1H), 6.87(d, J=6.7 Hz, 1H), 6.76(dd, J=7.6, 1.6 Hz, 1H), 6.66(ddd, J=8.2, 2.3, 1.0 Hz, 1H), 4.55(s, 2H). | 42 |
| 113 | 212o | (4-phenoxyphenyl) | N-(2-Amino-phenyl)-4-[(4-phenoxy-phenylamino)-methyl]-benzamide | $^1$H NMR: (Acetone-$d_6$) δ(ppm): 9.06(bs, 1H), 7.99(d, J=8.2 Hz, 2H), 7.55(d, J=8.4 Hz, 2H), 7.28(dd, J=8.8, 7.2 Hz, 2H), 7.02-6.97(m, 1H), 6.86(dd, J=8.8, 1.0 Hz, 2H), 6.83(d, J=9.0 Hz, 2H), 6.70(d, J=8.6 Hz, 2H), 6.6 (quint, J=7.4 Hz, 1H), 4.65(bs, 2H), 4.47(s, 2H). | 42 |

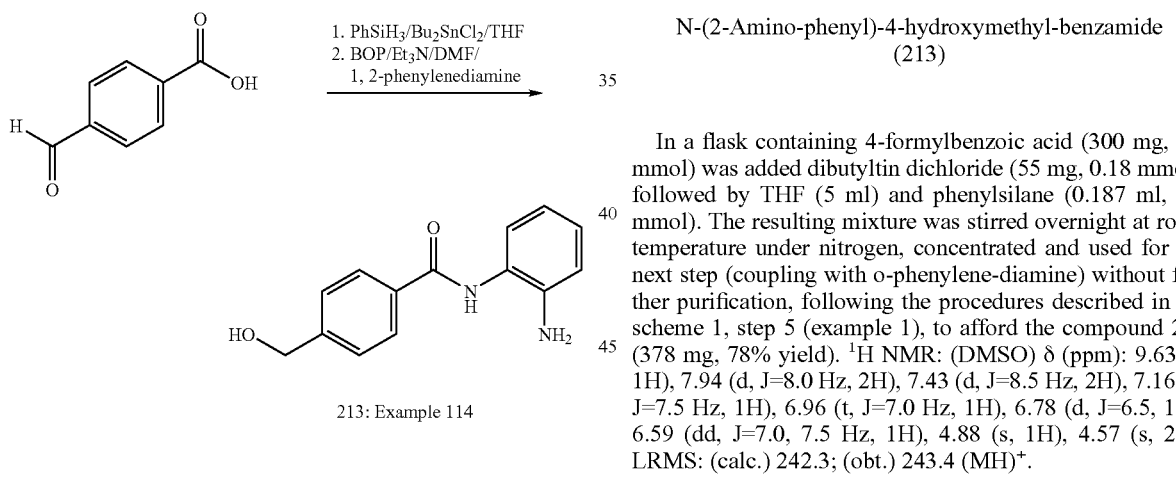

Scheme 43

Example 114

N-(2-Amino-phenyl)-4-hydroxymethyl-benzamide (213)

In a flask containing 4-formylbenzoic acid (300 mg, 1.8 mmol) was added dibutyltin dichloride (55 mg, 0.18 mmol), followed by THF (5 ml) and phenylsilane (0.187 ml, 1.8 mmol). The resulting mixture was stirred overnight at room temperature under nitrogen, concentrated and used for the next step (coupling with o-phenylene-diamine) without further purification, following the procedures described in the scheme 1, step 5 (example 1), to afford the compound 213 (378 mg, 78% yield). $^1$H NMR: (DMSO) δ (ppm): 9.63 (s, 1H), 7.94 (d, J=8.0 Hz, 2H), 7.43 (d, J=8.5 Hz, 2H), 7.16 (d, J=7.5 Hz, 1H), 6.96 (t, J=7.0 Hz, 1H), 6.78 (d, J=6.5 Hz, 1H), 6.59 (dd, J=7.0, 7.5 Hz, 1H), 4.88 (s, 1H), 4.57 (s, 2H). LRMS: (calc.) 242.3; (obt.) 243.4 (MH)$^+$.

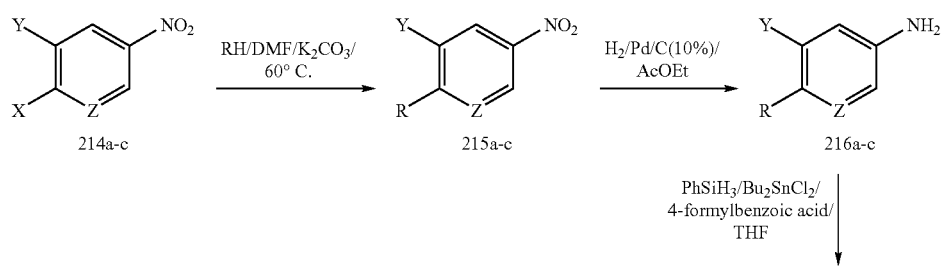

Scheme 44

-continued

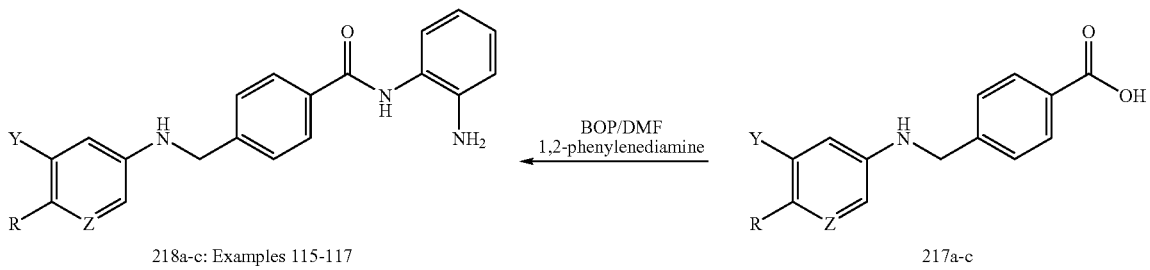

| Compound | Example | X | Y | Z | R |
|---|---|---|---|---|---|
| 218a | 115 | F | F | CH | morpholin-4-yl |
| 218b | 116 | F | H | CH | 2-(morpholin-4-yl)ethoxy |
| 218c | 117 | Br | H | N | morpholin-4-yl |

Example 115

N-(2-Amino-phenyl)-4-[(3-fluoro-4-morpholin-4-yl-phenylamino)-methyl]-benzamide (218a)

Step 1: 4-(2-Fluoro-4-nitro-phenyl)-morpholine (215a)

To a solution of 214a (3 g, 18.85 mmol) in DMF (20 mL) were added morpholine (1.6 ml, 18.85 mmol) and K₂CO₃ (10.4 g, 75.4 mmol) at room temperature. The reaction mixture was heated at 60° C. for 16 h, cooled, filtered and concentrated in vacuo. The residue was purified by flash chromatography on silica gel, eluent with AcOEt/hexane (40:60) to afford title compound 215a as a white solid (4.0 g, 89% yield). LRMS: 226.2 (calc.); 227.3 (obt.) (MH)⁺.

Step 2: 3-Fluoro-4-morpholin-4-yl-phenylamine (216a)

Title compound 216a was obtained by catalytic hydrogenation of nitro compound 215a, following the procedure described in the scheme 38, step 1 (example 92) (92% yield). LRMS: 196.2 (calc.); 197.2 (obt.) (MH)⁺.

Step 3: 4-[(3-Fluoro-4-morpholin-4-yl-phenylamino)-methyl]-benzoic acid (217a)

Title compound 226a was obtained via a reaction of 4-formylbenzoate with amine 216a, following the procedure described in the scheme 3, step 2 (example 12) (91% yield). LRMS: 330.4 (calc.); 331.5 (obt.) (MH)⁺.

Step 4: N-(2-Amino-phenyl)-4-[(3-fluoro-4-morpholin-4-yl-phenylamino)-methyl]-benzamide (218a)

Title compound 218a was obtained reacting acid 217a with 1,2-phenylenediamine following the procedures described in the scheme 1, step 5 (example 1) (40% yield). $^1$H NMR: (DMSO) δ (ppm): 9.57 (s, 1H), 7.91 (d, J=7.9 Hz, 2H), 7.44 (d, J=7.9 Hz, 2H), 7.14 (d, J=7.5 Hz, 1H), 6.95 (t, J=7.5; 7.0 Hz, 1H), 6.82-6.74 (m, 2H), 6.57 (dd, J=7.0; 7.5 Hz, 1H), 6.37-6.30 (m, 2H), 4.86 (bs, 2H), 4.30 (d, J=5.71 Hz, 2H), 3.66 (bs, 4H), 2.80 (bs, 4H). LRMS: (calc.) 420.2; (obt.) 421.2 (MH)⁺.

Examples 116-117 (Compounds 218b-c)

Examples 116-117 (compounds 218b-c) were prepared using the same procedures as described for the compound 218a (example 116, scheme 44) (table 3).

TABLE 7

| Ex | Cmpd | R | Y | Z | Name | Characterization | Scheme |
|---|---|---|---|---|---|---|---|
| 117 | 218b | (morpholine-ethoxy-OH group) | H | CH | N-(2-Amino-phenyl)-4-{[4-(2-morpholin-4-yl-ethoxy)-phenylamino]-methyl}-benzamide | $^1$H NMR: (DMSO-d$_6$) δ(ppm): 9.64(bs, 1H), 7.97(d, J=8.4 Hz, 2H), 7.52(d, J=7.9 Hz, 2H), 7.20 (d, J=7.5 Hz, 1H), 7.02(dd, J=7.0, 7.5 Hz, 1H), 6.83(d, J=7.91, 1H), 6.77(d, J=8.8 Hz, 2H), 6.65(t, J=7.5 Hz, 1H), 6.57(d, J=8.8 Hz, 2H), 4.36(bs, 2H), 4.07(bs, 2H), 3.72(bs, 4H), 3.00(bs, 2H), 2.82(bs, 4H). | 44 |
| 118 | 218c | (morpholine-NH group) | H | N | N-(2-Amino-phenyl)-4-[(6-morpholin-4-yl-pyridin-3-ylamino)-methyl]-benzamide | $^1$H NMR: (CDCl$_3$) δ(ppm): 9.59(bs, 1H), 7.91(d, J=8.3 Hz, 2H), 7.57(d, J=2.9 Hz, 1H), 7.46(d, J=8.3 Hz, 2H), 7.14(d, J=8.3 Hz, 1H), 7.97-6.93(m, 2H), 6.76(d, J=7.8 Hz, 1H), 6.64(d, J=8.8 Hz, 1H), 6.58(t, J=7.8 Hz, 1H), 4.88(bs, 2H), 4.30(d, J=5.8 Hz, 2H), 3.66-3.64(m, 4H), 3.16-3.14(m, 4H). | 44 |

Scheme 45

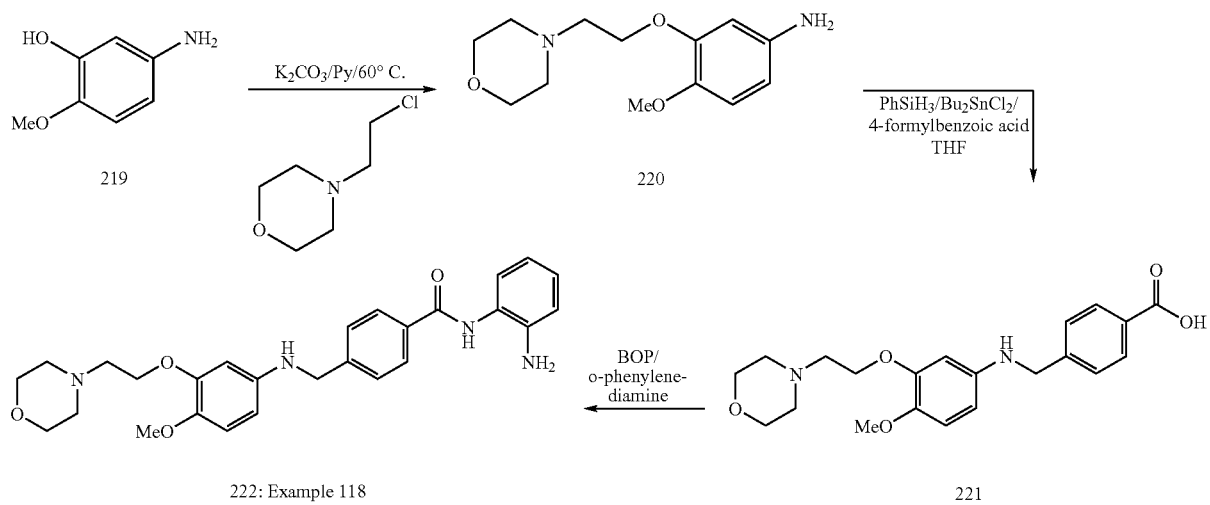

Example 118

N-(2-Amino-phenyl)-4-{[4-methoxy-3-(2-morpholin-4-yl-ethoxy)-phenylamino]-methyl}-benzamide (222)

Step 1: 4-Methoxy-3-(2-morpholin-4-yl-ethoxy)-phenylamine (220)

To a solution of 4-(2-chloro-ethyl)-morpholine (2.67 g, 14.4 mmol) in a solvent mixture pyridine (5 mL) and DMF (15 ml) were added amine 219 (2.00, 14.4 mmol) and K$_2$CO$_3$ (7.96 g, 57.6 mmol) at room temperature. The reaction mixture was heated at 60° C. overnight, cooled, filtered and concentrated in vacuo. The residue was purified by flash chromatography on silica gel eluting with 70:30 AcOEt/hexane to afford title compound 229 (3.6 g, 100% yield). LRMS: 252.3 (calc.); 253.3 (obt.) (MH)$^+$.

Step 2: 4-{[4-Methoxy-3-(2-morpholin-4-yl-ethoxy)-phenylamino]-methyl}-benzoic acid (221)

Title compound 221 was obtained reacting 4-formylbenzoate with amine 220, following the procedure described in the scheme 3, step 2 (example 12) (1.9 g, 99% yield). LRMS: 386.4 (calc.); 387.4 (obt.) (MH)⁺.

Step 3: N-(2-Amino-phenyl)-4-{[4-methoxy-3-(2-morpholin-4-yl-ethoxy)-phenylamino]-methyl}-benzamide (222)

Title compound 222 was obtained by coupling of the acid 221 (5.07 mmol) with 1,2-phenylenediamine (5.07 mmol) following the procedure described in the scheme 1, step 5 (example 1) (260 mg, 11% yield). $^1$H NMR: (DMSO) δ (ppm): 9.59 (s, 1H), 7.92 (d, J=7.5 Hz, 2H), 7.45 (d, J=7.9 Hz, 2H), 7.15 (d, J=7.9 Hz, 1H), 6.96 (dd, J=8.5; 6.5 Hz, 1H), 6.77 (d, J=8.5 Hz, 1H), 6.65 (d, J=8.5 Hz, 1H), 6.58 (t, J=7.5 Hz, 1H), 6.31 (d, J=2.5 Hz, 1H), 6.03 (d, J=8.5 Hz, 1H), 4.86 (bs, 2H), 4.30 (d, J=5.5 Hz, 2H), 3.95 (dd, J=5.9, 5.5 Hz, 2H), 3.59 (s, 3H), 3.56 (bs, 4H), 2.63 (bs, 2H), 2.44 (bs, 4H). LRMS: 476.6 (calc.); 477.6 (obt.) (MH)⁺.

Step 2: N-(2-Amino-phenyl)-4-(3,4-dimethoxy-phenylsulfamoyl)-benzamide (224)

A mixture of 223 (705 mg, 1.7 mmol), 1,2-phenylenediamine (199 mg, 1.84 mmol), Pd(OAc)₂ (0.25 mmol, 15%) and 1,1'-bis(diphenylphosphino) ferrocene (160 mg, 0.29 mmol) was suspended in degassed DMF (10 mL), treated with Et₃N (700 μL, 5.04 mmol), heated under CO atmosphere (balloon) for 18 h at 70° C. After evaporation of the DMF in vacuo, the residue was purified by flash chromatography (eluent AcOEt:hexane, 3:1) to give the title compound 224 (100 mg, 14% yield). $^1$H-NMR (CD₃OD-d4), δ (ppm): 10.05 (s, 1H), 9.76 (s, 1H), 8.06 (d, J=8.3 Hz, 2H), 7.79 (d, J=7.8 Hz, 2H), 7.11 (bs, 1H), 6.94 (bs, 1H), 6.77-6.69 (m, 3H), 6.54 (bs, 2H), 4.91 (bs, 2H), 3.62 (s, 3H).

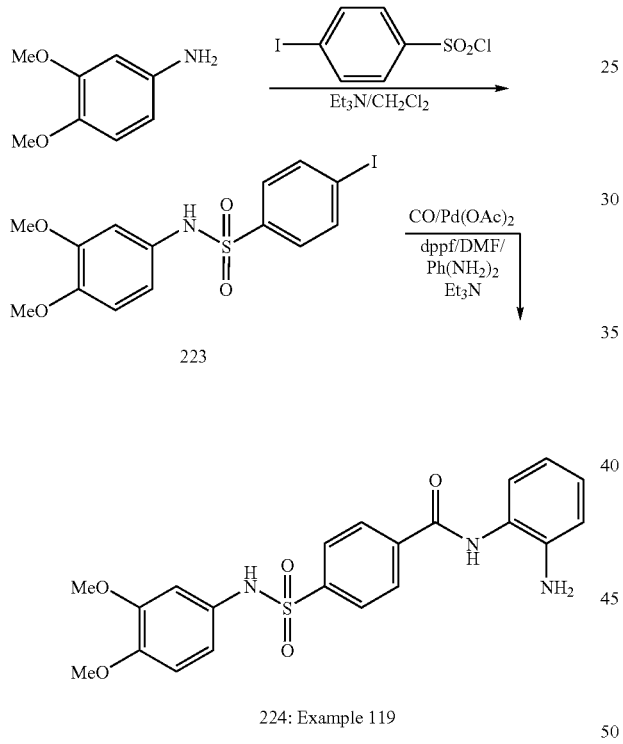

Scheme 46

224: Example 119

Example 119

N-(2-Amino-phenyl)-4-(3,4-dimethoxy-phenylsulfamoyl)-benzamide (224)

Step 1: N-(3,4-Dimethoxy-phenyl)-4-iodo-benzenesulfonamide (223)

The title compound 223 was obtained following the procedure described in the Patent application No WO 01/38322 A1, by reacting 3,4-dimethoxy-phenylamine with 4-iodo-benzenesulfonyl chloride (80% yield). LRMS: 419.2 (calc.); 420.2 (obt.) (MH)⁺.

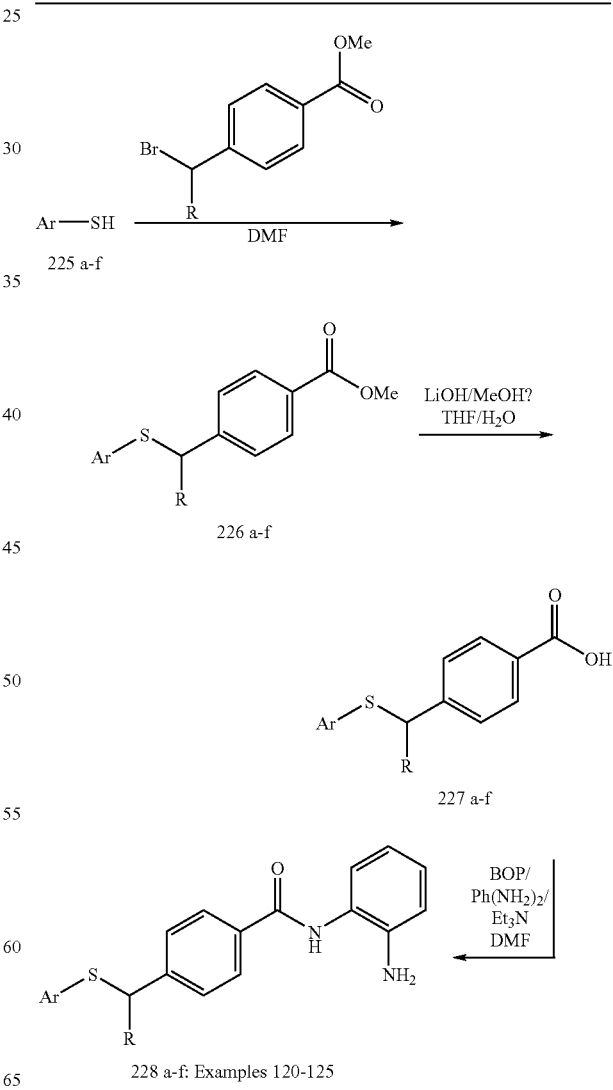

Scheme 47

228 a-f: Examples 120-125

-continued

| Compounds 225-228 | Example | R | Ar |
|---|---|---|---|
| a | 120 | H | 4-MeO-phenyl-pyrimidinyl |
| b | 121 | H | thiophene-pyrimidinyl |
| c | 122 | Me | pyridinyl-pyrimidinyl |
| d | 123 | Me | 4-MeO-phenyl-pyrimidinyl |
| e | 124 | H | pyridinyl-dihydrothiadiazolyl |
| f | 125 | H | 4-Cl-phenyl-pyridinyl |

Example 120

N-(2-Amino-phenyl)-4-[4-(4-methoxy-phenyl)-pyrimidin-2-ylsulfanylmethyl]-benzamide (228a)

Step 1: 4-[4-(4-Methoxy-phenyl)-pyrimidin-2-ylsulfanylmethyl]-benzoic acid methyl ester (226a)

To a solution of 4-(4-methoxy-phenyl)-pyrimidine-2-thiol (225a) (1.00 g, 4.58 mmol) in DMF (30 mL) was added 4-bromomethyl-benzoic acid methyl ester (1.05 g, 4.58 mmol). The mixture was heated at 60° C. for 1 h and evaporated to dryness to form the compound 226a, which was used in the next without purification. LRMS=366.4 (calc.), 367.4 (found).

Step 2: 4-[4-(4-Methoxy-phenyl)-pyrimidin-2-ylsulfanylmethyl]-benzoic acid (227a)

To a stirred solution of 226a (4.58 mmol) in THF (20 ml) and MeOH (20 ml) at room temperature was added a solution of LiOH—H$_2$O (960 mg, 22.9 mmol) in water (50 ml). The reaction mixture was stirred 18 h at room temperature, diluted in water and acidified with 1N HCl (pH 5-6) to form a precipitate which was collected by filtration, washed with water and dried to afford the title compound 227a (1.64 g, 99% yield). LRMS (calc.): 352.4, (found): 353.4.

Step 3: N-(2-Amino-phenyl)-4-[4-(4-methoxy-phenyl)-pyrimidin-2-ylsulfanylmethyl]-benzamide (228a)

The title compound 228a was obtained by coupling of acid 227a with 1,2-phenylenediamine following the procedures described in the scheme 1, step 5 (example 1) (80% yield). $^1$H NMR: (DMSO) δ (ppm): 9.57 (bs, 1H), 8.59 (d, J=5.5 Hz, 2H), 8.16 (d, J=7.0 Hz, 2H), 7.88 (d, J=8.2 Hz, 2H), 7.70 (d, J=5.0 Hz, 1H), 7.57 (d, J=8.2 Hz, 2H), 7.12-7.07 (m, 2H), 6.93 (dd, J=8.2, 7.0 Hz, 1H), 6.73 (dd, J=8.2, 1.6 Hz, 1H), 6.55 (dt, J=8.6, 1.1 Hz, 1H), 4.86 (bs, 2H), 4.55 (s, 2H), 3.83 (s, 3H) LRMS: (calc.) 442.5; (obt.) 443.5 (MH)$^+$.

Examples 121-125

Examples 121-125 (compounds 228b-f) were prepared using the same procedures as described for the compound 228a, example 121 (scheme 47, table 1) starting from the thiophenols 225b-f via the intermediates 226b-f and 227b-f (scheme 47).

TABLE 8

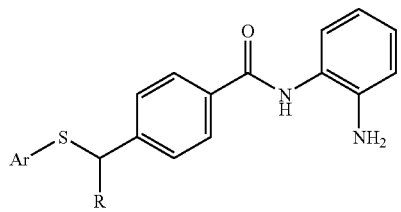

| Ex | Cmpd | Ar | R | Name | Characterization | Scheme |
|---|---|---|---|---|---|---|
| 121 | 228b | (4-thiophen-2-yl) | H | N-(2-Amino-phenyl)-4-(4-thiophen-2-yl-pyrimidin-2-ylsulfanylmethyl)-benzamide | $^1$H NMR: (DMSO-d$_6$) δ(ppm): 9.57 (bs, 1H), 8.59 (d, J=5.1 Hz, 1H), 8.07 (dd, J=1.2, 3.9 Hz, 1H), 7.87-7.82 (m, 3H), 7.68 (d, J=5.1 Hz, 1H), 7.59 (d, J=8.2, 2H), 7.24 (dd, J=5.1, 3.5 Hz, 1H), 7.10 (d, J=7.0 Hz, 1H), 6.93 (dt, J=7.8, 1.6 Hz, 1H), 6.73 (dd, J=7.8, 1.2 Hz, 1H), 6.55 (dt, J=7.4, 1.2 Hz, 1H), 4.87 (bs, 2H), 4.51 (s, 2H). | 47 |
| 122 | 228c | (pyridin-3-yl) | Me | N-(2-Amino-phenyl)-4-(4-pyridin-3-yl-pyrimidin-2-ylsulfanylmethyl)-benzaimide | $^1$H NMR: (DMSO-d$_6$) δ(ppm): 9.65 (bs, 1H), 9.45-9.21 (m, 1H), 8.66-8.60 (m, 2H), 8.41-8.39 (m, 1H), 7.77-7.76 (m, 3H), 7.52-7.41 (m, 3H), 7.05-6.98 (m, 1H), 6.81 (dd, J=6.8, 7.2 Hz, 1H), 6.61 (d, J=6.9 Hz, 1H), 6.42 (dd, J=7.0, 8.8 Hz, 1H), 4.74 (bs, 2H), 4.46 (s, 2H). | 47 |
| 123 | 228d | (4-methoxy-phenyl) | Me | N-(2-Amino-phenyl)-{1-[4-(4-methoxy-phenyl)-pyrimidin-2-ylsulfanyl]-ethyl}-benzamide | $^1$H NMR: (CDCl$_3$) δ(ppm): 9.58 (bs, 1H), 8.57 (d, J=5.3 Hz, 1H), 8.13 (dd, J=2.1, 6.8 Hz, 2H), 7.91 (d, J=8.0 Hz, 2H), 7.68 (d, J=5.5 Hz, 1H), 7.63 (d, J=8.2, 2H), 7.12 (m, 3H), 6.93 (dt, J=1.4, 7.8 Hz, 1H), 7.40 (dd, J=1.4, 8.0 Hz, 1H), 6.56 (dt, J=1.3, 7.6 Hz, 1H), 4.87 (s, 2H), 3.83 (s, 3H), 1.76 (d, J=7.0 Hz, 3H). | 47 |
| 124 | 228e | (5-pyridin-2-yl-4,5-dihydro-[1,3,4]thiadiazol) | H | N-(2-Amino-phenyl)-4-(5-pyridin-2-yl-4,5-dihydro-[1,3,4]thiadiazol-2-ylsulfanylmethyl)-benzamide | $^1$H NMR: (CD$_3$OD) δ(ppm): 9.60 (bs, 1H), 8.58 (bd, J=4.7 Hz, 1H), 8.24 (s, 1H), 7.90 (d, J=8.1 Hz, 2H), 7.87-7.80 (m, 2H), 7.52 (d, J=8.2 Hz, 2H), 7.43-7.39 (m, 1H), 7.11 (d, J=7.2 Hz, 1H), 6.93 (dt, J=1.6, 8.0 Hz, 1H), 6.74 (dd, J=1.4, 8.0 Hz, 1H), 6.55 (ddd, J=1.6, 6.3, 7.4 Hz, 1H), 4.88 (bs, 2H), 4.56 (s, 2H). | 47 |
| 125 | 228f | (4-chloro-phenyl)-pyridin-2-yl | H | N-(2-Amino-phenyl)-4-[6-(4-chloro-phenyl)-pyridin-2-ylsulfanylmethyl]-benzaimide | $^1$H NMR: (CD$_3$OD) δ(ppm): 9.57 (bs, 1H), 8.68 (d, J=5.2 Hz, 1H), 8.20 (bd, J=8.8 Hz, 2H), 7.88 (d, J=8.2 Hz, 2H), 7.80 (d, J=5.2 Hz, 1H), 7.62-7.55 (m, 4H), 7.10 (d, J=7.6 Hz, 1H), 6.92 (dt, J=1.6, 8.0 Hz, 1H), 6.72 (dd, J=1.4, 8.0 Hz, 1H), 6.54 (dt, J=1.2, 7.6 Hz, 1H), 4.86 (bs, 2H), 4.55 (s, 2H). | 47 |

Scheme 48

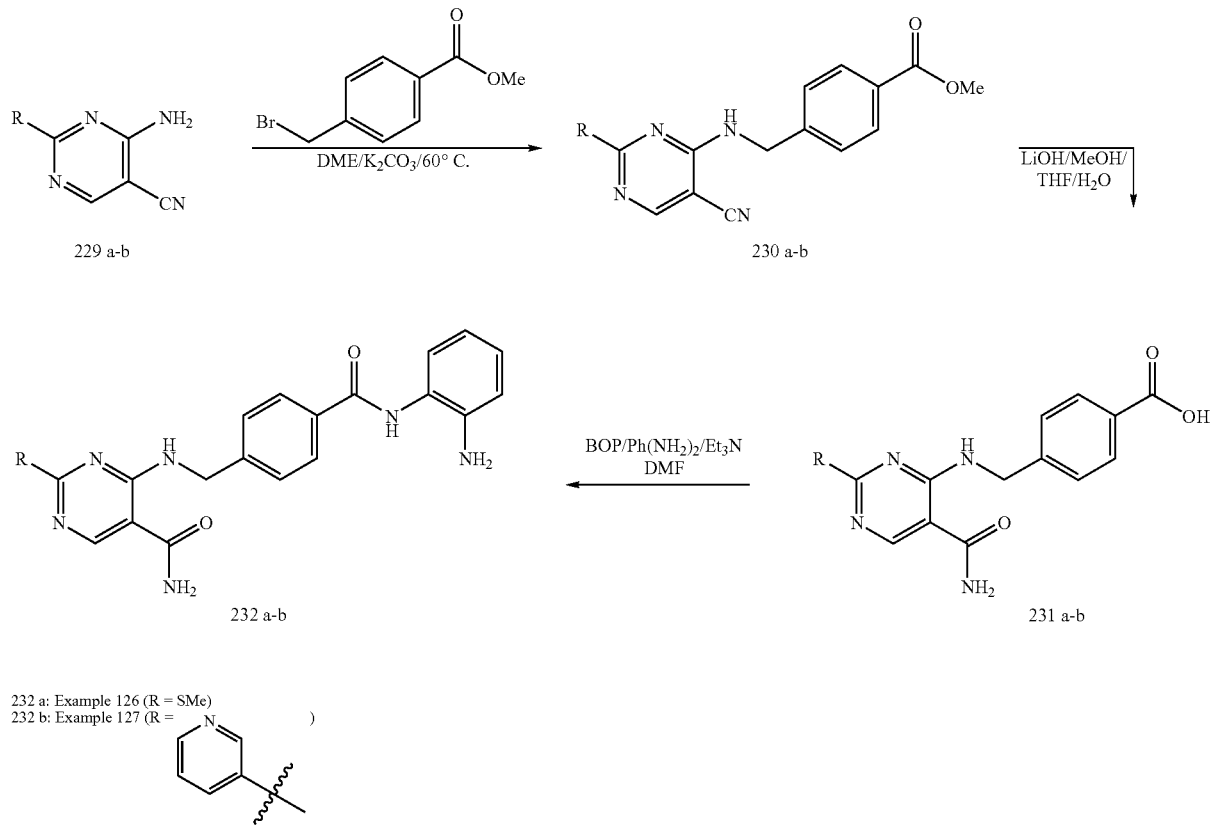

232 a: Example 126 (R = SMe)
232 b: Example 127 (R = 3-pyridyl)

Example 126

4-[4-(2-Amino-phenylcarbamoyl)-benzylamino]-2-methylsulfanyl-pyrimidine-5-carboxylic acid amide (232a)

Step 1: 4-[(5-Cyano-2-methylsulfanyl-pyrimidin-4-ylamino)-methyl]-benzoic acid methyl ester (230a)

To a solution of 4-amino-2-methylsulfanyl-pyrimidine-5-carbonitrile (229a) (200 mg, 1.2 mmol) in DME (10 ml) were added 4-bromomethyl-benzoic acid methyl ester (274 mg, 1.2 mmol) and $K_2CO_3$ (663 mg, 4.8 mmol) at room temperature. The reaction mixture was heated at 100° C. for 5 h, overnight at 60° C., cooled, filtered and concentrated in vacuo. The crude product was used in the next reaction without further purification. LRMS: 314.3 (calc.); 315.3 (obt.) $(MH)^+$.

Step 2: 4-[(5-Carbamoyl-2-methylsulfanyl-pyrimidin-4-ylamino)-methyl]-benzoic acid (231a)

Title compound 231a was obtained following the procedure described in example 121, step 2 (scheme 47) but substituting compound 226a for compound 230a (227 mg, 60% yield). LRMS (calc.): 318.3, (found): 319.3.

Step 3: 4-[4-(2-Amino-phenylcarbamoyl)-benzylamino]-2-methylsulfanyl-pyrimidine-5-carboxylic acid amide (232a)

Title compound 232a was obtained by a coupling reaction of acid 231a with 1,2-phenylenediamine following the procedure described in the scheme 1, step 5 (example 1) (80% yield). $^1$H NMR: (DMSO) δ (ppm): 9.39 (bs, 1H), 9.35 (bs, 2H), 8.32 (s, 1H), 7.71 (d, J=8.4 Hz, 2H), 7.22 (d, J=8.2 Hz, 2H), 6.94 (d, J=7.6 Hz, 1H), 6.75 (dt, J=1.4, 8.2, 1H), 6.56 (dd, J=1.5, 8.0 Hz, 1H), 6.39 (t, J=7.4 Hz, 1H), 4.54 (s, 2H), 2.30 (s, 3H). LRMS: (calc.) 408.5; (obt.) 409.5 $(MH)^+$.

Example 127

4-[4-(2-Amino-phenylcarbamoyl)-benzylamino]-2-pyridin-3-yl-pyrimidine-5-carboxylic acid amide (232b)

Title compound 232b was prepared following the same procedures as described for the compound 232a, example 126 (scheme 48) starting from the aminonitrile 229b via the intermediates 230b and 231b. $^1$H NMR: (DMSO-$d_6$) δ(ppm): 9.48 (bs, 3H), 8.86 (s, 1H), 8.74-8.73 (m, 1H), 8.64-8.61 (m, 1H), 8.19 (bs, 1H), 7.98 (d, J=8.8 Hz, 2H), 7.71 (bs, 1H), 7.60-7.57 (m, 3H), 7.18 (d, J=8.4 Hz, 1H), 7.00 (t, J=6.8 Hz, 1H), 6.81 (d, J=8.8 Hz, 1H), 6.63 (t, J=8.0 Hz, 1H), 4.95 (d, J=6.8 Hz, 2H).

Scheme 49

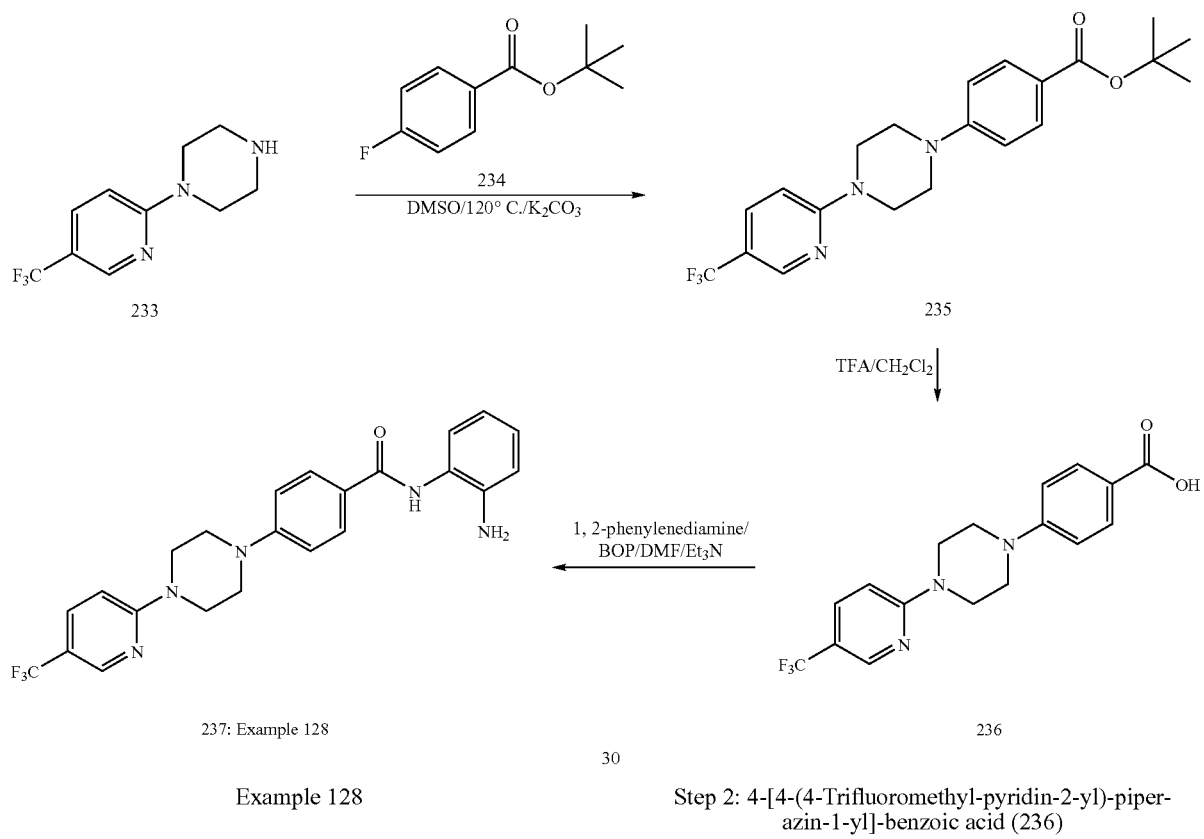

237: Example 128

236

Example 128

N-(2-aminophenyl)-4-(4-(5-(trifluoromethyl)pyridin-2-yl)piperazin-1-yl)benzamide (237)

Step 1: 4-[4-(4-Trifluoromethyl-pyridin-2-yl)-piperazin-1-yl]-benzoic acid tert-butyl ester (235)

To a solution of 1-(4-trifluoromethyl-pyridin-2-yl)-piperazine (233) (500 mg, 2.16 mmol) in DMSO were added 4-fluoro-benzoic acid tert-butyl ester (466 mg, 2.37 mmol) (234) and $K_2CO_3$ (1.2 g, 11.3 mmol). The mixture was heated for 16 h at 130° C., cooled, filtered and concentrated in vacuo. The residue was purified by flash chromatography (eluent AcOEt-hexane from 40:60 to pure AcOEt) to afford the title compound 244 (162 mg, 18% yield). LRMS: (calcd.) 406.4: (found) 407.4 $(MH)^+$.

Step 2: 4-[4-(4-Trifluoromethyl-pyridin-2-yl)-piperazin-1-yl]-benzoic acid (236)

The title compound 236 was obtained starting from the compound 235 following the procedure described in the scheme 28, step 5 (example 68) (99% yield). LRMS 350.3 (calcd.), 351.3 (found).

Step 3: N-(2-Amino-phenyl)-4-[4-(4-trifluoromethyl-pyridin-2-yl)-piperazin-1-yl]-benzamide (237)

The title compound 237 was obtained by coupling acid 236 with 1,2-phenylenediamine following the procedure described in the scheme 1, step 5 (example 1) (96% yield). $^1$H NMR: (DMSO) δ (ppm): 9.43 (bs, 1H), 8.43 (s, 1H), 7.93 (bs, 2H), 7.88 (d, J=8.8 Hz, 2H), 7.81 (dd, J=2.4, 8.8 Hz, 1H), 7.13 (d, J=8.0 Hz, 1H), 7.04-7.00 (m, 3H), 6.96 (t, J=7.6 Hz, 1H), 6.76 (d, J=8.0 Hz, 1H), 6.58 (t, J=7.6 Hz, 1H), 4.84 (bs, 2H), 3.82-3.79(m, 4H), 3.44-3.40 (m, 4H). LRMS: (calcd.) 440.4; (found.) 441.4 $(MH)^+$.

Scheme 50

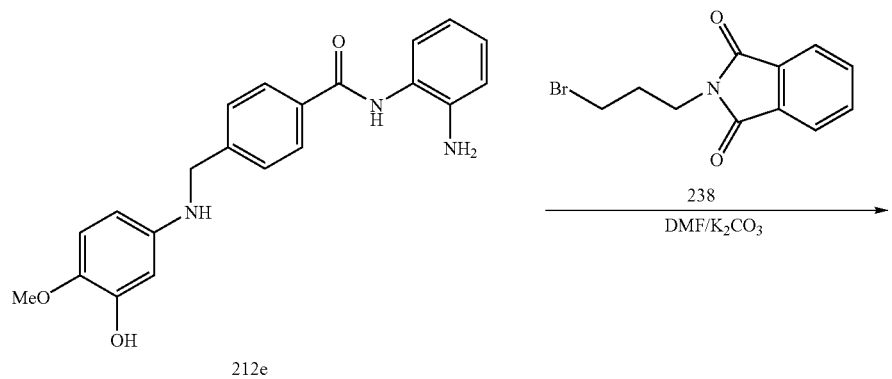

212e

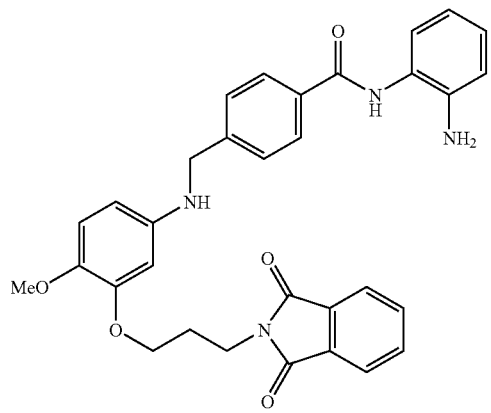

239: Example 129

Example 129

N-(2-Amino-phenyl)-4-({3-[3-(1,3-dioxo-1,3-dihydro-isoindol-2-yl)-propoxy]-4-methoxy-phenylamino}-methyl)-benzamide (239)

Step 1: N-(2-Amino-phenyl)-4-({3-[3-(1,3-dioxo-1,3-dihydro-isoindol-2-yl)-propoxy]-4-methoxy-phenylamino}-methyl)-benzamide (239)

To a solution of N-(2-amino-phenyl)-4-[(3-hydroxy-4-methoxy-phenylamino)methyl]-benzamide (212e) (586 mg, 0.66 mmol) in DMF (10 ml) were added 2-(3-bromopropyl)-isoindole-1,3-dione (238) (176 mg, 0.66 mmol) and $K_2CO_3$ (365 mg, 2.64 mmol) at room temperature. The reaction mixture was heated at 100° C. for 1 h then overnight at 60° C., cooled, filtered and concentrated in vacuo. The residue was purified by flash chromatography (eluent from AcOEt-hexane (40:60) to pure AcOEt) to afford 239 (168 mg, 46% yield). $^1$H NMR: (DMSO) δ (ppm): 9.57 (bs, 1H), 7.88 (d, J=8.0 Hz, 2H), 7.84-7.75 (m, 4H), 7.44 (d, J=8.0 Hz, 2H), 7.12 (d, J=7.2 Hz, 1H), 6.92 (t, J=8.8 Hz, 1H), 6.75 (dd, J=1.2, 7.6 Hz, 1H), 6.57 (d, J=8.4 Hz, 2H), 6.27 (d, J=2.4 Hz, 1H), 6.00-5.93 (m, 2H), 4.87 (s, 2H), 4.27 (d, J=6.0 Hz, 2H), 3.89 (dd, J=5.6, 6.0 Hz, 2H), 3.74 (dd, J=6.4, 6.8 Hz, 2H), 3.42 (s, 3H), 2.06-2.01 (m, 2H). LRMS: (calcd.) 550.4; (found.) 551.5 $(MH)^+$.

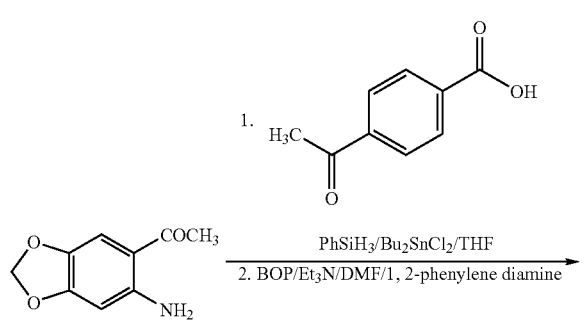

Scheme 51

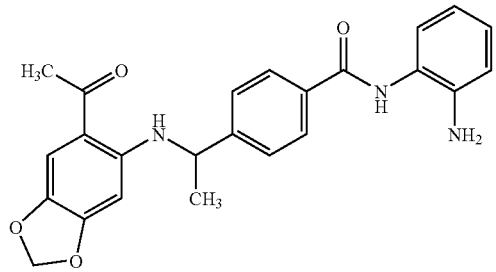

240: Example 130

Example 130

4-[1-(6-Acetyl-benzo[1,3]dioxol-5-ylamino)-ethyl]-N-(2-amino-phenyl)-benzamide (240)

Title compound 240 was prepared using the same procedures as described for the compound 212a, example 99 (scheme 42, table 1), starting from 1-(6-amino-benzo[1,3]dioxol-5-yl)-ethanone and 4-acetylbenzoic acid (scheme 51). $^1$H NMR: (DMSO-$d_6$) δ(ppm): 8.69 (s, 1H), 7.03 (d, J=7.8 Hz, 2H), 6.64 (d, J=7.8 Hz, 2H), 6.29 (dd, J=8.3, 7.8 Hz, 1H), 6.09 (t, J=7.8, 7.3 Hz, 1H), 5.90 (d, J=7.8, 1H), 5.72 (d, J=6.8 Hz, 1H), 5.70 (s, 1H), 5.16 (d, J=8.8 Hz, 1H), 4.88 (s, 1H), 4.84 (s, 1H), 4.07 (bd, 1H), 2.30 (s, 3H), 0.62 (d, J=6.83, 3H).

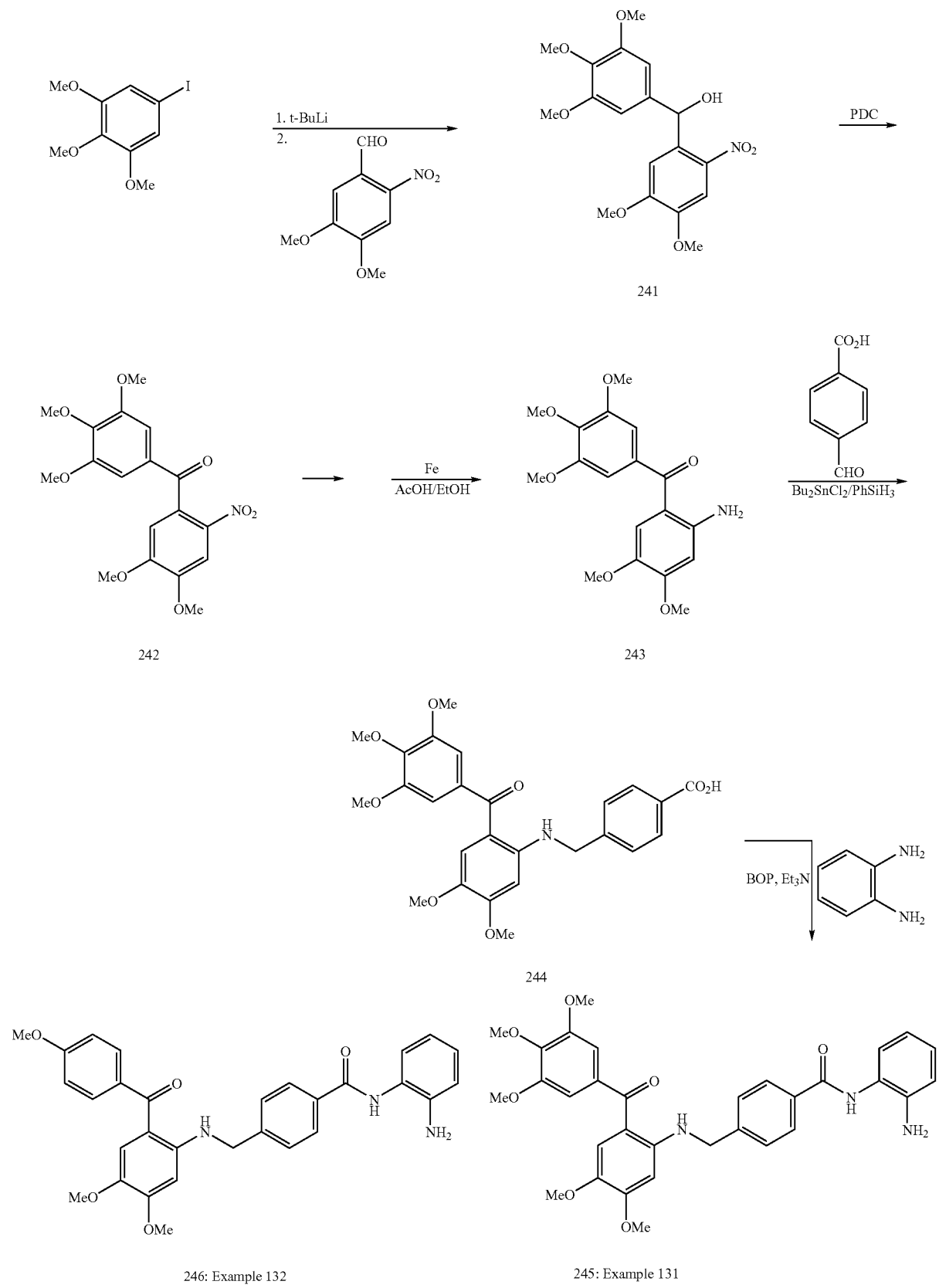
Scheme 52

Example 131

N-(2-Amino-phenyl)-4-{[4,5-dimethoxy-2-(3,4,5-trimethoxy-benzoyl)-phenylamino]-methyl}-benzamide (245)

Step 1: (4,5-Dimethoxy-2-nitro-phenyl)-(3,4,5-trimethoxy-phenyl)-methanol (241)

A flame-dried round-bottomed flask under $N_2$ atmosphere was charged with 5-iodo-1,2,3-trimethoxybenzene (2.92 g, 9.93 mmol) and THF (31 mL) was added. The solution was cooled down to −78° C. and 1.5 M solution of t-BuLi in pentane (13.6 mL, 20.57 mmol) was added dropwise. The mixture was stirred for 1 h and transferred via canula to a precooled (−78° C.) solution of 6-nitroveratraldehyde (2.02 g, 9.57 mmol) in THF (12 mL) under $N_2$ atmosphere. The resulting mixture was stirred for 2 h and slowly warmed up to 0° C., quenched with saturated aqueous solution of $NH_4Cl$ and allowed to warm-up to rt. Solvent was removed in vacuo and the residue was partitioned between water and DCM. Organic layer was collected and washed with brine, dried over $Na_2SO_4$ and concentrated in vacuo. The residue was purified by flash chromatography using EtOAc/DCM (9:91) affording the title compound 241 (1.46 g, 40% yield) $^1$H NMR (CDCl$_3$) δ (ppm): 7.61 (s, 1H), 7.16 (s, 1H), 6.58 (s, 2H), 6.45 (s, 1H), 6.09 (s, 1H), 3.97 (s, 3H), 3.93 (s, 3H), 3.84 (s, 3H), 3.83 (s, 6H). m/z: 402.4 (MH$^+$).

Step 2: (4,5-Dimethoxy-2-nitro-phenyl)-(3,4,5-trimethoxy-phenyl)-methanone (242)

Powdered 4 Å molecular sieves (583 mg) and pyridinium dichromate (2.17 g, 5.77 mmol) were successively added to a stirred solution of intermediate 241 (1.46 g, 3.84 mmol) in of anhydrous DCM (38.5 mL) at 0° C. The mixture was stirred at rt for 15 h. More PDC (290 mg, 0.770 mmol) was added and the mixture was stirred for another 4 h, The diluted with ether and filtered through a celite pad. The filtrate was concentrated and the brown solid was purified by flash chromatography using EtOAc/DCM (7:93) affording the title compound 242 (551 mg, 41%) as a yellow solid. $^1$H NMR (CDCl$_3$) δ (ppm): 7.72 (s, 1H), 6.99 (s, 2H), 6.86 (s, 1H), 4.06 (s, 3H), 4.00 (s, 3H), 3.93 (s, 3H), 3.84 (s, 6H). m/z: 378.4 (MH$^+$).

Step 3: (2-Amino-4,5-dimethoxy-phenyl)-(3,4,5-trimethoxy-phenyl)-methanone (243)

Iron powder (653 mg, 11.7 mmol) was added to a suspension of intermediate 199 (552 mg, 1.46 mmol) in a mixture of EtOH (5.11 mL), $H_2O$ (2.56 mL) and AcOH (5.11 mL) and 2 drops of concentrated HCl were added to the solution. The mixture was vigorously stirred while refluxing for 1 h, cooled down to rt and filtered through a celite pad. The filtrate was concentrated in vacuo and the aqueous residue partitioned between DCM and $H_2O$. The organic layer was washed with sat. NaHCO$_3$, dried over $Na_2SO_4$ and concentrated in vacuo affording the title compound 243 (393 mg, 77%). $^1$H NMR (CDCl$_3$) δ (ppm): 7.00 (s, 1H), 6.88 (s, 2H), 6.23 (s, 1H), 3.92 (m, 6H), 3.88 (s, 6H), 3.70 (s, 3H). m/z: 348.4 (MH$^+$).

Step 4: 4-{[4,5-Dimethoxy-2-(3,4,5-trimethoxy-benzoyl)-phenylamino]-methyl}-benzoic acid (244)

The title compound 244 was obtained following same procedure as for the reductive amination described in scheme 3, step 2 (example 12) starting from compound 243 (46% yield). m/z: 482.5 (MH$^+$).

Step 5: N-(2-Amino-phenyl)-4-{[4,5-dimethoxy-2-(3,4,5-trimethoxy-benzoyl)-phenylamino]-methyl}-benzamide (245)

The title compound 245 was obtained following the same procedure as for the BOP coupling described in scheme 1, step 5 (example 1) using compound 244 as starting material. (38% yield). $^1$H NMR: (DMSO-d$_6$) δ(ppm): 9.61 (s, 1H), 9.24 (t, J=5.7 Hz, 1H), 7.95 (d, J=8.2 Hz, 2H), 7.51 (d, J=8.2 Hz, 2H) 7.13 (d, J=8.0 Hz, 1H), 6.98 (s, 1H), 6.94 (td, J=7.6, 1.2 Hz, 1H) 6.84 (s, 2H), 6.75 (dd, J=8.0, 1.3 Hz, 1H), 6.57 (t, J=7.2 Hz, 1H), 6.35 (s, 1H), 4.89 (s, 2H), 4.62 (d, J=5.7 Hz, 2H), 3.79 (s, 6H), 3.76 (s, 3H), 3.73 (s, 3H), 3.54 (s, 3H). m/z: 572.5 (MH$^+$).

Example 132

N-(2-Amino-phenyl)-4-{[4,5-dimethoxy-2-(4-methoxy-benzoyl)-phenylamino]-methyl}-benzamide (246)

The title compound 246 was obtained following the same procedures described in example 131 but substituting the organolithium reagent obtained from 5-iodo-1,2,3-trimethoxybenzene and t-BuLi for the commercially available Grignard reagent 4-methoxyphenyl magnesium bromide (8.4% overall yield). $^1$H NMR: (DMSO-d$_6$) δ(ppm): 9.62 (s, 1H), 9.10 (t, J=5.7 Hz, 1H), 7.95 (d, J=8.2 Hz, 2H), 7.57 (d, J=8.8 Hz, 2H), 7.52 (d, J=8.2 Hz, 2H), 7.14 (d, J=6.6 Hz, 1H), 7.04 (d, J=8.8 Hz, 2H), 6.95 (td, J=8.2, 1.6 Hz, 2H), 6.94 (s, 1H), 6.76 (dd, J=7.8, 1.4 Hz, 1H), 6.58 (t, J=6.5 Hz, 2H), 6.35 (s, 2H), 4.90 (s, 2H), 4.62 (d, J=5.3 Hz, 2H), 3.84 (s, 3H), 3.76 (s, 3H), 3.54 (s, 3H). m/z: 512.6 (MH$^+$).

Scheme 53

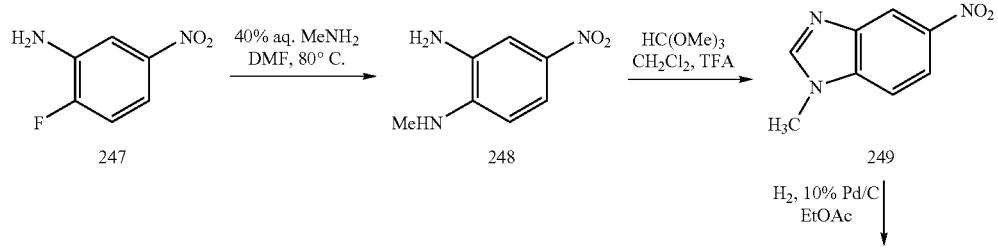

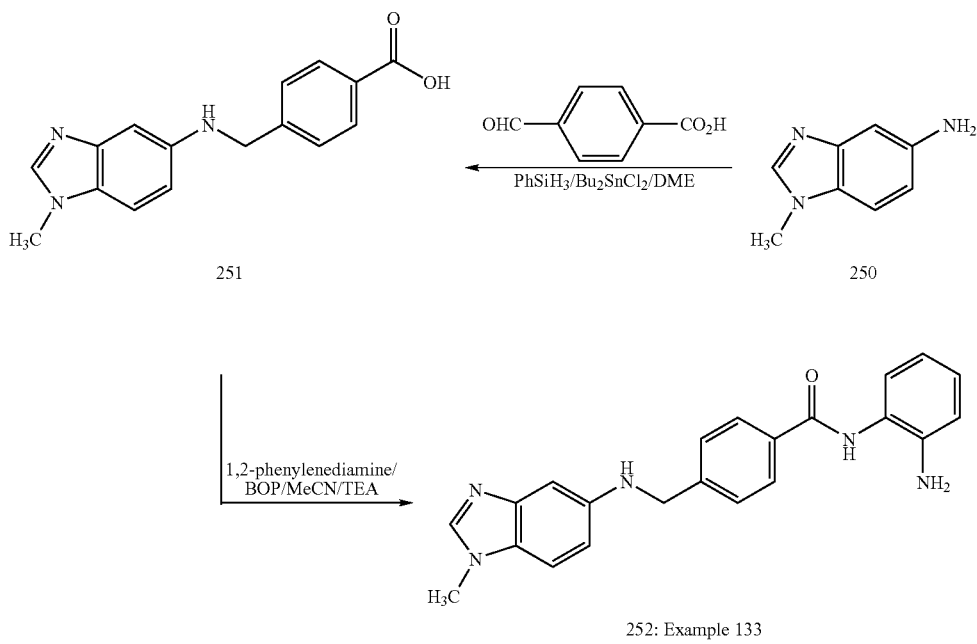

251

252: Example 133

Example 133

N-(2-Amino-phenyl)-4-[(1-methyl-1H-benzoimidazol-5-ylamino)-methyl]-benzamide (252)

Step 1. N1-Methyl-4-nitro-benzene-1,2-diamine (248)

A solution of fluoride 247 (5.41 g, 34.7 mmol) in DMF (40 mL) was treated with 40% w/w solution of $MeNH_2$ in water (10 mL, 128 mmol). The mixture stirred at 90° C. for 3 h, diluted with EtOAc, washed with saturated aqueous $NaHCO_3$. Organic phase was dried over $MgSO_4$, evaporated and the residue was purified by flash chromatography (eluent 50% EtOAc in $CH_2Cl_2$) to afford compound 248 (5.31 g, 92% yield). $^1$H NMR: ($CDCl_3$) δ (ppm): 7.75 (dd, J=2.6, 8.8 Hz, 1H), 7.53 (d, J=2.6 Hz, 1H), 6.45 (d, J=8.8 Hz, 1H), 4.24 (bs, 3H), 2.91 (s, 3H). LRMS: (calcd.) 167.2; (found) 168.1 $(MH)^+$.

Step 2. 1-Methyl-5-nitro-1H-benzoimidazole (249)

To a suspension of diamine 248 (1.14 g, 6.80 mmol) in $CH_2Cl_2$ (10 mL) was added trimethyl orthoformate (5 mL, 46 mmol, 6.7 eq) (or any other acylating agent of choice, 6 eq) followed by TFA (0.43 mL, 5.6 mmol, 0.8 eq) and the mixture was stirred at room temperature for 2 h. Precipitate was collected by filtration, washed with $CH_2Cl_2$ and dried to afford the title compound 249 as TFA salt (1.23 g, 62% yield). $^1$H NMR: ($CDCl_3$) δ (ppm): 8.57 (d, J=1.8 Hz, 1H), 8.20 (dd, J=1.8, 9.2 Hz, 1H), 8.18 (s, 1H), 7.54 (d, J=9.2 Hz, 1H), 3.94 (s, 3H). LRMS: (calc.) 177.2; (obt.) 178.1 $(MH)^+$.

Step 3. 1-Methyl-1H-benzoimidazol-5-ylamine (250)

Title compound 250 was obtained by catalytic hydrogenation of nitro compound 249 following the procedure described in the scheme 25, step 2 (example 64). LRMS: (calc.) 147.2; (obt.) 148.1 $(MH)^+$.

Step 4: 4-[(1-Methyl-1H-benzoimidazol-5-ylamino)-methyl]-benzoic acid (251)

Title compound 251 was obtained by reacting the amine 250 with 4-formyl-benzoic acid, following the procedure described in the scheme 3, step 2 (example 12). $^1$H NMR, (DMSO) δ (ppm): 8.24 (s, 1H), 7.89 (d, J=7.9 Hz, 2H), 7.49 (d, J=7.9 Hz, 2H), 7.35 (d, J=8.9 Hz, 1H), 6.80 (d, J=8.9 Hz, 1H), 6.61 (s, 1H), 4.39 (s, 2H), 3.77 (s, 3H). LRMS: (calc.) 281.3; (obt.) 282.3 $(MH)^+$.

Step 5: N-(2-Amino-phenyl)-4-[(1-methyl-1H-benzoimidazol-5-ylamino)-methyl]-benzamide (255)

Title compound 252 was obtained by coupling of acid 251 with 1,2-phenylenediamine following the procedure described in the scheme 1, step 5 (example 1). $^1$H NMR: (DMSO) δ (ppm): 9.57 (s, 1H), 8.00 (s, 1H), 7.91 (d, J=8.4 Hz, 2H), 7.51 (d, J=8.4 Hz, 2H), 7.28 (d, J=8.4 Hz, 1H), 7.15 (d, J=7.5 Hz, 1H), 6.96 (t, J=7.5 Hz, 1H), 6.76 (m, 2H), 6.62 (s, 1H), 6.57 (d, J=7.5 Hz, 1H), 6.17 (bs, 1H), 5.01 (bs, 2H), 4.40 (s, 2H), 3.73 (s, 3H). LRMS: (calc.) 371.4; (obt.) 372.4 $(MH)^+$.

Examples 134-140

Examples 134-140 (compounds 253-259) were prepared similarly to the example 134 (compound 252) according to the scheme 53 substituting trimethyl orthoformate by corresponding acyl chlorides.

TABLE 9

Characterization of compounds prepared as example 133 (scheme 53)

| Ex. | Cmpd | R | Name | Characterization | Scheme |
|---|---|---|---|---|---|
| 134 | 252 | Me | N-(2-Amino-phenyl)-4-[(1,2-dimethyl-1H-benzoimidazol-5-ylamino)-methyl]-benzamide | $^1$H NMR: (DMSO) δ (ppm): 9.50 (s, 1H), 7.92 (d, J=7.9 Hz, 2H), 7.50 (d, J=7.9 Hz, 2H), 7.31 (d, J=8.8 Hz, 1H), 7.15 (d, J=7.4 Hz, 1H), 6.96 (t, J=7.5 Hz, 1H), 6.74 (m, 2H), 6.59 (m, 2H), 6.30 (bs, 1H), 5.00 (bs, 2H), 4.40 (s, 2H), 3.68 (s, 3H), 2.49 (s, 3H). LRMS: (calc.) 385.5; (obt.) 386.4 (MH)$^+$. | 53 |
| 135 | 254 | MeOCH$_2$ | N-(2-Amino-phenyl)-4-[(2-methoxy-methyl-1-methyl-1H-benzoimidazol-5-ylamino)-methyl]-benzamide | $^1$H NMR: (DMSO) δ (ppm): 9.57 (s, 1H), 7.91 (d, J=7.9 Hz, 2H), 7.51 (d, J=7.9 Hz, 2H), 7.25 (d, J=8.8 Hz, 1H), 7.15 (d, J=7.5 Hz, 1H), 6.96 (t, J=7.9 Hz, 1H), 6.73 (m, 2H), 6.59 (m, 2H), 6.14 (bs, 1H), 4.96 (bs, 2H), 4.57 (bs, 2H), 4.38 (s, 2H), 3.68 (s, 3H), 3.27 (s, 3H). LRMS: (caic.) 415.5; (obt.) 416.5 (MH)$^+$. | 53 |
| 136 | 255 | CF$_3$ | N-(2-Amino-phenyl)-4-[(1-methyl-2-trifluoromethyl-1H-benzoimidazol-5-ylamino)-methyl]-benzamide | $^1$H NMR: (DMSO) δ (ppm): 9.57 (s, 1H), 7.90 (d, J=8.2 Hz, 2H), 7.49 (d, J=8.2, 2H), 7.46 (d, J=8.6 Hz, 1H), 7.12 (d, J=6.6 Hz, 1H), 6.96-6.92 (m, 2H), 6.75 (dd, J=1.6, 8.2 Hz, 1H), 6.64 (d, J=2.0 Hz, 1H), 6.56 (ddd, J=1.6, 7.4, 7.8 Hz, 1H), 6.45 (t, J =6.2 Hz, 1H), 4.88 (bs, 2H), 4.40 (d, J=5.9 Hz, 2H), 3.85 (d, J=0.8 Hz, 3H), LRMS: (calc.) 339.4; (obt.) 440.5 (MH)$^+$. | 53 |
| 137 | 256 | 3,4-dimethoxyphenyl | N-(2-Amino-phenyl)-4-{[2-(3,4-dimethoxy-phenyl)-1-methyl-1H-benzoimidazol-5-ylamino]-methyl}-benzamide | $^1$H NMR: (DMSO) δ (ppm): 9.58 (s, 1H), 7.92 (d, J=8.0 Hz, 2H), 7.52 (d, J=8.0 Hz, 2H), 7.32-7.27 (m, 3H), 7.14 (d, J=7.5 Hz, 1H), 7.09 (d, J=7.5 Hz, 1H), 6.95 (t, J=7.5, 1H), 6.77-6.73 (m, 2H), 6.62 (s, 1H), 6.58 (t, J=8.0, 1H), 6.16 (bs, 1H), 4.87 (bs, 2H), 4.40 (d, J=4.5, 2H), 3.83 (s, 3H), 3.81 (s, 3H), 3.77 (s, 3H). LRMS: (calc.) 507.6; (obt.) 508.4 (MH)$^+$. | 53 |
| 138 | 257 | 3,4,5-trimethoxyphenyl | N-(2-Amino-phenyl)-4-{[1-methyl-2-(3,4,5-trimethoxy-phenyl)-1H-benzoimidazol-5-ylamino]-methyl}-benzamide | $^1$H NMR: (DMSO) δ (ppm): 9.58 (s, 1H), 7.92 (d, J=8.0 Hz, 2H), 7.52 (d, J=8.0 Hz, 2H), 7.34 (d, J=9.0 Hz, 1H), 7.14 (d, J=8.0 Hz, 1H), 7.03 (s, 2H), 6.95 (t, J=8.0, 1H), 6.77 (m, 2H), 6.62 (s, 1H), 6.58 (t, J=7.0, 1H), 6.27 (bs, 1H), 4.41 (bs, 2H), 3.84 (s, 3H), 3.81 (s, 3H), 3.73 (s, 3H). LRMS: (calc.) 537.6; (obt.) 538.5 (MH)$^+$. | 53 |
| 139 | 258 | 5-bromopyridin-3-yl | N-(2-Amino-phenyl)-4-{[2-(5-bromo-pyridin 3-yl)-1-methyl-1H-benzoimidazol-5-ylamino]-methyl}-benzamide | $^1$H NMR: (DMSO) δ (ppm): 9.58 (s, 1H), 8.97 (s, 1H), 8.82 (s, 1H), 8.44 (s, 1H), 7.92 (d, J=7.0 Hz, 2H), 7.52 (d, J=7.0 Hz, 2H), 7.36 (d, J=8.0 Hz, 1H), 7.14 (d, J=7.5 Hz, 1H), 6.95 (m, 1H), 6.81 (d, J=8.0 Hz, 1H), 6.76 (d, J=8.0 Hz, 1H), 6.64 (s, 1H), 6.57 (m, 1H), 6.27 (s, 1H), 4.87 (bs, 2H), 4.41 (d, J=5.5, 2H), 3.83 (s, 3H) LRMS: (calc.) 527.4; (obt.) 528.3 (MH)$^+$. | 53 |

TABLE 9-continued

Characterization of compounds prepared as example 133 (scheme 53)

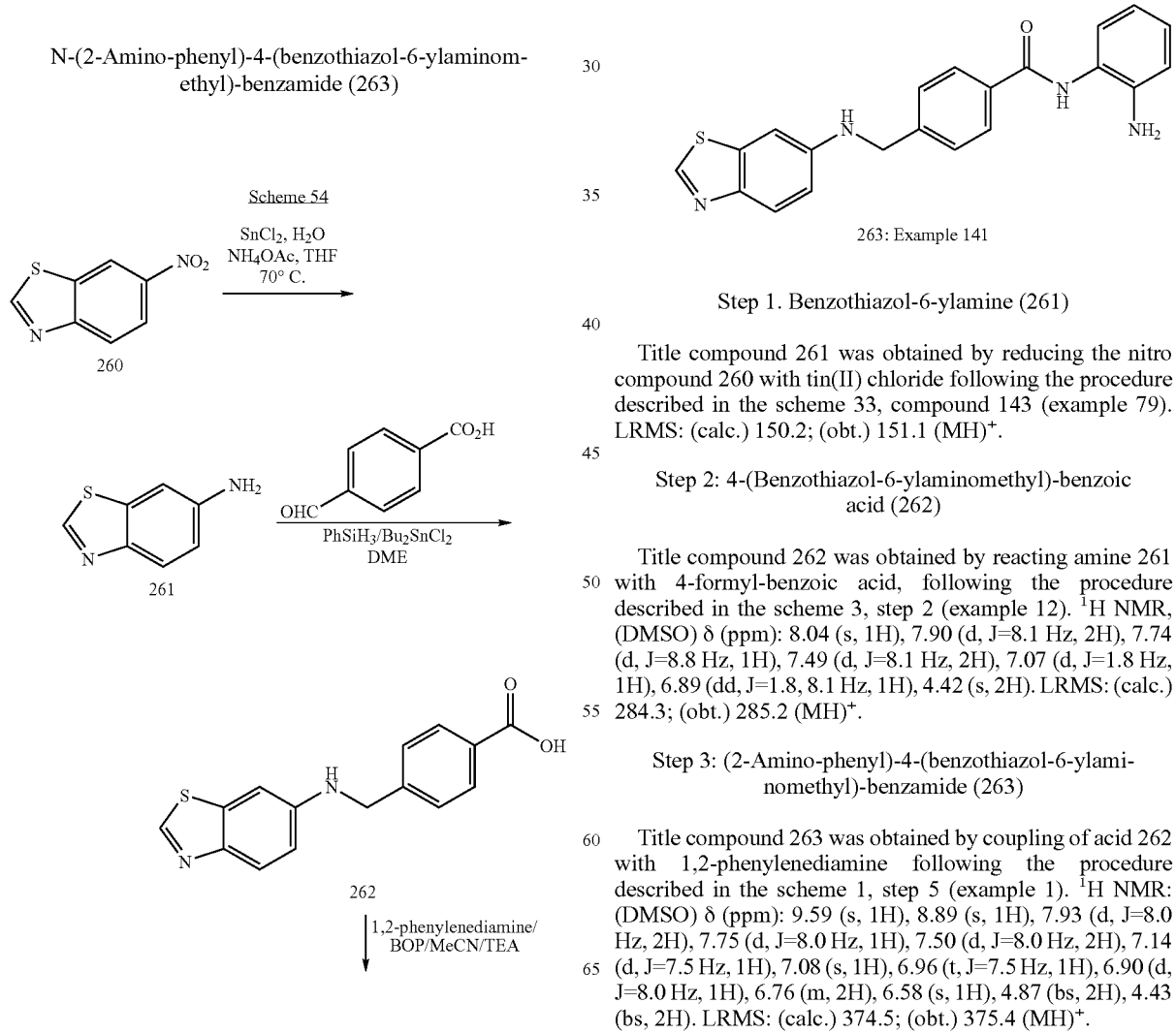

| Ex. | Cmpd | R | Name | Characterization | Scheme |
|---|---|---|---|---|---|
| 140 | 259 | (3-pyridyl) | N-(2-Amino-phenyl)-4-[(1-methyl-2-pyridin-3-yl-1H-benzoimidazol-5-ylamino)-methyl]-benzamide | $^1$H NMR: (DMSO) δ (ppm): 9.57 (s, 1H), 8.98 (s, 1H), 8.69 (s, 1H), 8.20 (d, J=8.5 Hz, 1H), 7.92 (d, J=8.0 Hz, 2H), 7.57 (m, 1H), 7.52 (d, J=8.0 Hz, 2H), 7.37 (d, J=9.0 Hz, 1H), 7.15 (d, J=7.5 Hz, 1H), 6.95 (t, J=7.5 Hz, 1H), 6.81 (d, J=8.5 Hz, 1H), 6.76 (d, J=8.0 Hz, 2H), 6.66 (s, 1H), 6.58 (t, J=7.5, 1H), 6.27 (bs, 1H), 4.90 (bs, 2H), 4.42 (bs, 2H), 3.81 (s, 3H) LRMS: (calc.) 448.52; (obt.) 449.2 (MH)$^+$. | 53 |

Example 141

N-(2-Amino-phenyl)-4-(benzothiazol-6-ylaminomethyl)-benzamide (263)

Step 1. Benzothiazol-6-ylamine (261)

Title compound 261 was obtained by reducing the nitro compound 260 with tin(II) chloride following the procedure described in the scheme 33, compound 143 (example 79). LRMS: (calc.) 150.2; (obt.) 151.1 (MH)$^+$.

Step 2: 4-(Benzothiazol-6-ylaminomethyl)-benzoic acid (262)

Title compound 262 was obtained by reacting amine 261 with 4-formyl-benzoic acid, following the procedure described in the scheme 3, step 2 (example 12). $^1$H NMR, (DMSO) δ (ppm): 8.04 (s, 1H), 7.90 (d, J=8.1 Hz, 2H), 7.74 (d, J=8.8 Hz, 1H), 7.49 (d, J=8.1 Hz, 2H), 7.07 (d, J=1.8 Hz, 1H), 6.89 (dd, J=1.8, 8.1 Hz, 1H), 4.42 (s, 2H). LRMS: (calc.) 284.3; (obt.) 285.2 (MH)$^+$.

Step 3: (2-Amino-phenyl)-4-(benzothiazol-6-ylaminomethyl)-benzamide (263)

Title compound 263 was obtained by coupling of acid 262 with 1,2-phenylenediamine following the procedure described in the scheme 1, step 5 (example 1). $^1$H NMR: (DMSO) δ (ppm): 9.59 (s, 1H), 8.89 (s, 1H), 7.93 (d, J=8.0 Hz, 2H), 7.75 (d, J=8.0 Hz, 2H), 7.50 (d, J=8.0 Hz, 2H), 7.14 (d, J=7.5 Hz, 1H), 7.08 (s, 1H), 6.96 (t, J=7.5 Hz, 1H), 6.90 (d, J=8.0 Hz, 1H), 6.76 (m, 2H), 6.58 (s, 1H), 4.87 (bs, 2H), 4.43 (bs, 2H). LRMS: (calc.) 374.5; (obt.) 375.4 (MH)$^+$.

Scheme 55

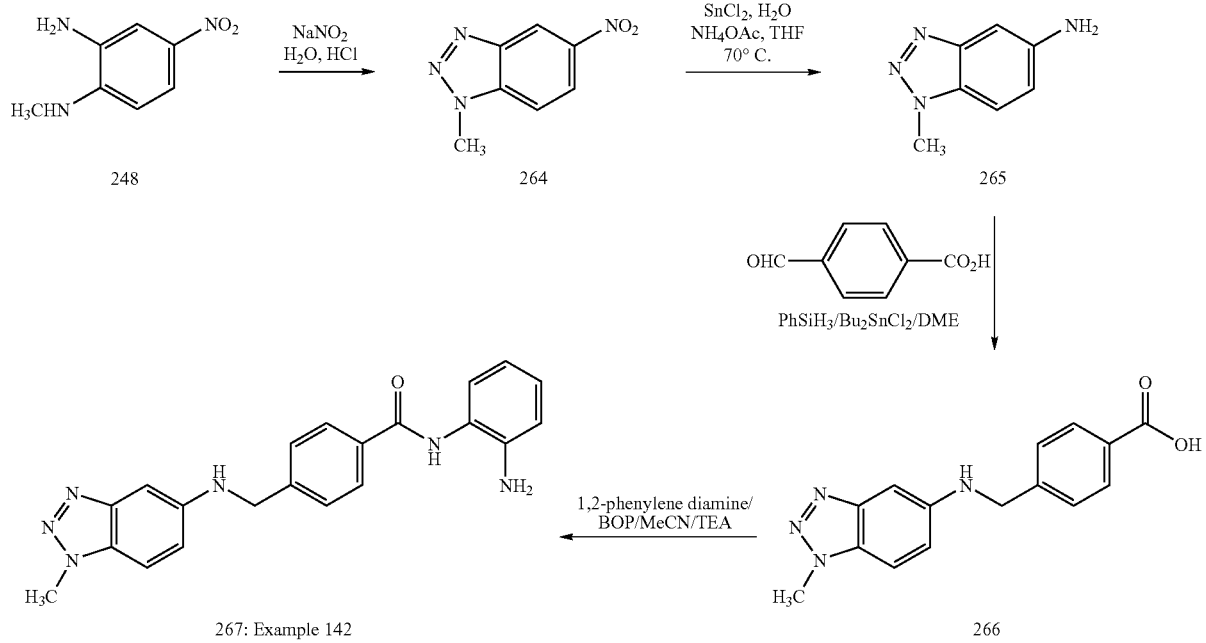

267: Example 142

Example 142

N-(2-Amino-phenyl)-4-[(1-methyl-1H-benzotriazol-5-ylamino)-methyl]-benzamide (267)

Step 1: 1-Methyl-5-nitro-1H-benzotriazole (264)

A stirred suspension of diamine 248 (1.13 g, 6.76 mmol) and concentrated HCl (5.6 mL, 67 mmol) in water (22 mL) at 0° C., was treated with a solution of NaNO$_2$ (586 mg, 8.5 mmol) in water (10 mL). The mixture was stirred at the same conditions for 3 h, warmed to room temperature, neutralized with a 5% w/v solution of KOH in water and filtered. The solid was washed with cold water and dried to afford title compound 264 (975 mg, 81% yield). $^1$H NMR: (DMSO) δ (ppm): 9.00 (d, J=1.3 Hz, 1H), 8.39 (dd, J=1.3, 8.8 Hz, 1H), 8.09 (d, J=8.8 Hz, 1H), 4.40 (s, 3H).

Step 2: 1-Methyl-1H-benzotriazol-5-ylamine (265)

Title compound 265 was obtained by reduction of the nitro compound 264 with tin(II) chloride, following the same procedure described in the scheme 33, compound 143 (example 79). $^1$H NMR: (CD$_3$OD) δ (ppm): 7.32 (d, J=8.8 Hz, 1H), 7.14 (d, J=1.7 Hz, 1H), 6.99 (dd, J=1.7, 8.8 Hz, 1H), 4.21 (s, 3H). LRMS: (calc.) 148.3; (obt.) 149.3 (MH)$^+$.

Step 3: 4-[(1-Methyl-1H-benzotriazol-5-ylamino)-methyl]-benzoic acid (266)

Title compound 266 was obtained by reacting amine 265 with 4-formyl-benzoic acid, following the procedure described in the scheme 3, step 2 (example 12). LRMS: (calc.) 282.3; (obt.) 283.3 (MH)$^+$.

Step 4: N-(2-Amino-phenyl)-4-[(1-methyl-1H-benzotriazol-5-ylamino)-methyl]-benzamide (267)

Title compound 267 was obtained by coupling of acid 266 with 1,2-phenylenediamine following the procedure described in the scheme 1, step 5 (example 1). $^1$H NMR: (DMSO) δ (ppm): 9.58 (s, 1H), 7.92 (d, J=8.0 Hz, 2H), 7.53 (m, 3H), 7.14 (d, J=8.0 Hz, 1H), 7.07 (dd, J=2.0, 8.5 Hz, 1H), 6.95 (t, J=7.5 Hz, 1H), 6.76 (d, J=8.0 Hz, 1H), 6.68 (s, 1H), 6.61 (s, 2H), 4.87 (bs, 2H), 4.42 (d, J=6.0 Hz, 2H), 4.16 (s, 3H). LRMS: (calc.) 372.4; (obt.) 373.5 (MH)$^+$.

Scheme 56

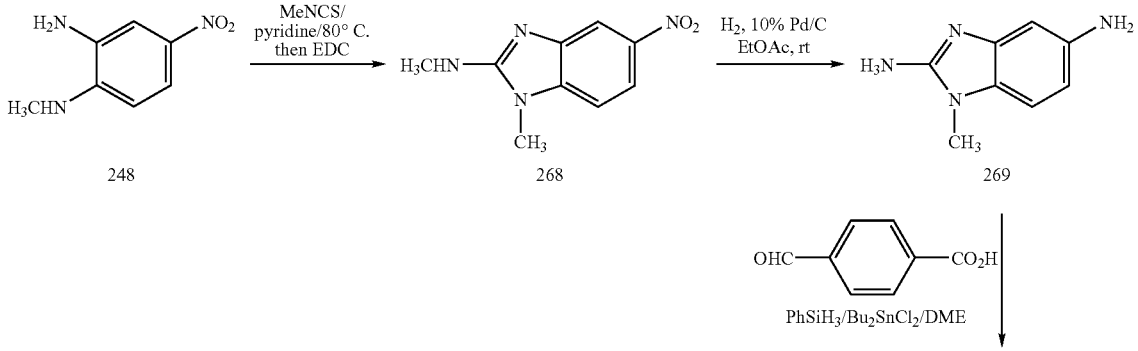

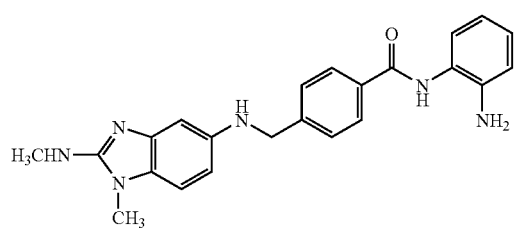

271: Example 143

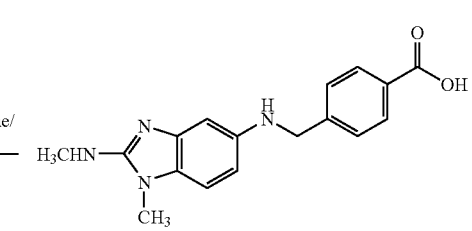

270

Example 143

N-(2-Amino-phenyl)-4-[(1-methyl-2-methylamino-1H-benzoimidazol-5-ylamino)-methyl]-benzamide (271)

Step 1: Methyl-(1-methyl-5-nitro-1H-benzoimidazol-2-yl)-amine (268)

A solution of diamine 248 (1.88 g, 11.2 mmol) in pyridine (20 mL) was treated with methyl isothiocyanate (970 mg, 12.9 mmol) and the mixture was stirred at 80° C. for 30 minutes, cooled down to 15° C., treated with solid EDC (3.03 g, 15.8 mmol, 1.40 eq) and the heating continued at 80° C. for 16 h. After removal of pyridine in vacuo, the residue was purified by flash chromatography (eluent 5% MeOH in $CH_2Cl_2$) to afford the title compound 268 (1.44 g, 62% yield). $^1$H NMR: ($CD_3OD$) δ (ppm): 8.12 (d, J=2.2 Hz, 1H), 7.94 (dd, J=2.2, 8.8 Hz, 1H), 7.04 (d, J=8.8 Hz, 1H), 4.44 (bs, 2H), 3.51 (s, 3H), 3.04 (s, 3H). LRMS: (calc.) 206.2; (obt.) 207.1 $(MH)^+$.

Step 2: Methyl-(1-methyl-5-amino-1H-benzoimidazol-2-yl)-amine (269)

Title compound 269 was obtained by catalytic hydrogenation of the nitro compound 268, following the procedure described in the scheme 25, step 2 (example 64). $^1$H NMR: ($CDCl_3$) δ (ppm): 6.70 (s, 1H), 6.62 (d, J=7.9 Hz, 1H), 6.29 (d, J=7.9 Hz, 1H), 5.97 (bs, 1H), 3.63 (bs, 2H), 3.15 (s, 3H), 2.90 (s, 3H). LRMS: (calc.) 176.2; (obt.) 177.3 $(MH)^+$.

Step 3: 4-[(1-Methyl-2-methylamino-1H-benzoimidazol-5-ylamino)-methyl]-benzoic acid (270)

Title compound 270 was obtained by reacting the amine 269 with 4-formyl-benzoic acid with, following the procedure described in the scheme 3, step 2 (example 12). $^1$H NMR: (DMSO) δ (ppm): 8.03 (bs, 1H), 7.88 (d, J=7.9 Hz, 2H), 7.47 (d, J=7.9 Hz, 2H), 7.02 (d, J=8.3 Hz, 1H), 6.46 (d, J=8.3 Hz, 1H), 6.44 (s, 1H), 4.35 (bs, 2H), 3.43 (s, 3H), 2.90 (d, J=3.5 Hz, 3H). LRMS: (calc.) 310.3; (obt.) 311.4 $(MH)^+$.

Step 4: N-(2-Amino-phenyl)-4-[(1-methyl-2-methylamino-1H-benzoimidazol-5-ylamino)-methyl]-benzamide (271)

Title compound 271 was obtained by coupling of the acid 270 with 1,2-phenylenediamine following the procedure described in the scheme 1, step 5 (example 1). $^1$H NMR: (DMSO) δ (ppm): 9.56 (s, 1H), 7.90 (d, J=7.9 Hz, 2H), 7.49 (d, J=7.9 Hz, 2H), 7.15 (d, J=7.5 Hz, 1H), 6.80 (d, J=8.4 Hz, 1H), 6.76 (d, J=8.4 Hz, 1H), 6.58 (t, J=7.5 Hz, 1H), 6.39 (s, 1H), 6.31 (m, 2H), 5.75 (t, J=5.7 Hz, 1H), 4.87 (s, 2H), 4.32 (d, J=5.7 Hz, 2H), 3.34 (s, 3H), 2.82 (d, J=4.4 Hz, 3H). LRMS: (calc.) 400.5; (obt.) 401.5 $(MH)^+$

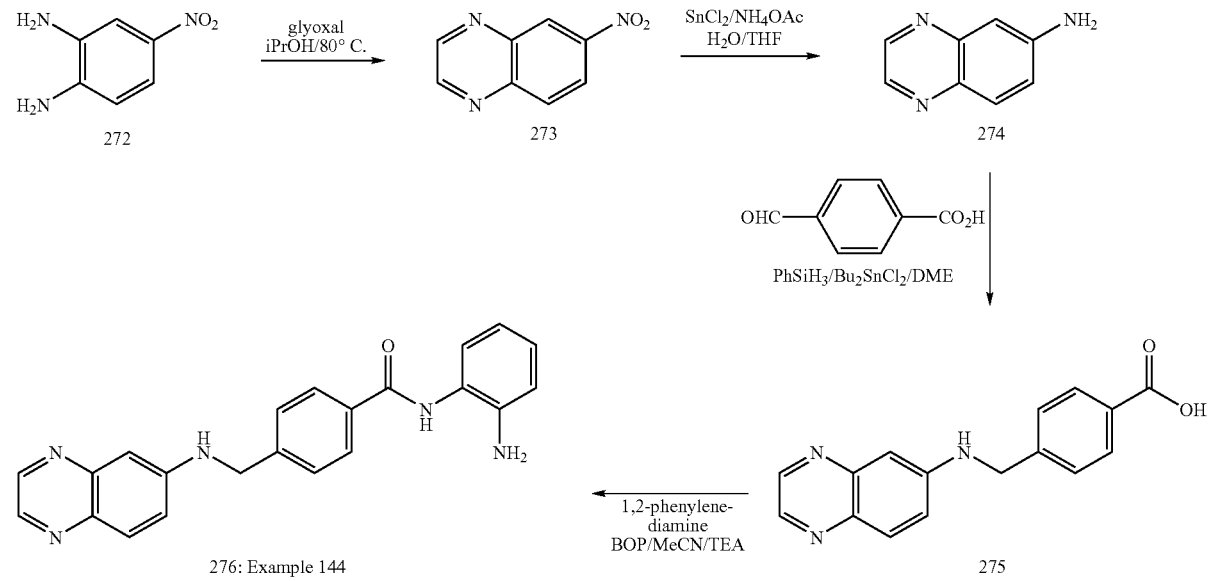

Scheme 57

Example 144

N-(2-Amino-phenyl)-4-(quinoxalin-6-ylaminomethyl)-benzamide (276)

Step 1: 6-Nitro-quinoxaline (273)

A solution of nitroaniline 272 (1.04 g, 6.76 mmol) in 2-propanol (35 mL) was treated with 40% aqueous glyoxal (0.85 mL, 7.4 mmol, 1.1 eq.) (or any other 1,2-dicarbonyl compound, 1.1 eq). The mixture was stirred at 80° C. for 2 h and concentrated in vacuo to afford the title compound 273, which was used for the next step without further purification. LRMS: (calc.) 175.1; (obt.) 176.1 (MH)$^+$.

Step 2: Quinoxalin-6-ylamine (274)

Title compound 274 was obtained by reduction of the nitro compound 273 with tin(II) chloride following the same procedure described in the scheme 33, compound 143 (example 79). LRMS: (calc.) 145.2; (obt.) 146.2 (MH)$^+$.

Step 3: 4-(Quinoxalin-6-ylaminomethyl)-benzoic acid (275)

Title compound 275 was obtained by reacting the amine 274 with 4-formyl-benzoic acid, following the procedures described in the scheme 3, step 2 (example 12). LRMS: (calc.) 279.3; (obt.) 280.2 (MH)$^+$.

Step 4: N-(2-Amino-phenyl)-4-(quinoxalin-6-ylaminomethyl)-benzamide (276)

Title compound 276 was obtained by coupling of acid 275 with 1,2-phenylenediamine following the procedure described in the scheme 1, step 5 (example 1). $^1$H NMR: (DMSO) δ (ppm): 9.61 (s, 1H), 8.56 (d, J=2.0 Hz, 1H), 8.43 (d, J=2.0 Hz, 1H), 7.93 (d, J=8.0 Hz, 2H), 7.75 (d, J=9.0 Hz, 1H), 7.52 (d, J=8.0 Hz, 2H), 7.40-7.36 (m, 2H), 7.13 (dd, J=1.6, 6.8 Hz, 1H), 6.95 (dt, J=1.6, 8.0 Hz, 1H), 6.76 (dd, J=1.2, 7.8 Hz, 1H), 6.67 (d, J=2.5 Hz, 1H), 6.59 (dd, J=1.2, 7.8 Hz, 1H), 5.05 (bs, 2H), 4.53 (d, J=5.7 Hz, 2H). LRMS: (calc.) 369.4; (obt.) 370.4 (MH)$^+$.

Example 145

N-(2-Amino-phenyl)-4-[(2,3-di-pyridin-2-yl-quinoxalin-6-ylamino)-methyl]-benzamide (277)

Title compound was prepared following the procedures depicted in scheme 57 for example 144 using in the first step 1,2-di-pyridin-2-yl-ethane-1,2-dione instead of glyoxal.

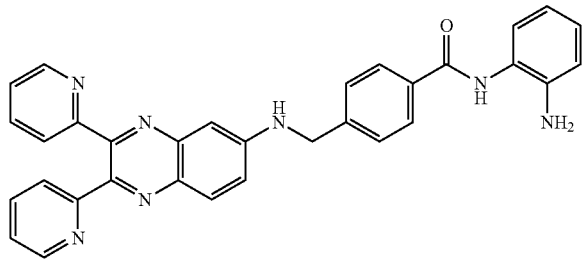

277: Example 145

$^1$H NMR: (DMSO) δ (ppm): 9.57 (s, 1H), 8.21 (m, 1H), 8.17 (m, 1H), 7.94 (d, J=8.0 Hz, 2H), 7.89-7.84 (m, 3H), 7.80 (dt, J=1.8, 7.6 Hz, 1H), 7.55 (m, 3H), 7.46 (dd, J=2.3, 9.0 Hz, 1H), 7.29-7.22 (m, 2H), 7.12 (d, J=7.6 Hz, 1H), 6.92 (m, 1H), 6.78 (d, J=2.3 Hz, 1H), 6.75 (dd, J=1.4, 8.3 Hz, 1H), 6.56 (t, J=7.6 Hz, 1H), 4.87 (bs, 2H), 4.58 (d, J=6.1 Hz, 2H), 4.34 (d, J=4.3 Hz, 1H). LRMS: (calc.) 523.6; (obt.) 524.5 (MH)$^+$.

Scheme 58

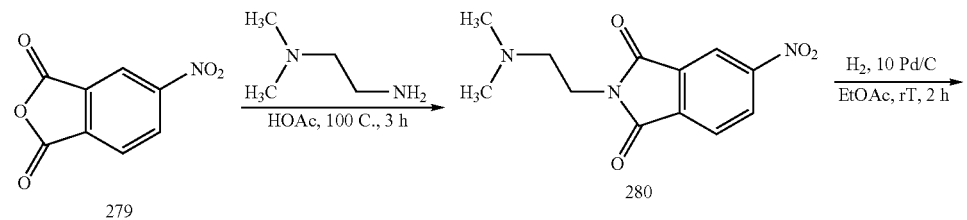

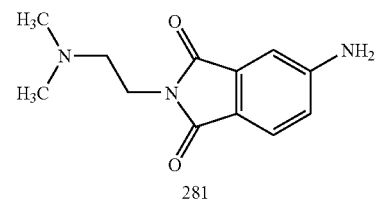

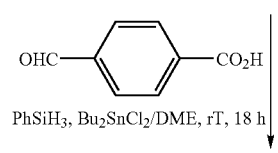

PhSiH$_3$, Bu$_2$SnCl$_2$/DME, rT, 18 h

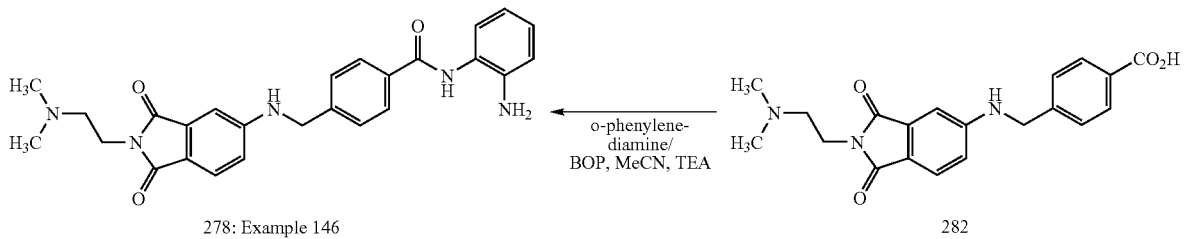

278: Example 146    282

Example 146

4-((2-(2-(dimethylamino)ethyl)-1,3-dioxoisoindolin-6-ylamino)methyl)-N-(2-aminophenyl)benzamide (278)

Step 1. 2-(2-(dimethylamino)ethyl)-5-nitroisoindoline-1,3-dione (280)

A solution of nitroftalic anhydride (279) (995 mg; 5.2 mmol) in acetic acid (12 mL) was treated with neat N1,N1-dimethylethane-1,2-diamine (0.75 mL; 5.8 mmol; 1.13 eq.) (or the corresponding amine, 1.3 eq.). The reaction mixture was stirred for 3 h at 100° C., cooled down to room temperature, concentrated in vacuo; the residue was dissolved in ethyl acetate (250 mL) and washed with saturated NaHCO$_3$, dried over MgSO$_4$, filtered and concentrated, to yield compound 280 as a yellow solid (1.19 g; 4.5 mmol; 87%). LRMS: 263.3 (calc.); 264.2 (obt.) (MH)$^+$.

Step 2. 5-amino-2-(2-(dimethylamino)ethyl)isoindoline-1,3-dione (281)

Title compound 281 was obtained by catalytic hydrogenation of the nitro compound 280 following the procedure described in the scheme 25, step 2 (example 64). LRMS: 233.3 (calc.); 234.2 (obt.) (MH)$^+$.

Step 3. 4-((2-(2-(dimethylamino)ethyl)-1,3-dioxoisoindolin-6-ylamino)methyl)benzoic acid (282)

Title compound 282 was obtained by reacting the amine 281 with 4-formyl-benzoic acid, following the procedure described in the scheme 3, step 2 (example 12). $^1$H NMR, (DMSO) δ (ppm): 7.89 (d, J=8.2 Hz, 2H), 7.78 (t, J=6.1 Hz, 1H), 7.53 (d, J=8.2 Hz, 1H), 7.43 (d, J=8.2 Hz, 2H), 6.91 (s, 1H), 4.53 (d, J=6.1 Hz, 2H), 3.80 (t, J=5.5 Hz, 2H), 3.32 (bs, 2H), 3.21 (bs, 2H), 2.74 (s, 6H). LRMS: 367.4 (calc.); 368.4 (obt.) (MH)$^+$.

Step 4. 4-((2-(2-(dimethylamino)ethyl)-1,3-dioxoisoindolin-6-ylamino)methyl)-N-(2-aminophenyl) benzamide (278)

Title compound 278 was obtained by coupling of acid 282 with 1,2-phenylenediamine following the procedure described in the scheme 1, step 5 (example 1). $^1$H NMR: (DMSO) δ (ppm): 9.52 (s, 1H), 7.85 (d, J=8.0 Hz, 2H), 7.63 (t, J=5.9 Hz, 1H), 7.42 (d, J=8.2 Hz, 2H), 7.37 (d, J=8.2 Hz, 2H), 7.05 (d, J=7.2 Hz, 1H), 6.87 (d, J=7.2 Hz, 1H), 6.82 (s, 1H), 6.76 (d, J=8.2 Hz, 2H), 6.67 (d, J=7.8 Hz, 1H), 6.49 (t, J=7.2 Hz, 1H), 4.81 (s, 2H), 4.45 (d, J=5.9 Hz, 2H), 3.48 (t, J=6.3 Hz, 2H), 2.32 (t, J=6.3 Hz, 2H), 2.04 (s, 6H). LRMS: (calc.) 457.5; (obt.) 458.5 (MH)$^+$.

Example 147

N-(2-Amino-phenyl)-4-[(1,3-dioxo-2-pyridin-3-ylmethyl-2,3-dihydro-1H-isoindol-5-ylamino)-methyl]-benzamide (283)

Title compound was prepared according to the reaction sequence depicted in scheme 58 for example 146, but using in the first step 3-aminomethylpyridine instead of N,N-dimethyl ethylenediamine.

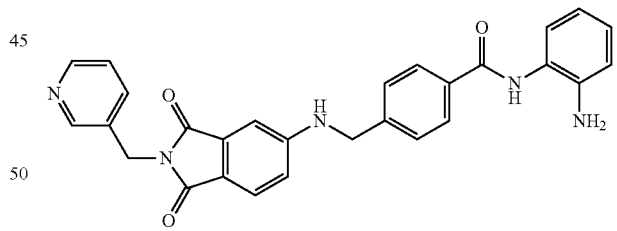

283: Example 147

$^1$H NMR: (DMSO) δ (ppm): 9.60 (s, 1H), 8.50 (s, 1H), 8.44 (t, J=3.7 Hz, 1H), 7.92 (d, J=8.0 Hz, 2H), 7.76 (t, J=6.3 Hz, 1H), 7.62 (dt, J=2.0, 3.9 Hz, 2H), 7.54 (d, J=8.2 Hz, 1H), 7.45 (d, J=8.0 Hz, 2H), 7.31 (dd, J=4.7, 7.6 Hz, 1H), 7.12 (d, J=6.6 Hz, 1H), 6.97-6.93 (m, 2H), 6.85 (d, J=8.4 Hz, 1H), 6.75 (dd, J=1.4, 8.0 Hz, 1H), 6.58 (dt, J=1.4, 7.6 Hz, 1H), 4.96 (bs, 2H), 4.70 (s, 2H), 4.53 (d, J=6.3 Hz, 2H). LRMS: (calc.) 477.5; (obt.) 478.5 (MH)$^+$.

TABLE 10

Characterization of examples 148-177 (compounds 284-313) prepared according to the schemes 19-30.

| Ex | Cmpd | Structure | Name | Characterization |
|---|---|---|---|---|
| 148 | 284 | 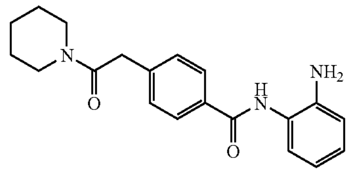 | N-(2-Amino-phenyl)-4-(2-oxo-2-piperidin-1-yl-ethyl)-benzamide | $^1$H NMR: (DMSO) δ (ppm): 9.61 (bs, 1H), 7.90 (d, J=8.2 Hz, 2H), 7.33 (d, J=8.2 Hz, 2H), 7.14 (d, J=7.6 Hz, 1H), 6.95 (ddd, J=7.6, 7.6, 1.5 Hz, 1H), 6.76 (dd, J=8.0, 1.2 Hz, 1H), 6.58 (ddd, J=7.4, 7.4, 1.2 Hz, 1H), 4.89 (s, 2H), 3.78 (s, 2H), 3.44-3.42 (m, 4H), 1.56-1.54 (m, 2H), 1.41-1.36 (m, 4H). MS: (calc.) 337.2; (obt.) 338.4 (MH)$^+$. |
| 149 | 285 | 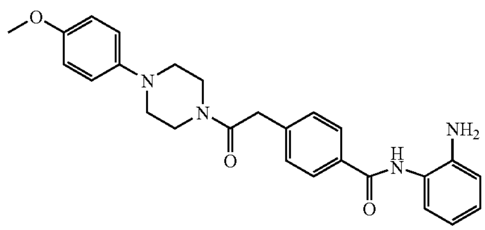 | N-(2-Amino-phenyl)-4-{2-[4-(4-methoxy-phenyl)-piperazin-1-yl]-2-oxo-ethyl}-benzamide | $^1$H NMR: (DMSO) δ (ppm): 9.60 (s, 1H), 7.88 (d, J=8.0 Hz, 2H), 7.33 (d, J=8.2 Hz, 2H), 7.11 (d, J=7.8 Hz, 1H), 6.93 (dd, J=7.6, 7.6 Hz, 1H), 6.86 (d, J=9.0 Hz, 2H), 6.78 (d, J=9.0 Hz, 2H), 6.74 (d, J=7.8 Hz, 1H), 6.55 (dd, J=7.4, 7.4 Hz, 1H), 4.88 (s,2H), 3.83 (s,2H), 3.65 (s,3H), 3.62-3.58 (m, 4H), 2.96-2.90 (m, 4H). MS: (calc.) 444.2; (obt.) 445.4 (MH)$^+$. |
| 150 | 286 | 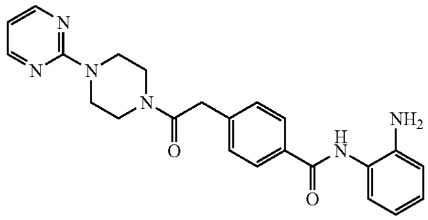 | N-(2-Amino-phenyl)-4-[2-oxo-2-(4-pyrimidin-2-yl-piperazin-1-yl)-ethyl]-benzamide | $^1$H NMR: (DMSO) δ (ppm): 9.62 (s, 1H), 8.36 (d, J=4.7 Hz, 2H), 7.90 (d, J=8.0 Hz, 2H), 7.36 (d, J=8.2 Hz, 2H), 7.13 (d, J=6.8 Hz, 1H), 6.95 (ddd, J=7.5, 7.5, 1.4 Hz, 1H), 6.76 (dd, J=8.0, 1.4 Hz, 1H), 6.70 (t, J=4.8 Hz, 1H), 6.57 (ddd, J=7.6, 7.6, 1.4 Hz, 1H), 4.90 (s, 2H), 3.87 (s, 2H), 3.72-3.68 (m, 4H), 3.62-3.55 (m, 4H). MS: (calc.) 416.2; (obt.) 417.4 (MH)$^-$. |
| 151 | 287 | 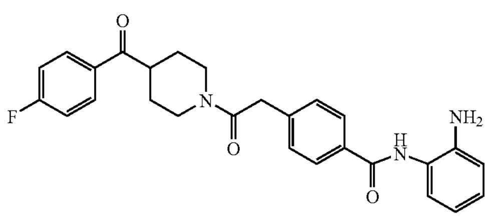 | N-(2-Amino-phenyl)-4-{2-[4-(4-fluoro-benzoyl)-piperidin-1-yl]-2-oxo-ethyl}-benzamide | $^1$H NMR: (DMSO) δ (ppm): 9.62 (s, 1H), 8.08-8.04 (m, 2H), 7.91 (d, J=8.0 Hz, 2H), 7.37-7.33 (m, 4H), 7.15 (d, J=7.2 Hz, 1H), 6.95 (ddd, J=7.5, 7.5, 1.4 Hz, 1H), 6.76 (dd, J=8.0, 1.4 Hz, 1H), 6.58 (ddd, J=7.6, 7.6, 1.4 Hz, 1H), 4.89 (s, 2H), 4.43-4.40 (m, 1H), 4.04-4.01 (m, 1H), 3.82 (s, 2H), 3.72-3.66 (m, 1H), 3.31-3.15(m, 1H), 1.82-1.74 (m, 2H), 1.40-1.34 (m, 2H). MS: (calc.) 459.2; (obt.) 460.5 (MH)$^+$. |
| 152 | 288 | 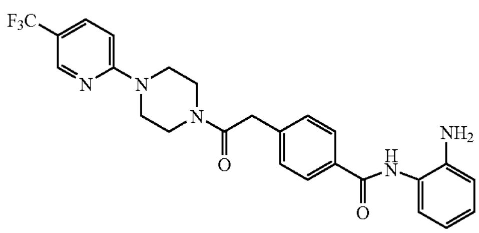 | N-(2-Amino-phenyl)-4-{2-oxo-2-[4-(5-trifluoromethyl-pyridin-2-yl)-piperazin-1-yl]-ethyl}-benzamide | $^1$H NMR: (DMSO) δ (ppm): 9.61 (s, 1H), 8.41 (s, 1H), 7.91 (d, J=8.0 Hz, 2H), 7.80 (dd, J=9.3, 2.4 Hz, 1H), 7.36 (d, J=8.4 Hz, 2H), 7.14 (d, J=7.6 Hz, 1H), 6.97-6.93 (m, 2H), 6.76 (dd, J=7.8, 1.4 Hz, 1H), 6.57 (ddd, J=7.6, 7.6, 1.4 Hz, 1H), 4.88 (s, 2H), 3.87 (s, 2H), 3.66-3.58 (m, 8H). MS: (calc.) 483.2; (obt.) 484.5 (MH)$^+$. |

TABLE 10-continued

Characterization of examples 148-177 (compounds 284-313)
prepared according to the schemes 19-30.

| Ex | Cmpd | Structure | Name | Characterization |
|---|---|---|---|---|
| 153 | 289 | 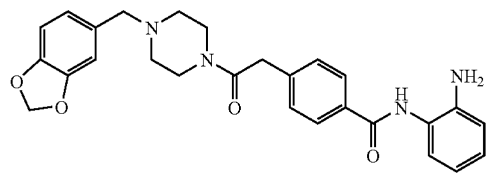 | N-(2-Amino-phenyl)-4-[2-(4-benzo[1,3]dioxol-5-ylmethyl-piperazin-1-yl)-2-oxo-ethyl]-benzamide | $^1$H NMR: (DMSO) δ (ppm): 9.60 (s, 1H), 7.89 (d, J= 8.2 Hz, 2H), 7.32 (d, J=8.2 Hz, 2H), 7.14 (d, J=7.6 Hz, 1H), 6.95 (ddd, J=7.6, 7.6, 1.8 Hz, 1H), 6.84-6.81 (m, 2H), 6.76 (dd, J=7.8, 1.2 Hz, 1H), 6.72 (dd, J= 8.0, 1.6 Hz, 1H), 6.58 (ddd, J=7.4, 7.4, 1.4 Hz, 1H), 5.97 (s, 2H), 4.89 (s, 2H), 3.78 (s, 2H), 3.49-3.46 (m, 4H), 3.37 (s, 2H), 2.29-2.27 (m, 4H). MS: (calc.) 372.2; (obt.) 373.5 (MH)$^+$. |
| 154 | 290 | 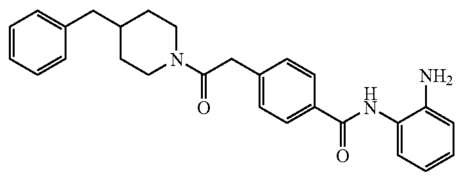 | N-(2-Amino-phenyl)-4-[2-(4-benzyl-piperidin-1-yl)-2-oxo-ethyl]-benzamide | $^1$H NMR: (400 MHz, DMSO-d$_6$,(ppm): 9.60 (s, 1H), 7.88 (d, J=8.2 Hz, 2H), 7.11 - 7.31 (m, 8H), 6.94 (d (dd), J=7.0 Hz, 1H), 6.75 (t (dd), J=7.8 Hz, 1H), 6.57 (d (dd), J=7.4 Hz, 1H), 4.87 (s, 2H), 4.34 (br. d, j= 12.5 Hz, 1H), 3.92 (br. d, j=13.9 Hz, 1H), 3.75 (s, 2H), 3.32 (s, 2H), 2.91 (br. t, j=11.3 Hz, 1H), 1.70-1.74 (m, 1H), 1.51-1.56 (m, 2H), 1.01-0.92 (m, 2H). |
| 155 | 291 | 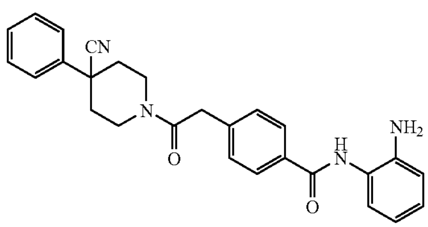 | N-(2-Amino-phenyl)-4-[2-(4-cyano-4-phenyl-piperidin-1-yl)-2-oxo-ethyl]-benzamide | $^1$H NMR: (400 MHz, DMSO-d$_6$,(ppm): 9.60 (s, 1H), 7.90 (d, J=8.0 Hz, 2H), 7.33-7.51 (m, 7H), 7.13 (d (dd), J=7.4 Hz, 1H), 6.93 (t (dd), J=9.4 Hz, 1H), 6 74 (d (dd), J=8.0 Hz, 1H), 6.56 (t (dd), j=7.8 Hz, 1H), 4.87 (s, 2H), 4.60 (br. d, j=13.9 Hz, 1H), 4.17 (br. d, j=14.7 Hz, 1H), 3.82-3.92 (m (instead of expected s), 2H), 3.26 (br. t, j=12.1 Hz, 1H), 2.85 (br. t, j=12.7 Hz, 1H), 2.12-2.16 (m, 2H), 1.89-1.94 (m, 2H). |
| 156 | 292 | 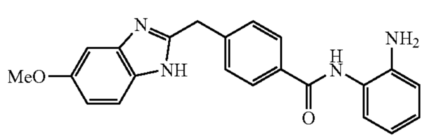 | N-(2-Amino-phenyl)-4-(5-methoxy-1H-benzoimidazol-2-ylmethyl)-benzamide | $^1$H NMR: (DMSO) δ (ppm): 12.12 (s, 1H), 9.59 (s, 1H), 7.91 (d, J=8.2 Hz, 2H), 7.42 (d, J=8.0 Hz, 2H), 7.35 (s, 1H), 7.14 (d, J=7.4 Hz, 1H), 6.97-6.93 (m, 2H), 6.77-6.73 (m, 2H), 6.58 (dd, J=7.1, 7.1 Hz, 1H), 4.87 (s, 2H), 4.21 (s, 2H), 3.75 (s, 3H). MS: (calc.) 372.2; (obt.) 373.5 (MH)$^+$. |
| 157 | 293 | 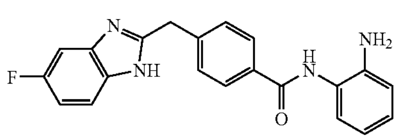 | N-(2-Amino-phenyl)-4-(5-fluoro-1H-benzoimidazol-2-ylmethyl)-benzamide | $^1$H NMR: (DMSO) δ (ppm): 12.42 (s, 1H), 9.59 (s, 1H 7.91 (d, J=8.2 Hz, 2H), 7.43 (m, 3H), 7.26 (m, 1H), 7.13 (d, J=6.7 Hz, 2H), 6.23-6.99 (m, 2H), 6.74 (d, J=1.4 Hz, 1H), 6.57 (dd, J=8.2, 8.2 Hz, 1H), 4.87 (s, 2H), 4.24 (s, 2H), 3.16 (s, 1H). MS: (calc.) 360.1; (obt.) 361.5 (MH)$^+$. |

TABLE 10-continued

Characterization of examples 148-177 (compounds 284-313) prepared according to the schemes 19-30.

| Ex | Cmpd | Structure | Name | Characterization |
|---|---|---|---|---|
| 158 | 294 | 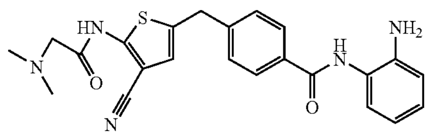 | N-(2-Amino-phenyl)-4-[4-cyano-5-(2-dimethylamino-acetylamino)-thiophen-2-ylmethyl]-benzamide | ¹H NMR: (DMSO) δ (ppm): 9.60 (bs, 1H), 7.93 (d, J= 8.1 Hz, 2H), 7.39 (d, J=8.1 Hz, 2H), 7.16 (d, J=7.3 Hz, 1H), 6.99-6.93 (m, 2H), 6.77 (d, J=7.3 Hz, 1H), 6.59 (dd, J=7.3, 7.3 Hz, 1H), 4.88 (bs, 2H), 4.12 (s, 2H), 3.33 (s, 2H), 2.36 (s, 6H). MS: (calc.) 432.2; (obt.) 433.5 (MH)⁻. |
| 159 | 295 | 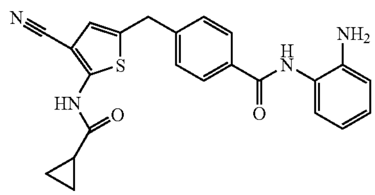 | N-(2-Amino-phenyl)-4-[4-cyano-5-(cyclopropanecarbonyl-amino)-thiophen-2-ylmethyl]-benzamide | ¹H NMR: (DMSO) δ (ppm): 11.85 (bs, 1H), 9.61 (bs, 1H), 7.92 (d, J=7.8 Hz, 2H), 7.39 (d, J=7.8 Hz, 2H), 7.15 (d, J=7.80 Hz, 1H), 6.98-6.95 (m, 2H), 7.11 (d, J =8.8 Hz, 2H), 6.99 (dd, J=7.7, 7.7 Hz, 1H), 6.77 (d, J= 6.3 Hz, 1H), 6.59 (dd, J=7.6, 7.6 Hz, 1H), 4.88 (bs, 2H), 4.12 (s, 2H), 2.14-2.13 (m, 1H), 0.90-0.84 (m, 4H). MS: (calc.) 392.1; (obt.) 393.4 (MH)⁻. |
| 160 | 296 | 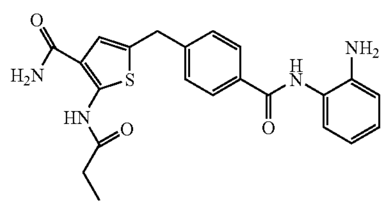 | 5-[4-(2-Amino-phenylcarbamoyl)-benzyl]-2-propionylamino thiophene-3-carboxylic acid amide | ¹H NMR: (DMSO) δ (ppm): 12.06 (s, 1H), 9.61 (s, 1H), 7.92 (d, J=8.2 Hz, 1H), 7.82 (bs, 1H), 7.45 (bs, 1H), 7.37 (d, J=8.2 Hz, 1H), 7.19 (s, 1H), 7.14 (d, J= 6.2 Hz, 1H), 6.95 (ddd, J=7.6, 7.6, 1.6 Hz, 1H), 6.76 (dd, J=8.2, 1.6 Hz, 1H), 6.57 (ddd, J=7.4, 7.4, 1.6 Hz, 1H), 4.98 (s, 2H), 4.10 (s, 2H), 2.44 (q, J=7.6 Hz, 2H), 1.09 (t, J=7.6 Hz, 2H). MS: (calc.) 422.1.; (obt.) 423.4. (MH)⁺. |
| 161 | 297 | 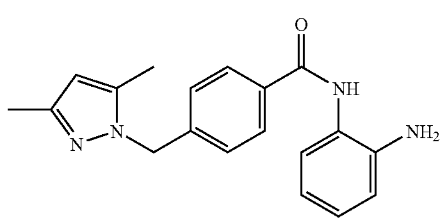 | N-(2-Amino-phenyl)-4-(3,5-dimethyl-pyrazol-1-ylmethyl)-benzamide | ¹H NMR: (400 MHz, DMSO-d₆,(ppm): 9.59 (s, 1H), 7.92 (d, J=8.2, 2H), 7.16 (d, J=8.4, 2H), 7.12 (d (dd), J=6.5, 1H), 6.94 (dd, J=1.4 Hz, j=7.8 Hz, 1H), 6.75 (dd, j=1.4 Hz, j=8.0 Hz, 1H), 6.57 (dd, j=1.4 Hz, 7.4 Hz, 1H), 5.86 (s, 1H), 5.26 (s, 2H), 4.88 (s, 2H), 2.16 (s, 3H), 2.11 (s, 3H) |
| 162 | 298 | 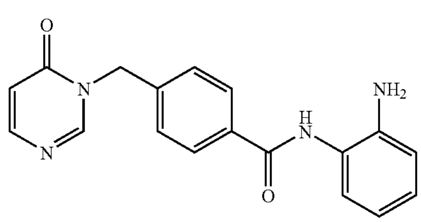 | N-(2-Amino-phenyl)-4-(6-oxo-6H-pyrimidin-1-ylmethyl)-benzamide | ¹H NMR: (DMSO) δ (ppm): 9.61 (s, 1H), 8.69 (s, 1H), 7.94-7.92 (m, 2H), 7.42 (d, J=7.8 Hz, 2H), 7.12 (d, J=7.4 Hz, 1H), 6.95 (dd, J=7.2, 7.2 Hz, 1H), 6.75 (d, J=7.2 Hz, 1H), 6.57 (dd, J=7.2, 7.2 Hz, 1H), 5.16 (s, 2H), 4.89 (s, 2H). MS: (calc.) 320.2; (obt.) 321.5 (MH)⁻. |

TABLE 10-continued

Characterization of examples 148-177 (compounds 284-313) prepared according to the schemes 19-30.

| Ex | Cmpd | Structure | Name | Characterization |
|---|---|---|---|---|
| 163 | 299 | 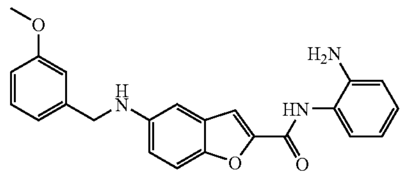 | 5-(3-Methoxy-benzylamino)-benzofuran-2 carboxylic acid (2-amino-phenyl)-amide | $^1$H NMR: (DMSO) δ(ppm): 9.69 (s, 1H), 7.45 (s, 1H), 7.40 (d, J=6.8 Hz, 1H), 7.26-7.18 (m, 2H), 6.97-6 73 (m, 8H), 6.60 (dd, J=7.3, 7.3 Hz, 1H), 6.22 (t, j=5.9 Hz, 1H), 4.92 (s, 2H), 4.27 (d, J=5.9 Hz, 2H), 3.73 (s, 3H). MS: (calc.) 387.1; (obt.) 388.4 (MH)$^+$. |
| 164 | 300 | 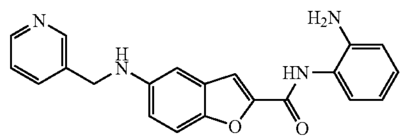 | 5-[(Pyridin-3-ylmethyl)-amino]-benzofuran-2-carboxylic acid (2-amino-phenyl)-amide | $^1$H NMR: (DMSO) δ (ppm): 9.69 (s, 1H), 8.62 (s, 1H), 8.44 (d, J=4.4 Hz, 1H), 7.78 (d, J=8.0 Hz, 1H), 7.45 (s, 1H), 7.41 (d, J=8.8 Hz, 1H), 7.35 (dd, J=8.1, 5.1 Hz, 1H), 7.18 (d, J=8.1 Hz, 1H), 6.97 (dd, J=7.0, 7.0 Hz, 1H), 6.88 (dd, J=8.8, 2.2 Hz, 1H), 6.79-6.77 (m, 2H), 6.59 (dd, J=6.9, 6.9 Hz, 1H), 6.27 (t, J=5.9 Hz, 1H), 4391 (s,2H), 4.33 (d, J=5.9 Hz, 1H). MS: (calc.) 358.1; (obt.) 359.4 (MH)$^+$. |
| 165 | 301 | 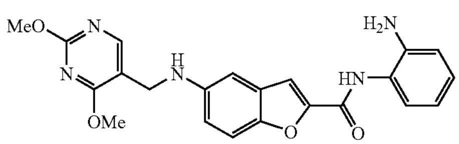 | 5-[(2,4-Dimethoxy-pyrimidin-5-ylmethyl)-amino]-benzofuran-2-carboxylic acid (2-amino-phenyl)-amide | $^1$H NMR: (DMSO) δ (ppm): 9.70 (s, 1H), 8.20 (s, 1H), 7.46 (s, 1H), 7.40 (d, J=8.8 Hz, 1H), 7.17 (dd, J=7.8, 1.2 Hz, 1H), 6.96 (ddd, J=7.6, 7.6, 1.5 Hz, 1H), 6.85 (dd, J=8.9, 2.3 Hz, 1H), 6.78-6.76 (m, 2H), 6.58 (ddd, J=7.5, 7.5, 1.4 Hz, 1H), 5.99 (t, J=5.8 Hz, 1H), 4.92 (s, 2H), 4.14 (d, J=5.9 Hz, 2H), 3.97 (s, 3H), 3.86 (s, 3H). MS: (calc.) 419.2; (obt.) 420.5 (MH)$^+$. |
| 166 | 302 | 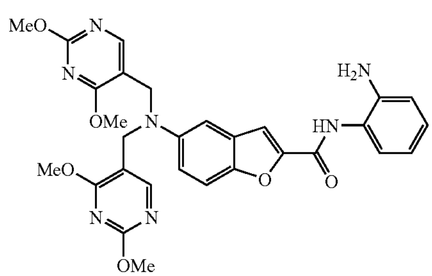 | 5-[Bis-(2,4-dimethoxy-pyrimidin-5-ylmethyl)-amino]-benzofuran-2-carboxylic acid (2-amino-phenyl)-amide | $^1$H NMR: (DMSO) δ (ppm): 9.72 (s, 1H), 7.66 (s, 2H), 7.47-7.39 (m, 2H), 7.15 (d, J=7.0 Hz, 1H), 6.98-6.92 (m, 3H), 6.75 (d, J=8.0 Hz, 1H), 6.56 (dd, J=7.5, 7.5 Hz, 1H), 4.91 (s, 2H), 4.47 (s, 4H), 3.90 (s, 6H), 3.82 (s, 6H). MS: (calc.) 571.2; (obt.) 572.5 (MH)$^+$. |
| 167 | 303 | 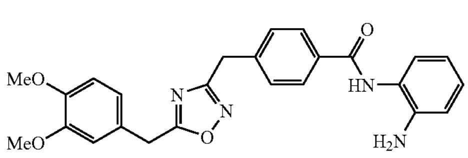 | N-(2-Amino-phenyl)-4-[5-(3,4-dimethoxy-benzyl)-[1,2,4]oxadiazol-3-ylmethyl]-benzamide | $^1$H NMR: (300 MHz, DMSO-d$_6$ (ppm): 9.61 (s, 1H), 7.92 (d, J=7.62 2H), 7.42 (d, J =8.21, 2H), 7.15 (d, J=7.62, 1H), 6.99-6.89 (m, 3H), 6.83-6.76 (m, 2H), 6.59 (t, J=7.03, 1H), 4.88 (brs, 2H), 4.23 (s, 2H), 4.16 (s, 2H), 3.72 (s, 3H), 3.71 (s, 3H) |

TABLE 10-continued

Characterization of examples 148-177 (compounds 284-313) prepared according to the schemes 19-30.

| Ex | Cmpd | Structure | Name | Characterization |
|---|---|---|---|---|
| 168 | 304 | 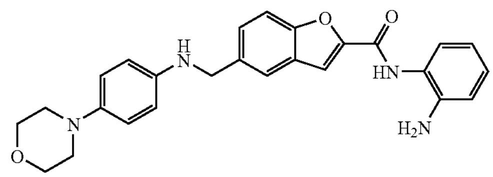 | 5-[(4-Morpholin-4-yl-phenylamino)-methyl]-benzofuran-2-carboxylic acid (2-amino-phenyl)-ainide | $^1$H NMR: (DMSO) δ (ppm): 9.01 (s, 1H), 6.92 (s, 1H), 6.84 (s, 1H), 6.80 (d, J=8.5, 1H), 6.65 (d, J=9.0, 1H), 6.36 (d, J=8.0, 1H), 6.16 (t, J=7.75, 1H), 5.96 (d, J=7.5, 1H), 5.89 (d, J =8.0, 2H), 5.77 (t, J=7.5, 1H), 5.71 (d, J=8.0, 2H), 5.05 (m, 1H), 4.12 (brs, 2H), 3.49 (brd, J=5.5, 2H), 2.87-2.83 (m, 4H), 2.06-2.02 (m, 4H). MS: (calc.) 442; (obt.) 443.5 (MH)$^+$. |
| 169 | 305 | 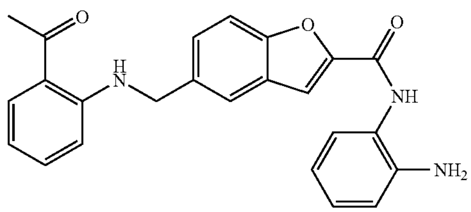 | 5-[(2-Acetyl-phenylamino)-methyl]-benzofuran-2-carboxylic acid (2-amino-phenyl)-amide | $^1$H NMR: (DMSO) δ (ppm): 9.85 (s, 1H), 9.26 (s, 1H), 7.86 (d, J=8.0, 1H), 7.75 (s, 1H), 7.69-7.67 (m, 2H), 7.47 (d, J=8.5, 1H), 7.33 (t, J=7.75, 1H), 7.19 (d, J=7.5, 1H), 6.99 (t, J=7.75, 1H), 6.78 (d, J=14.0, 1H), 6.77 (d, J=14.0, 1H), 6.62-6.59 (m, 2H), 4.96 (s, 2H), 4.59 (d, J=5.5, 2H), 2.57 (s, 3H). MS: (calc.) 399; (obt.) 400.2 (MH)$^+$. |
| 170 | 306 | 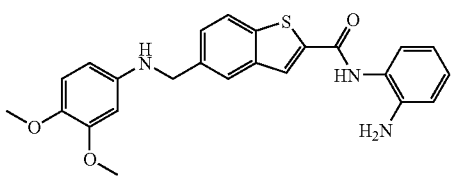 | 5-[(3,4-Dimethoxy-phenylamino)-methyl]-benzo[b]thiophene-2-carboxylic acid (2-amino-phenyl)- | $^1$H NMR: (DMSO) δ (ppm): 9.88 (s, 1H), 8.25 (s, 1H), 7.97 (d, J=8.5, 1H), 7.91 (s, 1H), 7.49 (d, J=8.5, 1H), 7.16 (d, J=7.5, 1H), 6.98 (t, J=7.25, 1H), 6.78 (d, J=8.0, 1H), 6.65 (d, J=8.0, 1H), 6.60 (t, J=7.5, 1H), 6.35 (s, 1H), 6.05 (d, J=9.0, 1H), 5.96 (s, 1H), 4.97 (s, 2H), 4.36 (d, J=5.0, 2H), 3.65 (s, 3H), 3.58 (s, 3H). MS: (calc.) 433.1; (obt.) 434.5 (MH)$^+$. |
| 171 | 307 | 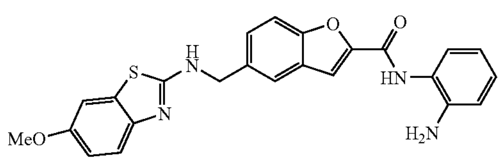 | 5-[(6-Methoxy-benzothiazol-2-ylamino)-methyl] benzofuran-2-carboxylic acid (2-amino-phenyl)-amide | MS: (calc.) 444.1; (obt.) 445.4 (MH)$^+$. |
| 172 | 308 | 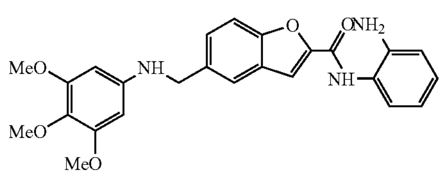 | 5-[(3,4,5-Trimethoxy-phenylamino)-methyl]-benzofuran-2-carboxylic acid (2-amino-phenyl)-amide | $^1$H NMR: (DMSO) δ (ppm): 9.82 (s, 1H), 7.75 (s, 1H); 7.67 (s, 1H); 7.63 (d, J=8.6 Hz, 1H); 7.47 (dd, J=8.6, 1.6 Hz, 1H); 7.16 (dd, J=7.8, 1.4, Hz, 1H); 6.96 (dt, J=8.0, 1.6 Hz, 1H); 6.76 (dd, J=8.0, 1.4 Hz, 1H); 6.58 (dt, J=7.6, 1.4 Hz, 1H); 6.11 (t, J=6.1 Hz, 1H); 5.90 (s, 2H); 4.95 (s, 2H); 4.34 (d, J=5.9 Hz, 2H); 3.63 (s, 6H); 3.49 (s, 3H). MS: (calc.) 447.2; (obt.) 448.5 (MH)$^+$. |

TABLE 10-continued

Characterization of examples 148-177 (compounds 284-313) prepared according to the schemes 19-30.

| Ex | Cmpd | Structure | Name | Characterization |
|---|---|---|---|---|
| 173 | 309 | 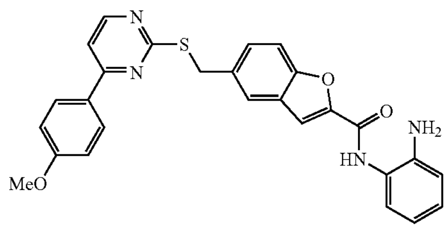 | 5-[4-(4-Methoxy-phenyl)-pyrimidin-2-ylsulfanylmethyl]-benzofuran-2-carboxylic acid (2-amino-phenyl)-amide | $^1$H NMR: (DMSO) δ (ppm): 9.85 (s, 1H), 8.63 (d, J=5.3 Hz, 1H), 8.19 (dd, J=6.8, 2.0 Hz, 2H); 7.89 (d, J=1.0 Hz, 1H); 7.73 (d, J=5.5 Hz, 1H); 7.66 (m, 2H); 7.59 (dd, J=8.6, 1.8 Hz, 1H); 7.17 (dd, J=7.6, 1.2 Hz, 1H); 7.10 (dd, J=6.8, 2.0 Hz, 2H); 6.98 (dt, J=8.0, 1.8 Hz, 1H); 6.78 (dd, J=7.8, 1.2 Hz, 1H); 6.59 (ddd, J=1.4, 7.6, 8.8 Hz, 1H); 4.97 (s, 2H); 4.64 (s, 2H); 3.86 (s, 3H). MS: (calc.) 482.5; (obt.) 483.5 (MH)$^+$. |
| 174 | 310 | 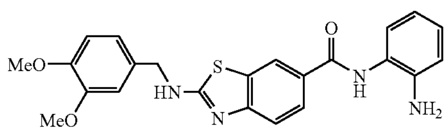 | 2-(3,4-Dimethoxy-benzylamino)-benzothiazole-6-carboxylic acid (2-amino-phenyl)-amide | $^1$H NMR: (DMSO) δ (ppm): 948 (s, 1H), 8.00 (d, J=2.0, 1H), 7.77 (dd, J=8.2, 1.6, 1H), 7.11 (d, J=6.7, 1H), 7.06-7.04 (m, 2H), 6.92 (dt, J=7.6, 1.6 Hz, 1H), 6.86-6.84 (m, 1H), 6.79 (d, J=8.2 Hz, 1H), 6.73 (dd, J=8.2, 1.6 Hz, 6.55 (dt, J=7.6, 1.2 Hz, 1H), 5.11 (s, 2H), 4.86 (brs, 2H), 3.71 (s, 3H), 3.69 (s, 3H). MS: (calc.) 434; (obt.) 435.4 (MH)$^+$. |
| 175 | 311 | 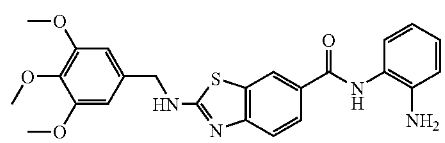 | 2-(3,4,5-Trimethoxy-benzylamino)-benzothiazole-6-carboxylic acid (2-amino-phenyl)-amide | $^1$H NMR: (DMSO) δ (ppm): 9.54 (s, 1H), 8.70 (brt, J=5.48, 1H), 8.30 (d, J=1.76, 1H), 7.86 (dd, J=8.32, 1.67, 1H), 7.45 (d, J=8.41, 1H), 7.15 (d, J=6.85, 1H), 6.94 (m, 1H), 6.76 (dd, J=7.93, 1.27, 1H), 6.72 (s, 2H), 6.58 (m, 1H), 4.89 (brs, 2H), 4.55 (d, J=5.48, 2H), 3.76 (s, 6H), 3.63 (s, 3H). MS: (calc.) 464; (obt.) 465.5 (MH)$^+$. |
| 176 | 312 | 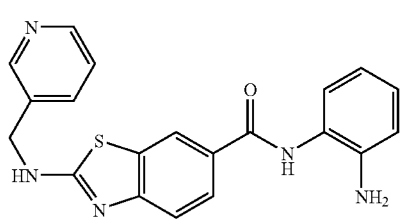 | 2-[(Pyridin-3-ylmethyl)-amino]-benzothiazole-6-carboxylic acid (2-amino-phenyl)-amide | $^1$H NMR: (DMSO) δ (ppm): 9.56 (s, 1H), 8.83 (t, J=5.9 Hz, 1H); 8.62 (d, J=1.4 Hz, 1H); 8.49 (dd, J=1.6, 4.7 Hz, 1H); 8.32 (d, J=1.8 Hz, 1H); 7.88 (dd, J=1.9, 6.4 Hz, 1H); 7.81 (m, 1H); 7.40 (m, 1H); 7.46 (d, J=8.4 Hz, 1H); 7.16 (d, J=6.4 Hz, 1H); 6.96 (dt, J=1.0, 8.6 Hz, 1H); 6.77 (dd, J=1.2, 7.8 Hz, 1H); 6.60 (dt, J=1.0, 8.8 Hz, 1H); 4.90 (s, 2H); 4.68 (d, J=5.7 Hz, 2H). MS: (calc.) 375.1; (obt.) 376.4 (MH)$^+$. |

TABLE 10-continued

Characterization of examples 148-177 (compounds 284-313) prepared according to the schemes 19-30.

| Ex | Cmpd | Structure | Name | Characterization |
|---|---|---|---|---|
| 177 | 313 | 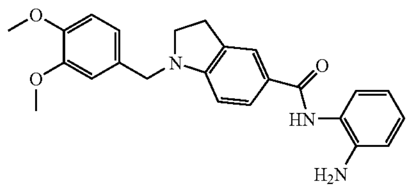 | 1-(3,4-Dimethoxy-benzyl)-2,3-dihydro-1H-indole-5-carboxylic acid (2-amino-phenyl)-amide | $^1$H NMR: (DMSO) δ (ppm): 9.29 (s, 1H), 7.71 (dd, J=8.22, 1.77, 1H), 7.66 (brm, 1H), 7.12 (dd, J=7.93, 1.47, 1H), 6.93-6.89 (m, 3H), 6.84 (dd, J=8.22, 1.96, 1H), 6.75 (dd, J=8.02, 1.37, 1H), 6.65 (d, J=8.41, 1H), 6 57 (dt, J=7.53, 1.30, 1H), 4.82 (s, 2H), 3.73 (s, 6H), 3.41 (t, J=8.51, 2H), 2.98 (t, J=8.51, 2H). MS: (calc.) 403; (obt.) 404.5 (MH)$^+$. |

Example 178

N-(2-Amino-phenyl)-4-{[4-(2,4-dimethyl-thiazol-5-yl)-pyrimidin-2-ylamino]-methyl}-benzamide (314)

314: Example 178

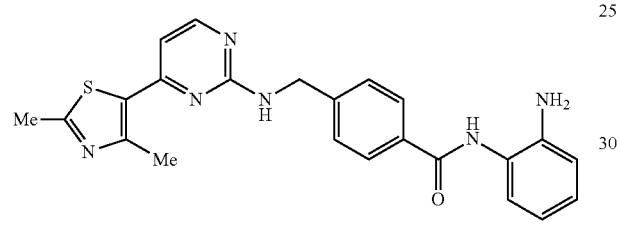

Title compound was obtained according to the scheme 6 similarly to the compound 26a (Example 29) using instead of 1-pyrazin-2-yl-ethanone as the starting material 1-(2,4-dimethyl-thiazol-5-yl)-ethanone (Table 11). Characterization of the title compound is provided in the Table 12.

TABLE 11

Heteroarylmethyl ketones used in the synthesis of examples 178-188

| Cmpd | Structure of Heteroary lmethyl ketone | Name of the Heteroary lmethyl ketone | Scheme | Example of the final product it was used for |
|---|---|---|---|---|
| | | 1-(2,4-Dimethyl-thiazol-5-yl)-ethanone | | 178 |
| | | 1-(2H-Pyrazol-3-yl)-ethanone | | 179 |
| | | 1-(2,4-Dimethyl-oxazol-5-yl)-ethanone | | 180 |
| 320 | | 1-(3-Hydroxymethyl-isoxazol-5-yl)-ethanone | 59 | 181 |

TABLE 11-continued

Heteroarylmethyl ketones used in the synthesis of examples 178-188

| Cmpd | Structure of Heteroarylmethyl ketone | Name of the Heteroarylmethyl ketone | Scheme | Example of the final product it was used for |
|---|---|---|---|---|
| 324 | (HOH₂C, Me, Me on isoxazole with C=O) | 1-(3-(Hydroxymethyl)-5-methylisoxazol-4-yl)ethanone | 60 | 182 |
| 327 | (1,2,3-triazole with C(O)Me) | 1-(3H-1,2,3-Triazol-4-yl)ethanone | 61 | 183, 184 |
| 333 | (2-methylimidazo[1,2-a]pyridine with C(O)Me) | 1-(2-Methylimidazo[1,2-a]pyridin-3-yl)ethanone | 62 | 185 |
|  | (H₂N-thiazole-Me with C(O)Me) | 1-(2-Amino-4-methylthiazol-5-yl)ethanone | | 186, 187 |

Example 179

N-(2-Amino-phenyl)-4-{[4-(2H-pyrazol-3-yl)-pyrimidin-2-ylamino]-methyl}-benzamide (315)

315: Example 179

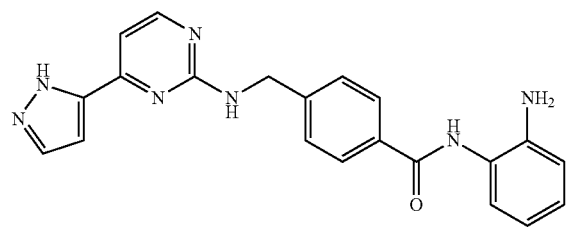

Title compound was obtained according to the scheme 6 similarly to the compound 26a (Example 29) using instead of 1-pyrazin-2-yl-ethanone as the starting material 1-(2H-pyrazol-3-yl)-ethanone (Table 11). Characterization of the title compound is provided in the Table 12.

Example 180

N-(2-Amino-phenyl)-4-{[4-(2,4-dimethyl-oxazol-5-yl)-pyrimidin-2-ylamino]-methyl}-benzamide (316)

316: Example 180

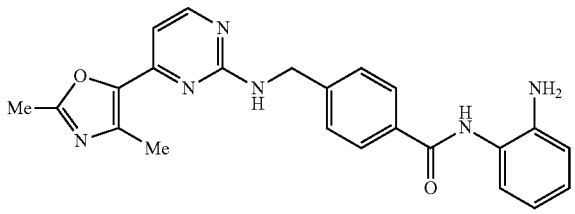

Title compound was obtained according to the scheme 6 similarly to the compound 26a (Example 29) using instead of 1-pyrazin-2-yl-ethanone as the starting material 1-(2,4-dimethyl-oxazol-5-yl)-ethanone (Table 11). Characterization of the title compound is provided in the Table 12.

Example 181

N-(2-Amino-phenyl)-4-{[4-(2,4-dimethyl-oxazol-5-yl)-pyrimidin-2-ylamino]-methyl}-benzamide (317)

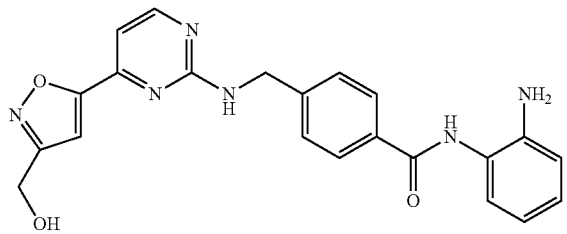

317: Example 181

Step 1. Ethyl 5-(2-methyl-1,3-dioxolan-2-yl)isoxazole-3-carboxylate (318)

A reaction mixture consisting of ethyl 5-acetylisoxazole-3-carboxylate (2.53 g, 13.8 mmol), ethylene glycol (1.29 g, 20.7 mmol) and p-TsOH (0.13 g, 0.69 mmol) in benzene (50 mL) was refluxed with the Dean-Stark adapter for 24 hours (scheme 59). Most of the solvent was removed under reduced pressure and the residue was partitioned between saturated NaHCO$_3$ and EtOAc. Organic layer was collected, washed with brine, water, and dried over MgSO$_4$. Evaporation of the dried extract under reduced pressure afforded the title compound as an oil (3.14 g, 100% yield), which was used for next step without further purification. $^1$H NMR (DMSO-d$_6$) δ (ppm): 6.89 (s, 1H), 4.35 (q, J=7.2 Hz, 2H), 4.07-4.01 (m, 2H), 4.01-3.94 (m, 2H), 1.70 (s, 3H), 1.32 (t, J=7.0 Hz, 3H). MS (m/z): 227.21 (calc) 228.1 (MH$^+$) (found).

Step 2. (5-(2-Methyl-1,3-dioxolan-2-yl)isoxazol-3-yl)methanol (319)

To a solution of the dioxolane 318 (3.14 g, 13.8 mmol) in a 1:2 mixture of EtOH-THF (45 mL) NaBH$_4$ (0.68 g, 18.0 mmol) was added. The reaction mixture was stirred at room temperature for 2 hours, treated with water and the organic solvents were evaporated. The aqueous phase was extracted with EtOAc and combined organic layers were successively washed with H$_2$O and brine, dried over MgSO$_4$ and concentrated under reduced pressure to afford the title compound as oil (2.39 g, 93% yield) which was used for next step without further purification. $^1$H NMR (DMSO-d$_6$) δ (ppm): 6.43 (s, 1H), 5.47 (t, J=5.9 Hz, 1H), 4.47 (d, J=5.9 Hz, 2H), 4.06-4.02 (m, 2H), 3.94-3.90 (m, 2H), 1.66 (s, 3H). MS (m/z): 185.18 (calc) 186.1 (MH+) (found).

Step 3. 1-(3-(Hydroxymethyl)isoxazol-5-yl)ethanone (320)

To a solution of the carbinol 319 (2.39 g, 12.9 mmol) in MeOH (30 mL) 10% HCl (30 mL) was added. The reaction mixture was stirred at 70° C. for 18 hours, cooled and neutralized to pH 6 using 1M NaOH solution. MeOH was evaporated and the resulting aqueous phase was extracted with EtOAc. The organic layer was washed with brine, dried under MgSO$_4$ and concentrated under reduced pressure to produce the title compound as a beige solid (1.67 g, 92% yield), which was used for next step without further purification. $^1$H NMR (DMSO-d$_6$) δ (ppm): 7.25 (s, 1H), 5.62 (t, J=6.1 Hz, 1H), 4.56 (d, J=5.9 Hz, 2H), 2.56 (s, 3H). MS (m/z): 141.12 (calc) 142.1 (MH+) (found)

Step 4. N-(2-Amino-phenyl)-4-{[4-(2,4-dimethyl-oxazol-5-yl)-pyrimidin-2-ylamino]-methyl}-benzamide (317)

Title compound was obtained according to the scheme 6 similarly to the compound 26a (Example 29) using instead of 1-pyrazin-2-yl-ethanone as the starting material the ketone 320 (Table 11). Structure and characterization of the title compound are presented in the Table 12.

Example 182

N-(2-aminophenyl)-4-((4-(3-(hydroxymethyl)-5-methylisoxazol-4-yl)pyrimidin-2-ylamino)methyl)benzamide (321)

321: Example 182

Step 1. Methyl 5-methyl-4-(2-methyl-1,3-dioxolan-2-yl)-isoxazole-3-carboxylate (322)

Title compound was obtained similarly to the dioxolane 318 in 82% yield according to the scheme 60. MS (m/z): 227.21 (calc) 228.1 (MH+) (found)

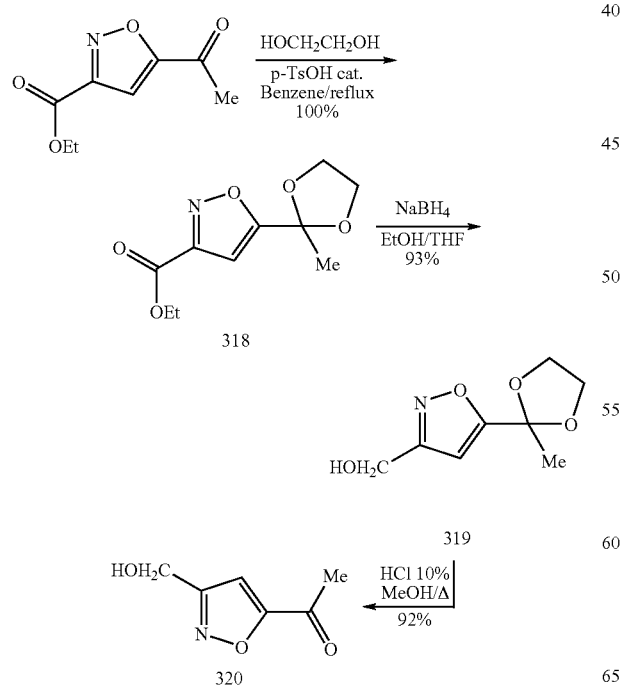

Step 2. (5-Methyl-4-(2-methyl-1,3-dioxolan-2-yl)isoxazol-3-yl)methanol (323)

Title compound was obtained similarly to the carbinol 319 in 94% yield according to the scheme 60. $^1$H NMR (DMSO-d$_6$) δ(ppm): 5.21 (t, J=5.7 Hz, 1H), 4.48 (d, J=5.7 Hz, 2H), 3.98-3.94 (m, 2H), 3.71-3.67 (m, 2H), 2.39 (s, 3H), 1.60 (s, 3H). MS (m/z): 199.20 (calc) 200.1 (MH+) (found)

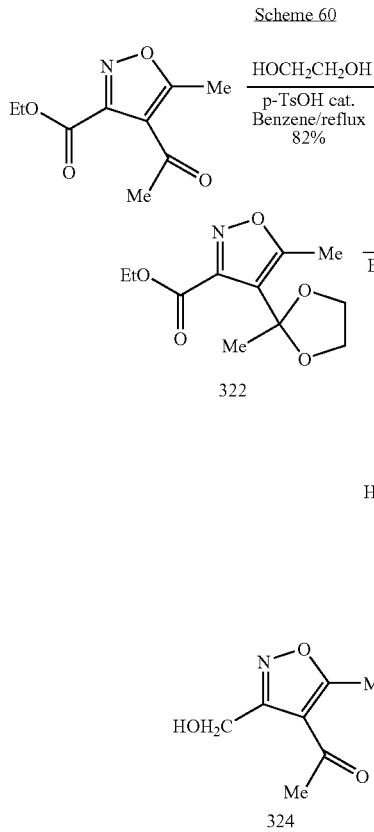

Scheme 60

Step 3. 1-(3-(Hydroxymethyl)-5-methylisoxazol-4-yl)ethanone (324)

Title compound was obtained similarly to the ketone 320 in 77% yield according to the scheme 60. $^1$H NMR (DMSO-d$_6$) δ (ppm): 5.45 (t, J=5.9 Hz, 1H), 4.66 (d, J=5.9 Hz, 2H), 2.66 (s, 3H), 2.51 (s, 3H). MS (m/z): 155.15 (calc) 156.1 (MH+) (found)

Step 4. N-(2-aminophenyl)-4-((4-(3-(hydroxymethyl)-5-methylisoxazol-4-yl)pyrimidin-2-ylamino)methyl)benzamide (317)

Title compound was obtained according to the scheme 6 similarly to the compound 26a (Example 29) using instead of 1-pyrazin-2-yl-ethanone as the starting material the ketone 324 (Table 11). Characterization of the title compound is provided in the Table 12.

Examples 183, 184

N-(2-aminophenyl)-4-((4-(1-methyl-1H-1,2,3-triazol-4-yl)pyrimidin-2-ylamino)methyl)benzamide (325) and N-(2-aminophenyl)-4-((4-(3-methyl-3H-1,2,3-triazol-4-yl)pyrimidin-2-ylamino)methyl)benzamide (326)

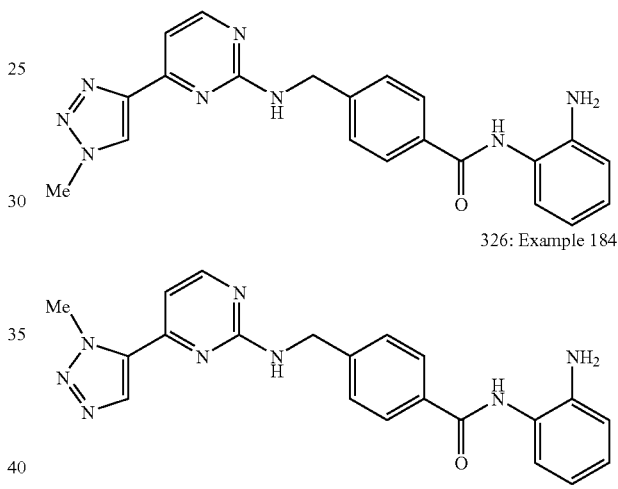

325: Example 183

326: Example 184

Step 1. 1-(3H-1,2,3-Triazol-4-yl)ethanone (327)

To a solution of 3-butyn-2-one (627 mg, 9.21 mmol) in xylene (10 mL) was added azidotributyltin (4.00 g, 12.0 mmol). The reaction mixture was stirred at 140° C. for 3 hours in a sealed flask. Xylene was evaporated and the residue was purified by flash chromatography, eluent EtOAc to afford the title compound (645 mg, 63% yield). $^1$H NMR (DMSO-d$_6$) δ(ppm): 8.51 (s, 1H), 2.56 (s, 3H). MS (m/z): 111.10 (calc) 112.1 (MH$^+$) (found)

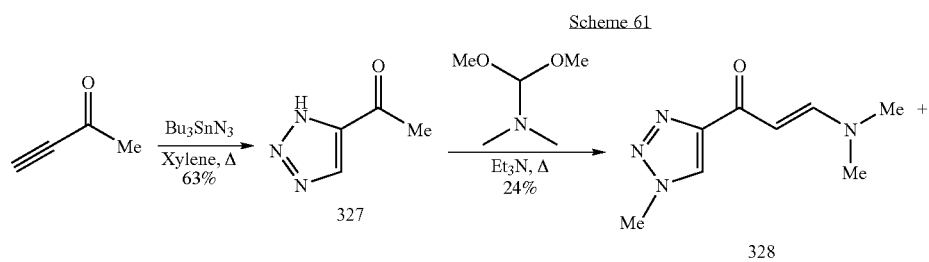

Scheme 61

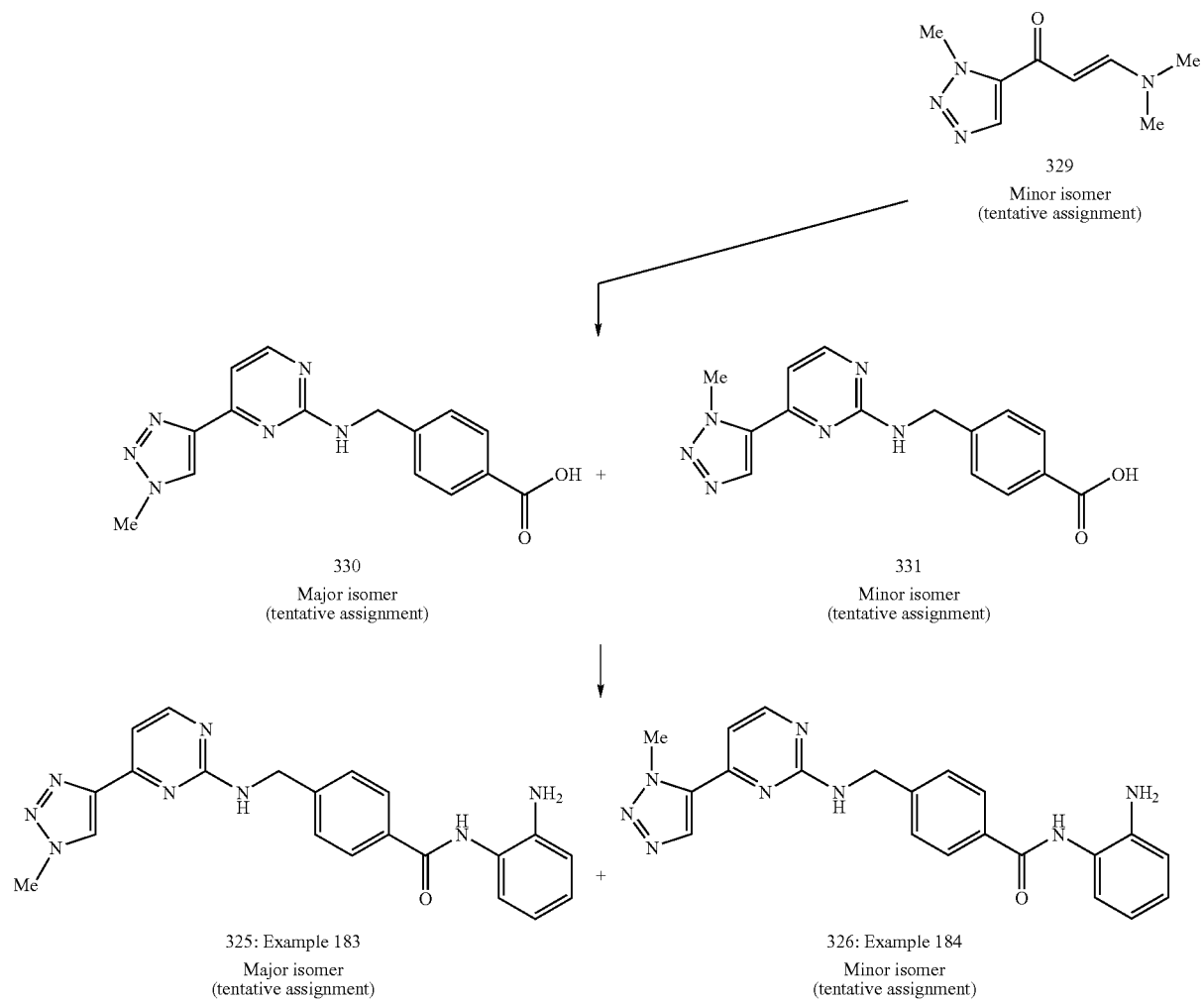

Step 2. (E)-3-(dimethylamino)-1-(1-methyl-1H-1,2,3-triazol-4-yl)prop-2-en-1-one (328) and (E)-3-(dimethylamino)-1-(3-methyl-3H-1,2,3-triazol-4-yl)prop-2-en-1-one (329)

Mixture of title compounds 328 and 329 was obtained in 24% yield according to the scheme 6 similarly to the compound 23a (Example 29, step 1) using instead of 1-pyrazin-2-yl-ethanone as the starting material ketone 327 (Table 11). MS (m/z): 180.21 (calc) 181.1 (MH+) (found).

$^1$H NMR (DMSO-d$_6$) δ (ppm) (328, major isomer, tentative assignment): 8.01 (s, 1H), 7.74 (d, J=12.3 Hz, 1H), 5.73 (d, J=12.3 Hz, 1H), 4.18 (s, 3H), 3.15 (s, 3H), 2.88 (s, 3H).

$^1$H NMR (DMSO-d$_6$) δ (ppm) (329, minor isomer, tentative assignment): 8.26 (s, 1H), 7.71 (d, J=10.8 Hz, 1H), 5.66 (d, J=12.1 Hz, 1H), 4.19 (s, 3H), 3.16 (s, 3H), 2.92 (s, 3H).

Step 3. 4-((4-(1-Methyl-1H-1,2,3-triazol-4-yl)pyrimidin-2-ylamino)methyl)benzoic acid (330) and 4-((4-(3-methyl-3H-1,2,3-triazol-4-yl)pyrimidin-2-ylamino)methyl)benzoic acid (331)

Mixture of title compounds was obtained in 80% yield according to the scheme 6 similarly to the compound 25a (Example 29, step 3) using instead of enamino ketone 23a as a starting material mixture of enamino ketones 328 and 329.

$^1$H NMR (DMSO-d$_6$) δ (ppm) (328, major isomer, tentative assignment): 12.80 (s, 1H), 8.33 (d, J=5.1 Hz, 1H), 8.17 (s, 1H), 7.94 (t, J=6.5 Hz, 1H), 7.85 (d, J=8.2 Hz, 2H), 7.42 (d, J=8.2 Hz, 2H), 7.02 (d, J=4.7 Hz, 1H), 4.60 (d, J=6.5 Hz, 2H), 4.22 (s, 3H). MS (m/z): 310.31 (calc) 311.2 (MH+) (found)

Step 4. N-(2-aminophenyl)-4-((4-(1-methyl-1H-1,2,3-triazol-4-yl)pyrimidin-2-ylamino)methyl)benzamide (325) and N-(2-aminophenyl)-4-((4-(3-methyl-3H-1,2,3-triazol-4-yl)pyrimidin-2-ylamino)methyl)benzamide (326)

Title compounds were obtained in 53 and 7% yields according to the scheme 6 similarly to the compound 26a (Example 29, step 4) using instead of acid 25a as a starting material mixture of acids 330 and 331. Characterization of the title compounds is provided in the Table 12.

Example 185

N-(2-Aminophenyl)-4-((4-(2-methylimidazo[1,2-a]pyridin-3-yl)pyrimidin-2-ylamino)methyl)benzamide (332)

332: Example 185

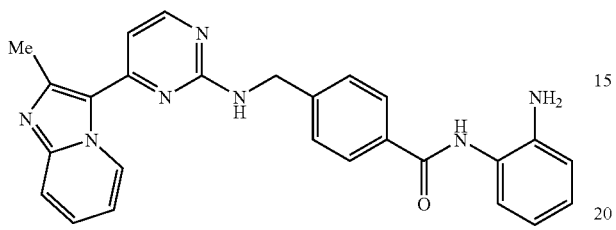

Step 1. 1-(2-Methylimidazo[1,2-a]pyridin-3-yl)ethanone (333)

1,1'-Azobis(cyclohexanecarbonitrile) (catalytic amount) was added to a solution of pentane-2,4-dione (1.00 g, 9.99 mmol) and N-bromosuccinimide (1.96 g, 10.99 mmol) in CHCl$_3$ (20 mL). The reaction mixture was stirred for 1 hour, filtered and the filtrate was concentrated under reduced pressure. The residue was re-dissolved in a 1:1 mixture of THF/Et$_2$O (20 mL), then pyridin-2-amine (723 mg, 7.68 mmol) was added and the reaction mixture was refluxed overnight. After cooling the solvent was removed under reduced pressure and the residue was purified by column chromatography, eluents EtOAc, then EtOAc-MeOH (96:4), to afford the title compound (475 mg 35% yield). $^1$H NMR (DMSO-d$_6$) δ (ppm): 9.59 (dt, J=6.8, 1.4 Hz, 1H), 7.68 (dt, J=8.8, 1.2 Hz, 1H), 7.56 (ddd, J=8.8, 6.8, 1.4 Hz, 1H), 7.17 (td, J=6.8, 1.4 Hz, 1H), 2.72 (s, 3H), 2.58 (s, 3H). MS (m/z): 174.20 (calc) 175.1 (MH$^+$) (found).

[M. Anderson, J. F. Beattie, et. al. Bioorg. Med. Chem. Lett.; 2003, 13; 3021-3026].

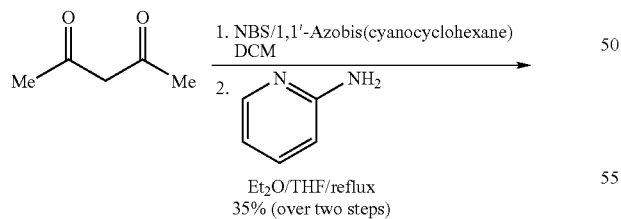

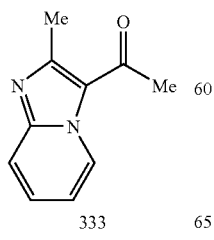

333

Step 2. N-(2-Aminophenyl)-4-((4-(2-methylimidazo[1,2-a]pyridin-3-yl)pyrimidin-2-ylamino)methyl)benzamide (332)

Title compound was obtained according to the scheme 6 similarly to the compound 26a (Example 29) using instead of 1-pyrazin-2-yl-ethanone as the starting material the ketone 333 (Table 11). Characterization of the title compound is provided in the Table 12.

Examples 186 and 187

4-((4-(2-Amino-4-methylthiazol-5-yl)pyrimidin-2-ylamino)methyl)-N-(2-aminophenyl)benzamide (334) and N-(2-aminophenyl)-4-((4-(5-(2-(dimethylamino)acetamido)-3-methylthiophen-2-yl)pyrimidin-2-ylamino)methyl)benzamide (335)

334: Example 186

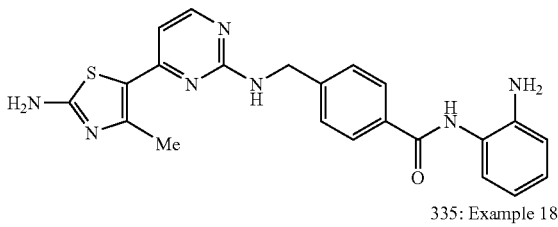

335: Example 187

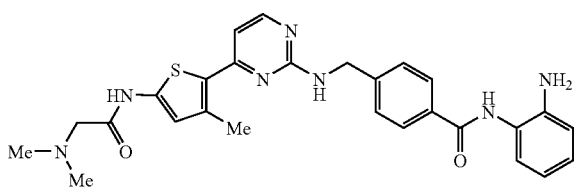

Step 1. 2-(bis-Boc-Amino-)-5-acetyl-4-methylthiazole (336)

Pyridine (1.11 g, 14.1 mmol) was added to a solution of Boc$_2$O (3.07 g, 14.1 mmol) and 1-(2-amino-4-methylthiazol-5-yl) (2.00 g, 12.8 mmol) in DCM (20 mL). The reaction mixture was stirred for 3 days at room temperature. The same amount of Boc$_2$O was added and the reaction mixture was stirred for another 3 days. DCM was evaporated under reduced pressure, water was added and the resultant mixture was extracted with EtOAc. The organic layer was washed with brine, dried over MgSO$_4$ and concentrated under reduced pressure to afford the title compound as orange oil (4.6 g, 100% yield). $^1$H NMR (DMSO-d$_6$) δ (ppm): 2.54 (s, 3H), 2.49 (s, 3H), 1.53 (s, 18H). MS (m/z): 356.44 (calc) 357.1 (MH+) (found)

Step 2. (E)-1-[2-(bis-Boc-Amino-)-4-methylthiazol-5-yl]-3-(dimethylamino)prop-2-en-1-one (337)

Following the procedure described for the synthesis of enamino ketone 23a (scheme 6) but substituting 1-(pyrazin-2-yl)-ethanone for the ketone 336, title compound was obtained in 16% yield. $^1$H NMR (DMSO-d$_6$) δ (ppm): 7.65 (d, J=12.1 Hz, 1H), 5.34 (d, J=12.1 Hz, 1H), 3.14 (s, 3H), 2.87 (s, 3H), 2.50 (s, 3H), 1.51 (s, 18H). MS (m/z): 411.52 (calc) 412.3 (MH$^+$) (found).

Scheme 63

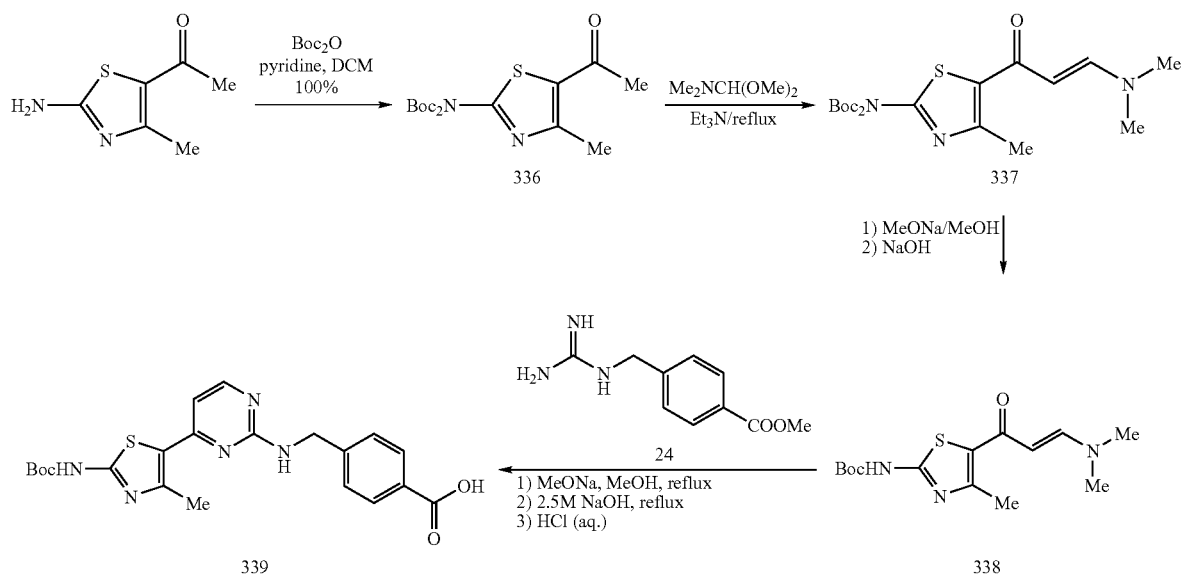

Step 3. (E)-1-[2-(Boc-Amino-)-4-methylthiazol-5-yl]-3-(dimethylamino)prop-2-en-1-one (338)

A solution of enamino ketone 337 (859 mg, 2.09 mmol) in methanol (12 mL) was treated with NaOMe solution (25% ww, 1.9 ml). The reaction mixture refluxed for 24 hours, treated with NaOH solution (1M, 3 ml), cooled to the room temperature, carefully neutralized (pH 7.5-8) with 1M HCl and extracted with EtOAc. Extract was dried over $MgSO_4$, filtered and evaporated to provide a residue corresponding to the title compound (721 mg, more than quantitative yield), which was used for the next step without further purification. MS (m/z): 311.40 (calc) 312.1 (MH+) (found).

Step 4. 4-((4-(2-(tert-Butoxycarbonylamino)-4-methylthiazol-5-yl)pyrimidin-2-ylamino)methyl)benzoic acid (339)

Following the procedure described for the synthesis of the acid 25a (scheme 6, step 3) but substituting enamino ketone 23a for the enamino ketone 338, title compound was obtained in 18% yield and was used for the next steps without further purification. MS (m/z): 441.50 (calc) 442.3 (MH+) (found).

Steps 5 and 6. 4-((4-(2-Amino-4-methylthiazol-5-yl)pyrimidin-2-ylamino)methyl)-N-(2-aminophenyl)benzamide (334)

Title compound was obtained according to the procedure described for the synthesis of compound 26a (scheme 6, step 4, coupling with 1,2-phenylene diamine) followed by the procedure described for the synthesis of the compound 117 (scheme 28, step 5, amino-group deprotection). Yield 78% over two steps. Characterization of the title compound is provided in the Table 12.

Step 7. 4-((4-(2-Amino-4-methylthiazol-5-yl)pyrimidin-2-ylamino)methyl)benzoic acid (340)

Title compound was obtained according to procedure described for the synthesis of the compound 117 (scheme 28, step 5, amino-group deprotection) in a quantitative yield (purity ca 90%). MS (m/z): 341.39 (calc) 342.1 (MH+) (found).

Scheme 64

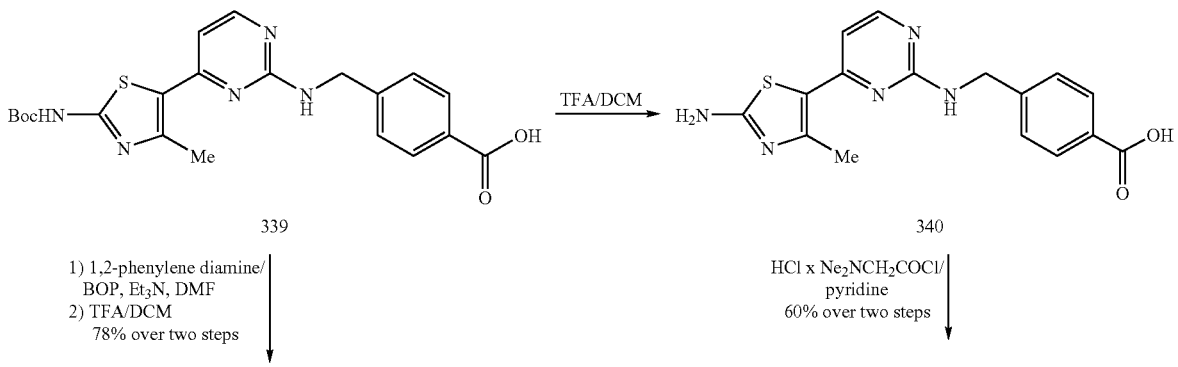

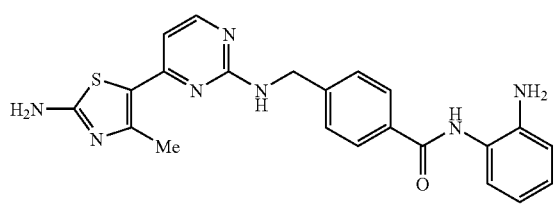

334

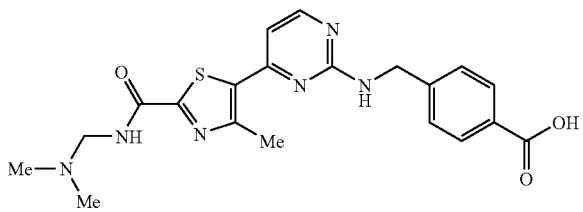

341

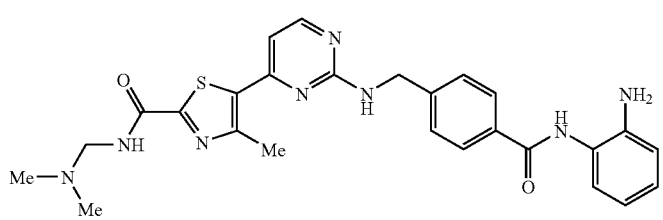

335

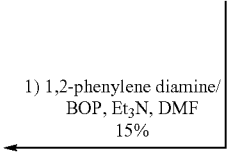

1) 1,2-phenylene diamine/
BOP, Et₃N, DMF
15%

Step 8. 4-((4-(2-((Dimethylamino)methylcarbamoyl)-4-methylthiazol-5-yl)pyrimidin-2-ylamino)methyl)benzoic acid (341)

Dimethylamino acetyl chloride hydrochloride (59.0 mg, 0.37 mmol) was added to a solution of the acid 340 (98.1 mg, 0.29 mmol) in pyridine (5 mL). The reaction mixture was stirred at room temperature for 1 day then another portion of dimethylaminoacetyl chloride hydrochloride (40 mg, 0.12 mmol) was added and the mixture was stirred at 40° C. for another day. Pyridine was evaporated under reduced pressure and MeOH was added. A solid material was formed which was collected by filtration and purified by preparative RP HPLC (column AQUASIL C-18; 5 µM; 230×21.2 mm; eluent 20-80% MeOH in water) to afford 24,5 mg of the title compound (20% yield). MS (m/z): 426.49 (calc) 427.2 (MH+) (found).

Step 9. N-(2-aminophenyl)-4-((4-(5-(2-(dimethylamino)acetamido)-3-methylthiophen-2-yl)pyrimidin-2-ylamino)methyl)benzamide (335)

Title compound was obtained according to the procedure described for the synthesis of compound 26a (scheme 6, step 4) in 15% yield (purified by preparative HPLC, column AQUASIL C-18; 5 µM; 230×21.2 mm; eluent 20-80% MeOH in water). Characterization of the title compound is provided in the Table 12.

Example 188

4-(4-(Pyridin-3-yl)pyrimidin-2-ylamino)-N-(2-aminophenyl)benzamide (342)

Step 1. 4-(4-(Pyridin-3-yl)pyrimidin-2-ylamino)benzoic acid (343)

Title compound was prepared according to the procedure described for the synthesis of compound 25a (scheme 6, step 3) replacing the guanindine 24 by 4-guanidinobenzoic acid (344) (Zlatoidsky P., Maliar T. *Eur. J. Med. Chem Chim. Ther.;* 1996, 31, 895-900) and (E)-3-(dimethylamino)-1-(pyrazin-2-yl)-prop-2-en-1-one (23a) by (E)-3-(dimethylamino)-1-(pyridin-3-yl)prop-2-en-1-one (345) (Zimmermann J., Buchdunger E., et al. *Bioorg. Med. Chem. Lett.,* 1996, 6, 1221-1226). Yield of the product 28%. MS (m/z): 292.29 (calc) 293.1 (MH+) (found).

Scheme 65

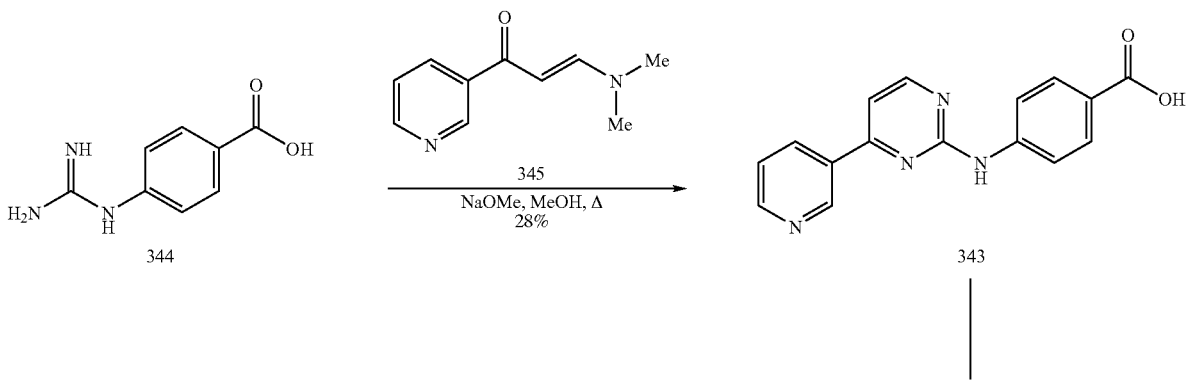

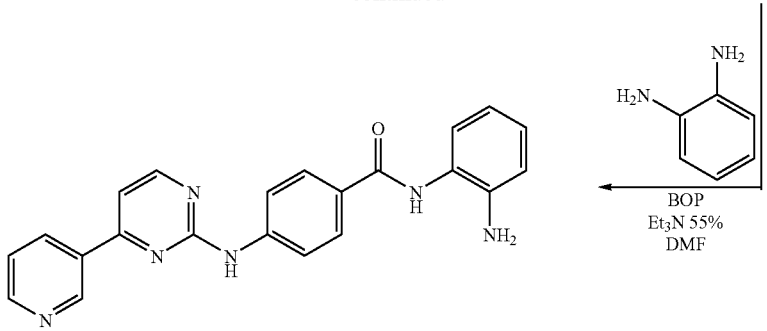

342: Example 188

Step 2. 4-(4-(Pyridin-3-yl)pyrimidin-2-ylamino)-N-(2-aminophenyl)benzamide (342)

Title compound was obtained in 54% yield according to the procedure described for the synthesis of compound 26a (scheme 6, step 4) replacing acid 25a by the acid 343. Characterization of the title compound is provided in the Table 12.

Scheme 65a

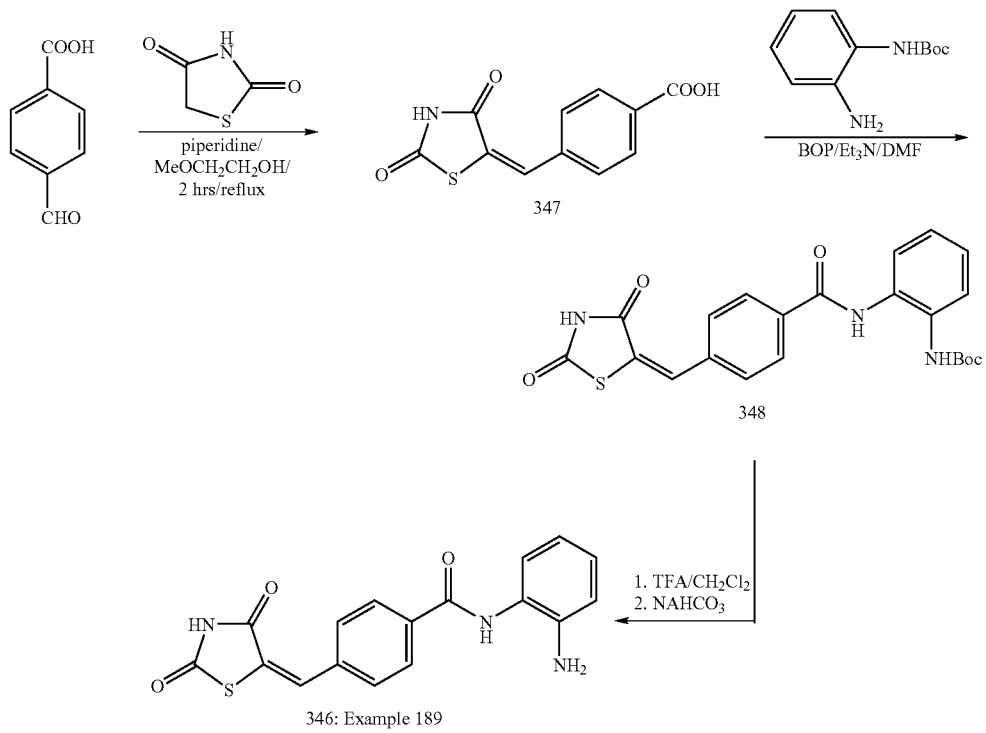

346: Example 189

Example 189

N-(2-Amino-phenyl)-4-(2,4-dioxo-thiazolidin-5-ylidenemethyl)-benzamide (346)

Step 1.
4-(2,4-Dioxo-thiazolidin-5-ylidenemethyl)-benzoic acid (347)

A solution of 4-formyl-benzoic acid (1.0 g, 6.7 mmol), thiazolidine-2,4-dione (0.78 g, 6.7 mmol) and piperidine (1.32 ml, 13.3 mmol) in 2-methoxy-ethanol (20 ml) was refluxed for 2 hrs, cooled to the room temperature, evaporated and the oily residue was re-dissolved in water. Acidification of this solution with conc. HCl (pH 1-2) produced a precipitate which was collected by filtration, dried and triturated with hot acetone to afford the title compound (1.06 g, 64% yield). LRMS: 249.2 (calcd.), 248.1 [M−H]⁻ (found).

Step 2. {2-[4-(2,4-Dioxo-thiazolidin-5-ylidenemethyl)-benzoylamino]-phenyl}-carbamic acid tert-butyl ester (348)

Following the procedure described for the synthesis of compound 115 (scheme 28) but substituting the acid 114 by the acid 347, title compound was obtained in 63% yield. LRMS: 439.5 (calcd.), 462.4 [M+Na]+ (found).

Step 3. N-(2-Amino-phenyl)-4-(2,4-dioxo-thiazolidin-5-ylidenemethyl)-benzamide (346)

Following the procedure described for the synthesis of compound 117 (scheme 28) but substituting the amide 116 by the amide 348, title compound was obtained in 37% yield. $^1$H NMR: (400 MHz, DMSO-d$_6$, δ (Ppm): 9.72 (s, 1H), 8.06 (d, j=8.2 Hz, 2H), 7.79 (s, 1H), 7.69 (d, J=8.4, 2H), 7.14 (d (dd) J=7.8, 1H), 6.95 (d (dd), J=1.6 Hz, J=9.0, 1H), 6.75 (dd, J=1.2 Hz, J=8.0 Hz, 1H), 6.56 (t (dd), J=7.2 Hz 1H). LRMS: 339.4 (calcd.), 340.4 [MH]+ (found).

Example 190

N-(2-Amino-phenyl)-4-(2,4-dioxo-thiazolidin-5-ylmethyl)-benzamide (349)

Step 1. 4-(2,4-Dioxo-thiazolidin-5-ylidenemethyl)-benzoic acid methyl ester (350)

A solution of 4-formyl-benzoic acid methyl ester (1.0 g, 6.7 mmol), thiazolidine-2,4-dione (0.78 g, 6.7 mmol) and piperidine (0.66 ml, 6.7 mmol) in 2-methoxy-ethanol (20 ml) was refluxed for 2 hrs, cooled to the room temperature and evaporated. The residue was triturated with CH$_2$Cl$_2$ to produce a crystalline material which was collected by filtration to afford the title compound (620 mg, 35% yield). LRMS: 263.3 (calcd.), 264.1 [MH]+ (found).

Step 2. 4-(2,4-Dioxo-thiazolidin-5-ylmethyl)-benzoic acid methyl ester (351)

A solution of the methyl ester 350 (615 mg, 2.32 mmol) in MeOH (120 ml) was hydrogenated over 10% Pd/C (615 mg, Degussa type) for 2 hours at room temperature. Another portion of Pd/C (300 mg) was added and the hydrogenation proceeded for another 3 hrs (monitored by MS). The reaction mixture was filtered through a celite pad, evaporated and the residue was purified by flash chromatography, eluent EtOAc—CH$_2$Cl$_2$ (1:2), to produce the title compound (570 mg, 92% yield). LRMS: 265.3 (calcd.), 266.1 [MH]+ (found).

Step 3. 4-(2,4-Dioxo-thiazolidin-5-ylmethyl)-benzoic acid (352)

A solution of methyl ester 351 (250 mg, 0.94 mmol) in AcOH (10 ml) was treated with conc. HCl (5 ml) and the reaction mixture was heated at 120° C. for 2 hrs, cooled and evaporated to produce a solid residue which was re-suspended in water and collected by filtration to afford the title compound (98 mg, 41% yield). LRMS: 251.3 (calcd.), 250.1 [M−H]− (found).

Step 4. N-(2-Amino-phenyl)-4-(2,4-dioxo-thiazolidin-5-ylmethyl)-benzamide (349)

Following the procedure described for the synthesis of compound 10a (scheme 2, Example 2) but replacing acid 9 by the acid 352, title compound was obtained in 51% yield. $^1$H NMR: (400 MHz, DMSO-d$_6$, δ (ppm): 12.04 (br s, 1H), 9.62 (s, 1H), 7.90 (d, j=8.2 Hz, 2H), 7.36 (d, J=8.2, 2H), 7.16 (d (dd) J=8.4, 1H), 7.13 (d (dd), J=6.7, 1H), 6.95 (dd, J=1.6 Hz, J=7.8 Hz, 1H), 6.75 (dd, j=1.4 Hz, j=8.0 Hz, 1H), 6.57 (dd, j=1.4 Hz, 7.6 Hz, 1H), 4.99 (dd, J=4.7 Hz, J=9.0 Hz, 1H), 4.96 (br s, 2H), 3.45 (dd, J=4.5 Hz, J=14.1 Hz, 1H), 3.22 (dd, J=9.0 Hz, J=14.3 Hz, 1H). LRMS: 341.3 (calcd.), 342.3 [MH]+ (found).

Scheme 66

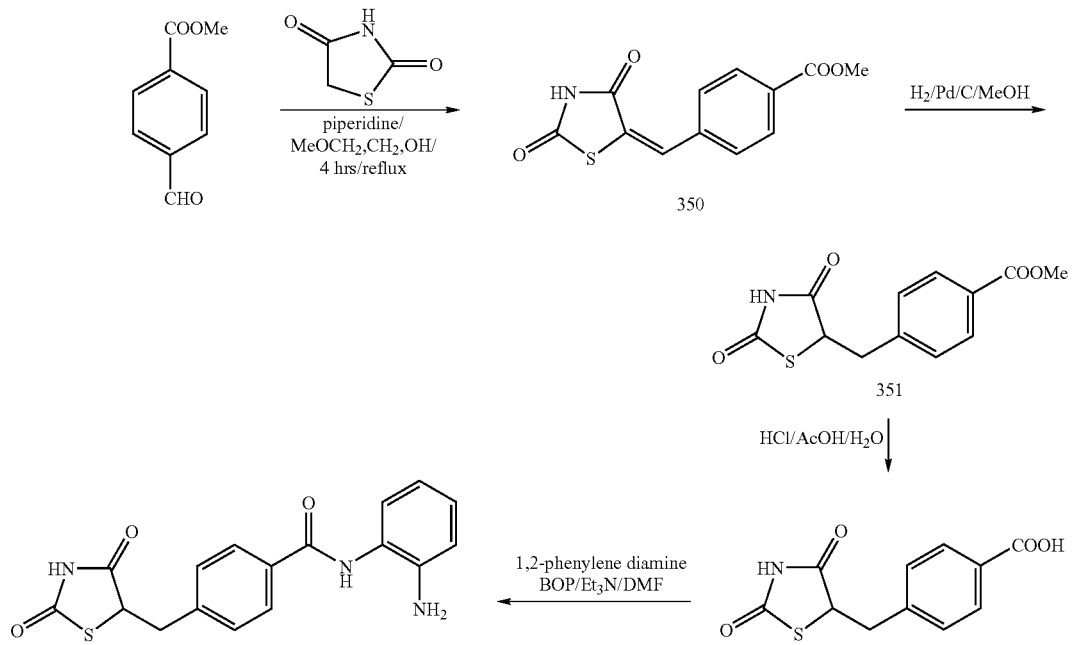

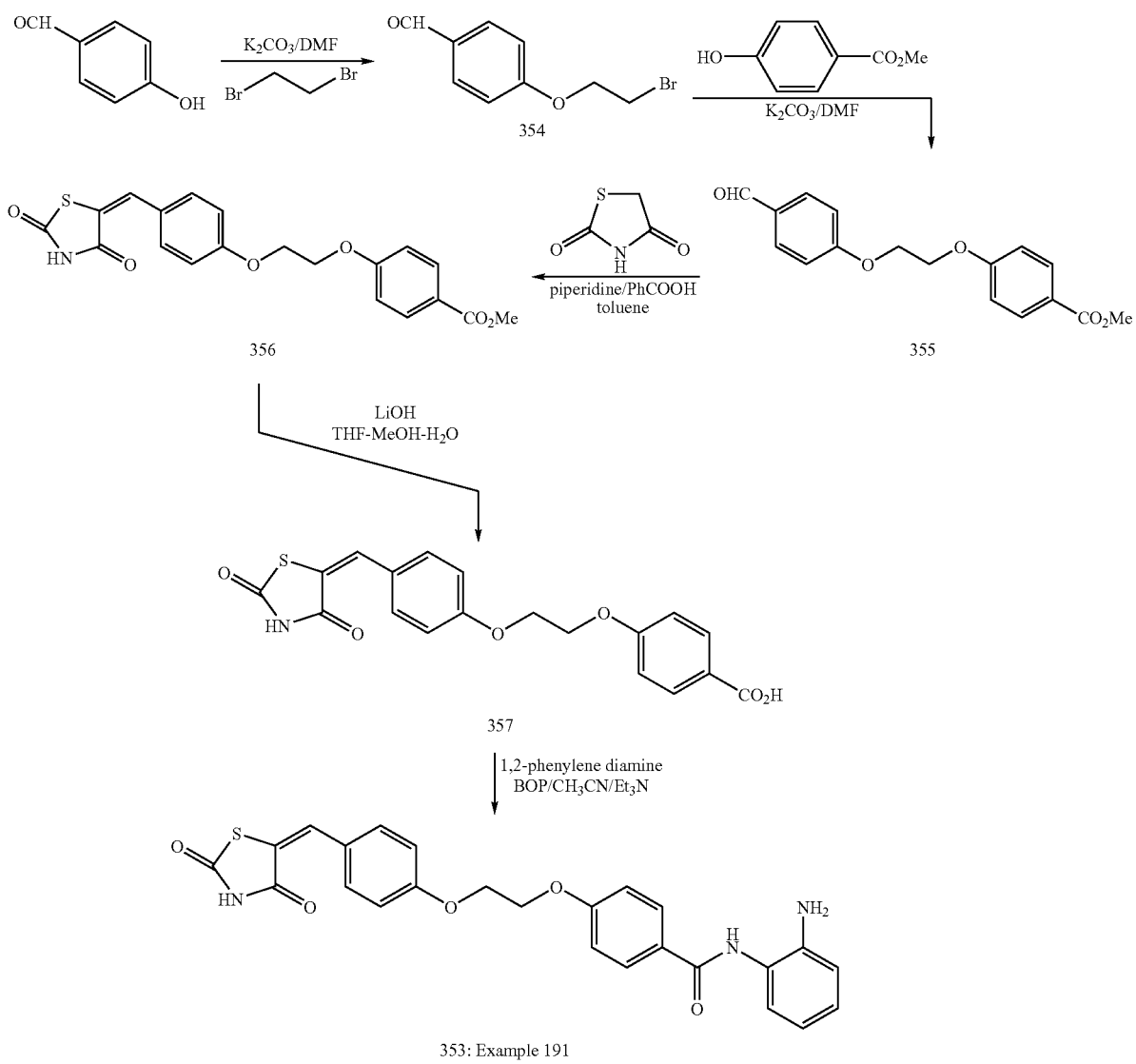

Scheme 67

353: Example 191

Example 191

(E)-N-(2-aminophenyl)-4-(2-(4-((2,4-dioxothiazolidin-5-ylidene)methyl)phenoxy)ethoxy)benzamide (353)

Step 1: 4-(2-bromoethoxy)benzaldehyde (354)

To a suspension of K$_2$CO$_3$ (4.52 g, 32.7 mmol), 1,2-dibromoethane (10.6 ml, 122.8 mmol) in DMF (12 mL) was added a solution of 4-hydroxybenzaldehyde (1.0 g, 8.2 mmol) in DMF (3 mL) at 0° C. The mixture was stirred at room temperature for 18 h., filtered and evaporated. The residue was purified by silica gel column chromatography with gradient of EtOAc-hexane (increasing percentage of EtOAc from 20 to 25%) to afford the title compound (1.21 g, 64% yield). $^1$H NMR: (CDCl$_3$) δ (ppm): 9.88 (s, 1H), 7.84 (d, J=8.0 Hz, 2H), 7.01 (d, J=8.0 Hz, 2H), 4.38 (t, J=6 Hz, 2H), 3.67 (t, J=6 Hz, 2H). LRMS (ESI): (calc.) 227.9, 229.9; (found) 229.1, 231.3 (MH)$^+$.

Step 2: Methyl 4-(2-(4-formylphenoxy)ethoxy)benzoate (355)

To a solution of 354 (1.21 g, 5.27 mmol) in DMF (10 mL) was added methyl 4-hydroxybenzoate (0.80 g, 5.27 mmol) and K$_2$CO$_3$ (2.91 g, 21.1 mmol). The resultant mixture was stirred at 60° C. for 6 h, filtered, and evaporated. The residue was purified by silica gel column chromatography, eluent EtOAc-hexane (1:2) to afford title compound (0.83 g, 53%). LRMS (ESI): (calc.) 300.3; (found) 301.4 (MH)$^+$.

Step 3: (E)-Methyl 4-(2-(4-((2,4-dioxothiazolidin-5-ylidene)methyl)phenoxy)ethoxy)benzoate (356)

To a solution of 355 (1.59 g, 3.86 mmol) in toluene (10 mL) was added thiazolidine-2,4-dione (542 mg, 4.63 mmol), benzoic acid (61.3 mg, 0.50 mmol) and piperidine (57 uL, 0.58 mmol). The resultant mixture was refluxed with the Dean- Stark adapter for ½ h and cooled to the room temperature. A precipitate formed which was collected by filtration to afford the title compound (1.41 g, 92%). $^1$H NMR: (DMSO-d$_6$) δ (ppm): 7.90 (d, J=8.8 Hz, 2H), 7.73 (s, 1H), 7.54 (d, J=8.8 Hz, 2H), 7.14 (d, J=8.8 Hz, 2H), 7.08 (d J=8.8 Hz, 2H), 4.42 (bs, 4H), 3.80 (s, 3H). LRMS (ESI): (calc.) 399.1; (found) 400.0 (MH)$^+$.

Step 4: (E)-4-(2-(4-((2,4-Dioxothiazolidin-5-ylidene)methyl)phenoxy)ethoxy)benzoic acid (compound 357)

To a solution of methyl ester 356 (647 mg, 1.62 mmol) in THF (15 mL) was added methanol (2 mL), water (2 mL) and lithium hydroxide monohydrate (340 mg, 8.11 mmol). The mixture was heated at 60° C. for 1 hour, acidified with 10% HCl solution and extracted with ethyl acetate. The organic extract was dried over MgSO$_4$, filtered, and evaporated to afford the title compound (141 mg, 22%). $^1$H NMR: (MeOD-d$_4$) δ (ppm): 7.97 (d, J=8.8 Hz, 2H), 7.75 (s, 1H), 7.53 (d, J=8.8 Hz, 2H), 7.12 (d, J=8.8 Hz, 2H), 7.04 (d, J=8.8 Hz, 2H), 4.44 (4H, bs). LRMS (ESI): (calc.) 385.4; (found) 392.3 (MLi)$^+$.

Step 5: (E)-N-(2-Aminophenyl)-4-(2-(4-((2,4-dioxothiazolidin-5-ylidene)methyl)phenoxy)ethoxy)benzamide (353)

Acid 357 (141 mg, 0.37 mmol), benzene-1,2-diamine (40 mg, 0.37 mmol) and BOP (161 mg, 0.37 mmol) were dissolved in CH$_3$CN (5 mL). Triethylamine (0.73 mmol, 203 µL) was added and the reaction was stirred for 18 hours at room temperature. The solvents were removed under reduced pressure and the residue was purified by silica gel column chromatography with gradient elution by EtOAc-hexane mixture (increasing percentage of EtOAc from 33 to 100%) to afford the title compound (34.2 mg, 19%). $^1$H NMR: (DMSO-d$_6$) δ (ppm): 10.00 (s, 1H), 8.44 (s, 1H), 7.96 (s, 1H), 7.57-7.65 (m, 3H), 7.49 (t, J=7.6 Hz, 2H), 7.36-7.43 (m, 2H), 7.31-7.35 (m, 1H), 4.59 (s, 2H), 4.23 (s, 2H), 3.74 (s, 3H), 3.11-3.20 (m, 2H), 2.37 (t, J=7.2 Hz, 2H), 1.60-1.71 (m, 2H), 1.45-1.55 (m, 2H), 1.32-1.43 (m, 2H). LRMS (ESI): (calc.) 460.5; (found) 461.3 (MH)$^+$.

Example 192

N-(2-Aminophenyl)-4-(2-(4-((2,4-dioxothiazolidin-5-yl)methyl)phenoxy)ethoxy)benzamide (358)

Step 1: Methyl 4-(2-(4-((2,4-dioxothiazolidin-5-yl)methyl)phenoxy)ethoxy)benzoate (359)

To a solution of 356 (scheme 67) (672 mg, 1.68 mmol) in 1,4-dioxane (10 mL) was added 10% Pd/C (2.3 g, 2.18 mmol). The resultant mixture was stirred under hydrogen atmosphere for 2 days at room temperature, filtered through a celite pad and concentrated under reduced pressure to afford 359 (379 mg, 56%). LRMS (ESI): (calc.) 401.4; (found) 424.2 (M+Na)$^+$. $^1$H NMR: (CDCl$_3$) δ (ppm): 8.15 (bs, 1H), 7.99 (d, J=8.8 Hz, 2H), 7.16 (d, J=8.8 Hz, 2H), 6.96 (d, J=8.8 Hz, 2H), 6.90 (d, J=8.8 Hz, 2H), 4.52 (dd, J=9.2, 4.0 Hz, 1H), 4.38-4.37 (m, 2H), 4.32-4.32 (m, 2H), 3.89 (s, 3H), 3.45 (dd, J=14.1, 4.0 Hz, 1H), 3.14 (dd, J=14.0, 9.2 Hz, 1H).

Step 2: 4-(2-(4-((2,4-Dioxothiazolidin-5-yl)methyl)phenoxy)ethoxy)benzoic acid (360)

To a solution of methyl ester 359 (872 mg, 2.17 mmol) in glacial AcOH (30 mL) was added conc. HCl (10 mL). The mixture was heated at 120° C. for 3 hours. The solvents were remove under reduced pressure to afford the title compound (833 mg, 99%). $^1$H NMR: (DMSO-d$_6$) δ (ppm): 12.61 (bs, 1H), 12.01 (s, 1H), 7.91 (d, J=8.8 Hz, 2H), 7.19 (d, J=8.8 Hz, 2H), 7.08 (d, J=8.8 Hz, 2H), 6.95 (d, J=8.8 Hz, 2H), 4.91 (dd, J=9.2, 4.4 Hz, 1H), 4.40-4.42 (m, 2H), 4.33-4.36 (m, 2H), 3.32 (d, J=4.0 Hz, 1H), 3.10 (dd, J=14.0, 9.6 Hz, 1H). LRMS (ESI): (calc.) 387.4; (found) 386.2 (M−H)$^−$.

Scheme 68

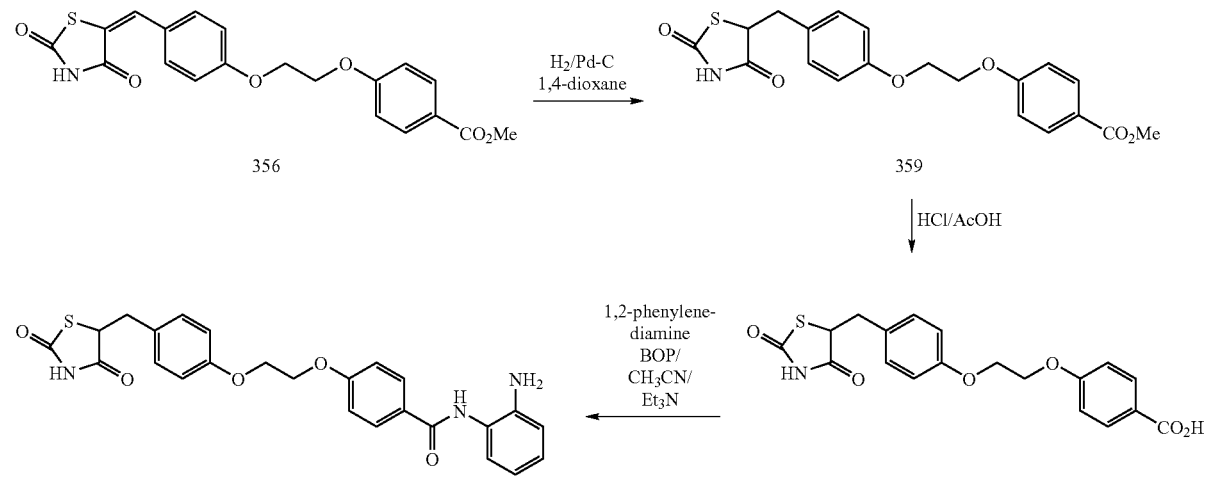

356

359

HCl/AcOH 1,2-phenylenediamine
BOP/
CH$_3$CN/
Et$_3$N

358: Example 192

360

Step 3: N-(2-aminophenyl)-4-(2-(4-((2,4-dioxothia-zolidin-5-yl)methyl)phenoxy)ethoxy)benzamide (358)

Following the same procedure as described for compound 393 (step 5, scheme 67, example 191) but substituting acid 357 for the acid 360 title compound was obtained as a beige solid (57 mg, 33% yield). $^1$H NMR: (DMSO-$d_6$) δ (ppm): 9.34 (s, 1H), 7.74-7.78 (m, 3H), 6.93-6.98 (m, 3H), 6.88 (d J=8.8 Hz, 2H), 6.73-6.78 (m, 3H), 6.57 (dd, J=8.0, 1.2 Hz, 1H), 6.38 (dt, J=8.0, 1.2 Hz, 1H), 4.68 (dd, J=8.8, 4.4 Hz, 2H), 4.19-4.21 (m, 2H), 3.11 (d, J=4.4 Hz, 1H), 2.88 (dd, J=14.0, 9.2 Hz, 1H). LRMS (ESI): (calc.) 477.4; (found) 478.4 (MH)$^+$.

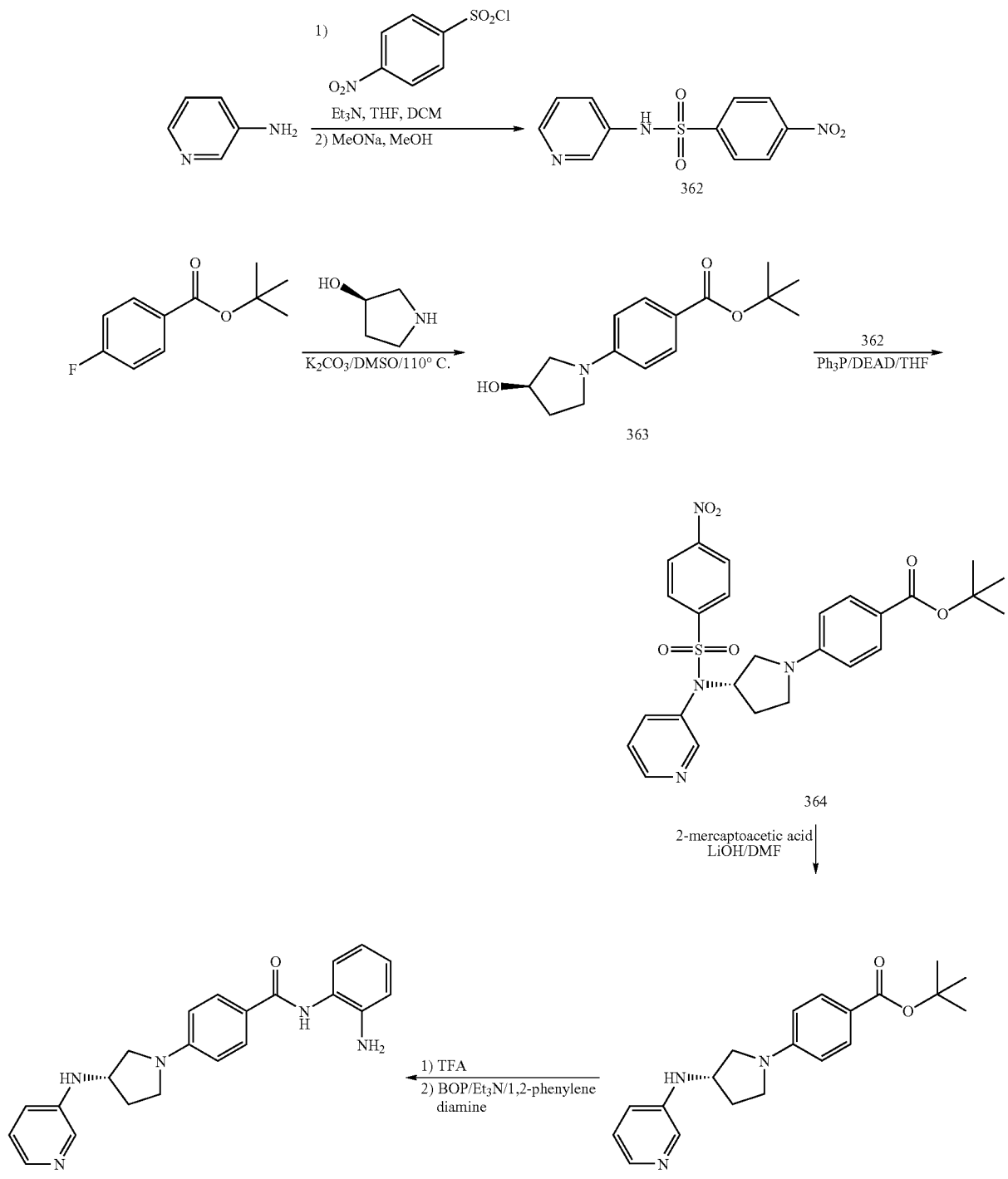

Scheme 69

361: Example 193

TABLE 12

Characterization of examples 178-188.

| Ex | Cpd | Structure | Name | Characterization | Scheme |
|---|---|---|---|---|---|
| 178 | 314 | 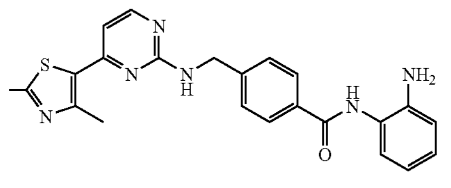 | N-(2-amino-phenyl)-4-((4-(2,4-dimethyl thiazol-5-yl)pyrimidin-2-ylamino)methyl) benzamide | $^1$H NMR (DMSO-d$_6$) δ(ppm): 9.56 (s, 1H), 8.30 (d, J=5.1 Hz, 1H), 7.92 (s, 1H), 7.89 (d, J=8.2 Hz, 2H), 7.43 (d, J=7.4 Hz, 2H), 7.12 (d, J=7.6 Hz, 1H), 6.94 (td, J=7.8, 1.4 Hz, 1H), 6.82 (d, j=5.1 Hz, 1H), 6.75 (dd, J=8.0, 1.4 Hz, 1H), 6.57 (td, J=7.6, 1.4 Hz, 1H), 4.87 (s, 2H), 4.56 (d, J=6.3 Hz, 2H), 2.61 (s, 3H), 2.56 (s, 3H). MS (m/z): 430.53 (calc) 431.1 (MH+) (found) | 6 |
| 179 | 315 | 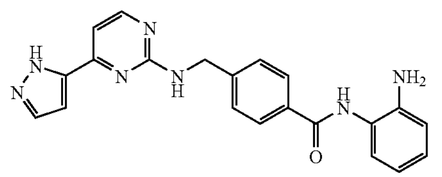 | 4-((4-(1H-pyrazol-5-yl)pyrimidin-2-ylamino)methyl)-N-(2-amino-phenyl)benzamide | $^1$H NMR (DMSO-d$_6$) δ (ppm): 13.16 (s, 1H), 9.56 (s, 1H), 8.26 (s, 1H), 7.89 (d, J=8.2 Hz, 2H), 7.80 (d, J=14.5 Hz, 2H), 7.47 (s, 2H), 7.13 (d, J=7.6 Hz, 1H), 7.08 (s, 0.5H), 6.94 (td, J=7.2, 1.6 Hz, 1H), 6.80 (s, 0.5H), 6.74 (dd, J=7.9, 1.6 Hz, 1H), 6.56 (td, J=6.9, 1.4 Hz, 1H), 4.86 (s, 2H), 4.60 (s, 2H). MS (m/z): 385.42 (calc) 386.2 (MH+) (found) | 6 |
| 180 | 316 | 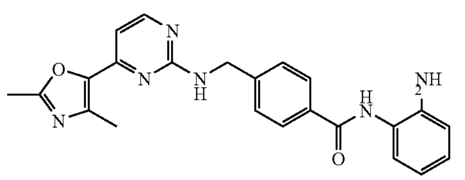 | N-(2-amino-phenyl)-4-((4-(2,4-dimethyloxazol-5-yl)pyrimidin-2-ylamino)methyl) benzamide | $^1$H NMR (DMSO-d$_6$) δ (ppm): 9.57 (s, 1H), 8.31 (d, J=4.5 Hz, 1H), 7.93-7.89 (m, 3H), 7.41 (d, J=8.2 Hz, 2H), 7.12 (d, J=7.6 Hz, 1H), 6.94 (td, J=7.2, 1.6 Hz, 1H), 6.76-6.73 (m, 2H), 6.56 (td, J=8.0, 1.2 Hz, 1H), 4.87 (s, 2H), 4.59 (d, J=6.5 Hz, 2H), 2.44 (s, 3H), 2.35 (s, 3H). MS (m/z): 414.46 (calc) 415.3 (MH+) (found) | 6 |
| 181 | 317 | 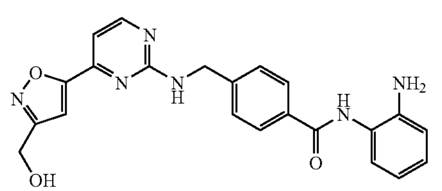 | N-(2-amino-phenyl)-4-((4(3-(hydroxymethyl) isoxazol-5-yl) pyrimidin-2-ylamino)methyl) benzamide | $^1$H NMR (MeOD-d$_4$) δ (ppm): 8.42 (d, J=5.1 Hz, 1H), 7.92 (d, J=8.0 Hz, 2H), 7.53 (d, J=8.8 Hz, 2H), 7.16 (d, J=8.4 Hz, 1H), 7.08 (d, J=4.9 Hz, 1H), 7.06-7.04 (m, 2H), 6.89 (d, J=8.0 Hz, 1H), 6.75 (t, J=7.6 Hz, 1H), 4.72 (s, 2H), 4.69 (s, 2H). MS (m/z): 416.43 (calc) 417.3 (MH+) (found) | 59, 6 |
| 182 | 321 | 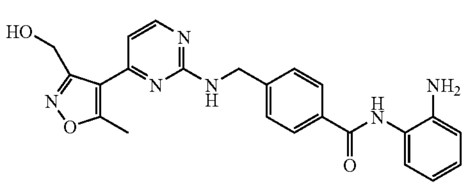 | N-(2-amino-phenyl)-4-((4(3-(hydroxymethyl)-5-methylisoxazol-4-yl)pyrimidin-2-ylamino)methyl) benzamide | $^1$H NMR (DMSO-d$_6$) δ (ppm): 9.54 (s, 1H), 8.34 (d, J=5.1 Hz, 1H), 7.94-7.88 (m, 3H), 7.42 (d, J=8.0 Hz, 2H), 7.13 (d, J=7.6 Hz, 1H), 6.94 (t, J=7.0 Hz, 2H), 6.75 (d, J=7.8 Hz, 1H), 6.57 (t, J=7.4 Hz, 1H), 5.53 (t, J=5.9 Hz, 1H), 4.87 (s, 2H), 4.65-4.59 (m, 4H). (CH$_3$ singlet is probably overlapped by DMSO signal) $^1$H NMR (MeOD-d$_4$) δ (ppm): 8.32 (d, J=5.3 Hz, 1H), 7.92 (d, J=8.2 Hz, 2H), 7.48 (d, J=8.2 Hz, 2H), 7.16 (d, J=7.6 Hz, 1H), 7.06 (t, J=7.2 Hz, 1H), 6.94 (d, J=5.3 Hz, 1H), 6.88 (d, J=8.2 Hz, 1H), 6.76 (t, J=6.3 Hz, 1H), 4.72 (s, 2H), 4.70 (s, 2H), 2.61 (s, 3H). MS (m/z): 430.46 (calc) 431.2 (MH+) (found) | 60, 6 |

TABLE 12-continued

Characterization of examples 178-188.

| Ex | Cpd | Structure | Name | Characterization | Scheme |
|---|---|---|---|---|---|
| 183 | 325 | 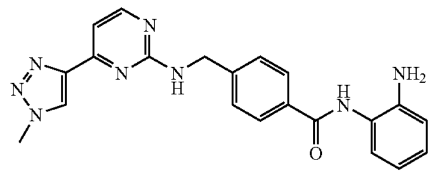 | N-(2-amino-phenyl)-4-((4-(1-methyl-1H-1,2,3-triazol-4-yl)pyrimidin-2-ylamino)methyl) benzamide | $^1$H NMR (DMSO-d$_6$) δ (ppm): 9.56 (s, 1H), 8.33 (d, J=4.9 Hz, 1H), 8.20 (s, 1H), 7.96 (t, J=6.3 Hz, 1H), 7.89 (d, J=8.2 Hz, 2H), 7.47 (s, 2H), 7.12 (d, J=7.8 Hz, 1H), 7.02 (d, J=4.7 Hz, 1H), 6.94 (td, J=7.2, 1.5 Hz, 1H), 6.75 (dd, J=7.9, 1.3 Hz, 1H), 6.57 (td, J=7.9, 1.4 Hz, 1H), 4.86 (s, 2H), 4.60 (d, J=6.3 Hz, 2H), 4.22 (s, 3H). MS (m/z): 400.44 (calc) 401.2 (MH+) (found) | 61 |
| 184 | 326 | 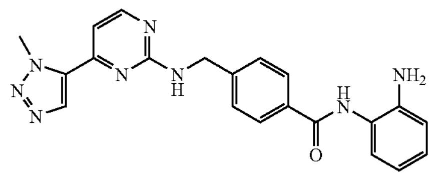 | N-(2-amino-phenyl)-4-((4-(3-methyl-3H-1,2,3-triazol-4-yl)pyrimidin-2-ylamino)methyl) benzamide | $^1$H NMR (DMSO-d$_6$) δ (ppm): 9.57 (s, 1H), 8.42 (s, 1H), 8.35 (s, 1H), 8.14 (s, 1H), 7.90 (d, J= 8.2 Hz, 2H), 7.43 (d, J=8.2 Hz, 2H), 7.13 (d, J=7.2 Hz, 1H), 7.08 (d, J=5.1 Hz, 1H), 6.94 (td, J=8.2, 1.6 Hz, 1H), 6.75 (dd, J=7.8, 1.2 Hz, 1H), 6.57 (t, J=8.2 Hz, 1H), 4.87 (s, 2H), 4.62 (d, J=6.3 Hz, 2H), 4.40 (s, 1H), 4.12 (s, 2H). MS (m/z): 400.44 (calc) 401.2 (MH+) (found) | 61 |
| 185 | 332 | 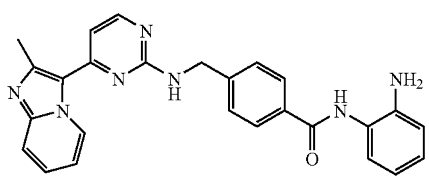 | N-(2-amino-phenyl)-4-((4-(2-methylH-imidazo[1,2-a]pyridin-3-yl)pyrimidin-2-ylamino)methyl) benzamide | $^1$H-NMR, DMSO-d6 δ (ppm): 9.60 (s, 1H); 8.97 (bs, 1H); 8.35 (bs, 1H); 8.03 (t, J=6.3 Hz, 1H); 7.94 (d, J=8.2 Hz, 2H); 7.56 (bs, 1H); 7.47 (d, J=8.2 Hz, 2H); 7.33 (bs, 1H); 7.13 (d, J=7.3 Hz, 1H); 6.94 (dt, J=1.4, 7.3 Hz, 1H); 6.85 (d, J=4.3 Hz, 1H); 6.75 (dd, J=1.0, 8.0 Hz, 1H); 6.71 (bs, 1H); 6.57 (t, J=7.3 Hz, 1H); 4.87 (bs, 2H); 4.62 (d, J=6.1 Hz, 2H); 2.59 (bs, 3H). MS (m/z): 449.51 (calc) 450.2 (MH+) (found) | 62, 6 |
| 186 | 334 | 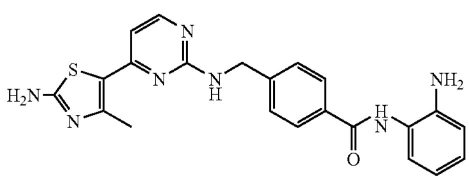 | 4-((4-(2-amino-4-methylthiazol-5-yl)pyrimidin-2-ylamino)methyl)-N-(2-amino-phenyl)benzamide | $^1$H NMR (MeOD-d$_4$) δ (ppm): 8.16 (d, J=5.9 Hz, 1H), 8.00 (d, J=8.2 Hz, 2H), 7.54 (d, J=8.0 Hz, 2H), 7.35-7.26 (m, 4H), 6.92 (d, J=6.1 Hz, 1H), 4.73 (s, 2H), 2.55 (s, 3H). MS (m/z): 431.51 (calc) 432.2 (MH+) (found) | 63 |
| 187 | 335 | 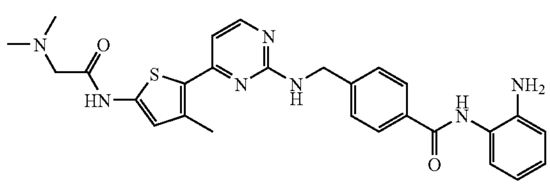 | N-(2-amino-phenyl)-4-((4-(5-(2-(dimethyl-amino)aceta mido)-3-methyl-thiophen-2-yl)pyrimidin-2-ylamino)methyl) benzamide | $^1$H NMR (MeOD-d$_4$) δ (ppm): 8.23 (d, J=5.3 Hz, 1H), 7.92 (d, J=8.0 Hz, 2H), 7.54 (d, J=8.0 Hz, 2H), 7.16 (d, J=7.4 Hz, 1H), 7.06 (t, J=7.2 Hz, 1H), 6.89-6.86 (m, 2H), 6.75 (t, J=7.6 Hz, 1H), 4.68 (s, 2H), 3.60 (s, 2H), 2.59 (s, 6H), 256 (s, 3H). MS (m/z): 516.62 (calc) 517.3 (MH+) (found) | 63 |
| 188 | 342 | 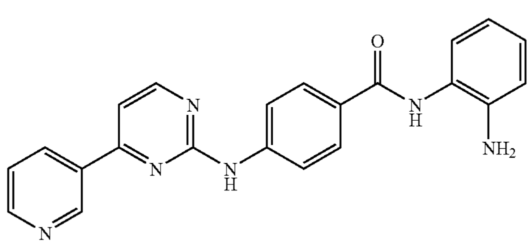 | N-(2-amino-phenyl)-4-(4-(pyridin-3-yl)pyrimidin-2-ylamino)benza-mide | $^1$H NMR (DMSO-d$_6$) δ (ppm): 10.10 (s, 1H), 9.52 (s, 1H), 9.35 (d, J=1.9 Hz, 1H), 8.73 (dd, J=4.9, 1.8 Hz, 1H), 8.66 (d, J=5.1 Hz, 1H), 8.52 (dt, j=8.2, 2.2 Hz, 1H), 7.96 (d, J=2.0 Hz, 4H), 7.61 (d, J=4.9 Hz, 1H), 7.59 (d, J=5.1 Hz, 1H), 7.15 (d, J=7.3 Hz, 1H), 6.95 (td, J=8.0, 1.6 Hz, 1H), 6.77 (dd, J=7.8, 1.2 Hz, 1H), 6.59 (td, J=7.4, 1.4 Hz, 1H), 4.89 (s, 2H). MS (m/z): 382.42 (calc) 383.3 (MH+) (found) | 64 |

Example 193

(S)—N-(2-Aminophenyl)-4-(3-(pyridin-3-ylamino)pyrrolidin-1-yl)benzamide (361)

Step 1: N-p-Nosyl-3-pyridine (362)

To a stirred solution of 2-aminopyridine (3.03 g, 32.2 mmol) in THF (15 mL) were successively added DCM (30 mL), 4-nitrobenzenesulfonyl chloride (1.50 g, 68.7 mmol), and Et$_3$N (9.88 mL, 70.9 mmol). The solution turned orange and a precipitate formed. The suspension was allowed to stir at room temperature for 1 h, solvents were evaporated under reduced pressure and the solid residue was suspended in methanol (200 mL). To the suspension a large excess (>10 eq) of sodium methoxide was added, the mixture was stirred at 50° C. for 3 h, quenched with HCl 1N (2 mL) and concentrated under reduced pressure at 80° C. until the volume became 50 mL. The concentrated solution was further acidified with 1N HCl until neutral pH. A precipitate formed which was collected by filtration to afford the title compound (7.67 g, 85% yield). $^1$H NMR (DMSO-d$_6$) δ (ppm): 10.88 (s, 1H), 8.36 (d, J=9.0 Hz, 2H), 8.28 (dd, J=6.1, 1.4 Hz, 1H), 8.27 (d, J=2.5 Hz, 1H), 7.50 (ddd, J=8.4, 2.7, 1.6 Hz, 1H), 7.30 (ddd, J=8.2, 4.7, 0.8 Hz, 1H). m/z: 280.1 (MH$^+$).

Step 2: tert-Butyl 4-((R)-3-hydroxypyrrolidin-1-yl)benzoate (363)

To a solution of t-butyl 4-fluorobenzoate (2.17 g, 11.0 mmol) and (R)-(+)-3-pyrrolidinol (1.00 g, 11.5 mmol) in DMSO (8 mL) was added potassium carbonate (1.53 g, 11.0 mmol). The mixture was stirred at 130° C. for 18 h and poured into stirring water (100 mL) while still hot. The resulting beige precipitate was collected by filtration and dried at 120° C. for 1.5 h to afford the title compound (2.64 g, 91% yield). $^1$H NMR (Acetone-d$_6$) δ (ppm): 7.78 (d, J=9.0 Hz, 2H), 6.54 (d, J=8.8 Hz, 2H), 4.58 (bs, 1H), 4.15 (bs, 1H), 3.55 (dd, J=10.36, 4.7 Hz, 1H), 3.49 (t, J=6.8 Hz, 1H), 3.42 (td, J=9.2, 2.3 Hz, 1H), 3.28 (d, J=10.8 Hz, 1H), 2.21-2.10 (m, 1H), 2.09-2.03 (m, 1H), 1.56 (s, 9H). m/z: 520.3 (MH$^+$).

Step 3: tert-Butyl 4-((S)-3-N-p-nosyl(pyridin-3-ylamino)pyrrolidin-1-yl)benzoate (364)

To a solution of compound 362 (6.00 g, 21.5 mmol) in THF (100 mL), were successively added carbinol 363 (5.66 g, 21.5 mmol), triphenylphosphine (6.76 g, 25.8 mmol) and diethyl azodicarboxylate (4.06 mL, 25.8 mmol). The mixture was stirred at room temperature for 18 h and the solvent was removed in vacuo. The residue was purified by flash chromatography using EtOAc/Hex (40:60) as an eluent to afford the title compound (4.68 g, 42% yield). $^1$H NMR (DMSO-d$_6$) d(ppm): 8.58 (dd, J=4.7, 1.4 Hz, 1H), 8.48 (d, J=8.0 Hz, 2H), 8.38 (d, J=2.0 Hz, 1H), 8.13 (d, J=9.0 Hz, 2H), 7.72 (d, J=9.0 Hz, 2H), 7.61 (ddd, J=8.0, 2.5, 1.6 Hz, 1H), 7.39 (dd, J=8.2, 4.9 Hz, 1H), 6.43 (d, J=9.0 Hz, 2H), 5.17 (quint, J=8.2 Hz, 1H), 3.77 (dd, J=10.4, 7.2 Hz, 1H), 3.36 (dd, J=10.4, 6.7 Hz, 1H), 3.26 (dd, J=15.1, 7.8 Hz, 1H), 3.06 (td, J=12.3, 3.3 Hz, 1H), 2.43-2.38 (m, 1H), 2.02-1.94 (m, 1H), 1.55 (s, 9H). m/z: 525.3 (MH$^+$)

Step 4: tert-Butyl 4-((S)-3-(pyridin-3-ylamino)pyrrolidin-1-yl)benzoate (365)

To a solution of the nitro compound 364 (4.68 g, 8.92 mmol) in DMF (45 mL), were successively added lithium hydroxide (1.31 g, 31.2 mmol) and thioglycolic acid (930 μL, 13.4 mmol). The mixture was stirred for 3 days at room temperature, the solvent was removed in vacuo at 80° C. and the residue was partitioned between EtOAc and H$_2$O. Organic layer was collected and extracted with HCl 1N. Acidic layer was collected and neutralized with a saturated NaHCO$_3$ solution. A white precipitate was formed which was extracted with EtOAc. The EtOAc solution was washed with brine, dried over MgSO4, and concentrated in vacuo to afford the title compound (1.65 g, 54% yield) as a white solid. $^1$H NMR: (Acetone-d$_6$) δ(ppm): 8.08 (d, J=2.2 Hz, 1H), 7.86 (d, J=4.3 Hz, 1H), 7.79 (d, J=9.0 Hz, 2H), 7.09 (dd, J=8.2, 4.3 Hz, 1H), 7.05 (ddd, J=8.2, 2.7, 1.6 Hz, 1H), 6.57 (d, J=8.8 Hz, 2H), 5.54 (d, J=6.5 Hz, 1H), 4.32 (sext, J=5.3 Hz, 1H), 3.78 (dd, J=10.2, 5.9 Hz, 1H), 3.56 (dd, J=17.0, 7.2 Hz, 1H), 3.47 (td, J=8.0, 5.1 Hz, 1H), 3.31 (dd, J=10.2, 3.9 Hz, 1H), 2.44 (sext., J=7.8 Hz, 1H), 2.13 (sext, J=5.1 Hz, 1H), 1.56 (s, 9H). m/z: 340.3 (MH$^+$).

Step 5: (S)—N-(2-Aminophenyl)-4-(3-(pyridin-3-ylamino)pyrrolidin-1-yl)benzamide (361)

To a suspension of compound 365 (19 mg, 0.56 mmol) in DCM 500 μL was added trifluoroacetic acid (200 μL). The solution was refluxed at 50° C. for 3 h and concentrated in vacuo to produce a white solid. This material was dissolved in DMF (500 μL) and was treated with Et$_3$N (16 μL, 0.118 mmol) and BOP (30 mg, 0.067 mmol). The reaction mixture was stirred for 10 min. and 1,2-henylenediamine (7 mg, 0.061 mmol) and another portion of Et$_3$N (23 μL, 0.168 mmol) were added. The mixture was stirred for 2 h at room temperature and DMF was removed in vacuo at 80° C. The residue was partitioned between EtOAc and H$_2$O. The organic layer was collected and extracted with 1N HCl and neutralized with sat. NaHCO$_3$. A precipitate formed which was extracted with EtOAc, dried over MgSO$_4$, and concentrated in vacuo. The residue was purified by flash chromatography using MeOH/CHCl$_3$ (7:93) as the eluent to afford the title compound (11 mg, 52% yield). $^1$H NMR: (CD$_3$OD) δ(ppm): 7.97 (d, J=2.7 Hz, 1H), 7.86 (d, J=8.8 Hz, 2H), 7.78 (dd, J=4.7, 1.0 Hz, 1H), 7.18-7.10 (m, 3H), 7.05 (td, J=7.4, 0.6 Hz, 1H), 6.89 (dd, J=7.8, 1.2 Hz, 1H), 6.76 (td, J=7.4, 1.4 Hz, 1H), 6.64 (d, J=8.8 Hz, 2H), 4.25 (quint, J=4.9 Hz, 1H), 3.77 (dd, J=10.2, 6.1 Hz, 1H), 3.57 (dd, J=17.0, 7.0 Hz, 1H), 3.49 (td, J=8.0, 5.3 Hz, 1H), 3.29 (q, J=6.7 Hz, 1H), 2.41 (sext, J=7.2 Hz, 1H), 2.10 (sext, J=4.9 Hz, 1H). m/z: 372.4 (MH$^+$).

Example 194

(R)—N-(2-Aminophenyl)-4-(3-(pyridin-3-ylamino)pyrrolidin-1-yl)benzamide (366)

The title compound was obtained following the same procedures described in scheme 69, example 193 but substituting (R)-(+)-3-pyrrolidinol for (S)-(−)-3-pyrrolidinol. (108 mg, 21% yield) $^1$H NMR: (DMSO-d$_6$) δ(ppm): 9.34 (s, 1H), 8.00 (d, J=2.3 Hz, 1H), 7.84 (d, J=8.8 Hz, 2H), 7.77 (dd, J=4.7, 1.2 Hz, 1H), 7.12 (d, J=7.6 Hz, 1H), 7.08 (dd, J=8.0, 4.5 Hz, 1H), 6.99-6.97 (m, 1H), 6.92 (t, J=7.8 Hz, 1H), 6.75 (d, J=7.8 Hz, 1H), 6.60-6.56 (m, 3H), 6.17 (d, J=6.8 Hz, 1H), 4.81 (s, 2H), 4.19-4.17 (m, 1H), 3.71 (dd, J=10.2, 6.5 Hz, 1H), 3.53-3.47 (m, 1H), 3.42-3.38 (m, 1H), 3.18 (dd, J=10.4, 4.1 Hz, 1H), 2.32 (sext, J=6.3 Hz, 1H), 1.99 (sext, J=4.7 Hz, 1H). m/z: 374.2 (MH$^+$).

Example 195

(S)—N-(2-Aminophenyl)-4-(3-(pyridin-3-yloxy)pyrrolidin-1-yl)benzamide (367)

The title compound was obtained following the same procedures described in scheme 69, example 193 but skipping steps 1 and 4 and substituting compound 362 for 3-hydroxypyridine (24 mg, 44% yield) $^1$H NMR: (Acetone-$d_6$) δ(ppm): 8.88 (s, 1H), 8.31 (d, J=2.9 Hz, 1H), 8.19 (d, J=4.7 Hz, 1H), 7.93 (d, J=8.8 Hz, 2H), 7.41 (ddd, J=8.4, 2.9, 1.4 Hz, 1H), 7.31 (ddd, J=8.4, 4.5, 0.6 Hz, 1H), 7.26 (d, J=7.8 Hz, 1H), 6.97 (td, J=7.8, 1.4 Hz, 1H), 6.85 (dd, J=8.0, 1.4 Hz, 1H), 6.66 (d, J=9.0 Hz, 2H), 6.65 (td, J=8.0, 1.4 Hz, 1H), 5.34-5.32 (m, 1H), 4.62 (s, 2H), 3.84 (dd, J=11.3, 4.7 Hz, 1H), 3.61-3.56 (m, 3H), 2.50-2.34 (m, 2H). m/z: 375.2 (MH$^+$).

Example 196

(R)—N-(2-Aminophenyl)-4-(3-(pyridin-3-yloxy)pyrrolidin-1-yl)benzamide (368)

The title compound was obtained following the same procedures described in scheme 69, example 193 skipping steps 1 and 4 and substituting compound 362 for 3-hydroxypyridine and (R)-(+)-3-pyrrolidinol for (S)-(−)-3-pyrrolidinol. (14 mg, 12% yield) $^1$H NMR: (Acetone-$d_6$) δ(ppm): 8.85 (s, 1H), 8.31 (d, J=2.9 Hz, 1H), 8.19 (dd, J=4.5, 1.2 Hz, 1H), 7.93 (d, J=8.8 Hz, 2H), 7.42 (ddd, J=8.4, 2.9, 1.4 Hz, 1H), 7.31 (ddd, J=8.4, 4.7, 0.8 Hz, 1H), 7.26 (d, J=7.8 Hz, 1H), 6.97 (td, J=7.2, 1.6 Hz, 1H), 6.85 (dd, J=7.8, 1.2 Hz, 1H), 6.68 (d, J=8.8 Hz, 6.66 (td, J=7.6, 1.4 Hz, 1H), 3.56-5.33 (m, 1H), 4.60 (bs, 2H), 3.86 (dd, J=11.3, 4.7 Hz, 1H), 3.62-3.57 (m, 3H), 2.50-2.35 (m, 2H). m/z: 375.2 (MH$^+$).

Example 197

(S)—N-(2-Aminophenyl)-4-(3-(phenylamino)pyrrolidin-1-yl)benzamide (369)

The title compound was obtained following the same procedures described in scheme 69, example 193 but substituting compound 3-aminopyridine for aniline. (7 mg, 16% yield) $^1$H NMR: (Acetone-$d_6$) δ(ppm): 8.84 (s, 1H), 7.91 (d, J=8.8 Hz, 2H), 7.25 (dd, J=7.8, 1.2 Hz, 1H), 7.12 (t, J=7.2 Hz, 2H), 6.96 (dt, J=8.0, 1.4 Hz, 1H), 6.85 (d, J=8.0 Hz, 1H), 6.71 (dd, J=8.8, 1.0 Hz, 2H), 6.66 (t, J=7.8 Hz, 1H), 6.62 (d, J=8.8 Hz, 2H), 5.26 (d, J=7.6 Hz, 1H), 4.60 (bs, 1H), 4.30 (quint, J=5.3 Hz, 1H), 3.79 (dd, J=10.0 Hz, 1H), 3.57 (q, J=9.6 Hz, 1H), 3.50-3.45 (m, 1H), 3.30 (dd, J=10.2, 3.9 Hz, 1H), 2.42 (sext, J=6.8 Hz, 1H). m/z: 373.1 (MH$^+$).

Example 198

(R)—N-(2-Aminophenyl)-4-(3-(phenylamino)pyrrolidin-1-yl)benzamide (370)

The title compound was obtained following the same procedures described in scheme 69, example 193 but substituting 3-aminopyridine for aniline and (R)-(+)-3-pyrrolidinol for (S)-3-pyrrolidinol. (22 mg, 23% yield) $^1$H NMR (CDCl$_3$) δ 7.79 (m, 2H), 7.2-7.4 (m, 2H), 7.05 (s, 1H), 6.8 (m, 3H) 6.65 (m, 2H), 6.53(m, 2H), 4.24 (br.s., 1H), 3.9(m, 2H), 3.73 (m, 1H), 3.26 (m, 1H), 2.37 (m, 1H), 2.09 (m, 1H) m/z: 373.3 (MH$^+$).

Example 199

(S)—N-(2-Aminophenyl)-4-(3-phenoxypyrrolidin-1-yl)benzamide (371)

The title compound was obtained following the same procedures described in scheme 69, example 193 but skipping steps 1 and 4 and substituting compound 362 for phenol. (50 mg, 33% yield) $^1$H NMR (CDCl$_3$) δ 7.79 (μ, 3H), 7.3 (m, 3H), 7.03 (m, 1H), 6.96 (m, 1H), 6.90 (d, 2H, J=8.8 Hz), 6.80 (m, 2H), 6.54 (d, J=8.8 Hz, 2H), 5.08 (br.s., 1H), 3.71 (dd, J=4.7 Hz, J=11.0 Hz, 1H), 3.6 (m, 3H), 2.41 (m, 1H), 2.31 (m, 1H) m/z: 374.2 (MH$^+$).

Example 200

(S)-Methyl-4-(1-(4-(2-aminophenylcarbamoyl)phenyl)pyrrolidin-3-yloxy)benzoate (372)

The title compound was obtained following the same procedures described in scheme 69, example 193 but skipping steps 1 and 4 and substituting compound 362 for methyl 4-hydroxybenzoate. (143 mg, 42% yield) $^1$H NMR (CDCl$_3$) δ 8.0 (m, 2H), 7.81 (m, 2H), 7.72 (s, 1H), 7.25 (m, 1H), 7.06 (m, 1H), 6.91(m, 2H), 6.84 (m, 2H), 6.59 (m, 2H), 5.16 (br.s., 1H), 3.9.(s, 3H), 3.78 (m, 1H), 3.60 (m, 3H), 2.4 (m, 2H) m/z: 432.4 (MH$^+$).

Example 201

(S)-4-(1-(4-(2-Aminophenyl carbamoyl)phenyl)pyrrolidin-3-yloxy)benzoic acid (373)

A solution of 372 (100 mg, 0.23 mmol) and KOH (100 mg, 1.78 mmol) in 1:1:1 mixture of THF/water/MeOH (6 mL) was stirred at room temperature for 5 days. The reaction mixture was concentrated and partitioned between water (5 mL) and ether (5 mL). Organic phase was discarded and the aqueous phase was acidified to pH=6 using 1M HCl solution and extracted with EtOAc. The extract was dried over Na$_2$SO4, filtered and concentrated. The residue was purified by flash chromatography, eluent MeOH-DCM (gradient of MeOH from 5 till 20% MeOH) to afford the title compound (20 mg, 21% yield). $^1$H NMR (DMSO) δ 9.34 (σ, 1H), 7.85 (m, 4H), 7.11 (d, 1H, J=7.8 Hz), 7.00 (d, J=8.4 Hz, 2H), 6.92 (d, 2H, J=7.7 Hz), 6.75 (d, J=8.0 Hz, 2H), 6.6 (m, 3H), 5.26 (br.s., 1H), 3.75 (m, 1H), [3.34 DMSO, 4H], 2.44 (m, 1H), 2.31 (m, 1H) m/z: 418.4 (MH$^+$).

Example 202

(S)—N-(2-Aminophenyl)-4-(3-(3,4,5-trimethoxyphenoxy)pyrrolidin-1-yl)benzamide (374)

The title compound was obtained following the same procedures described in scheme 69, example 193 but skipping steps 1 and 4 and substituting compound 362 for 3,4,5-trimethoxyphenol. (30 mg, 21%) $^1$H NMR (CDCl$_3$) δ 7.79 (d, 2H, J=8.8 Hz), 7.73 (s, 1H), 7.26 (d, 1H, J=7.4 Hz), 7.05 (t, J=7.7 Hz, 1H), 6.81 (d, 2H, J=7.7 Hz), 6.57 (d, J=8.7 Hz, 2H), 6.14 (s, 2H), 5.04 (br.s., 1H), 3.88 (s, 6H), 3.80 (s, 3H), 3.71 (dd, J=4.7 Hz, J=11.0 Hz, 1H), 3.6 (m, 3H), 2.41 (m, 1H), 2.31 (m, 1H) m/z: 464.4 (MH$^+$).

Example 203

(S)—N-(2-Aminophenyl)-4-(3-(benzo[d][1,3]dioxol-5-yloxy)pyrrolidin-1-yl)benzamide (375)

The title compound was obtained following the same procedures described in scheme 69, example 193 but skipping steps 1 and 4 and substituting compound 362 for benzo[d][1,3]dioxol-5-ol. (31 mg, 15%) $^1$H NMR (CDCl$_3$) δ 8.95 (s, 1H), 7.87 (d, 2H, J=8.0 Hz), 7.80 (d, 2H, J=8.7 Hz), 7.67 (s, 1H), 7.48 (s, 0.5H) 7.04 (m, 1H), 6.83(m, 1H), 6.71 (m, 1H), 6.57

(d, 2H), 6.48 (s, 1H), 6.33 (m, 1H), 5.93 (s, 2H), 4.96 (br.s., 1H), 3.67(m, 1H), 3.57 (m, 3H), 2.36 (m, 1H), 2.26 (m, 1H) m/z: 418.2 (MH⁺).

Example 204

(S)—N-(2-Aminophenyl)-4-(3-(4-phenoxyphenoxy)pyrrolidin-1-yl)benzamide (376)

The title compound was obtained following the same procedures described in scheme 69, example 193 but skipping steps 1 and 4 and substituting compound 362 for 4-phenoxyphenol. $^1$H NMR (CDCl$_3$) δ 7.81 (m,2H), 7.70 (s, 1H), 7.67 (s, 0.5H), 7.2-7.4 (m, 4H) 6.8-7.2 (m, 10H), 6.6(m, 2H), 5.05 (br.s., 1H), 3.6(m, 1H), 3.5 (m, 3H), 2.41 (m, 1H), 2.32 (m, 1H) m/z: 466.4 (MH⁺).

Example 205

(S)—N-(2-Aminophenyl)-4-(3-(4-nitrophenoxy)pyrrolidin-1-yl)benzamide (377)

The title compound was obtained following the same procedures described in scheme 69, example 193 but skipping steps 1 and 4 and substituting compound 362 for 4-nitrophenol. (12 mg, 6%) $^1$H NMR (CDCl$_3$) δ 8.12 (d, 2H, J=9.1 Hz), 7.72 (d, J=8.8 Hz, 2H), 7.18 (d, J=7.3 Hz, 1H), 6.97 (t, 1H, J=7.7 Hz), 6.87 (d, J=9.1 Hz, 2H), 6.50 (d, 2H, J=8.6 Hz), 5.09 (br.s., 1H), 3.71 (dd, J=4.5 Hz, J=11.3 Hz, 1H), 3.6 (m, 3H2.3 (m, 2H) m/z: 419.1 (MH⁺).

Example 206

(S)—N-(2-Aminophenyl)-4-(3-(pyridin-2-ylthio)pyrrolidin-1-yl)benzamide (378)

The title compound was obtained following the same procedures described in scheme 69, example 193 but skipping steps 1 and 4 and substituting compound 362 for pyridine-2-thiol. (22 mg, 28%) $^1$H NMR (CDCl$_3$) δ 8.44 (μ, 1H), 7.78 (d, J=8.8 Hz, 2H), 7.69 (s, 1H), 7.49 (t, 1H, J=7.4 Hz), 7.27 (m, 1H), 7.18 (d, 1H, J=8.0 Hz), 7.0-7.1 (m, 2H), 6.82 (d, 7.8 Hz, 2H), 6.55 (d, J=9.0 Hz, 2H), 4.55 (m, 1H), 3.9-4.0 (m, 3H), 3.4-3.6 (m, 4H) 2.6 (m, 1H), 2.2 (m, 1H) m/z: 391.0 (MH⁺).

TABLE 13

Characterization of examples 193-206 prepared according to the scheme 69.

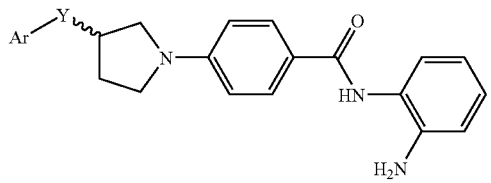

| Ex. | Cpd | Ar | Y | Name | Characterization |
|---|---|---|---|---|---|
| 193 | 361 | pyridin-3-yl | NH | (S)-N-(2-aminophenyl)-4-(3-(pyridin-3-ylamino)pyrrolidin-1-yl)benzamide | $^1$H NMR: (CD$_3$OD) δ (ppm): 7.97 (d, J=2.7 Hz, 1H), 7.86 (d, J=8.8 Hz, 2H), 7.78 (dd, J=4.7, 1.0 Hz, 1H), 7.18-7.10 (m, 3H), 7.05 (td, J=7.4, 0.6 Hz, 1H), 6.89 (dd, J=7.8, 1.2 Hz, 1H), 6.76 (td, J=7.4, 1.4 Hz, 1H), 6.64 (d, J=8.8 Hz, 2H), 4.25 (quint, J=4.9 Hz, 1H), 3.77 (dd, J=10.2, 6.1 Hz, 1H), 3.57 (dd, J=17.0, 7.0 Hz, 1H), 3.49 (td, J=8.0, 5.3 Hz, 1H), 3.29 (q, J=6.7 Hz, 1H), 2.41 (sext, J=7.2 Hz, 1H), 2.10 (sext, J=4.9 Hz, 1H). |
| 194 | 366 | pyridin-3-yl | NH | (R)-N-(2-aminophenyl)-4-(3-(pyridin-3-ylamino)pyrrolidin-1-yl)benzamide | $^1$H NMR: (DMSO-d$_6$) δ (ppm): 9.34 (s, 1H), 8.00 (d, J=2.3 Hz, 1H), 7.84 (d, J=8.8 Hz, 2H), 7.77 (dd, J=4.7, 1.2 Hz, 1H), 7.12 (d, J=7.6 Hz, 1H), 7.08 (dd, J=8.0, 4.5 Hz, 1H), 6.99-6.97 (m, 1H), 6.92 (t, J=7.8 Hz, 1H), 6.75 (d, J=7.8 Hz, 1H), 6.60-6.56 (m, 3H), 6.17 (d, J=6.8 Hz, 1H), 4.81 (s, 2H), 4.19-4.17 (m, 1H), 3.71 (dd, J=10.2, 6.5 Hz, 1H), 3.53-3.47 (m, 1H), 3.42-3.38 (m, 1H), 3.18 (dd, J=10.4, 4.1 Hz, 1H), 2.32 (sext, J=6.3 Hz, 1H), 1.99 (sext, J=4.7 Hz, 1H). |
| 195 | 367 | pyridin-3-yl | O | (S)-N-(2-aminophenyl)-4-(3-(pyridin-3-yloxy)pyrrolidin-1-yl)benzamide | $^1$H NMR: (Acetone-d$_6$) δ (ppm): 8.88 (s, 1H), 8.31 (d, J=2.9 Hz, 1H), 8.19 (d, J=4.7 Hz, 1H), 7.93 (d, J=8.8 Hz, 2H), 7.41 (ddd, J=8.4, 2.9, 1.4 Hz, 1H), 7.31 (ddd, J=8.4, 4.5, 0.6 Hz, 1H), 7.26 (d, J=7.8 Hz, 1H), 6.97 (td, J=7.8, 1.4 Hz, 1H), 6.85 (dd, J=8.0, 1.4 Hz, 1H), 6.66 (d, J=9.0 Hz, 2H), 6.65 td, J=8.0, 1.4 Hz, 1H), 5.34-5.32 (m, 1H), 4.62 (s, 2H), 3.84 (dd, J=11.3, 4.7 Hz, 1H), 3.61-3.56 (m, 3H), 2.50-2.34 (m, 2H). |

TABLE 13-continued

Characterization of examples 193-206 prepared according to the scheme 69.

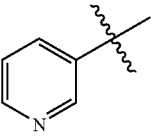

| Ex. | Cpd | Ar | Y | Name | Characterization |
|---|---|---|---|---|---|
| 196 | 368 | 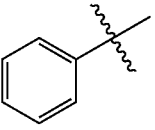 | O | (R)-N-(2-aminophenyl)-4-(3-(pyridin-3-yloxy)pyrrolidin-1-yl)benzamide | $^1$H NMR: (Acetone-$d_6$) δ (ppm): 8.85 (s, 1H), 8.31 (d, J=2.9 Hz, 1H), 8.19 (dd, J=4.5, 1.2 Hz, 1H), 7.93 (d, J=8.8 Hz, 2H), 7.42 (ddd, J=8.4, 2.9, 1.4 Hz, 1H), 7.31 (ddd, J=8.4, 4.7, 0.8 Hz, 1H), 7.26 (d, J=7.8, 1.6 Hz, 1H), 6.97 (td, J=7.2, 1.6 Hz, 1H), 6.85 (dd, J=7.8, 1.2 Hz, 1H), 6.68 (d, J=8.8 Hz, 2H), 6.66 (td, J=7.6, 1.4 Hz, 1H), 3.56-5.33 (m, 1H), 4.60 (bs, 2H), 3.86 (dd, J=11.3, 4.7 Hz, 1H), 3.62-3.57 (m, 3H), 2.50-2.35 (m, 2H). |
| 197 | 369 | 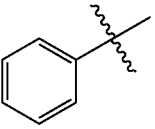 | NH | (S)-N-(2-aminophenyl)-4-(3-(phenylamino)pyrrolidin-1-yl)benzamide | $^1$H NMR: (Acetone-$d_6$) δ (ppm): 8.84 (s, 1H), 7.91 (d, J=8.8 Hz, 2H), 7.25 (dd, J=7.8, 1.2 Hz, 1H), 7.12 (t, J=7.2 Hz, 2H), 6.96 (dt, J=8.0, 1.4 Hz, 1H), 6.85 (d, J=8.0 Hz, 1H), 6.71 (dd, J=8.8, 1.0 Hz, 2H), 6.66 (t, J=7.8 Hz, 1H), 6.62 (d, J=8.8 Hz, 2H), 5.26 (d, J=7.6 Hz, 1H), 4.60 (bs, 1H), 4.30 (quint, J=5.3 Hz, 1H), 3.79 (dd, J=10.0 Hz, 1H), 3.57 (q, J=9.6 Hz, 1H), 3.50-3.45 (m, 1H), 3.30 (dd, J=10.2, 3.9 Hz, 1H), 2.42 (sext, J=6.8 Hz, 1H). |
| 198 | 370 | 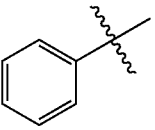 | NH | (R)-N-(2-aminophenyl)-4-(3-(phenylamino)pyrrolidin-1-yl)benzamide | $^1$H NMR (CDCl$_3$) δ (ppm) 7.79 (m, 2H), 7.2-7.4 (m, 2H), 7.05 (s, 1H), 6.8 (m, 3H) 6.65 (m, 2H), 6.53 (m, 2H), 4.24 (br.s., 1H), 3.9 (m, 2H), 3.73 (m, 1H), 3.26 (m, 1H), 2.37 (m, 1H), 2.09 (m, 1H) |
| 199 | 371 | 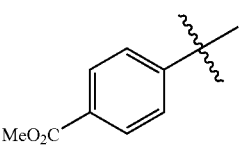 | O | (S)-N-(2-aminophenyl)-4-(3-phenoxypyrrolidin-1-yl)benzamide | $^1$H NMR (CDCl$_3$) δ (ppm) 7.79 (m, 3H), 7.3 (m, 3H), 7.03 (m, 1H), 6.96 (m, 1H), 6.90 (d, 2H, J=8.8 Hz), 6.80 (m, 2H), 6.54 (d, J=8.8 Hz, 2H), 5.08 (br.s., 1H), 3.71 (dd, J=4.7 Hz, J=11.0 Hz, 1H), 3.6 (m, 3H), 2.41 (m, 1H), 2.31 (m, 1H) |
| 200 | 372 | 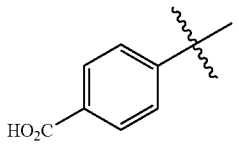 | O | (S)-methyl-4-(1-(4-(2-aminophenyl carbamoyl)phenyl)pyrrolidin-3-yloxy)benzoate | $^1$H NMR (CDCl$_3$) δ (ppm): 8.0 (m, 2H), 7.81 (m, 2H), 7.72 (s, 1H), 7.25 (m, 1H), 7.06 (m, 1H), 6.91 (m, 2H), 6.84 (m, 2H), 6.59 (m, 2H), 5.16 (br.s., 1H), 3.9 (s, 3H), 3.78 (m, 1H), 3.60 (m, 3H), 2.4 (m, 2H) |
| 201 | 373 | 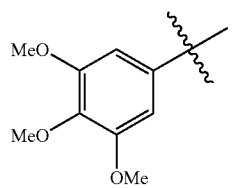 | O | (S)-4-(1-(4-(2-aminophenyl carbamoyl)phenyl)pyrrolidin-3-yloxy)benzoic acid | $^1$H NMR: (DMSO-$d_6$) δ (ppm): 9.34 (s, 1H), 7.85 (m, 4H), 7.11 (d, 1H, J=7.8 Hz), 7.00 (d, J=8.4 Hz, 2H), 6.92 (d, 2H, J=7.7 Hz), 6.75 (d, J=8.0Hz, 2H), 6.6 (m, 3H), 5.26 (br.s., 1H), 3.75 (m, 1H), [3.34 DMSO, 4H], 2.44 (m, 1H), 2.31 (m, 1H) |
| 202 | 374 | | O | (S)-N-(2-aminophenyl)-4-(3-(3,4,5-trimethoxyphenoxy)pyrrolidin-1-yl)benzamide | $^1$H NMR (CDCl$_3$) δ (ppm) 7.79 (d, 2H), J=8.8 Hz), 7.73 (s, 1H), 7.26 (d, 1H, J=7.4 Hz), 7.05 (t, J=7.7 Hz, 1H), 6.81 (d, 2H, J=7.7 Hz), 6.57 (d, J=8.7 Hz, 2H), 6.14 (s, 2H), 5.04 (br.s., 1H), 3.88 (s, 6H), 3.80 (s, 3H), 3.71 (dd, J=4.7 Hz, J=11.0 Hz, 1H), 3.6 (m, 3H), 2.41 (m, 1H), 2.31 (m, 1H) |

TABLE 13-continued

Characterization of examples 193-206 prepared according to the scheme 69.

| Ex. | Cpd | Ar | Y | Name | Characterization |
|---|---|---|---|---|---|
| 203 | 375 | benzo[d][1,3]dioxol-5-yl | O | (S)-N-(2-aminophenyl)-4-(3-(benzo[d][1,3]dioxol-5-yloxy)pyrrolidin-1-yl)benzamide | $^1$H NMR (CDCl$_3$) δ (ppm) 8.95 (s, 1H), 7.87 (d, 2H, J=8.0 Hz), 7.80 (d, J=8.7 Hz, 1H), 7.67 (s, 1H), 7.48 (s, .5H) 7.04 (m, 1H), 6.83 (m, 1H), 6.71 (m, 1H), 6.57 (d, 2H), 6.48 (s, 1H), 6.33 (m, 1H), 5.93 (s, 2H), 4.96 (br.s., 1H), 3.67 (m, 1H), 3.57 (m, 3H), 2.36 (m, 1H), 2.26 (m, 1H) |
| 204 | 376 | 4-phenoxyphenyl (PhO) | O | (S)-N-(2-aminophenyl)-4-(3-(4-phenoxyphenoxy)pyrrolidin-1-yl)benzamide | $^1$H NMR (CDCl$_3$) δ (ppm) 7.81 (m, 2H), 7.70 (s, 1H), 7.67 (s, .5H), 7.2-7.4 (m, 4H) 6.8-7.2 (m, 10H), 6.6 (m, 2H), 5.05 (br.s., 1H), 3.6 (m, 1H), 3.5 (m, 3H), 2.41 (m, 1H), 2.32 (m, 1H) |
| 205 | 377 | 4-nitrophenyl (O$_2$N) | O | (S)-N-(2-aminophenyl)-4-(3-(4-nitrophenoxy)pyrrolidin-1-yl)benzamide | $^1$H NMR (CDCl$_3$) δ (ppm) 8.12 (d, 2H, J=9.1 Hz), 7.72 (d, J=8.8 Hz, 2H), 7.18 (d, J=7.3 Hz, 1H), 6.97 (t, 1H, J=7.7 Hz), 6.87 (d, J=9.1 Hz, 2H), 6.50 (d, 2H, J=8.6 Hz), 5.09 (br.s., 1H), 3.71 (dd, J=4.5 Hz, J=11.3 Hz, 1H), 3.6 (m, 3H 2.3 (m, 2H) |
| 206 | 378 | pyridin-2-yl | S | (S)-N-(2-aminophenyl)-4-(3-(pyridin-2-ylthio)pyrrolidin-1-yl)benzamide | $^1$H NMR (CDCl$_3$) δ (ppm) 8.44 (m, 1H), 7.78 (d, J=8.8 Hz, 2H), 7.69 (s, 1H), 7.49 (t, 1H, J=7.4 Hz), 7.27 (m, 1H), 7.18 (d, 1H, J=8.0 Hz), 7.0-7.1 (m, 2H), 6.82 (d, 7.8 Hz, 2H), 6.55 (d, J=9.0 Hz, 2H), 4.55 (m, 1H), 3.9-4.0 (m, 3H), 3.4-3.6 (m, 4H) 2.6 (m, 1H), 2.2 (m, 1H) |

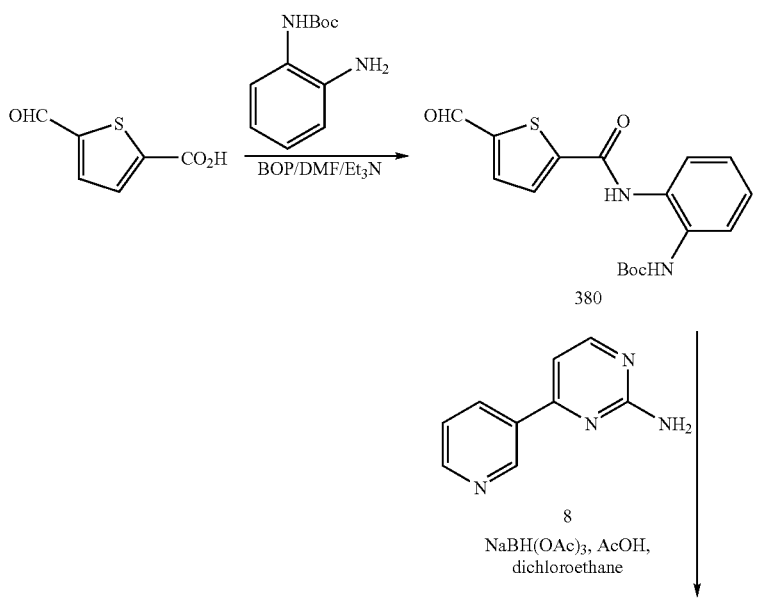

Scheme 70

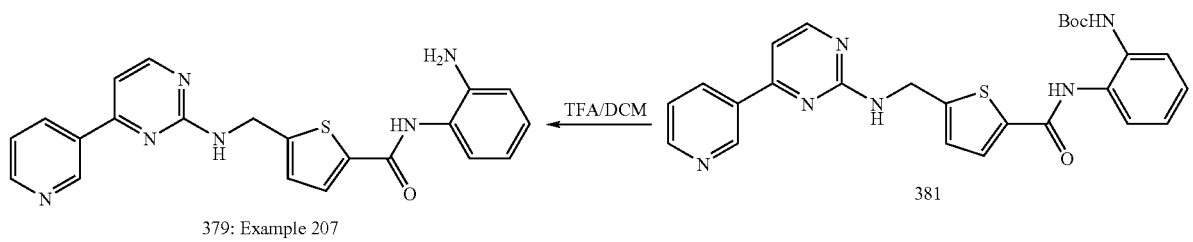

379: Example 207

Example 207

N-(2-Aminophenyl)-5-((4-(pyridin-2-yl)pyrimidin-2-ylamino)methyl)thiophene-2-carboxamide (379)

Step 1. tert-Butyl 2-(5-formylthiophene-2-carboxamido)phenylcarbamate (380)

A solution of 5-formylthiophene-2-carboxylic acid (350 mg, 2.24 mmol), tert-butyl 2-aminophenylcarbamate (467 mg, 2.24 mmol) and triethylamine (470 μL, 340 mg, 3.36 mmol) and BOP (1.1 g, 2.68 mmol) in DMF (10 mL) was stirred at room temperature for 2 hours. The reaction mixture was concentrated and purified by flash chromatography using 25% EtOAc in hexanes as an eluent, yielding 260 mg (33%) of the title compound. $^1$H NMR (CDCl3) δ9.95 (s, 1H), 9.7 (br. s, 1H), 7.84 (d, 1H, J=8.0 Hz), 7.74 (m, 2H), 7.15 (m, 2H), 6.72 (s, 1H), 1.56 (s, 9H). LRMS: (calc) 346.1; (found) 369.1 (M+Na)

Step 2. tert-Butyl 2-(5-((4-(pyridin-2-yl)pyrimidin-2-ylamino)methyl)thiophene-2-carboxamido)phenylcarbamate (381)

A solution of aldehyde 380 (260 mg, 0.75 mmol), 4-(pyridin-3-yl)pyrimidin-2-amine (85 mg, 0.5 mmol) and acetic acid (100 μL) in DCE (2 mL) was treated with NaBH(OAc)$_3$ (22 mg, 1 mmol) and the resultant mixture was stirred at room temperature overnight. It was then quenched by addition of saturated NaHCO$_3$ (5 mL) and the aqueous phase was extracted with EtOAc. Organic extract was dried with Na$_2$SO$_4$, filtered and concentrated to provide a crude product which was purified by flash chromatography using 80-20% mixture EtOAc-hexane as an eluent, to afford the title compound (35 mg, 14% yield). LRMS: (calc) 502.2; (found) 503.4 (M+H$^1$)

N-(2-Aminophenyl)-5-((4-(pyridin-2-yl)pyrimidin-2-ylamino)methyl)thiophene-2-carboxamide (379)

A solution of 381 (35 mg, 0.07 mmol) in 1:1 mixture of DCM and TFA (4 mL) was stirred at room temperature for 30 minutes. The reaction mixture was concentrated to produce a solid which was triturated with ether to afford the title compound as a TFA salt (26 mg, 75% yield). $^1$H NMR (MeOH-d4) δ9.31 (s, 1H), 8.68 (s, 1H), 8.66 (s, 1H), 8.43 (d, J=5.1 Hz, 1H), 7.77 (d, J=3.9 Hz, 1H), 7.68 (m, 1H), 7.1-7.5 (m, 6H). LRMS: (calc) 402.2; (found) 403.3 (M+H$^1$).

Scheme 71

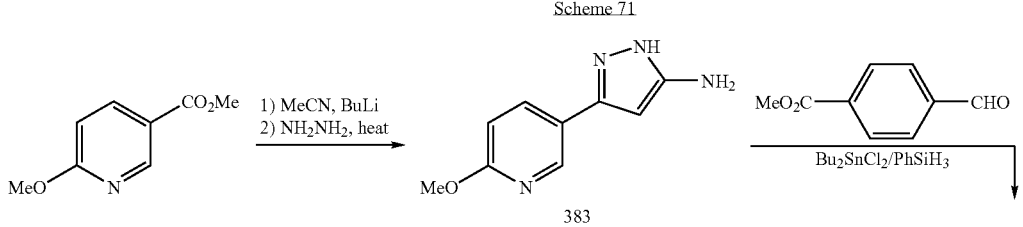

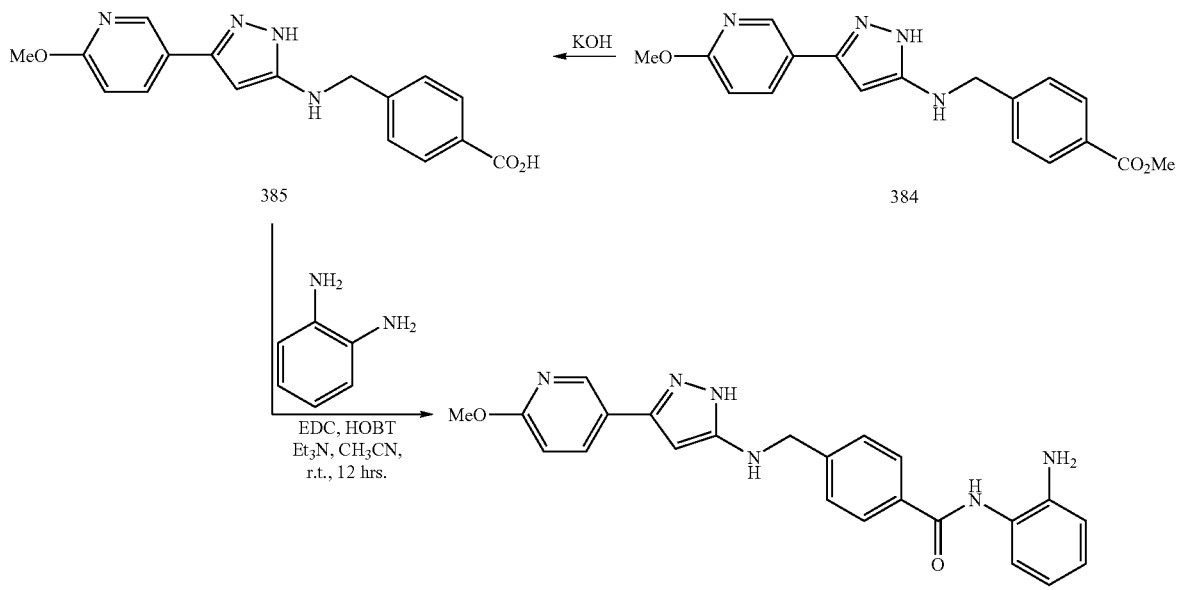

382: Example 208

Example 208

N-(2-Aminophenyl)-4-((3-(6-methoxypyridin-3-yl)-1H-pyrazol-5-ylamino)methyl)benzamide (382)

Step 1: 3-(6-Methoxypyridin-3-yl)-1H-pyrazol-5-amine (383)

MeCN (940 μL, 736 mg, 17.96 mmol) in THF (20 mL) was treated with 2.5 M solution of BuLi in hexanes (7.2 mL, 17.96 mmol) at −78° C. and the reaction mixture was allowed to stir at the same temperature for 30 min, treated with a solution of methyl 6-methoxynicotinate (2 g, 11.96 mmol) in THF (10 mL) at −78° C. and was stirred at room temperature for additional 2 hours. It was then quenched by addition of water (10 mL) and 1M solution of HCl (10 mL). The resultant mixture was concentrated in vacuo, the residue was mixed with hydrazine monohydrate (5 mL) in EtOH (30 mL), refluxed for 2 hours, cooled and concentrated under reduced pressure produce a solid which was purified by flash chromatography using 10% MeOH in DCM as an eluent, to afford the title compound (720 mg, 32% yield). $^1$H NMR (MeOH-d4) δ8.39 (s, 1H), 7.89 (d, J=8.6 Hz, 1H), 6.80 (d, J=8.6 Hz, 1H), 5.85 (s, 1H), 3.91 (s, 3H). LRMS: (calc) 190.1; (found) 191.1 (M+H$^1$).

Step 2: Methyl 4-((3-(6-methoxypyridin-3-yl)-1H-pyrazol-5-ylamino)methyl)benzoate (384)

A solution of amine 383 (720 mg, 3.79 mmol), methyl 4-formylbenzoate (745 mg, 4.54 mmol), and Bu$_2$SnCl$_2$ (230 mg, 0.76 mmol) in dry THF (5 mL) was stirred at room temperature for 2 hours. It was then treated with PhSiH$_3$ (514 μL, 451 mg, 4.17 mmol) and allowed to stir for another hour at room temperature. The reaction mixture was quenched by addition of MeOH and vigorous stirring for 45 min. It was then concentrated in vacuo and the residue was purified by flash chromatography using the gradient 50-100% EtOAc in hexane to afford the title compound (672 mg, 52% yield). LRMS: (calc) 338.1; (found) 339.2 (M+H$^1$)

Step 3: 4-((3-(6-Methoxypyridin-3-yl)-1H-pyrazol-5-ylamino)methyl)benzoic acid (385)

A solution of 384 (672 mg, 1.99 mmol) and KOH (300 mg, 5.35 mmol) in 1:1:1 mixture of THF, MeOH and water (9 mL) was stirred at room temperature overnight. The reaction mixture was acidified to pH=4 by addition of 1M HCl and concentrated in vacuo. The residue was triturated with water and the solid was collected by filtration and dried to afford the title compound (640 mg, 99% yield). LRMS: (calc) 324.1; (found) 325.2 (M+H$^1$)

Step 4: N-(2-Aminophenyl)-4-((3-(6-methoxypyridin-3-yl)-1H-pyrazol-5-ylamino)methyl)benzamide (382)

A solution of 385 (640 mg, 1.97 mmol) in MeCN (10 mL) was sequentially treated with Et$_3$N (831 μL, 603 mg, 5.96 mmol), EDC (571 mg, 2.98 mmol), HOBT (334 mg, 2.18 mmol) and 1,2-phenylene diamine (429 mg, 3.97 mmol) and allowed to stir overnight. The reaction mixture was concentrated and partitioned between DCM (15 mL) and saturated NH$_4$Cl (15 mL). The organic phase was collected, dried with Na$_2$SO$_4$, filtered and concentrated. The resultant solid was purified by flash chromatography using the gradient 3-15% MeOH in DCM to afford the title compound (113 mg, 14% yield). $^1$H NMR (DMSO-d$_6$) δ9.65 (s, 1H), 8.43 (s, 1H), 7.92 (m, 3H), 7.48 (d, J=8.0 Hz, 2H), 7.16 (d, J=7.4 Hz, 1H), 6.97 (t, J=7.6 Hz, 1H), 6.81 (t, J=8.2 Hz, 2H), 6.63 (t, J=7.4 Hz, 1H), 5.85 (s, 1H), 4.34 (s, 2H), 3.85 (s, 3H). LRMS: (calc) 414.2; (found) 415.3 (M+H$^1$)

Example 209

N-(2-aminophenyl)-4-((3-(pyridin-3-yl)-1H-pyrazol-5-ylamino)methyl)benzamide (386)

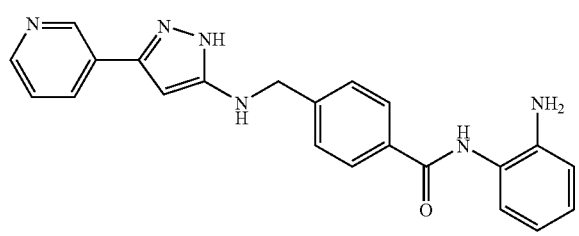

386: Example 209

Title compound was prepared according to the scheme 71 (example 208) starting from methyl nicotinate. $^1$H NMR (MeOH-d4) δ 8.80 (s, 1H), 8.43 (d, J=3.9 Hz, 1H), 8.04 (m, 2H), 7.94 (d, J=8.2 Hz, 2H), 7.53 (d, J=8.2 Hz, 1H), 7.43 (m, 1H), 7.15 (d, J=7.6 Hz, 1H), 7.05 (t, J=7.2 Hz, 2H), 6.88 (d, J=8.0 Hz, 1H), 6.75 (t, J=7.4 Hz, 1H), 5.94 (s, 1H), 4.45 (s, 2H). LRMS: (calc) 384.2; (found) 385.2 (M+H$^1$)

Example 210

N-(2-Aminophenyl)-4-((3-(3,4,5-trimethoxyphenyl)-1H-pyrazol-5-ylamino)methyl)benzamide (387)

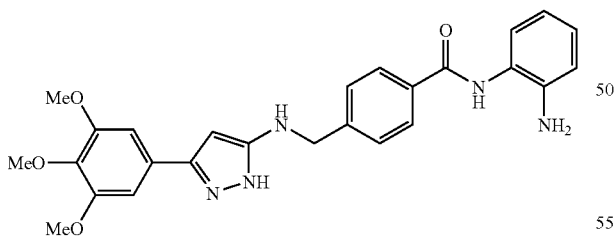

387: Example 210

Title compound was prepared according to the scheme 71 (example 208) starting from methyl 3,4,5-trimethoxybenzoate. $^1$H NMR (MeOH-d4) δ 7.92 (d, J=8.4 Hz, 2H), 7.53 (d, J=8.0 Hz, 2H), 7.16 (d, J=7.9 Hz, 1H), 7.06 (t, J=7.8 Hz, 1H), 6.93 (s, 2H), 6.88 (d, J=8.0 Hz, 1H), 6.75 (t, J=7.6 Hz, 1H), 5.89 (s, 1H), 4.45 (s, 2H), 3.87 (s, 6H), 3.77 (s, 3H). LRMS: (calc) 473.3; (found) 474.4 (M+H$^1$)

Example 211

N-(2-Aminophenyl)-4-((4-chloro-3-(3,4,5-trimethoxyphenyl)-1H-pyrazol-5-ylamino)methyl)benzamide (388)

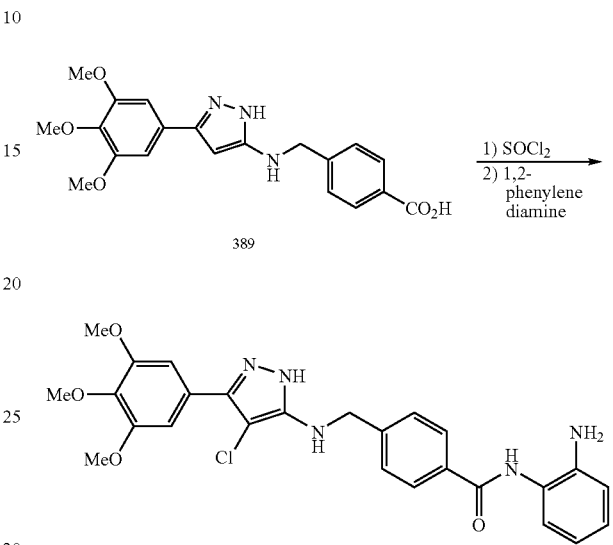

388: Example 211

Steps 1, 2 and 3. 4-((3-(3,4,5-Trimethoxyphenyl)-1H-pyrazol-5-ylamino)methyl)benzoic acid (389)

Title compound was obtained according to the scheme 71, steps 1, 2 and 3 using in the first step methyl 3,4,5-trimethoxybenzoate instead of methyl 6-methoxynicotinate. LRMS: (calc) 383.1; (found) 384.2 (M+H$^1$).

Step 4: N-(2-Aminophenyl)-4-((4-chloro-3-(3,4,5-trimethoxyphenyl)-1H-pyrazol-5-ylamino)methyl)benzamide (388)

A solution of 389 (30 mg, 0.08 mmol) in a 1:1 mixture of DCM and SOCl2 (2 mL) was stirred at room temperature for 30 min. The reaction mixture was concentrated and treated with a solution of 1,2-phenylene diamine (18 mg, 0.16 mmol) in THF (2 mL) and stirred at room temperature for 15 min, concentrated under reduced pressure to produce a solid which was purified by preparative HPLC (column AQUASIL C-18; 5 μM; 230×21.2 mm; eluent 30-95% MeOH in water) to afford the title compound (8 mg, 20% yield). $^1$H NMR (MeOH-d4) δ 7.92 (d, J=8.3 Hz, 2H), 7.52 (d, J=8.2 Hz, 2H), 7.17 (d, J=7.6 Hz, 1H), 7.06 (m, 3H), 6.89 (d, J=7.8 Hz, 1H), 6.75 (t, J=7.2 Hz, 1H), 4.55 (s, 2H), 3.89 (s, 6H), 3.80 (s, 3H). LRMS: (calc) 507.2; (found) 508.3 (M+H$^1$).

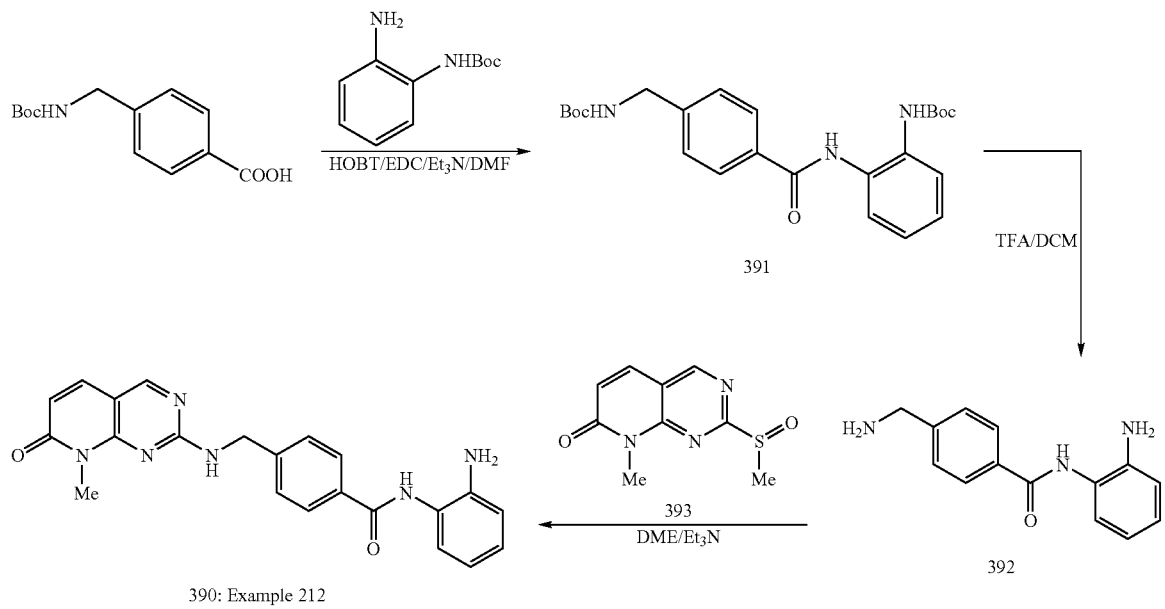

Example 212

N-(2-Aminophenyl)-4-((8-methyl-7-oxo-7,8-dihydropyrido[2,3-d]pyrimidin-2-ylamino)methyl)benzamide (389)

Step 1. tert-Butyl 2-(4-(Boc-aminomethyl)benzamido)phenylcarbamate (391)

A solution of 4-((tert-butoxycarbonylamino)methyl)benzoic acid (1 g, 3.98 mmol) in DMF (10 mL) was treated sequentially with EDC (930 mg, 4.84 mmol), HOBT (682 mg, 4.46 mmol) and Et$_3$N (670 μL, 489 mg, 4.84 mmol) at room temperature and allowed to stir overnight. The reaction mixture was concentrated under reduced pressure and partitioned between chloroform (10 mL) and water (10 mL). Organic phase was collected, washed with 1M HCl (10 mL) and saturated NaHCO$_3$ (10 mL), dried, filtered and evaporated to form a residue which was purified by flash chromatography using 30% EtOAc in hexanes as an eluent to afford the title compound (840 mg, 51%). LRMS: (calc) 441.2; (found) 442.2 (M+H$^1$)

Step 2. 4-(Aminomethyl)-N-(2-aminophenyl)benzamide (392)

A solution of 391 (840 mg, 1.9 mmol) in 2:1 mixture of DCM/TFA (6 mL) was stirred at room temperature for 2 hours. The reaction mixture was concentrated in vacuo to afford the title compound as a mixture of the mono and di-TFA salt. (1.33 g, 100% yield). LRMS: (calc) 241.2; (found) 242.2 (M+H$^1$).

Step 3. N-(2-Aminophenyl)-4-((8-methyl-7-oxo-7,8-dihydropyrido[2,3-d]pyrimidin-2-ylamino)methyl)benzamide (390)

A solution of sulfoxide 393 (Barvian, M. et al. *J. Med. Chem.* (2001) 44(6); 1016-1016) (166 mg, 0.74 mmol), bis-amine 392 (535 mg, 2.23 mmol) and triethylamine (620 μL, 4.46 mmol) in DME (3 mL) was stirred at room temperature for 3 hours. The reaction mixture was concentrated and partitioned between EtOAc (5 mL) and water (5 mL). Organic phase was collected and washed successively with saturated solutions of NH$_4$Cl (5 mL) and NaHCO$_3$ (5 mL), dried over Mg$_2$SO$_4$, filtered and concentrated to produce a residue which was triturated with 1:1 EtOAc/hexane solution to afford the title compound (48 mg, 16% yield). $^1$H NMR (CDCl$_3$) δ3.62 (s, 3H), 4.80 (m, 2H), 6.42 (d, J=10 Hz, 1H), 6.85 (d, J=8 Hz, 2H), 7.10 (m, 1H), 7.30 (m, 1H), 7.50 (m, 2H), 7.87 (s, 1H), 7.897 (m, 2H), 8.43 (s, 1H). LRMS: (calc) 400.0; (found) 401.0 (M+H$^1$)

Example 213

N-(2-Aminophenyl)-4-((7-oxo-7,8-dihydropyrido[2,3-d]pyrimidin-2-ylamino)methyl)benzamide (394)

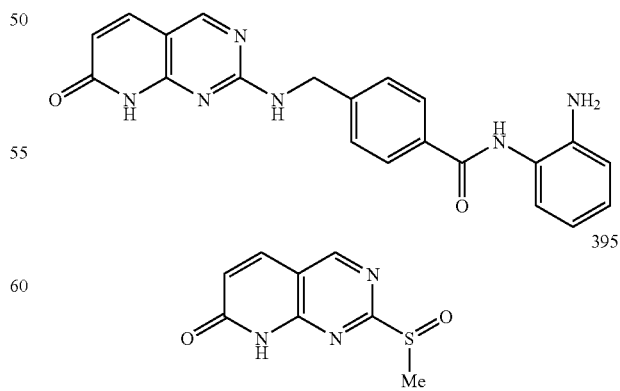

Title compound was prepared in a similar manner as the example 212 (scheme 72) starting from the sulfoxide 395 obtained by literature procedure similarly to the sulfoxide 393. ¹H NMR (DMSO) δ4.60 (s, 2H), 4.90 (s, 2H), 6.10 (d, J=10 Hz, 1H), 6.55 (t, J=7 Hz, 2H), 6.75 (m, 1H), 6.90 (t, J=7 Hz, 2H), 7.10 (m, 2H), 7.40 (m, 2H), 7.65 (m, 1H), 7.90 (m, 1H), 8.55 (s, 1H), 9.69 (s, 1H). LRMS: (calc) 386.0; (found) 387.0 (M+H¹).

and quenched by adding saturated NH₄Cl sat solution (5 mL). The organic phase was separated, dried over Na₂SO₄, filtered and concentrated to produce a residue which was purified by flash chromatography using 5% MeOH in DCM as an eluent to afford the title compound (110 mg, 79% yield). LRMS: (calc) 367.2; (found). 368.1 (M+H¹).

Scheme 73

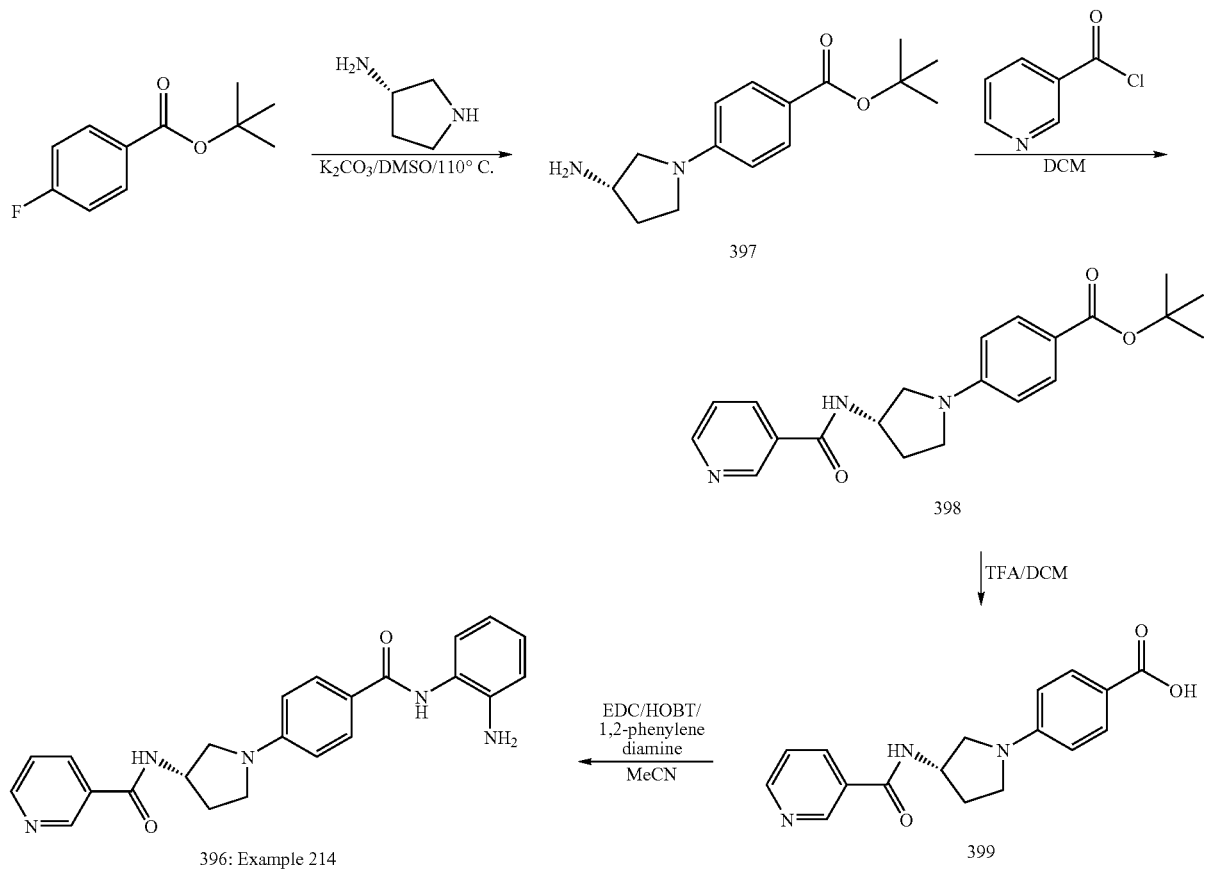

Example 214

(S)—N-(1-(4-(2-Aminophenyl carbamoyl)phenyl) pyrrolidin-3-yl)nicotinamide (396)

Step 1. (S)-tert-Butyl 4-(3-aminopyrrolidin-1-yl) benzoate (397)

Title compound was obtained similarly to the aminoester 363 using the same procedure as described in step 2, scheme 69. ¹H NMR (CDCl₃) δ 7.83 (d, J=8.8 Hz, 1H), 6.46 (d, J=8.8 Hz, 1H), 3.75 (m, 1H), 3.35-3.6 (m, 3H), 3.06 (dd, J=4.7 Hz, J=9.8 Hz, 1H), 2.26 (m, 1H), 1.85 (m, 1H), 1.57 (s, 9H), LRMS: (calc) 262.1; (found) 263.0 (M+H¹).

Step 2. (S)-tert-Butyl 4-(3-(nicotinamido)pyrrolidin-1-yl)benzoate (398)

A solution of 397 (100 mg, 0.38 mmol), Et₃N (160 µL, 1.14 mmol) and nicotinoyl chloride HCl salt (68 mg, 0.38 mmol) in DCM (2 mL) was stirred at room temperature for 1 hour

Step 3. (S)-4-(3-(Nicotinamido)pyrrolidin-1-yl)benzoic acid (399)

The title compound was obtained as the mixture of monosalt and disalt similarly to the compound 117 using the same procedure as described in step 5, scheme 28. LRMS: (calc) 311.1; (found) 312.1 (M+H¹).

Step 4. (S)—N-(1-(4-(2-Aminophenylcarbamoyl) phenyl)pyrrolidin-3-yl)nicotinamide (396)

A solution of 399 (93 mg, 0.3 mmol), phenylene diamine (65 mg, 0.6 mmol), EDC (86 mg, 0.45 mmol), HOBT (53 mg, 0.33 mmol) and Et₃N (125 µL, 91 mg, 0.9 mmol) in acetonitrile (2 mL) was stirred at room temperature overnight. The reaction mixture was concentrated and the residue was purified by flash chromatography using the gradient 5-20% MeOH in DCM as an eluent to afford the title compound (24 mg, 16% yield). ¹H NMR (CDCl₃) δ 8.97 (s, 1H), 8.66 (d, J=4.9 Hz, 1H), 8.21 (d, J=3.9 Hz, 1H), 7.87 (d, 2H, J=8.8 Hz), 7.52 (dd, J=5.1 Hz, J=8.0 Hz, 1H), 7.15 (d, 1H, J=7.9 Hz), 7.05 (t, J=8.1 Hz, 1H), 6.89 (d, J=7.6 Hz, 1H), 6.76 (t, J=7.3 Hz, 1H), 6.66 (d, J=9.0 Hz, 2H), 4.78 (m, 1H), 3.80 (dd, J=6.7

Hz, J=10.2 Hz, 1H), 3.61 (m, 1H), 3.49 (m, 1H), 3.41 (m, 1H), 2.4 (m, 1H), 2.2 (m, 1H). LRMS: (calc) 401.2; (found) 402.2 (M+H$^1$).

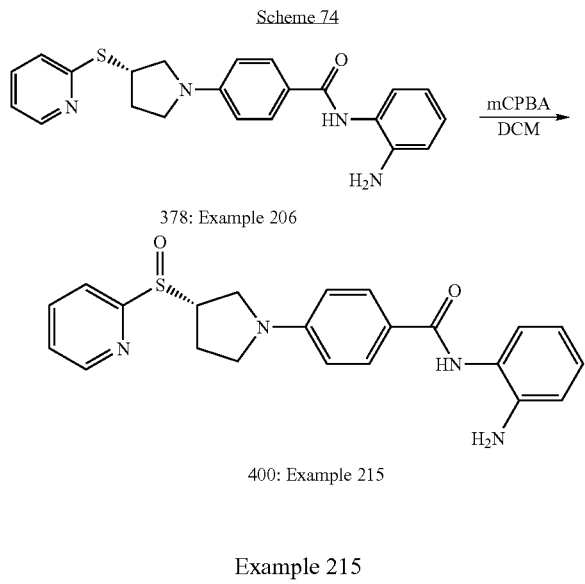

378: Example 206

400: Example 215

Example 215

N-(2-Aminophenyl)-4-((S)-3-((S)-pyridin-2-ylsulfinyl)pyrrolidin-1-yl)benzamide (400)

A solution of 378 (15 mg, 0.04 mmol) and mCPBA (6 mg, 0.04 mmol) in DCM (2 mL) was stirred at room temperature for 1 hour. The reaction mixture was concentrated and the residue was purified by flash chromatography using the gradient EtOAc to 5% MeOH in DCM as an eluent, to afford the title compound (13 mg, 80% yield). $^1$H NMR (CDCl$_3$) δ $^1$H NMR (CDCl$_3$) δ 8.63 (m, 1H), 8.58 (m, 1H), 7.6-8.0 (m, 10H), 7.40 (m, 2H), 7.25 (m, 1H), 7.05 (m, 2H), 6.85 (m, 3H), 6.58 (d, J=8.8 Hz, 2H), 6.50 (d, J=11.1 Hz, 2H), 3.7-4.0 (m, 6H), 3.2-3.5 (m, 4H), 2.4-2.8 (m, 3H), 2.95 (m, 1H). LRMS: (calc) 406.1; (found) 407.1 (M+H$^1$).

Assay Example 1

Inhibition of Histone Deacetylase Enzymatic Activity

1. Human HDAC-1

Assay 1. HDAC inhibitors were screened against a cloned recombinant human HDAC-1 enzyme expressed and purified from a Baculovirus insect cell expression system. For deacetylase assays, 20,000 cpm of the [$^3$H]-metabolically labeled acetylated histone substrate (M. Yoshida et al., *J. Biol. Chem.* 265(28): 17174-17179 (1990)) was incubated with 30 μg of the cloned recombinant hHDAC-1 for 10 minutes at 37° C. The reaction was stopped by adding acetic acid (0.04 M, final concentration) and HCl (250 mM, final concentration). The mixture was extracted with ethyl acetate and the released [$^3$H]-acetic acid was quantified by scintillation counting. For inhibition studies, the enzyme was preincubated with compounds at 4° C. for 30 minutes prior to initiation of the enzymatic assay. IC$_{50}$ values for HDAC enzyme inhibitors were determined by performing dose response curves with individual compounds and determining the concentration of inhibitor producing fifty percent of the maximal inhibition.

Assay 2. The following protocol was also used to assay the compounds of the invention. In the assay, the buffer used was 25 mM HEPES, pH 8.0, 137 mM NaCl, 2.7 mM KCl, 1 mM MgCl$_2$ and the substrate was Boc-Lys(Ac)-AMC in a 50 mM stock solution in DMSO. The enzyme stock solution was 4.08 μg/mL in buffer. The compounds were pre-incubated (2 μl in DMSO diluted to 13 μl in buffer for transfer to assay plate) with enzyme (20 μl of 4.08 μg/ml) for 10 minutes at room temperature (35 μl pre-incubation volume). The mixture was pre-incubated for 5 minutes at room temperature. The reaction was started by bringing the temperature to 37° C. and adding 16 μl substrate. Total reaction volume was 50 μl. The reaction was stopped after 20 minutes by addition of 50 μl developer, prepared as directed by Biomol (Fluor-de-Lys developer, Cat. # KI-105). A plate was incubated in the dark for 10 minutes at room temperature before reading ($λ_{Ex}$=360 nm, $λ_{Em}$=470 nm, Cutoff filter at 435 nm).

IC$_{50}$ values for representative compounds are presented in Table 14. Assay 1 was used to measure HDAC activity of compounds 10c, 13e, 16d, 26b, 44, 47, 61a, 61b, 63, 134, 138, and 308. Assay 2 was used to measure HDAC activity of compounds 361, 366, 367, 368, 369, 370, 371, 372, 373, 374, 375, 376, 377, and 378. In Table 14, "a" indicates activity of ≦0.1 μM, "b" indicates activity of ≦1 μM, "c" indicates activity of ≦5 μM, and "d" indicates activity of >5 μm. For the H4-Ac T24 EC vs. MS-275 assay in Table 14, "u" indicates less than 1, "v" indicates 1, and "w" indicates greater than 1. For the H3 Ac t24 assay in Table 14, "x" indicates activity of ≦1 μM, "y" indicates activity of ≦10 μM, and "z" indicates activity of ≦20 μM.

2. MTT Assay

HCT116 cells (2000/well) were plated into 96-well tissue culture plates one day before compound treatment. Compounds at various concentrations were added to the cells. The cells were incubated for 72 hours at 37° C. in 5% CO$_2$ incubator. MTT (3-[4,5-dimethylthiazol-2-yl]-2,5diphenyl tetrazolium bromide, Sigma) was added at a final concentration of 0.5 mg/ml and incubated with the cells for 4 hours before one volume of solubilization buffer (50% N,N-dimethylformamide, 20% SDS, pH 4.7) was added onto the cultured cells. After overnight incubation, solubilized dye was quantified by colorimetric reading at 570 nM using a reference at 630 nM using an MR700 plate reader (Dynatech Laboratories Inc.). OD values were converted to cell numbers according to a standard growth curve of the relevant cell line. The concentration which reduces cell numbers to 50% of that of solvent treated cells is determined as MTT IC$_{50}$. IC$_{50}$ values for representative compounds are presented in Table 14. In Table 14, "a" indicates activity of ≦0.1 μM, "b" indicates activity of ≦1 μM, and "c" indicates activity of ≦5 μM.

3. Histone H4 Acetylation in Whole Cells by Immunoblots

T24 human bladder cancer cells growing in culture were incubated with HDAC inhibitors for 16 h. Histones were extracted from the cells after the culture period as described by M. Yoshida et al. (*J. Biol. Chem.* 265(28): 17174-17179 (1990)). 20 g of total histone protein was loaded onto SDS/PAGE and transferred to nitrocellulose membranes. Membranes were probed with polyclonal antibodies specific for acetylated histone H-4 (Upstate Biotech Inc.), followed by horse radish peroxidase conjugated secondary antibodies (Sigma). Enhanced Chemiluminescence (ECL) (Amersham) detection was performed using Kodak films (Eastman Kodak). Acetylated H-4 signal was quantified by densitometry. Representative data are presented in Table 14. Data are presented as the ratio of the concentration effective for reducing the acetylated H-4 signal by 50% (EC$_{50}$) using the indicated compound of the invention to a control compound, MS-275. If the indicated ratio is 1, then the compound of the invention is as effective as the MS-275 control compound. If the ratio is less than 1, then the compound of the invention is more effective than the MS-275 control compound. Further information regarding the MS-275 compound can be found in Suzuki et al., *J. Med. Chem.* 1999, pp. 3001-3003.

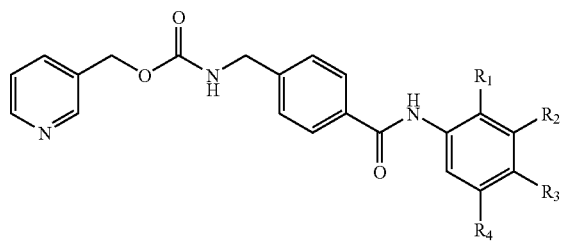

MS-275

4. Histone H3 Acetylation Assay

T24 human bladder cancer cells growing in culture are incubated with HDAC inhibitors for 16 h. Cell viability is determined by adding 10 µl Alamar Blue (BioSource, DAL1100). Cells are washed once with PBS and fixed with methanol precooled to −20° C. for 10 min. The cells are then washed twice in PBS. The fixed cells are blocked with 50 µl of PBS+0.1% Triton X-100. Cells are probed with rabbit-anti-acetyl-H3 (Upstate #06-599) as the primary antibody and then with goat-anti-rabbit-HRP (Sigma #A-0545) as the secondary antibody. Fluorescence is read by fluorometer at Ex:550, Em:610, Cutoff:590 (Auto PMT, 15 reads/well) after addition of Amplex-Red. Fluorescence signal is normalized against cell viability derived from Alamar Blue. Data is presented in Table 14 as $EC_{50}$. Maximum acetylation signal of MS-275 (fluorescence unit) is measured as $E_{max}$. The concentration of compound which gives 50% of $E_{max}$ is $EC_{50}$. In Table 14, "x" indicates activity of $\leq 1$ µM, "y" indicates activity of $\leq 10$ µM, and "z" indicates activity of $\leq 20$ µM.

TABLE 14

In vitro profile of selected HDAC inhibitors.

| Example | Compd | Structure | HDAC-1 $IC_{50}$ (µM) | MTT HCT116 $IC_{50}$ (µM) | H4-Ac T24 EC vs. MS-275 |
|---|---|---|---|---|---|
| 4 | 10c | 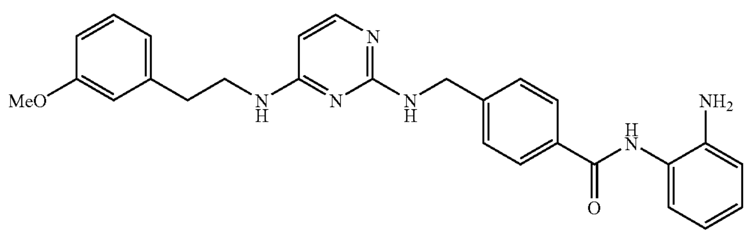 | c | b | v |
| 16 | 13e | 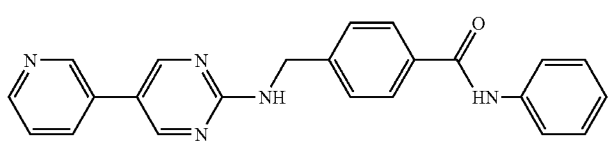 | c | b | v |
| 20 | 16d | 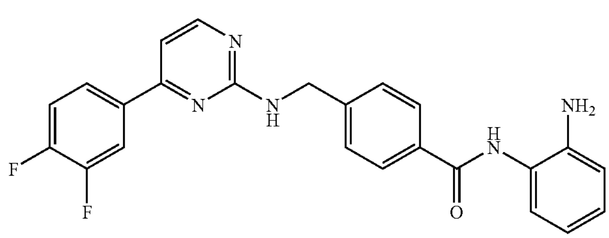 | b | b | v |
| 30 | 26b | 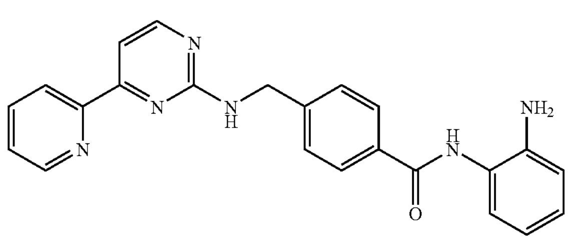 | c | a | v |

TABLE 14-continued
In vitro profile of selected HDAC inhibitors.
| 42 | 44 | 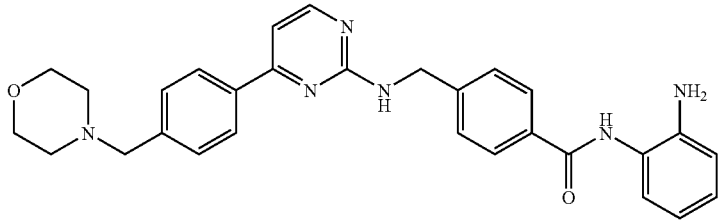 | c | a | v |
| 43 | 47 | 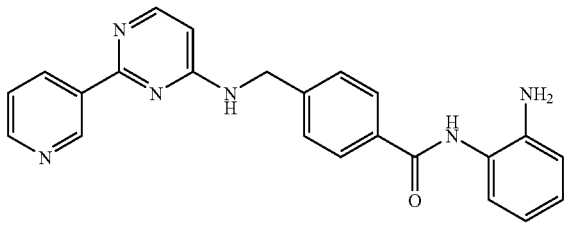 | c | b | u |
| 48 | 61a | 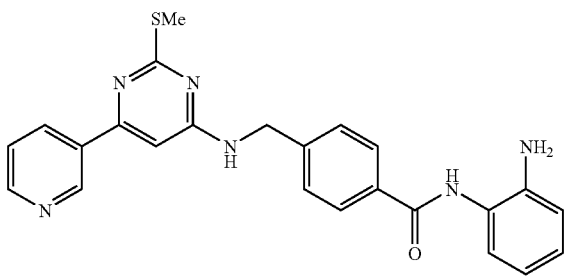 | c | a | v |
| 49 | 61b | 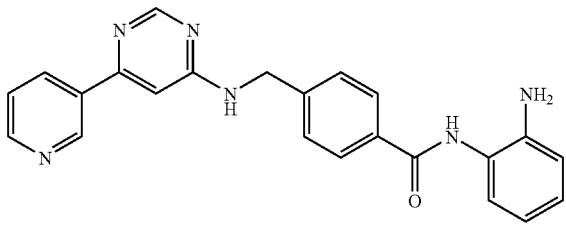 | c | a | u |
| 51 | 63 | 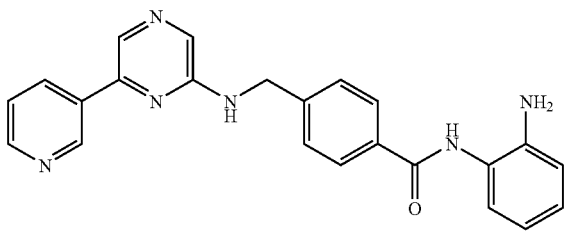 | c | b | v |
| 72 | 134 | 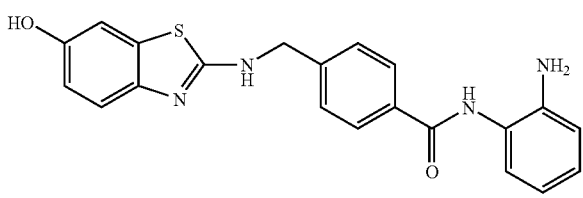 | c | b | u |

US 8,088,805 B2
TABLE 14-continued
In vitro profile of selected HDAC inhibitors.
| 76 | 138 |  | c | a | u |
| 173 | 308 |  | c | b | w |
| Example | Comp | Structure | HDAC1 IC$_{50}$ µM | MTT HCT116 IC$_{50}$ | H3 Ac t24 (µM) |
|---|---|---|---|---|---|
| 193 | 361 | 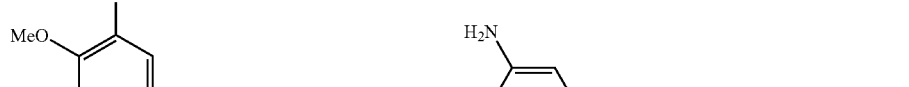 | a | b | y |
| 194 | 366 | 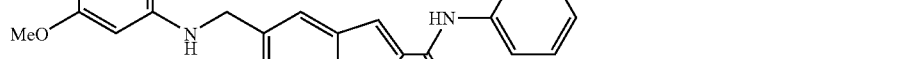 | b | c | z |
| 195 | 367 | 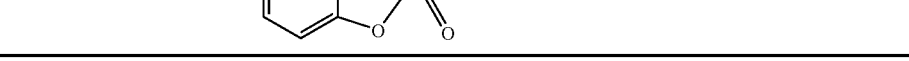 | b | b | y |
| 196 | 368 | 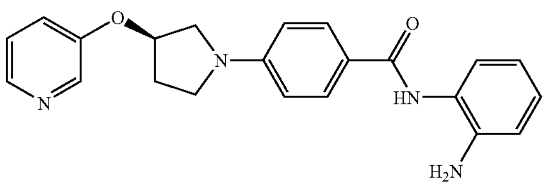 | b | b | |
| 197 | 369 | 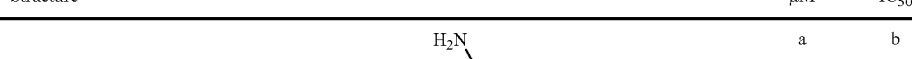 | b | b | x |
| 198 | 370 | 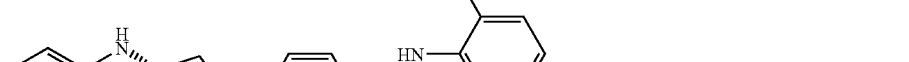 | c | c | |

TABLE 14-continued

In vitro profile of selected HDAC inhibitors.

| | | Structure | | | |
|---|---|---|---|---|---|
| 199 | 371 | (phenoxy-pyrrolidinyl-phenyl-C(O)NH-phenyl-NH2) | b | b | |
| 220 | 372 | (MeO2C-phenyl-O-pyrrolidinyl-phenyl-C(O)NH-phenyl-NH2) | a | b | |
| 201 | 373 | (HO2C-phenyl-O-pyrrolidinyl-phenyl-C(O)NH-phenyl-NH2) | b | d | |
| 202 | 374 | (3,4,5-triMeO-phenyl-O-pyrrolidinyl-phenyl-C(O)NH-phenyl-NH2) | a | b | x |
| 203 | 375 | (benzodioxol-O-pyrrolidinyl-phenyl-C(O)NH-phenyl-NH2) | a | d | x |
| 204 | 376 | (phenoxy-phenyl-O-pyrrolidinyl-phenyl-C(O)NH-phenyl-NH2) | c | c | |
| 205 | 377 | (4-NO2-phenyl-O-pyrrolidinyl-phenyl-C(O)NH-phenyl-NH2) | b | b | |
| 206 | 378 | (pyridyl-S-pyrrolidinyl-phenyl-C(O)NH-phenyl-NH2) | b | b | y |

Assay Example 2

Antineoplastic Effects of Histone Deacetylase Inhibitors on Human Tumor Xenografts In Vivo Eight to ten week old female BCD1 mice (Taconic Labs, Great Barrington, N.Y.) were injected subcutaneously in the flank area with $2 \times 10^6$ preconditioned HCT116 human colorectal carcinoma cells, SW48 colon cancer cells, and A549 lung cancer cells. Preconditioning of these cells was done by a minimum of three consecutive tumor transplantations in the same strain of nude mice. Subsequently, tumor fragments of approximately 30 mgs were excised and implanted subcutaneously in mice, in the left flank area, under Forene anesthesia (Abbott Labs, Geneva, Switzerland). When the tumors reached a mean volume of 100 $mm^3$, the mice were treated intraperitoneally by daily injection, with a solution of the histone deacetylase inhibitor in DMSO, at a starting dose of 10 mg/kg. The optimal dose of the HDAC inhibitor was established by dose response experiments according to standard protocols. Tumor volume was calculated every second day post infusion according to standard methods (e.g., Meyer et al., *Int. J. Cancer* 43: 851-856 (1989)). Treatment with the HDAC inhibitors according to the invention caused a significant reduction in tumor weight and volume relative to controls treated with vehicle only (i.e., no HDAC inhibitor).

Assay Example 3

Combined Antineoplastic Effect of Histone Deacetylase Inhibitors and Histone Deacetylase Antisense Oligonucleotides on Tumor Cells In Vivo The purpose of this example is to illustrate the ability of the combined use of a histone deacetylase inhibitor of the invention and a histone deacetylase antisense oligonucleotide to enhance inhibition of tumor growth in a mammal. Preferably, the antisense oligonucleotide and the HDAC inhibitor inhibit the expression and activity of the same histone deacetylase.

Mice bearing implanted HCT116 tumors (mean volume 100 $mm^3$) are treated daily with saline preparations containing from about 0.1 mg to about 30 mg per kg body weight of histone deacetylase antisense oligonucleotide. A second group of mice is treated daily with pharmaceutically acceptable preparations containing from about 0.01 mg to about 5 mg per kg body weight of HDAC inhibitor.

Some mice receive both the antisense oligonucleotide and the HDAC inhibitor. Of these mice, one group may receive the antisense oligonucleotide and the HDAC inhibitor simultaneously intravenously via the tail vein. Another group may receive the antisense oligonucleotide via the tail vein, and the HDAC inhibitor subcutaneously. Yet another group may receive both the antisense oligonucleotide and the HDAC inhibitor subcutaneously. Control groups of mice are similarly established which receive no treatment (e.g., saline only), a mismatch antisense oligonucleotide only, a control compound that does not inhibit histone deacetylase activity, and a mismatch antisense oligonucleotide with a control compound.

Tumor volume is measured with calipers. Treatment with the antisense oligonucleotide plus the histone deacetylase protein inhibitors according to the invention causes a significant reduction in tumor weight and volume relative to controls.

TABLE 12

| | | | | | % Inhibition (relative to vehicle control) | | |
|---|---|---|---|---|---|---|---|
| Compound | Example | Dose mg/kg | Route | No. of animals entered | HCT116 | SW48 | A549 |
| 10a | 2 | 30 | ip | 6 | 16.1 | 23.0 | — |
| 26b | 30 | 40 | ip | 6 | — | 75.1 | 74.4 |
| 26c | 32 | 30 | ip | 6 | 88.0 | 89.5 | — |
| 29a | 34 | 30 | ip | 6 | — | 70.2 | 31.8 |
| 31b | 37 | 30 | ip | 6 | 39.4 | 47.8 | — |
| 34a | 39 | 30 | ip | 6 | — | 25.5 | 67.1 |
| 58b | 47 | 30 | ip | 6 | 29.4 | 34.6 | — |
| 138 | 76 | 30 | ip | 6 | 79.8 | — | 83.7 |
| 158 | 82 | 30 | ip | 6 | — | 43.2 | 42.6 |
| 194 | 93 | 30 | ip | 6 | 54.5 | 23.1 | — |
| 212f | 104 | 30 | ip | 6 | 65.7 | 32.7 | — |
| 212h | 106 | 30 | ip | 6 | — | 44.0 | 54.4 |
| 252 | 133 | 30 | ip | 6 | 70.6 | 25.9 | — |
| 296 | 161 | 30 | ip | 6 | 63.9 | 53.4 | — |

We claim:

1. A compound of formula 1a-2:

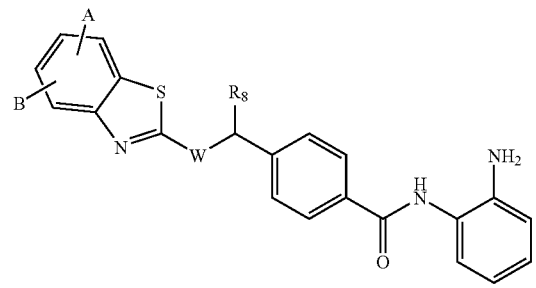

1a-2 wherein W is S or NH; $R_8$ is H or $C_1$-$C_4$ alkyl; and A is selected from $C_1$-$C_4$ alkyl, haloalkoxy and heteroarylalkoxy, alkoxyalkyl, haloalkyl, amino, nitro, alkylthio, acylamino, carbamoyl,

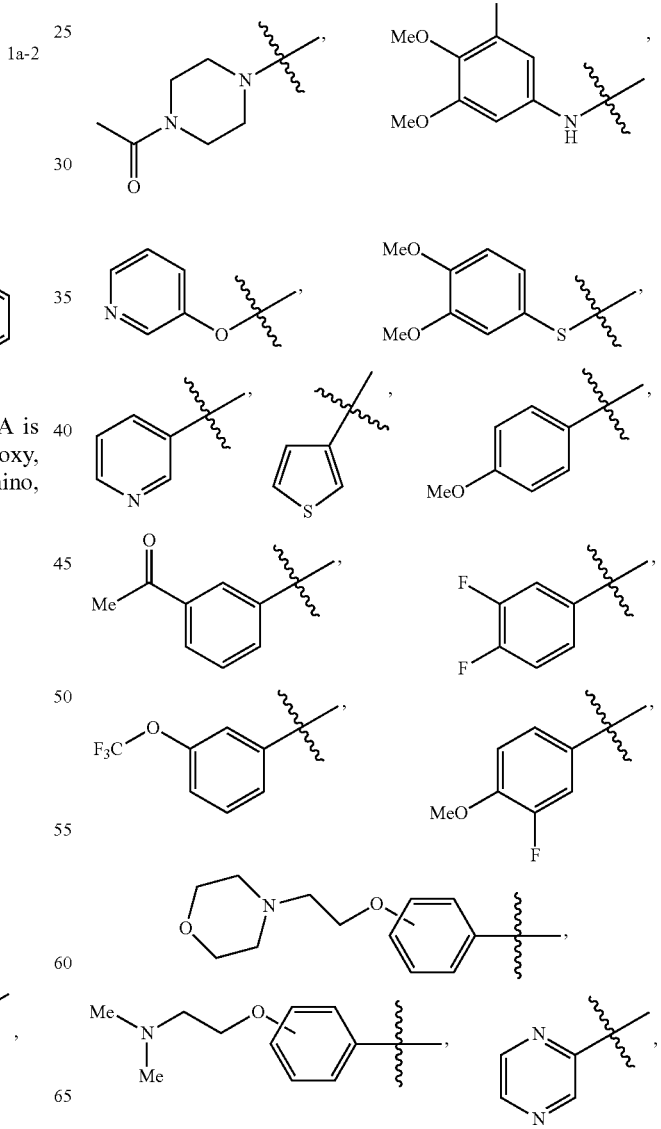

301
-continued
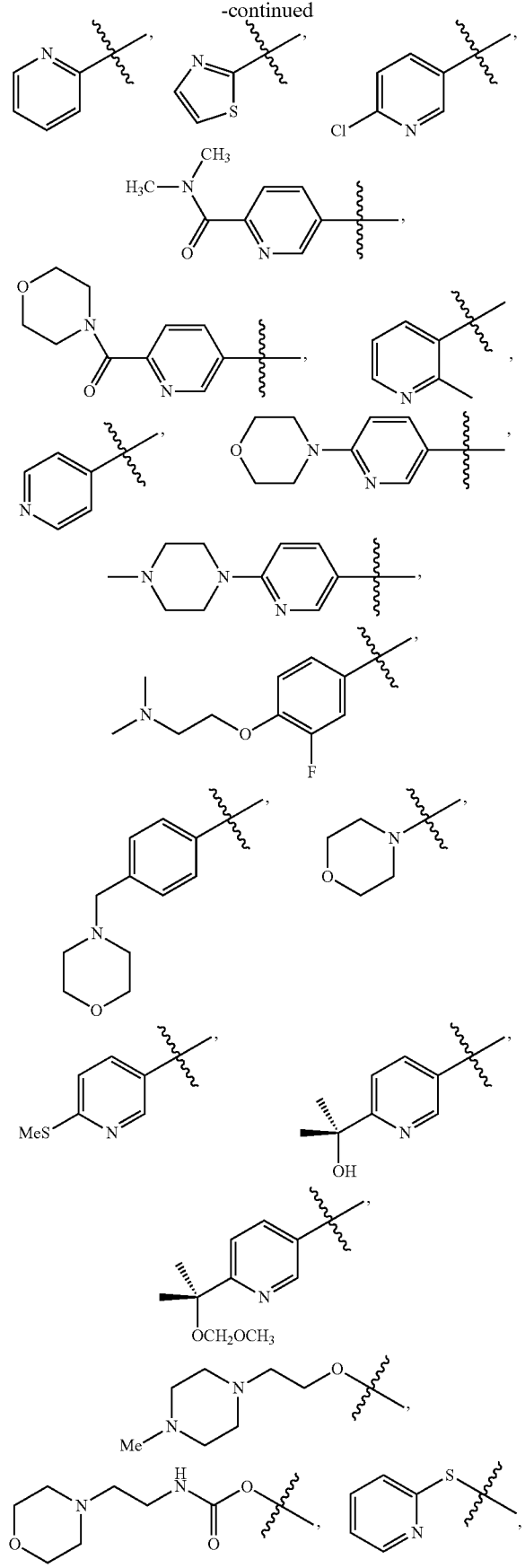
302
-continued
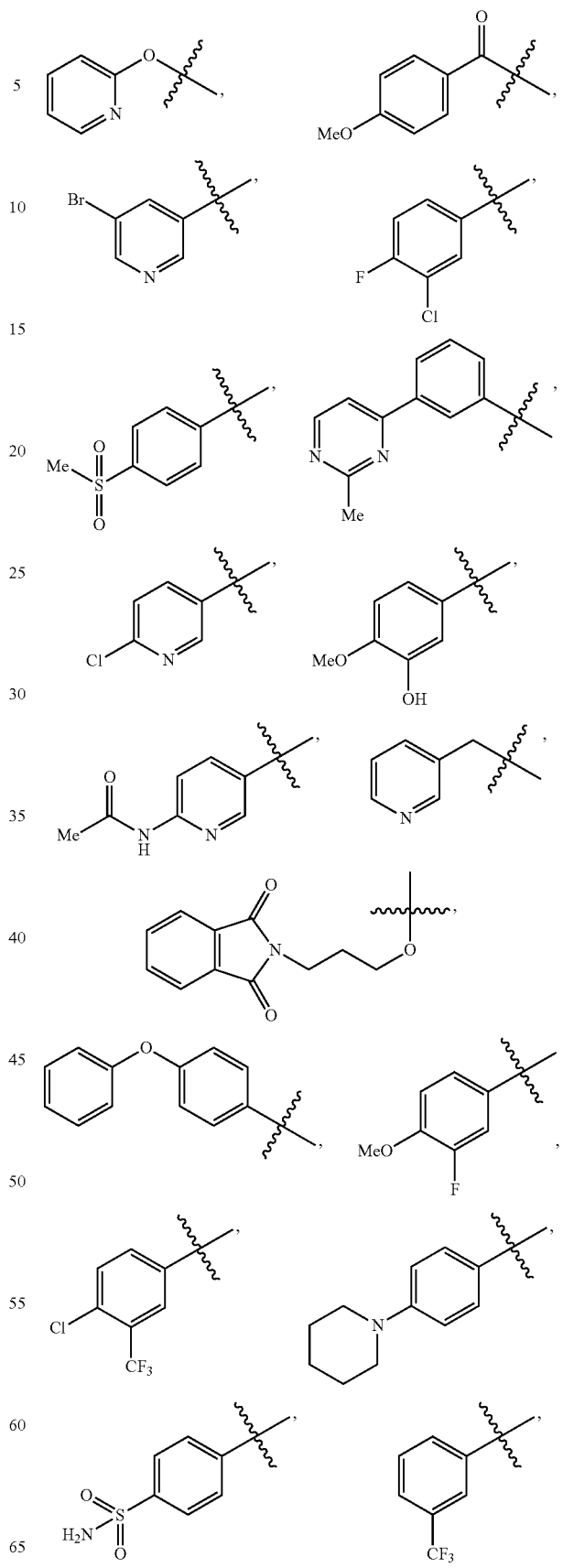

-continued
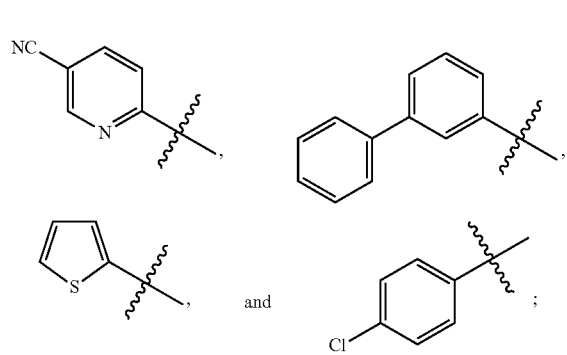
and B is selected from H, halogen, $C_1$-$C_4$ alkyl, haloalkoxy and heteroarylalkoxy, alkoxyalkyl, haloalkyl, nitro, alkylthio, acylamino, carbamoyl,
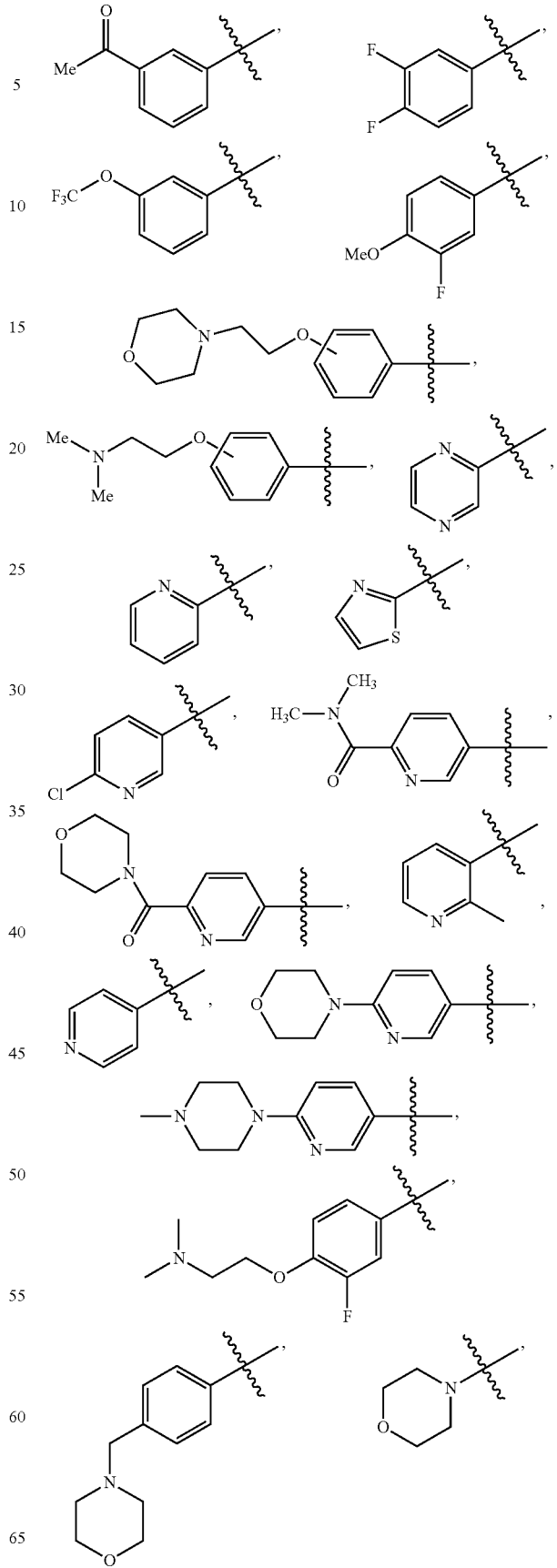

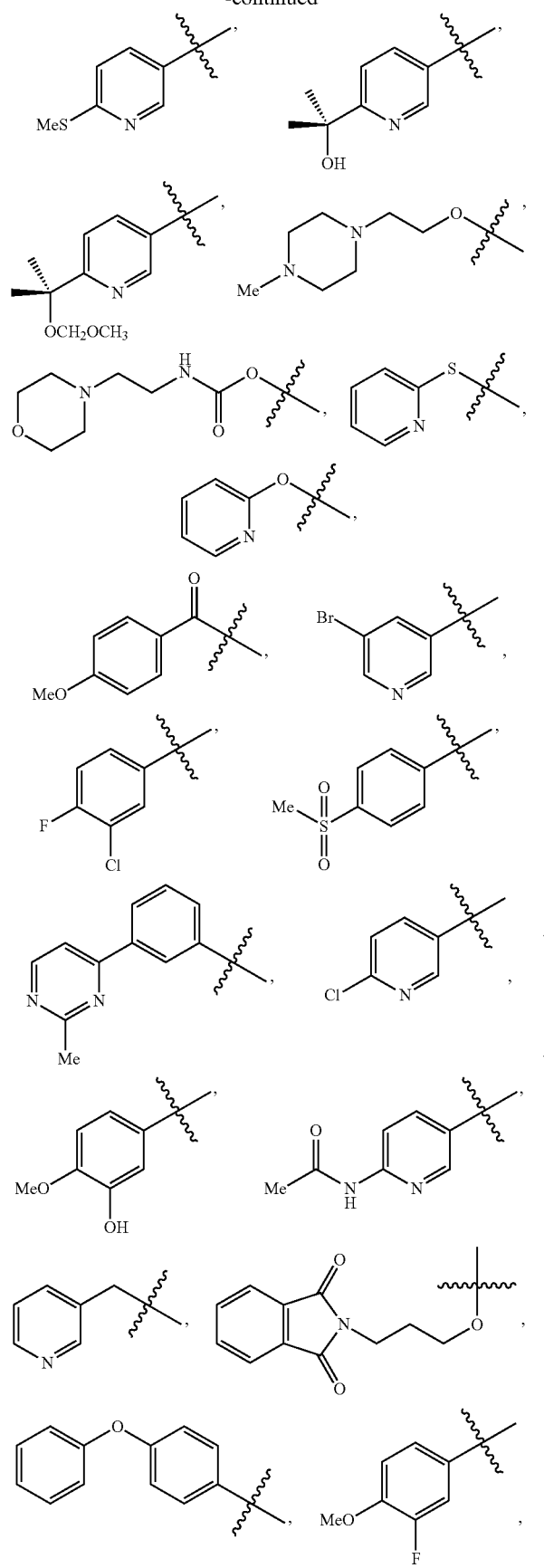
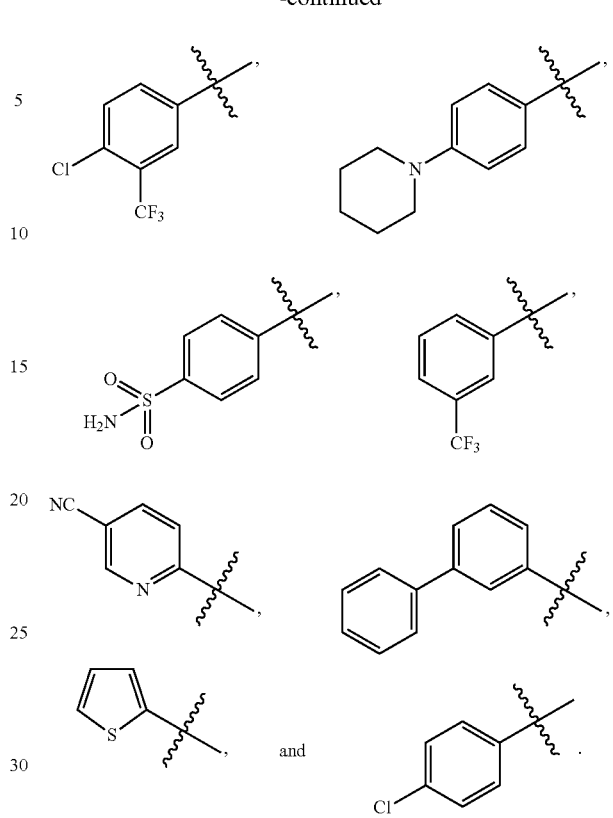
2. A composition comprising one or more compounds according to claim 1 and a pharmaceutically acceptable carrier, excipient, or diluent.
3. A compound of formula 1a-2:
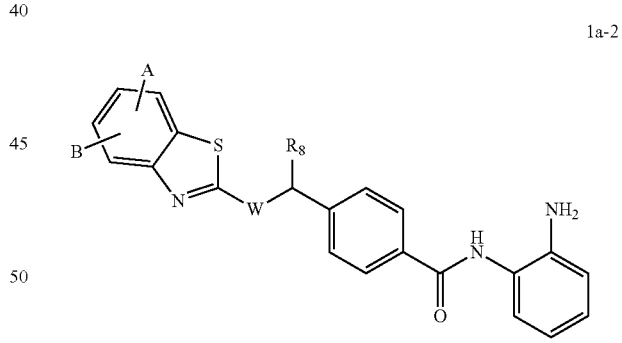
wherein W is S or NH; $R_8$ is H or $C_1$-$C_4$ alkyl; and A is selected from $C_1$-$C_4$ alkyl, haloalkoxy and heteroarylalkoxy, alkoxyalkyl, haloalkyl, nitro, alkylthio, acylamino, carbamoyl,
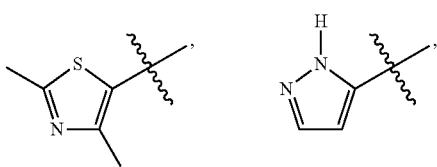

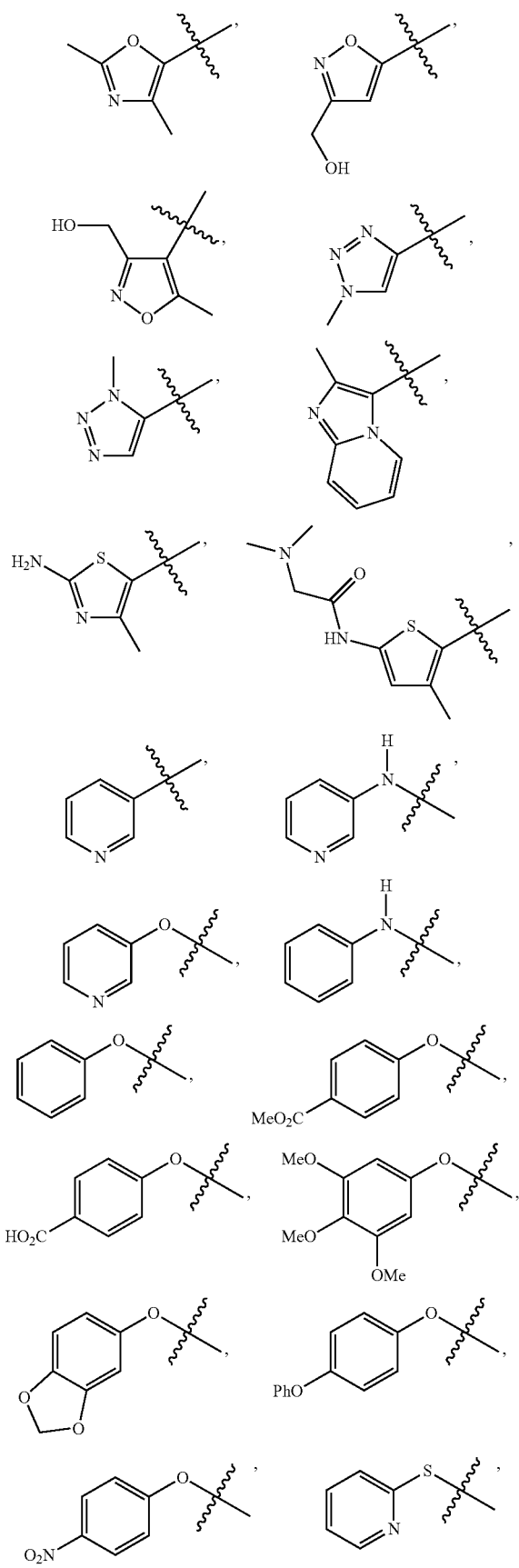
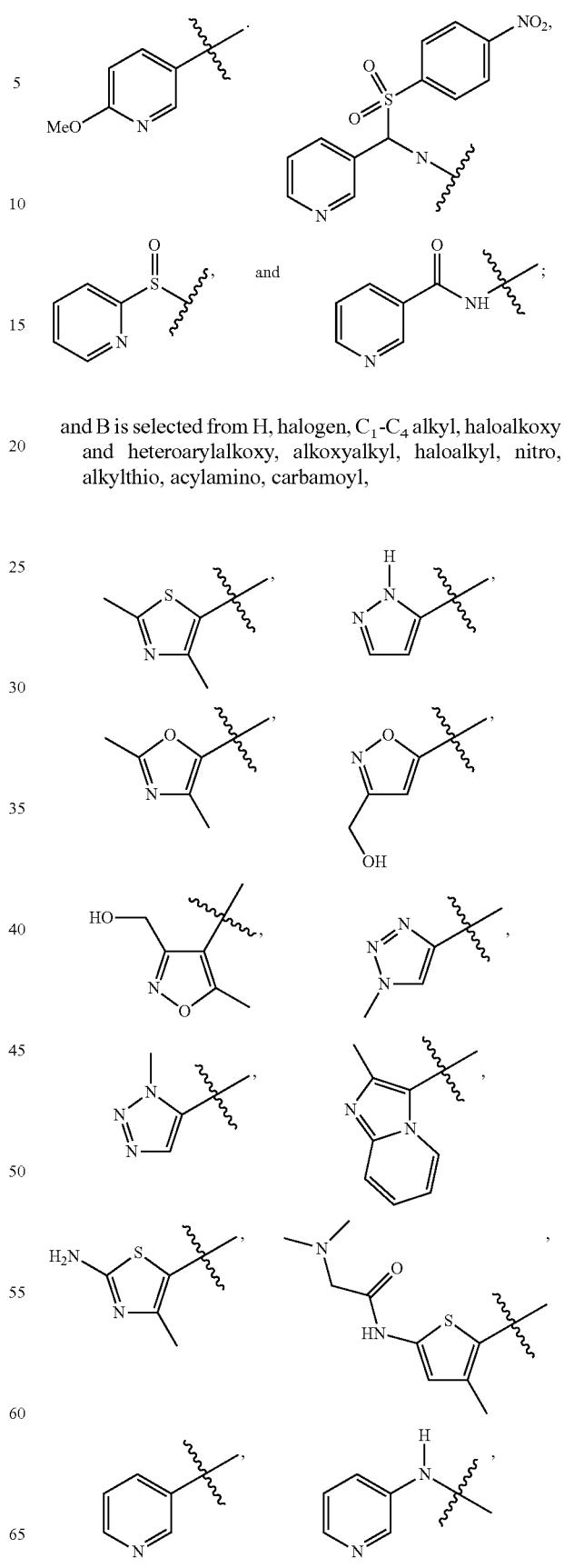
and B is selected from H, halogen, $C_1$-$C_4$ alkyl, haloalkoxy and heteroarylalkoxy, alkoxyalkyl, haloalkyl, nitro, alkylthio, acylamino, carbamoyl,

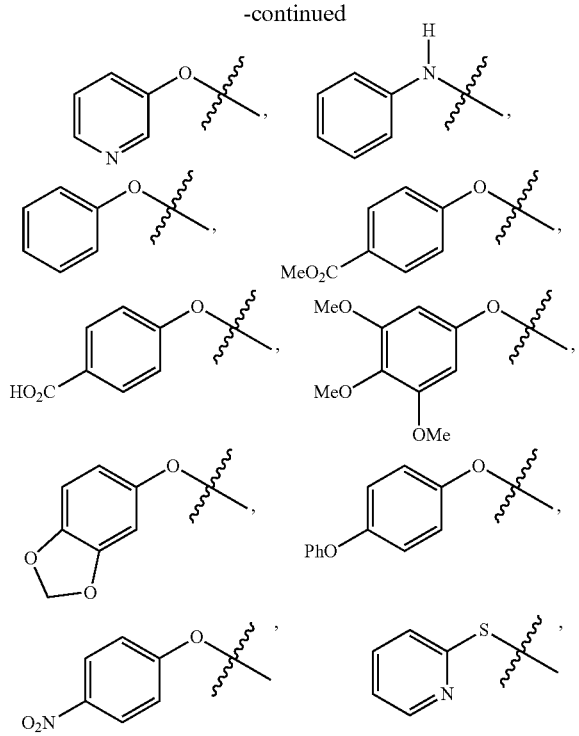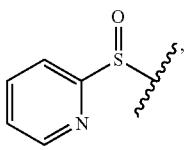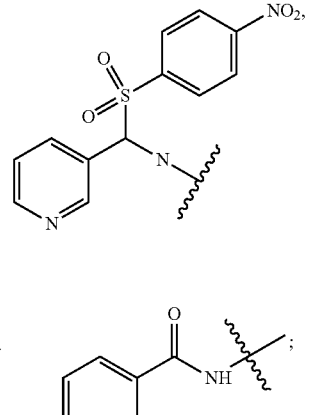
4. A composition comprising one or more compounds according to claim 3 and a pharmaceutically acceptable carrier, excipient, or diluent.
* * * * *

SEQUENCE LISTING

<160> NUMBER OF SEQ ID NOS: 17

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
gaaacgtgag ggactcagca        20

<210> SEQ ID NO 2
<211> LENGTH: 20
<212> TYPE: DNA
<213> ORGANISM: Artificial
<220> FEATURE:
<223> OTHER INFORMATION: Synthetic

<400> SEQUENCE: 2
ggaagccaga gctggagagg        20

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
gttaggtgag gcactgagga                                                 20

<210> SEQ ID NO 4
<211> LENGTH: 20
<212> TYPE: DNA
<213> ORGANISM: Artificial
<220> FEATURE:
<223> OTHER INFORMATION: Synthetic

<400> SEQUENCE: 4
gctgagctgt tctgatttgg                                                 20

<210> SEQ ID NO 5
<211> LENGTH: 20
<212> TYPE: DNA
<213> ORGANISM: Artificial
<220> FEATURE:
<223> OTHER INFORMATION: Synthetic

<400> SEQUENCE: 5
cgtgagcact tctcatttcc                                                 20

<210> SEQ ID NO 6
<211> LENGTH: 20
<212> TYPE: DNA
<213> ORGANISM: Artificial
<220> FEATURE:
<223> OTHER INFORMATION: Synthetic

<400> SEQUENCE: 6
cgctttcctt gtcattgaca                                                 20

<210> SEQ ID NO 7
<211> LENGTH: 20
<212> TYPE: DNA
<213> ORGANISM: Artificial
<220> FEATURE:
<223> OTHER INFORMATION: Synthetic

<400> SEQUENCE: 7
gcctttccta ctcattgtgt                                                 20

<210> SEQ ID NO 8
<211> LENGTH: 20
<212> TYPE: DNA
<213> ORGANISM: Artificial
<220> FEATURE:
<223> OTHER INFORMATION: Synthetic

<400> SEQUENCE: 8
gctgcctgcc gtgcccaccc                                                 20

<210> SEQ ID NO 9
<211> LENGTH: 20
<212> TYPE: DNA
<213> ORGANISM: Artificial
<220> FEATURE:
<223> OTHER INFORMATION: Synthetic

<400> SEQUENCE: 9
cgtgcctgcg ctgcccacgg                                                    20

<210> SEQ ID NO 10
<211> LENGTH: 20
<212> TYPE: DNA
<213> ORGANISM: Artificial
<220> FEATURE:
<223> OTHER INFORMATION: Synthetic

<400> SEQUENCE: 10
tacagtccat gcaacctcca                                                    20

<210> SEQ ID NO 11
<211> LENGTH: 20
<212> TYPE: DNA
<213> ORGANISM: Artificial
<220> FEATURE:
<223> OTHER INFORMATION: Synthetic

<400> SEQUENCE: 11
atcagtccaa ccaacctcgt                                                    20

<210> SEQ ID NO 12
<211> LENGTH: 20
<212> TYPE: DNA
<213> ORGANISM: Artificial
<220> FEATURE:
<223> OTHER INFORMATION: Synthetic

<400> SEQUENCE: 12
cttcggtctc acctgcttgg                                                    20

<210> SEQ ID NO 13
<211> LENGTH: 20
<212> TYPE: DNA
<213> ORGANISM: Artificial
<220> FEATURE:
<223> OTHER INFORMATION: Synthetic

<400> SEQUENCE: 13
caggctggaa tgagctacag                                                    20

<210> SEQ ID NO 14
<211> LENGTH: 20
<212> TYPE: DNA
<213> ORGANISM: Artificial
<220> FEATURE:
<223> OTHER INFORMATION: Synthetic

<400> SEQUENCE: 14
gacgctgcaa tcaggtagac                                                    20

<210> SEQ ID NO 15
<211> LENGTH: 20
<212> TYPE: DNA
<213> ORGANISM: Artificial
<220> FEATURE:
<223> OTHER INFORMATION: Synthetic

<400> SEQUENCE: 15
cttcagccag gatgcccaca                                                    20

<210> SEQ ID NO 16
<211> LENGTH: 20

```
<212> TYPE: DNA
<213> ORGANISM: Artificial
<220> FEATURE:
<223> OTHER INFORMATION: Synthetic

<400> SEQUENCE: 16
ctccggctcc tccatcttcc                                           20

<210> SEQ ID NO 17
<211> LENGTH: 20
<212> TYPE: DNA
<213> ORGANISM: Artificial
<220> FEATURE:
<223> OTHER INFORMATION: Synthetic

<400> SEQUENCE: 17
agccagctgc cacttgatgc                                           20
```